US008193227B2

(12) United States Patent
Flentge et al.

(10) Patent No.: US 8,193,227 B2
(45) Date of Patent: Jun. 5, 2012

(54) HIV PROTEASE INHIBITING COMPOUNDS

(75) Inventors: Charles A. Flentge, Salem, WI (US);
Hui-Ju Chen, Grayslake, IL (US);
David A. DeGoey, Salem, WI (US);
William J. Flosi, Evanston, IL (US);
David J. Grampovnik, Waukegan, IL (US); Peggy P. Huang, Lake Bluff, IL (US); Dale J. Kempf, Libertyville, IL (US); Larry L. Klein, Lake Forest, IL (US); Allan C. Krueger, Gurnee, IL (US); Darold L. Madigan, Elk Grove Village, IL (US); John T. Randolph, Libertyville, IL (US); Minghua Sun, Libertyville, IL (US); Ming C. Yeung, Grayslake, IL (US); Chen Zhao, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 329 days.

(21) Appl. No.: 11/009,841

(22) Filed: Dec. 10, 2004

(65) Prior Publication Data

US 2011/0003827 A1    Jan. 6, 2011

Related U.S. Application Data

(60) Provisional application No. 60/529,121, filed on Dec. 11, 2003.

(51) Int. Cl.
*A61K 31/415*    (2006.01)
*C07D 233/00*    (2006.01)

(52) U.S. Cl. ..... 514/386; 514/389; 514/392; 548/316.4; 548/321.5

(58) Field of Classification Search .................. 514/386, 514/389, 392; 548/316.4, 321.5
See application file for complete search history.

(56) References Cited

U.S. PATENT DOCUMENTS 5,914,332 A    6/1999  Sham et al.
5,977,137 A  * 11/1999  Tung et al. ............... 514/312
6,150,556 A    11/2000  Getman et al.
6,251,906 B1   6/2001  Chen et al.
2004/0039016 A1  2/2004  Ghosh et al.

FOREIGN PATENT DOCUMENTS

| WO | 94/05639  | 3/1994  |
| WO | 95/06030  | 3/1995  |
| WO | 95/33464  | 12/1995 |
| WO | 99/33792  | 7/1999  |
| WO | 99/33815  | 7/1999  |
| WO | 01/00635  | 1/2001  |
| WO | 02/06292  | 1/2002  |
| WO | 02/10124  | 2/2002  |
| WO | 02/092595 | 11/2002 |
| WO | 03/078438 | 9/2003  |

OTHER PUBLICATIONS van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*
"Fosamprenavir", Drugs of the Future, Barcelona, ES., vol. 26, No. 3, Mar. 2001, pp. 224-231.
Flynn, D.L., et al., "Chemical Library Purification Strategies Based on Principles of Complementary Molecular Reactivity and Molecular Recognition", *J. Am. Chem. Soc.*, 119:4874-4881 (1997).
Vazquez, M.L., et al., "Inhibitors of HIV-1 Protease Containing the Novel and Potent ®-(Hydroxyethyl)sulfonamide Isostere", *Journ. Of Medicinal Chem.*, 38(4):581-584 (1995).

* cited by examiner

*Primary Examiner* — Brandon Fetterolf
*Assistant Examiner* — Paul Zarek
(74) *Attorney, Agent, or Firm* — Bradley E. Davis

(57) ABSTRACT

A compound of the formula

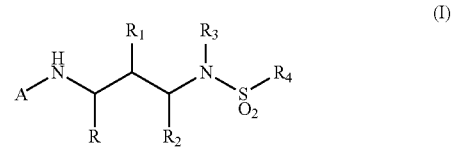

(I)

is disclosed as an HIV protease inhibitor. Methods and compositions for inhibiting an HIV infection are also disclosed.

19 Claims, No Drawings

HIV PROTEASE INHIBITING COMPOUNDS

This application claims priority to the provisional application Ser. No. 60/529,121 filed on Dec. 11, 2003.

TECHNICAL FIELD

The present invention relates to novel compounds and a composition and a method for inhibiting human immunodeficiency virus (HIV) protease, a composition and method for inhibiting or treating an HIV infection, processes for making the compounds and synthetic intermediates employed in the processes.

BACKGROUND OF THE INVENTION

The genome of the human immunodeficiency virus (HIV) encodes a protease that is responsible for the proteolytic processing of one or more polyprotein precursors such as the pol and gag gene products. HIV protease processes the gag precursor into core proteins and also processes the pol precursor into reverse transcriptase and protease.

The correct processing of the precursor polyproteins by HIV protease is necessary for the assembly of infectious virions. Therefore, inhibition of HIV protease provides a useful target for development of therapeutic agents for treatment of HIV infection.

In recent years, inhibitors of HIV protease have become an important class of therapeutic agents for inhibition and treatment of HIV infection in humans. HIV protease inhibitors are especially effective when administered in combination with other classes of HIV therapeutic agents, especially inhibitors of HIV reverse transcriptase, in "cocktails" of HIV therapeutic agents.

At the present time, the HIV protease inhibitors saquinavir, ritonavir, indinavir, nelfinavir, amprenavir, lopinavir/ritonavir, fosamprenavir, and atazanavir have been approved in the U.S. for treatment of HIV infection. There is a continuing need for improved HIV protease inhibitors that are very potent, that have reduced side-effects and that are effective against resistant strains of HIV.

SUMMARY OF THE INVENTION

The present invention provides a compound of formula (I)

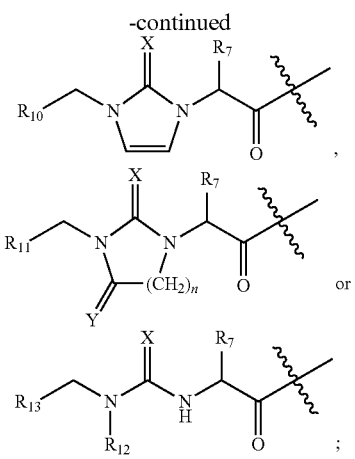

or a pharmaceutically acceptable salt form, stereoisomer, ester, salt of an ester, prodrug, salt of a prodrug, or combination thereof, wherein:

A is $R_5C(O)-$, $R_6SO_2-$,

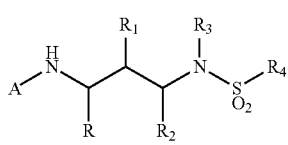

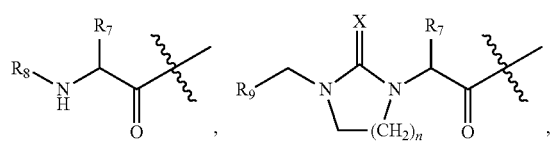

X is O, S or NH;
Y is O, S or NH;
R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, $-N(H)$alkyl, $-N($alkyl$)_2$, $-C(=O)$OH, $-C(=O)$Oalkyl, haloalkyl, hydroxyalkyl and alkoxyalkyl;
$R_1$ is $OR_a$, $-OSO_2R_a$, $-OSO_3R_a$, $-OPO_3R_a$, $-OC(=O)C(H)(R_{1a})NR_aR_b$ or $-OC(=O)C(H)(R_{1a})N(H)C(O)OR_a$;
$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, $-OR_a$, $-SR_a$, $-SOR_a$, $-SO_2R_a$, $-SO_2NR_aR_b$, $-C(=O)R_a$, $-NR_aR_b$, $-N(R_b)C(=O)R_a$, $-N(R_b)C(=O)OR_a$, $-N(R_b)SO_2R_a$, $-N(R_a)SO_2NR_aR_b$, $-N(R_b)C(=NH)NR_aR_b$, $-N(R_b)C(=O)NR_aR_b$, $-C(=O)NR_aR_b$ and $-C(=O)OR_a$;
$R_2$ is H;
$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkyl$SR_a$, -alkyl$SOR_a$, -alkyl$SO_2R_a$, -alkyl$NR_aR_b$, -alkyl$N(R_b)C(=O)OR_a$, -alkyl$N(R_b)C(=O)R_a$, -alkyl$N(R_b)SO_2R_a$ or -alkyl$N(R_b)SO_2NR_aR_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, $-SH$, $-S($alkyl$)$, $-SO_2($alkyl$)$, $-NH_2$, $-N(H)($alkyl$)$, $-N($alkyl$)_2$, $-N(H)C(=O)$alkyl, $-N($alkyl$)C(=O)$alkyl, $-C(=O)OH$, $-C(=O)O($alkyl$)$, $-C(=O)NH_2$, $-C(=O)N(H)($alkyl$)$, $-C(=O)N($alkyl$)_2$, $-C(=O)$alkyl, haloalkyl, hydroxyalkyl, alkoxyalkyl, cyanoalkyl, formylalkyl, nitroalkyl, -alkyl$SH$, -alkyl$S($alkyl$)$, -alkyl$SO_2$(alkyl), -alkyl$NH_2$, -alkyl$N(H)$(alkyl), -alkyl$N$(alkyl)$_2$, -alkyl$N(H)C(=O)$alkyl, -alkyl$N$(alkyl)$C(=O)$alkyl, -alkyl$C(=O)OH$, -alkyl$C(=O)O$(alkyl), -alkyl$C(=O)NH_2$, -alkyl$C(=O)N(H)$(alkyl), -alkyl$C(=O)N$(alkyl)$_2$, -alkyl$C(=O)$alkyl and $R_{3a}$;
$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_5$ is alkyl, haloalkyl, cyanoalkyl, hydroxyalkyl, alkoxyalkyl, haloalkoxyalkyl, -OalkylSO$_2$alkyl, —O-heterocycle, -alkyl-O-aryl or —O-alkyl-heteroaryl; wherein the heterocycle, aryl or heteroaryl moiety of —O-heterocycle, -alkyl-O-aryl and —O-alkyl-heteroaryl is independently substituted with 0, 1, 2 or 3 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_6$ is aryl or heteroaryl; wherein each $R_6$ is substituted with 0 or 1 substituent selected from the group consisting of —C(H)=NOH, —C(alkyl)=NOH, —C(H)=NO(alkyl), —C(alkyl)=NO(alkyl), —C(H)=NO(arylalkyl) and —C(alkyl)=NO(arylalkyl);

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_8$ is —C(=O)OR$_{8a}$ or —C(=O)alkylNR$_{8a}$R$_{8b}$, $R_{8a}$ and $R_{8b}$ are, at each occurrence, independently selected from the group consisting of alkyl, arylalkyl and heteroarylalkyl; wherein each R$_{8a}$ and R$_{8b}$ is independently substituted with 0, 1, 2, 3 or 4 substituents independently selected from the group consisting of alkyl, nitro, hydroxy, alkoxy, amino, formyl, halo, haloalkyl, hydroxyalkyl, alkoxyalky aminoalkyl and formylalkyl;

$R_9$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{10}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{10}$ is substituted with 0, 1, 2 or 3 substituents independently selected from the group consisting of alkyl, alkenyl, alkynyl, cyano, halo, nitro, oxo, —OR$_a$, —OC (=O)$R_a$, —$SR_a$, —$SOR_a$, —$SO_2R_a$, —$SO_2NR_a$, —$SO_2OR_a$, —$NR_aR_b$, —$N(R_b)NR_aR_b$, —$N(R_b)C(=O)R_a$, —$N(R_b)SO_2R_a$, —$N(R_b)C(=O)OR_a$, —$N(R_b)C(=O)NR_aR_b$, —$N(R_b)SO_2NR_aR_b$, —$C(=O)R_a$, —$C(=O)NR_aR_b$, —$C(=O)OR_a$, azidoalkyl, haloalkyl, nitroalkyl, cyanoalkyl, -alkyl$OR_a$, -alkylOC(=O)$R_a$, -alkyl$SR_a$, -alkyl$SOR_a$, -alkyl$SO_2R_a$, -alkyl$SO_2NR_a$, -alkyl$SO_2OR_a$, -alkyl$NR_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN($R_b$)N$R_aR_b$, -alkylN($R_b$)C(=O)$R_a$, -alkylN($R_b$)C(=O)O$R_a$, -alkylN($R_b$)C(=O)N$R_aR_b$, -alkylN($R_b$)SO$_2$N$R_aR_b$, -alkylN($R_b$)SO$_2R_a$, -alkylC(=O)$R_a$, -alkylC(=O)O$R_a$, -alkylC(=O)N$R_aR_b$ and $R_{10a}$;

$R_{10a}$ is cycloalkyl, cycloalkenyl, heterocycle, aryl or heteroaryl; wherein each $R_{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{11}$ is alkyl, alkenyl, alkynyl, —C(=O)N$R_aR_b$, —C(=O)O$R_a$, cycloalkyl, cycloalkenyl, aryl, heteroaryl or heterocycle; wherein each $R_{11}$ is substituted with 0, 1, 2 or 3 substituents independently selected from the group consisting of alkyl, alkenyl, alkynyl, cyano, halo, nitro, oxo, —O$R_a$, —OC(=O)$R_a$, —S$R_a$, —SO$R_E$, —SO$_2R_a$, —SO$_2$N$R_a$, —SO$_2$O$R_a$, —N$R_aR_b$, —N($R_b$)N$R_aR_b$, —N($R_b$)C(=O)$R_a$, —N($R_b$)SO$_2R_a$, —N($R_b$)C(=O)O$R_a$, —N($R_b$)C(=O)N$R_aR_b$, —N($R_b$)SO$_2$N$R_aR_b$, —C(=O)$R_a$, —C(=O)N$R_aR_b$, —C(=O)O$R_a$, azidoalkyl, haloalkyl, nitroalkyl, cyanoalkyl, -alkylOC(=O)$R_a$, -alkyl$SR_a$, -alkyl$SOR_a$, -alkyl$SO_2R_a$, -alkyl$SO_2NR_a$, -alkyl$SO_2OR_a$, -alkyl$NR_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN($R_b$)N$R_aR_b$, -alkylN($R_b$)C(=O)$R_a$, -alkylN($R_b$)C(=O)O$R_a$, -alkylN($R_b$)C(=O)N$R_aR_b$, -alkylN($R_b$)SO$_2$N$R_aR_b$, -alkylN($R_b$)SO$_2R_a$, -alkylC(=O)$R_a$, -alkylC(=O)O$R_a$, -alkylC(=O)N$R_aR_b$ and $R_{11a}$;

$R_{11a}$ is cycloalkyl, cycloalkenyl, heterocycle, aryl or heteroaryl; wherein each $R_{11a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{12}$ is alkyl, alkenyl, cycloalkyl, cycloalkenyl, cycloalkylalkyl or cycloalkenylalkyl; wherein each $R_{12}$ is substituted with 0, 1 or 2 substituents independently selected from the group consisting of hydroxy, alkoxy cyano, nitro and halo;

$R_{13}$ is alkyl, alkenyl, alkynyl, cycloalkyl, cycloalkenyl, aryl, heteroaryl or heterocycle; wherein each $R_{13}$ is substituted with 0, 1, 2 or 3 substituents independently selected from the group consisting of alkyl, alkenyl, alkynyl, cyano, halo, nitro, oxo, —O$R_a$, —OC(=O)$R_a$, —S$R_a$, —SO$R_a$, —SO$_2R_a$, —SO$_2$N$R_a$, —SO$_2$O$R_a$, —N$R_aR_b$, —N($R_a$)N$R_aR_b$, —N(ROC(=O)$R_a$, —N($R_b$)SO$_2R_a$, —N($R_b$)C(=O)O$R_a$, —N($R_b$)C(=O)N$R_aR_b$, —N($R_b$)SO$_2$N$R_aR_b$, —C(=O)$R_a$, —C(=O)N$R_aR_b$, —C(=O)O$R_a$, azidoalkyl, haloalkyl, nitroalkyl, cyanoalkyl, -alkyl$OR_a$, -alkylOC(=O)$R_a$, -alkyl$SR_a$, -alkyl$SOR_a$, -alkyl$SO_2R_a$, -alkyl$SO_2NR_a$, -alkyl$SO_2OR_a$, -alkyl$NR_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN($R_b$)N$R_aR_b$, -alkylN($R_b$)C(=O)$R_a$, -alkylN($R_b$)C(=O)O$R_a$, -alkylN($R_b$)C(=O)N$R_aR_b$, -alkylN($R_b$)SO$_2$N$R_aR_b$, -alkylN($R_b$)SO$_2R_a$, -alkylC(=O)$R_a$, -alkylC(=O)O$R_a$, -alkylC(=O)N$R_aR_b$ and $R_{13a}$;

$R_{13a}$ is cycloalkyl, cycloalkenyl, heterocycle, aryl or heteroaryl; wherein each $R_{13a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and $R_c$; alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —$NH_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

The present invention also provides the processes of making a compound of the present invention and intermediates employed in the processes.

The present invention further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention yet further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier.

The present invention still further provides a method of inhibiting the replication of an HIV virus comprising contacting said virus with a therapeutically effective amount of a compound or combination of compounds of the present invention, or a pharmaceutically acceptable salt form, stereoisomer, ester, salt of an ester, prodrug, salt of a prodrug, or combination thereof.

The present invention still further provides a method of inhibiting the replication of an HIV virus comprising contacting said virus with any one of the pharmaceutical composition of the present invention.

The present invention still further provides a method of inhibiting an HIV protease comprising contacting said HIV protease with a therapeutically effective amount of a compound or combination of compounds of the present invention, or a pharmaceutically acceptable salt form, stereoisomer, ester, salt of an ester, prodrug, salt of a prodrug, or combination thereof.

The present invention still further provides a method of inhibiting an HIV protease comprising contacting said HIV protease with any one of the pharmaceutical composition of the present invention.

The present invention also provides a method of treating or preventing an HIV infection comprising administering to a patient in need of such treatment a therapeutically effective amount of a compound or combination of compounds of the present invention, or a pharmaceutically acceptable salt form, stereoisomer, ester, salt of an ester, prodrug, salt of a prodrug, or combination thereof.

The present invention also provides a method of treating or preventing an HIV infection comprising administering to a patient in need of such treatment any one of the pharmaceutical composition of the present invention.

DETAILED DESCRIPTION OF THE INVENTION

As used in the present specification the following terms have the meanings indicated:

As used herein, the singular forms "a", "an", and "the" may include plural reference unless the context clearly dictates otherwise.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonylchloride and the like, anhydrides derived from reaction of the carboxylic acid with N,N'-carbonyldiimidazole and the like, N-hydroxysuccinimide derived esters, N-hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "alkanoyl" as used herein refers to an alkyl group attached to the parent molecular moiety through a carbonyl group. Examples of alkanoyl include methylcarbonyl, ethylcarbonyl, tert-butylcarbonyl and the like.

The term "alkyl," as used herein, refers to a group derived from a straight or branched chain saturated hydrocarbon containing 1, 2, 3, 4, 5, 6, 7, 8, 9 or 10 carbon atoms. Examples of alkyl groups include butyl, methyl, 1-methylpropyl, 2-methylbutyl, tert-butyl, isopropyl, and the like.

The term "alkylamino" as used herein refers to —N(H)R$^{90}$ wherein R$^{90}$ is alkyl.

The term "alkylaminocarbonyl" as used herein refers to an alkylamino group attached to the parent molecular moiety through a carbonyl group.

The term "alkenyl," as used herein, refers to a straight or branched chain group of 2, 3, 4, 5, 6, 7, 8, 9 or 10 carbon atoms containing at least one carbon-carbon double bond. Examples of alkenyl groups include alkyl, propenyl, 3-methyl-2-butenyl, and the like.

The term "alkynyl," as used herein, refers to a straight or branched chain hydrocarbon of 2, 3, 4, 5, 6, 7, 8, 9 or 10 carbon atoms containing at least one carbon-carbon triple bond. Examples of alkynyl groups include ethynyl, 2-methyl-3-butynyl, 3-pentynyl, and the like.

The term "alkoxy," as used herein, refers to an alkyl group attached to the parent molecular moiety through an oxygen atom. Examples of alkoxy groups include tert-butoxy, methoxy, isopropoxy, and the like.

The term "alkoxyalkyl," as used herein, refers to an alkyl group substituted by at least one alkoxy group.

The term "alkoxycarbonyl," as used herein, refers to an alkoxy group attached to the parent molecular moiety through a carbonyl group. Examples of alkoxycarbonyl groups include tert-butoxycarbonyl, ethoxycarbonyl, methoxycarbonyl, and the like.

The term "amino" as used herein, refers to —NH$_2$.

The term "aminoalkyl" as used herein, refers to an amino group appended to the parent molecular moiety through an alkyl group as defined herein.

The term "aryl" as used herein, refers to a phenyl group, or a bicyclic or tricyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Examples of aryl groups include anthracenyl, azulenyl, fluorenyl, indanyl, indenyl, naphthyl, phenyl, tetrahydronaphthyl, and the like. The aryl groups of the present invention can be connected to the parent molecular moiety through any substitutable carbon atom of the group. The aryl groups of the present invention can be substituted or unsubstituted.

The term "arylalkyl," as used herein, refers to an aryl group attached to the parent molecular moiety through an alkyl group.

The term "carbonyl" as used herein, refers to —C(=O).

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic, partially unsaturated, monocyclic, bicyclic or tricyclic ring system, having three to fourteen carbon atoms and zero heteroatom. Examples of cycloalkenyl groups include cyclohexenyl, octahydronaphthalenyl, norbornylenyl, and the like. The cycloalkenyl groups of the present invention can be unsubstituted or substituted.

The term "cycloalkenylalkyl," as used herein, refers to a cycloalkenyl group attached to the parent molecular moiety through an alkyl group.

The term "cycloalkyl," as used herein, refers to a saturated monocyclic, bicyclic, or tricyclic hydrocarbon ring system having three to fourteen carbon atoms and zero heteroatom. Examples of cycloalkyl groups include cyclopropyl, cyclobutyl, cyclopentyl, cyclohexyl, cycloheptyl, bicyclo[3.1.1]heptyl, 6,6-dimethylbicyclo[3.1.1]heptyl, adamantyl, and the like. The cycloalkyl groups of the present invention can be unsubstituted or substituted.

The term "cycloalkylalkyl," as used herein, refers to a cycloalkyl group attached to the parent molecular moiety through an alkyl group.

The term "dialkylamino" as used herein refers to —NR$^{90}$R$^{91}$, wherein R$^{90}$ and R$^{91}$ are alkyls.

The term "dialkylaminocarbonyl" as used herein refers to a dialkylamino group as defined herein, appended to the parent molecular moiety through a carbonyl group.

The term "formyl", as used herein, refers to a —C(O)H group.

The term "formylalkyl" as used herein, refers to a formyl group appended to the parent molecular moiety through an alkyl group.

The terms "halo," and "halogen," as used herein, refer to F, Cl, Br, and I.

The term "haloalkenyl," as used herein, refers to an alkenyl group substituted by one, two, three, or four halogen atoms.

The term "haloalkoxy" as used herein, refers to a haloalkyl group attached to the parent molecular moiety through an oxygen atom.

The term "haloalkoxyalkyl" as used herein, refers to a haloalkoxy group attached to the parent molecular moiety through an alkyl group, as defined herein.

The term "haloalkyl," as used herein, refers to an alkyl group substituted by one, two, three, or four halogen atoms.

The term "haloalkynyl," as used herein, refers to an alkynyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a heterocycle group, as defined herein, or an additional heteroaryl group. The term "heteroaryl" also includes tricyclic systems where a bicyclic system is fused to a phenyl group, a monocyclic cycloalkyl group, as defined herein, a heterocycle group, as defined herein, or an additional heteroaryl group. The heteroaryl groups are connected to the parent molecular moiety through any substitutable carbon or nitrogen atom in the groups. Examples of heteroaryl groups include benzothienyl, benzoxazolyl, benzimidazolyl, benzoxadiazolyl, benzofuranyl, dihydrobenzothiazolyl, furanyl (furyl), imidazolyl, 3H-[4,5-b]pyridinyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridoimidazolyl, pyridyl, pyridazinyl, pyrimidinyl, pyrazinyl, pyrazolyl, pyrrolyl, quinolinyl, tetrahydroquinolinyl, triazinyl, and the like. The heteroaryl groups of the present invention can be substituted or unsubstituted. In addition, the nitrogen heteroatoms can be optionally quaternized or oxidized to the N-oxide. Also, the nitrogen containing rings can be optionally N-protected.

The term "heteroarylalkyl", as used herein, refers to refers to a heteroaryl group attached to the parent molecular moiety through an alkyl group.

The term "heterocycle," as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic systems where a heterocycle ring is fused to a phenyl group, a monocyclic cycloalkenyl group, as defined herein, a monocyclic cycloalkyl group, as defined herein, or an additional monocyclic heterocycle group. The term "heterocycle" also includes tricyclic systems where a bicyclic system is fused to a phenyl group, a monocyclic cycloalkenyl group, as defined herein, a monocyclic cycloalkyl group, as defined herein, or an additional monocyclic heterocycle group. The heterocycle groups of the invention are connected to the parent molecular moiety through any substitutable carbon or nitrogen atom in the group. Examples of heterocycle groups include benzoxazinyl, 1,3-benzodioxol, dihydroindolyl, dihydropyridinyl, 1,3-dioxanyl, 1,4-dioxanyl, 1,3-dioxolanyl, tetrahydrofuranyl, hexahydrofurofuranyl, hexahydrofuropyranyl, isoindolinyl, morpholinyl, piperazinyl, pyrrolidinyl, tetrahydropyridinyl, piperidinyl, thiomorpholinyl, tetrahydropyranyl, and the like. The heterocycle groups of the present invention can be substituted or substituted. In addition, the nitrogen heteroatoms can be optionally quaternized or oxidized to the N-oxide. Also, the nitrogen containing heterocyclic rings can be optionally N-protected.

The term "heterocyclealkyl", as used herein, refers to refers to a heterocycle group attached to the parent molecular moiety through an alkyl group.

The term "hydroxy" or "hydroxyl" as used herein, refers to —OH.

The term "hydroxyalkyl," as used herein, refers to an alkyl group as substituted by at least one hydroxy group.

The term "nitro," as used herein, refers to —NO$_2$.

The term "nitroalkyl," as used herein, refers to an alkyl group substituted by at least one nitro group.

The term "oxo," as used herein, refers to =O.

The term "thioalkoxy", as used herein, refers to an alkyl group as defined herein, appended to the parent molecular moiety through a sulfur atom.

The term "thioalkoxyalkyl", as used herein, refers to an thioalkoxy group as defined herein, appended to the parent molecular moiety through a alkyl group.

It is understood that each of the terms alkanoyl, alkenyl, alkoxy, alkoxyalkyl, alkoxycarbonyl, alkyl, alkylamino, alkylaminocarbonyl, alkynyl, aminoalkyl, aryl, arylalkyl, cyanoalkyl, cycloalkenyl, cycloalkenylalkyl, cycloalkyl, cycloalkylalkyl, dialkylamino, dialkylaminocarbonyl, formylalkyl, haloalkenyl, haloalkoxy, haloalkoxyalkyl, haloalkynyl, haloalkyl, heteroaryl, heteroarylalkyl, heterocycle, heterocyclealkyl, hydroxyalkyl, nitroalkyl, thioalkoxy and thioalkoxyalkyl may be unsubstituted or substituted.

In a first embodiment, the present invention provides a compound of formula (I),

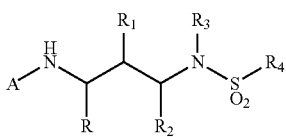

or a pharmaceutically acceptable salt form, stereoisomer, ester, salt of an ester, prodrug, salt of a prodrug, or combination thereof, wherein:

A is $R_5C(O)$—, $R_6SO_2$—,

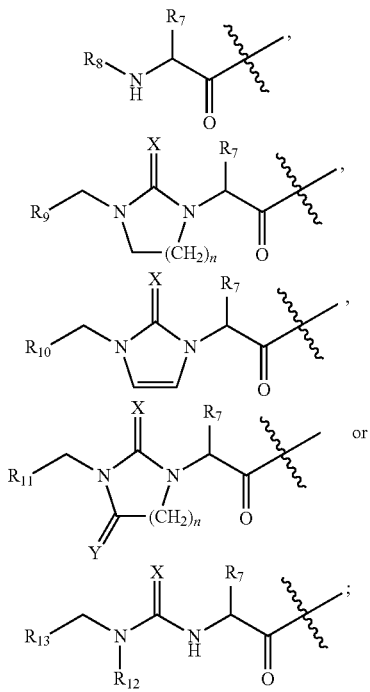

X is O, S or NH;
Y is O, S or NH;
R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —$NH_2$, —N(H)alkyl, —N(alkyl)$_2$, —C(=O)OH, —C(=O)Oalkyl, haloalkyl, hydroxyalkyl and alkoxyalkyl;
$R_1$ is $OR_a$, —$OSO_2R_a$, —$OSO_3R_a$, —$OPO_3R_a$, —OC(=O)C(H)(R$_{1a}$)NR$_a$R$_b$ or —OC(=O)C(H)(R$_{1a}$)N(H)C(O)OR$_a$;
$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, —$OR_a$, —$SR_a$, —$SOR_a$, —$SO_2R_a$, —$SO_2NR_aR_b$, —C(=O)R$_a$, —$NR_aR_b$, —N(R$_b$)C(=O)R$_a$, —N(R$_b$)C(=O)OR$_a$, —N(R$_b$)SO$_2$R$_a$, —N(R$_a$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;
$R_2$ is H;
$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSR$_a$, -alkylSOR$_a$, alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and $R_{3a}$;
$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;
$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —NR$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;
$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, $NH_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_5$ is alkyl, haloalkyl, cyanoalkyl, hydroxyalkyl, alkoxyalkyl, haloalkoxyalkyl, -Oalkyl$SO_2$alkyl, —O-heterocycle, -alkyl-O-aryl or —O-alkyl-heteroaryl; wherein the heterocycle, aryl or heteroaryl moiety of —O-heterocycle, -alkyl-O-aryl and —O-alkyl-heteroaryl is independently substituted with 0, 1, 2 or 3 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_6$ is aryl or heteroaryl; wherein each $R_6$ is substituted with 0 or 1 substituent selected from the group consisting of —C(H)=NOH, —C(alkyl)=NOH, —C(H)=NO(alkyl), —C(alkyl)=NO(alkyl), —C(H)=NO(arylalkyl) and —C(alkyl)=NO(arylalkyl);

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and $R_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_8$ is —C(=O)OR$_{8a}$ or —C(=O)alkylNR$_{8a}$R$_{8b}$, $R_{8a}$ and $R_{8b}$ are, at each occurrence, independently selected from the group consisting of alkyl, arylalkyl and heteroarylalkyl; wherein each $R_{8a}$ and $R_{8b}$ is independently substituted with 0, 1, 2, 3 or 4 substituents independently selected from the group consisting of alkyl, nitro, hydroxy, alkoxy, amino, formyl, halo, haloalkyl, hydroxyalkyl, alkoxyalky aminoalkyl and formylalkyl;

$R_9$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{10}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{10}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{10a}$;

$R_{10a}$ is cycloalkyl, cycloalkenyl, heterocycle, aryl or heteroaryl; wherein each $R_{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{11}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{11}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{11a}$;

R$_{11a}$ is cycloalkyl, cycloalkenyl, heterocycle, aryl or heteroaryl; wherein each R$_{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_{12}$ is alkyl, alkenyl, cycloalkyl, cycloalkenyl, cycloalkylalkyl or cycloalkenylalkyl; wherein each R$_{12}$ is substituted with 0, 1 or 2 substituents independently selected from the group consisting of hydroxy, alkoxy cyano, nitro and halo;

R$_{13}$ is alkyl, alkenyl, alkynyl, cycloalkyl, cycloalkenyl, aryl, heteroaryl or heterocycle; wherein each R$_{13}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{13a}$;

R$_{13a}$ is cycloalkyl, cycloalkenyl, heterocycle, aryl or heteroaryl; wherein each R$_{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_a$ and R$_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$; alternatively, R$_a$ and R$_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

For example, the present invention provides a compound of formula (I) wherein R$_1$ is OH and R$_2$ is H.

For example, the present invention provides a compound of formula (I) wherein R$_1$ is OH, R$_2$ is H, X is O and Y is O.

For example, the present invention provides a compound of formula (I) wherein wherein R$_1$ is OH, R$_2$ is H, X is O, Y is O, and R$_3$ is alkyl, cycloalkenylalkyl, cycloalkylalkyl, heterocleakyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (I) wherein R$_1$ is OH, R$_2$ is H, X is O, Y is O, R$_3$ is alkyl or cycloalkylalkyl and R$_4$ is aryl or heteroaryl.

For example, the present invention provides a compound of formula (I) wherein R$_1$ is OH, R$_2$ is H, X is O, Y is O, R$_3$ is alkyl or cycloalkylalkyl and R$_4$ is phenyl.

For example, the present invention provides a compound of formula (I) wherein R$_1$ is OH, R$_2$ is H, X is O, Y is O, R$_3$ is alkyl or cycloalkylalkyl and R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

For example, the present invention provides a compound of formula (I) wherein R$_1$ is OH, R$_2$ is H, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and R is phenylmethyl wherein R$_{4a}$ and R$_{4b}$ are independently selected from the group consisting of hydrogen and alkyl.

For example, the present invention provides a compound of formula (I) wherein R$_1$ is OH, R$_2$ is H, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is alkyl; wherein R$_{4a}$ and R$_{4b}$ are independently selected from the group consisting of hydrogen and alkyl.

For example, the present invention provides a compound of formula (I) wherein R$_1$ is OH, R$_2$ is H, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is alkyl; wherein R$_{4a}$ and R$_{4b}$ are independently selected from the group consisting of hydrogen and alkyl.

For example, the present invention provides a compound of formula (I) wherein R$_1$ is OH, R$_2$ is H, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is C1 alkyl, C2 alkyl, C3 alkyl, C4 alkyl or C5 alkyl; wherein R$_{4a}$ and R$_{4b}$ are independently selected from the group consisting of hydrogen and alkyl.

Exemplary compounds of the present invention having formula (I) include, but not limited to, the following:

hexahydrofuro[2,3-b]furan-3-yl(1S,2R)-1-benzyl-2-hydroxy-3-[({4-[(E)-(hydroxyimino)methyl]phenyl}sulfonyl)(isobutyl)amino]propylcarbamate;

tetrahydro-3-furanyl(1S,2R)-1-benzyl-2-hydroxy-3-[({4-[(E)-(hydroxyimino)methyl]phenyl}sulfonyl)(isobutyl)amino]propylcarbamate;

N-{(1S,2R)-1-benzyl-2-hydroxy-3-[({4-[(E)-(hydroxyimino)methyl]phenyl}sulfonyl)(isobutyl)amino]propyl}acetamide;

N-{(1S,2R)-1-benzyl-2-hydroxy-3-[({4-[(E)-(hydroxyimino)methyl]phenyl}sulfonyl)(isobutyl)amino]propyl}-2-(2,6-dimethylphenoxy)acetamide;

(3aS,7aR)-hexahydro-4H-furo[2,3-b]pyran-3-yl(1S,2R)-1-benzyl-2-hydroxy-3-[({4-[(E)-(hydroxyimino)methyl]phenyl}sulfonyl)(isobutyl)amino]propylcarbamate and (3aR,7aS)-hexahydro-4H-furo[2,3-b]pyran-3-yl(1S,2R)-1-benzyl-2-hydroxy-3-[({4-[(E)-(hydroxyimino)methyl]phenyl}sulfonyl)(isobutyl)amino]propylcarbamate;

3-furylmethyl(1S,2R)-1-benzyl-2-hydroxy-3-[({4-[(E)-(hydroxyimino)methyl]phenyl}sulfonyl)(isobutyl)amino]propylcarbamate;

2-pyridinylmethyl 2-({(1S,2R)-1-benzyl-2-hydroxy-3-[({4-[(E)-(hydroxyimino)methyl]phenyl}sulfonyl)(isobutyl)amino]propyl}amino)-2-oxoethylcarbamate;

2-(methylsulfonyl)ethyl(1S,2R)-1-benzyl-2-hydroxy-3-[({4-[(E)-(hydroxyimino)methyl]phenyl}sulfonyl)(isobutyl)amino]propylcarbamate;

(3aS,7aR)-hexahydro-4H-furo[2,3-b]pyran-3-yl(1S,2R)-1-benzyl-2-hydroxy-3-[({4-[(E)-(hydroxyimino)methyl]phenyl}sulfonyl)(isobutyl)amino]propylcarbamate;

(3aR,7aS)-hexahydro-4H-furo[2,3-b]pyran-3-yl(1S,2R)-1-benzyl-2-hydroxy-3-[({4-[(E)-(hydroxyimino)methyl]phenyl}sulfonyl)(isobutyl)amino]propylcarbamate;

3-pyridinylmethyl(1S,2R)-1-benzyl-2-hydroxy-3-[({4-[(E)-(hydroxyimino)methyl]phenyl}sulfonyl)(isobutyl)amino]propylcarbamate;

4-pyridinylmethyl(1S,2R)-1-benzyl-2-hydroxy-3-[({4-[(E)-(hydroxyimino)methyl]phenyl}sulfonyl)(isobutyl)amino]propylcarbamate;

1,3-thiazol-5-ylmethyl(1S,2R)-1-benzyl-2-hydroxy-3-[({4-[(E)-(hydroxyimino)methyl]phenyl}sulfonyl)(isobutyl)amino]propylcarbamate; and N-{(2R,3S)-2-hydroxy-3-[({4-(hydroxyimino)methyl]phenyl}sulfonyl)amino]-4-phenylbutyl}-4-[(E)-(hydroxyimino)methyl]-N-isobutylbenzenesulfonamide; or a pharmaceutically acceptable salt form, stereoisomer, ester, salt of an ester, prodrug, salt of a prodrug, or combination thereof.

In a second embodiment, the present invention provides a compound of formula (II)

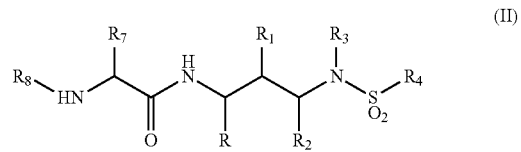

or a pharmaceutically acceptable salt form, stereoisomer, ester, salt of an ester, prodrug, salt of a prodrug, or combination thereof, wherein R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

R$_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

R$_{1a}$ is hydrogen, alkyl, alkenyl, alkynyl, cycloalkyl, cycloalkenyl, aryl, arylalkyl, heteroaryl or heteroarylalkyl; wherein each R$_{1a}$ is substituted with 0, 1 or 2 substituents independently selected from the group consisting of halo, alkyl, alkenyl, alkynyl, —OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(ROC(=O)NR$_a$R$_b$, —C(=O)NR$_a$R$_b$ and —C(=O)OR$_a$;

R$_2$ is H;

R$_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxy, -alkylSR$_a$, -alkylSOR$_a$, -alkylSO$_2$R$_a$, -alkylNR$_a$R$_b$, -alkylN(ROC(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

R$_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

R$_8$ is —C(=O)OR$_{8a}$ or —C(=O)alkylNR$_{8a}$R$_{8b}$;

R$_{8a}$ and R$_{8b}$ are, at each occurrence, independently selected from the group consisting of alkyl, arylalkyl and heteroarylalkyl; wherein each R$_{8a}$ and R$_{8b}$ is independently substituted with 0, 1, 2, 3 or 4 substituents independently selected from the group consisting of alkyl, nitro, hydroxy, alkoxy, amino, formyl, halo, haloalkyl, hydroxyalkyl, alkoxyalky aminoalkyl and formylalkyl;

R$_a$ and R$_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$; alternatively, R$_a$ and R$_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and R$_c$; and R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$.

For example, the present invention provides a compound of formula (II) wherein R$_1$ is OH and R$_2$ is H.

For example, the present invention provides a compound of formula (II) wherein R$_1$ is OH, R$_2$ is H and R$_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (II) wherein R$_1$ is OH, R$_2$ is H, R$_3$ is alkyl or cycloalkyl and R$_4$ is aryl or heteroaryl.

For example, the present invention provides a compound of formula (II) wherein R$_1$ is OH, R$_2$ is H, R$_3$ is alkyl or cycloalkylalkyl and R$_4$ is phenyl.

For example, the present invention provides a compound of formula (II) wherein R$_1$ is OH, R$_2$ is H, R$_3$ is alkyl or cycloalkylalkyl and R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

For example, the present invention provides a compound of formula (II) wherein R$_1$ is OH, R$_2$ is H, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and R$_7$ is alkyl; wherein R$_{4a}$ and R$_{4b}$ are independently selected from the group consisting of hydrogen and alkyl.

For example, the present invention provides a compound of formula (II) wherein R$_1$ is OH, R$_2$ is H, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen and alkyl.

For example, the present invention provides a compound of formula (II) wherein R$_1$ is OH, R$_2$ is H, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen and alkyl.

For example, the present invention provides a compound of formula (II) wherein R$_1$ is OH, R$_2$ is H, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is C1 alkyl, C2 alkyl, C3 alkyl, C4 alkyl or C5 alkyl and R is phenylmethyl; wherein R$_{4a}$ and R$_{4b}$ are independently selected from the group consisting of hydrogen and alkyl.

Exemplary compounds of the present invention of formula (II) include, but not limited to, the following:

tert-butyl (1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropylcarbamate;

benzyl(1S)-3-amino-1-[({(1S,2R)-1-benzyl-2-hydroxy-3-[({4-[(E)-(hydroxyimino)methyl]phenyl}sulfonyl)(isobutyl)amino]propyl}amino)carbonyl]-3-oxopropylcarbamate;

methyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropylcarbamate;

2-pyridinylmethyl(1R)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylpropylcarbamate;

2-pyridinylmethyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylpropylcarbamate;

benzyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylpropylcarbamate;

benzyl(1S,2R)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-hydroxypropylcarbamate;

tert-butyl(1S,2S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylbutylcarbamate;

benzyl(1S,2S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylbutylcarbamate;

tert-butyl (1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-3-(methylsulfonyl)propylcarbamate;

benzyl(1R)-1-[(aminosulfonyl)methyl]-2-({(1S,2R)-1-benzyl-2-hydroxy-3-[({4-[(E)-(hydroxyimino)methyl]phenyl}sulfonyl)(isobutyl)amino]propyl}amino)-2-oxoethylcarbamate;

benzyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-3-(methylsulfanyl)propylcarbamate;

benzyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-3-methylbutylcarbamate;

benzyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropylcarbamate;

benzyl(1S)-4-amino-1-[({(1S,2R)-1-benzyl-2-hydroxy-3-[({4-[(E)-(hydroxyimino)methyl]phenyl}sulfonyl)(isobutyl)amino]propyl}amino)carbonyl]butylcarbamate;

benzyl(1S)-2-({(1S,2R)-1-benzyl-2-hydroxy-3-[({4-[(E)-(hydroxyimino)methyl]phenyl}sulfonyl)(isobutyl)amino]propyl}amino)-1-(1H-imidazol-4-ylmethyl)-2-oxoethylcarbamate;

benzyl(1S)-2-({(1S,2R)-1-benzyl-2-hydroxy-3-[({4-[(E)-(hydroxyimino)methyl]phenyl}sulfonyl)(isobutyl)amino]propyl}amino)-1-(1H-indol-3-ylmethyl)-2-oxoethylcarbamate;

benzyl(1S,2R)-2-(2-amino-2-oxoethoxy)-1-[({(1S,2R)-1-benzyl-2-hydroxy-3-[({4-[(E)-(hydroxyimino)methyl]phenyl}sulfonyl)(isobutyl)amino]propyl}amino)carbonyl]propylcarbamate;

methyl(3S)-4-({(1S,2R)-1-benzyl-2-hydroxy-3-[({4-[(E)-(hydroxyimino)methyl]phenyl}sulfonyl)(isobutyl)amino]propyl}amino)-3-{[(benzyloxy)carbonyl]amino}-4-oxobutanoate;

2-pyridinylmethyl(1S,2S)-1-[({(1S,2R)-1-benzyl-3-[(cyclopentylmethyl)({4-[(E)-(hydroxyimino)methyl]phenyl}sulfonyl)amino]-2-hydroxypropyl}amino)carbonyl]-2-methylbutylcarbamate;

[6-(methoxymethyl)-2-pyridinyl]methyl(1S,2S)-1-[({(1S,2R)-1-benzyl-3-[(cyclopentylmethyl)({4-[(E)-(hydroxyimino)methyl]phenyl}sulfonyl)amino]-2-hydroxypropyl}amino)carbonyl]-2-methylbutylcarbamate;

[6-(methoxymethyl)-2-pyridinyl]methyl(1S)-1-[({(1S,2R)-1-benzyl-3-[(cyclopentylmethyl)({4-[(E)-(hydroxyimino)

methyl]phenyl}sulfonyl)amino]-2-hydroxypropyl}amino)carbonyl]-2,2-dimethylpropylcarbamate;

(2S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide;

(2R)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[({[(5-nitro-3-thienyl)methyl]amino}acetyl)amino]pentanamide; and benzyl(1S)-4-{[amino(imino)methyl]amino}-1-[({(1S,2R)-1-benzyl-2-hydroxy-3-[({4-[(E)-(hydroxyimino)methyl]phenyl}sulfonyl)(isobutyl)amino]propyl}amino)carbonyl]butylcarbamate; or a pharmaceutically acceptable salt form, stereoisomer, ester, salt of an ester, prodrug, salt of a prodrug, or combination thereof.

In a third embodiment, the present invention provides a compound of formula (III)

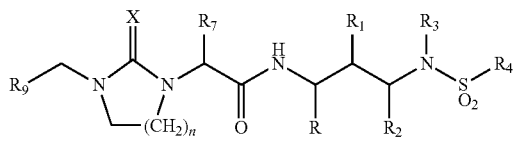

(III)

or a pharmaceutically acceptable salt form, stereoisomer, ester, salt of an ester, prodrug, salt of a prodrug, or combination thereof, wherein X is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

$R_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_a$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

$R_2$ is H;

$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSR$_a$, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylN(R$_{4a}$)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N($R_b$)C(=O)$R_a$, —N($R_b$)C(=O)O$R_a$, —N($R^b$)SO$_2$$R_a$, —N($R_b$)SO$_2$NR$_a$$R_b$, —N($R_b$)C(=NH)NR$_a$$R_b$, —N($R_b$)C(=O)NR$_a$$R_b$, —C(=O)NR$_a$$R_b$, —C(=O)O$R_a$ and $R_{1a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_9$ is alkyl, alkenyl, alkynyl, —C(=O)NR$_a$$R_b$, —C(=O)OR$_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —O$R_a$, —OC(=O)$R_a$, —S$R_a$, —SO$R_a$, —SO$_2$$R_a$, —SO$_2$NR$_a$, —SO$_2$O$R_a$, —NR$_a$$R_b$, —N($R_b$)NR$_a$$R_b$, —N($R_b$)C(=O)$R_a$, —N($R_b$)C(=O)O$R_a$, —N($R_b$)C(=O)NR$_a$$R_b$, —N($R_b$)SO$_2$$R_a$, —N($R_b$)SO$_2$NR$_a$$R_b$, —C(=O)$R_a$, —C(=O)NR$_a$$R_b$, —C(=O)O$R_a$, azidoalkyl, haloalkyl, nitroalkyl, cyanoalkyl, -alkylO$R_a$, -alkylOC(=O)$R_a$, -alkylS$R_a$, -alkylSO$R_a$, -alkylSO$_2$$R_a$, -alkylSO$_2$NR$_a$, -alkylSO$_2$O$R_a$, -alkylNR$_a$$R_b$, —C(H)=N(O$R_a$), —C(alkyl)=N(O$R_a$), —C(H)=NNR$_a$$R_b$, —C(alkyl)=NNR$_a$$R_b$, —C(H)(=NOR$_a$)NR$_a$$R_b$, —C(alkyl)(=NOR$_a$)NR$_a$$R_b$, -alkylN($R_b$)NR$_a$$R_b$, -alkylN($R_b$)C(=O)$R_a$, -alkylN($R_b$)C(=O)O$R_a$, -alkylN($R_b$)C(=O)NR$_a$$R_b$, -alkylN($R_b$)SO$_2$NR$_a$$R_b$, -alkylN($R_b$)SO$_2$$R_a$, -alkylC(=O)$R_a$, -alkylC(=O)O$R_a$, -alkylC(=O)NR$_a$$R_b$ and $R_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and $R_c$; alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

For example, the present invention provides a compound of formula (III) wherein $R_1$ is OH and $R_2$ is H.

For example, the present invention provides a compound of formula (III) wherein $R_1$ is OH, $R_2$ is H, X is O and $R_3$ is alkyl, cycloalkenylalkyl, cycloalkylalkyl, heterocyclealkyl, heteroarylalkyl, arylalkyl, hydroxyalkyl, alkoxyalkyl, -alkylS$R_a$, -alkylSO$R_a$, -alkylSO$_2$$R_a$ or -alkylNR$_a$$R_b$.

For example, the present invention provides a compound of formula (III) wherein $R_1$ is OH, $R_2$ is H, X is O, $R_3$ is alkyl or cycloalkyl and $R_4$ is aryl or heteroaryl.

For example, the present invention provides a compound of formula (III) wherein $R_1$ is OH, $R_2$ is H, X is O, $R_3$ is alkyl or cycloalkylalkyl and $R_4$ is phenyl.

For example, the present invention provides a compound of formula (III) wherein $R_1$ is OH, $R_2$ is H, X is O, $R_3$ is alkyl or cycloalkylalkyl and $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

For example, the present invention provides a compound of formula (III) wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and $R_7$ is alkyl; wherein R$_{4a}$ and R$_{4b}$ are independently selected from the group consisting of hydrogen and alkyl.

For example, the present invention provides a compound of formula (III) wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, $R_7$ is alkyl and R is phenylmethyl; wherein R$_{4a}$ and R$_{4b}$ are independently selected from the group consisting of hydrogen and alkyl.

For example, the present invention provides a compound of formula (III) wherein $R_1$ is OH, $R_2$ is H, X is O, $R_3$ is C3 alkyl, C4 alkyl, C5 alkyl, cyclopropylmethyl, cyclobutylmethyl or cyclopentylmethyl, $R_4$ is phenyl substituted with 0, 1, 2, 3 or 4 substituents selected from the group consisting of halo, $-OR_{4a}$, $-NR_{4a}R_{4b}$, and $-C(R_{4b})=NOR_{4a}$, and $R_7$ is alkyl and R is phenylmethyl; wherein $R_{4a}$ and $R_{4b}$ are independently selected from the group consisting of hydrogen and alkyl.

For example, the present invention provides a compound of formula (III) wherein $R_1$ is OH, $R_2$ is H, X is O, $R_3$ is C3 alkyl, C4 alkyl, C5 alkyl, cyclopropylmethyl, cyclobutylmethyl or cyclopentylmethyl, $R_4$ is phenyl substituted with 0, 1, 2, 3 or 4 substituents selected from the group consisting of halo, $-OR_{4a}$, $-NR_{4a}R_{4b}$ and $-C(R_{4b})=NOR_{4a}$, and $R_7$ is C1 alkyl, C2 alkyl, C3 alkyl, C4 alkyl, C5 alkyl and R is phenylmethyl; wherein $R_{4a}$ and $R_{4b}$ are independently selected from the group consisting of hydrogen and alkyl.

Exemplary compounds of the present invention of formula (III) include, but not limited to, the following:

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxoimidazolidin-1-yl)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(1-methyl-1H-benzimidazol-2-yl)methyl]-2-oxoimidazolidin-1-yl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-quinolinylmethyl)-1-imidazolidinyl]butanamide;

(2S)-2-(3-{[2-(acetylamino)-1,3-thiazol-4-yl]methyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[3-({2-[(dimethylamino)methyl]-1,3-thiazol-4-yl}methyl)-2-oxo-1-imidazolidinyl]-3-methylbutanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(tetrahydro-2-furanylmethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[2-(dimethylamino)ethyl]({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2-furylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(2-pyridinylmethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-{3-[(2,5-dimethyl-1,3-thiazol-4-yl)methyl]-2-oxo-1-imidazolidinyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-(3-nitrobenzyl)-2-oxo-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridinylmethyl)-1-imidazolidinyl]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-methyl-1H-benzimidazol-2-yl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(2-methoxyethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2-oxo-1-imidazolidinyl)-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridinylmethyl)-1-imidazolidinyl]pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[2-oxo-3-(3-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridinylmethyl)-1-imidazolidinyl]pentanamide;

(2S)—N-{(1S,2R)-1-benzyl-2-hydroxy-3-[({4-[(E)-(hydroxyimino)methyl]phenyl}sulfonyl)(2-hydroxypropyl)amino]propyl}-3-methyl-2-{3-[(2-methyl-1,3-thiazol-4-yl)methyl]-2-oxo-1-imidazolidinyl}butanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[2-oxo-3-(4-quinolinylmethyl)-1-imidazolidinyl]pentanamide;

(2S)—N-((1S,2R)-1-benzyl-2-hydroxy-3-{({4-[(E)-(hydroxyimino)methyl]phenyl}sulfonyl)[2-(2-thienyl)ethyl]amino}propyl)-3-methyl-2-{3-[(2-methyl-1,3-thiazol-4-yl)methyl]-2-oxo-1-imidazolidinyl}butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxo-1-imidazolidinyl}pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-quinolinylmethyl)-1-imidazolidinyl]pentanamide;

(2S,3S)-2-(3-{[2-(acetylamino)-1,3-thiazol-4-yl]methyl}-2-oxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)-2-(3-{[2-(acetylamino)-1,3-thiazol-4-yl]methyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-[3-(1H-benzimidazol-5-ylmethyl)-2-oxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S)—N-((1S,2R)-1-benzyl-2-hydroxy-3-{({4-[(E)-(hydroxyimino)methyl]phenyl}sulfonyl)[(1S)-1-(hydroxymethyl)-2-methylpropyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{({4-[(E)-(hydroxyimino)methyl]phenyl}sulfonyl)[(1R)-1-(hydroxymethyl)-2-methylpropyl]amino}propyl)-3-methyl-2-{3-[(2-methyl-1,3-thiazol-4-yl)methyl]-2-oxo-1-imidazolidinyl}butanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(4-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(4-methyl-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(6-methyl-2-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(2-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(methoxymethyl)-2-pyridinyl]methyl}-2-oxo-1-imidazolidinyl)-3-methyl-pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-(3-{[6-(methoxymethyl)-2-pyridinyl]methyl}-2-oxo-1-imidazolidinyl)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(2-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-(3-cyanobenzyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(trifluoromethyl)-1,3-thiazol-4-yl]methyl}-1-imidazolidinyl)pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(1-methyl-1H-benzimidazol-2-yl)methyl]-2-oxo-1-imidazolidinyl}pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(8-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(8-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(2-isopropyl-1,3-thiazol-4-yl)methyl]-2-oxo-1-imidazolidinyl}-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-{3-[(2-isopropyl-1,3-thiazol-4-yl)methyl]-2-oxo-1-imidazolidinyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-{3-[(2-isopropyl-1,3-thiazol-4-yl)methyl]-2-oxo-1-imidazolidinyl}-3-methylbutanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-{3-[(2-isopropyl-1,3-thiazol-4-yl)methyl]-2-oxo-1-imidazolidinyl}-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxo-1-imidazolidinyl)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2-oxo-1-imidazolidinyl)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]-4-pyridinyl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(7-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(6-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(2-pyridinyl)-1,3-thiazol-4-yl]methyl}-1-imidazolidinyl)pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(7-quinolinylmethyl)-1-imidazolidinyl]pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(6-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[(E)-(dimethylhydrazono)methyl]-1,3-thiazol-4-yl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(neopentyl)amino]propyl}-3-methyl-2-{3-[(1-methyl-1H-benzimidazol-2-yl)methyl]-2-oxo-1-imidazolidinyl}pentanamide;

(2S)—N4(1S,2R)-1-benzyl-2-hydroxy-3-{({4-[(E)-(hydroxyimino)methyl]phenyl}sulfonyl)[4-(2-pyridinyl)benzyl]amino}propyl)-3-methyl-2-{3-[(2-methyl-1,3-thia-zol-4-yl)methyl]-2-oxo-1-imidazolidinyl}butanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(1E)-N-hydroxyethanimi-doyl]-4-pyridinyl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({6-[(1E)-N-hydroxyethanimidoyl]-2-pyridinyl}methyl)-2-oxo-1-imidazolidinyl]-3-methylpentanamide;

(2S,3S)-2-{3-[(6-{[acetyl(methyl)amino]methyl}-2-pyridinyl)methyl]-2-oxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(3-{[2-(1-methylhydrazino)-1,3-thiazol-4-yl]methyl}-2-oxo-1-imidazolidinyl)pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(3-pyridinyl)-1,3-thiazol-4-yl]methyl}-1-imidazolidinyl)pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[(6-pyridin-2-yl-2-pyridinyl)methyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-4-quinolinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(4-methyl-2-quinolinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(6-isopropyl-2-pyridinyl)methyl]-2-oxo-1-imidazolidinyl}-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(6-methyl-2-pyridinyl)methyl]-2-oxo-1-imidazolidinyl}pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(4-methyl-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[4-(methoxymethyl)-2-pyridinyl]methyl}-2-oxo-1-imidazolidinyl)-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(4-quinolinylmethyl)-1-imidazolidinyl]butanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(3-pyridinylmethyl)-1-imidazolidinyl]pentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(3-pyridinylmethyl)-1-imidazolidinyl]butanamide;

(2S,3S)-2-{3-[(2-{[acetyl(methyl)amino]methyl}-1,3-thiazol-4-yl)methyl]-2-oxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(2-methyl-4-quinolinyl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(6-quinolinylmethyl)-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(7-quinolinylmethyl)-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(2-oxo-3-{[2-(2-pyridinyl)-1,3-thiazol-4-yl]methyl}-1-imidazolidinyl)butanamide;

{4-[(3-{(1S,2S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylbutyl}-2-oxo-1-imidazolidinyl)methyl]-1,3-thiazol-2-yl}methyl acetate;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(methoxymethyl)-2-pyridinyl]methyl}-2-oxo-1-imidazolidinyl)-3,3-dimethylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxo-1-imidazolidinyl)-3,3-dimethylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[3-(3-pyridinyl)benzyl]-1-imidazolidinyl}pentanamide;

(2S)-2-[3-({2-[(1S)-1-(acetylamino)ethyl]-1,3-thiazol-4-yl}methyl)-2-oxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3,3-dimethylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(3-{[2-(6-methyl-3-pyridinyl)-1,3-thiazol-4-yl]methyl}-2-oxo-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(2-oxo-3-{[2-(4-pyridinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(2-oxo-3-{[2-(2-thienyl)-1,3-thiazol-4-yl]methyl}-1-imidazolidinyl)butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(6-methyl-3-pyridinyl)methyl]-2-oxo-1-imidazolidinyl}pentanamide;

ethyl {6-[(3-{(1S,2S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylbutyl}-2-oxo-1-imidazolidinyl)methyl]-2-pyridinyl}methyl (methyl)carbamate;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(hydroxymethyl)-2-pyridinyl]methyl}-2-oxo-1-imidazolidinyl)-3,3-dimethylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[3-(1,3-thiazol-2-yl)benzyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[3-(2-pyridinyl)benzyl]-1-imidazolidinyl}pentanamide;

(2S)—N-{(1S,2R)-1-benzyl-2-hydroxy-3-[{4-[(E)-(hydroxyimino)methyl]phenyl}sulfonyl)(isobutyl)amino]propyl}-3,3-dimethyl-2-(3-{[2-(5-methyl-3-isoxazolyl)-1,3-thiazol-4-yl]methyl}-2-oxo-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(3-methyl-3H-imidazo[4,5-b]pyridin-2-yl)methyl]-2-oxo-1-imidazolidinyl}butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(2,4-dimethyl-3-pyridinyl)methyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[3-(3-furyl)benzyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[3-(4-pyrimidinyl)benzyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(6-methoxy-3-pyridinyl)methyl]-2-oxo-1-imidazolidinyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-(2-oxo-3-{[2-(2-pyrazinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxy-1-methylethyl)-2-pyridinyl]methyl}-2-oxo-1-imidazolidinyl)-3,3-dimethylbutanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(2-methyl-3-pyridinyl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(6-methyl-3-pyridinyl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(4-pyridazinylmethyl)-1-imidazolidinyl]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridazinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridazinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(3-methyl-3H-imidazo[4,5-b]pyridin-2-yl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxoimidazolidin-1-yl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-({2-[(methylamino)methyl]-1,3-thiazol-4-yl}methyl)-2-oxoimidazolidin-1-yl]butanamide;

(2S)—N-{(1S,2R)-1-benzyl-2-hydroxy-3-[({4-[(E)-(hydroxyimino)methyl]phenyl}sulfonyl)(pyrrolidin-2-ylmethyl)amino]propyl}-3-methyl-2-{3-[(2-methyl-1,3-thiazol-4-yl)methyl]-2-oxoimidazolidin-1-yl}butanamide;

(2S)-2-[3-(3-aminobenzyl)-2-oxoimidazolidin-1-yl]-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxido-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxidopyridin-4-yl)methyl]-2-oxoimidazolidin-1-yl}pentanamide;

(2S,3S)-2-(3-{[2-(aminomethyl)-1,3-thiazol-4-yl]methyl}-2-oxoimidazolidin-1-yl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-(3-{[2-(aminomethyl)-1,3-thiazol-4-yl]methyl}-2-oxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)-2-(3-{[2-(aminomethyl)-1,3-thiazol-4-yl]methyl}-2-oxo-1-imidazolidinyl)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]pyridin-4-yl}methyl)-2-oxo-2,3-dihydro-1H-imidazol-1-yl]-3-methylpentanamide;

(2R,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide;

(2S,3S)-2-(3-{3-[amino(hydroxyimino)methyl]benzyl}-2-oxo-1-imidazolidinyl)-N-{(1S,2R)-1-benzyl-2-hydroxy- 3-[({4-[(E)-(hydroxyimino)methyl]phenyl}sulfonyl)(isobutyl)amino]propyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[3-(hydroxymethyl)benzyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({6-[(hydroxyimino)methyl]-2-pyridinyl}methyl)-2-oxo-1-imidazolidinyl]-2,3-dimethylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxyethyl)-2-pyridinyl]methyl}-2-oxo-1-imidazolidinyl)-3,3-dimethylbutanamide;

(2S)—N-((1S,2R)-1-benzyl-2-hydroxy-3-{isobutyl[(4-methoxyphenyl)sulfonyl]amino}propyl)-2-{3-[(2-isopropyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-[2-oxo-3-(3-thienylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(2-ethyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3-methylbutanamide;

(2S)—N-(1S,2R)-1-benzyl-2-hydroxy-3-{isobutyl[(4-methoxyphenyl)sulfonyl]amino}propyl)-3-methyl-2-[2-oxo-3-(1,3-thiazol-2-ylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(3,5-dimethyl-1-phenyl-1H-pyrazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(5-ethyl-2-phenyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(5-ethyl-2-methyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(2,5-dimethyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(5-nitro-3-thienyl)methyl]-2-oxo-1-imidazolidinyl}butanamide;

(2S)-2-[3-(1-benzothien-3-ylmethyl)-2-oxo-1-imidazolidinyl]-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(1-methyl-1H-benzimidazol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-{3-[(1-methyl-1H-indol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-[2-oxo-3-(2-quinolinylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(2-cyclopropyl-1,3-thiazol-4-yl)methyl]-2-oxo-1-imidazolidinyl}-3-methylbutanamide;

(2S)-2-{3-[(2-acetyl-1,3-thiazol-4-yl)methyl]-2-oxo-1-imidazolidinyl}-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-{3-[(2-isobutyryl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(2-butyryl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(5-nitro-2-thienyl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-{3-[(2-nitro-1,3-thiazol-4-yl)methyl]-2-oxo-1-imidazolidinyl}butanamide;

(2S)-2(3-{[2-(azidomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)—N4(1S,2R)-1-benzyl-2-hydroxy-3-{isobutyl[(4-methoxyphenyl)sulfonyl]amino}propyl)-3-methyl-2-{2-oxo-3-[(2-propionyl-1,3-thiazol-4-yl)methyl]-1-imidazolidinyl}butanamide;

(2S)—N-((1S,2R)-1-benzyl-2-hydroxy-3-{isobutyl[(4-methoxyphenyl)sulfonyl]amino}propyl)-3,3-dimethyl-2-{3-[(2-methyl-1,3-thiazol-4-yl)methyl]-2-oxo-1-imidazolidinyl}butanamide;

(2S,3S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2-oxo-1-imidazolidinyl}pentanamide;

(2S)—N$^1$-((1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}butanediamide;

(4-{[34(1S)-1-{[(((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methyl acetate;

(2S)—N' 4(1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}pentanediamide;

(2S)-2-[3-(1-benzofuran-2-ylmethyl)-2-oxo-1-imidazolidinyl]-N4(1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-3-methyl-2-[2-oxo-3-(3-quinolinylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(4-methoxy-5-nitro-3-thienyl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[3-({2-[(methylsulfanyl)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-(3-{[2-(cyanomethyl)-1,3-thiazol-4-yl]methyl}-2-oxo-1-imidazolidinyl)-3-methylbutanamide;

(2S)-2-(3-{[2-(acetylamino)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-{3-[(8-hydroxy-2-quinolinyl)methyl]-2-oxo-1-imidazolidinyl}-3-methylbutanamide;

(2S,3S)—N-((1S,2R)-1-benzyl-2-hydroxy-3-{isobutyl[(4-methoxyphenyl)sulfonyl]amino}propyl)-3-methyl-2-{3-[(1-methyl-1H-benzimidazol-2-yl)methyl]-2-oxo-1-imidazolidinyl}pentanamide;

(2S)—N-((1S,2R)-1-benzyl-2-hydroxy-3-{isobutyl[(4-methoxyphenyl)sulfonyl]amino}propyl)-2-{3-[(4-methoxy-2-quinolinyl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[2-oxo-3-(2-quinoxalinylmethyl)-1-imidazolidinyl]butanamide;

(2S)—$N^1$-((1S,2R)-1-benzyl-2-hydroxy-3-{isobutyl[(4-methoxyphenyl)sulfonyl]amino}propyl)-$N^4$-methyl-2-{3-[(2-methyl-1,3-thiazol-4-yl)methyl]-2-oxo-1-imidazolidinyl}butanediamide;

(2S)—$N^1$-((1S,2R)-1-benzyl-2-hydroxy-3-{isobutyl[(4-methoxyphenyl)sulfonyl]amino}propyl)-$N^4$-ethyl-2-{3-[(2-methyl-1,3-thiazol-4-yl)methyl]-2-oxo-1-imidazolidinyl}butanediamide;

(2S,3S)—N-((1S,2R)-1-benzyl-2-hydroxy-3-{isobutyl[(4-methoxyphenyl)sulfonyl]amino}propyl)-3-methyl-2-[2-oxo-3-(4-quinolinylmethyl)-1-imidazolidinyl]pentanamide;

(2S,3S)-2-[3-(1H-benzimidazol-5-ylmethyl)-2-oxo-1-imidazolidinyl]-N-((1S,2R)-1-benzyl-2-hydroxy-3-{isobutyl[(4-methoxyphenyl)sulfonyl]amino}propyl)-3-methylpentanamide;

(2S)—N-((1S,2R)-1-benzyl-3-{(cyclopentylmethyl)[(4-methoxyphenyl)sulfonyl]amino}-2-hydroxypropyl)-2-(3-{[2-(methoxymethyl)-1,3-thiazol-4-yl]methyl}-2-oxo-1-imidazolidinyl)-3-methylbutanamide;

(2S,3S)—N-((1S,2R)-1-benzyl-2-hydroxy-3-{isobutyl[(4-methoxyphenyl)sulfonyl]amino}propyl)-3-methyl-2-[2-oxo-3-(2-quinolinylmethyl)-1-imidazolidinyl]pentanamide;

(2S,3S)—N-((1S,2R)-1-benzyl-3-{(cyclopentylmethyl)[(4-methoxyphenyl)sulfonyl]amino}-2-hydroxypropyl)-3-methyl-2-{3-[(1-methyl-1H-benzimidazol-2-yl)methyl]-2-oxo-1-imidazolidinyl}pentanamide;

(2S,3S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-2-[3-(3-cyanobenzyl)-2-oxo-1-imidazolidinyl]-3-methylpentanamide;

(2S)—N-((1S,2R)-1-benzyl-2-hydroxy-3-{isobutyl[(4-methoxyphenyl)sulfonyl]amino}propyl)-3,3-dimethyl-2-{3-[(1-methyl-1H-benzimidazol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-(formylamino)-2-{3-[(2-methyl-1,3-thiazol-4-yl)methyl]-2-oxo-1-imidazolidinyl}propanamide;

(2S)-3-[(aminocarbonyl)amino]-N-((1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}propanamide;

(2S,3S)—N-((1S,2R)-1-benzyl-2-hydroxy-3-{isobutyl[(4-methoxyphenyl)sulfonyl]amino}propyl)-2-(3-{[6-(methoxymethyl)-2-pyridinyl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-2-[3-({2-[(1E)-N-hydroxyethanimidoyl]-4-pyridinyl}methyl)-2-oxo-1-imidazolidinyl]-3-methylpentanamide;

(2S,3S)—N-((1S,2R)-1-benzyl-2-hydroxy-3-{isobutyl[(4-methoxyphenyl)sulfonyl]amino}propyl)-3-methyl-2-(2-oxo-3-{[2-(2-pyridinyl)-1,3-thiazol-4-yl]methyl}-1-imidazolidinyl)pentanamide;

(2S,3S)—N-((1S,2R)-1-benzyl-2-hydroxy-3-{isobutyl[(4-methoxyphenyl)sulfonyl]amino}propyl)-3-methyl-2-(2-oxo-3-{[2-(3-pyridinyl)-1,3-thiazol-4-yl]methyl}-1-imidazolidinyl)pentanamide;

(2S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3,3-dimethylbutanamide;

(2S)—N-((1S,2R)-1-benzyl-2-hydroxy-3-{isobutyl[(4-methoxyphenyl)sulfonyl]amino}propyl)-3,3-dimethyl-2-(2-oxo-3-{[2-(3-pyridinyl)-1,3-thiazol-4-yl]methyl}-1-imidazolidinyl)butanamide;

(2S,3S)—N-((1S,2R)-1-benzyl-2-hydroxy-3-{isobutyl[(4-methoxyphenyl)sulfonyl]amino}propyl)-3-methyl-2-(3-{[2-(2-methyl-1,3-thiazol-4-yl)-1,3-thiazol-4-yl]methyl}-2-oxo-1-imidazolidinyl)pentanamide;

(2S,3S)—N-((1S,2R)-1-benzyl-2-hydroxy-3-{isobutyl[(4-methoxyphenyl)sulfonyl]amino}propyl)-2-(3-{[2-(2-ethyl-4-pyridinyl)-1,3-thiazol-4-yl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-3-methyl-2-(3-{[2-(6-methyl-3-pyridinyl)-1,3-thiazol-4-yl]methyl}-2-oxo-1-imidazolidinyl)pentanamide;

(2S)—N-((1S,2R)-1-benzyl-2-hydroxy-3-{isobutyl[(4-methoxyphenyl)sulfonyl]amino}propyl)-3,3-dimethyl-2-{3-[(3-methyl-3H-imidazo[4,5-b]pyridin-2-yl)methyl]-2-oxo-1-imidazolidinyl}butanamide;

(2S,3S)—N-((1S,2R)-1-benzyl-2-hydroxy-3-{isobutyl[(4-methoxyphenyl)sulfonyl]amino}propyl)-3-methyl-2-{3-[(3-methyl-3H-imidazo[4,5-b]pyridin-2-yl)methyl]-2-oxo-1-imidazolidinyl}pentanamide;

(2S,3S)—N-((1S,2R)-1-benzyl-3-{(cyclopentylmethyl)[(4-methoxyphenyl)sulfonyl]amino}-2-hydroxypropyl)-3-methyl-2-(2-oxo-3-{[2-(3-pyridinyl)-1,3-thiazol-4-yl]methyl}-1-imidazolidinyl)pentanamide;

(2S,3S)—N-{(1S,2R)-1-benzyl-2-hydroxy-3-[[(4-methoxyphenyl)sulfonyl](neopentyl)amino]propyl}-3-methyl-2-(2-oxo-3-{[2-(3-pyridinyl)-1,3-thiazol-4-yl]methyl}-1-imidazolidinyl)pentanamide;

(2S)-2-(3-{[2-(aminomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)-2-[3-({2-[(acetylamino)methyl]-1,3-thiazol-4-yl}methyl)-2-oxo-1-imidazolidinyl]-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-(3-{[2-(hydroxymethyl)-1,3-thiazol-4-yl]methyl}-2-oxo-1-imidazolidinyl)-3-methylbutanamide;

(2S)—N-((1S,2R)-1-benzyl-2-hydroxy-3-{isobutyl[(4-methoxyphenyl)sulfonyl]amino}propyl)-2-[3-({2-[(dimethylamino)methyl]-1,3-thiazol-4-yl}methyl)-2-oxo-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(2-{[(methylsulfonyl)amino]methyl}-1,3-thiazol-4-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-2-[3-({2-[(hydroxyimino)methyl]-1,3-thiazol-4-yl}methyl)-2-oxo-1-imidazolidinyl]-3-methylbutanamide;

methyl(4-{[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methylcarbamate;

(2S)—N-((1S,2R)-1-benzyl-2-hydroxy-3-{isobutyl[(4-methoxyphenyl)sulfonyl]amino}propyl)-3-methyl-2-[3-({2-[(methylsulfonyl)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-[3-({2-[(diethylamino)methyl]-1,3-thiazol-4-yl}methyl)-2-oxo-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[3-({2-[(methylamino)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-[3-({2-[N-hydroxyethanimidoyl]-1,3-thiazol-4-yl}methyl)-2-oxo-1-imidazolidinyl]-3-methylbutanamide;

(2S,3S)-2-(3-{[2-(aminomethyl)-1,3-thiazol-4-yl]methyl}-2-oxo-1-imidazolidinyl)-N-((1S,2R)-1-benzyl-3-{(cyclopentylmethyl)[(4-methoxyphenyl)sulfonyl]amino}-2-hydroxypropyl)-3-methylpentanamide;

(2S,3S)-2-(3-{3-[amino(hydroxyimino)methyl]benzyl}-2-oxo-1-imidazolidinyl)-N-((1S,2R)-1-benzyl-2-hydroxy-3-{isobutyl[(4-methoxyphenyl)sulfonyl]amino}propyl)-3-methylpentanamide;

(2S)—N-((1S,2R)-1-benzyl-2-hydroxy-3-{isobutyl[(4-methoxyphenyl)sulfonyl]amino}propyl)-4-hydroxy-2-{3-[(1-methyl-1H-benzimidazol-2-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[[(4-aminophenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1R,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-2-{3-[(2-isopropyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-isopropyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-isopropyl-1,3-thiazol-4-yl)methyl]-2-oxo-1-imidazolidinyl}-3-methylbutanamide;

(2S)—N-{(1S,2R)-1-benzyl-2-hydroxy-3-[[(4-hydroxyphenyl)sulfonyl](isobutyl)amino]propyl}-2-{3-[(2-ethyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-3-[[(3-amino-4-hydroxyphenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-1-benzyl-2-hydroxy-3-[[(4-hydroxyphenyl)sulfonyl](isobutyl)amino]propyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(4-aminophenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(3-amino-4-chlorophenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(3-amino-4-hydroxyphenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-1-benzyl-2-hydroxy-3-[[(4-hydroxy-3-{[(1-methyl-1H-imidazol-4-yl)sulfonyl]amino}phenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dichloro-4-hydroxyphenyl)sulfonyl](isobutyl)amino]-2-hydroxypropyl}-3- methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[({4-hydroxy-3-[(3-pyridinylsulfonyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-hydroxy-3-[(methylsulfonyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-2-{3-[(2-cyclopropyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-cyclopropyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-cyclopropyl-1,3-thiazol-4-yl)methyl]-2-oxo-1-imidazolidinyl}-3-methylbutanamide;

(2S)—N-{(1S,2R)-1-benzyl-3-[[(3-ethyl-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dichloro-2-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl({4-[(methylsulfonyl)amino]phenyl}sulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-fluoro-4-hydroxy-2-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-chloro-4-hydroxy-2-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-hydroxy-5-methylphenyl)sulfonyl]isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-{[(methylamino)sulfonyl]amino}phenyl)sulfonyl](isobutyl)amino]propyl}-3-methyl-2-{3-[(2-methyl-1,3-thiazol-4-yl)methyl]-2-oxo-1-imidazolidinyl}butanamide;

ethyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

(2S)—N-{(1S,2R)-1-benzyl-2-hydroxy-3-[[(4-hydroxy-3-isopropylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(1-methyl-1H-benzimidazol-2-yl)methyl]-2-oxo-1-imidazolidinyl}butanamide;

(2S)—N-{(1S,2R)-1-benzyl-2-hydroxy-3-[[(4-hydroxy-3,5-dimethylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(2-nitro-1,3-thiazol-4-yl)methyl]-2-oxo-1-imidazolidinyl}butanamide;

(2S)—N-{(1S,2R)-3-[[(4-amino-3-hydroxyphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

{4-[(3-{(1S)-1-[({(1S,2R)-3-[[(3-amino-4-chlorophenyl)sulfonyl](isobutyl)amino]-1-benzyl-2-hydroxypropyl}amino)carbonyl]-2-methylpropyl}-2-oxo-1-imidazolidinyl)methyl]-1,3-thiazol-2-yl}methyl acetate;

(2S)—N-{(1S,2R)-1-benzyl-2-hydroxy-3-[{[4-hydroxy-3-(methylamino)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[3-(dimethylamino)-4-hydroxyphenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-{[(ethylamino)carbonyl]amino}-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

methyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

benzyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

(2S)—N-{(1S,2R)-3-[[(1-acetyl-2,3-dihydro-1H-indol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2-chloro-4-hydroxy-5-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-acetyl-4-hydroxyphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(2-amino-1,3-thiazol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-3-methyl-2-[2-oxo-3-(3-quinolinylmethyl)-1-imidazolidinyl]butanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(5-nitro-3-thienyl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-[2-oxo-3-(4-quinolinylmethyl)-1-imidazolidinyl]butanamide;

(2S)—N-{(1S,2R)-1-benzyl-2-hydroxy-3-[{[4-(2-hydroxyethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)-2-(3-{[2-(acetylamino)-1,3-thiazol-4-yl]methyl}-2-oxo-1-imidazolidinyl)-N-{(1S,2R)-3-[[(3-amino-4-chlorophenyl)sulfonyl](isobutyl)amino]-1-benzyl-2-hydroxypropyl}-3-methylbutanamide;

(2S)—N-{(1S,2R)-1-benzyl-3-[[(3-cyano-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S,3S)—N-{(1S,2R)-3-[[(3-amino-4-chlorophenyl)sulfonyl](isobutyl)amino]-1-benzyl-2-hydroxypropyl}-3-methyl-2-{3-[(1-methyl-1H-benzimidazol-2-yl)methyl]-2-oxo-1-imidazolidinyl}pentanamide;

(2S,3S)—N-{(1S,2R)-3-[[(3-amino-4-chlorophenyl)sulfonyl](isobutyl)amino]-1-benzyl-2-hydroxypropyl}-3-methyl-2-[2-oxo-3-(4-quinolinylmethyl)-1-imidazolidinyl]pentanamide;

(2S,3S)—N-{(1S,2R)-3-[[(3-amino-4-chlorophenyl)sulfonyl](isobutyl)amino]-1-benzyl-2-hydroxypropyl}-2-[3-(1H-benzimidazol-5-ylmethyl)-2-oxo-1-imidazolidinyl]-3-methylpentanamide;

(2S,3S)—N-{(1S,2R)-3-[[(3-amino-4-chlorophenyl)sulfonyl](isobutyl)amino]-1-benzyl-2-hydroxypropyl}-3-methyl-2-[2-oxo-3-(2-quinolinylmethyl)-1-imidazolidinyl]pentanamide;

(2S)—N-{(1S,2R)-3-[[(3-amino-4-chlorophenyl)sulfonyl](isobutyl)amino]-1-benzyl-2-hydroxypropyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-3-[[(4-aminophenyl)sulfonyl](isobutyl)amino]-1-benzyl-2-hydroxypropyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-3-[[(3-amino-4-chlorophenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3,3-dimethylbutanamide;

(2S,3S)—N-{(1S,2R)-3-[[(3-amino-4-chlorophenyl)sulfonyl](isobutyl)amino]-1-benzyl-2-hydroxypropyl}-3-methyl-2-(3-{[2-(2-methyl-1,3-thiazol-4-yl)-1,3-thiazol-4-yl]methyl}-2-oxo-1-imidazolidinyl)pentanamide;

(2S)—N-{(1S,2R)-1-benzyl-2-hydroxy-3-[({4-[(E)-(hydroxyimino)methyl]phenyl}sulfonyl)(neopentyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[{[4-((E)-{[(3-aminopropanoyl)oxy]imino}methyl)phenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(3-methoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-chlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dibromophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(1,2-dimethyl-1H-imidazol-4-yl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(1-methyl-1H-imidazol-4-yl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-bromo-5-chloro-2-pyridinyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-bromophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dimethoxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(4-acetylphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2,4,6-trichlorophenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,5-dichloro-3-thienyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(2-thienylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,4-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,3-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dimethyl-4-isoxazolyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-methoxy-4-methylphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-3-[{[4-(acetylamino)-3-chlorophenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoic acid;

(2S)—N-{(1S,2R)-1-benzyl-3-[[(3-fluoro-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(5-isoquinolinylsulfonyl)amino]propyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(3,4,5-trimethoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[2-chloro-5-(trifluoromethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[2-chloro-4-(trifluoromethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

4-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoic acid;

(2S)—N-{(1S,2R)-1-benzyl-2-hydroxy-3-[isobutyl(phenylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-bromo-2-methoxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-oxo-2,3-dihydro-1,3-benzoxazol-6-yl)sulfonyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(4-vinylphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2,3-dihydro-1-benzofuran-5-ylsulfonyl)(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[{[4-(1-hydroxyethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[(1,3-benzodioxol-5-ylsulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[(1-benzofuran-5-ylsulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(3-pyridinylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[{[2-(acetylamino)-4-methyl-1,3-thiazol-5-yl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-methyl-2,3-dihydro-1-benzofuran-5-yl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-{(Z)-[(benzyloxy)imino]methyl}-2-furyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

methyl 3-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoate;

(2S)—N-{(1S,2R)-3-[[(3-acetylphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(1-oxido-4-pyridinyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(3-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-bromo-2-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[4-(1,2-dihydroxyethyl)phenyl]sulfonyl}(isobutyl)amino]-2-hydroxypropyl}-3- methyl-2-{3-[(2-methyl-1,3-thiazol-4-yl)methyl]-2-oxo-1-imidazolidinyl}butanamide;

(2S)—N-{(1S,2R)-1-benzyl-3-[[(4-formylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[{[4-(hydroxymethyl)phenyl]sulfonyl}(isobutyl)amino]propyl}-3-methyl-2-{3-[(2-methyl-1,3-thiazol-4-yl)methyl]-2-Oxo-1-imidazolidinyl}butanamide;

(2S)—N-{(1S,2R)-1-benzyl-3-[{[4-(formylamino)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-2-(3-{[2-(hydroxymethyl)-1,3-thiazol-4-yl]methyl}-2-oxo-1-imidazolidinyl)-3-methylbutanamide;

(2S)—N-{(1S,2R)-3-[{[3-(acetylamino)-4-hydroxyphenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

tert-butyl 2-(2-hydroxy-5-{[[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate;

(2S)—N-{(1S,2R)-1-benzyl-3-[{[3-(formylamino)-4-hydroxyphenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-hydroxy-3-[(phenylacetyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

tert-butyl 3-(2-hydroxy-5-{[[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-3-oxopropylcarbamate;

(2S)—N-{(1S,2R)-1-benzyl-2-hydroxy-3-[isobutyl({4-[(methoxyimino)methyl]phenyl}sulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2,3-dihydro-1H-indol-5-ylsulfonyl)(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(2-amino-4-methyl-1,3-thiazol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[({3-[(3-aminopropanoyl)amino]-4-hydroxyphenyl}sulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

tert-butyl 2-(3-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate;

(2S)—N-{(1S,2R)-1-benzyl-2-hydroxy-3-[{[3-(hydroxymethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-formyl-2-furyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({5-[(E)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({5-[(Z)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[({4-[amino(hydroxyimino)methyl]phenyl}sulfonyl)(isobutyl)amino]-1-benzyl-2-hydroxypropyl}-3-methyl-2-{3-[(2-methyl-1,3-thiazol-4-yl)methyl]-2-oxoimidazolidin-1-yl}butanamide;

4-{[[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzamide;

4-{[[(2R,3S)-2-hydroxy-3-({(2S,3S)-3-methyl-2-[2-oxo-3-(3-pyridinylmethyl)-1-imidazolidinyl]pentanoyl}amino)-4-phenylbutyl](isobutyl)amino]sulfonyl}benzamide; and (2S,3S)—N-{(1S,2R)-1-benzyl-3-[[(4-cyanophenyl)sulfonyl](isobutyl)amino]-2-hydroxypropyl}-3-methyl-2-[2-oxo-3-(3-pyridinylmethyl)-1-imidazolidinyl]pentanamide; or a pharmaceutically acceptable salt form, stereoisomer, ester, salt of an ester, prodrug, salt of a prodrug, or combination thereof.

In a fourth embodiment, the present invention provides a compound of formula (IV)

$$(IV)$$

or a pharmaceutically acceptable salt form, stereoisomer, ester, salt of an ester, prodrug, salt of a prodrug, or combination thereof, wherein X is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl nitro, hydroxy, alkoxy, —NH$_3$—N(H)alkyl, —N(alkyl)$_2$, —C(=O)OH, —C(=O)Oalkyl, haloalkyl, hydroxyalkyl and alkoxyalkyl;

$R_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_a$)N(H)C(O)OR$_a$;

$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_a$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

$R_2$ is H;

$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

R$_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

R$_{10}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each R$_{10}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{10a}$;

R$_{10a}$ is cycloalkyl, cycloalkenyl, heterocycle, aryl or heteroaryl; wherein each R$_{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_a$ and R$_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$; alternatively, R$_a$ and R$_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, alkylC(=O)OH, -alkylC(=O)Oalkyl, -alkylC(=O)NH$_2$, -alkylC(=O)N(H)(alkyl), -alkylC(=O)N(alkyl)$_2$ and R$_c$; and R$_c$ is aryl, heteroaryl or heterocycle; wherein each II, is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$.

For example, the present invention provides a compound of formula (IV) wherein R$_1$ is OH and R$_2$ is H.

For example, the present invention provides a compound of formula (IV) wherein R$_1$ is OH, R$_2$ is H, X is O and R$_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (IV) wherein R$_1$ is OH, R$_2$ is H, X is O, R$_3$ is alkyl or cycloalkyl and R$_4$ is aryl or heteroaryl.

For example, the present invention provides a compound of formula (IV) wherein R$_1$ is OH, R$_2$ is H, X is O, R$_3$ is alkyl or cycloalkyl and R$_4$ is phenyl.

For example, the present invention provides a compound of formula (IV) wherein R$_4$ is OH, R$_2$ is H, X is O, R$_3$ is alkyl or cycloalkylalkyl and R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen or alkyl.

For example, the present invention provides a compound of formula (IV) wherein R$_1$ is OH, R$_2$ is H, X is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and R$_7$ is alkyl; wherein R$_{4a}$ and R$_{4b}$ are independently selected from the group consisting of hydrogen or alkyl.

For example, the present invention provides a compound of formula (IV) wherein R$_1$ is OH, R$_2$ is H, X is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen or alkyl.

For example, the present invention provides a compound of formula (IV) wherein R$_1$ is OH, R$_2$ is H, X is O, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen or alkyl.

For example, the present invention provides a compound of formula (IV) wherein R$_1$ is OH, R$_2$ is H, X is O, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is C1 alkyl, C2 alkyl, C3 alkyl, C4 alkyl or C5 alkyl and R is phenylmethyl; wherein R$_{4a}$ and R$_{4b}$ are independently selected from the group consisting of hydrogen or alkyl.

Exemplary compounds of the present invention of formula (IV) include, but not limited to, the following:

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxo-2,3-dihydro-1H-imidazol-1-yl}butanamide; and (2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]pyridin-4-yl}methyl)-2-oxo-2,3-dihydro-1H-imidazol-1-yl]-3-methylpentanamide; or a pharmaceutically acceptable salt form, stereoisomer, ester, salt of an ester, prodrug, salt of a prodrug, or combination thereof.

In a fifth embodiment, the present invention provides a compound of formula (V)

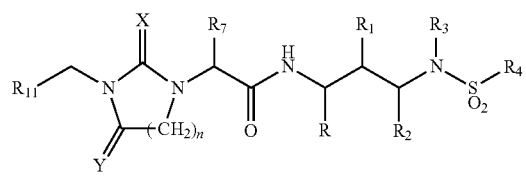

(V)

or a pharmaceutically acceptable salt form, stereoisomer, ester, salt of an ester, prodrug, salt of a prodrug, or combination thereof, wherein X is O, S or NH;

Y is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

R$_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

R$_{1a}$ is hydrogen, alkyl, alkenyl, alkynyl, cycloalkyl, cycloalkenyl, aryl, arylalkyl, heteroaryl or heteroarylalkyl; wherein each R$_{1a}$ is substituted with 0, 1 or 2 substituents independently selected from the group consisting of halo, alkyl, alkenyl, alkynyl, —OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_a$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

$R_2$ is H;

$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSR$_a$, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

$R_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

$R_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl), —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_{11}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each R$_{11}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{11a}$;

$R_{11a}$ is cycloalkyl, cycloalkenyl, heterocycle, aryl or heteroaryl; wherein each R$_{11a}$ is substituted with 0, 1, 2, 3 or 4 substituents independently selected from the group consisting of cyano, halo, nitro, oxo, alkyl, alkenyl, alkynyl, hydroxy, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$; alternatively, R$_a$ and R$_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

For example, the present invention provides a compound of formula (V) wherein R$_1$ is OH and R$_2$ is H.

For example, the present invention provides a compound of formula (V) wherein R$_1$ is OH, R$_2$ is H, X is O, Y is O and R$_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (V) wherein R$_1$ is OH, R$_2$ is H, X is O, Y is O, R$_3$ is alkyl or cycloalkyl and R$_4$ is aryl or heteroaryl.

For example, the present invention provides a compound of formula (V) wherein R$_1$ is OH, R$_2$ is H, X is O, Y is O, R$_3$ is alkyl or cycloalkyl and R$_4$ is phenyl.

For example, the present invention provides a compound of formula (V) wherein R$_1$ is OH, R$_2$ is H, X is O, Y is O, R$_3$ is alkyl or cycloalkylalkyl and R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

For example, the present invention provides a compound of formula (V) wherein R$_1$ is OH, R$_2$ is H, X is O, Y is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and R$_7$ is alkyl; wherein R$_{4a}$ and R$_{4b}$ are independently selected from the group consisting of hydrogen and alkyl.

For example, the present invention provides a compound of formula (V) wherein R$_1$ is OH, R$_2$ is H, X is O, Y is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen and alkyl.

For example, the present invention provides a compound of formula (V) wherein R$_1$ is OH, R$_2$ is H, X is O, Y is O, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R$_7$ is alkyl and R is phenylmethyl; wherein R$_{4a}$ and R$_{4b}$ are independently selected from the group consisting of hydrogen and alkyl.

For example, the present invention provides a compound of formula (V) wherein R$_1$ is OH, R$_2$ is H, X is O, Y is O, R$_3$ is C3 alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{11a}$R$_{11b}$ and —C(R$_{4b}$)=NOR$_{4a}$, R$_7$ is C1 alkyl, C2 alkyl, C3 alkyl, C4 alkyl or C5 alkyl and R is phenylmethyl; wherein R$_{4a}$ and R$_{4b}$ are independently selected from the group consisting of hydrogen and alkyl.

Exemplary compounds of the present invention of formula (V) include, but not limited to, the following:

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-(3-nitrobenzyl)-2,4-dioxo-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-methyl-1H-benzimidazol-2-yl)methyl]-2,4-dioxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(2-quinolinylmethyl)-1-imidazolidinyl]-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(3-methyl-3H-imidazo[4,5-b]pyridin-2-yl)methyl]-2,4-dioxo-1-imidazolidinyl}butanamide;

(2S)-2-[3-(1,3-benzodioxol-5-ylmethyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylbutanamide;

2-(3-benzyl-2,4-dioxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}acetamide;

(2S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(4-pyridinylmethyl)-1-imidazolidinyl]-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[3-({2-[(dimethylamino)methyl]-1,3-thiazol-4-yl}methyl)-2,4-dioxo-1-imidazolidinyl]-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2,4-dioxo-1-imidazolidinyl}butanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2,4-dioxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(2-pyridinylmethyl)-1-imidazolidinyl]-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(6-methyl-2-pyridinyl)methyl]-2,4-dioxo-1-imidazolidinyl}butanamide;

(2S)-2-(3-benzyl-2,4-dioxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)-2-[3-(3-acetylbenzyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2,4-dioxo-1-imidazolidinyl}butanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-{3-[(2-cyano-4-pyridinyl)methyl]-2,4-dioxo-1-imidazolidinyl}-3-methylbutanamide;

(2S)-2-{3-[(2-acetyl-4-pyridinyl)methyl]-2,4-dioxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)-2-{3-[3-(azidomethyl)benzyl]-2,4-dioxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(4-pyridinylmethyl)-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(3-pyridinylmethyl)-1-imidazolidinyl]-3-methylpentanamide;

(2S,3S)-2-(3-{[2-(acetylamino)-1,3-thiazol-4-yl]methyl}-2,4-dioxo-1-imidazolidinyl)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)-2-(3-{[2-(acetylamino)-1,3-thiazol-4-yl]methyl}-2,4-dioxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(2-pyrazinylmethyl)-1-imidazolidinyl]-3-methylbutanamide;

(2S,3S)-2-(3-{[2-(acetylamino)-1,3-thiazol-4-yl]methyl}-2,4-dioxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-(3-{3-[(methylamino)methyl]benzyl}-2,4-dioxo-1-imidazolidinyl)butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-(3-nitrobenzyl)-2,4-dioxo-1-imidazolidinyl]pentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(4-quinolinylmethyl)-1-imidazolidinyl]-3-methylbutanamide;

(2S,3S)-2-{3-[(6-amino-2-quinolinyl)methyl]-2,4-dioxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-{3-[(2-acetyl-4-pyridinyl)methyl]-2,4-dioxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-(3-{[2-(acetylamino)-1,3-thiazol-4-yl]methyl}-2,4-dioxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(3-methyl-3H-imidazo[4,5-b]pyridin-2-yl)methyl]-2,4-dioxo-1-imidazolidinyl}butanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(3-methyl-3H-imidazo[4,5-b]pyridin-2-yl)methyl]-2,4-dioxo-1-imidazolidinyl}butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(2-pyridinylmethyl)-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[2,4-dioxo-3-(4-quinolinylmethyl)-1-imidazolidinyl]-3-methylpentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-2-[2,4-dioxo-3-(4-quinolinylmethyl)-1-imidazolidinyl]-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[2,4-dioxo-3-(4-quinolinylmethyl)-1-imidazolidinyl]-3-methylpentanamide;

(2S)-2-[3-(3-aminobenzyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{3-[N-hydroxyethanimidoyl]benzyl}-2,4-dioxo-1-imidazolidinyl)-3-methylbutanamide;

(2S)-2-{3-[3-(aminomethyl)benzyl]-2,4-dioxo-1-imidazo-lidinyl}-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S,3S)-2-[3-(3-aminobenzyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]-4-pyridinyl}methyl)-2,4-dioxo-1-imidazolidinyl]-3-methylpentanamide;

(2S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2,4-dioxo-1-imidazolidinyl}butanamide;

(2S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2,4-dioxo-1-imidazolidinyl)-3-methylbutanamide;

(2S)-2-(3-benzyl-2,4-dioxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-[2,4-dioxo-3-(2-quinolinylmethyl)-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(1-methyl-1H-benzimidazol-2-yl)methyl]-2,4-dioxo-1-imidazolidinyl}butanamide;

ethyl[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2,5-dioxo-1-imidazolidinyl]acetate;

(2S)—N-((1S,2R)-1-benzyl-2-hydroxy-3-{isobutyl[(4-methoxyphenyl)sulfonyl]amino}propyl)-3-methyl-2-{3-[(3-methyl-3H-imidazo[4,5-b]pyridin-2-yl)methyl]-2,4-dioxo-1-imidazolidinyl}butanamide;

(2S)—N-((1S,2R)-1-benzyl-2-hydroxy-3-{isobutyl[(4-methoxyphenyl)sulfonyl]amino}propyl)-2-{3-[(6-methoxy-2-quinolinyl)methyl]-2,4-dioxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-[2,4-dioxo-3-(4-quinolinylmethyl)-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(6-nitro-2-quinolinyl)methyl]-2,4-dioxo-1-imidazolidinyl}butanamide;

(2S)-2-{3-[(6-amino-2-quinolinyl)methyl]-2,4-dioxo-1-imidazolidinyl}-N-((1S,2R)-1-benzyl-2-hydroxy-3-{isobutyl[(4-methoxyphenyl)sulfonyl]amino}propyl)-3-methylbutanamide;

(2S)-2-(3-{[2-(acetylamino)-1,3-thiazol-4-yl]methyl}-2,4-dioxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S,3S)-2-(3-{[2-(acetylamino)-1,3-thiazol-4-yl]methyl}-2,4-dioxo-1-imidazolidinyl)-N-((1S,2R)-1-benzyl-2-hydroxy-3-{isobutyl[(4-methoxyphenyl)sulfonyl]amino}propyl)-3-methylpentanamide;

(2S,3S)-2-{3-[(6-amino-2-quinolinyl)methyl]-2,4-dioxo-1-imidazolidinyl}-N-((1S,2R)-1-benzyl-2-hydroxy-3-{isobutyl[(4-methoxyphenyl)sulfonyl]amino}propyl)-3-methylpentanamide;

(2S,3S)—N-((1S,2R)-1-benzyl-2-hydroxy-3-{isobutyl[(4-methoxyphenyl)sulfonyl]amino}propyl)-2-[2,4-dioxo-3-(4-quinolinylmethyl)-1-imidazolidinyl]-3-methylpentanamide;

(2S,3S)—N-((1S,2R)-1-benzyl-3-{(cyclopentylmethyl)[(4-methoxyphenyl)sulfonyl]amino}-2-hydroxypropyl)-2-(3-{[2-(methoxymethyl)-1,3-thiazol-4-yl]methyl}-2,4-dioxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2,4-dioxo-1-imidazolidinyl)-3-methylpentanamide;

(2S,3S)—N-{(1S,2R)-1-benzyl-2-hydroxy-3-[[(4-methoxyphenyl)sulfonyl](neopentyl)amino]propyl}-2-(3-{[2-(methoxymethyl)-1,3-thiazol-4-yl]methyl}-2,4-dioxo-1-imidazolidinyl)-3-methylpentanamide;

(2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2,4-dioxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[2-(isobutylamino)-2-oxoethyl]-2,4-dioxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[2-(4-morpholinyl)-2-oxoethyl]-2,4-dioxo-1-imidazolidinyl}butanamide;

(2S)—N-((1S,2R)-1-benzyl-2-hydroxy-3-{isobutyl[(4-methoxyphenyl)sulfonyl]amino}propyl)-2-{3-[2-(dimethylamino)-2-oxoethyl]-2,4-dioxo-1-imidazolidinyl}-3-methylbutanamide;

(2S)-2-[3-(2-anilino-2-oxoethyl)-2,4-dioxo-1-imidazolidinyl]-N-((1S,2R)-1-benzyl-2-hydroxy-3-{isobutyl[(4-methoxyphenyl)sulfonyl]amino}propyl)-3-methylbutanamide;

(2S)—N-{(1S,2R)-1-benzyl-2-hydroxy-3-[[(4-hydroxyphenyl)sulfonyl](isobutyl)amino]propyl}-2-{3-[(2-ethyl-1,3-thiazol-4-yl)methyl]-2,4-dioxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-ethyl-1,3-thiazol-4-yl)methyl]-2,4-dioxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-ethyl-1,3-thiazol-4-yl)methyl]-2,4-dioxo-1-imidazolidinyl}-3-methylbutanamide;

(2S)—N-{(1S,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2,4-dioxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(2-methyl-1,3-thiazol-4-yl)methyl]-2,4-dioxo-1-imidazolidinyl}butanamide;

(2S)—N-{(1S,2R)-3-[[(3-amino-4-hydroxyphenyl)sulfonyl](isobutyl)amino]-1-benzyl-2-hydroxypropyl}-3-methyl-2-(3-{[2-methyl-1,3-thiazol-4-yl)methyl]-2,4-dioxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-2-(3-{[2-

(methoxymethyl)-1,3-thiazol-4-yl]methyl}-2,4-dioxo-1-imidazolidinyl)-3-methylbutanamide;

(2S)—N-{(1S,2R)-1-benzyl-2-hydroxy-3-[[(4-hydroxyphenyl)sulfonyl](isobutyl)amino]propyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-1-benzyl-2-hydroxy-3-[[(4-hydroxyphenyl)sulfonyl](isobutyl)amino]propyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-3-[[(4-aminophenyl)sulfonyl](isobutyl)amino]-1-benzyl-2-hydroxypropyl}-2-(3-{[2-(methoxymethyl)-1,3-thiazol-4-yl]methyl}-2,4-dioxo-1-imidazolidinyl)-3-methylbutanamide;

(2S)—N-{(1S,2R)-3-[[(3-amino-4-chlorophenyl)sulfonyl](isobutyl)amino]-1-benzyl-2-hydroxypropyl}-2-(3-benzyl-2,4-dioxo-1-imidazolidinyl)-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(3-methylbenzyl)-2,4-dioxo-1-imidazolidinyl]butanamide;

(2S)—N-{(1S,2R)-3-[[(3-amino-4-chlorophenyl)sulfonyl]isobutyl)amino]-1-benzyl-2-hydroxypropyl}-2-[3-(2-cyanobenzyl)-2,4-dioxo-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(3-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-2-{2,4-dioxo-3-[3-(trifluoromethoxy)benzyl]-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{2,4-dioxo-3-[4-(trifluoromethoxy)benzyl]-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(4-methylbenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-3-methyl-2-[3-(4-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-2-[2,4-dioxo-3-(2-quinolinylmethyl)-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(1-methyl-1H-benzimidazol-2-yl)methyl]-2,4-dioxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-2-[3-([1,1'-biphenyl]-4-ylmethyl)-2,4-dioxo-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-2-[3-(4-benzoylbenzyl)-2,4-dioxo-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(1-naphthylmethyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-3-methyl-2-[3-(2-naphthylmethyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-2-[2,4-dioxo-3-(4-vinylbenzyl)-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(4-methyl-3-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-3-methyl-2-[3-(2-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-3-methyl-2-[3-(2-methyl-3-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-2-{2,4-dioxo-3-[4-(1,2,3-thiadiazol-4-yl)benzyl]-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-[2,4-dioxo-3-(3-pyridinylmethyl)-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-2-[2,4-dioxo-3-(2-pyridinylmethyl)-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-2-[2,4-dioxo-3-(4-pyridinylmethyl)-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-2-[3-(2-methoxy-5-nitrobenzyl)-2,4-dioxo-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-2-[3-(2-fluoro-6-nitrobenzyl)-2,4-dioxo-1-imidazolidinyl]-3-methylbutanamide;

(2S)—N-{(1S,2R)-3-[[(3-amino-4-chlorophenyl)sulfonyl](isobutyl)amino]-1-benzyl-2-hydroxypropyl}-3-methyl-2-[3-(3-methyl-4-nitrobenzyl)-2,4-dioxo-1-imidazolidinyl]butanamide;

(2S)—N-{(1S,2R)-3-[[(3-amino-4-chlorophenyl)sulfonyl](isobutyl)amino]-1-benzyl-2-hydroxypropyl}-2-{3-[3-(methoxymethyl)benzyl]-2,4-dioxo-1-imidazolidinyl}-3-methylbutanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(1-methyl-1H-benzimidazol-2-yl)methyl]-2,4-dioxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-2-[3-(3-bromobenzyl)-2,4-dioxo-1-imidazolidinyl]-3-methylbutanamide;

(2S)-2-[3-(3-acetylbenzyl)-2,4-dioxo-1-imidazolidinyl]-N-{(1S,2R)-3-[[(3-amino-4-chlorophenyl)sulfonyl](isobutyl)amino]-1-benzyl-2-hydroxypropyl}-3-methylbutanamide;

(2S)—N-{(1S,2R)-3-[[(3-amino-4-chlorophenyl)sulfonyl] (isobutyl)amino]-1-benzyl-2-hydroxypropyl}-2-{2,4-di-oxo-3-[3-(2-pyrazinyl)benzyl]-1-imidazolidinyl}-3-methylbutanamide;

(2S)—N-{(1S,2R)-3-[[(3-amino-4-chlorophenyl)sulfonyl] (isobutyl)amino]-1-benzyl-2-hydroxypropyl}-2-{2,4-di-oxo-3-[3-(2-thienyl)benzyl]-1-imidazolidinyl}-3-methylbutanamide;

(2S)—N-{(1S,2R)-3-[[(3-amino-4-chlorophenyl)sulfonyl] (isobutyl)amino]-1-benzyl-2-hydroxypropyl}-3-methyl-2-{3-[(5-nitro-3-thienyl)methyl]-2,4-dioxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-2-{3-[(6-chloro-1,3-benzodioxol-5-yl)methyl]-2,4-dioxo-1-imidazolidinyl}-3-methylbutanamide;

(2S)—N-{(1S,2R)-3-[[(3-amino-4-chlorophenyl)sulfonyl] (isobutyl)amino]-1-benzyl-2-hydroxypropyl}-2-[3-(1,3-benzothiazol-2-ylmethyl)-2,4-dioxo-1-imidazolidinyl]-3-methylbutanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(6-nitro-1,3-benzodioxol-5-yl)methyl]-2,4-dioxo-1-imidazolidinyl}butanamide;

(2S)—N-{(1S,2R)-3-[[(3-amino-4-chlorophenyl)sulfonyl] (isobutyl)amino]-1-benzyl-2-hydroxypropyl}-3-methyl-2-{3-[(3-methyl-3H-imidazo[4,5-b]pyridin-2-yl)methyl]-2,4-dioxo-1-imidazolidinyl}butanamide;

(2S)-2-[3-(1,3-benzodioxol-5-ylmethyl)-2,4-dioxo-1-imidazolidinyl]-N-{(1S,2R)-1-benzyl-2-hydroxy-3-[[(4-hydroxy-3-methylphenyl)sulfonyl](isobutyl)amino]propyl}-3-methylbutanamide;

(2S)—N-{(1S,2R)-1-benzyl-2-hydroxy-3-[[(4-hydroxyphenyl)sulfonyl](isobutyl)amino]propyl}-3-methyl-2-{3-[(1-methyl-1H-benzimidazol-2-yl)methyl]-2,4-dioxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-2-[2,4-dioxo-3-(2-pyridinylmethyl)-1-imidazolidinyl]-3-methylbutanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(6-methyl-2-pyridinyl)methyl]-2,4-dioxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(4-methyl-3-pyridinyl)methyl]-2,4-dioxo-1-imidazolidinyl}butanamide;

(2S)-2-(3-{[2-(acetylamino)-1,3-thiazol-4-yl]methyl}-2,4-dioxo-1-imidazolidinyl)-N-{(1S,2R)-3-[[(3-amino-4-chlorophenyl)sulfonyl](isobutyl)amino]-1-benzyl-2-hydroxypropyl}-3-methylbutanamide;

(2S)—N-{(1S,2R)-1-benzyl-2-hydroxy-3-[[(4-hydroxy-3-methylphenyl)sulfonyl](isobutyl)amino]propyl}-2-{3-[(2-cyano-4-pyridinyl)methyl]-2,4-dioxo-1-imidazolidinyl}-3-methylbutanamide;

(2S)-2-{3-[(2-acetyl-4-pyridinyl)methyl]-2,4-dioxo-1-imidazolidinyl}-N-{(1S,2R)-1-benzyl-2-hydroxy-3-[[(4-hydroxy-3-methylphenyl)sulfonyl](isobutyl)amino]propyl}-3-methylbutanamide;

(2S)—N-{(1S,2R)-3-[[(3-amino-4-chlorophenyl)sulfonyl] (isobutyl)amino]-1-benzyl-2-hydroxypropyl}-2-{3-[3-(hydroxymethyl)benzyl]-2,4-dioxo-1-imidazolidinyl}-3-methylbutanamide;

(2S,3S)-2-(3-{[2-(acetylamino)-1,3-thiazol-4-yl]methyl}-2, 4-dioxo-1-imidazolidinyl)-N-{(1S,2R)-3-[[(3-amino-4-chlorophenyl)sulfonyl](isobutyl)amino]-1-benzyl-2-hydroxypropyl}-3-methylpentanamide;

(2S,3S)—N-{(1S,2R)-3-[[(3-amino-4-chlorophenyl)sulfonyl](isobutyl)amino]-1-benzyl-2-hydroxypropyl}-2-{3-[(6-amino-2-quinolinyl)methyl]-2,4-dioxo-1-imidazolidinyl}-3-methylpentanamide;

(2S,3S)—N-{(1S,2R)-3-[[(3-amino-4-chlorophenyl)sulfonyl](isobutyl)amino]-1-benzyl-2-hydroxypropyl}-2-[2,4-dioxo-3-(4-quinolinylmethyl)-1-imidazolidinyl]-3-methylpentanamide; and (2S)—N-{(1S,2R)-3-[{[4-((E)-{[(3-aminopropanoyl)oxy] imino}methyl)phenyl]sulfonyl}(cyclopentylmethyl) amino]-1-benzyl-2-hydroxypropyl}-3-methyl-2-{3-[(2-methyl-1,3-thiazol-4-yl)methyl]-2,4-dioxo-1-imidazolidinyl}butanamide; or a pharmaceutically acceptable salt form, stereoisomer, ester, salt of an ester, prodrug, salt of a prodrug, or combination thereof.

In a sixth embodiment the present invention provides a compound of formula (VI)

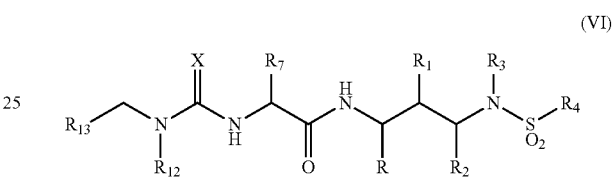

or a pharmaceutically acceptable salt form, stereoisomer, ester, salt of an ester, prodrug, salt of a prodrug, or combination thereof, wherein X is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —$NH_2$, —N(H)alkyl, —N(alkyl)$_2$, —C(=O)OH, —C(=O)Oalkyl, haloalkyl, hydroxyalkyl and alkoxyalkyl;

$R_1$ is H and $R_2$ is $OR_a$, —$OSO_2R_a$, —$OSO_3R_a$, —$OPO_3R_a$, —OC(=O)C(H)($R_{1a}$)$NR_aR_b$ or —OC(=O)C(H)($R_{1a}$)N(H)C(O)$OR_a$; or $R_1$ is $OR_a$, —$OSO_2R_a$, —$OSO_3R_a$, —$OPO_3R_a$, —OC(=O) C(H)($R_{1a}$)$NR_aR_b$ or —OC(=O)C(H)($R_{1a}$)N(H)C(O)$OR_a$;

$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, —$OR_a$, —$SR_a$, —$SOR_a$, —$SO_2R_a$, —$SO_2NR_aR_b$, —C(=O)$R_a$, —$NR_aR_b$, —N($R_b$)C(=O)$R_a$, —N($R_b$)C(=O)$OR_a$, —N($R_b$)$SO_2R_a$, —N($R_a$)$SO_2NR_aR_b$, —N($R_b$)C(=NH)$NR_aR_b$,    —N($R_b$)C(=O)$NR_aR_b$, —C(=O)$NR_aR_b$ and —C(=O)$OR_a$;

$R_2$ is H;

$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkyl$SR_a$, -alkyl$SOR_a$, -alkyl$SO_2R_a$, -alkyl$NR_aR_b$, -alkylN($R_b$)C(=O)$OR_a$, -alkylN($R_b$)C(=O) $R_a$, -alkylN($R_b$)$SO_2R_a$ or -alkylN($R_b$)$SO_2NR_aR_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

R$_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

R$_{12}$ is alkyl, alkenyl, cycloalkyl, cycloalkenyl, cycloalkylalkyl or cycloalkenylalkyl; wherein each R$_{12}$ is substituted with 0, 1 or 2 substituents independently selected from the group consisting of hydroxy, alkoxy cyano, nitro and halo;

R$_{13}$ is alkyl, alkenyl, alkynyl, cycloalkyl, cycloalkenyl, aryl, heteroaryl or heterocycle; wherein each R$_{13}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{13a}$;

R$_{13a}$ is cycloalkyl, cycloalkenyl, heterocycle, aryl or heteroaryl; wherein each R$_{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_a$ and R$_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and $R_c$; alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and $R_c$; and $R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$.

For example, the present invention provides a compound of formula (VI) wherein $R_1$ is OH and $R_2$ is H.

For example, the present invention provides a compound of formula (VI) wherein $R_1$ is OH, $R_2$ is H, X is O and $R_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (VI) wherein $R_1$ is OH, $R_2$ is H, X is O, $R_3$ is alkyl or cycloalkyl and $R_4$ is aryl or heteroaryl.

For example, the present invention provides a compound of formula (VI) wherein $R_1$ is OH, $R_2$ is H, X is O, $R_3$ is alkyl or cycloalkylalkyl and $R_4$ is phenyl.

For example, the present invention provides a compound of formula (VI) wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and $R_7$ is alkyl; wherein $R_{4a}$ and $R_{4b}$ are independently selected from the group consisting of hydrogen and alkyl.

For example, the present invention provides a compound of formula (VI) wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, $R_7$ is alkyl and $R_{12}$ is alkyl; wherein $R_{4a}$ and $R_{4b}$ are independently selected from the group consisting of hydrogen and alkyl.

For example, the present invention provides a compound of formula (VI) wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, $R_7$ is alkyl, $R_{12}$ is alkyl and R is phenylmethyl; wherein $R_{4a}$ and $R_{4b}$ are independently selected from the group consisting of hydrogen and alkyl.

For example, the present invention provides a compound of formula (VI) wherein $R_1$ is OH, $R_2$ is H, X is O, $R_3$ is C3 alkyl, C4 alkyl, C5 alkyl, cyclopropylmethyl, cyclobutylmethyl or cyclopentylmethyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, $R_7$ is alkyl, $R_{12}$ is methyl or ethyl, and R is phenylmethyl; wherein $R_{4a}$ and $R_{4b}$ are independently selected from the group consisting of hydrogen and alkyl.

For example, the present invention provides a compound of formula (VI) wherein $R_1$ is OH, $R_2$ is H, X is O, $R_3$ is C3 alkyl, C4 alkyl, C5 alkyl, cyclopropylmethyl, cyclobutylmethyl or cyclopentylmethyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, $R_7$ is C1 alkyl, C2 alkyl, C3 alkyl, C4 alkyl or C5 alkyl, $R_{12}$ is methyl or ethyl, and R is phenylmethyl; wherein $R_{4a}$ and $R_{4b}$ are independently selected from the group consisting of hydrogen and alkyl.

Exemplary compounds of the present invention of formula (VI) include, but not limited to, the following:

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-({[methyl(2-pyridinylmethyl)amino]carbonyl}amino)pentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-({[[(2-isopropyl-1,3-thiazol-4-yl)methyl](methyl)amino]carbonyl}amino)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-({[methyl(2-pyridinylmethyl)amino]carbonyl}amino)butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[({methyl[(2-methyl-1,3-thiazol-4-yl)methyl]amino}carbonyl)amino]butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-({[{[2-(methoxymethyl)-1,3-thiazol-4-yl]methyl}(methyl)amino]carbonyl}amino)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[({ethyl[(2-isopropyl-1,3-thiazol-4-yl)methyl]amino}carbonyl)amino]propanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-({[[(2-isopropyl-1,3-thiazol-4-yl)methyl](methyl)amino]carbonyl}amino)-3-methylbutanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-2-({[[(2-isopropyl-1,3-thiazol-4-yl)methyl](methyl)amino]carbonyl}amino)-3-methylbutanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-({[methyl(2-pyridinylmethyl)amino]carbonyl}amino)pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-({[methyl(2-pyridinylmethyl)amino]carbonyl}amino)pentanamide;

(2S,3R)—N-{(1S,2R)-1-benzyl-3-[(cyclobutylmethyl)({4-[(E)-(hydroxyimino)methyl]phenyl}sulfonyl)amino]-2-hydroxypropyl}-3-tert-butoxy-2-({[{[2-(methoxymethyl)-1,3-thiazol-4-yl]methyl}(methyl)amino]carbonyl}amino)butanamide;

(2S,3R)—N-{(1S,2R)-1-benzyl-3-[(cyclopentylmethyl)({4-[(E)-(hydroxyimino)methyl]phenyl}sulfonyl)amino]-2- hydroxypropyl}-3-tert-butoxy-2-({[{[2-(methoxymethyl)-1,3-thiazol-4-yl]methyl}(methyl)amino]carbonyl}amino)butanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-2-({[{[2-(methoxymethyl)-1,3-thiazol-4-yl]methyl}(methyl)amino]carbonyl}amino)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[{[2-(methoxymethyl)-1,3-thiazol-4-yl]methyl}(methyl)amino]carbonyl}amino)-3-methylpentanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[({methyl[(2-methyl-1,3-thiazol-4-yl)methyl]amino}carbonyl)amino]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[({methyl[(2-methyl-1,3-thiazol-4-yl)methyl]amino}carbonyl)amino]pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[({methyl[(2-methyl-1,3-thiazol-4-yl)methyl]amino}carbonyl)amino]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-tert-butoxy-2-[({methyl[(2-methyl-1,3-thiazol-4-yl)methyl]amino}carbonyl)amino]butanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-tert-butoxy-2-[({methyl[(2-methyl-1,3-thiazol-4-yl)methyl]amino}carbonyl)amino]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-({[methyl(3-nitrobenzyl)amino]carbonyl}amino)pentanamide;

methyl 4-{(5S,8S,9R)-8-benzyl-9-hydroxy-11-({4-[(E)-(hydroxyimino)methyl]phenyl}sulfonyl)-2,13-dimethyl-5-[(1S)-1-methylpropyl]-3,6-dioxo-2,4,7,11-tetraazatetradec-1-yl}-1,3-thiazol-2-ylcarbamate;

(2S)—N-{(1S,2R)-1-benzyl-3-[(cyclobutylmethyl)({4-[(E)-(hydroxyimino)methyl]phenyl}sulfonyl)amino]-2-hydroxypropyl}-2-({[{[2-(methoxymethyl)-1,3-thiazol-4-yl]methyl}(methyl)amino]carbonyl}amino)-3-methylbutanamide;

(2S,3S)-2-({[{[2-(acetylamino)-1,3-thiazol-4-yl]methyl}(methyl)amino]carbonyl}amino)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-({[methyl(3-pyridinylmethyl)amino]carbonyl}amino)pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-({[methyl(4-pyridinylmethyl)amino]carbonyl}amino)pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-({[{[2-(methoxymethyl)-1,3-thiazol-4-yl]methyl}(methyl)amino]carbonyl}amino)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[{[6-(methoxymethyl)-2-pyridinyl]methyl}(methyl)amino]carbonyl}amino)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-({[[(2-isopropyl-1,3-thiazol-4-yl)methyl](methyl)amino]carbonyl}amino)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[[(2-isopropyl-1,3-thiazol-4-yl)methyl](methyl)amino]carbonyl}amino)-3-methylpentanamide;

(2S,3S)-2-({[({6-[(Z)-amino(hydroxyimino)methyl]-2-pyridinyl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-({[{[6-(methoxymethyl)-2-pyridinyl]methyl}(methyl)amino]carbonyl}amino)-3,3-dimethylbutanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-({[{[6-(tert-butoxymethyl)-2-pyridinyl]methyl}(methyl)amino]carbonyl}amino)-3,3-dimethylbutanamide;

(2S,3R)—N-{(1S,2R)-1-benzyl-3-[(cyclobutylmethyl)({4-[(E)-(hydroxyimino)methyl]phenyl}sulfonyl)amino]-2-hydroxypropyl}-3-hydroxy-2-({[{[2-(methoxymethyl)-1,3-thiazol-4-yl]methyl}(methyl)amino]carbonyl}amino)butanamide;

(2S,3R)—N-{(1S,2R)-1-benzyl-3-[(cyclopentylmethyl)({4-[(E)-(hydroxyimino)methyl]phenyl}sulfonyl)amino]-2-hydroxypropyl}-3-hydroxy-2-({[{[2-(methoxymethyl)-1,3-thiazol-4-yl]methyl}(methyl)amino]carbonyl}amino)butanamide;

(2S,3S)-2-({[(3-aminobenzyl)(methyl)amino]carbonyl}amino)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3R)—N-{(1S,2R)-1-benzyl-2-hydroxy-3-[({4-[(E)-(hydroxyimino)methyl]phenyl}sulfonyl)(isobutyl)amino]propyl}-3-hydroxy-2-[({methyl[(2-methyl-1,3-thiazol-4-yl)methyl]amino}carbonyl)amino]butanamide;

(2S,3R)—N-{(1S,2R)-1-benzyl-3-[(cyclobutylmethyl)({4-[(E)-(hydroxyimino)methyl]phenyl}sulfonyl)amino]-2-hydroxypropyl}-3-hydroxy-2-[({methyl[(2-methyl-1,3-thiazol-4-yl)methyl]amino}carbonyl)amino]butanamide;

(2S,3S)-2-({[{[2-(aminomethyl)-1,3-thiazol-4-yl]methyl}(methyl)amino]carbonyl}amino)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-({[{[2-(aminomethyl)-1,3-thiazol-4-yl]methyl}(methyl)amino]carbonyl}amino)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)-2-({[{[2-(aminomethyl)-1,3-thiazol-4-yl]methyl}(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)-2-({[({2-[(1S)-1-aminoethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)-2-({[({2-[(1R)-1-aminoethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[({6-[N-hydroxyethanimidoyl]-2-pyridinyl}methyl)(methyl)amino]carbonyl}amino)-3-methylpentanamide; and (2S,3S)-2-({[({2-[(1S)-1-(acetylamino)ethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide; or a pharmaceutically acceptable salt form, stereoisomer, ester, salt of an ester, prodrug, salt of a prodrug, or combination thereof.

In a seventh embodiment, the present invention provides a compound of formula (VII)

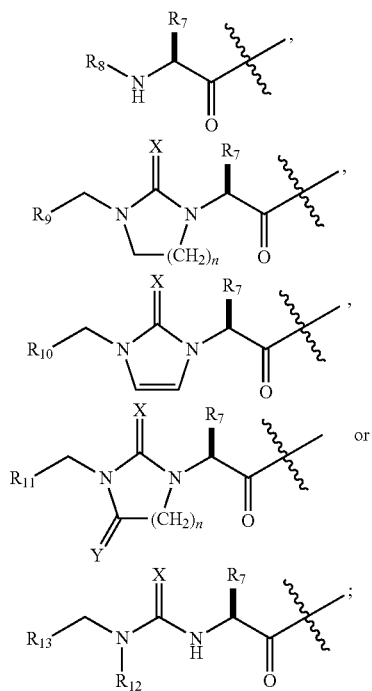

or a pharmaceutically acceptable salt form, stereoisomer, ester, salt of an ester, prodrug, salt of a prodrug, or combination thereof, wherein:

A is $R_5C(O)$—, $R_6SO_2$—,

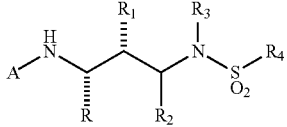

X is O, S or NH;
Y is O, S or NH;
R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —$NH_2$, —N(H)alkyl, —N(alkyl)$_2$, —C(=O)OH, —C(=O)Oalkyl, haloalkyl, hydroxyalkyl and alkoxyalkyl;

$R_1$ is $OR_a$, —$OSO_2R_a$, —$OSO_3R_a$, —$OPO_3R_a$, —OC(=O)C(H)($R_{1a}$)$NR_aR_b$ or —OC(=O)C(H)($R_{1a}$)N(H)C(O)$OR_a$;
$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, —$OR_E$, —$SR_a$, —$SOR_a$, —$SO_2R_a$, —$SO_2NR_aR_b$, —C(=O)$R_a$, —$NR_aR_b$, —N($R_b$)C(=O)$R_a$, —N($R_b$)C(=O)$OR_a$, —N($R_b$)$SO_2R_a$, —N($R_a$)$SO_2NR_aR_b$, —N($R_b$)C(=NH)$NR_aR_b$, —N($R_b$)C(=O)$NR_aR_b$, —C(=O)$NR_aR_b$ and —C(=O)$OR_a$;
$R_2$ is H;
$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkyl$SR_a$, -alkyl$SOR_a$, -alkyl$SO_2R_a$, -alkyl$NR_aR_b$, -alkylN($R_b$)C(=O)$OR_a$, -alkylN($R_b$)C(=O)$R_a$, -alkylN($R_b$)$SO_2R_a$ or -alkylN($R_b$)$SO_2NR_aR_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —$SO_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$, -alkylC(=O)alkyl and $R_{3a}$;
$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —$SO_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$ and -alkylC(=O)alkyl;
$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —$OR_{4a}$, —$SR_{4a}$, —$SOR_{4a}$, —$SO_2R_{4a}$, —$NR_{4a}R_{4b}$, —OC(=O)$R_{4a}$, —C(=O)$R_{4a}$, —C(=O)O$R_{4a}$, —C(=O)N$R_{4a}R_{4b}$, —N($R_{4b}$)C(=O)$R_{4a}$, —N($R_{4b}$)C(=O)O$R_{4a}$, —N($R_{4b}$)SO$_2R_{4a}$, —N($R_{4b}$)C(=O)N$R_{4a}R_{4b}$, —N($R_{4b}$)SO$_2$N$R_{4a}R_{4b}$, -alkylS$R_{4a}$, -alkylSO$R_{4a}$, -alkylSO$_2R_{4a}$, -alkylN$R_{4a}R_{4b}$, -alkylOC(=O)$R_{4a}$, -alkylC(=O)$R_{4a}$, -alkylC(=O)O$R_{4a}$, -alkylC(=O)N$R_{4a}R_{4b}$, -alkylN($R_{4b}$)C(=O)$R_{4a}$, -alkylN($R_{4b}$)C(=O)O$R_{4a}$, -alkylN($R_{4b}$)SO$_2R_{4a}$, -alkylN($R_{4b}$)C(=O)N$R_{4a}R_{4b}$, -alkylN($R_{4b}$)SO$_2$N$R_{4a}R_{4b}$, —N(H)C(=O)alkylN(H)C(=O)O$R_{4a}$, —N(H)C(=O)alkylN$R_{4a}R_{4b}$, —C($R_{4b}$)=NO$R_{4a}$, —C(N$R_{4a}R_{4b}$)=NO$R_{4a}$ and —C($R_{4b}$)=NOC(=O)alkylN$R_{4a}R_{4b}$;

$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_5$ is alkyl, haloalkyl, cyanoalkyl, hydroxyalkyl, alkoxyalkyl, haloalkoxyalkyl, —OalkylSO$_2$alkyl, —O-heterocycle, -alkyl-O-aryl or —O-alkyl-heteroaryl; wherein the heterocycle, aryl or heteroaryl moiety of —O-heterocycle, -alkyl-O-aryl and —O-alkyl-heteroaryl is independently substituted with 0, 1, 2 or 3 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_6$ is aryl or heteroaryl; wherein each $R_6$ is substituted with 0 or 1 substituent selected from the group consisting of —C(H)=NOH, —C(alkyl)=NOH, —C(H)=NO(alkyl), —C(alkyl)=NO(alkyl), —C(H)=NO(arylalkyl) and —C(alkyl)=NO(arylalkyl);

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —O$R_a$, —OalkylC(=O)N$R_aR_b$, —S$R_a$, —SO$R_a$, —SO$_2R_a$, —SO$_2$N$R_aR_b$, —C(=O)$R_a$, —N$R_aR_b$, —N($R_b$)C(=O)$R_a$, —N($R_b$)C(=O)O$R_a$, —N($R_b$)SO$_2R_a$, —N($R_b$)SO$_2$N$R_aR_b$, —N($R_b$)C(=NH)N$R_aR_b$, —N($R_b$)C(=O)N$R_aR_b$, —C(=O)N$R_aR_b$, —C(=O)O$R_a$ and $R_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(H)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)N(H)(alkyl) and -alkyl-C(=O)N(alkyl)$_2$;

$R_8$ is —C(=O)O$R_{8a}$ or —C(=O)alkylN$R_{8a}R_{8b}$, $R_{8a}$ and $R_{8b}$ are, at each occurrence, independently selected from the group consisting of alkyl, arylalkyl and heteroarylalkyl; wherein each $R_{8a}$ and $R_{8b}$ is independently substituted with 0, 1, 2, 3 or 4 substituents independently selected from the group consisting of alkyl, nitro, hydroxy, alkoxy, amino, formyl, halo, haloalkyl, hydroxyalkyl, alkoxyalky aminoalkyl and formylalkyl;

$R_9$ is alkyl, alkenyl, alkynyl, —C(=O)N$R_aR_b$, —C(=O)O$R_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —O$R_a$, —OC(=O)$R_a$, —S$R_a$, —SO$R_a$, —SO$_2R_a$, —SO$_2$N$R_a$, —SO$_2$O$R_a$, —N$R_aR_b$, —N($R_b$)N$R_aR_b$, —N($R_b$)C(=O)$R_a$, —N($R_b$)SO$_2R_a$, —N($R_b$)C(=O)O$R_a$, —N($R_b$)C(=O)N$R_aR_b$, —N($R_b$)SO$_2$N$R_aR_b$, —C(=O)$R_a$, —C(=O)N$R_aR_b$, —C(=O)O$R_a$, azidoalkyl, haloalkyl, nitroalkyl, cyanoalkyl, -alkylO$R_a$, -alkylOC(=O)$R_a$, -alkylS$R_a$, -alkylSO$R_a$, -alkylSO$_2R_a$, -alkylSO$_2$N$R_a$, -alkylSO$_2$O$R_a$, -alkylN$R_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN($R_b$)N$R_aR_b$, -alkylN($R_b$)C(=O)$R_a$, -alkylN($R_b$)C(=O)O$R_a$, -alkylN($R_b$)C(=O)N$R_aR_b$, -alkylN($R_b$)SO$_2$N$R_aR_b$, -alkylN($R_b$)SO$_2R_a$, -alkylC(=O)$R_a$, -alkylC(=O)O$R_a$, -alkylC(=O)N$R_aR_b$ and $R_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{10}$ is alkyl, alkenyl, alkynyl, —C(=O)N$R_aR_b$, —C(=O)O$R_a$, cycloalkyl, cycloalkenyl, aryl, heteroaryl or heterocycle; wherein each $R_{10}$ is substituted with 0, 1, 2 or 3 substituents independently selected from the group consisting of alkyl, alkenyl, alkynyl, cyano, halo, nitro, oxo, —O$R_a$, —OC(=O)$R_a$, —S$R_a$, —SO$R_a$, —SO$_2R_a$, —SO$_2$N$R_a$, —SO$_2$O$R_a$, —N$R_aR_b$, —N($R_b$)N$R_aR_b$, —N($R_b$)C(=O)$R_a$, —N($R_b$)SO$_2R_a$, —N($R_b$)C(=O)O$R_a$, —N($R_b$)C(=O)N$R_aR_b$, —N($R_b$)SO$_2$N$R_aR_b$, —C(=O)$R_a$, —C(=O)N$R_aR_b$, —C(=O)O$R_a$, azidoalkyl, haloalkyl, nitroalkyl, cyanoalkyl, -alkylOC(=O)$R_a$, -alkylS$R_a$, -alkylSO$R_a$, -alkylSO$_2R_a$, -alkylSO$_2$N$R_a$, -alkylSO$_2$O$R_a$, -alkylN$R_aR_b$, —C(H)=N(O$R_a$), —C(alkyl)=N(O$R_a$), —C(H)=NN$R_aR_b$, —C(alkyl)=NN$R_aR_b$, —C(H)(=NO$R_a$)N$R_aR_b$, —C(alkyl)(=NO$R_a$)N$R_aR_b$, -alkylN($R_b$)N$R_aR_b$, -alkylN($R_b$)C(=O)$R_a$, -alkylN($R_b$)C(=O)O$R_a$, -alkylN($R_b$)C(=O)N$R_aR_b$, -alkylN($R_b$)SO$_2$N$R_aR_b$, -alkylN($R_b$)SO$_2R_a$, -alkylC(=O)$R_a$, -alkylC(=O)O$R_a$, -alkylC(=O)N$R_aR_b$ and $R_{10a}$;

$R_{10a}$ is cycloalkyl, cycloalkenyl, heterocycle, aryl or heteroaryl; wherein each $R_{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{11}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{11}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{11a}$;

$R_{11a}$ is cycloalkyl, cycloalkenyl, heterocycle, aryl or heteroaryl; wherein each $R_{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{12}$ is alkyl, alkenyl, cycloalkyl, cycloalkenyl, cycloalkylalkyl or cycloalkenylalkyl; wherein each $R_{12}$ is substituted with 0, 1 or 2 substituents independently selected from the group consisting of hydroxy, alkoxy cyano, nitro and halo;

$R_{13}$ is alkyl, alkenyl, alkynyl, cycloalkyl, cycloalkenyl, aryl, heteroaryl or heterocycle; wherein each $R_{13}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(ROC(=O)R$_a$, —N(R$_b$)SO$_2$R$_a$, —N(R$_b$)C(=O)OR$_a$, —N(ROC(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(ROC(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{13a}$;

$R_{13a}$ is cycloalkyl, cycloalkenyl, heterocycle, aryl or heteroaryl; wherein each $R_{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and $R_c$; alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

For example, the present invention provides a compound of formula (VII) wherein $R_1$ is OH and $R_2$ is H.

For example, the present invention provides a compound of formula (VII) wherein $R_1$ is OH, $R_2$ is H, X is O and Y is O.

For example, the present invention provides a compound of formula (VII) wherein wherein $R_1$ is OH, $R_2$ is H, X is O, Y is O and $R_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO$_2$R$_a$ or -alkylNR$_a$R$_b$.

For example, the present invention provides a compound of formula (VII) wherein R$_1$ is OH, R$_2$ is H, X is O, Y is O, R$_3$ is alkyl or cycloalkylalkyl and R$_1$ is aryl or heteroaryl.

For example, the present invention provides a compound of formula (VII) wherein R$_1$ is OH, R$_2$ is H, X is O, Y is O, R$_3$ is alkyl or cycloalkylalkyl and R$_1$ is phenyl.

For example, the present invention provides a compound of formula (VII) wherein R$_1$ is OH, R$_2$ is H, X is O, Y is O, R$_3$ is alkyl or cycloalkylalkyl and R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

For example, the present invention provides a compound of formula (VII) wherein R$_1$ is OH, R$_2$ is H, X is O, Y is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and R is phenylmethyl; wherein R$_{4a}$ and R$_{4b}$ are independently selected from the group consisting of hydrogen and alkyl.

For example, the present invention provides a compound of formula (VII) wherein R$_1$ is OH, R$_2$ is H, X is O, Y is O, R$_3$ is alkyl or cycloalkylalkyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is alkyl; wherein R$_{4a}$ and R$_{4b}$ are independently selected from the group consisting of hydrogen and alkyl.

For example, the present invention provides a compound of formula (VII) wherein R$_1$ is OH, R$_2$ is H, R$_3$ is C3, alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is alkyl; wherein R$_{4a}$ and R$_{4b}$ are independently selected from the group consisting of hydrogen and alkyl.

For example, the present invention provides a compound of formula (VII) wherein R$_1$ is OH, R$_2$ is H, R$_3$ is C3, alkyl, C4 alkyl, C5 alkyl, cyclopropylmethyl, cyclobutylmethyl or cyclopentylmethyl, R$_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, R is phenylmethyl and R$_7$ is C1 alkyl, C2 alkyl, C3 alkyl, C4 alkyl or C5 alkyl; wherein R$_{4a}$ and R$_{4b}$ are independently selected from the group consisting of hydrogen and alkyl.

In an eighth embodiment, the present invention provides a pharmaceutical composition comprising a therapeutically effective amount of a compound, or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, and a pharmaceutically acceptable carrier.

In a ninth embodiment, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, five or six second HIV protease inhibitors, and a pharmaceutically acceptable carrier.

For example, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

In a tenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV reverse transcriptase inhibitors, and a pharmaceutically acceptable carrier.

For example, the present invention provides a pharmaceutical composition comprising a therapeutically effective amount of a compound, or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calamide A, GW5634, BMS-56190 (DPC-083), DPC-961, MIV-150, TMC-120 and TMC-125, and a pharmaceutically acceptable carrier.

In an eleventh embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV entry/fusion inhibitors, and a pharmaceutically acceptable carrier.

For example, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

In a twelfth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV integrase inhibitors, and a pharmaceutically acceptable carrier.

For example, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three or four HIV integrase inhibitors selected from the group consisting of S-1360, zintevir (AR-177), L-870812 and L-870810, and a pharmaceutically acceptable carrier.

In a thirteenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two, three, four, five or six HIV budding/maturation inhibitors, and a pharmaceutically acceptable carrier.

For example, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, PA-457, and a pharmaceutically acceptable carrier.

In a fourteenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors, one, two or three HIV reverse transcriptase inhibitors, and a pharmaceutically acceptable carrier.

For example, the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

In a fifteenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors, one, two or three HIV entry/fusion inhibitors, and a pharmaceutically acceptable carrier.

For example, the present invention provides a pharmaceutical composition comprising a therapeutically effective amount of a compound or combination of compounds of formulae (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

In a sixteenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors, one, two or three HIV integrase inhibitors, and a pharmaceutically acceptable carrier.

For example, the present invention provides a pharmaceutical composition comprising a therapeutically effective amount of a compound, or combination of compounds of formulae (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV integrase inhibitors selected from the group consisting of S-1360, zintevir (AR-177), L-870812 and L-870810, and a pharmaceutically acceptable carrier.

In a seventeenth embodiment the present invention provides a pharmaceutical composition comprising a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors, one, two or three HIV budding/maturation inhibitors, and a pharmaceutically acceptable carrier.

For example, the present invention provides a pharmaceutical composition comprising a therapeutically effective amount of a compound or combination of compounds of formulae (I), (II), (III), (IV), (V), (VI) or (VII), or a pharmaceutically acceptable salt form, stereoisomer, ester, salt of an ester, prodrug, salt of a prodrug, or combination thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, PA-457, and a pharmaceutically acceptable carrier.

In an eighteenth embodiment, the present invention provides a method of inhibiting the replication of an HIV virus comprising contacting said virus with a therapeutically effective amount of a compound or combination of formula (I), (II), (III), (IV), (V), (VI) or (VII), or a pharmaceutically acceptable salt form, stereoisomer, ester, salt of an ester, prodrug, salt of a prodrug, or combination thereof.

In a nineteenth embodiment, the present invention provides a method of inhibiting the replication of HIV comprising contacting said virus with any one of the pharmaceutical composition as disclosed hereinabove.

In a twentieth embodiment, the present invention provides a method of treating or preventing an HIV infection comprising administering to a patient in need of such treatment a therapeutically effective amount of a compound or combination of compounds of formula (I), (II), (III), (IV), (V), (VI) or (VII), or a pharmaceutically acceptable salt form, stereoisomer, ester, salt of an ester, prodrug, salt of a prodrug, or combination thereof.

In a twenty-first embodiment the present invention provides a method of treating or preventing an HIV infection comprising administering to a patient in need of such treatment any one of the pharmaceutical composition as disclosed hereinabove.

In a twenty-second embodiment the present invention provides a method of inhibiting an HIV protease comprising contacting said HIV protease with a therapeutically effective amount of a compound or combination of formula (I), (II), (III), (IV), (V), (VI) or (VII), or a pharmaceutically acceptable salt form, stereoisomer, ester, salt of an ester, prodrug, salt of a prodrug, or combination thereof.

In a twenty-third embodiment the present invention provides a method of inhibiting an HIV protease comprising contacting said protease with any one of the pharmaceutical compositions as disclosed hereinabove.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

As used herein, the terms "S" and "R" configuration are as defined by the IUPAC 1974 Recommendations for Section E, Fundamental Stereochemistry, Pure Appl. Chem. (1976) 45, 13-30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of Formula (I), (II), (III), (IV), (V), (VI) or (VII), are meant to be included in this invention.

When any variable (for example A, R, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_a$, $R_b$, $R_c$, n, etc.) occurs more than one time in any substituent or in the compound of formula (I), (II), (III), (IV), (V), (VI) or (VII), or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can be used in the form of salts derived from inorganic or organic acids. These salts include but are not limited to the following: 4-acetamido-benzoate, acetate, adipate, alginate, carbonate, 4-chlorobenzenesulfonate, citrate, aspartate, benzoate, benzenesulfonate, bisulfate, butyrate, camphorate, camphorsulfonate, cholate, digluconate, cyclopentanepropionate, dichloroacetate, dodecylsulfate, ethanedisulfonate, ethanesulfonate, ethylsuccinate, formate, fumarate, galactarate, D-gluconate, D-glucuronate, glucoheptanoate, glutarate, lycerophosphate, glycolate, hemisulfate, heptanoate, hexanoate, hydrochloride, hydrobromide, hydroiodide, 2-hydroxyethanesulfonate (isethionate), 3-hydroxy-2-naphthoate, 1-hydroxy-2-naphthoate, lactate, lactobionate, laurate, maleate, malonate, mandelate, methanesulfonate, nicotinate, 1,5-naphthalene-disulfonate, 2-naphthalenesulfonate, oleate, oxalate, pamoate, palmitate, pectinate, persulfate, 3-phenylpropionate, picrate, pivalate, propionate, L-pyroglutamate, sebacate, stearate, succinate, tartrate, terephthalate, thiocyanate, p-toluenesulfonate, undecanoate, undecylenoate and valerate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as aluminum, sodium, lithium, potassium, calcium, magnesium or zinc or with organic bases such as diethylethanolamine, diethanolamine, ethylenediamine, guanidine, meglumine, olamine (ethnolamine), piperazine, piperidine, triethylamine, tromethamine, benzathine, benzene-ethanamine, adenine, cytosine, diethylamine, glucosamine, guanine, nicotinamide, hydrabamine, tributylamine, deanol, epolamine or triethanolamine.

Representative salts of the compounds of the present invention include, but not limited to, hydrochloride, methanesulfonate, sulfonate, phosphonate, isethionate and trifluoroacetate.

The compounds of the present invention can also be used in the form of prodrugs. Examples of such prodrugs include compounds wherein one, two or three hydroxy groups in the compound of this invention are functionalized with $R^{15}$ wherein $R^{15}$ is

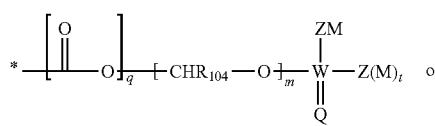
(VIII)

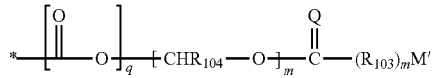
(IX)

wherein $R_{103}$ is $C(R_{105})_2$, O or $—N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, Li, Na, K, Mg, Ca, Ba, $—N(R_{105})_2$, alkyl, alkenyl, and $R_{106}$; wherein 1 to 4 $—CH_2$ radicals of the alkyl or alkenyl, other than the $—CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $—OR_{105}$, $—R_{105}$, $—N(R_{105})_2$, $—CN$, $—C(O)OR_{105}$, $—C(O)N(R_{105})_2$, $—SO_2N(R_{105})$, $—N(R_{105})C(O)R_{105}$, $—C(O)R_{105}$, $—S(O)R_{105}$, $—SO_2R_{105}$, $—OCF_3$, $—SR_{106}$, $—SOR_{106}$, $—SO_2R_{106}$, $—N(R_{105})SO_2R_{105}$, halo, $—CF_3$ and $NO_2$;

Z is $CH_2$, O, S, $—N(R_{105})$, or, when M is absent, H;

Q is O or S;

W is P or S; wherein when W is S, Z is not S;

M' is H, alkyl, alkenyl or $R_{106}$; wherein 1 to 4 $—CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $—OR_{105}$, $—R_{105}$, $—N(R_{105})_2$, $—CN$, $—C(O)OR_{105}$, $—C(O)N(R_{105})_2$, $—SO_2N(R_{105})$, $—N(R_{105})C(O)R_{105}$, $—C(O)R_{105}$, $—SR_{105}$, $—S(O)R_{105}$, $—SO_2R_{105}$, $—OCF_3$, $—SR_{106}$, $—SOR_{106}$, $—SO_2R_{106}$, $—N(R_{105})SO_2R_{105}$, halo, $—CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatom selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $—OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring system is substituted with 0, 1, 2, 3 or 4 substituents selected from the group consisting of oxo, $—OR_{105}$, $—R_{105}$, $—N(R_{105})_2$, $—N(R_{105})C(O)R_{105}$, $—C(O)OR_{105}$, $—C(O)N(R_{105})_2$, halo and $—CF_3$;

q is 0 or 1;

m is 0 or 1; and t is 0 or 1.

Representative examples of $R^{15}$ of formula (VIII) or (IX) that can be utilized for the functionalization of the hydroxy groups in the compound of the present invention include, but not limited to, the following:

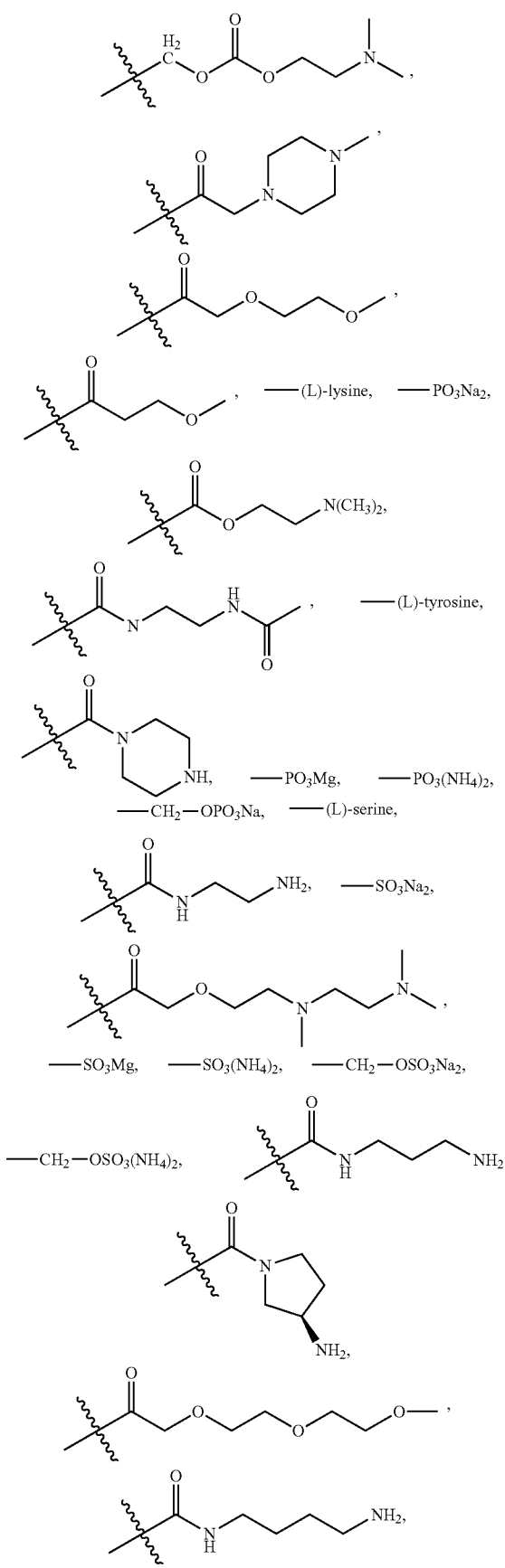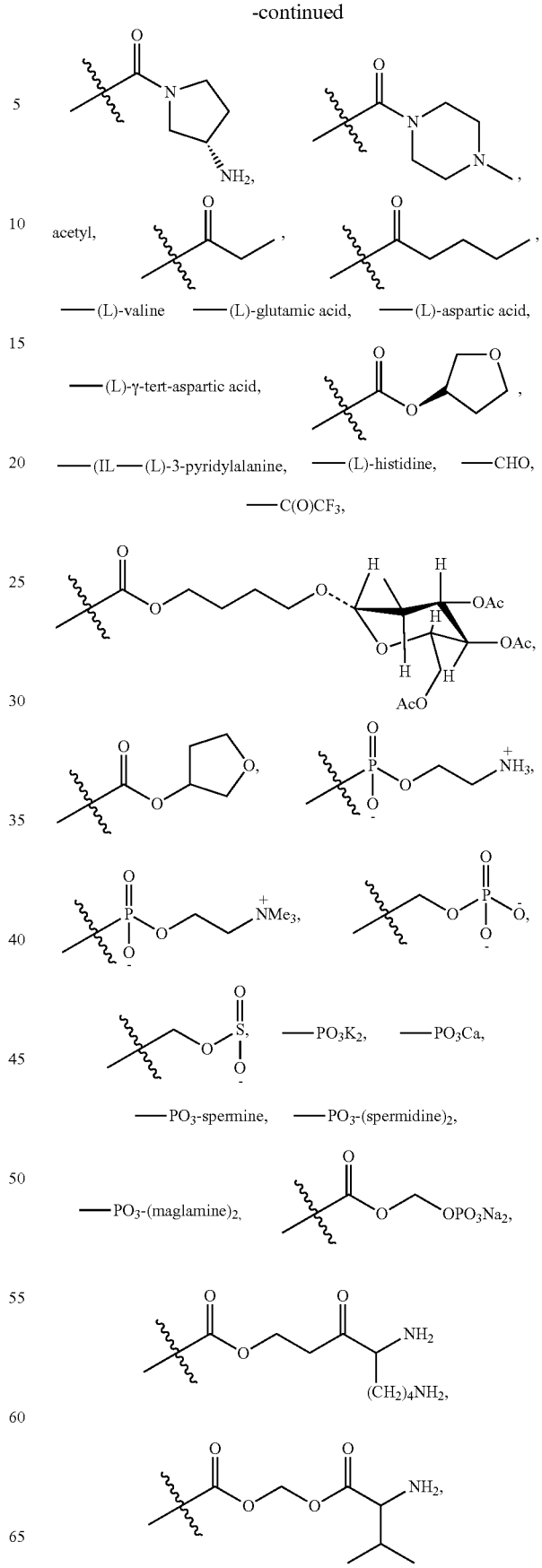

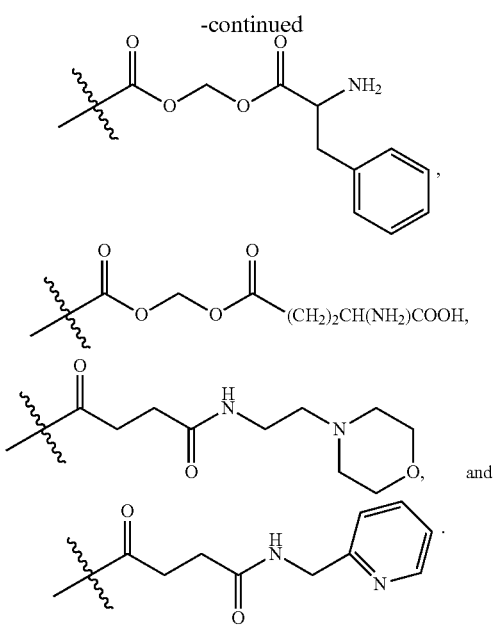

It will be understood by those of skill in the art that component M or M' in the formulae set forth herein will have either a covalent, a covalent/zwitterionic, or an ionic association with either Z or $R_{103}$ depending upon the actual choice for M or M'. When M or M' is hydrogen, alkyl, alkenyl or $R_{106}$, then M or M', is covalently bound to —$R_{103}$ or Z. If M is a mono or bivalent metal or other charged species (i.e. $NH_4^+$), there is an ionic interaction between M and Z and the resulting compound is a salt.

These prodrugs of the compound of the present invention serve to increase the solubility of these compounds in the gastrointestinal tract. These prodrugs also serve to increase solubility for intravenous administration of the compound. These prodrugs may be prepared by using conventional synthetic techniques. One of skill in the art would be well aware of conventional synthetic reagents to convert one or more of the hydroxy groups of the compounds of the present invention to a desired prodrug, functionalized by the substituents of formula (VIII) or (IX) as defined above.

The prodrugs of this invention are metabolized in vivo to provide the compound of this invention.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 20 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., Methods in Cell Biology, Volume XIV, Academic Press, New York, N.Y. (1976), p. 33.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, BCH-189, AzdU, carbovir, ddA, d4C, d4T (stavudine), 3TC (lamivudine) DP-AZT, FLT (fluorothymidine), BCH-189, 5-halo-3'-thia-dideoxycytidine, PMEA, bis-POMPMEA, zidovudine (AZT), MSA-300, trovirdine, R82193, L-697,661, BI-RG-587 (nevirapine), abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125 and the like), retroviral protease inhibitors (for example, HIV protease inhibitors such as ritonavir, lopinavir, saquinavir, amprenavir (VX-478), fosamprenavir, nelfinavir (AG1343), tipranavir, indinavir, atazanavir, TMC-126, TMC-114, mozenavir (DMP-450), JE-2147 (AG1776), L-756423, RO0334649, KNI-272, DPC-681, DPC-684, GW640385X, SC-52151, BMS 186,318, SC-55389a, BILA 1096 BS, DMP-323, KNI-227, and the like), HEPT compounds, L,697, 639, R82150, U-87201E and the like), HIV integrase inhibitors (S-1360, zintevir (AR-177), L-870812 L-870810 and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclor, castanosperminem rCD4/CD4-IgG, CD4-PE40, butyl-DNJ, hypericin, oxamyristic acid, dextran sulfate and pentosan polysulfate. Other agents that can be administered in combination with the compound of the present invention include HIV entry/fusion inhibitor (enfuvirtide (T-20), T-1249, PRO 2000, PRO 542, PRO 140, AMD-3100, BMS-806, FP21399, GW873140, Schering C (SCH-C), Schering D (SCH-D), TNX-355, UK-427857 and the like) and HIV budding/maturation inhibitor such as PA-457. Immunomodulators that can be administered in combination with the compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, cyclosporin, rapamycin, FK-565, FK-506, G-CSF, GM-CSF, hyperthermia, isopinosine, IVIG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24)) can be used in combination with the compound of the present invention.

Other agents that can be used in combination with the compound of this inventim are ansamycin LM 427, apurinic acid, ABPP, Al-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenyloin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

For example, a compound of this invention can be administered in combination with ritonavir. Such a combination is especially useful for inhibiting HIV protease in a human.

Such a combination is also especially useful for inhibiting or treating an HIV infection in a human. When used in such a combination the compound of this invention and ritonavir can be administered as separate agents at the same or different times or they can be formulated as a single composition comprising both compounds.

When administered in combination with a compound, or combination of compounds of this invention, ritonavir causes an improvement in the pharmacokinetics (i.e., increases half-life, increases the time to peak plasma concentration, increases blood levels) of the compound of this invention.

Another combination can comprise of a compound, or combination of compounds of the present invention with ritonavir and one or more reverse transcriptase inhibitors (for example, lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150 TMC-120, TMC-125 and the like). Such a combination is useful for inhibiting or treating an HIV infection in a human.

When used in such a combination the compound or combination of compounds of the present invention and ritonavir and one or more reverse transcriptase inhibitors can be administered as separate agents at the same or different times or they can be formulated as compositions comprising two or more of the compounds.

It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

Antiviral Activity

Determination of Activity Against Wild-Type HIV or the Passaged Variants

MT4 cells were infected with 0.003 multiplicity of infection (MOI) of wild-type HIV-1 or the passaged mutant variants at $1\times10^6$ cells/mL for 1 h, washed twice to remove unabsorbed virus and resuspended to $1\times10^5$ cells/mL of medium, seeded in a 96-well plate at 1004/well, and treated with an equal volume of solution of inhibitor in a series of half log dilutions in RPMI 1640 (Rosewell Park Memorial Institute) media (Gibco) containing 10% fetal bovine serum (FBS), in triplicate. The final concentration of DMSO in all wells was 0.5%. The virus control culture was treated in an identical manner except no inhibitor was added to the medium. The cell control was incubated in the absence of inhibitor or virus. Plates were incubated for 5 days in a $CO_2$ incubator at 37° C. On day 5, stock solution of 3-[4,5-dimethylthiazol-2-yl]-2,5-diphenyltetrazolium bromide (MTT) (4 mg/mL in PBS, Sigma cat. # M 5655) was added to each well at 25 µL per well. Plates were further incubated for 4 hrs, then treated with 20% sodium dodecyl sulfate (SDS) plus 0.02 N HCl at 50 µL per well to lyse the cells. After an overnight incubation, optical density (O.D.) was measured by reading the plates at 570/650 nm wavelengths on a Bio-Tek microtitre plate reader. Percent cytopathic effect (CPE) reduction was calculated from the formula below:

((O.D. test well−O.D. infected control well)/(O.D. uninfected control well−O.D. infected control well))×100

$EC_{50}$ values were determined from the plot of log (Fa/Fu) vs. log(compound concentration) using the median-effect equation (Chou, 1975, Proc. Int. Cong. Pharmacol. $6^{th}$ p. 619) wherein Fa is the fraction inhibited by the compound, and Fu is the fraction uninhibited (1-Fa).

When tested by the above method, the compounds of the present invention exhibit $EC_{50}$ in the range of 1 nM to 100 nM.

Determination of Anti-HIV Activity in the Presence of Human Serum

The above antiviral assay was performed in 96-well tissue culture plates containing 50% human serum (HS) (Sigma) plus 10% FBS (Gibco/BRL, Grand Island, N.Y.). Compounds were dissolved in DMSO, diluted at half log concentrations in DMSO, then transferred to media without serum at four times the final concentration. These solutions were added to 96-well plates at 50 µL per well, in triplicate. Cells were separately infected with 0.003 MOI of HIV-1 at $1\times10^6$ cells/mL for 1 h, washed twice to remove unadsorbed virus and resuspended to $2\times10^5$ cells/mL of media without serum. The cell suspension (50 µL) was seeded at $1\times10^4$ cells per well. Uninfected cells were included as control. Final DMSO concentration in all wells was 0.5% including uninfected and infected control wells. Cultures were incubated for 5 days in a $CO_2$ incubator at 37° C. $EC_{50}$ values were measured using MTT uptake as described above.

When tested by the above method, compounds of the present invention exhibit $EC_{50}$ in the range of 10 nM to 1 µM.

Generation of HIV-1 Resistant to ABT-378/r (A 17) by In Vitro Passage

MT4 cells ($2\times10^6$) were infected with pNL4-3 at an MOI of 0.03 for 2 h, washed, then cultured in the presence of ABT-378 and ritonavir at concentration ratio of 5:1. The concentration of ABT-378 and ritonavir used in the initial passage was 1 nM and 0.2 nM respectively. Viral replication was monitored by determination of p24 antigen levels in the culture supernatant (Abbott Laboratories), as well as by observation for any cytopathic effect (CPE) present in the cultures. When p24 antigen levels were positive, the viral supernatant was harvested for the proceeding passage. Following each passage, the drug concentrations in the subsequent passage were gradually increased. After 5 months of selection, 1.5 µM of ABT-378 can be used in the final passage. The A17 virus was generated after 17 passages of pNL4-3 in the presence of ABT-378 and ritonavir at concentration ratio of 5:1.

When tested by the above method, compounds of the present invention exhibit $EC_{50}$ in the range of 1 nM to 1 µM.

Synthetic Methods

Abbreviations which have been used in the descriptions of the scheme and the examples that follow are: DMF is N,N-dimethylformamide, DMSO is dimethylsulfoxide, THF is tetrahydrofuran, NMMO is 4-methylmorpholine N-oxide, HOBT is 1-hydroxybenzotriazole hydrate, DCC is 1,3-dicyclohexylcarbodiimide, EDAC is 1-(3-dimethylaminopropyl)-3-ethylcarbodiimide hydrochloride, DMAP is 4-(dimethylamino)pyridine, TFA is trifluoroacetic acid, and DEPBT is 3-(diethoxyphosphoryloxy)-1,2,3-benzotriazin-4(3H)-one.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, R, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and n are as defined above unless otherwise noted below.

This invention is intended to encompass compounds having formula (I), (II), (III), (IV), (V), (VI) or (VII) when prepared by synthetic processes or by metabolic processes. Preparation of the compounds of the invention by metabolic processes includes those occurring in the human or animal body (in vivo) or processes occurring in vitro.

Compounds of the invention can be prepared according to the methods described in Schemes 1-5 as shown below.

Scheme 1

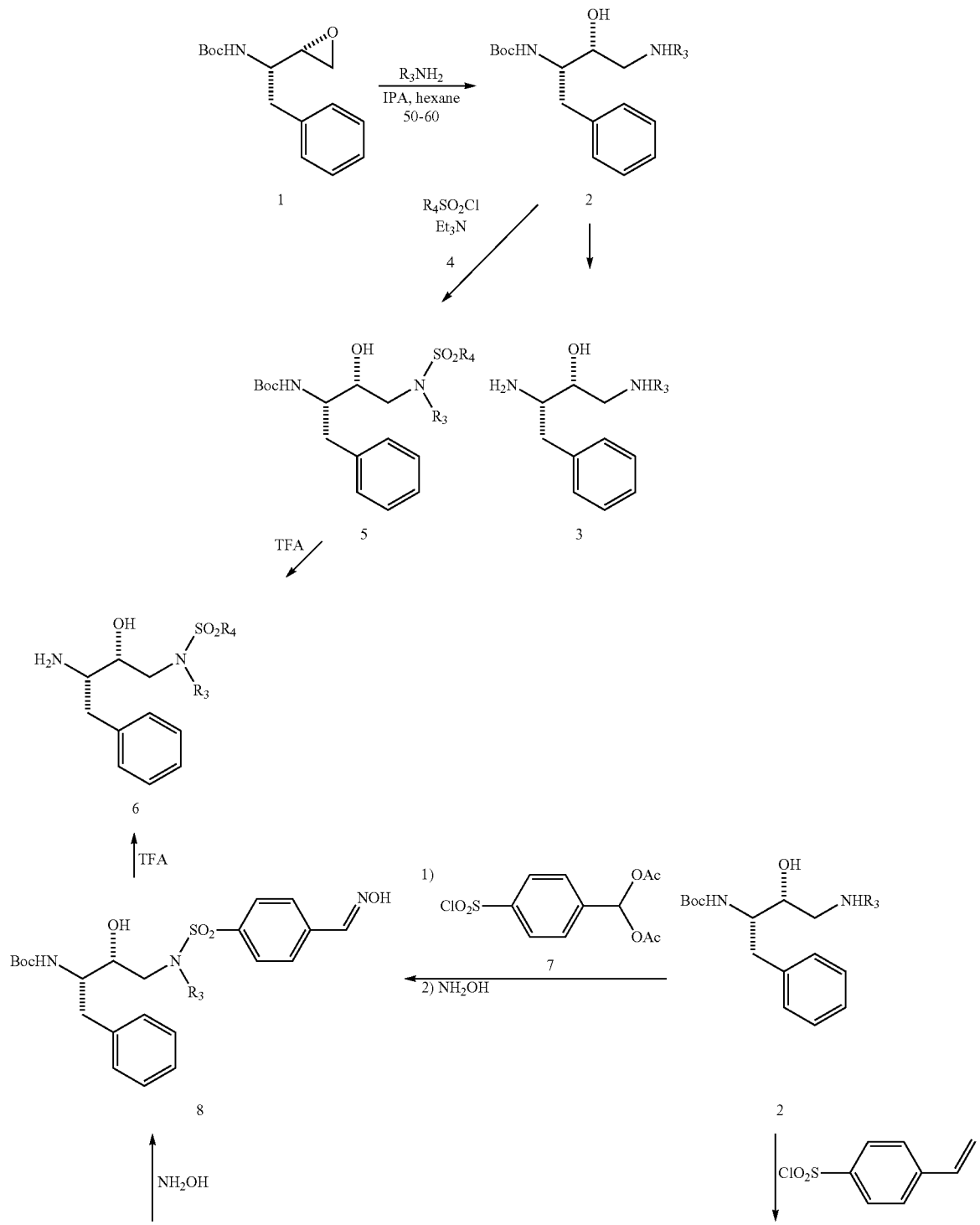

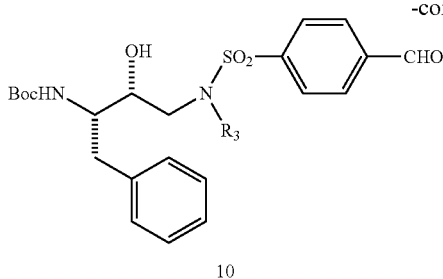

10

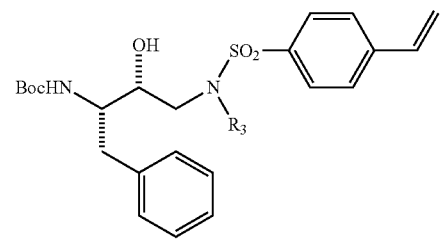

9

Compounds of formula (I) wherein $P_1$ is an N-protecting group (for example tert-butyloxycarbonyl or benzyloxycarbonyl), can be treated with an amine having formula $R^3NH_2$ (for example isobutylamine, cyclopentymethylamine, cyclobutylmethylamine, and the like) in an alcoholic solvent such as, but not limited to, ethanol or methanol at a temperature of about 25° C. to about 80° C., to give compounds of the formula (2). Compounds of formula (2) can be deprotected with an acid (for example, trifluoroacetic acid, hydrochloric acid, methanesulfonic acid, toluenesulfonic acid, sulfuric acid, aluminum chloride and the like) in an inert solvent (for example, dioxane, dichloromethane, chloroform, methanol, tetrahydrofuran, acetonitrile and the like) at a temperature from about 0° C. to about room temperature, to provide (3).

Treatment of compound (2) with sulfonyl chlorides of formula (4), such as, but not limited to, 4-methoxybenzenesulfonyl chloride in the presence of an organic amine base (for example, triethylamine, diisobutylethyl amine, pyridine, and the like), at a temperature of about 25° C. to about 80° C., in an inert solvent such as, but not limited to, dichloromethane, diethyl ether, tetrahydrofuran, chloroform, N,N-dimethylformamide, and the like, or mixtures thereof, give compounds of formula (5). Compounds of formula (5) can be deprotected to compounds of formula (6) using the conditions for the transformation of (2) to (3).

Compounds of formula (6) wherein $R_4$ is 4-[hydroxyimino)methyl]phenyl can be obtained by (a) treating compounds of formula (2) with 4-(diacetoxymethyl)benzenesulfonyl chloride (7), (b) treating the product from step (a) with hydroxylamine, and (c) deprotection of the corresponding oxime of formula (8).

Alternatively, compounds of formula (6) wherein $R_4$ is 4-[hydroxyimino)methyl]phenyl can also be obtained by (a) treating compounds of formula (2) with 4-vinylbenzenesulfonyl chloride, (b) oxidation of the product of step (a) with an oxidizing agent such as, but not limited to, osmium tetroxide, in the presence of sodium metaperiodate to give aldehydes of formula (10), (c) treating compounds of formula (10) with hydroxylamine to give compounds of formula (8), and (d) deprotection of compounds of formula (8).

Scheme 2

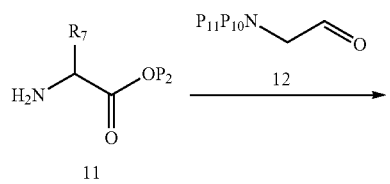

11

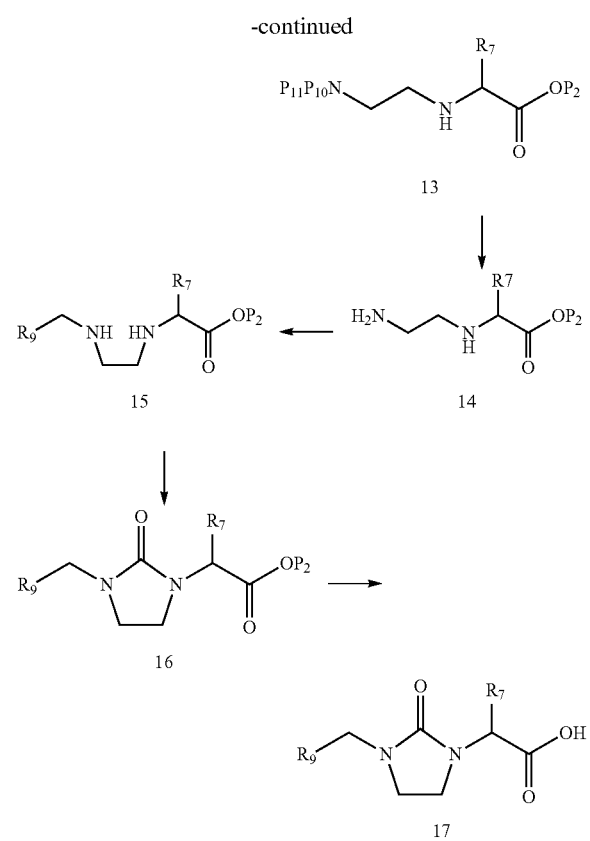

Amino acid esters of formula (11), wherein $P_2$ is lower alkyls (for example methyl, ethyl, tert-butyl and the like), can be treated with a suitably protected aldehyde of formula (12) (for example, $P_{10}$ and $P_{11}$ together with the nitrogen atom they are attached, form a phthalimido group) in the presence of a reducing agent under acidic conditions (for example, in the presence of acetic acid or hydrochloric acid) in an inert solvent, or mixture of solvents, such as methyl sulfoxide, methanol, dichloromethane, and the like, at a temperature of about room temperature to about 50° C., to provide compounds of formula (13). Examples of the reducing agent include, but are not limited to, sodium triacetoxyborohydride, sodium borohydride, sodium cyanoborohydride, and $BH_3$-pyridine.

Removal of the phthalimido group can be achieved using hydrazine in a suitable solvent such as ethanol and the like, at a temperature of about room temperature to about 100° C., to provide compounds of formula (14).

Compounds of formula (14) can be converted to compounds of formula (15) by (a) treating compounds of formula (14) with an aldehyde having formula $R_9CHO$, optionally in the presence of a drying agent (for example, magnesium sulfate, silica gel and the like) in an inert solvent, or mixture of solvents, such as dichloromethane, benzene, toluene, methanol, ethanol, methyl sulfoxide, and the like, at a temperature from about room temperature to about 100° C., and (b) reacting the product of step (a) with a reducing agent at about room temperature. Examples of the reducing agent include, but are not limited to, sodium triacetoxyborohydride, sodium borohydride, sodium cyanoborohydride, and $BH_3$-pyridine.

The diamine of formula (15) can be treated with a carbonylating agent in an inert solvent, or mixture of solvents, such as dichloromethane, 1,2 dichloroethane, toluene, acetonitrile, and the like, at a temperature of about room temperature to about 100° C., to provide compounds of formula (16). Examples of the carbonylating agent include, but are not limited to, 4-nitrophenyl carbonate, phosphene, diphosgene, triphosgene, carbonyl diimidazole, disuccinimidyl carbonate.

Conversion of compounds of formula (16) to the corresponding acids having formula (17) can be achieved by acid hydrolysis (for example acetic acid, trifluoroacetic acid, toluenesulfonic acid, formic acid, hydrochloric acid and the like) or base hydrolysis (for example sodium hydroxide, potassium hydroxide, lithium hydroxide, cesium carbonate, and the like) in a solvent, or mixture of solvents such as N,N-dimethylformamide, toluene, benzene, dichloromethane, ethyl acetate, water, methanol and the like, at a temperature of about 0° C. to about 100° C.

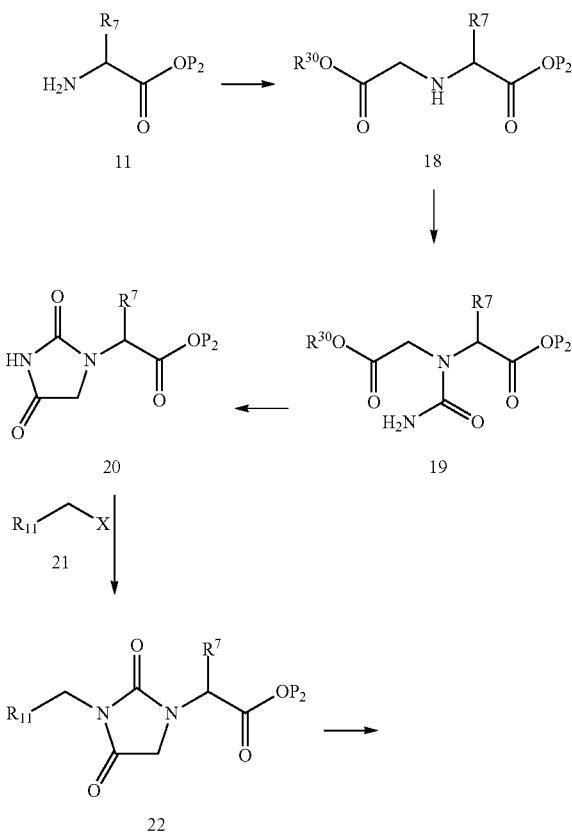

Scheme 3

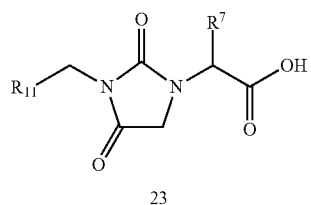

23

Amino acid esters having formula (11), wherein $P_2$ is lower alkyls (for example, methyl, ethyl, tert-butyl and the like) can be treated with compounds of formula $R^{30}OC(O)CH_2X$, wherein $R^{30}$ is lower alkyls and X is Br, Cl, or I, in an inert solvent, or mixture of solvents, such as N,N-dimethylformamide, dichloromethane, 1,2-dichloroethane, acetonitrile, toluene, benzene, diethyl ether and the like, at a temperature of about room temperature to about 50° C., to provide (18).

Compounds of formula (18) can be converted to compounds of formula (19) by (a) treating with chlorosulfonyl isocyanate (or compounds of formula $XSO_2NCO$, wherein X is Br, Cl, or I, and the like) in an inert solvent, or mixture of solvents, such as dichloromethane, 1,2-dichloroethane, dioxane, toluene, N,N-dimethylformamide, tetrahydrofuran diethyl ether and the like, at a temperature of about −10° C. to about room temperature, and (b) treating the product of step (a) with water at about room temperature. Alternatively, (18) can be reacted with a carbonylating agent such as, but not are limited to, 4-nitrophenyl carbonate, phosphene, diphosgene, triphosgene, carbonyl diimidazole, disuccinimidyl carbonate, followed by reaction with ammonia.

Cyclization of the compounds of formula (19) to provide compounds of formula (20) can be achieved be treating with an organic amine base such as triethyl amine, diisopropylethyl amine, imidazole, pyridine, N-methylmorpholine and the like, or an inorganic base such as sodium bicarbonate, sodium carbonate, cesium carbonate and the like, in an inert solvent, or mixture of solvents, such as methanol, ethanol, N,N-dimethylformamide, dioxane, xylene, tetrahydrofuran and the like, at a temperature of about room temperature to about 70° C.

Imides of formula (20) can be converted to compounds of formula (22) by (a) deprotonation with a base in an inert solvent, or mixture of solvents, such as dichloromethane, 1,2-dichloroethane, tetrahydrofuran, diethyl ether, tert-butyl methyl ether, and the like, at a temperature of about −78 to about 0° C., and (b) treating product of step (a) with an alkyl halide of formula (21), wherein X is Cl, Br or I, at a temperature of about room temperature to about 100° C. Examples of the base include, but are not limited to, sodium hydride, potassium hydride, lithium diisopropyl amide, lithium bis(trimethylsilyl)amide.

Alternatively, compounds of formula (20) can be converted to compounds of formula (22) by treating with an alcohol having formula $R_{11}CH_2OH$, in the presence of triphenylphosphine and diethyl azodicarboxylate, in an inert solvent such as dichloromethane, tetrahydrofuran, dioxane or N,N-dimethylformamide, at a temperature of about 0° C. to about 25° C.

Conversion of compounds of formula (22) can be converted to compounds of formula (23) using the conditions for the transformation of compounds of formula (16) to compounds of formula (17).

Scheme 4

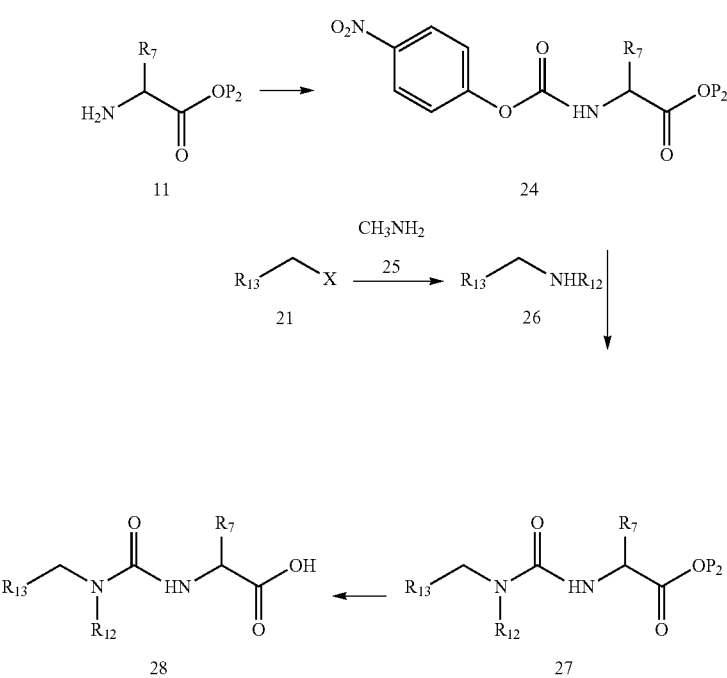

Amino acid esters having formula (11) wherein $P_2$ is lower alkyls (for example, methyl, ethyl, tert-butyl and the like) can be treated with compounds such as, but not limited to, bis-(4-nitrophenyl)carbonate in an inert solvent, or mixture of solvents, such as N,N-dimethylformamide, dichloromethane, 1,2-dichloroethane, acetonitrile, toluene, benzene, diethyl ether and the like at a temperature of about room temperature to about 50° C., to provide (24).

Treatment of alkyl halides of formula (21) wherein X is Cl, Br or I, with an amine of formula $R_{12}NH_2$ at a temperature of about 0° C. to about 50° C. in an open container or in a sealed vessel gives compounds of formula (26). Compounds of formula (26) is treated with (24) in an inert solvent, or mixture of solvents, such as N,N-dimethylformamide, dichloromethane, 1,2-dichloroethane, acetonitrile, toluene, benzene, diethyl ether, and the like, at a temperature of about room temperature to about 100° C., to provide compounds of formula (27).

Conversion of compounds of formula (2'7) to compounds of formula (2S) can be achieved by using the conditions for the transformation of compounds of formula (16) to compounds of formula (17).

Scheme 5

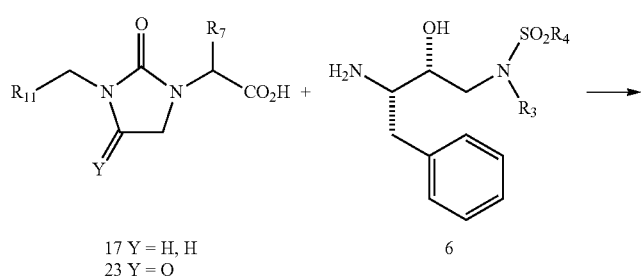

101

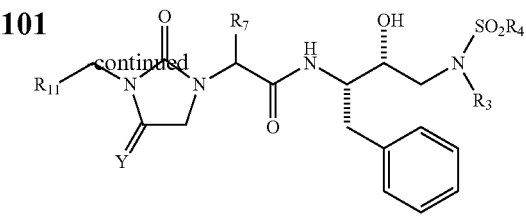

-continued

102

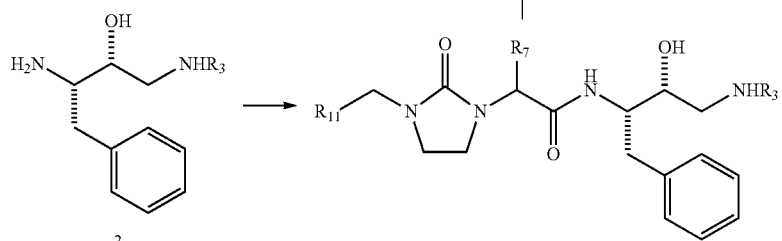

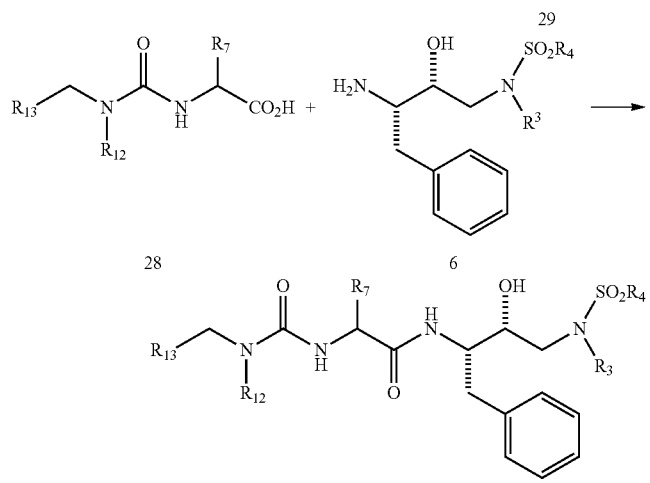

Compounds of formula (6) can be reacted with carboxylic acids of formula (17) or (23), or the corresponding salts, and an activating agent, optionally in the presence of 1-hydroxy-7-azabenzotriazole (HOAT), 1-hydroxybenzotriazole hydrate (HOBT) or 3-hydroxy-1,2,3-benzotriazin-4(3H)-one (HOOBT), and optionally in the presence of an inorganic base (for example, $NaHCO_3$, $Na_2CO_3$, $KHCO_3$, $K_2CO_3$, NaOH or KOH, and the like) in an inert solvent (for example, 1:1 ethyl acetate/water or isopropyl acetate/water or toluene/water or tetrahydrofuran/water and the like) at about room temperature, or an organic amine base (for example, imidazole, 1-methylimidazole, 2-methylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine or N-methylmorpholine and the like) in an inert solvent (for example, ethyl acetate, isopropyl acetate, tetrahydrofuran, toluene, acetonitrile, N,N-dimethylformamide, dichloromethane and the like) at a temperature of about 0° C. to about 50° C. to provide compounds of formula (30). Examples of the activating agent include, but are not limited to, 1,1'-carbonyldiimidazole (CDI), 1,3-dicyclohexylcarbodiimide (DCC), 1,3-diisopropylcarbodiimide, 1-(3-dimethylaminopropyl)-3-ethylcarbodiimide hydrochloride (EDAC), DEPBT (3-(diethoxyphosphoryloxy)-1,2,3-benzotriazin-4(3H)-one), PyBOP (benzotriazole-1-yl-oxy-tris-pyrrolidinophosphonium hexafluorophosphate), and 1,3-di-tert-butylcarbodiimide. Alternatively, a salt or an activated ester derivative of acid (17) or (23) (for example, the acid chloride, prepared by reaction of the carboxylic acid with thionyl chloride in ethyl acetate or tetrahydrofuran or oxalyl chloride in toluene/N,N-dimethylformamide) can be reacted with (6).

Alternatively, compounds of formula (30) can be obtained by (a) treating compounds of formula (3) with compounds of formula (17) using the conditions for the transformation of compound of formula (6) to (30), and (b) treating the product from step (a) with a compound having formula $R_4SO_2Cl$, using the conditions for the transformation of compounds of formula (2) to compounds of formula (5).

Compounds of formula (6) can also be coupled to acids having formula (2S) using the coupling conditions for the transformation of compounds of formula (6) to (30).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

It will be understood that the term "purification" used hereinafter, unless otherwise stated, means column chromatography using a silica gel column and eluting the column with a solvent system as specified in the experimental details.

Compounds of the invention were named by ACD/ChemSketch version 4.01 (developed by Advanced Chemistry Development, Inc., Toronto, ON, Canada) or were given names consistent with ACD nomenclature.

Example 1 tert-butyl(1S,2R)-1-benzyl-2-hydroxy-3-(isobutylamino)propylcarbamate

To a solution of (2R,3S)-3-N-tert-butoxycarbonylamino-1,2-epoxy-4-phenylbutane (10 g) in 2-propanol (100 mL) was added isobutylamine (11.4 mL, 3 equivalents), and the mixture was heated at 80° C. for 2.5 hours. After evaporation of the solvents, 11.86 g (93%) of the amine was produced in pure enough form for use in the next step. $^1$H NMR (300 MHz, CDCl$_3$) δ ppm 0.90 (d, J=1.47 Hz, 3H), 0.92 (d, J=1.47 Hz, 3H), 1.35 (s, 9H), 1.59 (s, 1H), 1.70 (m, 1H), 2.41 (d, J=6.99 Hz, 2H), 2.68 (d, J=4.78 Hz, 2H), 2.88 (d, J=8.09 Hz, 1H), 2.97 (d, J=4.41 Hz, 1H), 3.01 (d, J=4.78 Hz, 1H), 3.45 (q, J=5.52 Hz, 1H), 3.80 (s, 1H), 4.68 (d, J=8.09 Hz, 1H), 7.21 (m, 3H), 7.29 (m, 2H).

The compounds listed in Table 1, wherein X$_3$ represents the point of attachment to the core structure (A), were prepared by the procedure of Example 1.

TABLE 1

| Ex. | R$_3$ |
|---|---|
| 2 | cyclobutylmethyl |
| 3 | (pyridin-2-yl)methyl |
| 4 | 3-methyl-2-methylbutoxy |
| 5 | (tetrahydrofuran-2-yl)methyl |
| 6 | 2-methyl-1-methoxypropan-2-yl |
| 7 | 2-(dimethylamino)ethyl |
| 8 | 2-methoxyethyl |
| 9 | neopentyl |
| 10 | cyclopentylmethyl |
| 11 | 2-hydroxy-2-methylpropyl |
| 12 | [4-(pyridin-2-yl)phenyl]methyl |
| 13 | (furan-2-yl)methyl |

TABLE 1-continued (A)

| Ex. | R₃ |
|---|---|
| 14 | X₃—CH₂—(thiophene) |
| 15 | X₃—CH₂—(cyclopropyl) |

Example 16 tert-butyl(1S,2R)-1-benzyl-2-hydroxy-3-{isobutyl[(4-vinylphenyl)sulfonyl]amino}propylcarbamate To a solution of Example 1 (11.86 g) in dichloromethane (100 mL) was added triethylamine (TEA) (19.6 mL, 4 equivalents) followed by dropwise addition of vinylbenzenesulfonyl chloride (8.36 g, 1.2 equivalents) at 25° C. for 3 hrs. The mixture was partitioned in 1N sodium bicarbonate (NaHCO₃) and ethyl acetate (EtOAc). The organic extract was concentrated, and the residue was chromatographed on silica gel, eluting with ethyl acetate/hexanes (1:4) to afford the title compound (9.6 g, 54%). ¹H NMR (300 MHz, CDCl₃): δ ppm 0.87 (d, J=6.44 Hz, 3H), 0.90 (d, J=6.78 Hz, 3H), 1.34 (s, 9H), 1.86 (m, 1H), 2.84 (dd, J=13.39, 6.61 Hz, 2H), 2.97 (m, 3H), 3.11 (m, 3H), 3.79 (s, 1H), 4.61 (s, 1H), 5.44 (d, J=10.85 Hz, 1H), 5.88 (d, J=17.63 Hz, 1H), 6.75 (dd, J=17.63, 10.85 Hz, 1H), 7.25 (m, 5H), 7.51 (d, J=8.48 Hz, 2H), 7.72 (d, J=8.48 Hz, 2H).

Example 17 tert-butyl(1S,2R)-1-benzyl-2-hydroxy-3-[({4-[(hydroxyimino)methyl]phenyl}sulfonyl)(isobutyl)amino]propylcarbamate Method A Part 1 tert-butyl(1S,2R)-1-benzyl-3-[[(4-formylphenyl)sulfonyl](isobutyl)amino]-2-hydroxypropylcarbamate To Example 16 (8 g) in 80% tetrahydrofuran/water (120 mL) at 25° C. was added OsO₄ solution (2.9 mL, 4% by weight in water) followed by sodium periodate (6.76 g 2 equivalents). The mixture was stirred at 25° C. for 16 hrs, quenched with 10% sodium thiosulfate solution, and extracted with ethyl acetate. The organic extract was concentrated, and the residue was chromatographed on silica gel, eluting with 3% methanol/dichloromethane to give the title compound (7 g, 87%).

Part 2 tert-butyl(1S,2R)-1-benzyl-2-hydroxy-3-[({4-[(hydroxyimino)methyl]phenyl}sulfonyl)(isobutyl)amino]propylcarbamate A solution of hydroxylamine hydrochloride (2.08 g) in methanol (20 mL) was treated with a solution of KOH (1.68 g, 1 equivalent) in methanol (10 mL) at 0° C., stirred for 30 min, and filtered to give a 1 M solution of hydroxylamine. This solution (15 mL, 1.5 equivalents) was added to a solution of the product of Part 1 of method A (7 g) in methanol (25 mL), at 25° C. and stirred for 1 h. The reaction mixture was partitioned between ethyl acetate and brine. The organic extract was concentrated. The residue was chromatographed on silica gel using 5% methanol/CHCl₃. A second purification was performed using 15% ethyl acetate in dichloromethane to give the product (6.85 g, 95%).

Method B

Part 1

(acetyloxy)[4-(chlorosulfonyl)phenyl]methyl acetate

A solution of p-toluenesulfonyl chloride (40.2 g) in acetic acid:acetic anhydride (800 mL, 1:1) was treated with conc. sulfuric acid (64 mL, 5 equivalents) at 0-5° C. Chromium trioxide (80 g, 4 equivalents) was added at such a rate that the temperature remained below 10° C. The mixture was stirred at 5-10° C. until reaction was completed as indicated by TLC. The mixture was quenched with ice water (2 L), and the solids were filtered, washed with water, and dried. The solids were combined with saturated NaHCO₃ (1 L) at 25° C. for 2 hrs, filtered, dissolved in dichloromethane (1 L), dried over Na₂SO₄, filtered and concentrated. The residue was recrystallized from 2-3 volumes of hot acetone/pentane and cooling for 16 hrs. The crystals are filtered, and washed with cold pentane to give the product (24 g, 38%). ¹H NMR (CDCl₃): δ 8.09 (d, J=9 Hz, 2H), 7.77 (d, J=9 Hz, 2H), 7.73 (s, 1H), 2.16 (s, 6H).

Part 2

(acetyloxy)(4-{[{(2R,3S)-3-[(tert-butoxycarbonyl)amino]-2-hydroxy-4-phenylbutyl}(isobutyl)amino]sulfonyl}phenyl)methyl acetate A solution of Example 1 (12.82 g) in tetrahydrofuran (95 mL) was treated with triethylamine (15.9 mL), followed by a solution of the product of Part 1 of method B (14.0 g) in tetrahydrofuran (95 mL) and stirred at 25° C. for 4 hrs. The mixture was treated with saturated NaHCO₃ solution (125 mL), and the solvents were evaporated. The residue was diluted with water and extracted with ethyl acetate (3×), and the combined organic layers were dried over Na₂SO₄, filtered and concentrated to give the product.

107
Part 3 tert-butyl(1S,2R)-1-benzyl-2-hydroxy-3-[({4-[hydroxyimino)methyl]phenyl}sulfonyl)(isobutyl) amino]propylcarbamate A solution of the product of Part 2 of method B (23.1 g) in ethanol (254 mL) was treated sequentially with hydroxylamine hydrochloride (5.29 g) and triethylamine (21.2 mL), stirred at 75° C. for 4 hrs, cooled to 25° C., and concentrated. The residue was diluted with ethyl acetate and washed sequentially with water (3×) and saturated NaCl solution. The organic layer was separated, and concentrated. The solids formed was recrystallized by addition of about 2-3 volumes (relative to solid) of boiling ethyl acetate, followed by hexanes (2-3 volumes relative to ethyl acetate) until crystallization began. The mixture was kept at 25° C. for 18 h, and the solids were filtered and washed with hexanes to give the product (14.38 g, 73%). $^1$H NMR (300 MHz, CDCl$_3$) δ ppm 0.86 (d, J=6.44 Hz, 3H), 0.89 (d, J=6.78 Hz, 3H), 1.35 (s, 9H), 1.85 (m, 1H), 2.95 (m, 2H), 2.94 (s, 1H), 3.13 (m, 2H), 3.80 (s, 2H), 3.87 (s, 1H), 4.63 (d, J=5.76 Hz, 1H), 7.25 (m, 5H), 7.70 (d, J=8.48 Hz, 2H), 7.78 (d, J=8.48 Hz, 2H), 8.16 (s, 1H).

108
Example 18

N-[(2R,3S)-3-amino-2-hydroxy-4-phenylbutyl]-4-[(E)-(hydroxyimino)methyl]-N-isobutylbenzenesulfonamide A solution of Example 17 in dichloromethane (60 mL) was treated with 80% trifluoroacetic acid at 0° C. for 3 h. The solvents were evaporated, and the cis and trans oximes were treated with 5% trifluoroacetic acid in dichloromethane (20 mL) at 25° C. for 16 h. The solvents were evaporated, and the residue was partitioned between ethyl acetate and 1N NaHCO$_3$. After evaporating the solvents, the residue was filtered through a silica gel plug using 5% methanol in ethyl acetate (1% NH$_4$OH) and re-evaporated to give 3.62 g (91%). The trans isomer was separated from the cis by repeatedly crystallizing the solids from 5% methanol in ethyl acetate (50 mL). Approximately 3 g of pure trans isomer was recovered after six recrystallizations.

The compounds listed in Table 2 wherein X$_3$ represents the point of attachment to the core structure (B) were prepared by method A or method B as exemplified in Example 17 and Example 18.

TABLE 2

(B)

[Core structure (B): H$_2$N-(2R,3S)-3-amino-2-hydroxy-4-phenylbutyl chain with OH, linked to N(R$_3$)-SO$_2$-phenyl-CH=N-OH]

| Ex | Met. | R$_3$ | Ex | Method | R$_3$ | Ex | Mehod | R$_3$ |
|----|------|-------|----|--------|-------|----|-------|-------|
| 19 | A | cyclobutylmethyl (X$_3$-CH$_2$-cyclobutyl) | 20 | B | X$_3$-CH$_2$-(2-pyridyl) | 21 | B | X$_3$-CH(iPr)-CH$_2$-O |
| 22 | B | X$_3$-CH$_2$-(tetrahydrofuran-2-yl) | 23 | B | X$_3$-CH(iPr)-CH$_2$-O (stereo) | 24 | B | X$_3$-CH$_2$CH$_2$-N(CH$_3$)$_2$ |
| 25 | B | X$_3$-CH$_2$CH$_2$-O-CH$_3$ | 26 | A | neopentyl (X$_3$-CH$_2$-C(CH$_3$)$_3$) | 27 | A | X$_3$-CH$_2$-cyclopentyl |
| 28 | B | X$_3$-CH$_2$-CH(CH$_3$)-O | 29 | A | X$_3$-CH$_2$-(4-(2-pyridyl)phenyl) | 30 | B | X$_3$-CH$_2$-(2-furyl) |

TABLE 2-continued

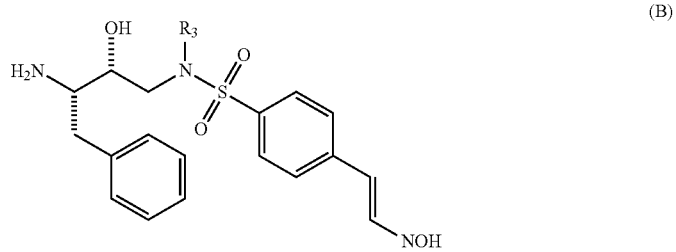

(B)

| Ex | Met. | R₃ | Ex | Method | R₃ | Ex | Mehod | R₃ |
|---|---|---|---|---|---|---|---|---|
| 31 | B |  | | | | | | |

Example 32

(2S,3S)-3-methyl-2-{3-[(6-methyl-2-pyridinyl)methyl]-2-oxo-1-imidazolidinyl}pentanoic acid

Example 32A (1,3-dioxo-1,3-dihydro-2H-isoindol-2-yl)acetaldehyde

To a solution of phthalimide diethylacetal (15 g) in tetrahydrofuran (THF) (30 mL) was added 10% aqueous HCl (18 mL). After heating at 75° C. for 5 hrs, the solution was allowed to cool to RT, and ethyl acetate (100 mL) was added. The solution was extracted with saturated sodium carbonate solution (100 mL), brine (100 mL), and the organic layer was separated and dried over magnesium sulfate ($MgSO_4$). The solution was filtered and evaporated to provide 11.2 g of the titled compound.

Example 32B tert-butyl (2S,3S)-2-{[2-(1,3-dioxo-1,3-dihydro-2H-isoindol-2-yl)ethyl]amino}-3-methylpentanoate To a solution of Example 32A (12.1 g) in methanol (20 mL) was added L-isoleucine tert-butyl ester hydrochloride (13.0 g, 58 mmol), sodium cyanoborohydride (7.3 g, 116 mmol), and acetic acid (2 mL). The resulting solution was stirred for 3 hrs at 25° C. and the methanol removed under vacuum, dichloromethane (500 mL) added, and the solution extracted with aq. $NaHCO_3$ (2×300 mL). Evaporation and purification of the organic layer gave 12.9 g of the title compound.

Example 32C tert-butyl (2S,3S)-2-[(2-aminoethyl)amino]-3-methylpentanoate

To a solution of Example 32B (12.9 g) in ethanol (400 mL) was added hydrazine hydrate (11.2 mL). The solution was then heated to 70° C. for 2 hrs. After cooling to 25° C., the resulting solid was dissolved in 1N NaOH solution (200 mL) and water (200 mL). The solution was then extracted with dichloromethane (3×200 mL), the organic extracts combined, dried and evaporated to provide 6.8 g of the title compound.

Example 32D tert-butyl (2S,3S)-3-methyl-2-[(2-{[(6-methyl-2-pyridinyl)methyl]amino}ethyl)amino]pentanoate 6-Methyl-2-pyridinecarboxaldehyde (4.25 g) was dissolved in dichloromethane (80 mL) and combined with Example 32C (8 g, 1 equivalent) and $MgSO_4$ (15 g), and the mixture was stirred at 25° C. for 2.5 hrs. The mixture was filtered, rinsed with dichloromethane, and the solvents were evaporated. The residue was dissolved in methanol (80 mL) and treated with $NaBH_4$ at 0° C. for 0.5 h. The solvents were evaporated, and the residue was partitioned between saturated $NaHCO_3$ and ethyl acetate. The organic layer was separated, washed with brine, dried over $Na_2SO_4$, and the solvents were evaporated to give 11 g of the title compound.

Example 32E tert-butyl (2S,3S)-3-methyl-2-{3-[(6-methyl-2-pyridinyl)methyl]-2-oxo-1-imidazolidinyl}pentanoate A solution of the product of Example 32D in N,N-dimethylformamide (60 mL) was treated with bis-(p-nitrophenyl) carbonate (12.6 g, 1.2 equivalents) at 50° C. for 5 hrs. The solvents were evaporated, and the residue was partitioned between water and ethyl acetate. The organic layer was separated, washed with brine, dried over $Na_2SO_4$, filtered, and the solvents were evaporated, and the residue was purified using ethyl acetate:hexanes (2:1) to give 7.3 g (57%) of the title compound.

Example 32F (2S,3S)-3-methyl-2-{3-[(6-methyl-2-pyridinyl)methyl]-2-oxo-1-imidazolidinyl}pentanoic acid A solution of the product of Example 32E (7.3 g) in dichloromethane (50 mL) and trifluoroacetic acid (50 mL) and the mixture was stirred at 25° C. for 3.5 hrs. The solvents were evaporated and the crude acid was used directly without purification.

The compounds listed in Table 3, wherein $X_7$ and $X_9$ represents the points of connection to the core structure (C), were prepared by the procedures as exemplified in Examples 32A-32F, substituting the corresponding aldehydes to 6-methyl-2-pyridinecarboxaldehyde, and substituting the corresponding amino acid esters or the salts of the amino acid esters for L-isoleucine tert-butyl ester hydrochloride.

TABLE 3-continued (C)

Structure: R9-N(C=O)-N(CH2CH2)-CH(R7)-CO2H (imidazolidinone)

| Ex. | R9 | R7 |
|---|---|---|
| 47 | 2-phenyl-5-ethyl-thiazol-4-yl (X9) | isopropyl (X7) |
| 48 | 2-methylquinolin-4-yl (X9) | tert-butyl (X7) |
| 49 | benzothiophen-3-yl (X9) | isopropyl (X7) |
| 50 | quinolin-6-yl (X9) | tert-butyl (X7) |
| 51 | 1-methylindol-2-yl (X9) | isopropyl (X7) |
| 52 | quinolin-7-yl (X9) | tert-butyl (X7) |
| 53 | quinolin-2-yl (X9) | isopropyl (X7) |
| 54 | 2-(pyridin-2-yl)thiazol-4-yl (X9) | tert-butyl (X7) |
| 55 | 2-acetylthiazol-4-yl (X9) | isopropyl (X7) |
| 56 | 3-(pyridin-3-yl)phenyl (X9) | tert-butyl (X7) |
| 57 | 2-isobutyryl-thiazol-4-yl (X9) | isopropyl (X7) |
| 58 | 3-(pyridin-3-yl)phenyl (X9) | sec-butyl (X7) |
| 59 | 2-butyryl-thiazol-4-yl (X9) | isopropyl (X7) |
| 60 | 2-(1-acetamidoethyl)thiazol-4-yl (X9) | tert-butyl (X7) |
| 61 | 5-nitrothiophen-2-yl (X9) | isopropyl (X7) |
| 62 | 2-(6-methylpyridin-3-yl)thiazol-4-yl (X9) | tert-butyl (X7) |

TABLE 3-continued (C)

[Structure: R9-N(CH2CH2)N(-C(=O)-)-CH(R7)-CO2H imidazolidinone]

| Ex. | R9 | R7 |
|---|---|---|
| 63 | 4-X9-thiazol-2-yl-CH2-N3 (azidomethyl thiazole) | isopropyl-X7 |
| 64 | 2-(pyridin-4-yl)-4-X9-thiazole | tert-butyl-X7 |
| 65 | 2-propanoyl-4-X9-thiazole | isopropyl-X7 |
| 66 | 2-(thiophen-2-yl)-4-X9-thiazole | tert-butyl-X7 |
| 67 | 1-methyl-2-X9-benzimidazole | isopropyl-X7 |
| 68 | 2-methyl-3-X9-pyridine | sec-butyl-X7 |
| 69 | 2-nitro-4-X9-thiophene | isopropyl-X7 |
| 70 | 6-methyl-3-X9-pyridine (2-methyl-5-X9-pyridine) | sec-butyl-X7 |
| 71 | 2-nitro-4-X9-thiazole | isopropyl-X7 |
| 72 | 6-(N-ethoxycarbonyl-N-methyl-aminomethyl)-2-X9-pyridine | sec-butyl-X7 |
| 73 | 2-(acetoxymethyl)-4-X9-thiazole | isopropyl-X7 |
| 74 | 3-(thiazol-2-yl)-X9-phenyl | sec-butyl-X7 |
| 75 | 2-X9-benzofuran | isopropyl-X7 |
| 76 | 3-(pyridin-2-yl)-X9-phenyl | sec-butyl-X7 |
| 77 | 3-X9-quinoline | isopropyl-X7 |
| 78 | 2,4-dimethyl-3-X9-pyridine | sec-butyl-X7 |

TABLE 3-continued

![structure C: R9-CH2-N(C=O)N-CH(R7)-CO2H imidazolidinone]

| Ex. | R9 | R7 |
|---|---|---|
| 79 | 3-methoxy-2-nitro-thiophen-4-yl (X9) | isopropyl (X7) |
| 80 | 3-(furan-3-yl)phenyl (X9) | sec-butyl (X7) |
| 81 | 2-(methylthiomethyl)thiazol-4-yl (X9) | isopropyl (X7) |
| 82 | 3-(pyrimidin-4-yl)phenyl (X9) | sec-butyl (X7) |
| 83 | 2-(cyanomethyl)thiazol-4-yl (X9) | isopropyl (X7) |
| 84 | 6-methoxypyridin-3-yl (X9) | sec-butyl (X7) |
| 85 | quinolin-4-yl (X9) | isopropyl (X7) |
| 86 | 2-(pyrazin-2-yl)thiazol-4-yl (X9) | tert-butyl (X7) |
| 87 | 5-methyl-2-nitro-thiazol-4-yl (X9) | isopropyl (X7) |
| 88 | pyridazin-4-yl (X9) | tert-butyl (X7) |
| 89 | 1-methylimidazol-2-yl (X9) | isopropyl (X7) |
| 90 | pyridazin-4-yl (X9) | sec-butyl (X7) |
| 91 | 2-acetamidothiazol-4-yl (X9) | isopropyl (X7) |
| 92 | 2-(5-methylisoxazol-3-yl)thiazol-4-yl (X9) | tert-butyl (X7) |
| 93 | 8-hydroxyquinolin-2-yl (X9) | isopropyl (X7) |

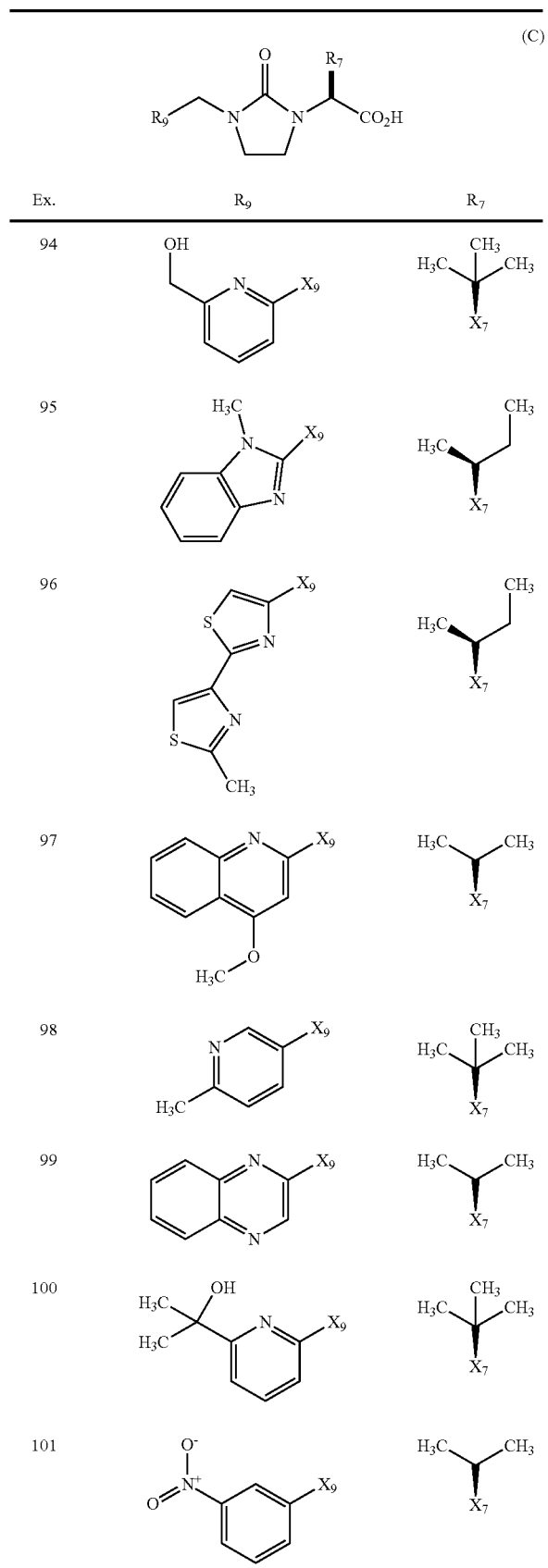
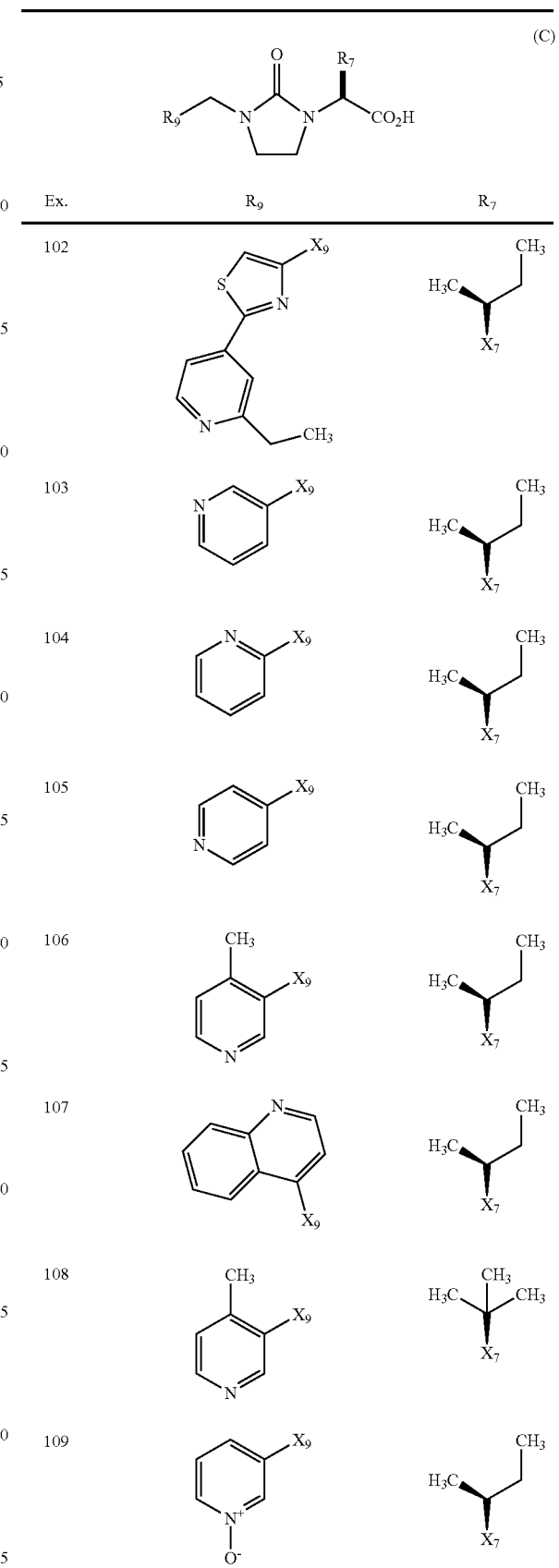

TABLE 3-continued (C)

Structure: R9–N(CH2CH2)N(C(=O))–CH(R7)–CO2H (imidazolidinone with R9 on one N and CH(R7)CO2H on the other)

| Ex. | R9 | R7 |
|---|---|---|
| 110 | 4-(methoxymethyl)thiazol-2-yl (X9 at 4-position, -CH2-OCH3 at 2-position via thiazole) | tert-butyl (X7) |
| 111 | pyridine N-oxide (X9 at 4-position) | sec-butyl (X7), (S) |
| 112 | 2-(6-methylpyridin-3-yl)thiazol-4-yl (X9) | sec-butyl (X7), (S) |
| 113 | 2-acetamidothiazol-4-yl (X9) | sec-butyl (X7), (S) |
| 114 | 2-(pyridin-3-yl)thiazol-4-yl (X9) | sec-butyl (X7), (S) |
| 115 | 1H-benzimidazol-5-yl (X9) | sec-butyl (X7), (S) |
| 116 | pyridazin-4-yl (X9) | sec-butyl (X7), (S) |
| 117 | 6-(methoxymethyl)pyridin-2-yl (X9) | sec-butyl (X7), (S) |
| 118 | 2-isopropylthiazol-4-yl (X9) | tert-butyl (X7) |
| 119 | quinolin-2-yl (X9) | sec-butyl (X7), (S) |
| 120 | pyridazin-3-yl (X9) | sec-butyl (X7), (S) |
| 121 | 3-cyanophenyl (X9) | sec-butyl (X7), (S) |
| 122 | 6-acetylpyridin-2-yl (X9) | tert-butyl (X7) |
| 123 | 2-(trifluoromethyl)thiazol-4-yl (X9) | sec-butyl (X7), (S) |
| 124 | 6-(methoxycarbonyl)pyridin-2-yl (X9) | tert-butyl (X7) |
| 125 | quinolin-8-yl (X9) | sec-butyl (X7), (S) |

TABLE 3-continued (C)

| Ex. | R9 | R7 |
|---|---|---|
| 126 | 2-(2-hydroxypropan-2-yl)pyridin-6-yl (X9) | sec-butyl (X7) |
| 127 | 2-(1-(hydroxyimino)ethyl)pyridin-4-yl (X9) | sec-butyl (X7) |
| 128 | 2-(hydroxymethyl)pyridin-6-yl (X9) | sec-butyl (X7) |
| 129 | quinolin-7-yl (X9) | sec-butyl (X7) |
| 130 | 2-methylquinolin-4-yl (X9) | sec-butyl (X7) |
| 131 | quinolin-6-yl (X9) | sec-butyl (X7) |
| 132 | 5-methylthiophen-2-yl (X9) | sec-butyl (X7) |
| 133 | 2-(pyridin-2-yl)thiazol-4-yl (X9) | sec-butyl (X7) |
| 134 | 2-(1-acetamidoethyl)thiazol-4-yl (X9) | sec-butyl (X7) |
| 135 | 2-((dimethylhydrazono)methyl)thiazol-4-yl (X9) | sec-butyl (X7) |
| 136 | imidazo[1,2-a]pyridin-3-yl (X9) | sec-butyl (X7) |
| 137 | 2-(1-(hydroxyimino)ethyl)pyridin-6-yl (X9) | sec-butyl (X7) |
| 138 | 2-methylpyridin-6-yl (X9) | tert-butyl (X7) |
| 139 | 2-((N-methylacetamido)methyl)pyridin-6-yl (X9) | sec-butyl (X7) |
| 140 | 2,2'-bipyridin-6-yl (X9) | sec-butyl (X7) |
| 141 | 2-(1-methylhydrazinyl)thiazol-4-yl (X9) | sec-butyl (X7) |

TABLE 3-continued

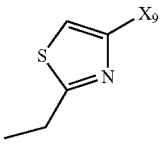

| Ex. | $R_9$ | $R_7$ |
|---|---|---|
| 142 | 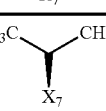 | 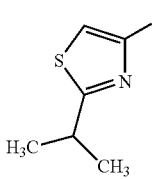 |

Example 143

(2S)-3-methyl-2-{3-[(2-methyl-1,3-thiazol-4-yl)methyl]-2-oxoimidazolidin-1-yl}butanoic acid

Example 143A

2-{[(2-methyl-1,3-thiazol-4-yl)methyl]amino}ethanol

2-Methyl-4-(chloromethyl)thiazole (2.24 g) was treated with ethanolamine (11.6 mL, 10 equivalents) in dichloromethane at 25° C. for 16 hrs. The solvent was evaporated and the residue partitioned between ethyl acetate and brine. The organic layer was separated and extracted with ethyl acetate (5×). The organic layers were combined and washed with brine, dried over $Na_2SO_4$, and the solvents were evaporated to give 2.4 g (85%) of title compound.

Example 143B tert-butyl 2-hydroxyethyl[(2-methyl-1,3-thiazol-4-yl)methyl]carbamate The product of Example 143A (2.4 g) was treated with di-t-butyl dicarbonate (2.85 g, 1 equivalent) in tetrahydrofuran/1M $NaHCO_3$ (2:1) and stirred at 25° C. for 16 hrs. The solvents were evaporated, and the residue was acidified with 10% citric acid and extracted with ethyl acetate (3×). The combined organic layer was washed with brine, dried over $Na_2SO_4$ and evaporated. The crude product was purified using 1% methanol/dichloromethane to give 1.91 g (52%) of title compound.

Example 143C methyl(2S)-3-methyl-2-[(2-{[(2-methyl-1,3-thiazol-4-yl)methyl]amino}ethyl)amino]butanoate A solution of the product of Example 143B (2.26 g) in dichloromethane (20 mL) was treated with oxalyl chloride (5.4 mL, 1.5 equivalents) at −78° C., and stirred for 15 min. DMSO (1.02 mL, 2 equivalents) was added dropwise at −78° C., stirred for 15 min, and quenched with triethylamine (4 mL, 4 equivalents) as the mixture warmed to 0° C. The mixture was quenched with 20% $KH_2PO_4$, and partitioned between dichloromethane and water. The organic layer was washed with brine, dried over $Na_2SO_4$, filtered, and the solvents were evaporated. To this crude product was added methanol/water (7:2), (L)-valine methyl ester (1.21 g, 1 equivalent), sodium acetate trihydrate (1.96 g, 2 equivalents), and $NaCNBH_3$ (0.95 g, 2 equivalents) was added portionwise over 30 min. After stirring for 1 hour the mixture was partitioned between saturated $NaHCO_3$ and extracted with ethyl acetate (2×). The combined organic layer was washed with brine, dried with $Na_2SO_4$, and evaporated. The residue was treated with dichloromethane/trifluoacetic acid (10 mL, 1:1) and stirred at 25° C. for 2 hrs and concentrated.

Example 143D (2S)-3-methyl-2-{3-[(2-methyl-1,3-thiazol-4-yl)methyl]-2-oxo-1-imidazolidinyl}butanoic acid A solution of the product of Example 143C (5.4 g) in tetrahydrofuran (80 mL) was treated with carbonydiimidazole (6.1 g, 2 equivalents) at 25° C. for 2 hrs. The mixture was quenched with 10% citric acid, the organic layer was separated, washed with water, brine, dried over $Na_2SO_4$, filtered, and the solvents were evaporated A solution of the residue (3.3 g) in dioxane (20 mL) was treated with 1M LiOH (20 mL) at 25° C. for 2 hrs. The solvents were evaporated, and the residue was acidified with 10% HCl, extracted with dichloromethane/2-propanol (3:1), the organic layer was separated, dried over $Na_2SO_4$, filtered, and the solvents evaporated to give 1.5 g of the title compound.

The compounds listed in Table 4, wherein $X_7$ and $X_9$ represents the points of connection to the core structure (C), were prepared by the procedures as exemplified in Examples 143A-143D, substituting the corresponding halides for 2-methyl-4-(chloromethyl)thiazole, and substituting the corresponding amino acid esters for (L)-valine methyl ester.

TABLE 4

| Ex. | $R_9$ | $R_7$ |
|---|---|---|
| 144 | 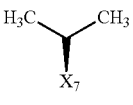 | 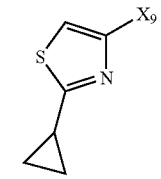 |
| 145 | 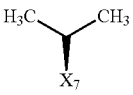 | 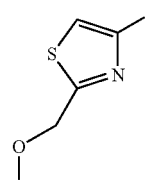 |
| 146 | 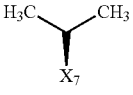 | |

TABLE 4-continued

| Ex. | R$_9$ | R$_7$ |
|---|---|---|
| 147 | (2-(1-methylethyl)thiazol-4-yl with X$_9$) | (CH$_3$, H$_3$C-CH with X$_7$) |

Example 148

(2S)-3,3-dimethyl-2-{3-[(1-methyl-1H-benzimidazol-2-yl)methyl]-2-oxoimidazolidin-1-yl}butanoic acid

Example 148A

N-(2,2-dimethoxyethyl)-N-[(1-methyl-1H-benzimidazol-2-yl)methyl]amine

A solution of 1-methyl-2-formylbenzimidazole (1 g) in methanol (27 mL) and acetic acid (0.54 mL) was treated with aminoacetaldehyde diethylacetal (0.9 g, 1 equivalent) and NaCNBH$_3$ (0.85 g, 2 equivalents) at 25° C., stirred for 1 hour. The mixture was partitioned between water and ethyl acetate. The organic layer was separated, washed sequentially with saturated NaHCO$_3$ and brine, and concentrated. The residue was chromatographed on silica gel, eluting with 8% methanol/dichloromethane to give 1.2 g (64%) of the title compound.

Example 148B 9H-fluoren-9-ylmethyl 2,2-dimethoxyethyl[(1-methyl-1H-benzimidazol-2-yl)methyl]carbamate A solution of the product of Example 148A (1.2 g) in dichloromethane (30 mL) was treated with 9-fluorenylmethyl succinimide (1.6 g, 1.05 equivalents) at 0° C. for 16 hours. The mixture was partitioned between water and ethyl acetate. The organic layer was separated, washed sequentially with 10% NaHCO$_3$ and brine, dried over Na$_2$SO$_4$, filtered and concentrated. The residue was chromatographed on silica gel, eluting with ethyl acetate:dichloromethane (1:1) to give 1.83 g (84%) of the title compound.

Example 148C 9H-fluoren-9-ylmethyl(1-methyl-1H-benzimidazol-2-yl)methyl(2-oxoethyl)carbamate A solution of the product of Example 148B (0.2 g) in tetrahydrofuran (0.2 mL) was treated with 30% HCl (0.2 mL), stirred at 75° C. for 6 hours, cooled to 25'C and concentrated. The residue was partitioned between 10% NaHCO$_3$ and ethyl acetate, the organic layer was separated and washed with brine, dried over Na$_2$SO$_4$, filtered and concentrated to give the title compound (175 mg).

Example 148D methyl(2S)-2-[(2-{[(9H-fluoren-9-ylmethoxy)carbonyl][(1-methyl-1H-benzimidazol-2-yl)methyl]amino}ethyl)amino]-3,3-dimethylbutanoate A solution of the product of Example 148C (0.178 g) and (L)-methyl t-leucinate hydrochloride (76.1 mg, 1 equivalent) in methanol (1.7 mL) and acetic acid (17 µL) was treated with NaCNBH$_3$ (54 mg, 2 equivalents) at 25° C. for 3.5 hours. The mixture was partitioned between water and ethyl acetate. The organic layer was separated and washed with 1N NaHCO$_3$ and brine, and concentrated. The residue was chromatographed on silica gel, eluting with ethyl acetate:dichloromethane (3:1) to give 0.19 g (83%) of the title compound.

Example 148E methyl(2S)-3,3-dimethyl-2-{3-[(1-methyl-1H-benzimidazol-2-yl)methyl]-2-oxoimidazolidin-1-yl}butanoate A solution of the product of Example 148D (0.19 g) in N,N-dimethylformamide (3.5 mL) was treated with diethylamine (0.35 mL), stirred at 25° C. for 1.5 hours and concentrated. A solution of the residue in dichloroethane (7 mL) was treated with bis-(p-nitrophenyl) carbonate (0.128 g, 1.2 equivalents), stirred at 60° C. for 16 hours and concentrated. The residue was chromatographed on silica gel, eluting with ethyl acetate:dichloromethane (3:2) to give 80 mg (64%) of the title compound.

Example 148F (2S)-3,3-dimethyl-2-{3-[(1-methyl-1H-benzimidazol-2-yl)methyl]-2-oxoimidazolidin-1-yl}butanoic acid A solution of the product of Example 148E (37 mg) in tetrahydrofuran (0.26 mL) and water (0.13 mL) was treated with LiOH (6.1 mg, 1.4 equivalents), stirred at 25° C. for 16 hours, quenched with 1N HCl (0.15 mL) at 0° C., and the solvents were evaporated to give the crude product to be used without further purification.

The compounds listed in Table 5, wherein X$_7$ and X$_9$ represent respectively the points of connection to the core structure (C), were prepared by the procedures as exemplified in Example 148A-148F, substituting the corresponding aldehydes for 1-methyl-2-formylbenzimidazole, and substituting the corresponding amino acid esters for (L)-methyl t-leucinate hydrochloride.

TABLE 5

| Ex. | R$_9$ | R$_7$ |
|---|---|---|
| 149 | (2-methylthiazol-4-yl with X$_9$) | (C(CH$_3$)$_2$ with X$_7$) |
| 150 | (2-methylthiazol-4-yl with X$_9$) | (H$_3$C-CH$_2$-NH-C(=O)-CH$_2$- with X$_7$) |
| 151 | (2-methylthiazol-4-yl with X$_9$) | (CH$_3$, H$_3$C-CH with X$_7$) |

TABLE 5-continued

| Ex. | R9 | R7 |
|---|---|---|
| 152 | 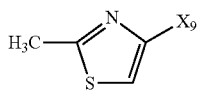 | 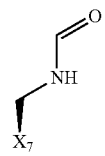 |
| 153 | 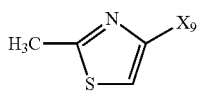 | 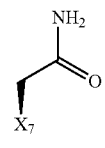 |
| 154 | 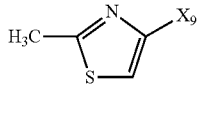 | 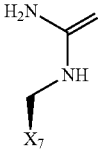 |
| 155 | 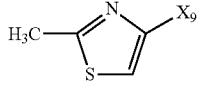 | 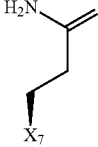 |
| 156 | 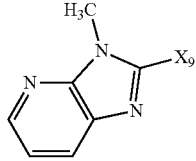 | 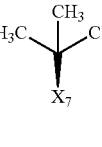 |
| 157 | 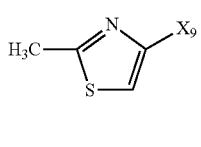 | 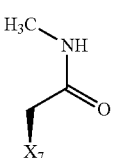 |
| 158 | 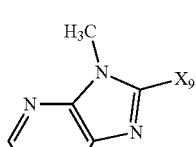 | 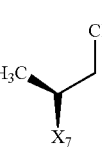 |

Example 159

(2S)-2-[3-({2-[(dimethylamino)methyl]-1,3-thiazol-4-yl}methyl)-2-oxo-1-imidazolidinyl]-3-methylbutanoic acid

Example 159A tert-butyl (2S)-2-[3-({2-[(dimethylamino)methyl]-1,3-thiazol-4-yl}methyl)-2-oxo-1-imidazolidinyl]-3-methylbutanoate Example 273D (0.2 g, 0.54 mmol) was dissolved in toluene:ethanol (2.2 mL, 1:1) and treated with dimethylamine (0.54 mL, 2M in tetrahydrofuran, 2 equivalents) at 70° C. for 3 h. The mixture was cooled to 25° C. and treated with sodium borohydride (20 mg, 3 equivalents) at 25° C. for 68 h. The solvents were evaporated, and the crude residue was partitioned between ethyl acetate and saturated sodium bicarbonate. The organic layer was separated, washed with brine, dried over magnesium sulfate, and the solvents were evaporated. The crude residue was purified using ethyl acetate-ethyl acetate/10% methanol to give 0.11 g (53%) of the title compound.

Example 159B (2S)-2-[3-({2-[(dimethylamino)methyl]-1,3-thiazol-4-yl}methyl)-2-oxo-1-imidazolidinyl]-3-methylbutanoic acid Example 159A was dissolved in dichloromethane:trifluoroacetic acid (2.4 mL, 1:1) at 25° C. for 1 h. The solvents were evaporated to give the title compound used directly for the next step.

Example 160

(2S)-3-methyl-2-{3-[(2-methyl-1,3-thiazol-4-yl)methyl]-2-oxo-2,3-dihydro-1H-imidazol-1-yl}butanoic acid

Example 160A

N-(2,2-diethoxyethyl)-N-[(2-methyl-1,3-thiazol-4-yl)methyl]amine

4-Chloromethyl-2-methylthiazole (0.6 g, 4 mmol) was added to aminoacetaldehyde diethyl acetal (5 mL, 10 equivalents) dissolved in tetrahydrofuran (15 mL) at 25° C., and the mixture was stirred for 16 h. The solvents were evaporated and the excess aldehyde was distilled from the crude mixture. The crude residue was purified using dichloromethane—dichloromethane/10% methanol to give 0.76 g (76%) of the title compound.

Example 160B methyl(2S)-3-methyl-2-{3-[(2-methyl-1,3-thiazol-4-yl)methyl]-2-oxo-2,3-dihydro-1H-imidazol-1-yl}butanoate Example 160A (0.76 g, 3.1 mmol) was dissolved in tetrahydrofuran (12 mL) and treated with (L)-methyl valinate p-nitrophenylcarbamate (0.92 g, 1 equivalent), triethylamine (0.43 mL, 2 equivalents), and DMAP (60 mg, 1.5 equivalents) at 25° C. for 2 days. The solvents were evaporated, and the crude residue was partitioned between ethyl acetate/10% sodium carbonate, the organic layer was separated, dried over magnesium sulfate, and the solvents were evaporated. The crude material was dissolved in formic acid (30 mL) at 25° C. for 16 h. the solvents were evaporated and the crude residue was purified using dichloromethane-ethyl acetate to give 0.51 g (53%) of the title compound.

Example 160C

Example 160B (0.1 g, 0.32 mmol) was dissolved in tetrahydrofuran:water (1.5 mL, 2:1) and treated with lithium hydroxide (40 mg, 3 equivalents) at 25° C. for 30 min. The mixture was combined with 1N HCl (1 mL) and partitioned between ethyl acetate and brine. The organic layer was separated and dried over magnesium sulfate, and the solvents were evaporated to give 95 mg (100%) of the title compound.

Example 161

(2S)-N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxoimidazolidin-1-yl)-3-methylbutanamide

Method A

Example 146 (62 mg) was combined with HOBT (39 mg, 1.5 equivalents) and EDAC (55 mg, 1.5 equivalents) in N,N-dimethylformamide (3 mL) and stirred for 1 h at 25° C. To this mixture was added N-methylmorpholine (MAIM) (42 μL, 2 equivalents) and Example 18 (80 mg, 1 equivalent). The mixture was stirred for 16 hrs, evaporated under vacuum, and purified using 3% methanol/dichloromethane to give 54 mg (39%) of the title compound. $^1$H NMR (300 MHz, CDCl$_3$) δ ppm 0.77 (d, J=6.44 Hz, 3H), 0.82 (d, J=6.44 Hz, 3H), 0.86 (d, J=6.78 Hz, 3H), 0.90 (d, J=6.78 Hz, 3H), 1.85 (m, 1H), 2.15 (m, 1H), 3.00 (m, 10H), 3.49 (s, 3H), 3.64 (d, J=10.85 Hz, 1H), 3.79 (m, 1H), 4.17 (m, 1H), 4.41 (d, J=15.26 Hz, 1H), 4.51 (d, J=15.26 Hz, 1H), 4.71 (s, 2H), 6.51 (d, J=8.48 Hz, 1H), 7.11 (s, 1H), 7.17 (m, 5H), 7.70 (d, J=8.48 Hz, 2H), 7.79 (d, J=8.48 Hz, 2H), 8.15 (s, 1H).

Example 162

(2S)-N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(1-methyl-1H-benzimidazol-2-yl)methyl]-2-oxoimidazolidin-1-yl}butanamide

Method B

Example 148F (36 mg) was dissolved in N,N-dimethylformamide (1.0 mL) and treated with Example 18 (44 mg, 1 equivalent), HOBT (14.4 mg, 1 equivalent), N-methylmorpholine (57 μL, 5 equivalents), and benzotriazole-1-yl-oxy-tris-pyrrolidino-phosphonium hexafluorophosphate (PyBOP) (54.6 mg, 1 equivalent) at 25° C. for 16 hrs. The solvents were evaporated, and the residue was purified using 9% methanol/dichloromethane to give 48 mg (62%) of the title compound. $^1$H NMR (300 MHz, CDCl$_3$) δ ppm 0.87 (d, J=6.44 Hz, 3H), 0.91 (d, J=6.44 Hz, 3H), 0.94 (s, 9H), 1.90 (m, 1H), 2.75 (m, 2H), 2.90 (m, 1H), 3.09 (m, 7H), 3.30 (dd, J=8.99, 4.92 Hz, 1H), 3.81 (s, 3H), 3.85 (m, 1H), 4.05 (m, 1H), 4.67 (d, J=15.26 Hz, 1H), 4.86 (d, J=15.26 Hz, 1H), 6.20 (d, J=8.48 Hz, 1H), 7.12 (m, 5H), 7.32 (m, 3H), 7.75 (m, 5H), 8.19 (s, 1H).

The compounds listed in Table 6, wherein $X_3$, $X_7$ and $X_9$ represent respectively the points of connection to the core structure (D), were prepared by coupling the corresponding acids (Examples 32-160) with the corresponding amines (Examples 1-31) using procedure exemplified by Example 161 (method A) and Example 162 (method B).

TABLE 6

| Cpd # | Method | $R_9$ | $R_7$ | $R_3$ |
|---|---|---|---|---|
| 163 | A | 4-$X_9$-2-nitrothiophen-5-yl | $X_7$-isopropyl | $X_3$-isobutyl |
| 164 | A | 4-$X_9$-quinolin-4-yl | $X_7$-isopropyl | $X_3$-isobutyl |
| 165 | A | N-(4-$X_9$-thiazol-2-yl)acetamide | $X_7$-isopropyl | $X_3$-isobutyl |

TABLE 6-continued
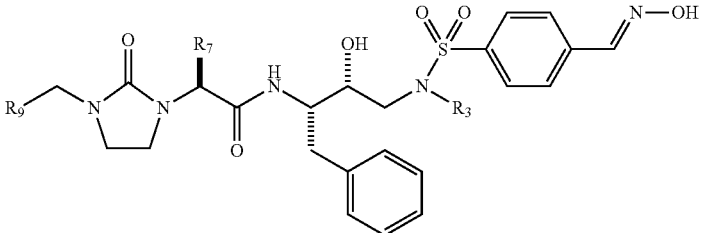
(D)
| Cpd # | Method | R9 | R7 | R3 |
|---|---|---|---|---|
| 166 | A | 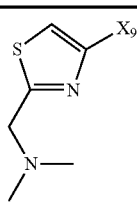 | 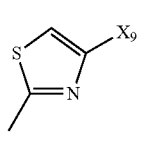 | 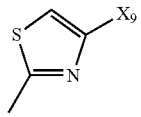 |
| 167 | A | 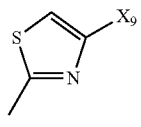 | 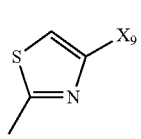 | 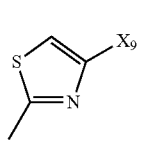 |
| 168 | A | 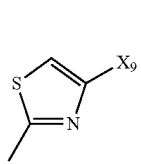 | 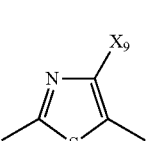 | 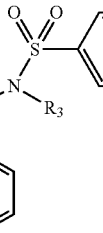 |
| 169 | A |  | 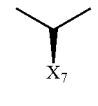 | 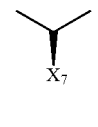 |
| 170 | A | 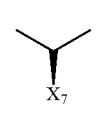 | 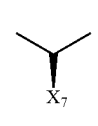 |  |
| 171 | A | 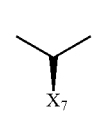 |  | 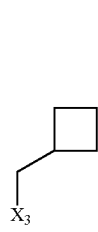 |
| 172 | A | 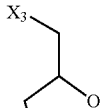 | 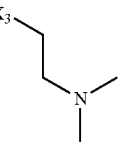 | 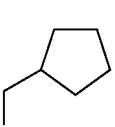 |
| 173 | A | 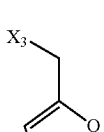 | 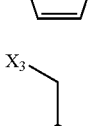 | 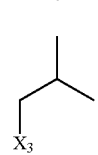 |

TABLE 6-continued
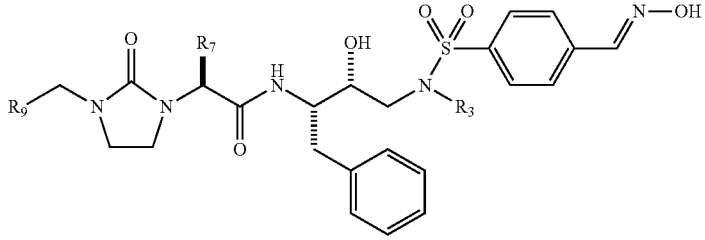
(D)
| Cpd # | Method | R9 | R7 | R3 |
|---|---|---|---|---|
| 174 | A | 3-nitrophenyl-X9 | iPr-X7 | iBu-X3 |
| 175 | A | pyridin-3-yl-X9 | iPr-X7 | iBu-X3 |
| 176 | B | 1-methylbenzimidazol-2-yl-X9 | sec-Bu-X7 | iBu-X3 |
| 177 | A | 2-methylthiazol-4-yl-X9 | iPr-X7 | 2-methoxyethyl-X3 |
| 178 | A | 2-(methoxymethyl)thiazol-4-yl-X9 | iPr-X7 | cyclobutylmethyl-X3 |
| 179 | A | pyridin-3-yl-X9 | sec-Bu-X7 | iBu-X3 |
| 180 | A | pyridin-3-yl-X9 | sec-Bu-X7 | cyclobutylmethyl-X3 |
| 181 | A | pyridin-4-yl-X9 | sec-Bu-X7 | iBu-X3 |

TABLE 6-continued

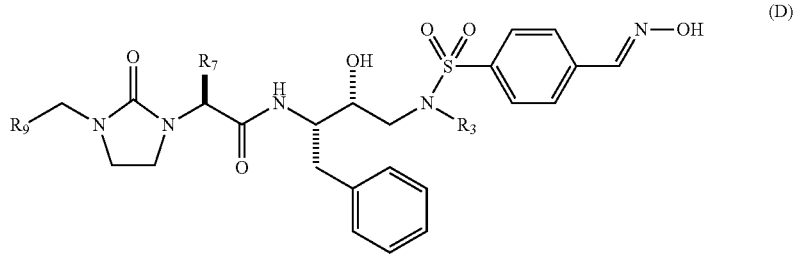

(D)

| Cpd # | Method | R9 | R7 | R3 |
|---|---|---|---|---|
| 182 | A | 4-pyridyl-X9 | sec-butyl-X7 | cyclobutylmethyl-X3 |
| 183 | A | 2-methylthiazol-4-yl-X9 | isopropyl-X7 | X3-CH2-CH(OH)-CH3 |
| 184 | A | quinolin-4-yl-X9 | sec-butyl-X7 | cyclobutylmethyl-X3 |
| 185 | A | 2-methylthiazol-4-yl-X9 | isopropyl-X7 | X3-CH2CH2-(thiophen-2-yl) |
| 186 | A | 2-methylthiazol-4-yl-X9 | sec-butyl-X7 | isobutyl-X3 |
| 187 | A | 2-methylthiazol-4-yl-X9 | sec-butyl-X7 | cyclobutylmethyl-X3 |
| 188 | A | quinolin-4-yl-X1 | sec-butyl-X7 | isobutyl-X3 |
| 189 | A | 2-acetamidothiazol-4-yl-X9 | sec-butyl-X7 | cyclobutylmethyl-X3 |

TABLE 6-continued (D)

| Cpd # | Method | R₉ | R₇ | R₃ |
|---|---|---|---|---|
| 190 | A | 2-acetamido-thiazol-4-yl (X₉) | sec-butyl (X₇) | isobutyl (X₃) |
| 191 | B | 1H-benzimidazol-5-yl (X₉) | sec-butyl (X₇) | isobutyl (X₃) |
| 192 | A | 2-methylthiazol-4-yl (X₉) | isopropyl (X₇) | 2-(hydroxymethyl)-3-methylbutyl (X₃) |
| 193 | A | 2-methylthiazol-4-yl (X₉) | isopropyl (X₇) | 2-(hydroxymethyl)-3-methylbutyl (X₃) |
| 194 | A | quinolin-4-yl (X₉) | sec-butyl (X₇) | cyclopentylmethyl (X₃) |
| 195 | A | 4-methylpyridin-3-yl (X₉) | sec-butyl (X₇) | isobutyl (X₃) |
| 196 | A | 6-methylpyridin-2-yl (X₉) | sec-butyl (X₇) | isobutyl (X₃) |
| 197 | A | pyridin-2-yl (X₉) | sec-butyl (X₇) | isobutyl (X₃) |

TABLE 6-continued
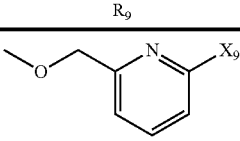
(D)
| Cpd # | Method | R9 | R7 | R3 |
|---|---|---|---|---|
| 198 | A | 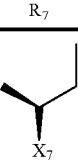 | 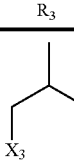 | 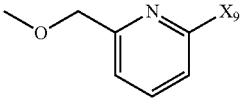 |
| 199 | A | 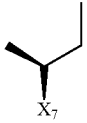 | 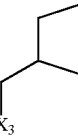 | 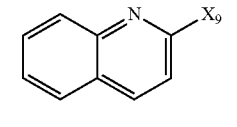 |
| 200 | B |  | 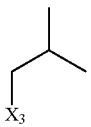 | 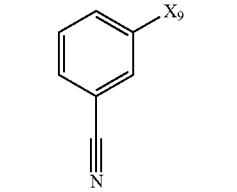 |
| 201 | A |  | 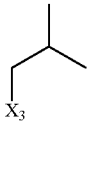 | 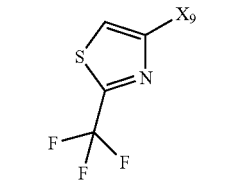 |
| 202 | A |  | 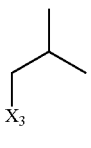 | 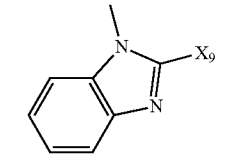 |
| 203 | B | 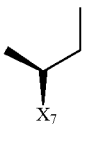 | 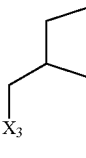 | 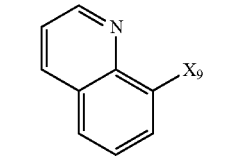 |
| 204 | B |  | 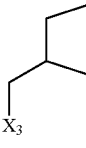 | 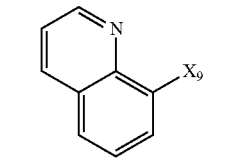 |
| 205 | B |  | 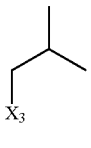 | |

TABLE 6-continued
(D)
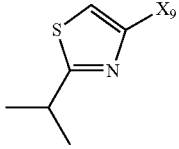
| Cpd # | Method | R$_9$ | R$_7$ | R$_3$ |
|---|---|---|---|---|
| 206 | A | 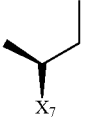 | 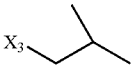 | 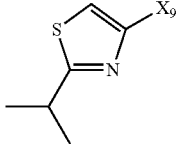 |
| 207 | A | 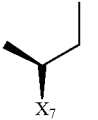 | 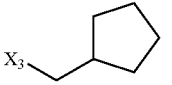 | 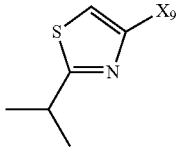 |
| 208 | A | 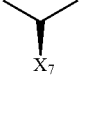 | 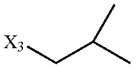 | 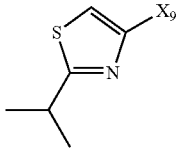 |
| 209 | A | 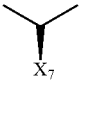 | 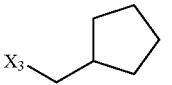 | 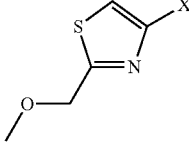 |
| 210 | A | 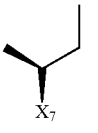 | 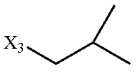 | 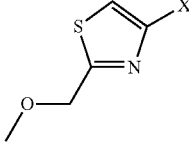 |
| 211 | A | 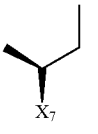 | 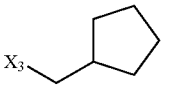 | 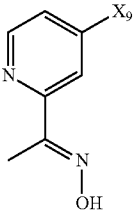 |
| 212 | A | 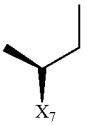 | 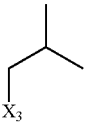 | |

TABLE 6-continued
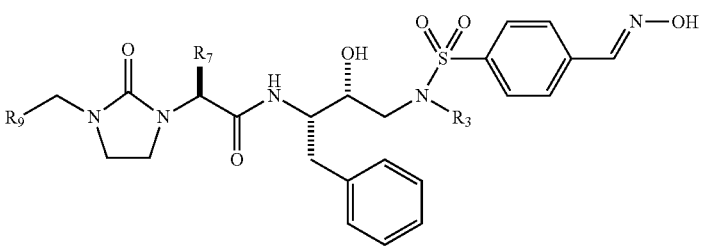
(D)
| Cpd # | Method | R₉ | R₇ | R₃ |
|---|---|---|---|---|
| 213 | B | 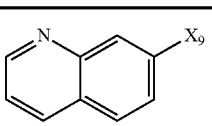 | 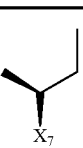 | 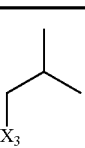 |
| 214 | B | 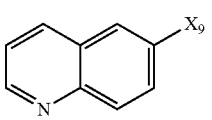 | 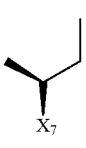 | 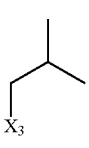 |
| 215 | A | 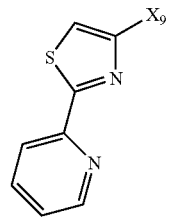 |  | 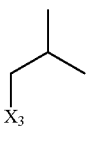 |
| 216 | B | 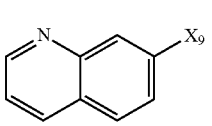 | 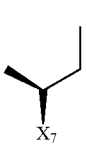 | 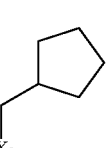 |
| 217 | B | 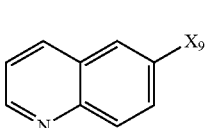 | 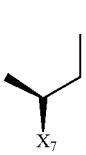 | 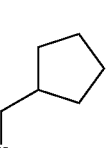 |
| 218 | A | 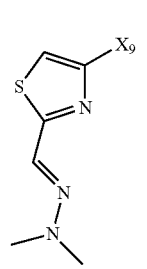 | 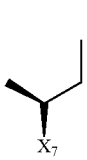 | 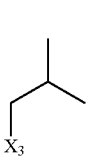 |
| 219 | A | 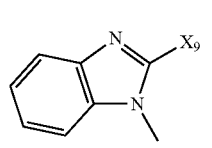 | 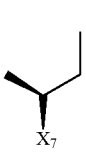 | 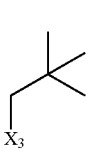 |

TABLE 6-continued
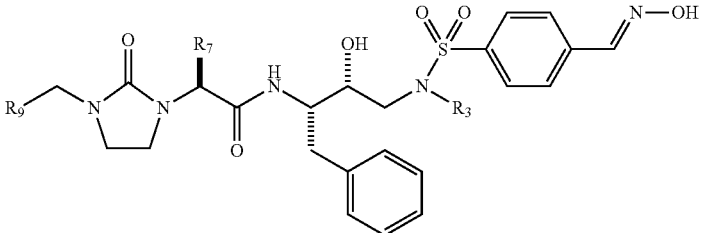
(D)
| Cpd # | Method | R9 | R7 | R3 |
|---|---|---|---|---|
| 220 | A | 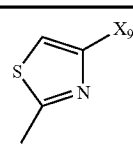 |  | 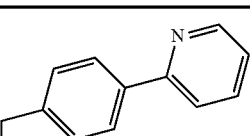 |
| 221 | A | 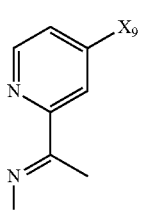 | 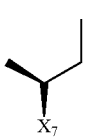 | 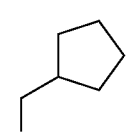 |
| 222 | A | 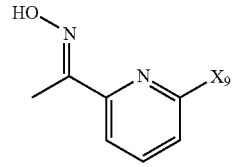 | 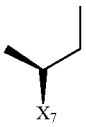 | 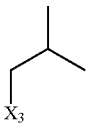 |
| 223 | A | 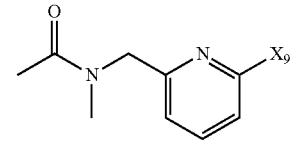 | 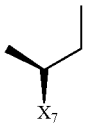 | 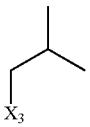 |
| 224 | A | 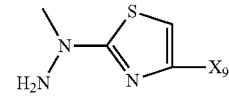 | 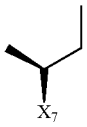 | 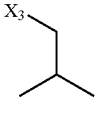 |
| 225 | A | 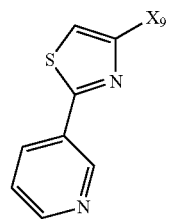 | 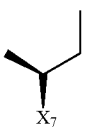 | 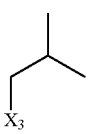 |
| 226 | A | 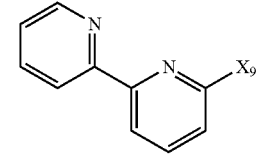 | 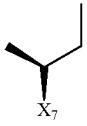 | 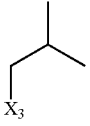 |

TABLE 6-continued
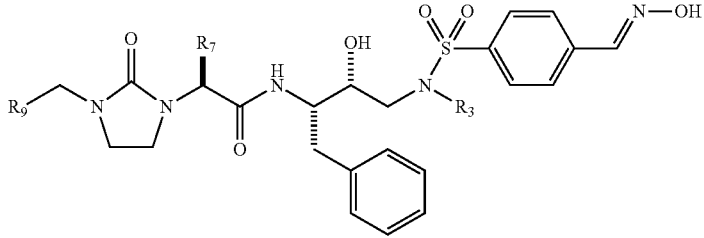
(D)
| Cpd # | Method | R9 | R7 | R3 |
|---|---|---|---|---|
| 227 | B | 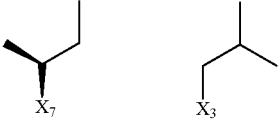 | 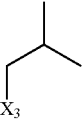 | 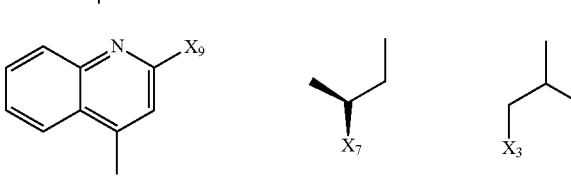 |
| 228 | B | 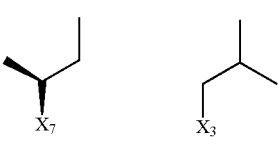 | 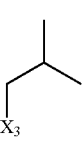 |  |
| 229 | A | 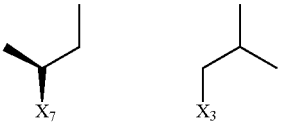 | 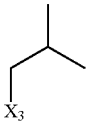 | 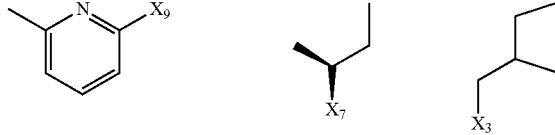 |
| 230 | A | 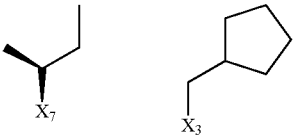 | 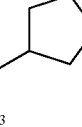 | 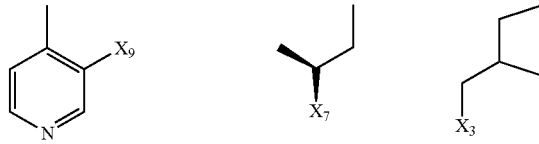 |
| 231 | A | 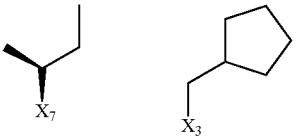 | 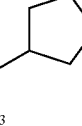 | 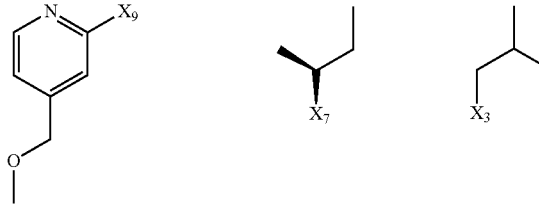 |
| 232 | A | 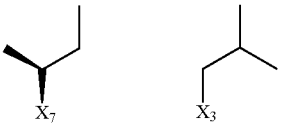 | 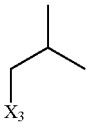 | 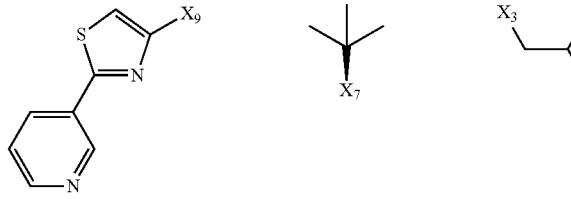 |
| 233 | A | 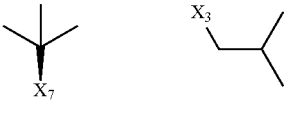 | 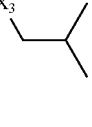 | |

TABLE 6-continued
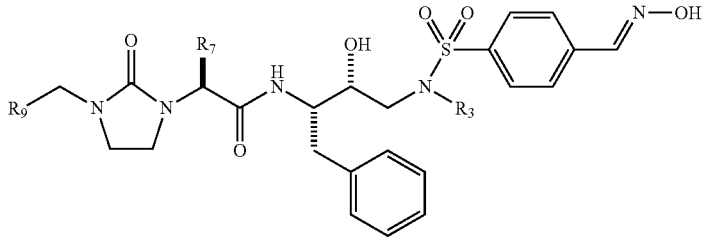
(D)
| Cpd # | Method | R₉ | R₇ | R₃ |
|---|---|---|---|---|
| 234 | B | 4-quinolinyl (X₉) | t-Bu (X₇) | isobutyl (X₃) |
| 235 | A | 3-pyridyl (X₉) | sec-butyl (X₇) | cyclopentylmethyl (X₃) |
| 236 | A | 3-pyridyl (X₉) | t-Bu (X₇) | isobutyl (X₃) |
| 237 | A | 2-(N-methyl-N-acetyl-aminomethyl)-4-thiazolyl (X₉) | sec-butyl (X₇) | isobutyl (X₃) |
| 238 | B | 2-methyl-4-quinolinyl (X₉) | t-Bu (X₇) | isobutyl (X₃) |
| 239 | B | 6-quinolinyl (X₉) | t-Bu (X₇) | isobutyl (X₃) |
| 240 | B | 6-isoquinolinyl (X₉) | t-Bu (X₇) | isobutyl (X₃) |

TABLE 6-continued (D)

| Cpd # | Method | R₉ | R₇ | R₃ |
|---|---|---|---|---|
| 241 | A | 2-(pyridin-2-yl)thiazol-4-yl (X₉) | tert-butyl (X₇) | isobutyl (X₃) |
| 242 | A | (4-X₉-thiazol-2-yl)methyl acetate | sec-butyl (X₇) | isobutyl (X₃) |
| 243 | A | 6-(methoxymethyl)pyridin-2-yl (X₉) | tert-butyl (X₇) | isobutyl (X₃) |
| 244 | A | 2-(methoxymethyl)thiazol-4-yl (X₉) | tert-butyl (X₇) | isobutyl (X₃) |
| 245 | A | 3-(pyrimidin-5-yl)phenyl (X₉) | sec-butyl (X₇) | isobutyl (X₃) |
| 246 | A | 2-(1-acetamidoethyl)thiazol-4-yl (X₉) | tert-butyl (X₇) | isobutyl (X₃) |

TABLE 6-continued

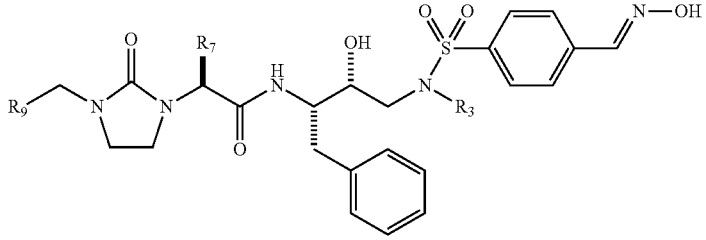

(D)

| Cpd # | Method | R₉ | R₇ | R₃ |
|---|---|---|---|---|
| 247 | A | 2-(6-methylpyridin-3-yl)thiazol-4-yl-X₉ | t-Bu-X₇ | isobutyl-X₃ |
| 248 | A | 2-(pyridin-4-yl)thiazol-4-yl-X₉ | t-Bu-X₇ | isobutyl-X₃ |
| 249 | A | 2-(thiophen-2-yl)thiazol-4-yl-X₉ | t-Bu-X₇ | isobutyl-X₃ |
| 250 | A | 2-methylpyridin-3-yl-X₉ | sec-Bu-X₇ | isobutyl-X₃ |
| 251 | A | 6-methylpyridin-3-yl-X₉ | sec-Bu-X₇ | isobutyl-X₃ |
| 252 | A | 6-((ethoxycarbonyl(methyl)amino)methyl)pyridin-2-yl-X₉ | sec-Bu-X₇ | isobutyl-X₃ |
| 253 | A | 6-(hydroxymethyl)pyridin-2-yl-X₉ | t-Bu-X₇ | isobutyl-X₃ |

TABLE 6-continued
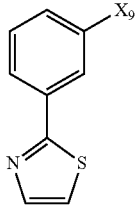
(D)
| Cpd # | Method | R9 | R7 | R3 |
|---|---|---|---|---|
| 254 | A | 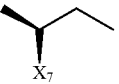 | 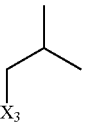 | 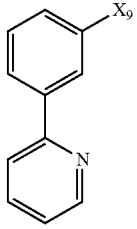 |
| 255 | A | 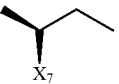 | 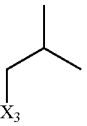 | 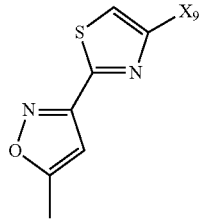 |
| 256 | A |  | 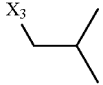 | 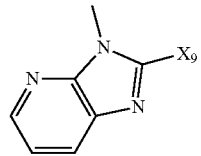 |
| 257 | B | 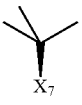 | 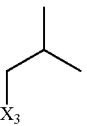 | 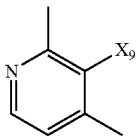 |
| 258 | A | 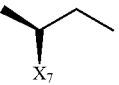 | 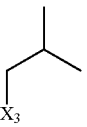 | 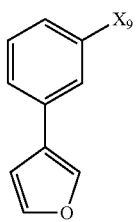 |
| 259 | A | 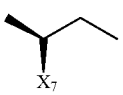 | 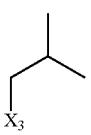 | |

TABLE 6-continued

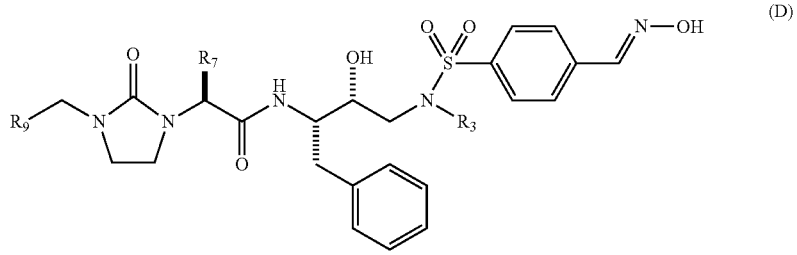
(D)

| Cpd # | Method | R₉ | R₇ | R₃ |
|---|---|---|---|---|
| 260 | A | 3-(pyrimidin-4-yl)phenyl-X₉ | sec-butyl-X₇ | isobutyl-X₃ |
| 261 | A | 6-methoxypyridin-3-yl-X₉ | sec-butyl-X₇ | isobutyl-X₃ |
| 262 | A | 2-(pyrazin-2-yl)thiazol-4-yl-X₉ | tert-butyl-X₇ | isobutyl-X₃ |
| 263 | A | 2-methylpyridin-3-yl-X₉ | tert-butyl-X₇ | isobutyl-X₃ |
| 264 | A | 2-methylpyridin-3-yl-X₉ | sec-butyl-X₇ | cyclopentylmethyl-X₃ |
| 265 | A | 6-methylpyridin-3-yl-X₉ | tert-butyl-X₇ | isobutyl-X₃ |
| 266 | B | pyridazin-4-yl-X₉ | tert-butyl-X₇ | isobutyl-X₃ |
| 267 | B | pyridazin-5-yl-X₉ | sec-butyl-X₇ | isobutyl-X₃ |

TABLE 6-continued

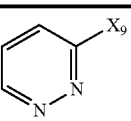

| Cpd # | Method | R9 | R7 | R3 |
|---|---|---|---|---|
| 268 | B | 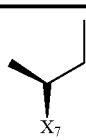 | 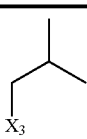 | 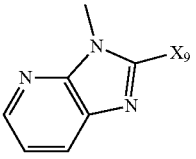 |
| 269 | B | 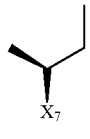 | 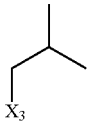 | |

Example 270

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxoimidazolidin-1-yl}butanamide Example 756 (13 mg, 0.019 mmol) was dissolved in ethanol (0.5 mL) and treated with hydroxylamine hydrochloride (3.9 mg, 3 equivalents) for 3 hrs at 25° C. The solvents were evaporated, and the residue was purified using 8% methanol/dichloromethane to give 5 mg (38%) of the title compound.

Example 271

(2,2-diethoxyethylidyne)-λ$^4$-sulfanylamine 1,1-Diethoxyacetamide (10 g, 0.068 mol) was dissolved in tetrahydrofuran (250 mL) and treated with P$_4$S$_{10}$ (3 g, 0.1 eq) at 25° C. for 16 h. The solvents were evaporated and diluted with ethyl acetate and water. The organic layer was washed with saturated sodium bicarbonate, brine, dried over magnesium sulfate, and the solvents were evaporated to give 7.13 g (64%) of the crude product used directly for the next step.

Example 272 ethyl 2-(diethoxymethyl)-1,3-thiazole-4-carboxylate

Example 271 (7.13 g, 0.044 mol) was dissolved in ethanol (90 mL) and treated with ethyl bromopyruvate (5.5 mL, 1 equivalent) and 3 A molecular sieves (20 g) and the mixture was heated at 80° C. for 30 min. The mixture was filtered and the solvents were evaporated. The crude residue was partitioned between ethyl acetate and saturated sodium bicarbonate. The organic layer was washed with brine and dried over magnesium sulfate. The solvents were evaporated and the crude residue was purified using dichloromethane with increasing amounts of ethyl acetate up to 10% to give 9.5 g (84%) of the thiazole.

Example 273

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-({2-[(methylamino)methyl]-1,3-thiazol-4-yl}methyl)-2-oxoimidazolidin-1-yl]butanamide

Example 273A

[2-(diethoxymethyl)-1,3-thiazol-4-yl]methanol

Example 273B 2-(diethoxymethyl)-1,3-thiazole-4-carbaldehyde

Example 272 (7.8 g, 30 mmol) was dissolved in toluene (60 mL) and treated with diisobutyl aluminum hydride (42 mL, 1.4 equivalents, 1M in toluene) at −78° C. for 45 min. The mixture was quenched with ethyl acetate (50 mL) and warmed to 25° C. while adding sodium potassium tartrate (10 mL, 10%) for 2 h. the mixture was extracted with ethyl acetate, the organic layer was washed with brine, dried over magnesium sulfate, and the solvents were evaporated. Two products were purified using ethyl acetate:hexane (1:1) to give 0.8 g (10%) of Example 273A and the remaining fractions consisted of crude Example 273B.

Example 273C tert-butyl (2S)-2-(3-{[2-(diethoxymethyl)-1,3-thiazol-4-yl]methyl}-2-oxo-1-imidazolidinyl)-3-methylbutanoate Example 273B (0.144 g, 0.57 mmol) was dissolved in benzene:ethanol (3 mL, 1:1) treated with the valine analog of Example 32C (0.14 g, 1 equivalent) and the mixture was heated to 70° C. for 1 h. The mixture was cooled to 25° C. and treated with sodium borohydride (75 mg, 3 equivalents) for 2 h. The mixture was partitioned between ethyl acetate and water, the organic layer was washed with saturated sodium bicarbonate, dried over magnesium sulfate and the solvents were evaporated. The crude residue was dissolved in dichloroethane (25 mL) and treated with bis-(p-nitrophenylcarbonate) (0.245 g, 1.2 equivalents) and heated to 60° C. for 16 h. The solvents were evaporated and the crude residue was purified using dichloromethane (100%) to hexane (100%) to hexane:ethyl acetate (1:1) to give 0.115 g (39% for 4 steps) of the title compound.

Example 273D tert-butyl (2S)-2-{3-[(2-formyl-1,3-thiazol-4-yl)methyl]-2-oxo-1-imidazolidinyl}-3-methylbutanoate Example 273C (0.1 g, 0.24 mmol) was dissolved in acetone (10 mL) and treated with 1M HCl (1 mL) at 70° C. for 45 min. The solvents were evaporated and the crude residue was partitioned between ethyl acetate and saturated sodium bicarbonate, dried over magnesium sulfate, filtered, and the solvents were evaporated to give 89 mg (99%) of the title compound.

Example 273E tert-butyl (2S)-3-methyl-2-[3-({2-[(methylamino)methyl]-1,3-thiazol-4-yl}methyl)-2-oxo-1-imidazolidinyl]butanoate Example 273D (0.2 g, 0.54 mmol) was dissolved in toluene (1.1 mL) and ethanol (1.1 mL) and treated with methylamine solution in tetrahydrofuran (0.54 mL, 2M, 2 equivalents) and stirred at 70° C. for 3 h. The mixture was cooled to 25° C. and combined with sodium borohydride (20 mg, 3 equivalents) and stirred for 18 h. The solvents were evaporated, and the residue was partitioned between ethyl acetate and saturated sodium bicarbonate. The organic layer separated, washed with brine and dried over sodium sulfate. The solvents were evaporated and the crude residue was purified using chloroform-95% chloroform/5% methanol to give 0.118 g (56%) of the title compound.

Example 273F tert-butyl (2S)-2-{3-[(2-{[[(9H-fluoren-9-ylmethoxy)carbonyl](methyl)amino]methyl}-1,3-thiazol-4-yl)methyl]-2-oxo-1-imidazolidinyl}-3-methylbutanoate Example 273E (0.115 g, 0.3 mmol) was dissolved in dichloromethane (3 mL), cooled to 0° C., combined with triethylamine (90 μL, 2.2 equivalents) and fluorenylmethyl chloroformate (86 mg, 1.1 equivalents). The mixture was stirred at 0° C. for 1 h, then at 25° C. for 18 h. The solvents were evaporated, and the crude residue was purified using ethyl acetate:hexanes (1:1) to give 0.138 g (76%) of the title compound.

Example 273G 9H-fluoren-9-ylmethyl{4-[(3-{(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylpropyl}-2-oxo-1-imidazolidinyl)methyl]-1,3-thiazol-2-yl}methyl(methyl)carbamate Example 273F (10 mg, 0.017 mmol) was dissolved in trifluoroacetic acid:dichloromethane (1:1, 0.3 mL) at 25° C. for 90 min. The solvents were evaporated, and the crude residue was dissolved in dimethylformamide (0.2 mL) and treated with N-methyl morpholine (3.4 mg, 1.5 equivalents), HOBT (3.4 mg, 1.5 equivalents), EDAC (4.8 mg, 1.5 equivalents), and Example 18 (10 mg, 1.5 equivalents). The mixture was stirred at 25° C. for 68 h. The solvents were evaporated and the crude residue was purified using C-18 column to give 8 mg (51%) of the title compound.

Example 273H (2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-({2-[(methylamino)methyl]-1,3-thiazol-4-yl}methyl)-2-oxo-1-imidazolidinyl]butanamide Example 273G (8 mg, 0.008 mmol) was dissolved in acetonitrile (0.1 mL) and treated with diethylamine (2 μL, 3 equivalents) at 25° C. for 1 h. The solvents were evaporated and the residue was purified using C-18 to give 6.5 mg (92%) of the title compound.

Example 274

(2S)—N-{(1S,2R)-1-benzyl-2-hydroxy-3-[({4-[(E)-(hydroxyimino)methyl]phenyl}sulfonyl)(pyrrolidin-2-ylmethyl)amino]propyl}-3-methyl-2-{3-[(2-methyl-1,3-thiazol-4-yl)methyl]-2-oxoimidazolidin-1-yl}butanamide

Example 274A (2R,3S)-3-amino-1-azido-4-phenylbutan-2-ol

A solution of (2R,3S)-3-N-tert-butoxycarbonylamino-1,2-epoxy-4-phenylbutane (1.17 g) in ethanol:water (45 mL, 4:1) was treated with lithium azide (1.09 g, 5 equivalents) and NH$_4$Cl (1.19 g, 5 equivalents), stirred at 75° C. for 2 hours and concentrated. The residue was partitioned between water and ethyl acetate. The organic layer was separated, dried over MgSO$_4$, filtered and concentrated. A solution of the residue in dichloromethane/trifluoroacetic acid (40 mL, 1:1) was stirred at 25° C. for 1 hour and concentrated to give the title compound.

Example 274B (2S)—N-[(1S,2R)-3-azido-1-benzyl-2-hydroxypropyl]-3-methyl-2-{3-[(2-methyl-1,3-thiazol-4-yl)methyl]-2-oxoimidazolidin-1-yl}butanamide A solution of the product of Example 274A (0.825 g) in N,N-dimethylformamide (30 mL) was treated with EDAC (0.744 g, 1.2 equivalents), HOBT (0.65 g, 1.2 equivalents), N methyl morpholine (0.88 mL, 2 equivalents) and Example 143D (1.19 g, 1 equivalent), stirred at 25° C. for 1 hour and concentrated. The residue was purified by HPLC reverse phase chromatography using water (0.1% trifluoroacetic acid):acetonitrile (95:5) to acetonitrile (100%) to give 1.3 g (67%) of title compound.

Example 274C (2S)—N-[(1S,2R)-3-amino-1-benzyl-2-hydroxypropyl]-3-methyl-2-{3-[(2-methyl-1,3-thiazol-4-yl)methyl]-2-oxoimidazolidin-1-yl}butanamide A solution of the product of Example 274B (1.3 g) in tetrahydrofuran:water (25 mL, 4:1) was treated with triphenylphosphine (1.4 g, 2 equivalents), stirred at 70° C. for 2 hours and concentrated. The residue was partitioned between 1N HCl and dichloromethane. The aqueous layer was separated and made basic using 1N NaOH, extracted with dichloromethane and the organic extract was concentrated. The residue was purified by HPLC reverse phase chromatography using water (0.1% trifluoroacetic acid):acetonitrile (95:5) to acetonitrile (100%) to give 0.76 g (62%) of the title compound.

Example 274D tert-butyl 2-[({(2R,3S)-2-hydroxy-3-[((2S)-3-methyl-2-{3-[(2-methyl-1,3-thiazol-4-yl)methyl]-2-oxoimidazolidin-1-yl}butanoyl)amino]-4-phenylbutyl}amino)methyl]pyrrolidine-1-carboxylate A solution of the product of Example 274C (59 mg) in ethanol:benzene (1 mL, 1:1) was treated with N-t-butoxylcarbonyl-(L)-prolinal (26 mg, 1 equivalent), stirred at 70° C. for 1 hour, cooled at 25° C., treated with NaBH$_4$ (14 mg, 3 equivalents) at 25° C. and stirred for 16 hours. The mixture was quenched with saturated NH$_4$Cl and partitioned between water and ethyl acetate. The organic layer was separated, dried over MgSO$_4$, filtered and concentrated to give 85 mg of the crude title compound.

Example 274E tert-butyl 2-[(({4-[(hydroxyimino)methyl]phenyl}sulfonyl){(2R,3S)-2-hydroxy-3-[((2S)-3-methyl-2-{3-[(2-methyl-1,3-thiazol-4-yl)methyl]-2-oxoimidazolidin-1-yl}butanoyl)amino]-4-phenylbutyl}amino)methyl]pyrrolidine-1-carboxylate A solution of the product of Example 274D (85 mg) in dichloromethane (0.6 mL) was treated with triethylamine (17 μL, 2 equivalents) and 4-formylbenzenesulfonyl chloride (12 mg, 1 equivalent), stirred at 25° C. for 2 hours and concentrated. A solution of the residue in methanol (1 mL) was treated with hydroxylamine hydrochloride, stirred at 25° C. for 16 hours and concentrated. The residue was purified by HPLC reverse phase chromatography using water (0.1% trifluoroacetic acid):acetonitrile (95:5) to acetonitrile (100%) to give 16 mg (20% over 3 steps) of the title compound.

Example 274F (2S)—N-{(1S,2R)-1-benzyl-2-hydroxy-3-[({4-[(E)-(hydroxyimino)methyl]phenyl}sulfonyl)(pyrrolidin-2-ylmethyl)amino]propyl}-3-methyl-2-{3-[(2-methyl-1,3-thiazol-4-yl)methyl]-2-oxoimidazolidin-1-yl}butanamide A solution of the product of Example 274E (12 mg) in dichloromethane (0.5 mL) and trifluoroacetic acid (0.5 mL) was stirred at 25° C. for 1 hour and concentrated. The residue was purified by HPLC reverse phase chromatography using water (0.1% trifluoroacetic acid):acetonitrile (95:5) to acetonitrile (100%) to give 10 mg (95%) of the title compound.

Example 275

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxo-2,3-dihydro-1H-imidazol-1-yl}butanamide Example 160C (62 mg, 0.22 mmol) was combined with HOBT (43 mg, 1.5 equivalents) and EDAC (60 mg, 1.5 equivalents) in N,N-dimethylformamide (3 mL) and stirred for 1 hour at 25° C. To this mixture was added N-methyl morpholine (43 μL, 3 equivalents) Example 18 (88 mg, 1.1 equivalents). The mixture was stirred for 16 hours, evaporated, and chromatographed, eluting with 2.5% methanol/dichloromethane to give 60 mg (41%) of title compound.

Example 276

(2S)-2-[3-(3-aminobenzyl)-2-oxoimidazolidin-1-yl]-N-{(1S,2R)-1-benzyl-2-hydroxy-3-[({4-[(E)-(hydroxyimino)methyl]phenyl}sulfonyl)(isobutyl)amino]propyl}-3-methylbutanamide Example 174 (68 mg, 0.09 mmol) was dissolved in ethyl acetate (1 mL) was treated with 10% Pd/C (14 mg) for 2 h. After work-up, the crude residue was purified using 3% methanol/chloroform to give 53 mg (82%) of the title compound.

Example 277

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxido-3-pyridinyl)methyl]-2-oxo-1-imidazolidinyl}pentanamide Example 179 (14.8 mg) was dissolved in tetrahydrofuran (0.25 mL) and treated with m-chloroperbenzoic acid (6 mg, 1.5 equivalents) at 25° C. for 3 h. The solvents were evaporated, and the residue was purified using 7% methanol/dichloromethane to give 12.5 mg (83%) of the title compound.

Example 278

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxidopyridin-4-yl)methyl]-2-oxoimidazolidin-1-yl}pentanamide Example 181 (10.4 mg) was dissolved in tetrahydrofuran (0.25 mL) and treated with m-chloroperbenzoic acid (6 mg, 1.5 equivalents) at 25° C. for 3 h. The solvents were evaporated, and the residue was purified using 7% methanol/dichloromethane to give 10.5 mg (98%) of the title compound.

Example 279

(2S,3S)-2-(3-{[2-(aminomethyl)-1,3-thiazol-4-yl]
methyl}-2-oxoimidazolidin-1-yl)-N-{(1S,2R)-1-
benzyl-2-hydroxy-3-[({4-[(E)-(hydroxyimino)me-
thyl]phenyl}sulfonyl)(isobutyl)amino]propyl}-3-
methylpentanamide

Example 279A tert-butyl(2S,3S)-2-(3-{[2-(diethoxymethyl)-1,3-
thiazol-4-yl]methyl}-2-oxo-1-imidazolidinyl)-3-
methylpentanoate Example 273B (0.86 g, 4 mmol) was dissolved in ethanol: benzene (12 mL, 1:1) and treated with Example 32C (0.55 g, 2.4 mmol) at 70° C. for 1 h. The mixture is cooled to 25° C. and treated with sodium borohydride (0.275 g, 3 equivalents) for 2 h. The mixture is quenched with methanol and the solvents were evaporated. The crude residue was dissolved in dichloroethane (100 mL) and treated with bis-p-nitrophenyl carbonate (0.9 g, 1.2 eq) at 70° C. for 16 h. The solvents were evaporated, and the crude residue was partitioned between ethyl acetate and saturated sodium bicarbonate, the organic layer was separated, washed with brine, dried over magnesium sulfate and the solvents were evaporated. The crude residue was purified using dichloromethane:hexanes (1:1)-hexanes-hexanes/ethyl acetate (1:1) to give 0.72 g (66%) of the title compound.

Example 279B tert-butyl (2S,3S)-2-{3-[(2-formyl-1,3-thiazol-4-yl)
methyl]-2-oxo-1-imidazolidinyl}-3-methylpen-
tanoate Example 279A (0.72 g, 1.6 mmol) was dissolved in acetone (35 mL) and treated with 1N HCl (3.5 mL) at 70° C. for 45 min. The solvents were evaporated, and the residue was partitioned between ethyl acetate and saturated sodium bicarbonate. The organic layer was separated and washed with brine, dried over magnesium sulfate, and the solvents were evaporated to give 0.584 g (97% crude) of the title compound.

Example 279C tert-butyl (2S,3S)-2-(3-{[2-(hydroxymethyl)-1,3-
thiazol-4-yl]methyl}-2-oxo-1-imidazolidinyl)-3-
methylpentanoate Example 279B (0.2 g, 0.54 mmol) was dissolved in ethanol (5 mL) and treated with sodium borohydride (30 mg, 1.5 equivalents) and stirred for 2 h. The solvents were evaporated, and the residue was partitioned between ethyl acetate and water. The organic layer separated, washed with brine and dried over magnesium sulfate. The solvents were evaporated and the crude residue was used directly for the next reaction.

Example 279D tert-butyl (2S,3S)-3-methyl-2-{3-[(2-{[(methylsulfo-
nyl)oxy]methyl}-1,3-thiazol-4-yl)methyl]-2-oxo-1-
imidazolidinyl}pentanoate Example 279C (0.2 g, 0.3 mmol) was dissolved in dichloromethane (5 mL), cooled to 0° C., combined with triethylamine (0.22 mL, 3 equivalents) and methanesulfonyl chloride (0.06 mL, 1.5 equivalents). The mixture was stirred at 0° C. for 90 min. The solvents were evaporated, and the crude residue was diluted with ethyl acetate and washed with 10% citric acid, saturated sodium bicarbonate, brine, and dried over magnesium sulfate to give 0.25 g of crude Example 279D residue which was used directly for the next reaction.

Example 279E tert-butyl (2S,3S)-2-(3-{[2-(azidomethyl)-1,3-thia-
zol-4-yl]methyl}-2-oxo-1-imidazolidinyl)-3-methyl-
pentanoate Example 279D (0.25 g) was dissolved in dimethylformamide (4 mL) treated with lithium azide (0.255 g, 10 equivalents) and stirred at 50° C. for 1 h. The solvents were evaporated and the residue was diluted with ethylacetate and washed with water, brine, and dried over magnesium sulfate. The solvents were evaporated to give 0.192 g crude azide.

Example 279F (2S,3S)-2-(3-{[2-({[(9H-fluoren-9-ylmethoxy)carbo-
nyl]amino}methyl)-1,3-thiazol-4-yl]methyl}-2-oxo-
1-imidazolidinyl)-3-methylpentanoic acid Example 279E (0.19 g, 0.47 mmol) was dissolved in tetrahydrofuran (4 mL) and water (1 mL) and treated with triphenylphosphine (0.247 g, 2 equivalents) and stirred at 50° C. for 1 h. The solvents were evaporated and the crude residue (0.127 g) was dissolved in acetonitrile (2.5 mL) and water (0.7 mL) and treated with sodium bicarbonate (67 mg, 2.4 equivalents) and fluorenylmethyl chloroformate (103 mg, 1.2 equivalents) and stirred at 25° C. for 90 min. The solvents were evaporated and the crude residue was diluted with ethyl acetate and washed with water, brine, dried over magnesium sulfate, and filtered. The solvents were evaporated and the crude residue was purified using chloroform:ethyl acetate 4:1-1:1 to give 0.2 g (70%) of the ester. This ester was dissolved in dichloromethane:trifluoroacetic acid (5 mL, 3:2) and stirred at 25° C. for 2 h. The solvents were evaporated to give 0.12 g of the title compound.

Example 279G (2S,3S)—N-{(1S,2R)-1-benzyl-2-hydroxy-3-[({4-
[(E)-(hydroxyimino)methyl]phenyl}sulfonyl)(isobu-
tyl)amino]propyl}-2-{3-[(2-{[(9H-fluoren-9-ylm-
ethyl)amino]methyl}-1,3-thiazol-4-yl)methyl]-2-
oxoimidazolidin-1-yl}-3-methylpentanamide Example 279F (15 mg, 0.027 mmol) was dissolved in N,N-dimethylformamide (0.3 mL) and treated with EDAC (8 mg, 1.5 equivalents), HOBT (6 mg, 1.5 equivalents), N-methyl morpholine (7 µL, 2.5 equivalents), followed by Example 18 (17 mg, 1.5 equivalents) at 25° C. for 16 hrs. The solvents were evaporated, and the residue was purified by HPLC reverse phase chromatography using water (0.1% trifluoroacetic acid):acetonitrile (75:25) to acetonitrile (100%) to give 12.3 mg (46%) of the title compound.

Example 279H (2S,3S)-2-(3-{[2-(aminomethyl)-1,3-thiazol-4-yl]
methyl}-2-oxo-1-imidazolidinyl)-N-{(1S,2R)-1-
benzyl-2-hydroxy-3-[({4-[(E)-(hydroxyimino)me-
thyl]phenyl}sulfonyl)(isobutyl)amino]propyl}-3-
methylpentanamide Example 279G (12 mg) was dissolved in acetonitrile (0.2 mL) and treated with diethylamine (3 µL, 3 equivalents) at 25° C. for 2 h. The solvents were evaporated, and the residue was purified by HPLC reverse phase chromatography using water (0.1% trifluoroacetic acid):acetonitrile (75:25) to acetonitrile (100%) to give 9.8 mg (92%) of the title compound.

Example 280

(2S,3S)-2-(3-{[2-(aminomethyl)-1,3-thiazol-4-yl]methyl}-2-oxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide

Example 280A 9H-fluoren-9-ylmethyl{4-[(3-{(1S,2S)-1-[({(1S,2R)-1-benzyl-3-[(cyclobutylmethyl)({4-[(E)-(hydroxyimino)methyl]phenyl}sulfonyl)amino]-2-hydroxypropyl}amino)carbonyl]-2-methylbutyl}-2-oxo-1-imidazolidinyl)methyl]-1,3-thiazol-2-yl}methylcarbamate In a similar manner to Example 279G, Example 280A was prepared using Example 279F (15 mg, 0.027 mmol), N-methyl morpholine (7 μL, 2.5 equivalents), HOBT (6 mg, 1.5 equivalents), EDAC (8 mg, 1.5 equivalents) and Example 19 (18 mg, 1.5 equivalents) in dimethylfomamide (0.3 mL) to give 11.8 mg (46%) after purification on C-18 using 75% water/0.1% trifluoroacetic acid/25% acetonitrile-100% acetonitrile.

Example 280B 9H-fluoren-9-ylmethyl{4-[(3-{(1S,2S)-1-[({(1S,2R)-1-benzyl-3-[(cyclobutylmethyl)({4-[(E)-(hydroxyimino)methyl]phenyl}sulfonyl)amino]-2-hydroxypropyl}amino)carbonyl]-2-methylbutyl}-2-oxo-1-imidazolidinyl)methyl]-1,3-thiazol-2-yl}methylcarbamate In a similar manner to Example 279H, Example 280A (11 mg, 0.013 mmol) was treated with diethylamine (3 μL). The crude product was purified by C-18 using 95% water/0.1% trifluoroacetic acid/5% acetonitrile-100% acetonitrile to give 7.8 mg (76%) of the title compound.

Example 281

(2S,3S)-2-(3-{[2-(aminomethyl)-1,3-thiazol-4-yl]methyl}-2-oxo-1-imidazolidinyl)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide In a similar manner to Example 280, Example 281 was prepared using Example 279F (75 mg, 0.14 mmol), N-methyl morpholine (38 μL, 2.5 equivalents), HOBT (28 mg, 1.5 equivalents), EDAC (39 mg, 1.5 equivalents) and Example 27 (91 mg, 1.5 equivalents) in dimethylfomamide (1.2 mL) to give 79.5 mg (60%) after purification on C-18 using 75% water/0.1% trifluoroacetic acid/25% acetonitrile-100% acetonitrile. This product was treated with diethylamine (20 μL, 3 equivalents) as in Example 279H. The crude product was purified by C-18 using 95% water/0.1% trifluoroacetic acid/5% acetonitrile-100% acetonitrile to give 49 mg (70%) of the title compound.

Example 282

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]pyridin-4-yl}methyl)-2-oxo-2,3-dihydro-1H-imidazol-1-yl]-3-methylpentanamide Example 405 (30 mg, 0.039 mmol) was dissolved in ethanol (1 mL) and treated with NaBH$_4$ (7 mg, 5 equivalents) at 25° C. for 16 hrs. The mixture was partitioned between water and ethyl acetate. The organic layer was separated, dried over NaSO$_4$, filtered and the solvents were evaporated. The residue was dissolved in dichloromethane (1 mL) and trifluoroacetic acid (1 mL) at 25° C. for 1 h and the mixture was partitioned between water and ethyl acetate, the organic layer was washed with saturated NaHCO$_3$, water, brine, and dried over NaSO$_4$, filtered and the solvents were evaporated. The residue was purified using 7% methanol/dichloromethane to give 25.5 mg (88%) of the title compound.

Example 283

(2R,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide

Example 283A tert-butyl (2S,3S)-2-[3-({2-[(isopropylamino)methyl]-1,3-thiazol-4-yl}methyl)-2-oxo-1-imidazolidinyl]-3-methylpentanoate A solution of Example 273D (65 mg) in toluene:ethanol (0.7 mL, 1:1) was treated with isopropylamine (0.14 mL, 10 equivalents), stirred at 70° C. in a capped vial for 2 hrs. The mixture was cooled to 25° C. and NaBH$_4$ (19 mg, 3 equivalents) was added and the mixture was stirred at 25° C. for 3 days. The solvents were evaporated, and the residue was partitioned between ethyl acetate and saturated NaHCO$_3$, the organic layer was separated and washed with brine, dried over MgSO$_4$, filtered and evaporated to give 59 mg of the title compound.

Example 283B (2S,3S)-2-{3-[(2-{[[(9H-fluoren-9-ylmethoxy)carbonyl](isopropyl)amino]methyl}-1,3-thiazol-4-yl)methyl]-2-oxo-1-imidazolidinyl}-3-methylpentanoic acid A solution of the product of Example 283A (59 mg) in acetonitrile (0.9 mL) and water (0.3 mL) was treated with NaHCO$_3$ (34 mg, 2.4 equivalents) followed by 9-fluorenylmethyl chloroformate (53 mg, 1.2 equivalents) at 25° C. for 1.5 h. The solvents were evaporated and the residue was purified using ethyl acetate:chloroform (1:4) to give 47 mg (40%) of FMOC-amine which was dissolved in dichloromethane (0.5 mL) and trifluoroacetic acid (0.5 mL) and stirred at 25° C. for 1 h. The solvents were evaporated, and the acid was used directly for the next step.

Example 283C 9H-fluoren-9-ylmethyl{4-[(3-{(1S,2S)-1-[({(1S,2R)-1-benzyl-3-[(cyclopentylmethyl)({4-[(E)-(hydroxyimino)methyl]phenyl}sulfonyl)amino]-2-hydroxypropyl}amino)carbonyl]-2-methylbutyl}-2-oxo-1-imidazolidinyl)methyl]-1,3-thiazol-2-yl}methyl(isopropyl)carbamate A solution of crude Example 283B dissolved in N,N-dimethylformamide (0.6 mL) was treated with EDAC (16 mg, 1.2 equivalents), HOBT (11 mg, 1.2 equivalents) and N-methylmorpholine (18 μL, 2.4 equivalents) followed by the Example 27 (36 mg, 1.2 equivalents) at 25° C. for 16 hrs. The solvents were evaporated, and the residue was purified using HPLC reverse phase chromatography using water (0.1% trifluoroacetic acid):acetonitrile (95:5) to acetonitrile (100%) to give 38.5 mg (55%) of the title compound.

Example 283D (2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide

Example 284

(2R,3R)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide A solution of Example 283C (38.5 mg, 0.038 mmol) in acetonitrile (0.5 mL) and diethylamine (9 μL, 3 equivalents) was stirred at 25° C. for 1 h. The solvents were evaporated and the residue was purified by HPLC reverse phase chromatography using water (0.1% trifluoroacetic acid):acetonitrile (95:5) to acetonitrile (100%) to give 30.9 mg of amines. The two products were separated by preparative TLC using 0.5 mm silica gel plates, eluting with 5% methanol/chloroform/0.2% ammonium hydroxide to give 7.3 mg of Example 283D and 7.4 mg of Example 284.

Example 285

(2S,3S)-2-(3-{3-[amino(hydroxyimino)methyl]benzyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylpentanamide Example 201 (65 mg) was dissolved in ethanol (1 mL) and treated with triethylamine (0.13 mL, 10 equivalents) and hydroxylamine hydrochloride (25 mg, 4 equivalents) at 50° C. for 6 h. The mixture was partitioned between water and ethyl acetate, the organic layer was separated, dried over Na$_2$SO$_4$, filtered and the solvents were evaporated. The residue was purified using 3% methanol/chloroform to give 57 mg (84%) of the title compound.

Example 286

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[3-(hydroxymethyl)benzyl]-2-oxo-1-imidazolidinyl}-3-methylpentanamide

Example 286A

6-[(trityloxy)methyl]pyridine-2-carbaldehyde 2,6-Dimethanol pyridine (1 g) was prepared per J. Org. Chem. 63, 3884-3894 (1998) to give 330 mg (12%) of the mono-trityl analog. The trityl ether (0.33 g) was dissolved in dichloromethane (2 mL) and stirred at 25° C. with manganese dioxide (0.5 g, 7 equivalents) for 3 days. The mixture was filtered through Celite©, and purified using dichloromethane to give 0.284 g (86%) of the title compound.

Example 286B tert-butyl (2S,3S)-3-methyl-2-[2-oxo-3-({6-[(trityloxy)methyl]pyridin-2-yl}methyl)imidazolidin-1-yl]pentanoate A solution of the product of Example 286A (0.28 g) in dichloromethane (5 mL) was treated with Example 32C (0.17 g, 1 equivalent) and MgSO$_4$ (1 g) and the mixture was stirred at 25° C. for 2 h. The mixture was filtered and the solvents were evaporated. The residue was dissolved in methanol (5 mL) and treated with NaBH$_4$ (42 mg, 1.5 equivalents) at 25° C. for 1 h. The mixture was partitioned between water and ethyl acetate, the organic layer was separated and dried over Na$_2$SO$_4$, filtered and the solvents were evaporated. The residue was used directly for the next step. The crude diamine was dissolved in N,N-dimethylformamide (15 mL) and treated with bis-(p-nitrophenylcarbonate (0.27 g, 1.2 equivalents) at 50° C. for 3 h. The mixture was partitioned between water and ethyl acetate and the organic layer was separated, washed with saturated NaHCO$_3$, dried over NaSO$_4$, filtered and the solvents were evaporated. The residue was purified using 5% ethyl acetate in dichloromethane to give 0.35 g (76%) of the title compound.

Example 286C (2S,3S)-3-methyl-2-[2-oxo-3-({6-[(trityloxy)methyl]pyridin-2-yl}methyl)imidazolidin-1-yl]pentanoic acid A solution of the product of Example 286B (0.35 g) in trifluoroacetic acid:dichloromethane (3 mL, 2:1) was stirred at 25° C. for 2 hrs. The solvents were evaporated and the residue was directly used for the next step.

Example 286D (2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-({6-[(trityloxy)methyl]pyridin-2-yl}methyl)imidazolidin-1-yl]pentanamide A solution of the product of Example 286C (0.35 g, 0.59 mmol) in N,N-dimethylformamide (4 mL) was combined with EDAC (0.17 g, 1.5 equivalents), HOBT (0.12 g, 1.5 equivalents), N-methylmorpholine (0.13 mL, 2 equivalents) followed by the Example 18 (0.27 g, 1.1 equivalents). The mixture was stirred at 25° C. for 16 hrs and partitioned between saturated NaHCO$_3$ and ethyl acetate. The organic layer was separated and dried over Na$_2$SO$_4$, filtered and the solvents were evaporated. The residue was purified first using 2% methanol/chloroform followed by ethyl acetate:hexanes (1:2) to give 0.243 g (43%) of the title compound.

Example 286E (2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(hydroxymethyl)pyridin-2-yl]methyl}-2-oxoimidazolidin-1-yl)-3-methylpentanamide A solution of the product of Example 286D (0.166 g) in methanol:dichloromethane (2 mL, 3:2) at 0° C. was treated with concentrated HCl (1 mL). The mixture was stirred at 25° C. for 30 min and partitioned into sat NaHCO$_3$ and dichloromethane. The organic layer was separated and dried over NaSO$_4$, filtered, and the solvents were evaporated. The residue was purified using 4% methanol/chloroform to give 69 mg (56%) of the title compound.

Example 287

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({6-[(hydroxyimino)methyl]-2-pyridinyl}methyl)-2-oxo-1-imidazolidinyl]-2,3-dimethylpentanamide Example 286E (10 mg, 0.014 mmol) was dissolved in dichloromethane (50 mL) and treated with MnO$_2$ (72 mg, 50 equivalents) at 25° C. for 16 hrs. Continue to add enough MnO$_2$ to complete the reaction. The mixture was filtered through Celite®, and the solvents were evaporated. The crude aldehyde was dissolved in methanol (1 mL) and treated with hydroxylamine hydrochloride (10 mg, 1.1 equivalents) at 25° C. for 1.5 h. The mixture was partitioned between sat NaHCO$_3$ and ethyl acetate, the organic layer was separated, dried over Na$_2$SO$_4$, filtered and the solvents were evaporated. The residue was purified using ethyl acetate:hexanes (2:1) to give 1.7 mg (17%) of the title compound.

Example 288

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxyethyl)-2-pyridinyl]methyl}-2-oxo-1-imidazolidinyl)-3,3-dimethylbutanamide

Example 288A (2S)-2-{3-[(6-acetyl-2-pyridinyl)methyl]-2-oxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3,3-dimethylbutanamide Example 122 (0.17 g) was dissolved in N,N-dimethylformamide (2 mL) and treated with EDAC (0.19 g, 2.7 equivalents), HOBT (0.134 g, 2.7 equivalents), N-methylmorpholine (88 µL, 2.1 equivalents) and Example 18 (0.28 g, 1.78 equivalents) at 25° C. for 2.5 days. The mixture was partitioned between 1N NaHCO$_3$ and ethyl acetate. The organic layer was separated, dried over Na$_2$SO$_4$, filtered and the solvents were evaporated. The residue was purified using ethyl acetate:hexanes (3:2) followed by using 3% methanol/dichloromethane to give 99 mg (35%) of the title compound.

Example 288B (2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxyethyl)pyridin-2-yl]methyl}-2-oxoimidazolidin-1-yl)-3,3-dimethylbutanamide A solution of the product of Example 288A (86 mg) in methanol (1.5 mL) was treated with NaBH$_4$ (8.8 mg, 2 equivalents) at 0° C. The mixture was stirred for 1 h at 25° C. and quenched by adding acetone (0.2 mL). The solvents were evaporated, and the residue was purified using 7% methanol/dichloromethane to give 83 mg (96%) of the title compound.

Example 289

(2S,3S)-3-methyl-2-{3-[(6-methyl-2-pyridinyl)methyl]-2,4-dioxo-1-imidazolidinyl}pentanoic acid

Example 289A tert-butyl(2S,3S)-2-[(2-ethoxy-2-oxoethyl)amino]-3-methylpentanoate To a solution of (L)-iso-leucine tert-butyl ester hydrochloride (5 g, 22.34 mmol) in N,N-dimethylformamide (30 mL) was added triethylamine (3.1 mL, 22.34 mmol), and the mixture was stirred for 1 h. The reaction was filtered to remove solid salts, and the filtrate was treated with triethylamine (9.3 mL, 67.0 mmol) and ethyl bromoacetate (9.9 mL, 67.0 mmol), and the reaction was stirred for 3 h at 25° C. The reaction was partitioned between ethyl acetate and water, and the organic was washed with brine and dried over MgSO$_4$, filtered and evaporated to give 5.7 g (93%) of the product which was used without further purification.

Example 289B tert-butyl (2S,3S)-2-[(aminocarbonyl)(2-ethoxy-2-oxoethyl)amino]-3-methylpentanoate To Example 289A (5.7 g, 20.9 mmol) in dichloromethane (60 mL) at 0° C. was added chlorosulfonyl isocyanate (2.7 mL, 31.0 mmol) and the mixture was stirred at 0° C. for 16 h. Water (60 mL) was added to the cold reaction and the mixture was warmed to room temperature and stirred for 4 h. The reaction was partitioned between dichloromethane and water, and the organic was washed with brine and dried over MgSO$_4$, filtered and evaporated to give 6.83 g of the product which was used without further purification.

Example 289C tert-butyl (2S,3S)-2-(2,4-dioxo-1-imidazolidinyl)-3-methylpentanoate To Example 289B (6.8 g, 20.9 mmol) in methanol (30 mL) was added triethylamine (5.6 mL, 40.2 mmol), and the mixture was stirred at 50° C. for 2 h. The solvent was evaporated and the residue was chromatographed on silica gel eluting with a gradient starting with dichloromethane and ending with 30% ethyl acetate in dichloromethane to give 2.53 g (47%) of the title compound

Example 289D tert-butyl (2S,3S)-3-methyl-2-{3-[(6-methyl-2-pyridinyl)methyl]-2,4-dioxo-1-imidazolidinyl}pentanoate To Example 289C (0.107 g, 0.396 mmol) in dichloromethane (2 mL) at 0° C. were added 6-methyl-2-pyridinemethanol (0.053 mg, 0.435 mmol), triphenylphosphine (0.135 g, 0.515 mmol), followed by diethyl azodicarboxylate (0.080 mL, 0.515 mmol), and the mixture was stirred at room temperature for 16 h. Water (2 mL) was added and the reaction was stirred for 2 h at room temperature. The reaction was partitioned between dichloromethane and water, and the organic was washed with brine and dried over $MgSO_4$, filtered and evaporated. The residue was purified using a gradient starting with dichloromethane and ending with 30% ethyl acetate in dichloromethane to give 0.154 g (94% yield) of the title compound.

Example 289E (2S,3S)-3-methyl-2-{3-[(6-methyl-2-pyridinyl)methyl]-2,4-dioxo-1-imidazolidinyl}pentanoic acid To Example 289D (0.154 g, 0.410 mmol) in dichloromethane (3 mL) was added trifluoracetic acid (3 mL), and the mixture was stirred at room temperature for 16 h. The solvent was evaporated and the product was purified by reversed phase (C18) chromatography eluting with a gradient starting with 5% acetonitrile in water (0.1% trifluoroacetic acid) and ending with acetonitrile to give 0.153 g (93%) as the trifluoroacetic acid salt.

Example 290

(2S)-2-{3-[(2-ethyl-1,3-thiazol-4-yl)methyl]-2,4-dioxol-imidazolidinyl}-3-methylbutanoic acid

Example 290A tert-butyl (2S)-2-[(2-ethoxy-2-oxoethyl)amino]-3-methylbutanoate To a solution of (L)-valine tert-butyl ester hydrochloride (4.94 g, 23.6 mmol) in N,N-dimethylformamide (55 mL) was added triethylamine (3.28 mL, 1 equivalent), and the mixture was stirred for 1 h. The reaction was filtered to remove solid salts, and the filtrate was treated with triethylamine (9.85 mL, 3 equivalents) and ethyl bromoacetate (7.84 mL, 3 equivalents), and the reaction was stirred for 3 h at 25° C. The reaction was partitioned between ethyl acetate and water, and the organic was washed with brine and dried over $MgSO_4$, filtered and evaporated to give 4.48 g (78%) of the product which was used without further purification.

Example 290B tert-butyl (2S)-2-[(aminocarbonyl)(2-ethoxy-2-oxoethyl)amino]-3-methylbutanoate Example 290A (4.48 g, 18.3 mmol) was dissolved in dichloromethane (30 mL) at 0° C. and was treated with chlorosulfonyl isocyanate (2.07 mL, 1.3 equivalents) and the mixture was stirred at 0° C. for 16 h. Water (60 mL) was added to the cold reaction and the mixture was warmed to 25° C. and stirred for 4 h. The reaction was partitioned between dichloromethane and water, and the organic was washed with brine and dried over $MgSO_4$, filtered and evaporated to give crude product which was used without further purification.

Example 290C tert-butyl (2S)-2-(2,4-dioxo-1-imidazolidinyl)-3-methylbutanoate Example 290B (crude product) was dissolved in methanol (30 mL) and was treated with triethylamine (5.07 mL, 2 equivalents), and the mixture was stirred at 50° C. for 2 h. The solvent was evaporated and the residue was purified using dichloromethane (100%)-25% ethyl acetate/dichloromethane to give 2.97 g (63%) of the title compound.

Example 290D tert-butyl (2S)-2-{3-[(2-ethyl-1,3-thiazol-4-yl)methyl]-2,4-dioxo-1-imidazolidinyl}-3-methylbutanoate Example 290C (0.076 g, 0.297 mmol) was dissolved in N,N-dimethylformamide (1.5 mL) at 0° C. and treated with sodium hexamethyldisilazide (0.33 mL, 1.1 equivalents, 1M in tetrahydrofuran) and the mixture is stirred for 1 h. The 4-chloromethyl-2-ethylthiazole (0.048 mg, 1 equivalent) was added (dissolved in 0.5 mL N,N-dimethylformamide) and the mixture was warmed to 25° C. for 2 h, heated to 75° C. for 18 h. The mixture was quenched with saturated ammonium chloride and partitioned between ethyl acetate and water, and the organic was washed with brine and dried over $MgSO_4$, filtered and evaporated. The residue was purified using hexanes (100%)—65% hexanes/ethyl acetate to give 77 mg (68% yield) of the title compound.

Example 290E (2S)-2-{3-[(2-ethyl-1,3-thiazol-4-yl)methyl]-2,4-dioxo-1-imidazolidinyl}-3-methylbutanoic acid Example 290E (75 mg, 0.196 mmol) was dissolved in dichloromethane (1 mL) and trifluoracetic acid (1 mL), and the mixture was stirred at room temperature for 1 h. The solvent was evaporated and the crude product was used directly for coupling procedures.

The compounds listed in Table 7, wherein $X_{11}$ and $X_7$ represents the points of connection to the core structure (E), were prepared by the procedures as exemplified in Examples 289A-289E and Examples 290A-290E.

TABLE 7
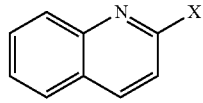
| Ex. | R₁₁ | R₇ |
|---|---|---|
| 291 | 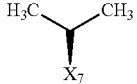 | 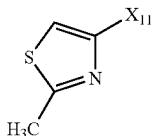 |
| 292 | 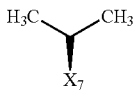 | 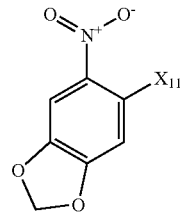 |
| 293 | 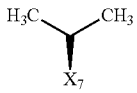 | 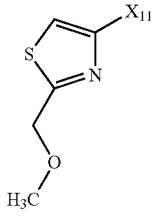 |
| 294 | 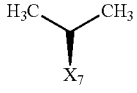 | 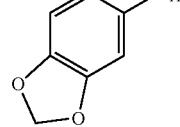 |
| 295 | 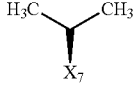 | 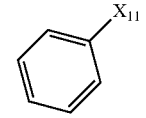 |
| 296 | 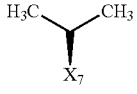 | 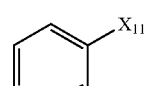 |
| 297 | 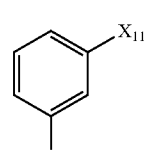 | H |
| 298 | 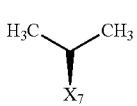 | 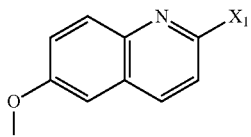 |
TABLE 7-continued
| Ex. | R₁₁ | R₇ |
|---|---|---|
| 299 | 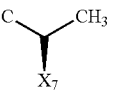 | 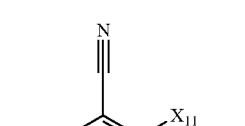 |
| 300 | 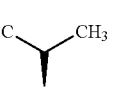 | 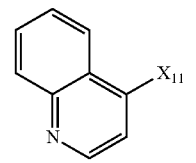 |
| 301 | 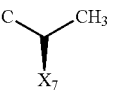 | 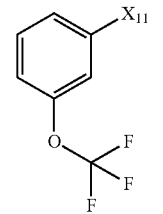 |
| 302 | 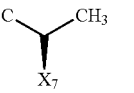 | 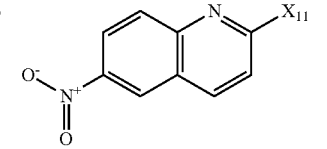 |
| 303 | 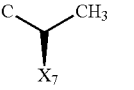 | 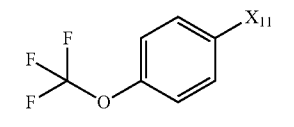 |
| 304 | 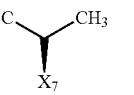 | 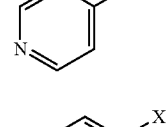 |
| 305 | 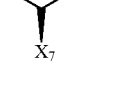 | 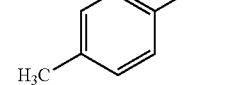 |
| 306 | 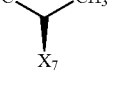 | |

TABLE 7-continued structure (E): R11-CH2-N(C=O)N(CH(R7)CO2H)-C(=O)-CH2- (hydantoin with R11 on one N via CH2 and CH(R7)CO2H on other N)

| Ex. | R11 | R7 |
|---|---|---|
| 307 | 3-(hydroxyiminomethyl)phenyl- (X11 at meta; CH=N-OH) | isopropyl (H3C-CH(X7)-CH3) |
| 308 | 4-nitrophenyl- (X11 para; NO2 as O-/N+=O) | isopropyl |
| 309 | pyridin-2-yl- (X11) | isopropyl |
| 310 | 4-biphenylyl- (X11) | isopropyl |
| 311 | 6-methylpyridin-2-yl- (H3C on pyridine, X11) | isopropyl |
| 312 | 4-benzoylphenyl- (X11 para; C(=O)-phenyl) | isopropyl |
| 313 | 4-methylpyridin-3-yl- (CH3 on pyridine, X11) | isopropyl |
| 314 | naphthalen-1-yl- (X11) | isopropyl |
| 315 | 6-amino-quinolin-2-yl- (H2N on quinoline, X11) | isopropyl |
| 316 | naphthalen-2-yl- (X11) | isopropyl |
| 317 | 3-acetylphenyl- (X11 meta; C(=O)CH3) | isopropyl |
| 318 | 4-vinylphenyl- (X11 para; CH=CH2) | isopropyl |
| 319 | 3-(1-hydroxyiminoethyl)phenyl- (X11 meta; C(CH3)=N-OH) | isopropyl |
| 320 | 4-methyl-3-nitrophenyl- (X11; H3C and NO2) | isopropyl |
| 321 | 2-acetamidothiazol-4-yl- (X11; NHC(=O)CH3 on thiazole) | isopropyl |

TABLE 7-continued (E)

| Ex. | R₁₁ | R₇ |
|---|---|---|
| 322 | 2-nitrophenyl (X₁₁) | isopropyl (X₇) |
| 323 | 2-cyanopyridin-4-yl (X₁₁) | isopropyl (X₇) |
| 324 | 2-methyl-3-nitrophenyl (X₁₁) | isopropyl (X₇) |
| 325 | 2-acetylpyridin-4-yl (X₁₁) | isopropyl (X₇) |
| 326 | 4-(1,2,3-thiadiazol-4-yl)phenyl (X₁₁) | isopropyl (X₇) |
| 327 | 3-(azidomethyl)phenyl (X₁₁) | sec-butyl (X₇) |
| 328 | pyridin-3-yl (X₁₁) | isopropyl (X₇) |
| 329 | pyridin-3-yl (X₁₁) | sec-butyl (X₇) |
| 330 | 2-methoxy-5-nitrophenyl (X₁₁) | isopropyl (X₇) |
| 331 | pyridin-3-yl (X₁₁) | sec-butyl (X₇) |
| 332 | 3-fluoro-6-nitrophenyl (X₁₁) | isopropyl (X₇) |
| 333 | 2-acetamido-thiazol-4-yl (X₁₁) | sec-butyl (X₇) |
| 334 | 2-methyl-4-nitrophenyl (X₁₁) (position as drawn) | isopropyl (X₇) |
| 335 | 3-(hydroxymethyl)phenyl (X₁₁) | isopropyl (X₇) |

TABLE 7-continued (E)

| Ex. | R11 | R7 |
|---|---|---|
| 336 | 3-(methoxymethyl)phenyl | isopropyl |
| 337 | pyrazin-2-yl | isopropyl |
| 338 | 3-cyanophenyl | isopropyl |
| 339 | 3-((methylamino)methyl)phenyl | isopropyl |
| 340 | 3-bromophenyl | isopropyl |
| 341 | 3-nitrophenyl | (S)-sec-butyl |
| 342 | ethoxycarbonyl | (S)-sec-butyl |
| 343 | 6-aminoquinolin-2-yl | (S)-sec-butyl |
| 344 | 3-(N'-hydroxycarbamimidoyl)phenyl | isopropyl |
| 345 | 2-acetylpyridin-4-yl | (S)-sec-butyl |
| 346 | 3-(pyrazin-2-yl)phenyl | isopropyl |
| 347 | 2-(1-(hydroxyimino)ethyl)pyridin-4-yl | (S)-sec-butyl |
| 348 | 3-(thiophen-2-yl)phenyl | isopropyl |
| 349 | quinolin-4-yl | (S)-sec-butyl |

TABLE 7-continued (E)

| Ex. | R₁₁ | R₇ |
|-----|-----|-----|
| 350 | 1-methyl-1H-imidazo[4,5-b]pyridin-2-yl (X₁₁) | isopropyl (X₇) |
| 351 | pyridin-2-yl (X₁₁) | sec-butyl (X₇) |
| 352 | 3-nitrophenyl (X₁₁) | isopropyl (X₇) |
| 353 | phenylcarbonyl (X₁₁) | sec-butyl (X₇) |
| 354 | 5-nitrothiophen-2-yl, 4-X₁₁ | isopropyl (X₇) |
| 355 | 2-(methoxymethyl)-1,3-thiazol-4-yl (X₁₁) | sec-butyl (X₇) |
| 356 | 6-chlorobenzo[1,3]dioxol-5-yl (X₁₁) | isopropyl (X₇) |
| 357 | phenylaminocarbonyl (X₁₁) | sec-butyl (X₇) |
| 358 | 1,3-benzothiazol-2-yl (X₁₁) | isopropyl (X₇) |
| 359 | pyridin-3-ylaminocarbonyl (X₁₁) | sec-butyl (X₇) |
| 360 | 1-methyl-1H-benzimidazol-2-yl (X₁₁) | isopropyl (X₇) |

Example 361

(2S)-2-[3-({2-[(dimethylamino)methyl]-1,3-thiazol-4-yl}methyl)-2,4-dioxo-1-imidazolidinyl]-3-methylbutanoic acid

Example 361A tert-butyl (2S)-2-(3-{[2-(diethoxymethyl)-1,3-thiazol-4-yl]methyl}-2,4-dioxo-1-imidazolidinyl)-3-methylbutanoate Example 290C (25 mg, 0.098 mmol) was dissolved in dichloromethane (1 mL) and treated with Example 273A (21.2 mg, 1 equivalent), triphenylphosphine (31 mg, 1.2 equivalents), and diethyldiazodicarboxylate (18.2 pt, 1.2 equivalents), the mixture was stirred at 25° C. for 1 h, quenched with water, the organic layer was separated, dried over magnesium sulfate, filtered, and the solvents were evaporated. The crude residue was purified using dichloromethane (100%)—20% ethyl acetate/dichloromethane to give 28 mg (63%) of the title compound.

Example 361B tert-butyl (2S)-2-{3-[(2-formyl-1,3-thiazol-4-yl)methyl]-2,4-dioxo-1-imidazolidinyl}-3-methylbutanoate Example 361A (0.31 g, 0.68 mmol) was dissolved in acetone (14 mL) and 1M HCl (1.4 mL) and heated to 70° C. for 1 h. The solvents were evaporated, and the residue was partitioned between ethyl acetate and brine, the organic layer was separated, washed with water, dried over magnesium sulfate, and the solvents were evaporated to give crude 0.189 g (73%) of the title compound.

Example 361C tert-butyl (2S)-2-[3-({2-[(dimethylamino)methyl]-1,3-thiazol-4-yl}methyl)-2,4-dioxo-1-imidazolidinyl]-3-methylbutanoate Example 361B (0.12 g, 0.31 mmol) was dissolved in ethanol:benzene (1.2 mL, 1:1) and treated with dimethylamine (0.79 mL, 2M in tetrahydrofuran) and heated to 70° C. for 2 h. The mixture was cooled to 25° C. and treated with sodium cyanoborohydride (39.5 mg, 2 equivalents) and acetic acid (90 μL, 5 equivalents) and the reaction was quenched by saturated ammonium chloride after 1 h. The mixture was partitioned between water and ethyl acetate, the organic layer was separated, washed with brine, dried over magnesium sulfate and the solvents were evaporated. The crude residue was purified using dichloromethane (100%)-4% methanol/dichloromethane to give 63 mg (49%) of the title compound.

Example 361D (2S)-2-[3-({2-[(dimethylamino)methyl]-1,3-thiazol-4-yl}methyl)-2,4-dioxo-1-imidazolidinyl]-3-methylbutanoic acid Example 361C (52 mg, 0.127 mmol) was dissolved in trifluoroacetic acid/dichloromethane (2 mL, 1:1) at 25° C. for 1 h. The solvents were evaporated to give the crude acid trifluoroacetic acid salt.

Example 362

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2,4-dioxo-1-imidazolidinyl)-3-methylbutanamide Example 294 (47 mg) is combined with HOBT (28 mg, 1.5 equivalent) and EDAC (32 mg, 1.5 equivalents) in N,N-dimethylformamide (1 mL) and stirred for 1 h at 25° C. To this mixture is added N-methylmorpholine (NMM) (30 μL, 2 equivalents) and Example 18 (57 mg, 1 equivalent). The mixture is stirred for 16 h, evaporated under vacuum, and purified by HPLC (reverse phase; 95% water (0.1% trifluoroacetic acid)/5% acetonitrile to 100% acetonitrile; flow=10 mL/minute; time=30 minute) to give 51 mg (50%) of the title compound. $^1$H NMR (300 MHz, CDCl$_3$) δ ppm 0.79 (t, J=7.12 Hz, 6H), 0.86 (d, J=6.44 Hz, 3H), 0.93 (d, J=6.44 Hz, 3H), 1.84 (m, 1H), 2.08 (m, 1H), 2.66 (dd, J=13.90, 10.85 Hz, 1H), 2.84 (m, 1H), 3.12 (m, 5H), 3.47 (s, 3H), 3.60 (d, J=17.97 Hz, 1H), 3.85 (m, 2H), 4.23 (m, J=4.41 Hz, 1H), 4.70 (s, 2H), 4.73 (d, J=14.58 Hz, 1H), 4.81 (d, J=15.26 Hz, 1H), 6.39 (d, J=8.82 Hz, 1H), 7.07 (m, 5H), 7.24 (s, 1H), 7.72 (d, J=8.14 Hz, 2H), 7.80 (d, J=8.48 Hz, 2H), 8.17 (s, 1H).

The compounds listed in Table 8, wherein $X_7$, $X_{11}$, and $X_3$ represent respectively the points of connection to the core structure (F), were prepared by coupling the corresponding acids (Example 291-360) with the corresponding amines (Example 1-31), using the procedure as exemplified by Example 362 (Method A) or Example 162 (Method B).

TABLE 8

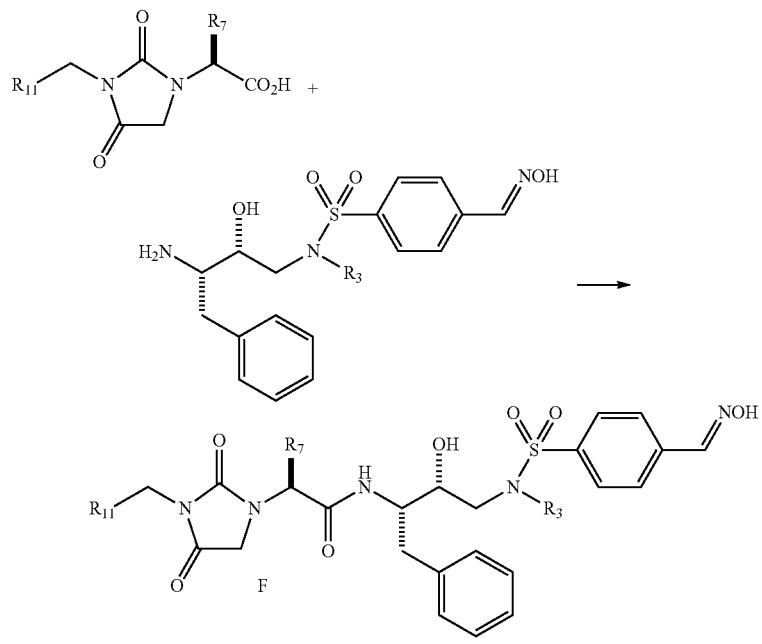

| Ex. | Method | $R_{11}$ | $R_7$ | $R_3$ |
|---|---|---|---|---|
| 363 | A | 3-nitrophenyl-$X_{11}$ | (CH$_3$)$_2$CH-$X_7$ | (CH$_3$)$_2$CHCH$_2$-$X_3$ |

TABLE 8-continued
| | | | | |
|---|---|---|---|---|
| 364 | B | 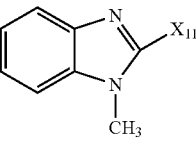 | 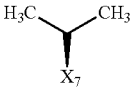 | 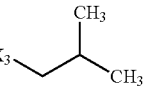 |
| 365 | B | 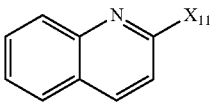 | 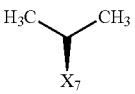 | 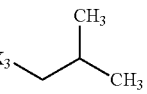 |
| 366 | A | 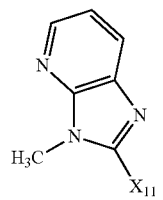 | 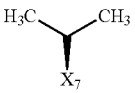 | 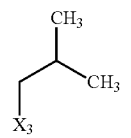 |
| 367 | A | 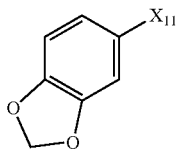 | 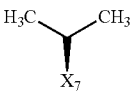 | 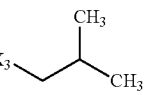 |
| 368 | A | 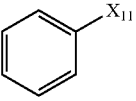 | H |  |
| 369 | A | 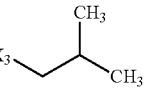 | 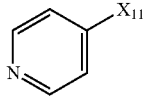 | 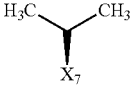 |
| 370 | A | 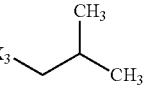 | 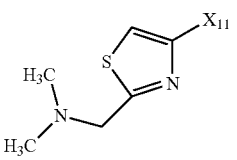 | 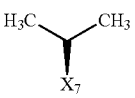 |
| 371 | A | 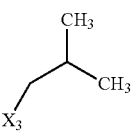 | 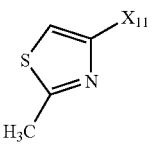 | 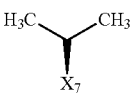 |
| 372 | A | 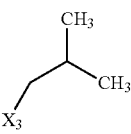 | 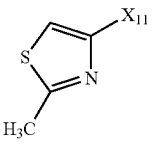 | 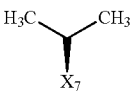 |
| 373 | A | 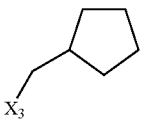 | 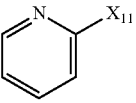 | 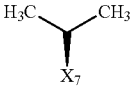 |
| 374 | A | 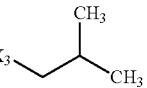 | 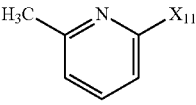 | 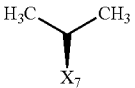 |

TABLE 8-continued

| | | | | |
|---|---|---|---|---|
| 375 | A | phenyl-$X_{11}$ | $H_3C-CH(X_7)-CH_3$ | $X_3-CH_2-CH(CH_3)_2$ |
| 376 | A | 3-acetylphenyl-$X_{11}$ | $H_3C-CH(X_7)-CH_3$ | $X_3-CH_2-CH(CH_3)_2$ |
| 377 | A | 2-(methoxymethyl)thiazol-4-yl-$X_{11}$ | $H_3C-CH(X_7)-CH_3$ | cyclopentyl-$CH_2-X_3$ |
| 378 | A | 2-methylthiazol-4-yl-$X_{11}$ | $H_3C-CH(X_7)-CH_3$ | cyclobutyl-$CH_2-X_3$ |
| 379 | A | 2-(methoxymethyl)thiazol-4-yl-$X_{11}$ | $H_3C-CH(X_7)-CH_3$ | cyclobutyl-$CH_2-X_3$ |
| 380 | A | 2-cyanopyridin-4-yl-$X_{11}$ | $H_3C-CH(X_7)-CH_3$ | $X_3-CH_2-CH(CH_3)_2$ |
| 381 | A | 2-acetylpyridin-4-yl-$X_{11}$ | $H_3C-CH(X_7)-CH_3$ | $X_3-CH_2-CH(CH_3)_2$ |
| 382 | A | 3-(azidomethyl)phenyl-$X_{11}$ | $H_3C-CH(X_7)-CH_3$ | $X_3-CH_2-CH(CH_3)_2$ |
| 383 | A | pyridin-4-yl-$X_{11}$ | $H_3C-CH(X_7)-CH_2-CH_3$ | $X_3-CH_2-CH(CH_3)_2$ |

TABLE 8-continued

| 384 | A | 3-pyridyl-X₁₁ | H₃C-CH(X₇)-CH₂-CH₃ (sec-butyl) | isobutyl-X₃ |
| 385 | A | 4-X₁₁-2-(acetylamino)thiazole | H₃C-CH(X₇)-CH₂-CH₃ | cyclopentylmethyl-X₃ |
| 386 | A | 4-X₁₁-2-(acetylamino)thiazole | H₃C-CH(X₇)-CH₂-CH₃ | isobutyl-X₃ |
| 387 | A | 2-X₁₁-pyrazine | isopropyl-X₇ | isobutyl-X₃ |
| 388 | A | 4-X₁₁-2-(acetylamino)thiazole | isopropyl-X₇ | isobutyl-X₃ |
| 389 | A | 3-(methylaminomethyl)phenyl-X₁₁ | isopropyl-X₇ | isobutyl-X₃ |
| 390 | A | 3-nitrophenyl-X₁₁ | H₃C-CH(X₇)-CH₂-CH₃ | isobutyl-X₃ |
| 391 | A | 4-X₁₁-quinoline | isopropyl-X₇ | isobutyl-X₃ |
| 392 | B | 6-amino-2-X₁₁-quinoline | H₃C-CH(X₇)-CH₂-CH₃ | isobutyl-X₃ |

TABLE 8-continued
| | | | | |
|---|---|---|---|---|
| 393 | A | 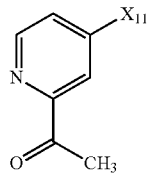 | 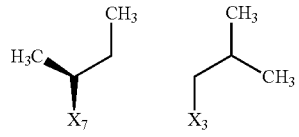 | 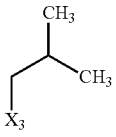 |
| 394 | A | 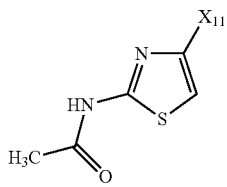 | 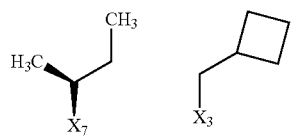 | 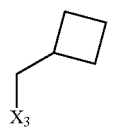 |
| 395 | A | 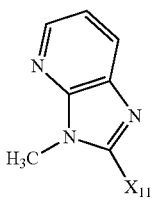 | 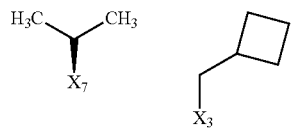 | 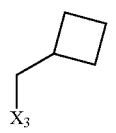 |
| 396 | A | 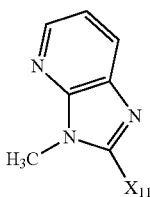 | 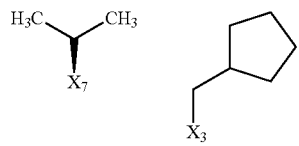 | 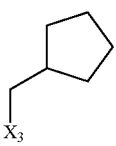 |
| 397 | A | 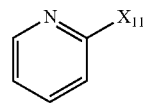 | 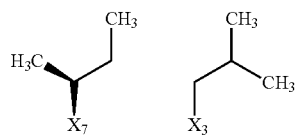 | 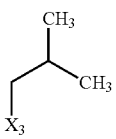 |
| 398 | A | 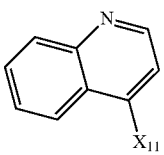 | 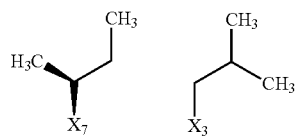 | 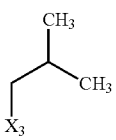 |
| 399 | A | 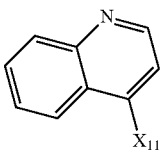 | 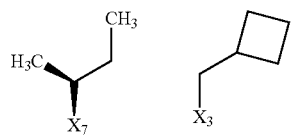 | 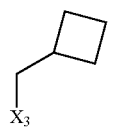 |
| 400 | A | 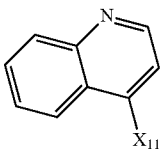 | 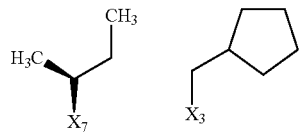 | 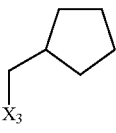 |

Example 401

(2S)-2-[3-(3-aminobenzyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylbutanamide Example 363 (75 mg) was dissolved in ethyl acetate (1 mL) and combined with 10% Pd/C (30 mg), a hydrogen balloon, and stirred at 25° C. for 2 h. The mixture was filtered, and the solvents were evaporated. The residue was purified using 2% methanol/CHCl$_3$ to give 45 mg (63%) of the title compound.

Example 402

(2S)—N-{(1S,2R)-1-benzyl-2-hydroxy-3-[({4-[(E)-(hydroxyimino)methyl]phenyl}sulfonyl)(isobutyl)amino]propyl}-2-(3-{3-[N-hydroxyethanimidoyl]benzyl}-2,4-dioxo-1-imidazolidinyl)-3-methylbutanamide Example 376 (90 mg, 0.12 mmol) was dissolved in ethanol (2 mL) and treated with hydroxylamine hydrochloride (34 mg, 4 equivalents) and triethylamine (0.17 mL, 10 equivalents) at 50° C. for 3 h. The mixture was cooled to 25° C. and partitioned between water and ethyl acetate. The organic layer was dried with sodium sulfate and the solvents were evaporated. The crude residue was purified using 1% methanol/chloroform to give 55 mg (60%) of the title compound.

Example 403

(2S)-2-{3-[3-(aminomethyl)benzyl]-2,4-dioxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylbutanamide Example 382 (10 mg, 0.013 mmol) was dissolved in ethyl acetate (0.5 mL) and combined with Lindlar's catalyst (6 mg) and a hydrogen balloon and stirred for 2 h. The mixture was filtered, and the solvents were evaporated. The residue was purified on florasil using 10% methanol/dichloromethane to give 5 mg (50%) of the title compound.

Example 404

(2S,3S)-2-[3-(3-aminobenzyl)-2,4-dioxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylpentanamide Example 390 (66 mg, 0.088 mmol) was dissolved in ethyl acetate (1 mL) and treated with 10% Pd/C (20 mg) and stirred at 25° C. under a hydrogen balloon for 3.5 h. The catalyst was filtered, and the solvents were evaporated. The crude residue was purified using 2% methanol/chloroform to give 51 mg (80%) of the title compound.

Example 405

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]-4-pyridinyl}methyl)-2,4-dioxo-1-imidazolidinyl]-3-methylpentanamide Example 381 (20 mg, 0.026 mmol) was dissolved in ethanol (0.3 mL) and treated with hydroxylamine hydrochloride (7 mg, 4 equivalents) and triethylamine (37 μL, 10 equivalents) at 50° C. for 6 h. The mixture was cooled to 25° C. and partitioned between water and ethyl acetate. The organic layer was dried with sodium sulfate and the solvents were evaporated. The crude residue was purified using 5% methanol/chloroform to give 19 mg (100%) of the title compound.

Example 406 methyl(2S,3S)-3-methyl-2-{[(4-nitrophenoxy)carbonyl]amino}pentanoate

To a solution of (L)-methyl iso-leucinate hydrochloride (2.5 g, 13.75 mmol) in dichloromethane (35 mL) at 0° C. were added 4-nitrophenyl chloroformate (3.05, 15.13 mmol) and N-methylmorpholine (3.2 mL, 29.11 mmol), and the mixture was stirred at room temperature for 64 hours. The reaction was partitioned between dichloromethane and saturated NaHCO$_3$, and the organic was washed with brine and dried over MgSO$_4$, filtered and evaporated to give the product (4.19 g, 98% yield), which was used without further purification.

Example 407 methyl(2S)-3-methyl-2-{[(4-nitrophenoxy)carbonyl]amino}butanoate (L)-Methyl valinate (1 g) was dissolved in dichloromethane (10 mL) and treated with bis-(4-nitrophenyl)carbonate (1.2 g, 1.1 equivalents) and N-methylmorpholine (1.5 mL, 2.5 equivalents) at 0° C. for 4 h. The reaction was quenched with 1M NaHCO$_3$, and the organic layer was separated, washed with brine, dried with Na$_2$SO$_4$, filtered, and evaporated. The residue is purified using ethyl acetate/hexanes (2:3) to give 1.65 g (96%) of the title compound.

Example 408

(2S)-3-methyl-2-[({methyl[(2-methyl-1,3-thiazol-4-yl)methyl]amino}carbonyl)amino]butanoic acid

Example 408A

N-methyl(2-methyl-1,3-thiazol-4-yl)methanamine

2-Methyl-4-(chloromethyl)thiazole (2.94 g, CAS#39238-07-8) was dissolved in 40% methylamine (39 mL, 25 equivalents) at 25° C. for 1 h. The mixture was evaporated and purified using 10% methanol/dichloromethane with 0.5% NH$_4$OH to give 2.83 g (99%) of the amine.

Example 408B methyl(2S)-3-methyl-2-[({methyl[(2-methyl-1,3-thiazol-4-yl)methyl]amino}carbonyl)amino]butanoate Example 408A (2.83 g) was dissolved in tetrahydrofuran (80 mL) and treated with triethyl amine (2.8 mL, 1 equivalent), DMAP (0.28 g, 0.02 equivalent), and Example 407 (5.9 g, 1 equivalent) at 25° C. for 16 h. The mixture was quenched with 10% K$_2$CO$_3$, and the organic layer was separated, dried with Na2SO4, filtered, and evaporated to give the crude thiazole ester which was used directly in the next step.

Example 408C (2S)-3-methyl-2-[({methyl[(2-methyl-1,3-thiazol-4-yl)methyl]amino}carbonyl)amino]butanoic acid Example 408B (0.57 g) was dissolved in dioxane (8 mL) and treated with 1.4M LiOH (8 mL, in water) at 25° C. for 1 h. The mixture was quenched with 1M HCl (4 mL), and the solvents were evaporated, and the residue was purified using 5% methanol/dichloromethane to give 0.52 g (96%) of the acid.

The compounds listed in Table 9, wherein $X_{13}$ and $X_7$ represents the points of connection to the core structure (G), were prepared by coupling of the p-nitrophenyl carbamates of the corresponding amino acid methyl esters with the corresponding arylamines, heteroarylamines, and alkylamines by the procedures as exemplified in Example 406-408C.

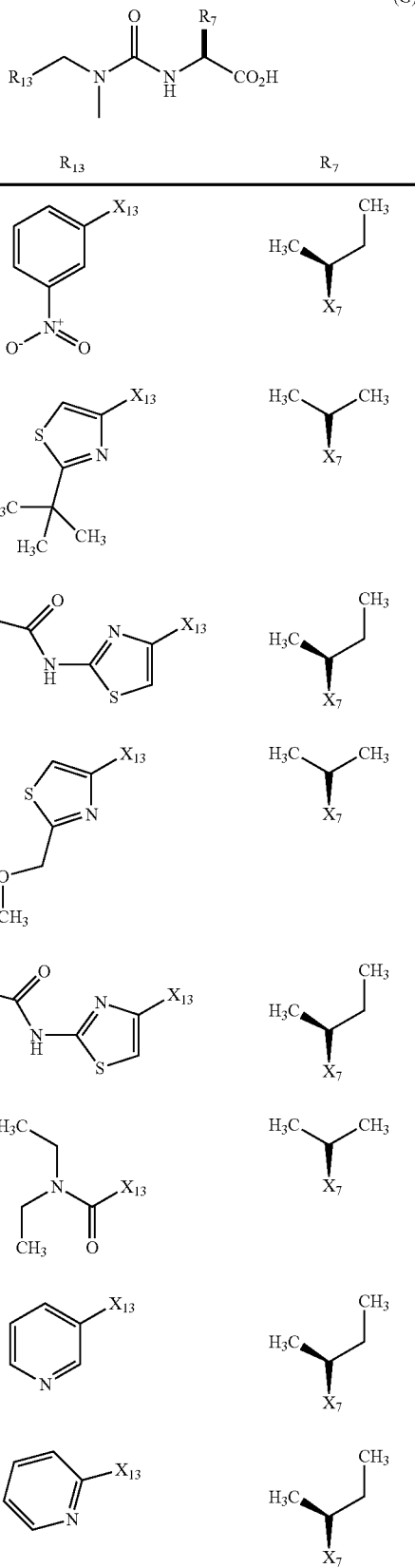

TABLE 9-continued (G)

| Ex. | R13 | R7 |
|---|---|---|
| 422 | 4-pyridyl-X13 | (S)-sec-butyl (CH3, H3C-CH2-) |
| 423 | 2-pyridyl-X13 | isopropyl (H3C-CH-CH3) |
| 424 | 6-(methoxymethyl)-2-pyridyl-X13 | (S)-sec-butyl |
| 425 | 2-isopropyl-thiazol-4-yl-X13 | methyl-X7 |
| 426 | 2-isopropyl-thiazol-4-yl-X13 | (S)-sec-butyl |
| 427 | PhNHC(O)-X1 | isopropyl |
| 428 | 6-(N-hydroxycarbamimidoyl)-2-pyridyl-X13 | (S)-sec-butyl |
| 429 | 2-(methoxymethyl)thiazol-4-yl-X13 | (R)-2-methoxy-3-methylbutan-2-yl |
| 430 | 6-(methoxymethyl)-2-pyridyl-X13 | tert-butyl |

TABLE 9-continued (G)

| Ex. | R13 | R7 |
|---|---|---|
| 431 | 2-(methoxymethyl)thiazol-4-yl-X13 | (S)-sec-butyl |
| 432 | 6-((2-methoxy-2-methylpropoxy)methyl)-2-pyridyl-X13 | tert-butyl |
| 433 | 2-((S)-1-acetamidoethyl)thiazol-4-yl-X13 | (S)-sec-butyl |

Example 434

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-({[methyl(2-pyridinylmethyl)amino]carbonyl}amino)pentanamide Method A Example 421 (20 mg, 0.071 mmol) is combined with HOBT (9.6 mg, 1.5 equivalent) and EDAC (14 mg, 1.5 equivalents) in N,N-dimethylformamide (1 mL) and stirred for 1 h at 25° C. To this mixture is added N-methylmorpholine (NMM) (5.3 µL, 1 equivalent) and Example 18 (20 mg, 1 equivalent). The mixture is stirred for 16 h, evaporated under vacuum, and purified by silica gel chromatography using 7% methanol/dichloromethane to give 13.4 mg (41%) of the title compound. $^1$H NMR (300 MHz, CDCl$_3$) δ ppm 0.77 (m, 6H), 0.83 (d, J=6.78 Hz, 3H), 0.88 (d, J=6.44 Hz, 3H), 0.97 (d, J=3.73 Hz, 1H), 1.88 (m, J=6.78 Hz, 2H), 2.85 (m, 2H), 2.98 (m, 8H), 3.07 (m, 2H), 3.37 (dd, J=14.92, 4.75 Hz, 1H), 3.85 (s, 1H), 4.14 (m, 1H), 4.22 (s, 2H), 4.31 (d, J=15.60 Hz, 1H), 7.18 (m, 5H), 7.28 (s, 1H), 7.70 (d, J=8.48 Hz, 2H), 7.77 (s, 1H), 7.82 (d, J=8.48 Hz, 2H), 8.12 (s, 1H), 8.20 (s, 1H).

Example 435

(2S)—N-{(1S,2R)-1-benzyl-2-hydroxy-3-[({4-[(E)-(hydroxyimino)methyl]phenyl}sulfonyl)(isobutyl)amino]propyl}-2-({[[(2-isopropyl-1,3-thiazol-4-yl)methyl](methyl)amino]carbonyl}amino)-3-methylbutanamide

Method E

Example 409 (activated as O-succinimide ester) (75 mg, 0.18 mmol) was dissolved in dichloromethane (1 mL) and N,N-dimethylformamide (0.5 mL) and treated with Example 18 (85 mg, 1.1 equivalents) and N-methylmorpholine (24.3 µL, 1.2 equivalents) at 25° C. for 16 h. The mixture was partitioned between dichloromethane and 1N NaHCO$_3$. The organic layer was separated, the solvents were evaporated, and the residue was purified using 4% methanol/dichloromethane to give 70 mg (53%) of the title compound. $^1$H NMR (300 MHz, CD$_3$OD) δ ppm 0.75 (d, J=3.05 Hz, 3H), 0.78 (d, J=3.05 Hz, 3H), 0.84 (d, J=6.78 Hz, 3H), 0.89 (d, J=6.78 Hz, 3H), 1.36 (d, J=6.44 Hz, 6H), 1.92 (m, 2H), 2.64 (dd, J=13.90, 10.51 Hz, 1H), 2.94 (s, 3H), 3.08 (m, 5H), 3.14 (m, 1H), 3.44 (dd, J=14.92, 3.39 Hz, 1H), 3.79 (m, 1H), 3.95 (d, J=7.46 Hz, 1H), 4.06 (m, 1H), 4.47 (t, J=16.28 Hz, 2H), 7.10 (m, 3H), 7.16 (s, 1H), 7.20 (m, 2H), 7.76 (d, J=8.48 Hz, 2H), 7.82 (d, J=6.44 Hz, 2H), 8.13 (s, 1H).

The compounds listed in Table 10, wherein $X_{13}$, $X_7$ and $X_3$ represent respectively the points of connection to the core structure (H), were prepared by coupling the corresponding acids (Example 409-433) with the corresponding amines (Example 1-31) using the procedures as exemplified by Example 434 (Method A) or Example 435 (Method E).

TABLE 10

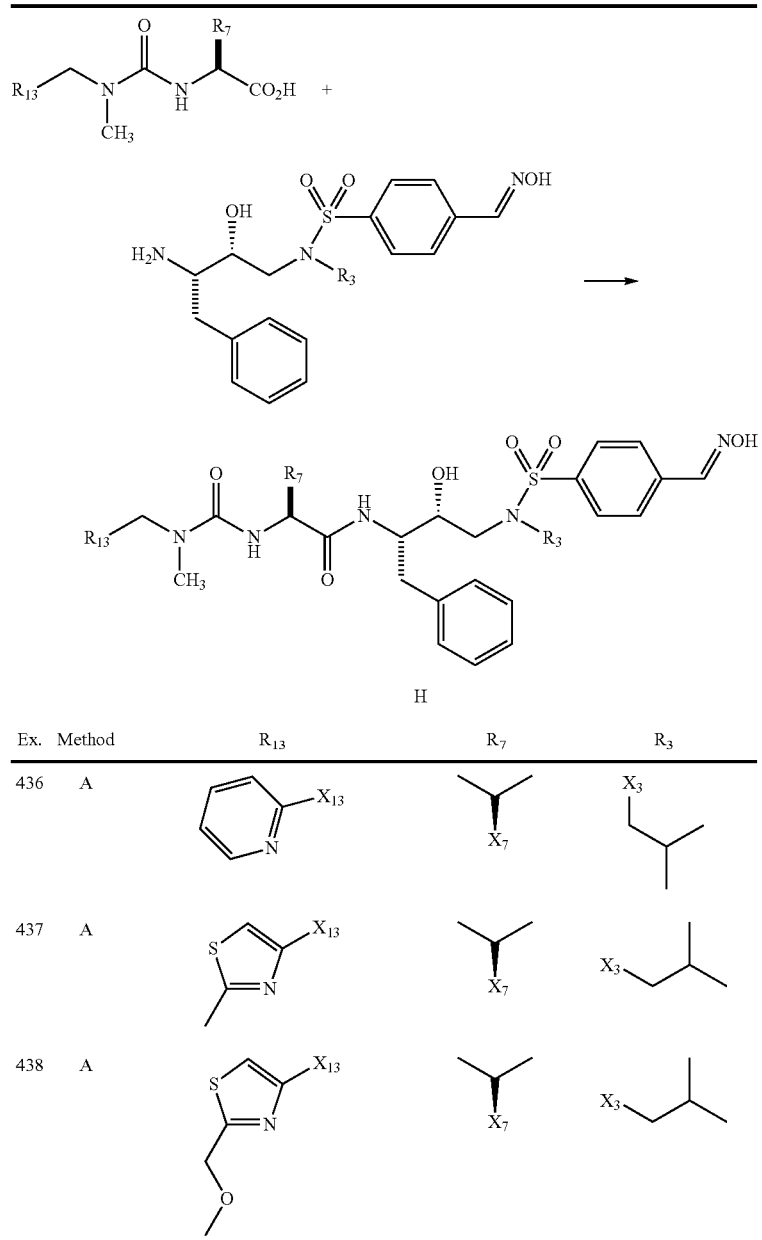

TABLE 10-continued
| | | | | |
|---|---|---|---|---|
| 439 | A | 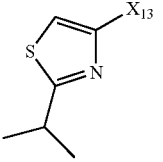 |  | 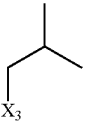 |
| 440 | E | 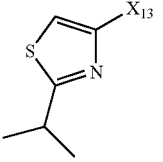 |  | 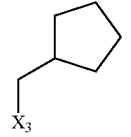 |
| 441 | E | 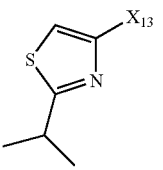 |  | 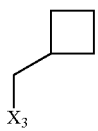 |
| 442 | A | 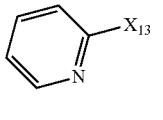 |  | 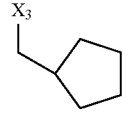 |
| 443 | A | 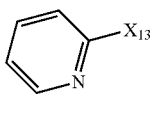 |  | 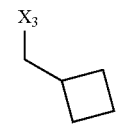 |
| 444 | A | 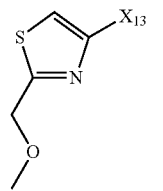 | 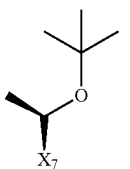 | 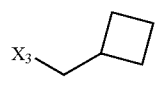 |
| 445 | A | 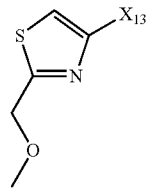 | 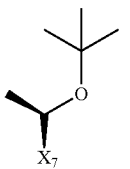 | 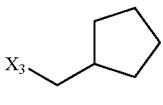 |
| 446 | A | 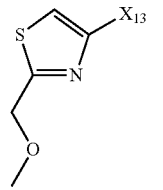 | 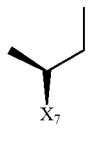 | 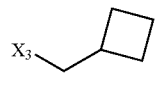 |
| 447 | A | 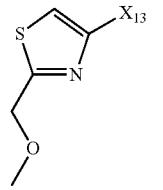 | 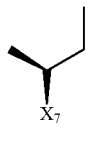 | 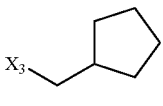 |

TABLE 10-continued

| 448 | A | 2-methylthiazol-4-yl (X13) | isopropyl (X2) | cyclobutylmethyl (X3) |
| 449 | A | 2-methylthiazol-4-yl (X13) | sec-butyl (X7) | isobutyl (X3) |
| 450 | A | 2-methylthiazol-4-yl (X13) | sec-butyl (X7) | cyclobutylmethyl (X3) |
| 451 | A | 2-methylthiazol-3-yl (X13) | (S)-1-(tert-butoxy)ethyl (X7) | isobutyl (X3) |
| 452 | A | 2-methylthiazol-4-yl (X13) | (S)-1-(tert-butoxy)ethyl (X7) | cyclobutylmethyl (X3) |
| 453 | A | 3-nitrophenyl (X13) | sec-butyl (X7) | isobutyl (X3) |
| 454 | A | 2-(methoxycarbonylamino)thiazol-4-yl (X13) | sec-butyl (X7) | isobutyl (X3) |
| 455 | A | 2-(methoxymethyl)thiazol-4-yl (X13) | isopropyl (X2) | cyclobutylmethyl (X3) |
| 456 | A | 2-acetamidothiazol-4-yl (X13) | sec-butyl (X7) | cyclobutylmethyl (X3) |
| 457 | A | pyridin-3-yl (X13) | sec-butyl (X7) | isobutyl (X3) |

TABLE 10-continued
| 458 | A | 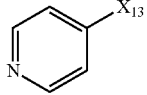 | 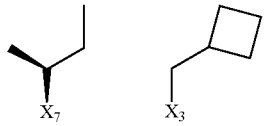 | 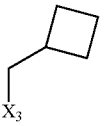 |
| --- | --- | --- | --- | --- |
| 459 | A | 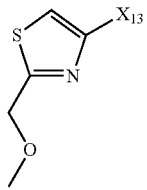 | 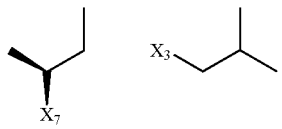 | 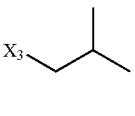 |
| 460 | A | 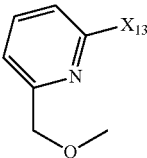 |  | 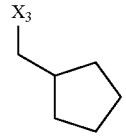 |
| 461 | A | 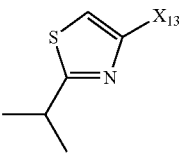 | 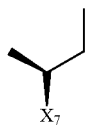 | 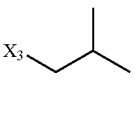 |
| 462 | A | 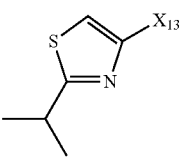 | 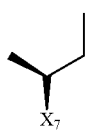 | 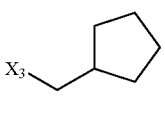 |
| 463 | A | 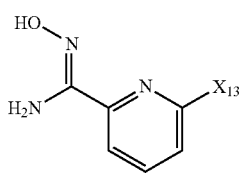 | 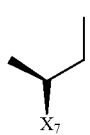 | 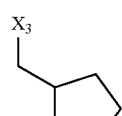 |
| 464 | A | 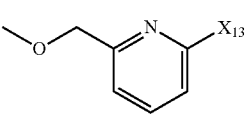 |  | 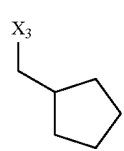 |
| 465 | A | 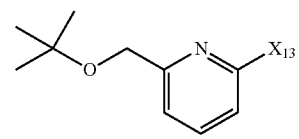 |  | 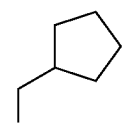 |

Example 466

(2S,3R)—N-{(1S,2R)-1-benzyl-3-[(cyclobutylmethyl)({4-[(E)-(hydroxyimino)methyl]phenyl}sulfonyl)amino]-2-hydroxypropyl}-3-hydroxy-2-({[{[2-(methoxymethyl)-1,3-thiazol-4-yl]methyl}(methyl)amino]carbonyl}amino)butanamide Example 444 (57 mg, 0.073 mmol) was treated with trifluoroacetic acid:dichloromethane (4 mL, 1:1) at 25° C. for 1 h. The solvents were evaporated and the crude solid was triturated with ethyl acetate:hexanes 1:5 to give 53 mg (99%) of the title compound.

Example 467

(2S,3R)—N-{(1S,2R)-1-benzyl-3-[(cyclopentylmethyl)({4-[(E)-(hydroxyimino)methyl]phenyl}sulfonyl)amino]-2-hydroxypropyl}-3-hydroxy-2-({[{[2-(methoxymethyl)-1,3-thiazol-4-yl]methyl}(methyl)amino]carbonyl}amino)butanamide Example 445 (41 mg, 0.051 mmol) was dissolved in dichloromethane:trifluoroacetic acid (4 mL, 1:1) at 25° C. for 1 h. The solvents were evaporated and the mixture was triturated with hexanes to precipitate 38 mg (100%) of the title compound.

Example 468

(2S,3S)-2-({[(3-aminobenzyl)(methyl)amino]carbonyl}amino)-N-{(1S,2R)-1-benzyl-2-hydroxy-3-[({4-[(E)-(hydroxyimino)methyl]phenyl}sulfonyl)(isobutyl)amino]propyl}-3-methylpentanamide Example 453 (19 mg, 0.026 mmol) was dissolved in ethyl acetate (1 mL) and treated with 10% Pd/C (6 mg) at 25° C. for 3.5 h. The catalyst was filtered and the solvents were evaporated. The crude residue was purified using 5% methanol/chloroform to give 17 mg (94%) of the title compound.

Example 469

(2S,3R)—N-{(1S,2R)-1-benzyl-2-hydroxy-3-[({4-[(E)-(hydroxyimino)methyl]phenyl}sulfonyl)(isobutyl)amino]propyl}-3-hydroxy-2-[({methyl[(2-methyl-1,3-thiazol-4-yl)methyl]amino}carbonyl)amino]butanamide Example 451 (25 mg) was dissolved in dichloromethane (2 mL) was treated with trifluoroacetic acid (2 mL) and stirred at 25° C. for 1 h. The solvents were evaporated. The residue was partitioned with saturated NaHCO₃ and chloroform, and the organic layer was dried over Na₂SO₄ and evaporated to give 20 mg (98%) of the title compound.

Example 470

(2S,3R)—N-{(1S,2R)-1-benzyl-3-[(cyclobutylmethyl)({4-[(E)-(hydroxyimino)methyl]phenyl}sulfonyl)amino]-2-hydroxypropyl}-3-hydroxy-2-[({methyl[(2-methyl-1,3-thiazol-4-yl)methyl]amino}carbonyl)amino]butanamide Example 452 was treated in a similar manner as in Example 469 to give the title compound.

Example 471

(2S,3S)-2-({[{[2-(aminomethyl)-1,3-thiazol-4-yl]methyl}(methyl)amino]carbonyl}amino)-N-{(1S,2R)-1-benzyl-2-hydroxy-3-[({4-[(E)-(hydroxyimino)methyl]phenyl}sulfonyl)(isobutyl)amino]propyl}-3-methylpentanamide

Example 471A tert-butyl 2-amino-2-thioxoethylcarbamate

Boc-glycine (2.34 g, 0.134 mmol) was dissolved in dichloromethane (130 mL) and treated with Lawesson's reagent (2.9 g, 0.52 equivalents) and the mixture was stirred at 25° C. for 16 h. The mixture was filtered and the solvents were evaporated. The residue was purified using dichloromethane:ethyl acetate (1:1) to give 2.56 g (100%) of the thioamide.

Example 471B tert-butyl{4-[(methylamino)methyl]-1,3-thiazol-2-yl}methylcarbamate Example 471A (0.5 g) was dissolved in isopropanol (10 mL) and treated with dichloroacetone (0.33 g, 1 equivalent) and the mixture was stirred at 25° C. for 16 h. The solvents were evaporated, and the crude residue was dissolved in isopropanol (2 mL) and treated with 40% methylamine in water (5 mL, 25 equivalents). The solvents were evaporated, and the residue was partitioned between ethyl acetate and sat NaHCO₃. The organic layer was separated, dried over MgSO₄, filtered, and the solvents were evaporated to give 0.48 g of the title compound.

Example 471C methyl(2S,3S)-2-({[[(2-{[(tert-butoxycarbonyl)amino]methyl}-1,3-thiazol-4-yl)methyl](methyl)amino]carbonyl}amino)-3-methylpentanoate Example 471B (0.48 g) was dissolved in tetrahydrofuran (10 mL) and treated with triethyl amine (0.78 mL, 3 equivalent), DMAP (34 mg, 15 mol %) followed by Example 406 (0.7 g, 1.2 equivalent) and the mixture was heated to 66° C. for 16 h. The mixture was partitioned between ethyl acetate and saturated NaHCO₃, the organic layer was separated, washed with brine and dried over MgSO₄, filtered, and the solvents were evaporated. The residue was purified using ethyl acetate to give 0.37 g (46%) of the title compound.

Example 471D (2S,3S)-2-({[[(2-{[(tert-butoxycarbonyl)amino]methyl}-1,3-thiazol-4-yl)methyl](methyl)amino]carbonyl}amino)-3-methylpentanoic acid Example 471C (0.37 g) was dissolved in tetrahydrofuran:water (4 mL, 3:1) and treated with LiOH (0.11 g, 3 equivalents) and the mixture was stirred at 25° C. for 30 min. The mixture was quenched with 1N HCl (2.75 mL) and partitioned between ethyl acetate and brine, the organic layer was

Example 471E tert-butyl (4-{(5S,8S,9R)-8-benzyl-9-hydroxy-11-({4-[(E)-(hydroxyimino)methyl]phenyl}sulfonyl)-2,13-dimethyl-5-[(1S)-1-methylpropyl]-3,6-dioxo-2,4,7,11-tetraazatetradec-1-yl}-1,3-thiazol-2-yl)methylcarbamate Example 471D (35 mg) was dissolved in N,N-dimethylformamide (0.85 mL) and treated with EDAC (25 mg, 1.5 equivalents), HOBT (17 mg, 1.5 equivalents), N-methylmorpholine (10 µL, 1.1 equivalents) followed by Example 18 (35 mg, 1 equivalent), and the mixture was stirred at 25° C. for 16 h. The solvents were evaporated and the residue was purified by HPLC reverse phase chromatography using water (0.1% trifluoroacetic acid):acetonitrile (95:5) to acetonitrile (100%) to give 74 mg (100%) of the title compound.

Example 471F tert-butyl (4-{(5S,8S,9R)-8-benzyl-9-hydroxy-11-({4-[(E)-(hydroxyimino)methyl]phenyl}sulfonyl)-2,13-dimethyl-5-[(1S)-1-methylpropyl]-3,6-dioxo-2,4,7,11-tetraazatetradec-1-yl}-1,3-thiazol-2-yl)methylcarbamate Example 471E was dissolved in dichloromethane (2 mL) and trifluoroacetic acid (2 mL) and stirred at 25° C. for 30 min. The solvents were evaporated, and the residue was purified by HPLC reverse phase chromatography using water (0.1% trifluoroacetic acid):acetonitrile (95:5) to acetonitrile (100%) to give 61 mg (81%) of the title compound.

Example 472

(2S,3S)-2-({[{[2-(aminomethyl)-1,3-thiazol-4-yl]methyl}(methyl)amino]carbonyl}amino)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide Example 472 was prepared as for Example 471F using Example 471D and Example 19 followed by deprotection as in Example 471F to give the title compound.

Example 473

(2S,3S)-2-({[{[2-(aminomethyl)-1,3-thiazol-4-yl]methyl}(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide Example 473 was prepared as for Example 471F using Example 471D and Example 27 followed by deprotection as in Example 471F to give the title compound.

Example 474

(2S,3S)-2-({[({2-[(1S)-1-aminoethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide

Example 474A tert-butyl (1S)-2-amino-1-methyl-2-oxoethylcarbamate

To a solution containing Boc-L-alanine (1.0 g, 5.29 mmol) in a mixture of tetrahydrofuran (25 mL) and N,N-dimethylformamide (5 mL) were added EDAC (1.5 g, 7.82 mmol) and N-hydroxysuccinimide (0.91 g, 7.91 mmol) and the mixture was stirred at room temperature for 16 hours. Aqueous ammonium hydroxide solution (15 mL, 28%) was added and the mixture was stirred for 0.5 hours at room temperature. The reaction was partitioned between ethyl acetate and water, and the organic was washed with brine and dried over MgSO$_4$, filtered and evaporated to give the product (0.483 g, 49% yield), which was used without further purification.

Example 474B tert-butyl(1S)-2-amino-1-methyl-2-thioxoethylcarbamate

To Example 474A (0.48 g, 2.55 mmol) in dichloromethane (25 mL) was added Lawesons Reagent (0.54 g, 1.34 mmol), and the mixture was stirred at room temperature for 16 hours. The solvent was evaporated and the residue was purified using dichloromethane-35% ethyl acetate in dichloromethane to give the product (0.52 g, 100% yield).

Example 474C ethyl 2-{(1S)-1-[(tert-butoxycarbonyl)amino]ethyl}-1,3-thiazole-4-carboxylate To Example 474B (0.914 g, 4.48 mmol) in DME (7 mL) at −20° C. were added pulverized KHCO$_3$ (3.55 g, 35.46 mmol) and ethyl bromopyruvate (1.65 mL, 13.15 mmol), and the mixture was stirred at −20° C. for 1 hour. A solution of trifluoroacetic anhydride (2.5 ml, 17.70 mmol) and 2,6-lutidine (4.4 mL, 37.78 mmol) in dimethylether (4.5 mL) was added to the reaction at −20° C. and the reaction was stirred at that temperature for 2 hours. The reaction was poured into water and was partitioned between ethyl acetate and water, and the organic was washed with brine and dried over MgSO$_4$, filtered and evaporated. The residue was purified using dichloromethane-15% ethyl acetate in dichloromethane to give the product (1.26 g, 94% yield).

Example 474D tert-butyl (1S)-1-{4-[(methylamino)methyl]-1,3-thiazol-2-yl}ethylcarbamate To Example 474C (0.50 g, 1.67 mmol) in a mixture of tetrahydrofuran (15 mL) and methanol (1 mL) was added LiBH$_4$ (0.15 g, 6.89 mmol) and the mixture was stirred at room temperature for 5 hours. The reaction was partitioned between dichloromethane and water, and the organic was washed with brine and dried over MgSO$_4$, filtered and evaporated. To a solution of this product (1.67 mmol) were added triethylamine (0.70 mL, 5.02 mmol) and methanesulfonyl chloride (0.195 mL, 2.52 mmol) at 0° C. and the reaction was stirred at this temperature for 0.5 hours. The reaction was partitioned between dichloromethane and water, and the organic was washed with brine and dried over MgSO$_4$, filtered and evaporated to give the crude mesylate. To an aqueous solution of methylamine (5 mL, 40%) was added a solution of the mesylate (1.67 mmol) in 2-propanol (2 mL) and the mixture was stirred at room temperature for 1.5 hours. The solvent was removed under reduced pressure to give the product (0.305 g), which was used without further purification.

Example 474F methyl(2S,3S)-2-({[[(2-{(1S)-1-[(tert-butoxycarbonyl)amino]ethyl}-1,3-thiazol-4-yl)methyl](methyl)amino]carbonyl}amino)-3-methylpentanoate Example 474D (0.305 g, 1.13 mmol) was dissolved in tetrahydrofuran (6 mL) and treated with Example 406 (0.525 g, 1.69 mmol), triethylamine (0.47 mL, 3.37 mmol), and DMAP (0.020 g, 0.16 mmol), at room temperature and the mixture was stirred at 80° C. for 16 hours. The reaction was cooled and partitioned between ethyl acetate and saturated NaHCO$_3$, and the organic was washed with brine and dried over MgSO$_4$, filtered and evaporated. The residue was purified using dichloromethane-ethyl acetate to give the product (0.344 g, 69% yield).

Example 474G (2S,3S)-2-({[[(2-{(1S)-1-[(tert-butoxycarbonyl)amino]ethyl}-1,3-thiazol-4-yl)methyl](methyl)amino]carbonyl}amino)-3-methylpentanoic acid To Example 474F (0.344 g, 0.778 mmol) in dioxane (3 mL) was added an aqueous solution of lithium hydroxide (3.0 mL, 0.5 M), and the reaction was stirred for 0.5 hours at room temperature. Aqueous HCl (1.62 mL, 1 N) was added and the reaction was partitioned between ethyl acetate and water, and the organic was washed with brine and dried over MgSO$_4$, filtered and evaporated to give the product, which was used without further purification.

Example 474H tert-butyl (1S)-1-(4-{(5S,8S,9R)-8-benzyl-12-cyclopentyl-9-hydroxy-11-({4-[(E)-(hydroxyimino)methyl]phenyl}sulfonyl)-2-methyl-5-[(1S)-1-methylpropyl]-3,6-dioxo-2,4,7,11-tetraazadodec-1-yl}-1,3-thiazol-2-yl)ethylcarbamate Example 474G (35 mg) was dissolved in N,N-dimethylformamide (0.85 mL) and treated with EDAC (25 mg, 1.5 equivalents), HOBT (17 mg, 1.5 equivalents), N-methylmorpholine (10 μL, 1.1 equivalents) followed by Example 27 (35 mg, 1 equivalent), and the mixture was stirred at 25° C. for 16 h. The solvents were evaporated and the residue was purified by HPLC reverse phase chromatography using water (0.1% trifluoroacetic acid):acetonitrile (95:5) to acetonitrile (100%) to give 74 mg (100%) of the title compound.

Example 474I (2S,3S)-2-({[({2-[(1S)-1-aminoethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide Example 474H was dissolved in dichloromethane (2 mL) and trifluoroacetic acid (2 mL) and stirred at 25° C. for 30 min. The solvents were evaporated, and the residue was purified by HPLC reverse phase chromatography using water (0.1% trifluoroacetic acid):acetonitrile (95:5) to acetonitrile (100%) to give 61 mg (81%) of the title compound.

Example 475

(2S,3S)-2-({[({2-[(1R)-1-aminoethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide In a similar manner to Example 474 but starting with Boc-(D)-alanine, Example 475 was prepared via coupling and deprotection.

Example 476

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[({6-[N-hydroxyethanimidoyl]-2-pyridinyl}methyl)(methyl)amino]carbonyl}amino)-3-methylpentanamide

Example 476A

1-[6-(hydroxymethyl)-2-pyridinyl]ethanone

The title compound was prepared according to the procedure as described in Katsura, Y. et. al., *Journal of Medicinal Chemistry*, 37, 57-66 (1994).

Example 476B

1-[6-(chloromethyl)-2-pyridinyl]ethanone

To Example 476A (0.23 g, 1.52 mmol) in N,N-dimethylformamide (2 mL) at 0° C. was treated phosphorus oxychloride (0.283 mL, 3.04 mmol). The mixture was stirred 3 hours at 0° C., quenched with 1M sodium bicarbonate, and extracted with ethyl acetate. The organic layer was evaporated, and the residued was purified using 10% ethyl acetate/hexane to give 86 mg (33.4%) of the title compound.

Example 476C

1-{6-[(methylamino)methyl]-2-pyridinyl}ethanone

Example 476B (86 mg, 0.5 mmol) at 25° C. was treated with 2 M methylamine in tetrahydrofuran (2 mL, 4 mmol). The reaction was stirred at 25° C. for 16 hour, the solvent was concentrated and the residue was purified using 10% methanol/dichloromethane with 0.5% ammonium hydroxide to give 53 mg (72.6%) of the title compound.

Example 476D tert-butyl (2S,3S)-2-({[[(6-acetyl-2-pyridinyl)methyl](methyl)amino]carbonyl}amino)-3-methylpentanoate To Example 476C (50 mg, 0.3 mmol), Example 406 (107 mg, 0.3 mmol) in N,N-dimethylformamide (2 mL) at 25° C. was treated with diisopropylethylamine (64 µL, 0.36 mmol) followed by N,N-dimethylaminopyridine (5.2 mg, 0.042 mmol). The mixture was stirred for 16 hour, quenched with 1M sodium bicarbonate, and extracted with ethyl acetate. The organic layer was evaporated, and the residued was purified using 30% ethyl acetate/hexane to give 97 mg (84.4%) of the title compound.

Example 476E (2S,3S)-2-({[[(6-acetyl-2-pyridinyl)methyl](methyl)amino]carbonyl}amino)-3-methylpentanoic acid Example 476D (97 mg, 0.257 mmol) at 25° C. was treated with 80% trifluoroacetic acid in dichloromethane (1.5 mL). The reaction was stirred at 25° C. for 3 hour, the solvent was concentrated and the residue was dissolved in water (0.5 mL) and purified using 7% methanol/dichloromethane to give 100 mg (89.3%) of the title compound.

Example 476F (2S,3S)-2-({[[(6-acetyl-2-pyridinyl)methyl](methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide Example 476E (99 mg, 0.31 mmol) was dissolved in N,N-dimethylformamide (3 mL) and combined with EDAC (88 mg, 1.5 equivalents), HOBT (62 mg, 1.5 equivalents), and N methylmorpholine (34 µL, 1 equivalent) followed by addition of Example 27 (164 mg, 1.2 equivalents). The mixture was stirred for 4 d at 25° C., quenched with 1N NaHCO$_3$, and extracted with ethyl acetate. The solvents were evaporated and the residue was purified using 5% methanol/dichloromethane to give 84 mg (47%) of the ketone.

Example 476G (2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-({[({6-[N-hydroxyethanimidoyl]-2-pyridinyl}methyl)(methyl)amino]carbonyl}amino)-3-methylpentanamide Example 476F (75 mg) was dissolved in methanol (2 mL) and combined with hydroxylamine hydrochloride (14 mg, 2 equivalents). The mixture was stirred at 25° C. for 16 h. The solvents were evaporated and the residue was purified using 10% methanol/dichloromethane to give 54 mg (70%) of the title compound.

Example 477

(2S,3S)-2-({[({2-[(1S)-1-(acetylamino)ethyl]-1,3-thiazol-4-yl}methyl)(methyl)amino]carbonyl}amino)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide Example 474I (0.87 g) was dissolved in dichloromethane (0.2 mL) and treated with triethyl amine (3.2 µL, 2 equivalents) and acetic anhydride (1.3 µL, 1.2 equivalents), and the mixture was stirred at 25° C. for 3 h. The solvents were evaporated, and the residue was purified by HPLC reverse phase chromatography using water (0.1% trifluoroacetic acid):acetonitrile (95:5) to acetonitrile (100%) to give 11.3 mg (100%) of the title compound.

Example 478 tert-butyl (1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropylcarbamate

Method D (L)-Boc-t-leucine (55 mg, 0.024 mmol) was dissolved in tetrahydrofuran (10 mL) and treated with triethyl amine (66 µL, 2 equivalents), 3-(diethylphosphoryloxy)-1,2,3-benzotriazin-4(3H)-one (DEPBT) (86 mg, 1.2 equivalents), and Example 18 (0.1 g, 1 equivalent) at 25° C. for 16 h. The mixture was partitioned between ethyl acetate and 10% Na$_2$CO$_3$, the organic layer was separated, washed with water, brine, dried over Na$_2$S$_O$, and the solvents were evaporated. The residue was purified using ethyl acetate:hexanes (1:2) to give 0.114 g (76%) of the title compound. $^1$H NMR (300 MHz, CDCl$_3$) δ ppm 0.87 (m, 15H), 1.42 (s, 9H), 1.85 (m, 1H), 2.84 (m, 1H), 2.95 (m, 1H), 3.02 (m, 1H), 3.13 (m, 1H), 3.69 (d, J=8.46 Hz, 1H), 3.85 (m, 2H), 4.12 (q, J=7.11 Hz, 1H), 4.19 (m, 1H), 4.94 (s, 1H), 6.00 (d, J=8.46 Hz, 1H), 7.22 (m, 5H), 7.70 (d, J=8.82 Hz, 2H), 7.76 (d, J=8.46 Hz, 2H), 8.16 (s, 1H).

Example 479 hexahydrofuro[2,3-b]furan-3-yl(1S,2R)-1-benzyl-2-hydroxy-3-[({4-[(E)-(hydroxyimino)methyl]phenyl}sulfonyl)(isobutyl)amino]propylcarbamate

Example 479A hexahydrofuro[2,3-b]furan-3-yl 4-nitrophenyl carbonate

To a solution of (3S,3aR,6aS)- and (3R,3aS,6aR)-3-hydroxy-4H-hexahydrofuro[2,3-b]furan (see compound 15 in: Gosh, A. K.; Kincaid, J. F.; Walters, D. E.; Chen, Y.; Chaudhuri, N. C.; Thompson, W. J.; Culberson, C.; Fitzgerald, P. M. D.; Lee. H. Y.; McKee, S. P.; Munson, P. M.; Duong, T. T.; Darke, P. L.; Zugay, J. A.; Schleif, W. A.; Axel, M. G.; Lin, J.; Huff, J. R. *Journal of Medicinal Chemistry* 1996, 39, 3278-3290.) (1.5 g, 11.5 mmol) in dichloromethane (40 mL) at 0° C. were added N-methylmorpholine (1.9 mL, 17.3 mmol) and 4-nitrophenyl chloroformate (2.9 g, 14.4 mmol), and the mixture was stirred for 16 hours at 0° C. The solvent was evaporated under reduced pressure and the residue was chromatographed on silica gel, eluting with 25% ethyl acetate in hexanes to give the product (291 g, 86% yield).

Example 479B hexahydrofuro[2,3-b]furan-3-yl(1S,2R)-1-benzyl-2-hydroxy-3-[({4-[(E)-(hydroxyimino)methyl]phenyl}sulfonyl)(isobutyl)amino]propylcarbamate Method F Example 479A (10.6 mg, 0.036 mmoles, 1.5 equivalents) was combined with Example 18 (10 mg, 0.024 mmoles) in tetrahydrofuran (0.5 mL) at 25° C. for 24 h. The solvent was evaporated under vacuum, and the residue was purified using 2% methanol/dichloromethane to give 10.9 mg (80% yield) of the title compound. $^1$H NMR (300 MHz, CDCl$_3$) δ ppm 0.87 (dd, J=6.44, 3.73 Hz, 3H), 0.93 (m, 3H), 1.84 (s, 2H), 2.85 (m, 2H), 3.01 (m, 3H), 3.16 (m, 1H), 3.59 (dd, J=9.66, 6.61 Hz, 1H), 3.69 (m, 1H), 3.85 (m, 3H), 3.96 (m, 2H), 4.93 (dd, J=16.95, 8.14 Hz, 1H), 5.01 (s, 1H), 5.66 (m, 1H), 7.27 (m, 5H), 7.55 (d, J=2.03 Hz, 1H), 7.72 (d, J=8.48 Hz, 2H), 7.78 (m, 2H), 8.16 (s, 1H).

The compounds listed in Table 11, wherein $X_3$ and $X_5$ represent respectively the points of connection to the core structure (I), were prepared by coupling available activated acids and carbonates with Examples 1-31 as exemplified in Example 434 (Method A) or Example 162 (Method 131, Example 435 (Method E), or Example 479 (Method F).

TABLE 11

| Ex. | Method | $R_5$ | $R_3$ |
|---|---|---|---|
| 480 | F | tetrahydrofuran-3-yl-O-X$_5$ | X$_3$-isobutyl |
| 481 | A | benzyl-O-C(O)-NH-CH(C(O)NH$_2$)-X$_5$ | X$_3$-isobutyl |
| 482 | A | methyl-O-C(O)-NH-CH(t-Bu)-X$_5$ | X$_3$-isobutyl |
| 483 | B | —X$_5$ | X$_3$-isobutyl |
| 484 | A | pyridin-2-yl-CH$_2$-O-C(O)-NH-CH(iPr)-X$_5$ | X$_3$-isobutyl |
| 485 | A | pyridin-2-yl-CH$_2$-O-C(O)-NH-CH(iPr)-X$_5$ | X$_3$-isobutyl |

TABLE 11-continued

[Structure I: R5-C(=O)-NH-CH(CH2-Ph)-CH(OH)-CH2-N(R3)-SO2-C6H4-CH=NOH]

| Ex. | Method | R5 | R3 |
|---|---|---|---|
| 486 | A | 2,6-dimethylphenyl-O-CH2-X5 | X3-CH2-CH(CH3)2 |
| 487 | A | Ph-CH2-O-C(=O)-NH-CH(iPr)-X5 | X3-CH2-CH(CH3)2 |
| 488 | A | Ph-CH2-O-C(=O)-NH-CH(CH(OH)CH3)-X5 | X3-CH2-CH(CH3)2 |
| 489 | F | hexahydrofuro[2,3-b]pyran-3-yl-O-X5 | X3-CH2-CH(CH3)2 |
| 490 | F | furan-3-yl-CH2-O-X5 | X3-CH2-CH(CH3)2 |
| 491 | A | pyridin-2-yl-CH2-O-C(=O)-NH-CH2-X5 | X3-CH2-CH(CH3)2 |
| 492 | E | tBu-O-C(=O)-NH-CH(sec-Bu)-X5 | X3-CH2-CH(CH3)2 |
| 493 | E | Ph-C(=O)-NH-CH(sec-Bu)-X5 | X3-CH2-CH(CH3)2 |

TABLE 11-continued
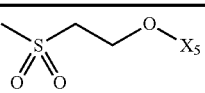
| Ex. | Method | R₅ | R₃ |
|---|---|---|---|
| 494 | E | 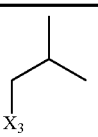 | 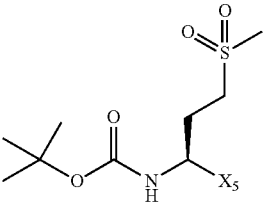 |
| 495 | A | 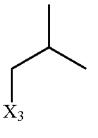 | 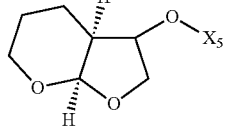 |
| 496 | F | 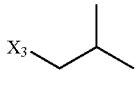 | 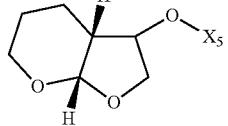 |
| 497 | F | 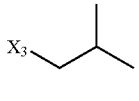 | 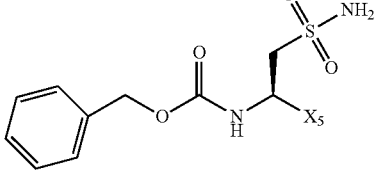 |
| 498 | A |  | 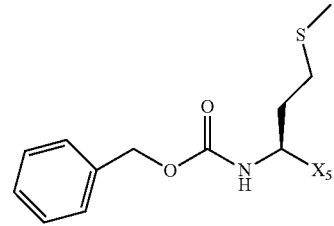 |
| 499 | E |  | 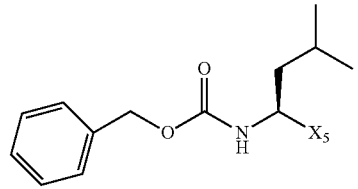 |
| 500 | A |  | |

TABLE 11-continued
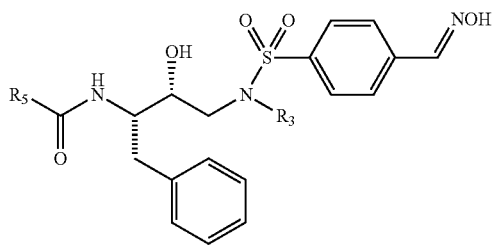
I
| Ex. | Method | R$_5$ | R$_3$ |
|---|---|---|---|
| 501 | A | 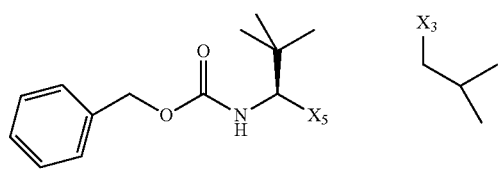 | X$_3$ |
| 502 | A | 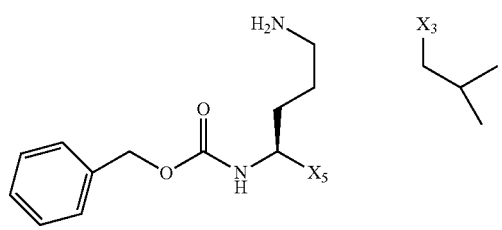 | X$_3$ |
| 503 | A | 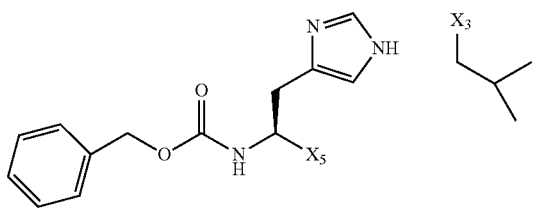 | X$_3$ |
| 504 | E | 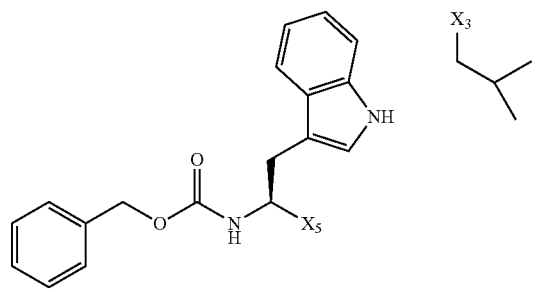 | X$_3$ |
| 505 | A | 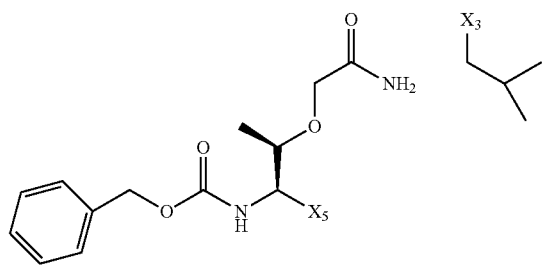 | X$_3$ |

TABLE 11-continued

| Ex. | Method | R5 | R3 |
|---|---|---|---|
| 506 | A | (methyl ester, Cbz-protected amino acid with X5) | X3 isobutyl |
| 507 | A | (2-pyridylmethyl carbamate of (S)-2-methylbutyl-X5) | X3 cyclopentylmethyl |
| 508 | A | (6-(methoxymethyl)-2-pyridylmethyl carbamate of (S)-2-methylbutyl-X5) | X3 cyclopentylmethyl |
| 509 | A | (6-(methoxymethyl)-2-pyridylmethyl carbamate of tert-butyl-X5) | X3 cyclopentylmethyl |
| 510 | F | (3-pyridyl-CH2-O-X5) | X3 isobutyl |
| 511 | F | (4-pyridyl-CH2-O-X5) | X3 isobutyl |
| 512 | F | (thiazol-5-yl-CH2-O-X5) | X3 isobutyl |

Example 513

(2S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide

Example 513A methyl(2S)-2-[(chloroacetyl)amino]-3,3-dimethylbutanoate (L)-methyl t-leucinate hydrochloride (1 g) was dissolved in ethyl acetate (6 mL) and water (4 mL) and treated with $K_2CO_3$ (1.66 g, 3 equivalents) followed by chloroacetyl chloride (0.53 mL, 1.2 equivalents) at 25° C. for 2 h. The organic layer was separated, washed with 10% citric acid, and the solvents were evaporated. The residue was purified by ethyl acetate:hexanes (1:4) to give 1.22 g (100%) of the chloro ester.

Example 513B methyl(2S)-2-({[(3-fluorobenzyl)amino]acetyl}amino)-3,3-dimethylbutanoate Example 513A (1.22 g) was dissolved in tetrahydrofuran (5 mL) and treated with 3-fluorobenzyl amine (1.9 mL, 3 equivalents) at 60° C. for 16 h. The solvents were evaporated and the residue partitioned between 1N $NaHCO_3$ and ethyl acetate. The organic layer was separated and purified using ethyl acetate:hexanes (3:2) to give 1.22 g (71%) of the title compound.

Example 513C methyl(2S)-2-({[(tert-butoxycarbonyl)(3-fluorobenzyl)amino]acetyl}amino)-3,3-dimethylbutanoate Example 513B (1.22 g) was dissolved in dioxane (14 mL) and treated with 1N $NaHCO_3$ (9 mL, 2.3 equivalents) followed by $Boc_2O$ (1.11 g, 1.3 equivalents) at 25° C. for 16 h. The mixture was partitioned between water and ethyl acetate, the organic layer separated, and the solvents were evaporated. The residue was purified using ethyl acetate:hexanes (1:4) to give 1.55 g (96%) of the protected amine.

Example 513D 2-({[(tert-butoxycarbonyl)(3-fluorobenzyl)amino]acetyl}amino)-3,3-dimethylbutanoic acid Example 513C (1 g) was dissolved in tetrahydrofuran (6 mL) and treated with LiOH (0.133 g, 1.3 equivalents) in water (3 mL) at 0° C. for 16 h. The solvents were evaporated, and the residue was partitioned between water and ethyl acetate. The aqueous layer was separated, acidified with 10% citric acid to pH 2-3, and extracted with ethyl acetate. The organic layer was separated, and the solvents were evaporated. The residue was purified using 10% methanol/dichloromethane to give 0.9 g (93%) of the acid as epimers at the alpha center which were not separable.

Example 513E tert-butyl 2-({(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropyl}amino)-2-oxoethyl(3-fluorobenzyl)carbamate Example 513D (0.125 g) was dissolved in N,N-dimethylformamide (2 mL) and treated with EDAC (82 mg, 1.5 equivalents), HOBT (58 mg, 1.5 equivalents), followed by Example 18 (0.12 g, 0.9 equivalent) at 25° C. for 3 d. The mixture was partitioned between 1N $NaHCO_3$ and ethyl acetate. The organic layer was separated, and the solvents were evaporated. The residue was separated using ethyl acetate:hexanes (1:1) to give 0.21 g of Example 514E and 0.36 g of Example 513E.

Example 513F (2S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide Example 513E (0.105 g) was dissolved in 80% trifluoroacetic acid (3 mL) at 25° C. for 2 h. The solvents were evaporated, and the residue was purified using 10% methanol/ethyl acetate w/0.5% $NH_4OH$ to give 53 mg (58%) of the title compound.

Example 514

(2R)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide

Example 514E tert-butyl 2-({(1R)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2,2-dimethylpropyl}amino)-2-oxoethyl(3-fluorobenzyl)carbamate

Example 514F (2R)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3,3-dimethylbutanamide Example 514E (0.11 g) was deprotected as for Example 513F to give 74 mg (81%) of the title compound.

Example 515

(2S,3S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3-methylpentanamide

Example 515A

N-Boc-glycyl-(L)-isoleucine (0.5 g) was dissolved in tetrahydrofuran (25 mL) and treated with $Boc_2O$ (0.64 g, 1.1 equivalents) and 1N NaOH (2.66 mL, 1 equivalent) at 25° C. for 2 h. The mixture was partitioned between NaHCO₃ and dichloromethane. The aqueous layer was separated, acidified with 10% citric acid, and extracted with dichloromethane. The organic layer was separated, dried with MgSO4, filtered, and the solvents were evaporated to give 0.3 g (39%) of the Boc compound.

Example 515B tert-butyl 2-({(1S,2S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-2-methylbutyl}amino)-2-oxoethylcarbamate Example 515A (34 mg) was dissolved in N,N-dimethylformamide (3 mL) and treated with EDAC (25 mg, 1.1 eq), HOBT (18 mg, 1.1 equivalents), and Example 18 (50 mg, 1 equivalent) at 25° C. for 16 h. The mixture was partitioned dichloromethane and 1N NaHCO₃, the organic layer was separated, dried over MgSO₄, and the solvents were evaporated. The residue was purified using ethyl acetate:hexanes (2:1) to give 67 mg (82%) of the amide.

Example 515C (2S,3S)-2-[(aminoacetyl)amino]-N-{(1S,2R)-1-benzyl-2-hydroxy-3-[({4-[(E)-(hydroxyimino)methyl]phenyl}sulfonyl)(isobutyl)amino]propyl}-3-methylpentanamide Example 515B (0.44 g) was dissolved in dichloromethane (2 mL) and trifluoroacetic acid (8 mL) at 25° C. for 2.5 h. The solvents were evaporated, and the residue was dissolved in dichloromethane, washed with 0.5N NH₄OH, dried with MgSO4, filtered, and the solvents were evaporated to give 0.378 g (100%) of the title compound.

Example 515D (2S,3S)—N-{(1S,2R)-1-benzyl-2-hydroxy-3-[({4-[(E)-(hydroxyimino)methyl]phenyl}sulfonyl)(isobutyl)amino]propyl}-2-({[(3-fluorobenzyl)amino]acetyl}amino)-3-methylpentanamide Example 515C (12 mg) was dissolved in methanol (1 mL) and benzene (1 mL) and treated with 3-fluorobenzaldehyde (2.2 µL, 1 equivalent), and this mixture is heated to 50° C. for 1.5 h. The mixture is cooled and treated with NaBH₄ (3.8 mg, 5 equivalents) at 25° C. for 1 h. The mixture was quenched with water and dichloromethane, the organic layer was separated, dried with MgSO4, filtered, and the solvents were evaporated. The residue was purified using ethyl acetate with 1% NH₄OH to give 4.7 mg (33%) of the title compound.

Example 517

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[({[(5-nitro-3-thienyl)methyl]amino}acetyl)amino]pentanamide In a similar manner to Example 515D, the title compound was prepared by coupling 2-nitrothiophene-3-carboxaldehyde with Example 515C.

Example 518 benzyl(1S)-4-{[amino(imino)methyl]amino}-1-[({(1S,2R)-1-benzyl-2-hydroxy-3-[({4-[(E)-(hydroxyimino)methyl]phenyl}sulfonyl)(isobutyl)amino]propyl}amino)carbonyl]butylcarbamate Example 518A benzyl(1S)-1-[({(1S,2R)-1-benzyl-2-hydroxy-3-[({4-[(E)-(hydroxyimino)methyl]phenyl}sulfonyl)(isobutyl)amino]propyl}amino)carbonyl]-4-[((Z)-[(tert-butoxycarbonyl)amino]{[(Z)-tert-butoxycarbonyl]imino}methyl)amino]butylcarbamate Z-Arginine(Boc)₂OH cyclohexylamine salt (22 mg) was dissolved in water, acidified with 10% citric acid and extracted with ethyl acetate. The organic layer was separated, dried over Na₂SO₄, and the solvents were evaporated to give the free acid. This acid was dissolved in N,N-dimethylformamide (0.5 mL) and treated with EDAC (13.7 mg, 1.5 equivalents), HOBT (9.66 mg, 1.5 equivalents), and N-methylmorpholine (5.3 µL, 1 equivalent) followed by the Example 18 (20 mg, 1 equivalent) at 25° C. for 2 d. The mixture was partitioned between 1N NaHCO₃ and ethyl acetate. The organic layer was separated, and the solvents were evaporated. The residue was purified using 5% ethyl acetate/hexanes to give 21 mg (48%) of the di-Boc compound.

Example 518B benzyl(1S)-4-{[amino(imino)methyl]amino}-1-[({(1S,2R)-1-benzyl-2-hydroxy-3-[({4-[(E)-(hydroxyimino)methyl]phenyl}sulfonyl)(isobutyl)amino]propyl}amino)carbonyl]butylcarbamate Example 518A (21 mg) was dissolved in 80% trifluoroacetic acid (1 mL) at 25° C. for 2 h. The solvents were evaporated and purified by preparative TLC using 0.25 mm plates and 8% methanol/dichloromethane/1% NH₄OH to give 9 mg (55%) of the title compound.

Example 519

(2S)-2-amino-N-{(1S,2R)-1-benzyl-2-hydroxy-3-[({4-[(E)-(hydroxyimino)methyl]phenyl}sulfonyl)(isobutyl)amino]propyl}-3,3-dimethylbutanamide Example 478 was treated with trifluoroacetic acid as for Example 518B to give the title compound.

Example 520

N-{(2R,3S)-2-hydroxy-3-[({4-(hydroxyimino)methyl]phenyl}sulfonyl)amino]-4-phenylbutyl}-4-[(E)-(hydroxyimino)methyl]-N-isobutylbenzenesulfonamide Example 520A (acetyloxy){4-[({(1S,2R)-1-benzyl-2-hydroxy-3-[({4-[(E)-(hydroxyimino)methyl]phenyl}sulfonyl)(isobutyl)amino]propyl}amino)sulfonyl]phenyl}methyl acetate Example 18 (78.6 mg) was dissolved in tetrahydrofuran (1 mL) and N,N-dimethylformamide (0.1 mL) and treated with the product of Example 17 from Part 1 of Method B, (70.5 mg, 1.2 equivalents) and triethyl amine (78 μL, 3 equivalents) at 25° C. for 2 h. The solvents were evaporated, and the residue was purified using dichloromethane to give 87 mg (68%) of the sulfonamide.

Example 520B

N-{(2R,3S)-2-hydroxy-3-[({4-[(hydroxyimino)methyl]phenyl}sulfonyl)amino]-4-phenylbutyl}-4-[(E)-(hydroxyimino)methyl]-N-isobutylbenzenesulfonamide Example 520A (87 mg) was dissolved in ethanol (1.2 mL) and treated with hydroxylamine hydrochloride (19 mg, 1.5 equivalents) and triethyl amine (91 μL, 3.5 equivalents) at 75° C. for 1 h. The solvents were evaporated, and the residue was purified using dichloromethane to give 88 mg (100%) of the title compound.

Example 521

N-[(2R,3S)-3-amino-2-hydroxy-4-phenylbutyl]-N-isobutyl-4-methoxybenzenesulfonamide

Example 521A tert-butyl(1S,2R)-1-benzyl-2-hydroxy-3-{isobutyl[(4-methoxyphenyl)sulfonyl]amino}propylcarbamate To a solution of (2R,3S)-3-N-tert-butoxycarbonylamino-1,2-epoxy-4-phenylbutane (0.2 g, 0.76 mmol) in 2-propanol (4 mL) was added the isobutylamine (1.5 mL, 20 equivalents), and the mixture was heated at 80° C. for 2 hours. The solvents were evaporated, and the crude residue was dissolved in dichloromethane (8 mL) and treated with triethylamine (0.32 mL, 3 equivalents) and p-methoxybenzenesulfonyl chloride (0.173 g, 1.1 equivalents) and the mixture is stirred at 25° C. for 1 h. The solvents were evaporated and the crude residue was purified using 0.5% methanol/dichloromethane to give 0.356 g (92%) of the title compound.

Example 521B

N-[(2R,3S)-3-amino-2-hydroxy-4-phenylbutyl]-N-isobutyl-4-methoxybenzenesulfonamide Example 521A (47 mg, 0.093 mmol) was dissolved in trifluoroacetic acid:dichloromethane (4 mL, 1:1) at 25° C. for 1 h. The solvents were evaporated to give 38 mg (100%) of the title compound.

The compounds listed in Table 12, wherein $X_3$ represents respectively the points of connection to the core structure (J), were prepared by the procedures as exemplified in Example 521A and Example 521B, substituting cyclopentylmethylamine and neopentylamine, respectively, for isobutylamine

TABLE 12

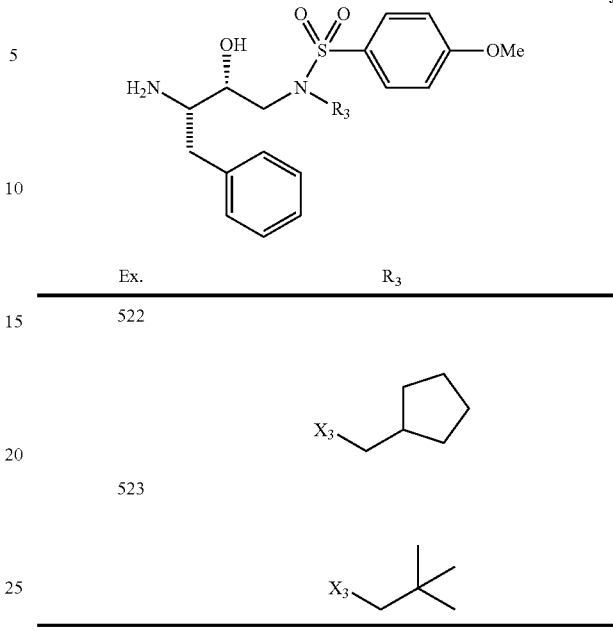

| Ex. | $R_3$ |
|---|---|
| 522 | (cyclopentylmethyl) |
| 523 | (neopentyl) |

Example 524

(2S)—N-((1S,2R)-1-benzyl-2-hydroxy-3-{isobutyl[(4-methoxyphenyl)sulfonyl]amino}propyl)-2-{3-[(2-isopropyl-1,3-thiazol-4-yl)methyl]-2-oxo-1-imidazolidinyl}-3-methylbutanamide

Method C

Example 144 (25 mg) was combined with N-hydroxysuccinimide (10 mg, 1.1 equivalents) and DCC (18 mg, 1.1 equivalents) in dichloromethane (1 mL) and stirred for 1 h at 25° C. The solids are filtered, and to this mixture was added N-methylmorpholine (9 μL, 1 equivalent) and Example 521B (31 mg, 1 equivalent). The mixture was stirred for 16 h, evaporated, and was purified using 1% methanol/chloroform to give 33 mg (60%) of the title compound. $^1$H NMR (300 MHz, DMSO-d$_6$) δ ppm 0.69 (dd, J=10.51, 6.44 Hz, 3H), 0.81 (dd, J=6.61, 2.88 Hz, 3H), 1.30 (d, J=2.37 Hz, 3H), 1.32 (d, J=2.37 Hz, 3H), 1.94 (m, 1H), 2.40 (dd, J=13.73, 11.02 Hz, 1H), 3.04 (m, 6H), 3.28 (s, 3H), 3.40 (m, 1H), 3.61 (s, 1H), 3.75 (d, J=10.85 Hz, 1H), 3.83 (s, 3H), 3.87 (s, 1H), 4.02 (s, 2H), 4.30 (d, J=15.60 Hz, 1H), 4.39 (d, J=13.22 Hz, 1H), 4.43 (d, J=7.80 Hz, 1H), 4.93 (d, J=6.44 Hz, 1H), 5.56 (d, J=7.80 Hz, 2H), 7.07 (m, 7H), 7.24 (s, 1H), 7.71 (d, J=8.82 Hz, 2H), 7.86 (d, J=9.49 Hz, 1H).

The compounds listed in Table 13, wherein $X_9$, $X_7$, and $X_3$ represent respectively the points of connection to the core structure (J), were prepared by coupling the corresponding acids (Examples 32-160) with the corresponding amines (Examples 521-523) as exemplified in Example 362 (Method A) or Example 161 (Method B), Example 524 (Method C) and Example 478 (Method D).

TABLE 13
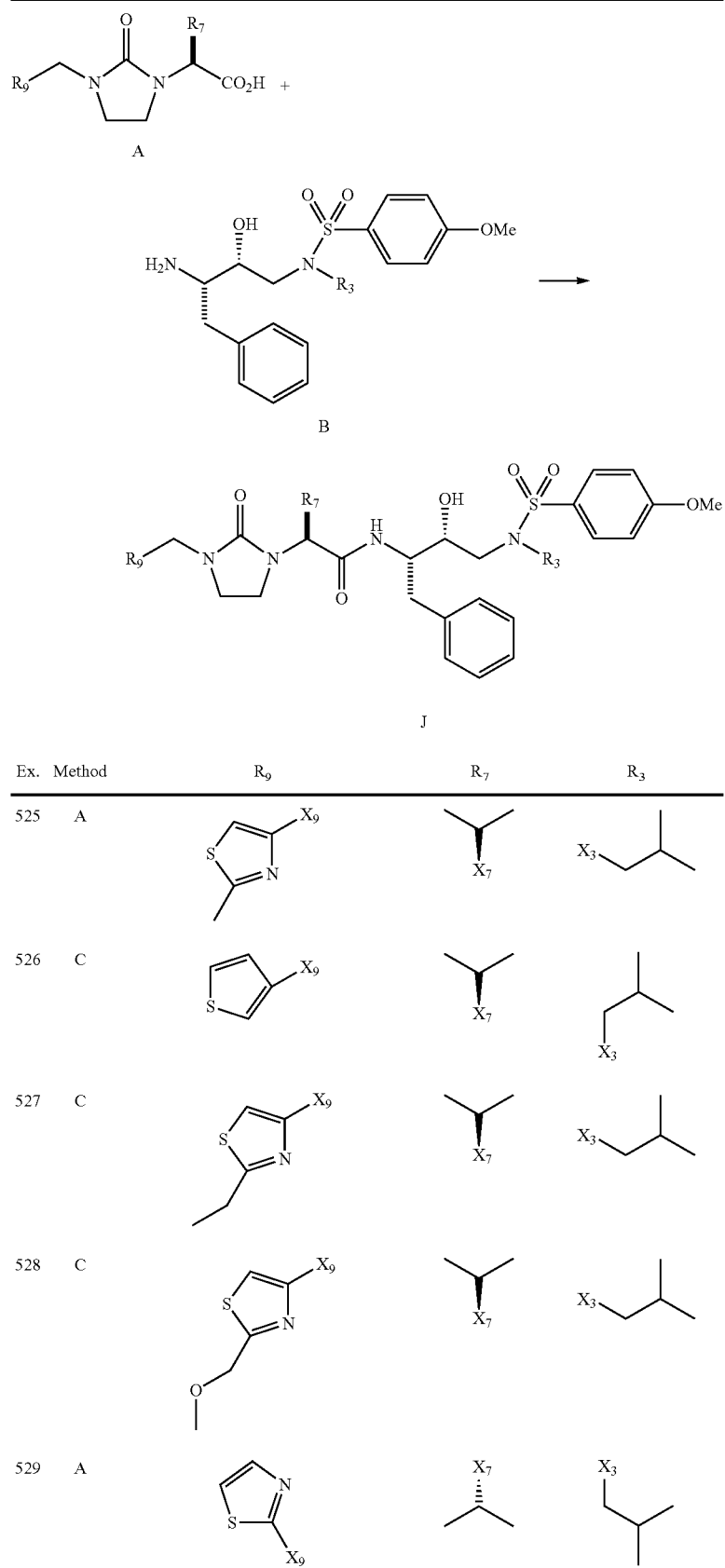

TABLE 13-continued
| | | | | |
|---|---|---|---|---|
| 530 | A | 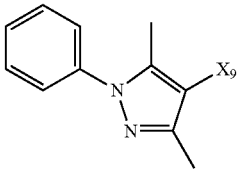 |  | 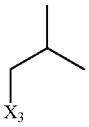 |
| 531 | A | 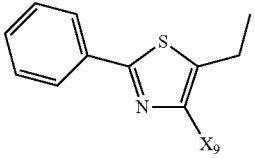 |  | 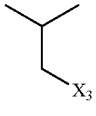 |
| 532 | A | 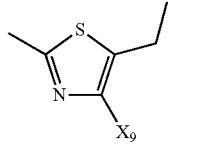 |  | 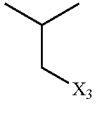 |
| 533 | A | 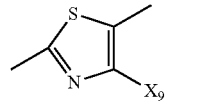 |  | 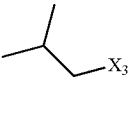 |
| 534 | A | 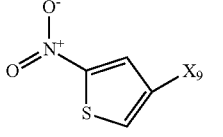 |  | 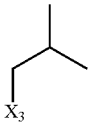 |
| 535 | A | 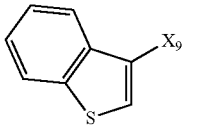 |  | 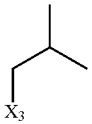 |
| 536 | A | 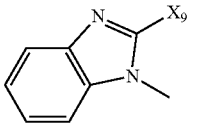 |  | 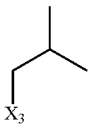 |
| 537 | A | 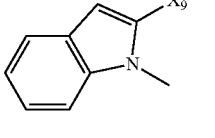 |  | 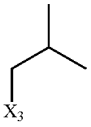 |
| 538 | A | 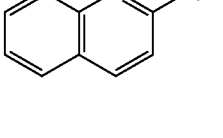 |  | 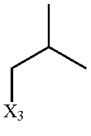 |
| 539 | C | 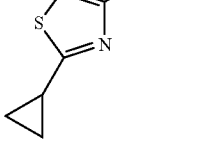 |  | 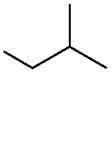 |

TABLE 13-continued
| | | | | |
|---|---|---|---|---|
| 540 | A | 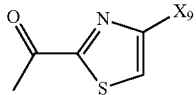 |  | 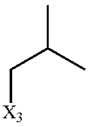 |
| 541 | A | 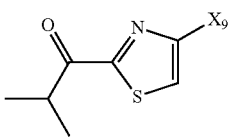 |  | 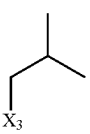 |
| 542 | A | 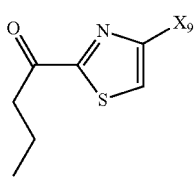 |  | 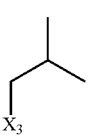 |
| 543 | A | 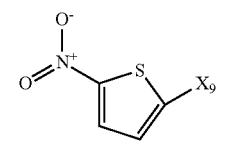 |  | 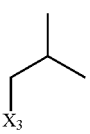 |
| 544 | A | 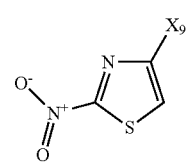 |  | 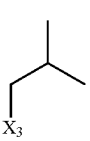 |
| 545 | A | 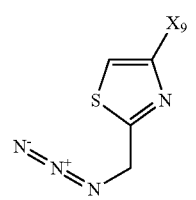 |  | 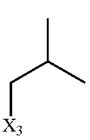 |
| 546 | A | 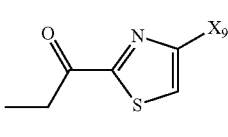 |  | 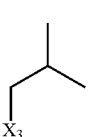 |
| 547 | A | 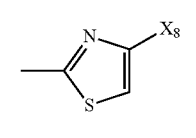 |  | 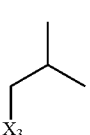 |
| 548 | A | 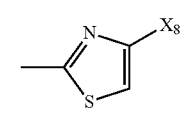 |  | 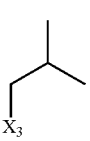 |
| 549 | A | 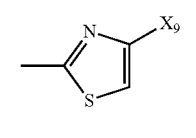 | 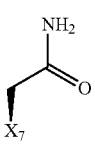 | 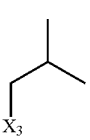 |

TABLE 13-continued

| 550 | A | thiazole-CH2-O-C(O)CH3 (X9 on thiazole) | X7-CH(CH3)2 | X3-CH2CH(CH3)2 |
| 551 | A | 2-methyl-thiazole-X9 | H2N-C(O)-CH2CH2-X7 | X3-CH2CH(CH3)2 |
| 552 | A | benzofuran-X9 | X7-CH(CH3)2 | X3-CH2CH(CH3)2 |
| 553 | A | quinoline-X9 | X7-CH(CH3)2 | X3-CH2CH(CH3)2 |
| 554 | A | 2-nitro-3-methoxy-thiophene-X9 | X7-CH(CH3)2 | X3-CH2CH(CH3)2 |
| 555 | A | thiazole-CH2-S-CH3 (X9 on thiazole) | X7-CH(CH3)2 | X3-CH2CH(CH3)2 |
| 556 | A | thiazole-CH2-CN (X9 on thiazole) | X7-CH(CH3)2 | X3-CH2CH(CH3)2 |
| 557 | A | 2-acetamido-thiazole-X9 | X7-CH(CH3)2 | X3-CH2CH(CH3)2 |

US 8,193,227 B2
TABLE 13-continued
| | | | | |
|---|---|---|---|---|
| 558 | B | 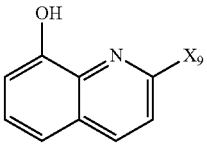 |  | 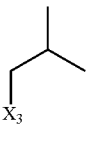 |
| 559 | B | 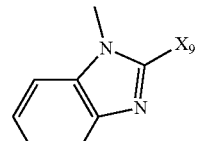 |  | 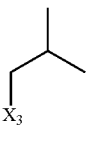 |
| 560 | B | 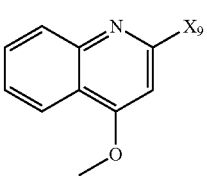 |  | 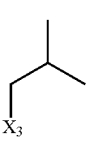 |
| 561 | B | 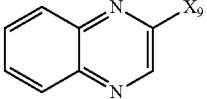 |  |  |
| 562 | B | 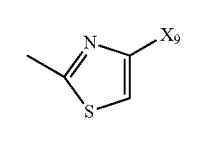 | 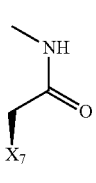 | 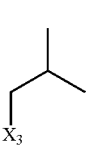 |
| 563 | B | 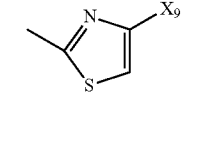 | 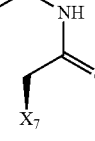 | 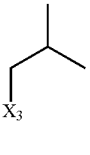 |
| 564 | A | 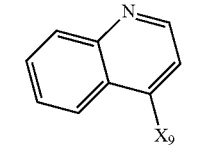 | 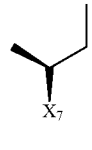 | 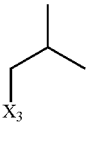 |
| 565 | B | 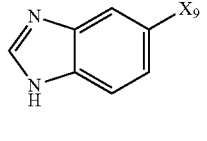 | 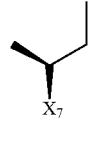 | 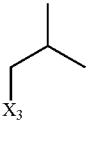 |
| 566 | A | 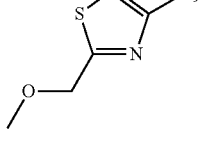 |  | 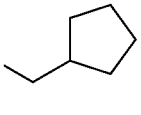 |
| 567 | B | 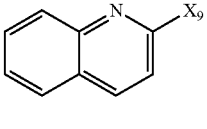 |  | 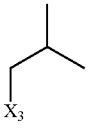 |

TABLE 13-continued

| | | | | |
|---|---|---|---|---|
| 568 | B | 1-methylbenzimidazol-2-yl-X₉ | sec-butyl-X₇ | cyclopentylmethyl-X₃ |
| 569 | A | 2-(methoxymethyl)thiazol-4-yl-X₉ | sec-butyl-X₇ | isobutyl-X₃ |
| 570 | A | 3-cyanophenyl-X₉ | sec-butyl-X₇ | isobutyl-X₃ |
| 571 | B | 1-methylbenzimidazol-2-yl-X₉ | tert-butyl-X₇ | isobutyl-X₃ |
| 572 | B | 2-methylthiazol-4-yl-X₉ | CHO-NH-CH₂-X₇ | isobutyl-X₃ |
| 573 | B | 2-methylthiazol-4-yl-X₉ | H₂N-CO-NH-CH₂-X₇ | isobutyl-X₃ |
| 574 | A | 6-(methoxymethyl)pyridin-2-yl-X₉ | sec-butyl-X₇ | isobutyl-X₃ |
| 575 | A | 2-(1-hydroxyiminoethyl)pyridin-4-yl-X₉ | sec-butyl-X₇ | isobutyl-X₃ |
| 576 | A | 2-(pyridin-2-yl)thiazol-4-yl-X₉ | sec-butyl-X₇ | isobutyl-X₃ |

TABLE 13-continued
| 577 | A | 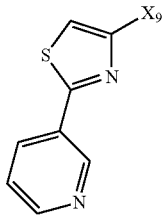 |  | 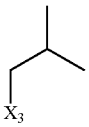 |
| --- | --- | --- | --- | --- |
| 578 | A | 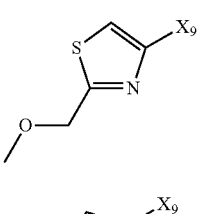 |  | 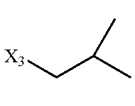 |
| 579 | D | 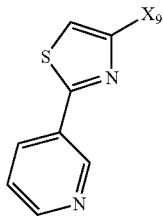 | 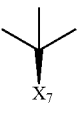 | 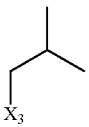 |
| 580 | D | 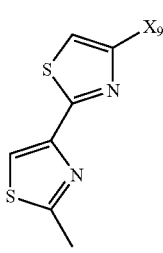 | 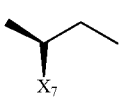 | 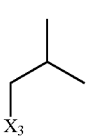 |
| 581 | D | 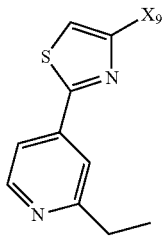 | 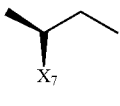 | 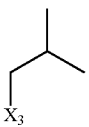 |
| 582 | A | 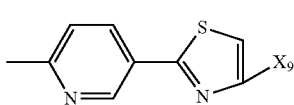 | 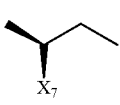 | 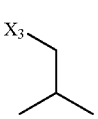 |
| 583 | B | 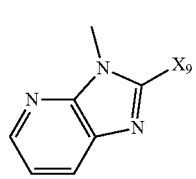 |  | 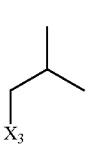 |
| 584 | B | 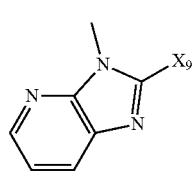 | 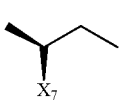 | 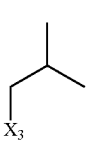 |

TABLE 13-continued

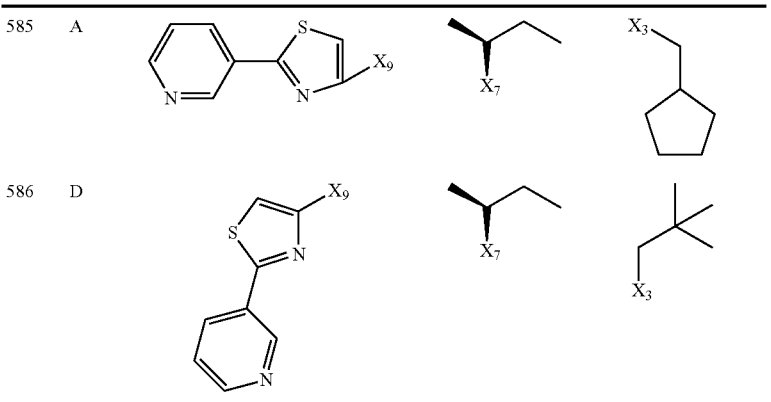

| | | | | |
|---|---|---|---|---|
| 585 | A | [pyridine-thiazole with X9] | [sec-butyl with X7] | [cyclopentylmethyl with X3] |
| 586 | D | [thiazole-pyridine with X9] | [sec-butyl with X7] | [neopentyl with X3] |

Example 587

(2S)-2-(3-{[2-(aminomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide

Example 587A tert-butyl (2S)-2-(3-{[2-(hydroxymethyl)-1,3-thiazol-4-yl]methyl}-2-oxo-1-imidazolidinyl)-3-methylbutanoate Example 273D (509 mg) was dissolved in ethanol (14 mL) added NaBH$_4$ (57.6 mg, 1.1 equivalents). The mixture was stirred at 25° C. for 3 h and quenched with sat. NH$_4$Cl and the mixture was partitioned between ethyl acetate and water. The organic layer was separated, washed with brine, dried over MgSO$_4$. The solvents were evaporated to give 452 mg (88%) crude alcohol.

Example 587B tert-butyl (2S)-3-methyl-2-{3-[(2-{[(methylsulfonyl)oxy]methyl}-1,3-thiazol-4-yl)methyl]-2-oxo-1-imidazolidinyl}butanoate Example 587A (452 mg) was dissolved in dichloromethane (12 mL) added triethylamine (683 µL, 4 equivalents), cooled to 0° C. and methanesulfonyl chloride (190 µL, 2 equivalents). After 30 min. the solvents were evaporated. The residue was partitioned between ethyl acetate and 10% citric acid solution. The organic layer was separated and washed with 10% NaHCO$_3$, brine, dried over MgSO$_4$, filtered, and the solvents were evaporated to give 335 mg (61%) of the title compound.

Example 587C (2S)-2-(3-{[2-(azidomethyl)-1,3-thiazol-4-yl]methyl}-2-oxo-1-imidazolidinyl)-3-methylbutanoic acid Example 587B (335 mg) was dissolved in N,N-dimethylformamide (5 mL) and LiN$_3$ (366 mg, 10 equivalents) and the mixture was heated to 50° C. for 2.5 h. The solvents were evaporated and partitioned between ethyl acetate and brine, and the organic layer was separated, dried over MgSO$_4$, filtered, and concentrated to give 292 mg of crude azide. The crude azide was dissolved in dichloromethane (2 mL) and trifluoroacetic acid (2 mL) and stirred at 25° C. for 2 h. The solvents were evaporated to give 244 mg (96%) acid.

Example 587D (2S)-2-(3-{[2-(azidomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide Example 587C (244 mg) was dissolved in N,N-dimethylformamide (7 mL) and HOBT (146 mg, 1.5 equivalents), EDAC (168 mg, 1.5 equivalents), triethylamine (0.2 mL, 2 equivalents) followed by Example 521B (352 mg, 1.2 equivalents). The mixture was stirred at 25° C. for 16 h. The solvents were evaporated, and the residue was purified using dichloromethan:ethyl acetate (100:0 to 0:100) to give 333 mg (64%) of the azide.

Example 587E (2S)-2-(3-{[2-(aminomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide Example 587D (270 mg, 0.37 mmol) was dissolved in tetrahydrofuran (3 mL) and water (0.7 mL) followed by triphenylphosphine (TPP) (195 mg, 2 equivalents). The mixture was heated to 50° C. for 1 h. The mixture was partitioned between dichloromethane and water. The organic layer was separated, washed with brine, dried over MgSO$_4$ and the solvents were evaporated. The residue was purified using dichloromethane:ethyl acetate (1:1 to 100:0 to 10% methanol/dichloromethane) to give 215 mg (83%) of the title compound.

Example 588

(2S)-2-[3-({2-[(acetylamino)methyl]-1,3-thiazol-4-yl}methyl)-2-oxo-1-imidazolidinyl]-N-((1S,2R)-1-benzyl-2-hydroxy-3-{isobutyl[(4-methoxyphenyl)sulfonyl]amino}propyl)-3-methylbutanamide Example 587E (11 mg, 0.016 mmol) was dissolved in dichloromethane (0.15 mL) and treated with acetic anhydride (2.2 µL, 1.5 equivalents) and triethylamine (6.6 µL, 3 equivalents) at 25° C. for 1 h. The mixture was quenched with citric acid and washed with 10% NaHCO₃, brine, dried over MgSO₄, filtered, and the solvents were evaporated. The residue was purified using dichloromethane:methanol (100:0 to 95:5) to give 9.8 mg (84%) of the title compound.

Example 589

(2S)—N-((1S,2R)-1-benzyl-2-hydroxy-3-{isobutyl[(4-methoxyphenyl)sulfonyl]amino}propyl)-2-(3-{[2-(hydroxymethyl)-1,3-thiazol-4-yl]methyl}-2-oxo-1-imidazolidinyl)-3-methylbutanamide

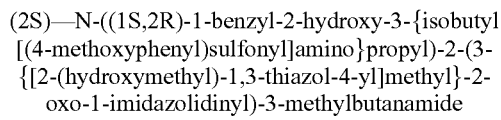

Example 550 (45 mg, 0.062 mmol) was dissolved in tetrahydrofuran:water (1 mL, 2:1) and treated with LiOH (8 mg) at 25° C. for 30 min. The mixture is quenched with 1N HCl (0.2 mL) and partitioned between ethyl acetate and water, the organic layer is separated, washed with brine and dried over MgSO₄, filtered, and the solvents were evaporated to give 43 mg (100%) of the title compound.

Example 590

(2S)—N-((1S,2R)-1-benzyl-2-hydroxy-3-{isobutyl[(4-methoxyphenyl)sulfonyl]amino}propyl)-2-[3-({2-[(dimethylamino)methyl]-1,3-thiazol-4-yl}methyl)-2-oxo-1-imidazolidinyl]-3-methylbutanamide

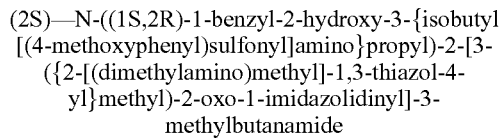

Example 587E (50 mg, 0.071 mmol) was dissolved in acetonitrile (0.7 mL) added formaldehyde (27 μL, 5 equivalents) acetic acid (8.1 μL, 2 equivalents), NaCNBH₃ (9 mg, 2 equivalents). The mixture was stirred at 25° C. for 3 h. The solvents were evaporated and the residue was purified using dichloromethane:methanol (95:5) to give 9 mg (17%) of the title compound.

Example 591

(2S)—N-((1S,2R)-1-benzyl-2-hydroxy-3-{isobutyl[(4-methoxyphenyl)sulfonyl]amino}propyl)-3-methyl-2-{3-[(2-{[(methylsulfonyl)amino]methyl}-1,3-thiazol-4-yl)methyl]-2-oxo-1-imidazolidinyl}butanamide

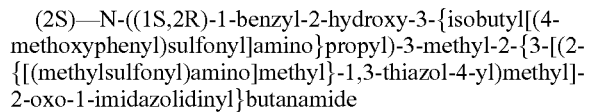

Example 587E (16.5 mg, 0.023 mmol) was dissolved in dichloromethane (0.25 mL) and treated with mesyl chloride (2 μL, 1.1 equivalents) and triethylamine (9.8 μL, 3 equivalents) at 0° C. for 1 h. The solvents were evaporated and the residue was purified using 5% methanol/dichloromethane to give 12 mg (66%) of the title compound.

Example 592

(2S)—N-((1S,2R)-1-benzyl-2-hydroxy-3-{isobutyl[(4-methoxyphenyl)sulfonyl]amino}propyl)-2-[3-({2-[(hydroxyimino)methyl]-1,3-thiazol-4-yl}methyl)-2-oxo-1-imidazolidinyl]-3-methylbutanamide

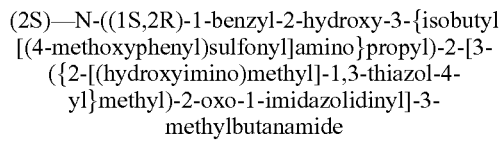

Example 587E (10.2 mg, 0.0145 mmol) was dissolved in dichloromethane (0.2 mL) at 0° C. was treated with m-chloroperbenzoic acid (7 mg, 2 equivalents) and the mixture was stirred for 2 h. The mixture was quenched with 50% NaHCO₃ and extracted with ethyl acetate. The organic layer was separated and dried over MgSO₄, filtered, and the solvents were evaporated. The residue was purified by HPLC reverse phase chromatography using water (0.1% trifluoroacetic acid):acetonitrile (95:5) to acetonitrile (100%) to give 7 mg (45%) of the title compound.

Example 593 methyl(4-{[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methylcarbamate

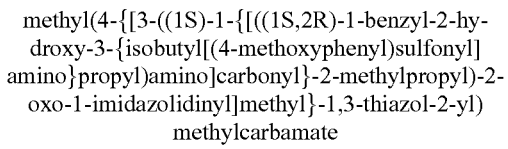

Example 587E (16.7 mg, 0.023 mmol) was dissolved in dichloromethane (0.4 mL) was treated with triethylamine (6.6 μL, 2 equivalents) and methyl chloroformate (2 μL, 1.1 equivalents) at 0° C. for 30 min. The solvents were evaporated and the residue was purified by HPLC reverse phase chromatography using water (0.1% trifluoroacetic acid):acetonitrile (95:5) to acetonitrile (100%) to give 12 mg (67%) of the title compound.

Example 594

(2S)—N-((1S,2R)-1-benzyl-2-hydroxy-3-{isobutyl[(4-methoxyphenyl)sulfonyl]amino}propyl)-3-methyl-2-[3-({2-[(methylsulfonyl)methyl]-1,3-thiazol-4-yl}methyl)-2-oxo-1-imidazolidinyl]butanamide Example 594A tert-butyl(2S)-3-methyl-2-[3-({2-[(methylsulfanyl)methyl]-1,3-thiazol-4-yl}methyl)-2-oxo-1-imidazolidinyl]butanoate

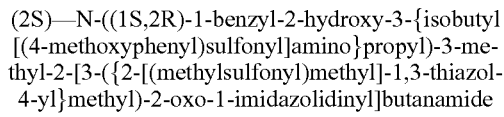

Example 587B (28 mg, 0.062 mmol) was dissolved in N,N-dimethylformamide (0.6 mL) and treated with sodium methylthiolate (4.8 mg, 1.1 equivalents) at 25° C. for 16 h. The mixture was partitioned between saturated NH₄Cl and ethyl acetate. The organic layer was separated and dried over MgSO₄, filtered, and the solvents were evaporated. The residue was purified using ethyl acetate:dichloromethane (1:1) to give 17.4 mg (70%) of the title compound.

Example 594B (2S)—N-((1S,2R)-1-benzyl-2-hydroxy-3-{isobutyl[(4-methoxyphenyl)sulfonyl]amino}propyl)-3-methyl-2-[3-({2-[(methylsulfanyl)methyl]-1,3-thiazol-4-yl}methyl)-2-oxo-1-imidazolidinyl]butanamide

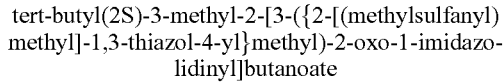

Example 594A (57 mg, 0.142 mmol) was dissolved in dichloromethane (1 mL) and trifluoroacetic acid (1 mL) and stirred at 25° C. for 1 h. The solvents were evaporated and the crude acid used directly for the next step. The acid was dissolved in N,N-dimethylformamide (1 mL) and treated with EDAC (33 mg, 1.5 equivalents), HOBT (29 mg, 1.5 equivalents), N methylmorpholine (0.16 mL, 1 equivalent) followed by the Example 18 (58 mg, 1 equivalent) and the mixture was stirred at 25° C. for 16 h. The solvents were evaporated and the residue was purified using dichloromethane:ethyl acetate (1:1) to give 12 mg (11%) of the title compound.

Example 594C (2S)—N-((1S,2R)-1-benzyl-2-hydroxy-3-{isobutyl[(4-methoxyphenyl)sulfonyl]amino}propyl)-3-methyl-2-[3-({2-[(methylsulfonyl)methyl]-1,3-thiazol-4-yl}methyl)-2-oxo-1-imidazolidinyl]butanamide

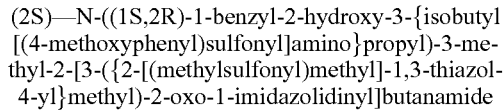

Example 594B (13 mg, 0.017 mmol) was dissolved in dichloromethane (0.4 mL) and treated with m-chloroperbenzoic acid (8.7 mg, 2 equivalents) at 25° C. for 30 min. The solvents were evaporated and the residue was purified by HPLC reverse phase chromatography using water (0.1% trifluoroacetic acid):acetonitrile (95:5) to acetonitrile (100%) to give 11.2 mg (82%) of the title compound.

Example 595

(2S)—N-((1S,2R)-1-benzyl-2-hydroxy-3-{isobutyl[(4-methoxyphenyl)sulfonyl]amino}propyl)-2-[3-({2-[(diethylamino)methyl]-1,3-thiazol-4-yl}methyl)-2-oxo-1-imidazolidinyl]-3-methylbutanamide

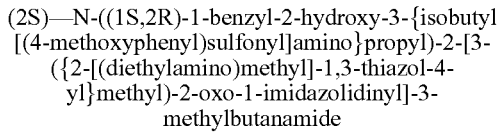

Example 587E was treated in a similar manner as for Example 590 using acetaldehyde instead of formaldehyde was to prepare the title compound.

Example 596

(2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2-oxo-1-imidazolidinyl}-3-methylbutanamide

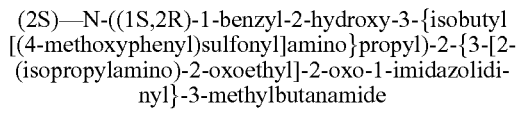

Example 620B (5.8 mg, 0.008 mmol) was dissolved in ethanol (0.3 mL) and treated with NaBH$_4$ (5 mg) and the mixture was stirred at 25° C. for 16 h. The solvents were evaporated and the residue was directly used for the next step. The imidazolone was dissolved in HOAc (1 mL) and treated with Pd(OH)$_2$ and a hydrogen balloon. The mixture was stirred for 16 h, filtered, and the solvents were evaporated. The residue was purified by HPLC reverse phase chromatography using water (0.1% trifluoroacetic acid):acetonitrile (95:5) to acetonitrile (100%) to give 2.7 mg (46% from imide) of the title compound.

Example 597

(2S)—N-((1S,2R)-1-benzyl-2-hydroxy-3-{isobutyl[(4-methoxyphenyl)sulfonyl]amino}propyl)-3-methyl-2-[3-({2-[(methylamino)methyl]-1,3-thiazol-4-yl}methyl)-2-oxo-1-imidazolidinyl]butanamide Example 597A tert-butyl (2S)-3-methyl-2-[3-({2-[(methylamino)methyl]-1,3-thiazol-4-yl}methyl)-2-oxo-1-imidazolidinyl]butanoate

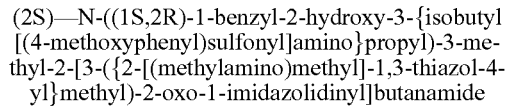

Example 273D (200 mg, 0.54 mmol) was dissolved in toluene:ethanol (2.2 mL, 1:1) was added 2M methylamine in tetrahydrofuran (0.54 mL, 2 equivalents) was heated to 70° C. for 2 h. The mixture was cooled to 25° C. and NaBH$_4$ (20 mg, 3 equivalents) was added and the mixture was stirred at 25° C. for 16 h. The solvents were evaporated and the residue was partitioned between ethyl acetate and sat. NaHCO$_3$, the organic layer was separated and washed with brine, dried over MgSO$_4$, filtered, and evaporated. The residue was purified using chloroform:methanol (95:5) to give 118 mg (56%) of the title compound.

Example 597B tert-butyl (2S)-2-{3-[(2-[[(9H-fluoren-9-ylmethoxy)carbonyl](methyl)amino]methyl-1,3-thiazol-4-yl)methyl]-2-oxo-1-imidazolidinyl}-3-methylbutanoate

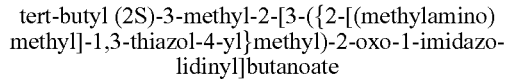

Example 597A (118 mg, 0.3 mmol) was dissolved in dichloromethane (3 mL) a 0° C. and triethylamine (90 µL, 2.2 equivalents) followed by FMOC-Cl (86 mg, 1.1 equivalents). The mixture was stirred at 25° C. for 16 h. The solvents were evaporated and the residue was purified using ethyl acetate:hexanes (1:1) to give 138 mg (76%) of protected amine.

Example 597C 9H-fluoren-9-ylmethyl(4-{[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methyl(methyl)carbamate

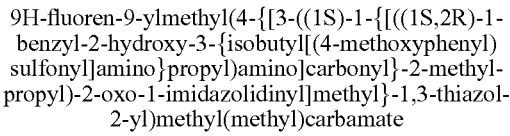

Example 597B (60 mg, 0.099 mmol) was dissolved in dichloromethane (0.5 mL) and trifluoroacetic acid (0.5 mL) and stirred at 25° C. for 1 h. The solvents were evaporated and the acid was used directly for the next step. The crude acid was dissolved in N,N-dimethylformamide (1 mL) with HOBT (20 mg, 1.5 equivalents) EDAC (29 mg, 1.5 equivalents), and N-methylmorpholine (27 µL, 2.5 equivalents) followed by the Example 18 (40 mg, 1 equivalent). The mixture was stirred at 25° C. for 16 h and the solvents were evaporated. The residue was purified using HPLC reverse phase chromatography using water (0.1% trifluoroacetic acid):acetonitrile (95:5) to acetonitrile (100%) to give 40 mg (42%) of the title compound.

Example 597D (2S)—N-((1S,2R)-1-benzyl-2-hydroxy-3-{isobutyl[(4-methoxyphenyl)sulfonyl]amino}propyl)-3-methyl-2-[3-({2-[(methylamino)methyl]-1,3-thiazol-4-yl}methyl)-2-oxo-1-imidazolidinyl]butanamide

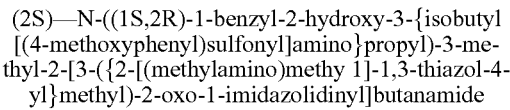

Example 597C (40 mg, 0.042 mmol) was dissolved in acetonitrile (0.5 mL) and diethylamine (10 µL, 3 equivalents), and the mixture was stirred at 25° C. for 1 h. The solvents were evaporated and the residue was purified by HPLC reverse phase chromatography using water (0.1% trifluoroacetic acid):acetonitrile (95:5) to acetonitrile (100%) to give 13 mg (37%) of the title compound.

Example 598

(2S)—N-((1S,2R)-1-benzyl-2-hydroxy-3-{isobutyl[(4-methoxyphenyl)sulfonyl]amino}propyl)-2-[3-({2-[N-hydroxyethanimidoyl]-1,3-thiazol-4-yl}methyl)-2-oxo-1-imidazolidinyl]-3-methylbutanamide

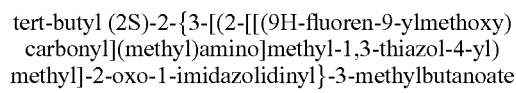

Example 540 was treated in a similar manner to Example 476G to give the title compound.

Example 599

(2S,3S)-2-(3-{[2-(aminomethyl)-1,3-thiazol-4-yl]methyl}-2-oxo-1-imidazolidinyl)-N-((1S,2R)-1-benzyl-3-{(cyclopentylmethyl)[(4-methoxyphenyl)sulfonyl]amino}-2-hydroxypropyl)-3-methylpentanamide

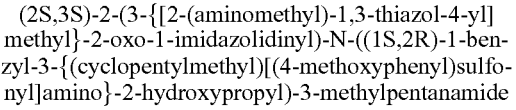

Example 599A 9H-fluoren-9-ylmethyl(4-{[3-((1S,2S)-1-{[((1S,2R)-1-benzyl-3-{(cyclopentylmethyl)[(4-methoxyphenyl)sulfonyl]amino}-2-hydroxypropyl)amino]carbonyl}-2-methylbutyl)-2-oxo-1-imidazolidinyl]methyl}-1,3-thiazol-2-yl)methylcarbamate

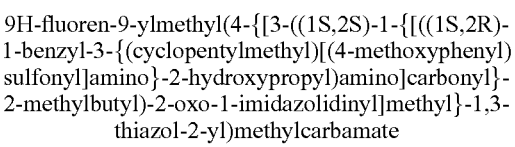

Example 279F (15 mg, 0.027 mmol) was dissolved in N,N-dimethylformamide (0.3 mL) and treated with Example 522 (18 mg, 1.5 equivalents), EDAC (8 mg, 1.5 equivalents), HOBT (6 mg, 1.5 equivalents), and N-methylmorpholine (7 µL, 2.5 equivalents) at 25° C. for 16 h. The solvents were evaporated, and the residue was purified by HPLC reverse phase chromatography using water (0.1% trifluoroacetic acid):acetonitrile (75:25) to acetonitrile (100%) to give 12 mg (46%) of the title compound.

Example 599B (2S,3S)-2-(3-{[2-(aminomethyl)-1,3-thiazol-4-yl]methyl}-2-oxo-1-imidazolidinyl)-N-((1S,2R)-1-benzyl-3-{(cyclopentylmethyl)[(4-methoxyphenyl)sulfonyl]amino}-2-hydroxypropyl)-3-methylpentanamide Example 599A (12 mg, 0.012 mmol) was dissolved in acetonitrile (0.2 mL) and treated with diethylamine (3 µL, 3 equivalents) at 25° C. for 2 h. The solvents were evaporated, and the residue was purified by HPLC reverse phase chromatography using water (0.1% trifluoroacetic acid):acetonitrile (95:5) to acetonitrile (100%) to give 10.6 mg (100%) of the title compound.

Example 600

(2S,3S)-2-(3-{3-[amino(hydroxyimino)methyl]benzyl}-2-oxo-1-imidazolidinyl)-N-((1S,2R)-1-benzyl-2-hydroxy-3-{isobutyl[(4-methoxyphenyl)sulfonyl]amino}propyl)-3-methylpentanamide Example 570 (80 mg, 0.11 mmol) was dissolved in ethanol (1 mL) and treated with hydroxylamine hydrochloride (32 mg, 4 equivalents) and triethylamine (0.16 mL, 10 equivalents) at 50° C. for 9 h. The mixture was partitioned between water and ethyl acetate, the organic layer was separated, dried over $Na_2SO_4$, and the solvents were evaporated. The residue was purified using ethyl acetate to give 35 mg (42%) of the title compound.

Example 601

(2S)—N-((1S,2R)-1-benzyl-2-hydroxy-3-{isobutyl[(4-methoxyphenyl)sulfonyl]amino}propyl)-4-hydroxy-2-{3-[(1-methyl-1H-benzimidazol-2-yl)methyl]-2-oxo-1-imidazolidinyl}butanamide Example 601A benzyl(1S)-1-{[((1S,2R)-1-benzyl-2-hydroxy-3-{isobutyl[(4-methoxyphenyl)sulfonyl]amino}propyl)amino]carbonyl}-3-hydroxypropylcarbamate Example 521B (167 mg, 0.41 mmol) was dissolved in pyridine (0.4 mL) and treated with Z-aminobutyrolactone (193 mg, 2 equivalents) (CAS#35677-89-5) and heated to 100° C. for 2 d. The solvents were evaporated and the residue was purified using ethyl acetate to give 235 mg (66%) of the title compound.

Example 601B (2S)-2-amino-N-((1S,2R)-1-benzyl-2-hydroxy-3-{isobutyl[(4-methoxyphenyl)sulfonyl]amino}propyl)-4-hydroxybutanamide Example 601A (73 mg, 0.11 mmol) was dissolved in methanol (2 mL) and treated with $Pd(OH)_2$/C and stirred with a hydrogen balloon at 25° C. for 3 h. The mixture was filtered, rinsed with methanol, and the solvents were evaporated. The amine was used directly without purification.

Example 601C 9H-fluoren-9-ylmethyl 2-[((1S)-1-{[((1S,2R)-1-benzyl-2-hydroxy-3-{isobutyl[(4-methoxyphenyl)sulfonyl]amino}propyl)amino]carbonyl}-3-hydroxypropyl)amino]ethyl[(1-methyl-1H-benzimidazol-2-yl)methyl]carbamate Example 601B (58 mg, 0.11 mmol) and Example 148C (49 mg, 1 equivalent) were dissolved in methanol (0.5 mL) and HOAc (5 µL) and treated with $NaCNBH_3$ (15.4 mg, 2 equivalents) at 25° C. for 2 h. The mixture was partitioned between water and ethyl acetate, the organic layer was separated and washed with 10% $NaHCO_3$, brine and the solvents were evaporated. The residue was purified using 9% methanol/dichloromethane to give 81 mg (78%) of the title compound.

Example 601D (2S)—N—((1S,2R)-1-benzyl-2-hydroxy-3-{isobutyl[(4-methoxyphenyl)sulfonyl]amino}propyl)-4-hydroxy-2-{3-[(1-methy 1-1H-benzimidazol-2-yl)methyl]-2-oxo-1-imidazolidinyl}butanamide Example 601C (81 mg, 0.088 mmol) was dissolved in N,N-dimethylformamide (0.9 mL) and treated with diethylamine (90 µL) at 25° C. for 1 h. The solvents were evaporated and the residue was dissolved in dichloroethane (1.8 mL) and treated with bis(p-nitrophenyl) carbonate (34 mg, 1.1 equivalents) and heated to 50° C. for 16 h. The mixture was partitioned with ethyl acetate and 1N $Na_2CO_3$ and stirred for 1 h, and the organic layer was separated. This layer was washed several times with 1N $Na_2CO_3$, separated, and the solvents were evaporated. The residue was purified using 9% methanol/dichloromethane to give 46 mg (72%) the title compound.

Example 602

(2S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2,4-dioxo-1-imidazolidinyl}butanamide Method C Example 292 (50 mg) was combined with N-hydroxysuccinimide (28 mg, 1.1 equivalents) and DCC (49 mg, 1.1 equivalents) in dichloromethane (1 mL) and stirred for 1 h at 25° C. The solids are filtered, and to this mixture was added N-methylmorpholine (35 µL, 1 equivalent) and Example 521B (72 mg, 1 equivalent). The mixture was stirred for 16 h, evaporated, and was purified using 1% methanol/chloroform to give 74 mg (65%) of the title compound. $^1$H NMR (300 MHz, $CDCl_3$) δ ppm 0.80 (dd, J=8.99, 6.61 Hz, 6H), 0.87 (d, J=6.44 Hz, 3H), 0.93 (m, 3H), 1.82 (m, 1H), 2.08 (m, 1H), 2.30 (m, 1H), 2.78 (m, 2H), 3.01 (m, 2H), 3.07 (m, 2H), 3.23 (m, 1H), 3.58 (d, J=17.97 Hz, 1H), 3.81 (m, 3H), 3.88 (s, 3H), 3.94 (m, 1H), 4.23 (m, 1H), 4.73 (d, J=6.10 Hz, 2H), 4.81 (s, 1H), 4.86 (d, J=10.17 Hz, 1H), 6.21 (d, J=9.49 Hz, 1H), 6.99 (m, 2H), 7.11 (m, 6H), 7.72 (m, 2H), 8.02 (s, 1H).

The compounds listed in Table 14, wherein $X_{11}$, $X_7$, and $X_3$ represent respectively the points of connection to the core structure (E), were prepared by coupling the corresponding acids (Examples 291-360) with the corresponding amines (Examples 521-523) as exemplified in Example 362 (Method A) or Example 162 (Method B) or Example 602 (Method C).

TABLE 14
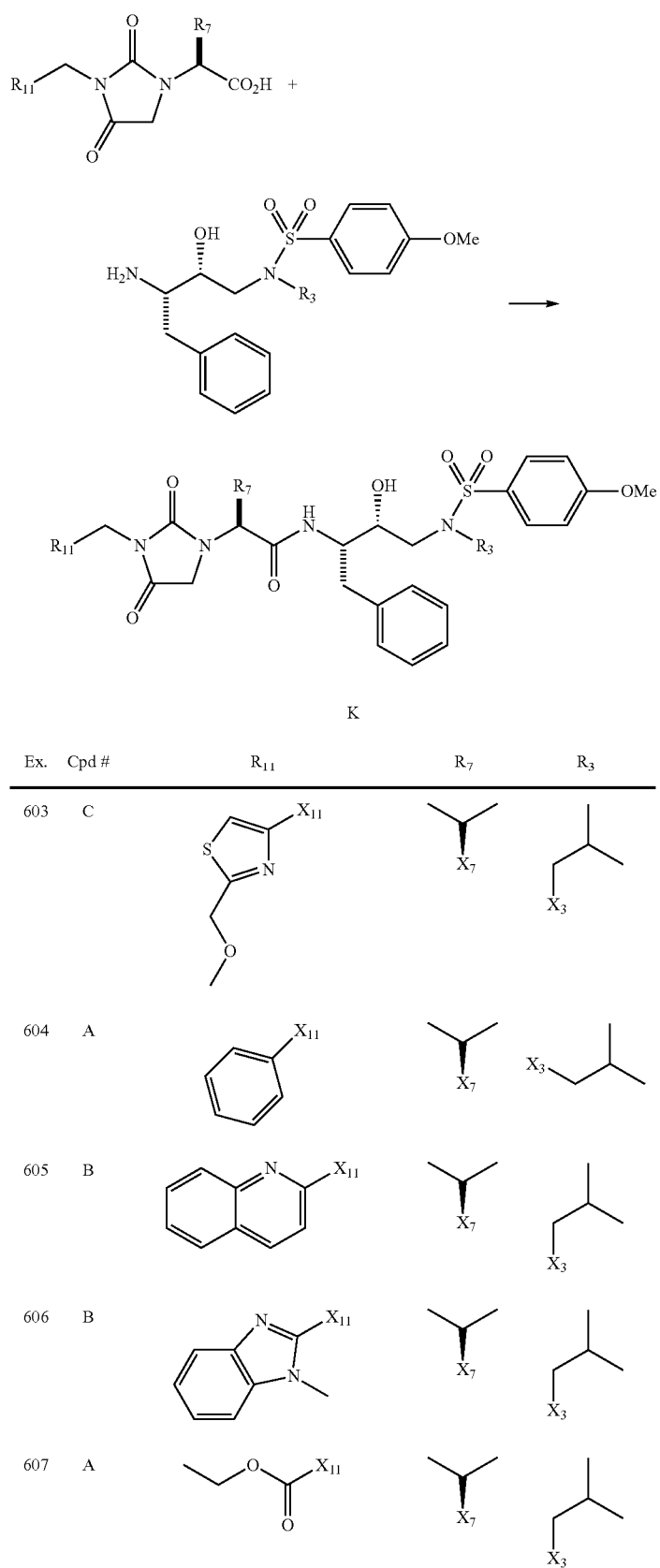
| Ex. | Cpd # | $R_{11}$ | $R_7$ | $R_3$ |
|---|---|---|---|---|
| 603 | C | thiazol-2-yl-CH$_2$OMe (X$_{11}$ at 4-position) | isopropyl (X$_7$) | isobutyl (X$_3$) |
| 604 | A | phenyl (X$_{11}$) | isopropyl (X$_7$) | isobutyl (X$_3$) |
| 605 | B | quinolin-2-yl (X$_{11}$) | isopropyl (X$_7$) | isobutyl (X$_3$) |
| 606 | B | 1-methylbenzimidazol-2-yl (X$_{11}$) | isopropyl (X$_7$) | isobutyl (X$_3$) |
| 607 | A | ethoxycarbonyl (X$_{11}$) | isopropyl (X$_7$) | isobutyl (X$_3$) |

TABLE 14-continued

| | | | | |
|---|---|---|---|---|
| 608 | A | 3-methyl-3H-imidazo[4,5-b]pyridin-2-yl-X₁₁ | X₇ (isopropyl) | X₃ (isobutyl) |
| 609 | B | 6-methoxyquinolin-2-yl-X₁₁ | X₇ (isopropyl) | X₃ (isobutyl) |
| 610 | B | quinolin-4-yl-X₁₁ | X₇ (isopropyl) | X₃ (isobutyl) |
| 611 | B | 6-nitroquinolin-2-yl-X₁₁ | X₇ (isopropyl) | X₃ (isobutyl) |
| 612 | B | 6-aminoquinolin-2-yl-X₁₁ | X₇ (isopropyl) | X₃ (isobutyl) |
| 613 | A | 2-acetamidothiazol-4-yl-X₁₁ | X₇ (isopropyl) | X₃ (isobutyl) |
| 614 | A | 2-acetamidothiazol-4-yl-X₁₁ | X₇ (sec-butyl, stereo) | X₃ (isobutyl) |
| 615 | B | 6-aminoquinolin-2-yl-X₁₁ | X₇ (sec-butyl, stereo) | X₃ (isobutyl) |
| 616 | A | quinolin-4-yl-X₁₁ | X₇ (sec-butyl, stereo) | X₃ (isobutyl) |

TABLE 14-continued

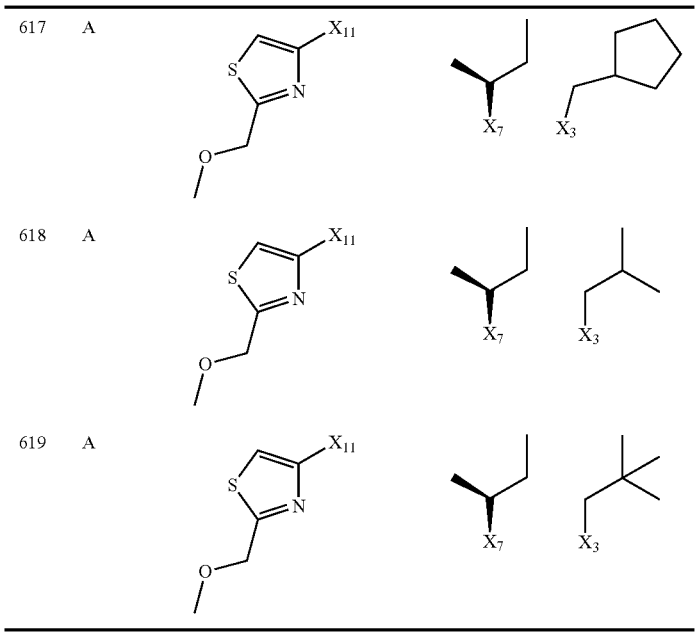

| | | | | |
|---|---|---|---|---|
| 617 | A | thiazole-CH2-O-CH3 (X11) | sec-butyl (X7) | cyclopentylmethyl (X3) |
| 618 | A | thiazole-CH2-O-CH3 (X11) | sec-butyl (X7) | isobutyl (X3) |
| 619 | A | thiazole-CH2-O-CH3 (X11) | sec-butyl (X7) | neopentyl (X3) |

Example 620

(2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2,4-dioxo-1-imidazolidinyl}-3-methylbutanamide

Example 620A

[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2,5-dioxo-1-imidazolidinyl]acetic acid Example 607 (161 mg, 0.24 mmol) was dissolved in tetrahydrofuran:water (0.9 mL, 3:1) and treated with LiOH (11 mg, 1.1 equivalents) at 25° C. for 2 h. The mixture was quenched with trifluoroacetic acid (20 µL), the solvents were evaporated and the residue was purified using 10% methanol (2% HOAc)/ethyl acetate to give 0.125 g (81%) of the acid.

Example 620B (2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2,4-dioxo-1-imidazolidinyl}-3-methylbutanamide Example 620A (24 mg, 0.037 mmol) was dissolved in N,N-dimethylformamide (0.4 mL) and treated with EDAC (10 mg, 1.5 equivalents), HOBT (7.5 mg, 1.5 equivalents), followed by isopropylamine (5 µL, 1 equivalent) and the mixture was stirred at 25° C. for 16 h. The solvents were evaporated, and the residue was purified using acetonitrile to give 12 mg (47%) of the title compound.

The compounds listed in Table 15, wherein $X_0$ represents the point of connection to the core structure (L), were prepared using the procedures as exemplified in Example 620A and Example 620B.

TABLE 15

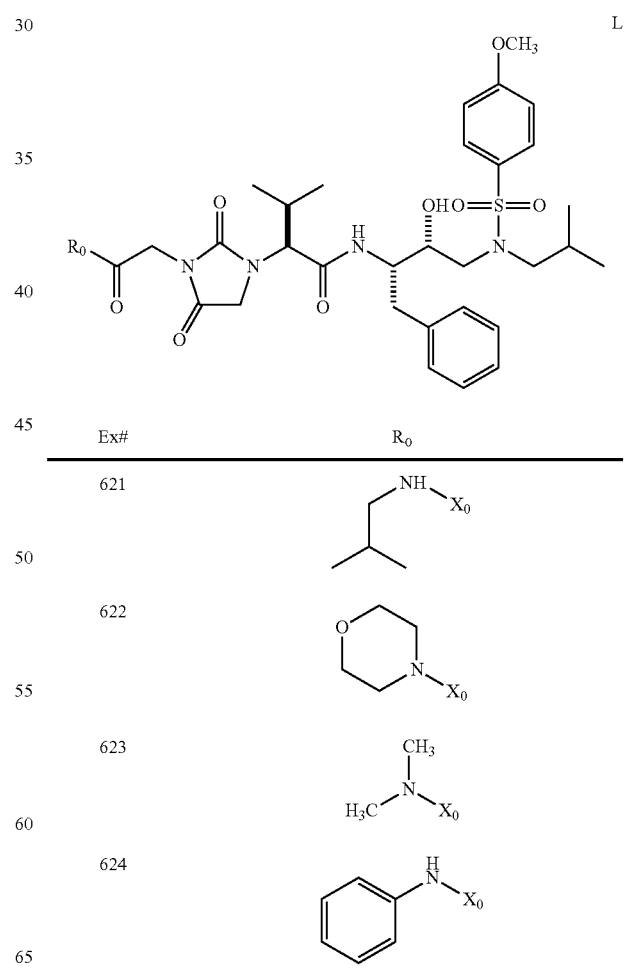

| Ex# | $R_0$ |
|---|---|
| 621 | isobutyl-NH-$X_0$ |
| 622 | morpholinyl-$X_0$ |
| 623 | (CH3)2N-$X_0$ |
| 624 | phenyl-NH-$X_0$ |

Example 625

N-[(2R,3S)-3-amino-2-hydroxy-4-phenylbutyl]-4-hydroxy-N-isobutylbenzenesulfonamide

Example 625A

N-[(2R,3S)-3-amino-2-hydroxy-4-phenylbutyl]-4-(benzyloxy)-N-isobutylbenzenesulfonamide Example 1 (0.13 g, 0.39 mmol) was dissolved in dichloromethane (4 mL) and treated with triethylamine (0.12 mL, 2.2 equivalents) and p-benzyloxybenzenesulfonyl chloride (0.12 g, 1.1 equivalents) at 25° C. for 18 h. The crude mixture was purified using chloroform to give 0.22 g (97%) of the title compound.

Example 625B

N-[(2R,3S)-3-amino-2-hydroxy-4-phenylbutyl]-4-hydroxy-N-isobutylbenzenesulfonamide Example 625A (0.22 g, 0.38 mmol) was dissolved in ethyl acetate (4 mL) and treated with Pd(OH)$_2$/C (0.1 g) and a hydrogen balloon at 25° C. for 2 h. The crude mixture was filtered, and the solvents were evaporated to give 0.2 g crude solid. This material was dissolved in dichloromethane:trifluoroacetic acid (6 mL, 1:1) at 25° C. for 1 h. The solvents was evaporated, the crude residue was azeotroped twice with toluene to give 0.205 g (100%) crude amine as the trifluoroacetic acid salt.

Example 626

4-amino-N-[(2R,3S)-3-amino-2-hydroxy-4-phenylbutyl]-N-isobutylbenzenesulfonamide

Example 626A tert-butyl(1S,2R)-1-benzyl-2-hydroxy-3-{isobutyl[(4-nitrophenyl)sulfonyl]amino}propylcarbamate Example 1 (0.64 g, 1.9 mmol) was dissolved in dichloromethane (20 mL) and treated with triethylamine (0.8 mL, 3 equivalents) and p-nitrobenzenesulfonyl chloride (0.46 g, 1.1 equivalents) at 25° C. and stirred for 4 h. The reaction mixture was evaporated and purified using 7% ethyl acetate/dichloromethane to give 0.88 g (89%) of the title compound.

Example 626B 4-amino-N-[(2R,3S)-3-amino-2-hydroxy-4-phenyl butyl]-N-isobutylbenzenesulfonamide Example 626A (0.88 g, 1.7 mmol) was dissolved in ethyl acetate (17 mL) and treated with 20% Pd(OH)$_2$/C (230 mg, 0.2 equivalent) and a hydrogen balloon at 25° C. for 1 h. The crude mixture was filtered and the solvents were removed by evaporation. This material was dissolved in dichloromethane: trifluoroacetic acid (10 mL, 1:1) at 25° C. for 1 h. The solvents were evaporated, the crude residue was azeotroped twice with ethyl acetate to give 0.75 g (100%) of crude product as the trifluoroacetic acid salt.

Example 627

3-amino-N-[(2R,3S)-3-amino-2-hydroxy-4-phenylbutyl]-4-chloro-N-isobutylbenzenesulfonamide

Example 627A tert-butyl(1S,2R)-1-benzyl-3-[[(4-chloro-3-nitrophenyl)sulfonyl](isobutyl)amino]-2-hydroxypropylcarbamate Example 1 (0.64 g, 1.9 mmol) was dissolved in dichloromethane (20 mL) and treated with triethylamine (0.8 mL, 3 equivalents) and p-chloro-o-nitrobenzenesulfonyl chloride (0.54 g, 1.1 equivalent) at 25° C. and stirred for 4 h. The reaction mixture was evaporated and purified using 5% ethyl acetate/dichloromethane to give 0.88 g (85%) of the title compound.

Example 627B 3-amino-N-[(2R,3S)-3-amino-2-hydroxy-4-phenylbutyl]-4-chloro-N-isobutylbenzenesulfonamide Example 627A (0.85 g, 1.53 mmol) was dissolved in ethanol:acetic acid (20 mL 1:1) and treated with iron (330 mg, 4 equivalents). The reaction was heated to 70° C. for 1 h. The reaction was evaporated and extracted twice with ethyl acetate. The organic layer was washed twice with saturated NaHCO$_3$, dried over MgSO$_4$, filtered, and evaporated to give 0.91 g of crude product. This material was treated with dichloromethane:trifluoroacetic acid (20 mL, 1:1) at 25° C. for 1 h. The solvents were evaporated to yield 0.80 g of Example 627B (100%).

Example 628

3-amino-N-[(2R,3S)-3-amino-2-hydroxy-4-phenylbutyl]-4-hydroxy-N-isobutylbenzenesulfonamide

Example 628A 4-(benzyloxy)-3-nitrobenzenesulfonyl chloride

To 10 g (41.5 mmol) of 4-hydroxy-3-nitro-benzenesulfonic acid sodium salt dissolved in ethanol (250 mL) was added benzyl bromide (5.4 mL, 1.1 equivalents), 15% NaOH solution (13.2 mL, 1.2 equivalents), and water (40 mL). The mixture was heated to 70° C. for 5 h. Additional benzyl bromide (5.4 mL) and 15% NaOH solution (13 mL) was added and heating was continued for an additional 18 h. The ethanol was removed by evaporation. The reaction was filtered through a pad of Celite, washed with water, and dried in a vacuum oven at 50° C. to give 7 g of material. A portion of this material (1.5 g, 4.56 mmol) was combined with phosphorous pentachloride (1.14 g, 1.2 equivalents) and phosphorous oxychloride (1.4 mL, 3.3 equivalents) and heated to 100° C. for 18 h. The reaction mixture was partitioned between chloroform and water. The organic layer was washed with a brine solution, dried over MgSO$_4$, filtered, and evaporated to leave 1.4 g of crude title compound which was used in the subsequent step.

Example 6288 tert-butyl(1S,2R)-1-benzyl-3-[{[4-(benzyloxy)-3-nitrophenyl]sulfonyl}(isobutyl)amino]-2-hydroxypropylcarbamate Example 1 (1.5 g, 4.4 mmol) was dissolved in 25 mL of dichloromethane and treated with Example 628A (1.4 g, 4.2 mmol) and triethylamine (1.3 mL, 2.2 equivalents). The reaction was stirred at 25° C. for 3 h. The crude mixture was purified using chloroform to give 1.83 mg (74%) of the title compound.

Example 628C 3-amino-N-[(2R,3S)-3-amino-2-hydroxy-4-phenylbutyl]-4-hydroxy-N-isobutylbenzenesulfonamide Example 628B (450 mg, 0.72 mmol) was dissolved in ethyl acetate (60 mL) and treated with 20% Pd(OH)$_2$/C (200 mg, 0.1 equivalent) and a hydrogen filled balloon at 25° C. for 3 h. The reaction was filtered and evaporated to leave 376 mg of crude material. This was dissolved in dichloromethane:trifluoroacetic acid (6 mL, 1:1) and stirred at 25° C. for 1.5 h. The solvents were removed by evaporation and the product was azeotroped with toluene (3×). The material was dissolved in ethyl acetate, washed with saturated NaHCO$_3$ solution, washed with brine, dried over MgSO$_4$, filtered, and evaporated to leave 328 mg (100%) of the title compound.

Example 629

N-(5-{[[(2R,3S)-3-amino-2-hydroxy-4-phenylbutyl](isobutyl)amino]sulfonyl}-2-hydroxyphenyl)-1-methy 1-1H-imidazole-4-sulfonamide

Example 629A (1R,2S)-1-{[{[4-(benzyloxy)-3-nitrophenyl]sulfonyl}(isobutyl)amino]methyl}-2-[(tert-butoxycarbonyl)amino]-3-phenylpropyl acetate Example 628B (1.83 g, 2.9 mmol) was dissolved in dichloromethane (30 mL) and treated with triethylamine (0.6 mL, 1.5 equivalents), acetic anhydride (0.3 mmol, 1.1 equivalents), and a catalytic amount of 4-(dimethylamino)pyridine. The reaction was stirred at 25° C. for 18 h and purifie using ethyl acetate/hexane to yield 1.82 g (93%) of the title compound.

Example 629B (1R,2S)-1-{[{[3-amino-4-(benzyloxy)phenyl]sulfonyl}(isobutyl)amino]methyl}-2-[(tert-butoxycarbonyl)amino]-3-phenylpropyl acetate Example 629A (1.8 g, 2.7 mmol) was dissolved ethanol (25 mL) and acetic acid (5 mL). The solution was treated with iron powder (600 mg, 4 equivalents) and heated to 50° C. for 1.5 h. The solvents were removed by evaporation. The reaction was dissolved in chloroform and washed with a saturated solution of NaHCO$_3$, washed with brine, dried over MgSO$_1$, filtered and evaporated. The residue was purified using chloroform and ethyl acetate to give 651 mg (38%) of the title compound.

Example 629C (1R,2S)-1-{[[(4-(benzyloxy)-3-{[(1-methyl-1H-imidazol-4-yl)sulfonyl]amino}phenyl)sulfonyl](isobutyl)amino]methyl}-2-[(tert-butoxycarbonyl)amino]-3-phenylpropyl acetate Example 629B (75 mg, 0.12 mmol) was dissolved in 1 mL of dichloromethane and treated with triethylamine (0.049 mL, 3 equivalents), 1-methylimidazole-4-sulfonyl chloride (32 mg, 1.5 equivalents), and a catalytic amount of 4-(dimethylamino)pyridine. The reaction was stirred at 40° C. for 4 h. The reaction was purified using 2% methanol/CHCl$_3$ to give 36 mg (39%) of the title compound.

Example 629D tert-butyl(1S,2R)-1-benzyl-2-hydroxy-3-[[(4-hydroxy-3-{[(1-methyl-1H-imidazol-4-yl)sulfonyl]amino}phenyl)sulfonyl](isobutyl)amino]propylcarbamate Example 629C (24 mg, 0.031 mmol) was dissolved in 1 mL of methanol and treated with 20% Pd(OH)$_2$/C (20 mg) and stirred at 25° C. under a hydrogen balloon atmosphere for 1 h. The reaction was filtered and evaporated to give 19 mg of crude product. This material (19 mg, 0.027 mmol) was dissolved in 0.5 mL of methanol and treated with KO$_3$ (4.2 mg, 1.1 equivalents) and stirred at 25° C. for 3 h. The reaction was evaporated and purified using 7% methanol/CHCl$_3$ to give 5.1 mg of the title compound (26%).

Example 629E

N-(5-{[[(2R,3S)-3-amino-2-hydroxy-4-phenylbutyl](isobutyl)amino]sulfonyl}-2-hydroxyphenyl)-1-methyl-1H-imidazole-4-sulfonamide Example 629D (5 mg, 0.008 mmol) was dissolved in dichloromethane:trifluoroacetic acid (0.5 mL, 2:1) and stirred at 25° C. for 1 h. The reaction was evaporated and azeotroped with toluene (3×) to give the title compound.

Example 630

N-(5-{[[(2R,3S)-3-amino-2-hydroxy-4-phenylbutyl](isobutyl)amino]sulfonyl}-2-hydroxyphenyl)-3-pyridinesulfonamide

Example 630A 3-pyridinesulfonyl chloride

A mixture of 3-pyridinesulfonic acid (1.0 g, 6.3 mmol), phosphorous pentachloride (1.6 g, 1.2 mmol), and phosphorous oxychloride (2.0 mL, 3.3 mmol) was combined and stirred at 100° C. for 18 h. The reaction was cooled to 25° C., diluted with CHCl$_3$, and bubbled with HCl gas. The resulting precipitate was collected by filtration, washed with CHCl$_3$, and dried in vacuo to yield 1.12 g of the title compound (84%).

Example 630B (1R,2S)-1-{[({4-(benzyloxy)-3-[(3-pyridinylsulfonyl)amino]phenyl}sulfonyl)(isobutyl)amino]methyl}-2-[(tert-butoxycarbonyl)amino]-3-phenylpropyl acetate Example 629B (75 mg, 0.12 mmol) was dissolved in 1.2 mL of dichloromethane and treated with pyridine (0.033 mL, 3.5 equivalents) and Example 630A (43 mg, 1.7 equivalents) at 25° C. and stirred for 72 h. The reaction was evaporated and purified using 25% ethyl acetate/chloroform to yield 67 mg of the title compound (72%).

Example 630C tert-butyl(1S,2R)-1-benzyl-2-hydroxy-3-[({4-hydroxy-3-[(3-pyridinylsulfonyl)amino]phenyl}sulfonyl)(isobutyl)amino]propylcarbamate Example 630B (67 mg, 0.086 mmol) was dissolved in 1 mL of methanol and treated with $K_2CO_3$ (15 mg, 1.2 equivalents) at 25° C. for 18 h. The reaction was diluted with chloroform and washed with a saturated solution of $NH_4Cl$, which was back extracted with chloroform. The organics were combined and washed with brine, dried over $MgSO_4$, filtered, and evaporated to yield 66 mg of crude product. This material was dissolved in 1 mL of methanol and treated with 20% Pd(OH)$_2$/C (30 mg, 0.5 mmol) and stirred at 25° C. under hydrogen balloon pressure for 2 h. The reaction was filtered, evaporated, and purified using 5% methanol/CHCl$_3$ to give 22.8 mg (40%) of the title compound.

Example 630D

N-(5-{[[(2R,3S)-3-amino-2-hydroxy-4-phenylbutyl](isobutyl)amino]sulfonyl}-2-hydroxyphenyl)-3-pyridinesulfonamide Example 630C (22 mg, 0.034 mmol) was dissolved in dichloromethane:trifluoroacetic acid (0.4 mL, 1:1) and stirred at 25° C. for 1.5 h. The reaction was evaporated and azeotroped with toluene (3x) to give the title compound.

Example 631

N-[(2R,3S)-3-amino-2-hydroxy-4-phenylbutyl]-4-hydroxy-N-isobutyl-3-[(methylsulfonyl)amino]benzenesulfonamide

Example 631A (1R,2S)-1-{[({4-(benzyloxy)-3-[(methylsulfonyl)amino]phenyl}sulfonyl)(isobutyl)amino]methyl}-2-[(tert-butoxycarbonyl)amino]-3-phenylpropyl acetate Example 628B (75 mg, 0.11 mmol) was dissolved in 1.1 mL of dichloromethane, cooled to −78° C. and treated with pyridine (0.027 mL, 3 equivalents), and methanesulfonyl chloride (0.016 mL, 1.8 equivalents). The reaction was allowed to warm to 25° C. and stirred for 18 h. The reaction mixture was evaporated and purified using 20% ethyl acetate/chloroform to give 91 mg of the title compound (99%).

Example 631B tert-butyl(1S,2R)-1-benzyl-2-hydroxy-3-[({4-hydroxy-3-[(methylsulfonyl)amino]phenyl}sulfonyl)(isobutyl)amino]propylcarbamate Example 631A (90 mg, 0.13 mmol) was dissolved in 1.3 mL of methanol, treated with $K_2CO_3$ (21 mg, 1.2 equivalents), and stirred at 25° C. for 1.5 h. The reaction was diluted with chloroform and washed with a saturated solution of $NH_4Cl$, which was back extracted with CHCl$_3$. The organics were combined and washed with brine, dried over $MgSO_4$, filtered, and evaporated to yield 83 mg of crude product. This material was dissolved in 1.2 mL of methanol and treated with 20% Pd(OH)$_2$/C (40 mg) and stirred at 25° C. under hydrogen balloon pressure for 2 h. The reaction was filtered, evaporated, and purified using 5% methanol/CHCl$_3$ to give 38 mg (52%) of the title compound.

Example 631C

N-[(2R,3S)-3-amino-2-hydroxy-4-phenylbutyl]-4-hydroxy-N-isobutyl-3-[(methylsulfonyl)amino]benzenesulfonamide Example 631B (35 mg, 0.060 mmol) was dissolved in dichloromethane:trifluoroacetic acid (0.3 mL, 1:1) and stirred at 25° C. for 1.5 h. The reaction was evaporated and azeotroped with toluene (3x) to give the title compound.

Example 632

N-[(2R,3S)-3-amino-2-hydroxy-4-phenylbutyl]-3,5-dichloro-4-hydroxy-N-isobutylbenzenesulfonamide 3,5-dichloro-4-hydroxy benzenesulphonyl chloride (97 mg, 0.372 mmol) was dissolved in 1 mL of dichloromethane and treated with N,O-bis(trimethylsilyl)acetamide (0.092 mL, 1 equivalent) and stirred at 25° C. for 5 h. The reaction mixture was treated with Example 1 (100 mg, 0.8 equivalents) and triethylamine (0.109 mL, 2.1 equivalents) and stirred an additional hour. The reaction was diluted with dichloromethane washed with water, dried over $MgSO_4$, filtered, and evaporated to give 240 mg of a foamy solid. This material was stirred with dichloromethane:trifluoroacetic acid (4.5 mL, 2:1) for 1.5 h. The reaction was evaporated, redissolved in 10% methanol/dichloromethane, washed with saturated NaHCO$_3$ solution, and purified using 10% methanol/dichloromethane to give 80 mg of the title compound (58%).

Example 633

N-[(2R,3S)-3-amino-2-hydroxy-4-phenylbutyl]-3,5-dichloro-2-hydroxy-N-isobutylbenzenesulfonamide 3,5-dichloro-6-hydroxy benzenesulphonyl chloride (97 mg, 0.372 mmol) was dissolved in 1 mL of dichloromethane and treated with N,O-bis(trimethylsilyl)acetamide (0.092 mL, 1 equivalent) and stirred at 25° C. for 5 h. The reaction mixture was treated with Example 1 (100 mg, 0.8 equivalents) and triethylamine (0.109 mL, 2.1 equivalents) and stirred an additional hour. The reaction was diluted with dichloromethane washed with water, dried over $MgSO_4$, and evaporated to give 240 mg of a foamy solid. This material was stirred with dichloromethane:trifluoroacetic acid (4.5 mL, 2:1) for 1.5 h. The reaction was evaporated, redissolved in 10% methanol/dichloromethane, washed with saturated NaHCO$_3$ solution, and purified using 10% methanol/dichloromethane to give 79 mg of the title compound (57%).

Example 634

N-[(2R,3S)-3-amino-2-hydroxy-4-phenylbutyl]-4-hydroxy-N-isobutyl-3-methylbenzenesulfonamide Example 634A 4-(benzyloxy)-3-methylbenzenesulfonyl chloride O-Cresol-4-sulfonic acid (6 g, 31.88 mmol) was stirred with benzyl bromide (9.5 mL, 2.5 equivalent), 15% aqueous NaOH (34 mL, 4 equivalents), and ethanol (150 mL) at 67° C. for 22 h. The solvent was evaporated and the reaction was slurried with 10 mL of water, filtered, and the resulting white solid was washed with water twice. The material was dried in vacuo to give 8.2 g of the O-benzylated sodium salt. A portion of this material (4.0 g, 15.1 mmol) was stirred with phosphorous pentachloride (4.4 g, 1.5 equivalents) for 10 minutes. The mixture was partitioned between dichloromethane and water. The organic layer was separated, dried over MgSO$_4$, filtered and the solvent was removed by evaporation to give 3.29 g (77%) of the title compound.

Example 634B tert-butyl(1S,2R)-1-benzyl-3-[{[4-(benzyloxy)-3-methylphenyl]sulfonyl}(isobutyl)amino]-2-hydroxypropylcarbamate Example 1 (100 mg, 0.30 mmol) dissolved in 2 mL of dichloromethane was combined with Example 634A (1 mg, 1.2 equivalents) and triethylamine (0.0125 mL, 3 equivalents) and stirred for 4 h. The reaction was purified using 1% methanol/dichloromethane to give 200 mg (100%) of crude title compound.

Example 634C

N-[(2R,3S)-3-amino-2-hydroxy-4-phenylbutyl]-4-hydroxy-N-isobutyl-3-methylbenzenesulfonamide Example 634B (200 mg crude, 0.3 mmol) was dissolved in 2 mL of ethanol and treated with 10% Pd/C (100 mg). The reaction was stirred under hydrogen balloon pressure for 24 h. The reaction was filtered, evaporated, and purified using 1% methanol/dichloromethane to give 80 mg of the debenzylated product. This material was stirred with dichloromethane:trifluoroacetic acid (3 mL, 2:1) for 2.5 h. The solvents were evaporated, and the product was dissolved in dichloromethane, washed with NaHCO$_3$, dried over MgSO$_4$, filtered and concentrated to yield 70 mg (57%) of the title compound.

Example 635

N-[(2R,3S)-3-amino-2-hydroxy-4-phenylbutyl]-5-fluoro-4-hydroxy-N-isobutyl-2-methylbenzenesulfonamide Example 635A 5-fluoro-4-hydroxy-2-methylbenzenesulfonyl chloride To a solution of chlorosulfonic acid (1.5 g, 13.3 mmol) dissolved in 10 mL of dichloromethane was added 2-fluoro-5-methylphenol (1.1 g, 8.86 mmol) dropwise. After 10 minutes, the reaction was quenched by adding to ice water. The reaction was extracted with dichloromethane, washed with brine, dried over MgSO$_4$, filtered, and concentrated to give 150 mg (7.5%) of the title compound.

Example 635B

N-[(2R,3S)-3-amino-2-hydroxy-4-phenylbutyl]-5-fluoro-4-hydroxy-N-isobutyl-2-methylbenzenesulfonamide Example 635A (95 mg, 0.424 mmol) was dissolved in 1 mL of dichloromethane, treated with N,O-bis(trimethylsilyl)acetamide (0.105 mL, 1 equivalent), and stirred at 25° C. for 5 h. The reaction mixture was treated with Example 1 (100 mg, 0.7 equivalent), triethylamine (0.109 mL, 2.1 equivalents), and stirred an additional hour. The reaction was diluted with dichloromethane washed with water, dried over MgSO$_4$, filtered, and evaporated give a foamy solid. This material was stirred with dichloromethane:trifluoroacetic acid (4.5 mL, 2:1) for 1.5 h. The reaction was evaporated, redissolved in 10% methanol/dichloromethane, washed with saturated NaHCO$_3$ solution, and purified using 10% methanol/dichloromethane to give 53 mg of the title compound (42%).

Example 636

N-[(2R,3S)-3-amino-2-hydroxy-4-phenylbutyl]-5-chloro-4-hydroxy-N-isobutyl-2-methylbenzenesulfonamide Example 636A 5-chloro-4-hydroxy-2-methylbenzenesulfonyl chloride To a solution of chlorosulfonic acid (1.22 g, 10.5 mmol) dissolved in 10 mL of dichloromethane was added 2-chloro-5-methylphenol (1.0 g, 7.0 mmol) dropwise. After 10 minutes, the reaction was quenched by pouring it into ice water. The reaction was extracted with dichloromethane, washed with brine, dried over MgSO$_4$, filtered, and concentrated to give 120 mg (7.1%) of the title compound.

Example 636B

N-[(2R,3S)-3-amino-2-hydroxy-4-phenylbutyl]-5-chloro-4-hydroxy-N-isobutyl-2-methylbenzenesulfonamide Example 636A (120 mg, 0.50 mmol) was dissolved in 1 mL of dichloromethane, treated with N,O-bis(trimethylsilyl)acetamide (0.123 mL, 1 equivalent), and stirred at 25° C. for 5 h. The reaction mixture was treated with Example 1 (117 mg, 0.7 equivalent), triethylamine (0.106 mL, 2.1 equivalents), and stirred an additional hour. The reaction was diluted with dichloromethane, washed with water, dried over MgSO$_4$, filtered, and evaporated to give a foamy solid. This material was stirred with dichloromethane:trifluoroacetic acid (4.5 mL, 2:1) for 1.5 h. The reaction was evaporated, redissolved in 10% methanol/dichloromethane, washed with saturated NaHCO$_3$ solution, and purified using 10% methanol/dichloromethane to give 33 mg (21%) of the title compound.

Example 637

N-[(2R,3S)-3-amino-2-hydroxy-4-phenylbutyl]-3-chloro-4-hydroxy-N-isobutyl-5-methylbenzene-sulfonamide

Example 637A 3-chloro-4-hydroxy-5-methylbenzenesulfonyl chloride

To a solution of chlorosulfonic acid (1.22 g, 10.5 mmol) dissolved in 10 mL of dichloromethane was added 2-chloro-5-methylphenol (1.0 g, 7.0 mmol) dropwise. After 10 minutes, the reaction was quenched by pouring it into ice water. The reaction was extracted with dichloromethane, washed with brine, dried over MgSO$_4$, filtered, and concentrated to give 190 mg (11.3%) of the title compound.

Example 637B

N-[(2R,3S)-3-amino-2-hydroxy-4-phenylbutyl]-3-chloro-4-hydroxy-N-isobutyl-5-methylbenzene-sulfonamide Example 637A (190 mg, 0.788 mmol) was dissolved in 2 mL of dichloromethane, treated with N,O-bis(trimethylsilyl)acetamide (0.194 mL, 1 equivalent), and stirred at 25° C. for 5 h. The reaction mixture was treated with Example 1 (183 mg, 0.7 equivalent), triethylamine (0.230 mL, 2.1 equivalents), and stirred an additional hour. The reaction was diluted with dichloromethane, washed with water, dried over MgSO$_4$, and evaporated to give a foamy solid. This material was stirred with dichloromethane:trifluoroacetic acid (4.5 mL, 2:1) for 2 h. The reaction was evaporated, redissolved in 10% methanol/dichloromethane, washed with saturated NaHCO$_3$ solution, and purified using 7% methanol/dichloromethane to give 110 mg (46%) of the title compound.

Example 638

N-[(2R,3S)-3-amino-2-hydroxy-4-phenylbutyl]-2-chloro-4-hydroxy-N-isobutyl-5-methylbenzene-sulfonamide

Example 638A 2-chloro-4-hydroxy-5-methylbenzenesulfonyl chloride

To a solution of chlorosulfonic acid (3.69 g, 31.65 mmol) dissolved in 30 mL of dichloromethane was added 3-chloro-6-methylphenol (3.0 g, 21.1 mmol) dropwise. After 10 minutes, the reaction was quenched by pouring it into ice water. The reaction was extracted with dichloromethane, washed with brine, dried over MgSO$_4$, filtered, and concentrated to give 120 mg (2.4%) of the title compound.

Example 638B

N-[(2R,3S)-3-amino-2-hydroxy-4-phenylbutyl]-2-chloro-4-hydroxy-N-isobutyl-5-methylbenzene-sulfonamide Example 638A (120 mg, 0.497 mmol) was dissolved in 2 mL of dichloromethane, treated with N,O-bis(trimethylsilyl)acetamide (0.135 mL, 1.1 equivalents), and stirred at 25° C. for 5 h. The reaction mixture was treated with Example 1 (132 mg, 0.7 equivalent), triethylamine (0.164 mL, 2.1 equivalents), and stirred an additional hour. The reaction was diluted with dichloromethane, washed with water, dried over MgSO$_4$, filtered, and evaporated to give a foamy solid. This material was stirred with dichloromethane:trifluoroacetic acid (4.5 mL, 2:1) for 2 h. The reaction was evaporated, redissolved in 10% methanol/dichloromethane, washed with saturated NaHCO$_3$ solution, and purified using 7% methanol/dichloromethane to give 25 mg (14.5%) of the title compound.

Example 639

N-[(2R,3S)-3-amino-2-hydroxy-4-phenylbutyl]-4-hydroxy-N-isobutyl-3-{[(methylamino)sulfonyl]amino}benzenesulfonamide

Example 639A 4-hydroxy-3-nitrobenzenesulfonyl chloride

To a solution of chlorosulfonic acid (12.0 mL, 180 mmol) at 0° C. was added 2-nitrophenol (8.35 g, 60.0 mmol) in small portions over 1 h. The reaction was heated to 60° C. for 20 minutes and allowed to stir for 18 h at 25° C. The reaction was quenched by pouring it into 100 g of ice. The reaction was extracted with chloroform (3×), washed with cold water (2×), dried over MgSO$_4$, filtered, and concentrated to give 9.06 g (64%) of the title compound.

Example 639B tert-butyl(1S,2R)-1-benzyl-2-hydroxy-3-[[(4-hydroxy-3-nitrophenyl)sulfonyl](isobutyl)amino]propylcarbamate Example 639A (1.06 g, 4.46 mmol) was dissolved in 22 mL of dichloromethane, treated with N,O-bis(trimethylsilyl)acetamide (1.1 mL, 1 equivalent), and stirred at 25° C. for 3 h. The reaction mixture was treated with Example 1 (1.5 g, 1 equivalent) in 10 mL of dichloromethane, triethylamine (2.0 mL, 3 equivalents), and stirred over 72 h. The reaction was washed with water, dried over MgSO$_4$, filtered, and evaporated. This material was dissolved in tetrahydrofuran (20 mL) and treated with tetrabutylammonium fluoride (15.0 mL, 3 equivalents) for 2 h. at 25° C. Ethyl acetate was added and the reaction was washed with 10% citric acid, water (2×), and brine. The reaction was dried over MgSO$_4$, filtered and concentrated to give 2.1 g (87.5%) of the title compound.

Example 639C tert-butyl(1S,2R)-1-benzyl-3-{isobutyl[(3-nitro-4-{[2-(trimethylsilyl)ethoxy]methoxy}phenyl)sulfonyl]amino}-2-{[2-(trimethylsilyl)ethoxy]methoxy}propylcarbamate Example 639B (1.0 g, 1.86 mmol) in 10 mL of N,N-dimethylformamide was treated with 2-(trimethylsilyl)ethoxymethyl chloride (1.30 mL, 4.0 equivalents) and N,N-diisopropylethylamine (2.0 mL, 6 equivalents) at 50° C. for 18 h. The reaction was diluted with ethyl acetate and washed with water (2×) followed by brine. The organic layer was dried over MgSO$_4$, filtered, concentrated, and purified using 5% ethyl acetate/dichloromethane to give 870 mg (58%) of the title compound.

Example 639D tert-butyl(1S,2R)-3-[[(3-amino-4-{[2-(trimethylsilyl)ethoxy]methoxy}phenyl)sulfonyl](isobutyl)amino]-1-benzyl-2-{[2-(trimethylsilyl)ethoxy]methoxy}propylcarbamate Example 639C (800 mg, 1.0 mmol) was dissolved in 5 mL of ethyl acetate and treated with 20% Pd(OH)$_2$/C (200 mg, 0.28 equivalent) under hydrogen balloon pressure for 3 h. The reaction was filtered, concentrated and purified using 5% ethyl acetate/chloroform to give 599 mg (78%) of the title compound.

Example 639E tert-butyl(1S,2R)-1-benzyl-3-{isobutyl[(3-{[(methylamino)sulfonyl]amino}-4-{[2-(trimethylsilyl)ethoxy]methoxy}phenyl)sulfonyl]amino}-2-{[2-(trimethylsilyl)ethoxy]methoxy}propylcarbamate Example 639D (100 mg, 0.13 mmol) in 1.3 mL of dichloromethane was treated with pyridine (0.025 mL, 2.4 equivalents) and N-methyl sulfamoyl chloride (ref: JOC 1976, 41, 4028)(0.014 mL, 1.2 equivalent) at 25° C. for 18 h. The reaction was concentrated and purified using 10% ethyl acetate/chloroform to give 106 mg (95%) of the title compound.

Example 639F

N-[(2R,3S)-3-amino-2-hydroxy-4-phenylbutyl]-4-hydroxy-N-isobutyl-3-{[(methylamino)sulfonyl]amino}benzenesulfonamide Example 639E (25 mg, 0.03 mmol) was dissolved in methanol (0.22 mL) and 4 N HCl (0.07 mL, 9.3 equivalents). The reaction was stirred at 25° C. for 18 h. The reaction was concentrated to give 15 mg (100%) of the title compound.

Example 640 ethyl 5-{[[(2R,3S)-3-amino-2-hydroxy-4-phenylbutyl](isobutyl)amino]sulfonyl}-2-hydroxyphenylcarbamate

Example 640A tert-butyl(1S,2R)-1-benzyl-3-[[(3-[(ethoxycarbonyl)amino]-4-{[2-(trimethylsilyl)ethoxy]methoxy}phenyl)sulfonyl](isobutyl)amino]-2-{[2-(trimethylsilyl)ethoxy]methoxy}propylcarbamate Example 639D (50 mg, 0.065 mmol) was dissolved in 0.7 mL of dichloromethane and treated with pyridine (0.012 mL, 2.4 equivalents) and ethyl chloroformate (0.007 mL, 1.2 equivalents). The reaction was stirred at 25° C. for 18 h, and the crude mixture was purified using 10% ethyl acetate/chloroform to give 49.6 (90%) of the title compound.

Example 640B ethyl 5-{[[(2R,3S)-3-amino-2-hydroxy-4-phenylbutyl](isobutyl)amino]sulfonyl}-2-hydroxyphenylcarbamate Example 640A (57 mg, 0.067 mmol) was dissolved in 0.75 mL of methanol, treated with 4 N HCl (0.25 mL, 15 equivalents) and stirred at 25° C. for 2 h. The solvents were evaporated to yield 32 mg of the title compound (100%).

Example 641

N-[(2R,3S)-3-amino-2-hydroxy-4-phenylbutyl]-4-hydroxy-N-isobutyl-3-(methylamino)benzenesulfonamide

Example 641A tert-butyl(1S,2R)-1-benzyl-3-{isobutyl[(3-(methylamino)-4-{[2-(trimethylsilyl)ethoxy]methoxy}phenyl)sulfonyl]amino}-2-{[2-(trimethylsilyl)ethoxy]methoxy}propylcarbamate Example 639D (125 mg, 0.16 mmol) was dissolved in 1.8 mL of acetonitrile and treated with formaldehyde (0.065 mL, 5 equivalents), sodium cyanoborohydride (20 mg, 2 equivalents), and acetic acid (0.018 mL, 2 equivalents). The reaction was stirred for 18 h at 25° C., and the crude mixture was purified using 10% ethyl acetate/chloroform to give 39 mg (31%) of the title compound.

Example 641B

N-[(2R,3S)-3-amino-2-hydroxy-4-phenylbutyl]-4-hydroxy-N-isobutyl-3-(methylamino)benzenesulfonamide Example 641A (36 mg, 0.05 mmol) was dissolved in 0.3 mL of methanol and treated with 4 N HCl (0.3 mL, 24 equivalents). Stirring was continued at 25° C. for 2 h. The reaction was concentrated to yield 21 mg of the title compound (100%).

Example 642

N-[(2R,3S)-3-amino-2-hydroxy-4-phenylbutyl]-3-(dimethylamino)-4-hydroxy-N-isobutylbenzenesulfonamide

Example 642A tert-butyl(1S,2R)-1-benzyl-3-[[(3-(dimethylamino)-4-{[2-(trimethylsilyl)ethoxy]methoxy}phenyl)sulfonyl](isobutyl)amino]-2-{[2-(trimethylsilyl)ethoxy]methoxy}propylcarbamate Example 639D (125 mg, 0.16 mmol) was dissolved in 1.8 mL of acetonitrile and treated with formaldehyde (0.065 mL, 5 equivalents), sodium cyanoborohydride (20 mg, 2 equivalents), and acetic acid (0.018 mL, 2 equivalents). The reaction was stirred for 18 h. at 25° C. Purification was performed using 10% ethyl acetate/chloroform to give 54 mg (43%) of the title compound.

Example 642B

N-[(2R,3S)-3-amino-2-hydroxy-4-phenylbutyl]-3-(dimethylamino)-4-hydroxy-N-isobutylbenzene-sulfonamide Example 642A (54 mg, 0.07 mmol) was dissolved in 0.4 mL of methanol and treated with 4 N HCl (0.4 mL, 23 equivalents). Stirring was continued at 25° C. for 2 h. The reaction was concentrated to yield 30 mg of the title compound (100%).

Example 643

N-[(2R,3S)-3-amino-2-hydroxy-4-phenylbutyl]-3-{[(ethylamino)carbonyl]amino}-4-hydroxy-N-isobu-tylbenzenesulfonamide

Example 643A tert-butyl(1S,2R)-1-benzyl-3-[[(3-{[(ethylamino)carbonyl]amino}-4-{[2-(trimethylsilyl)ethoxy]methoxy}phenyl)sulfonyl](isobutyl)amino]-2-{[2-(trimethylsilyl)ethoxy]methoxy}propylcarbamate Example 639D (50 mg, 0.065 mmol) was dissolved in 0.2 mL of toluene and treated with ethyl isocyanate (0.1 mL, 20 equivalents). The reaction was stirred at 50° C. for 18 h. Purification was performed using 10% ethyl acetate/chloroform to give 35.3 (64%) of the title compound.

Example 643B

N-[(2R,3S)-3-amino-2-hydroxy-4-phenylbutyl]-3-{[(ethylamino)carbonyl]amino}-4-hydroxy-N-isobu-tylbenzenesulfonamide Example 643A (35 mg, 0.042 mmol) was dissolved in 0.25 mL of methanol and treated with 4 N HCl (0.25 mL, 24 equivalents). Stirring was continued at 25° C. for 2 h. The reaction was concentrated to yield 30 mg of the title compound (100%).

Example 644 methyl 5-{[[(2R,3S)-3-amino-2-hydroxy-4-phenyl-butyl](isobutyl)amino]sulfonyl}-2-hydroxyphenyl-carbamate

Example 644A tert-butyl(1S,2R)-1-benzyl-3-{isobutyl[(3-[(methoxycarbonyl)amino]-4-{[2-(trimethylsilyl)ethoxy]methoxy}phenyl)sulfonyl]amino}-2-{[2-(trimethyl-silyl)ethoxy]methoxy}propylcarbamate Example 639D (57 mg, 0.074 mmol) was dissolved in 0.8 mL of dichloromethane and treated with pyridine (0.014 mL, 2.4 equivalents) and methyl chloroformate (0.007 mL, 1.2 equivalents). The reaction was stirred at 25° C. for 18 h. Purification was performed using 10% ethyl acetate/chloroform to give 58.0 (95%) of the title compound.

Example 644B methyl 5-{[[(2R,3S)-3-amino-2-hydroxy-4-phenyl-butyl](isobutyl)amino]sulfonyl}-2-hydroxyphenyl-carbamate Example 644A (56 mg, 0.068 mmol) was dissolved in 0.3 mL of methanol and treated with 4 N HCl (0.3 mL, 18 equivalents) and stirred at 25° C. for 2 h. The reaction was concentrated to yield 31 mg of the title compound (100%).

Example 645 benzyl 5-{[[(2R,3S)-3-amino-2-hydroxy-4-phenyl-butyl](isobutyl)amino]sulfonyl}-2-hydroxyphenyl-carbamate

Example 645A benzyl 5-{[((2R,3S)-3-[(tert-butoxycarbonyl)amino]-4-phenyl-2-{[2-(trimethylsilyl)ethoxy]methoxy}butyl)(isobutyl)amino]sulfonyl}-2-{[2-(trimethylsilyl)ethoxy]methoxy}phenylcarbamate Example 639D (57 mg, 0.074 mmol) was dissolved in 0.8 mL of dichloromethane and treated with pyridine (0.014 mL, 2.4 equivalents) and benzyl chloroformate (0.013 mL, 1.2 equivalents). The reaction was stirred at 25° C. for 18 h. Purification was performed using 10% ethyl acetate/chloroform to give 51.4 (78%) of the title compound.

Example 645B benzyl 5-{[[(2R,3S)-3-amino-2-hydroxy-4-phenylbutyl](isobutyl)amino]sulfonyl}-2-hydroxyphenylcarbamate Example 645A (49 mg, 0.056 mmol) was dissolved in 0.3 mL of methanol and treated with 4 N HCl (0.3 mL, 21 equivalents). Stirring was continued at 25° C. for 2 h. The reaction was concentrated to yield 30 mg (100%) of the title compound.

Example 646

4-amino-N-[(2R,3S)-3-amino-2-hydroxy-4-phenyl-butyl]-3-hydroxy-N-isobutylbenzenesulfonamide hydrate

Example 646A 2-oxo-2,3-dihydro-1,3-benzoxazole-6-sulfonyl chloride

Benzoxazolinone (13.5 g, 0.1 mol) was added slowly to a 0° C. solution of chlorosulfonic acid (33.29 mL, 5 equivalents). The reaction was warmed to 25° C. and stirred for 0.5 h, heated to 60° C. for 3 h. The reaction was cooled to 25° C., poured into ice, filtered, and rinsed with water. The resulting white solid was redissolved in 500 mL of diethyl ether and washed with water (2×), dried over $Na_2SO_4$, filtered and concentrated to 100 mL volume. Hexane was added (100 mL) and the white precipitate was filtered and placed under vacuum to yield 17 g (73%) of the title compound.

Example 646B tert-butyl(1S,2R)-1-benzyl-2-hydroxy-3-{isobutyl[(2-oxo-2,3-dihydro-1,3-benzoxazol-6-yl)sulfonyl]amino}propylcarbamate Example 1 (200 mg, 0.6 mmol) was dissolved in 4 mL of dichloromethane and treated with Example 646A (175 mg, 1.25 equivalents) and triethylamine (0.21 mL, 2.5 equivalents). Stirring was maintained for 16 h. at 25° C. The reaction was purified using 2% methanol/dichloromethane to give 370 mg (58%) of the title compound.

Example 646C 4-amino-N-[(2R,3S)-3-amino-2-hydroxy-4-phenylbutyl]-3-hydroxy-N-isobutylbenzenesulfonamide Example 646B (370 mg, 0.694 mmol) was dissolved in 0.5 mL of dichloromethane and treated with trifluoroacetic acid (1.7 mL). The reaction was stirred for 3 h at 25° C., quenched with 50 mL of water, and made alkaline to pH=9 with sodium bicarbonate. Extract with ethyl acetate, filter off the precipitate, dry the organic layer over $Na_2SO_4$, filter, and concentrate to give 290 mg of the intermediate. A portion of this material (120 mg, 0.23 mmol) was dissolved in 1 mL of methanol, treated with 3 mL of 30% NaOH solution, and heated to 80° C. for 3 h. The solvents were evaporated and the crude residue was extracted with ethyl acetate. The material was purified using 10% methanol/dichloromethane (w/1% $NH_4OH$) to yield 67 mg (60%) of the title compound.

Example 647

N-[(2R,3S)-3-amino-2-hydroxy-4-phenylbutyl]-4-(2-hydroxyethyl)-N-isobutylbenzenesulfonamide

Example 647A tert-butyl(1S,2R)-1-benzyl-2-hydroxy-3-{isobutyl[(4-vinylphenyl)sulfonyl]amino}propylcarbamate Example 1 (2.27 g, 6.8 mmol) in 20 mL of dichloromethane at 25° C. was treated with triethylamine (3.75 mL, 4 equivalents) followed by dropwise addition of 4-vinylbenzene sulfonyl chloride (1.6 g, 1.2 equivalents). Stirring was continued for 16 h. after which the reaction was quenched with 1 N $NaHCO_3$, and evaporated. The material was purified using 20% ethyl acetate/hexane to give 1.5 g (44%) of the title compound.

Example 647B tert-butyl(1S,2R)-1-benzyl-2-hydroxy-3-[{[4-(2-hydroxyethyl)phenyl]sulfonyl}(isobutyl)amino]propylcarbamate Example 647A (100 mg, 0.2 mmol) was dissolved in 3 mL of tetrahydrofuran at 0° C. and treated with borane-methyl sulfide complex (2 M/tetrahydrofuran, 0.3 mL, 3 equivalents). Stirring was continued for 3 h after which water (0.8 mL), followed by an aqueous solution of 1N NaOH (0.3 ml) was added. The reaction allowed to warm to 25° C. and 30% $H_2O_2$ (0.2 mL) was added. After stirring for 30 min., the reaction was partitioned between brine and ethyl acetate. The organic layer was concentrated and the material was purified using 40% ethyl acetate/hexanes to give 45 mg (43.5%) of the title compound.

Example 647C

N-[(2R,3S)-3-amino-2-hydroxy-4-phenylbutyl]-4-(2-hydroxyethyl)-N-isobutylbenzenesulfonamide Example 647B (37 mg, 0.0712 mmol) was dissolved in 0.2 mL of dichloromethane and treated with 0.8 mL of trifluoroacetic acid and stirred at 25° C. for 3 h. The reaction was evaporated and purified using 5% methanol/dichloromethane (w/0.5% $NH_4OH$) to give 16 mg (53.5%) of the title compound.

Example 648

N-[(2R,3S)-3-amino-2-hydroxy-4-phenylbutyl]-N-isobutyl-4-[(methylsulfonyl)amino]benzenesulfonamide

Example 648A tert-butyl(1S,2R)-1-benzyl-2-hydroxy-3-{isobutyl[(4-nitrophenyl)sulfonyl]amino}propylcarbamate Example 1 (400 mg, 1.2 mmol) was dissolved in 8 mL of dichloromethane and treated with p-nitro benzenesulfonyl chloride (0.316 g, 1.2 equivalents) and triethylamine (0.414 mL, 2.5 equivalents). The reaction was stirred at 25° C. for 16 h, and purified using 2% methanol/dichloromethane to give 0.56 g (90%) of the title compound.

Example 648B tert-butyl(1S,2R)-3-[[(4-aminophenyl)sulfonyl](isobutyl)amino]-1-benzyl-2-hydroxypropylcarbamate Example 648A (0.56 g, 1.07 mmol) in 10 mL of ethyl acetate was treated with 20% $Pd(OH)_2$/C (0.35 g, 0.2 equivalent) under a hydrogen balloon atmosphere for 2 h. The reaction was filtered, evaporated, and purified using 5% methanol/dichloromethane to give 520 mg (98%) of the title compound.

Example 648C

N-[(2R,3S)-3-amino-2-hydroxy-4-phenylbutyl]-N-isobutyl-4-[(methylsulfonyl)amino]benzenesulfonamide Example 648B (150 mg, 0.3 mmol) in 0.5 mL of dichloromethane was treated with pyridine (0.5 mL, 20 equivalents) and methanesulfonyl chloride (0.06 mL, 2.2 equivalents) at 25° C. for 5 h. The reaction was quenched with 1 N $NaHCO_3$, diluted with dichloromethane, concentrated, and purified using 1% methanol/20% ethyl acetate/dichloromethane to give 150 mg (87%) of product. This material was dissolved in 0.2 mL of dichloromethane and treated with 0.5 ml, of trifluoroacetic acid at 25° C. for 3 h. The reaction was quenched with 10 mL of water, made alkaline with 1 N $NaHCO_3$ and extracted with ethyl acetate. This material was purified using 5% methanol/dichloromethane (w/1% $NH_4OH$) to give 109 mg (88%) of the title compound.

Example 649

(2S)—N-{(1S,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide Example 143 (59 mg, 0.198 mmol) was combined with N-hydroxysuccinimide (25 mg, 1.1 equivalents) and DCC (45 mg, 1.1 equivalents) in dichloromethane (1 mL) and stirred for 1 h at 25° C. The solids are filtered, and to this mixture is added N-methylmorpholine (22 μL, 1 equivalent) and Example 625B (100 mg, 1 equivalent). The mixture was stirred for 16 h, evaporated, and purified using 1.5% methanol/CHCl$_3$ to give 42 mg (32%) of the title compound. $^1$H NMR (300 MHz, CDCl$_3$) δ ppm 0.74 (d, J=6.44 Hz, 3H), 0.81 (d, J=6.78 Hz, 3H), 0.90 (m, 6H), 1.86 (dd, J=13.90, 7.12 Hz, 1H), 2.13 (m, 1H), 2.69 (s, 3H), 2.79 (m, 2H), 2.94 (dd, J=7.46, 2.71 Hz, 2H), 2.99 (m, 1H), 3.04 (d, J=3.73 Hz, 1H), 3.10 (d, J=8.48 Hz, 1H), 3.16 (dd, J=8.82, 4.41 Hz, 1H), 3.24 (m, 2H), 3.59 (d, J=10.85 Hz, 1H), 3.78 (m, 1H), 3.85 (d, J=3.05 Hz, 1H), 4.04 (dd, J=9.49, 5.09 Hz, 1H), 4.42 (s, 2H), 6.44 (d, J=8.82 Hz, 1H), 6.92 (m, 2H), 6.96 (s, 1H), 7.17 (m, 5H), 7.65 (m, 2H).

The compounds listed in Table 16, wherein $X_7$, $X_9$, and $X_4$ represent respectively the points of connection to the core structure (M), were prepared by coupling the corresponding acids (Examples 31-160) with the corresponding amines (Examples 625-648) as exemplified in Example 362 (Method A), Example 162 (Method B), Example 524 (Method C) and Example 478 (Method D).

TABLE 16

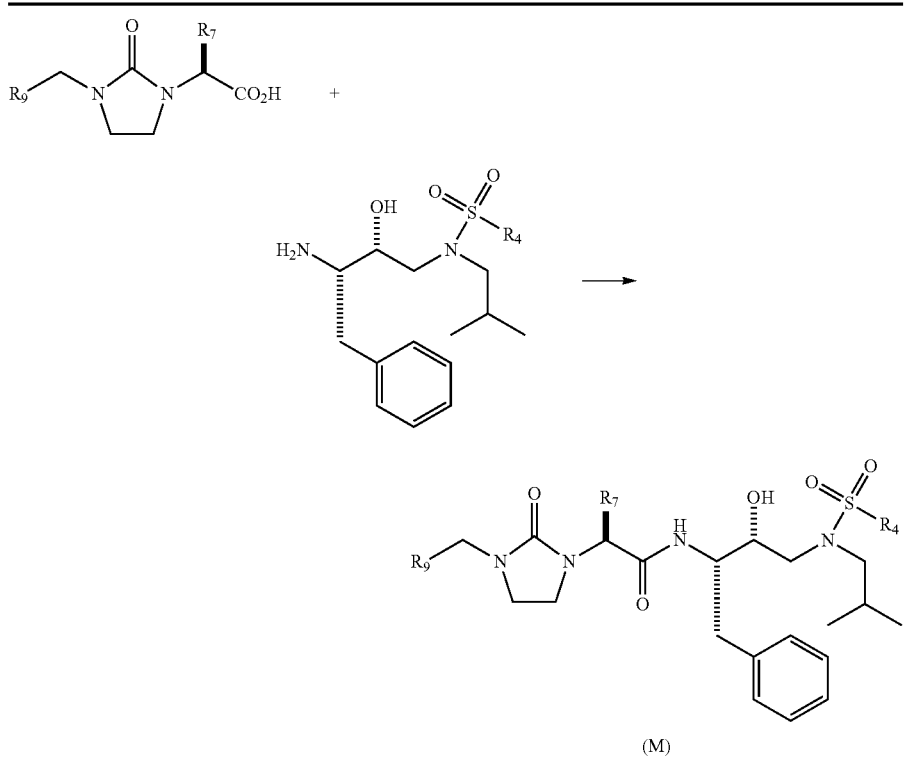

| Ex. | Method | $R_9$ | $R_7$ | $R_4$ |
|---|---|---|---|---|
| 650 | C | 2-methyl-thiazol-4-yl ($X_9$) | isopropyl ($X_7$) | 4-hydroxyphenyl ($X_4$) |
| 651 | C | 2-methyl-thiazol-4-yl ($X_9$) | isopropyl ($X_7$) | 2-chloro-5-amino-phenyl ($X_4$) |

TABLE 16-continued
| 652 | C | 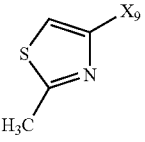 | 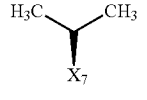 | 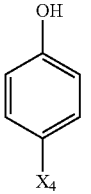 |
| 653 | C | 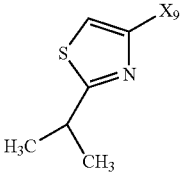 | 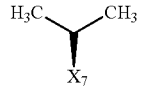 | 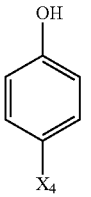 |
| 654 | C | 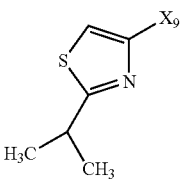 | 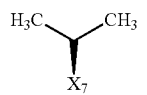 | 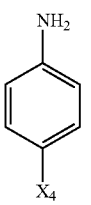 |
| 655 | C | 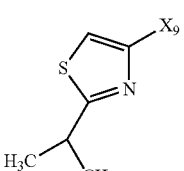 | 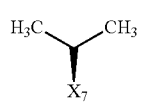 | 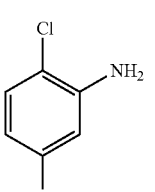 |
| 656 | C | 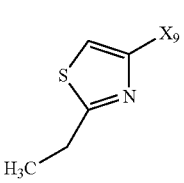 | 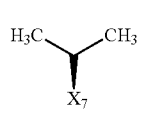 | 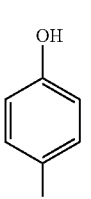 |
| 657 | C | 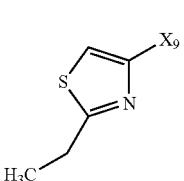 | 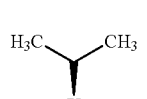 | 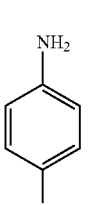 |
| 658 | C | 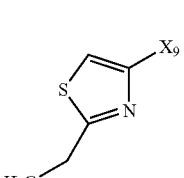 | 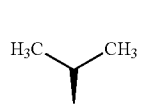 | 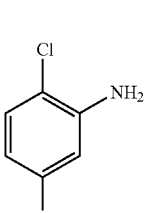 |

TABLE 16-continued
| | | | | |
|---|---|---|---|---|
| 659 | C | 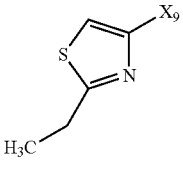 | 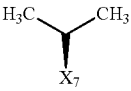 | 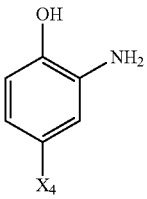 |
| 660 | C | 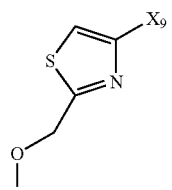 | 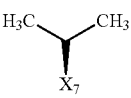 | 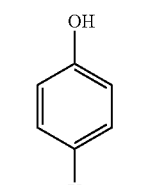 |
| 661 | C | 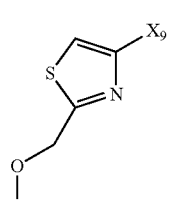 | 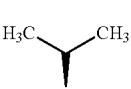 | 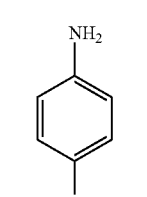 |
| 662 | C | 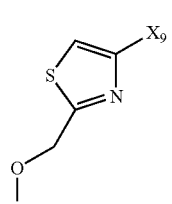 | 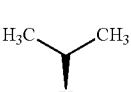 | 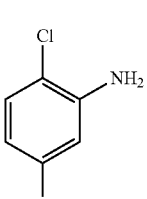 |
| 663 | C | 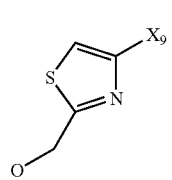 | 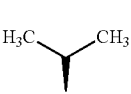 | 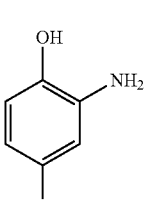 |
| 664 | C | 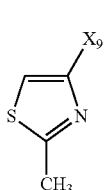 | 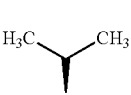 | 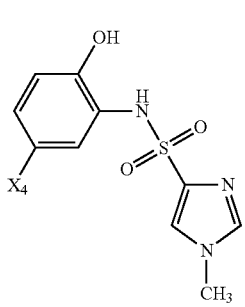 |
| 665 | A | 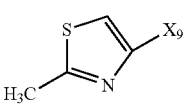 | 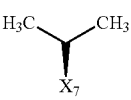 | 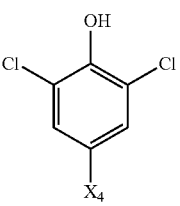 |

TABLE 16-continued

| | | | | |
|---|---|---|---|---|
| 666 | A | 2-nitrothiophene-4-$X_9$ | isopropyl-$X_7$ | 4-hydroxyphenyl-$X_4$ |
| 667 | C | 2-methylthiazole-4-$X_9$ | isopropyl-$X_7$ | 2-hydroxy-5-$X_4$-phenyl-NH-SO$_2$-(pyridin-3-yl) |
| 668 | C | 2-methylthiazole-4-$X_9$ | isopropyl-$X_7$ | 2-hydroxy-5-$X_4$-phenyl-NH-SO$_2$-CH$_3$ |
| 669 | C | 2-cyclopropylthiazole-4-$X_9$ | isopropyl-$X_7$ | 4-hydroxyphenyl-$X_4$ |
| 670 | C | 2-cyclopropylthiazole-4-$X_9$ | isopropyl-$X_7$ | 2-chloro-5-$X_4$-3-amino-phenyl |
| 671 | C | 2-cyclopropylthiazole-4-$X_9$ | isopropyl-$X_7$ | 4-$X_4$-aniline |
| 672 | A | 2-methylthiazole-4-$X_9$ | isopropyl-$X_7$ | 2-ethyl-4-hydroxy-5-$X_4$-phenyl |
| 673 | A | 2-methylthiazole-4-$X_9$ | isopropyl-$X_7$ | 3,5-dichloro-2-hydroxy-$X_4$-phenyl |

TABLE 16-continued

| 674 | A | 2-methylthiazol-4-yl (X9) | isopropyl (X7) | 4-hydroxy-3-methylphenyl (X4) |
| 675 | A | 2-methylthiazol-4-yl (X9) | isopropyl (X7) | 4-(methylsulfonamido)phenyl (X4) |
| 676 | A | 2-methylthiazol-4-yl (X9) | isopropyl (X7) | 2-fluoro-5-methyl-4-X4-phenol |
| 677 | A | 2-methylthiazol-4-yl (X9) | isopropyl (X7) | 2-chloro-5-methyl-4-X4-phenol |
| 678 | A | 2-methylthiazol-4-yl (X9) | isopropyl (X7) | 2-chloro-6-methyl-4-X4-phenol |
| 679 | C | 2-methylthiazol-4-yl (X9) | isopropyl (X7) | 2-hydroxy-5-X4-phenyl N-methylsulfamide |
| 680 | C | 2-methylthiazol-4-yl (X9) | isopropyl (X7) | ethyl (2-hydroxy-5-X4-phenyl)carbamate |

TABLE 16-continued
| | | | | |
|---|---|---|---|---|
| 681 | A | 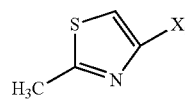 | 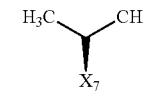 | 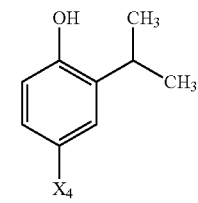 |
| 682 | A | 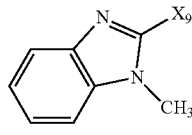 | 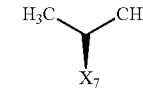 | 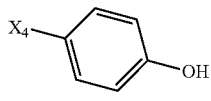 |
| 683 | A | 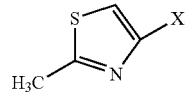 | 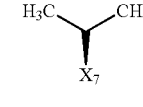 | 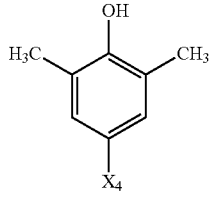 |
| 684 | A | 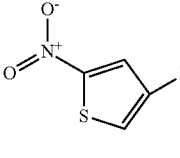 | 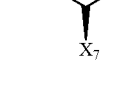 | 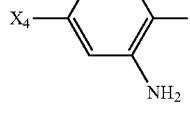 |
| 685 | A | 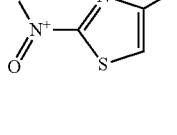 | 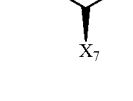 | 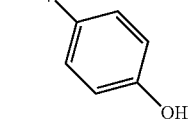 |
| 686 | A | 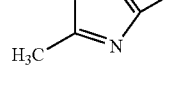 |  | 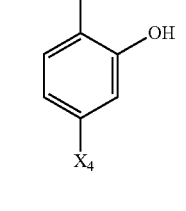 |
| 687 | A | 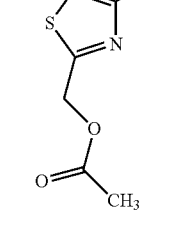 |  | 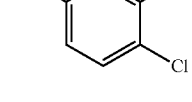 |
| 688 | C | 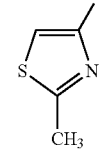 | 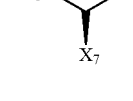 | 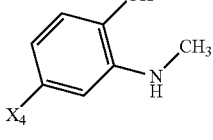 |

TABLE 16-continued
| 689 | C | 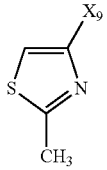 | 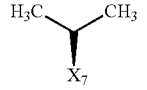 | 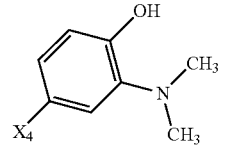 |
| --- | --- | --- | --- | --- |
| 690 | C | 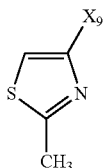 | 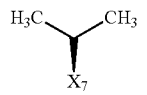 | 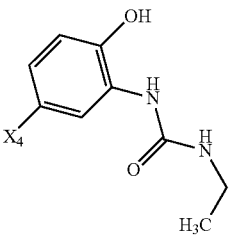 |
| 691 | C | 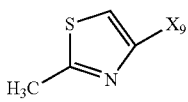 | 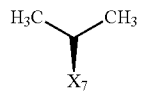 | 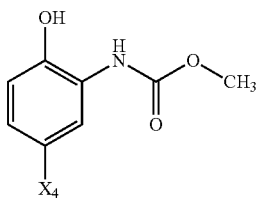 |
| 692 | C | 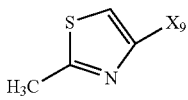 | 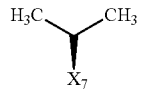 | 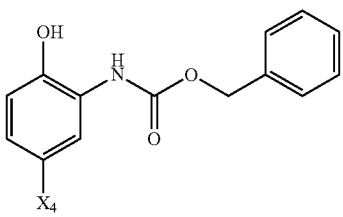 |
| 693 | A | 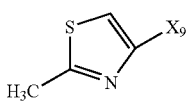 | 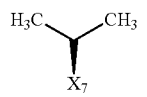 | 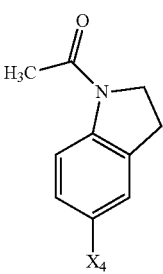 |
| 694 | A | 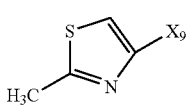 | 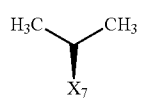 | 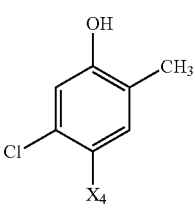 |
| 695 | A | 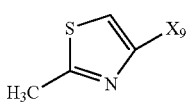 | 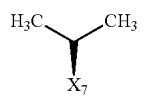 | 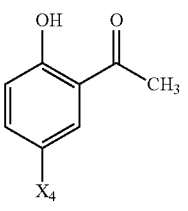 |

TABLE 16-continued
| 696 | A | 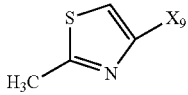 | 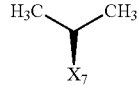 | 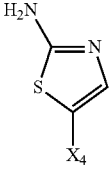 |
| 697 | A | 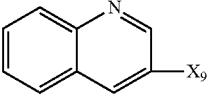 | 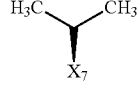 | 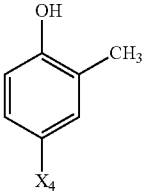 |
| 698 | A | 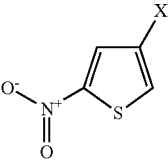 | 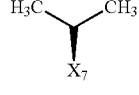 | 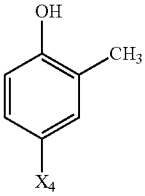 |
| 699 | A | 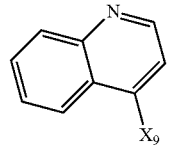 | 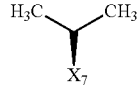 | 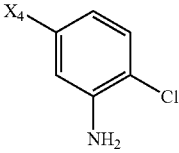 |
| 700 | A | 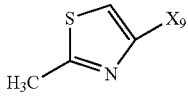 | 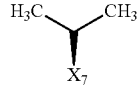 | 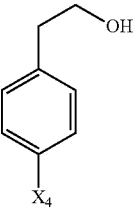 |
| 701 | A | 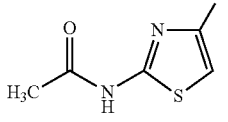 | 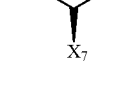 | 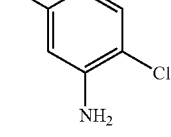 |
| 702 | A | 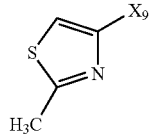 | 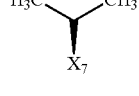 | 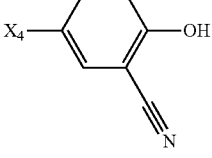 |
| 703 | B | 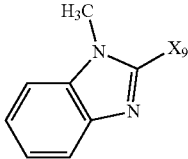 | 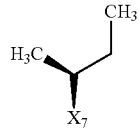 | 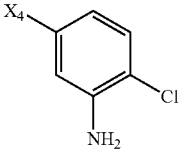 |

TABLE 16-continued
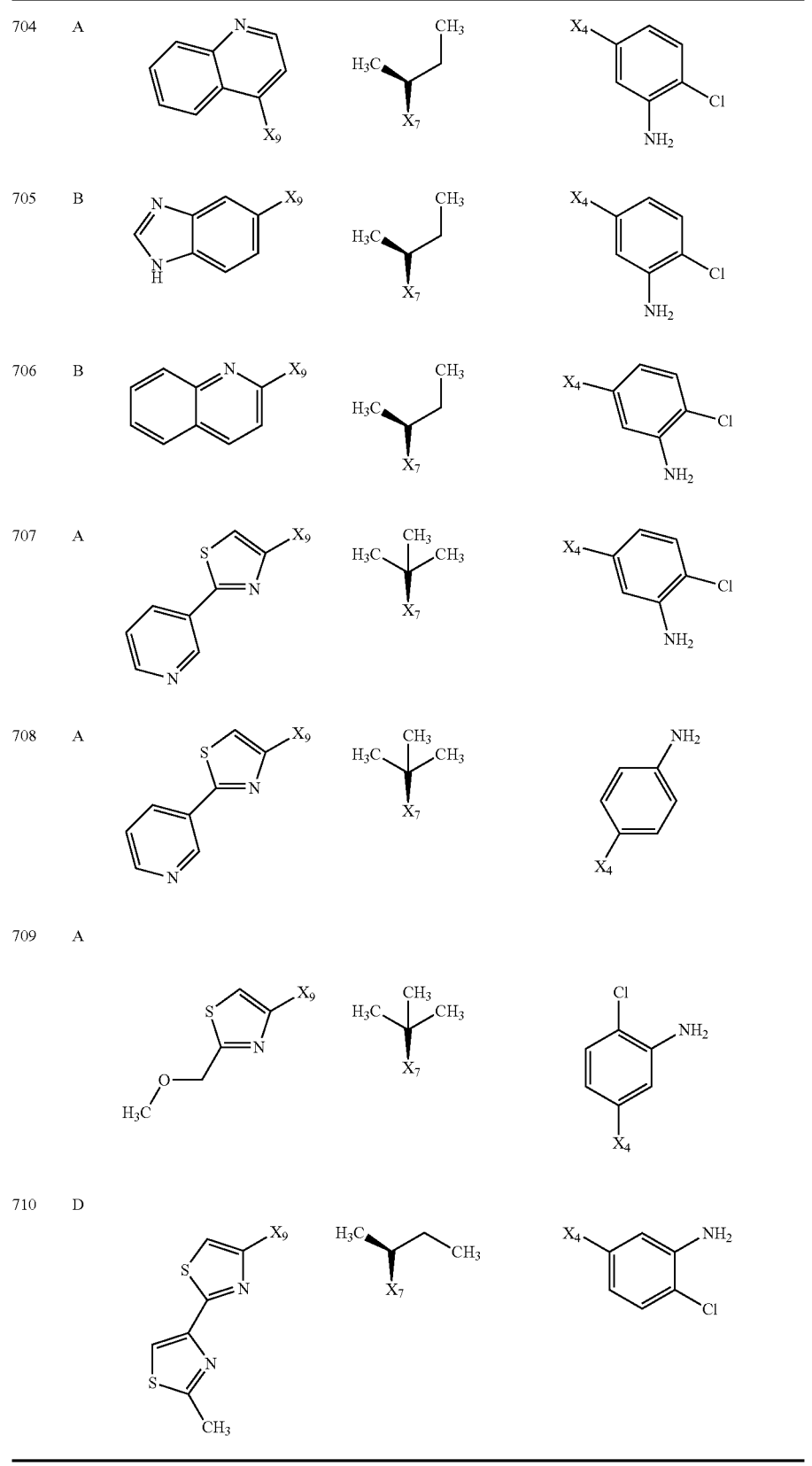

Example 711

(2S)—N-{(1S,2R)-1-benzyl-2-hydroxy-3-[({4-[(E)-(hydroxyimino)methyl]phenyl}sulfonyl)(neopentyl)amino]propyl}-3-methyl-2-{3-[(2-methyl-1,3-thiazol-4-yl)methyl]-2-oxo-1-imidazolidinyl}butanamide Example 143D (64 mg, 0.21 mmol) was dissolved in N,N-dimethylformamide (3 mL) and treated with EDAC (66.3 mg, 2 equivalents), HOBT (58 mg, 2 equivalents), Example 26 (111 mg, 1.2 equivalents), and N-methylmorpholine (47 µL, 2 equivalents) at 25° C. for 16 h. The solvents were evaporated and the crude residue was purified by HPLC reverse phase chromatography using water (0.1% trifluoroacetic acid):acetonitrile (95:5) to acetonitrile (100%) to give 73 mg (47%) of the title compound.

Example 712

(2S)—N-{(1S,2R)-3-[{[4-((E)-{[(3-aminopropanoyl)oxy]imino}methyl)phenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide

Example 712A (2S)—N-{(1S,2R)-3-[{[4-((E)-{[(3-aminopropanoyl)oxy]imino}methyl)phenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 270 (127 mg, 0.18 mmol) was dissolved in dichloromethane (1.8 mL) and treated with Boc-β-alanine hydroxysuccinimide ester (75 mg, 1.4 equivalents), N-methylmorpholine (40 µL, 2 equivalents) and DMAP (30 mg, 1.4 equivalents) at 25° C. for 18 h. The solvents were evaporated and the crude residue was purified by HPLC reverse phase chromatography using water (0.1% trifluoroacetic acid):acetonitrile (95:5) to acetonitrile (100%) to give 123 mg (78%) of the title compound.

Example 712B (2S)—N-{(1S,2R)-3-[{[4-((E)-{[(3-aminopropanoyl)oxy]imino}methyl)phenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 712A (150 mg, 0.17 mmol) was dissolved in dichloromethane:trifluoroacetic acid (3 mL, 2:1) at 25° C. for 30 min. The solvents were evaporated and the crude residue was purified by HPLC reverse phase chromatography using water (0.1% trifluoroacetic acid):acetonitrile (95:5) to acetonitrile (100%) to give 76 mg (50%) of the title compound.

Example 713

(2S)—N-[(1S,2R)-1-benzyl-2-hydroxy-3-(isobutylamino)propyl]-3-methyl-2-{3-[(2-methyl-1,3-thiazol-4-yl)methyl]-2-oxo-1-imidazolidinyl}butanamide

Example 713A (2R,3S)-3-amino-1-(isobutylamino)-4-phenyl-2-butanol

Example 1 (3 g, 8.9 mmol) in dichloromethane (2 mL) was treated with trifluoroacetic acid (8 mL, 12 equivalents) and stirred for 5 h at 25° C. The mixture was quenched with water (50 mL), the aqueous layer was made alkaline to pH 9 with NaHCO$_3$. The mixture was stirred for 3 h, and the solids were filtered and dried in vacuo to give 2.5 g (100%) of the diamine.

Example 713B (2S)—N-[(1S,2R)-1-benzyl-2-hydroxy-3-(isobutylamino)propyl]-3-methyl-2-{3-[(2-methyl-1,3-thiazol-4-yl)methyl]-2-oxo-1-imidazolidinyl}butanamide Example 143D (1 g, 3.4 mmol) was combined with the Example 713A (1.5 g, 1.5 equivalents) in N,N-dimethylformamide (50 mL) and to this mixture was added HOBT (0.6 g, 1.5 equivalents) and EDAC (0.86 g, 1.5 equivalents). The mixture was stirred for 16 h at 25° C. and quenched with NaHCO$_3$, extracted with ethyl acetate, and evaporated. The residue was purified using 10% methanol/dichloromethane to give 1.14 g (74%) of the title compound.

Example 714

(2S)—N-((1S,2R)-1-benzyl-2-hydroxy-3-{isobutyl[(3-methoxyphenyl)sulfonyl]amino}propyl)-3-methyl-2-{3-[(2-methyl-1,3-thiazol-4-yl)methyl]-2-oxo-1-imidazolidinyl}butanamide Example 713B (20 mg, 0.04 mmol) was dissolved in dichloromethane (0.5 mL) and treated with triethylamine (13.7 µL, 2.5 equivalents) followed by 3-methoxybenzene sulfonyl chloride (9.8 mg, 1.2 equivalents) at 25° C. for 16 h. The solvents were evaporated, and the residue was purified using chloroform to give 20.2 mg (76%) of the title compound. $^1$H NMR (300 MHz, CDCl$_3$) δ ppm 0.76 (d, J=6.44 Hz, 3H), 0.81 (d, J=6.78 Hz, 3H), 0.87 (d, J=6.44 Hz, 3H), 0.92 (d, J=6.44 Hz, 3H), 1.55 (s, 1H), 1.84 (m, 1H), 2.13 (m, 1H), 2.69 (s, 3H), 2.84 (dd, J=13.56, 6.78 Hz, 1H), 3.01 (m, 1H), 3.13 (m, 1H), 3.22 (m, 1H), 3.63 (d, J=11.19 Hz, 1H), 3.76 (m, 1H), 3.83 (d, J=3.05 Hz, 1H), 3.86 (d, J=5.09 Hz, 3H), 4.16 (m, 1H), 4.41 (m, 2H), 6.45 (d, J=8.82 Hz, 1H), 6.92 (d, J=6.10 Hz, 1H), 7.09 (m, 1H), 7.12 (m, 1H), 7.15 (d, J=3.73 Hz, 1H), 7.19 (m, 5H), 7.31 (m, 2H), 7.38 (m, 2H), 7.43 (m, 1H).

The compounds listed in Table 17, wherein X$_4$ represents the point of connection to the core structure (N), were prepared using the procedure as exemplified in Example 714, substituting the corresponding sulfonyl chlorides for 3-methoxybenzene sulfonyl chloride:

TABLE 17
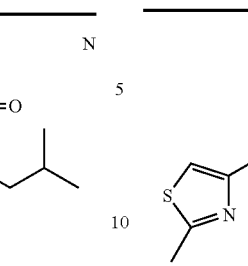
| Ex. | R4 |
|---|---|
| 715 | 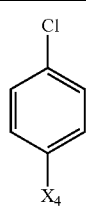 |
| 716 | 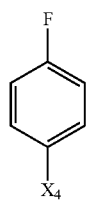 |
| 717 | 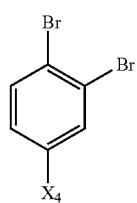 |
| 718 | 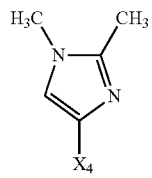 |
| 719 | 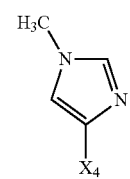 |
| 720 | 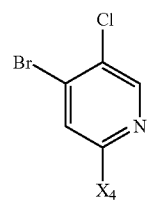 |
TABLE 17-continued
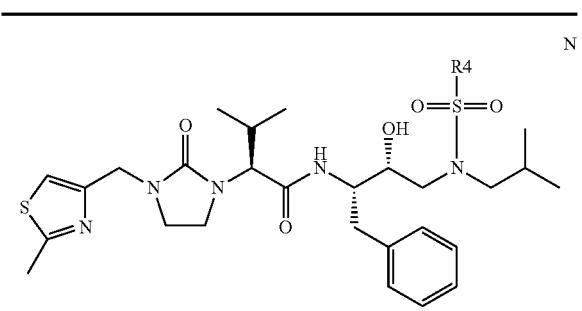
| Ex. | R4 |
|---|---|
| 721 | 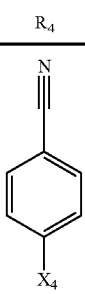 |
| 722 | 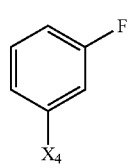 |
| 723 | 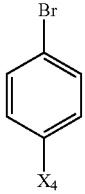 |
| 724 | 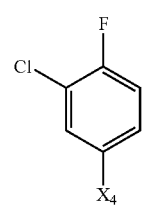 |
| 725 | 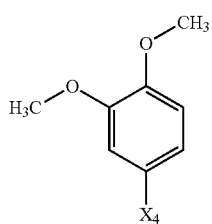 |
| 726 | 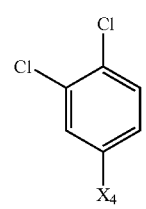 |

TABLE 17-continued
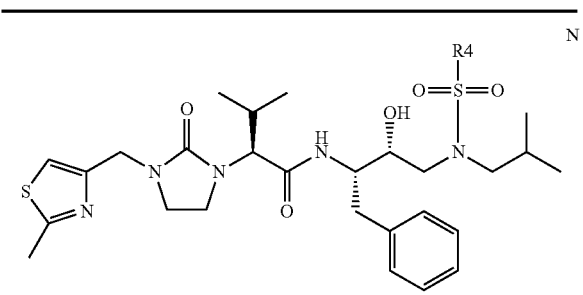
| Ex. | R4 |
|---|---|
| 727 | 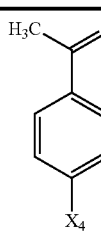 |
| 728 | 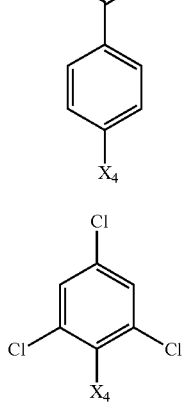 |
| 729 | 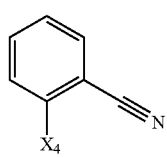 |
| 730 | 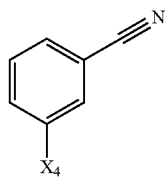 |
| 731 | 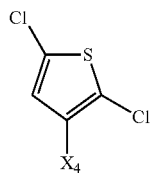 |
| 732 | 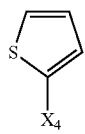 |
| 733 | 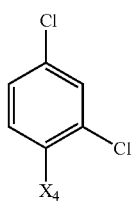 |
TABLE 17-continued
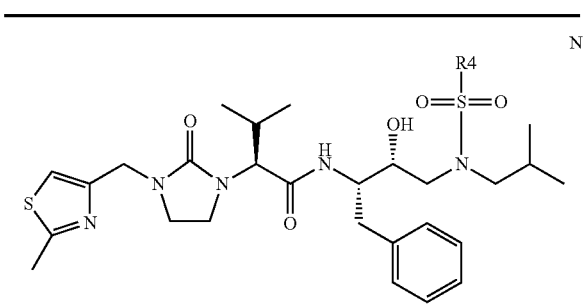
| Ex. | R4 |
|---|---|
| 734 | 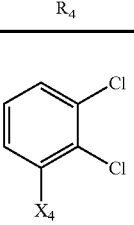 |
| 735 | 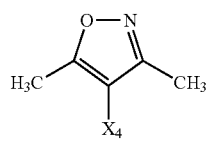 |
| 736 | 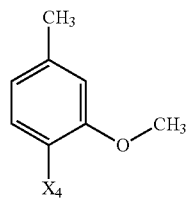 |
| 737 | 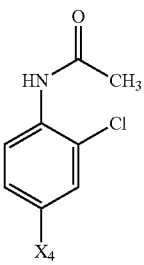 |
| 738 | 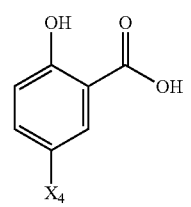 |
| 739 | 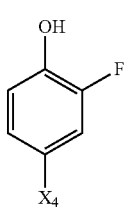 |

TABLE 17-continued
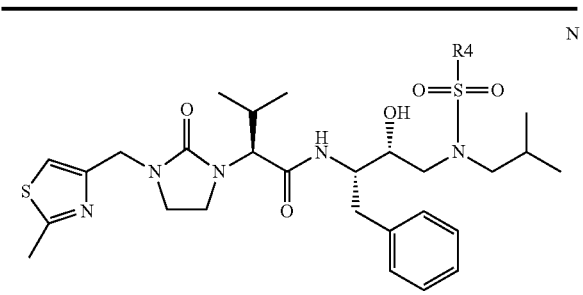
| Ex. | R4 |
|---|---|
| 740 | 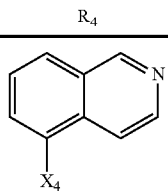 |
| 741 | 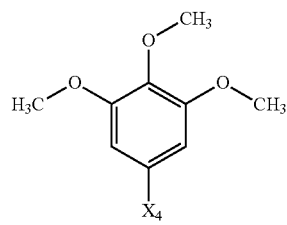 |
| 742 | 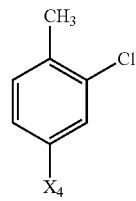 |
| 743 | 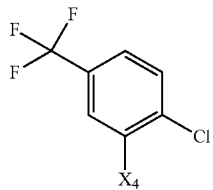 |
| 744 | 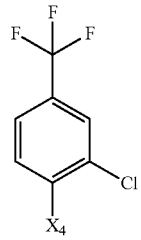 |
| 745 | 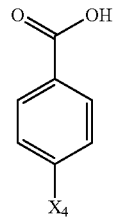 |
TABLE 17-continued
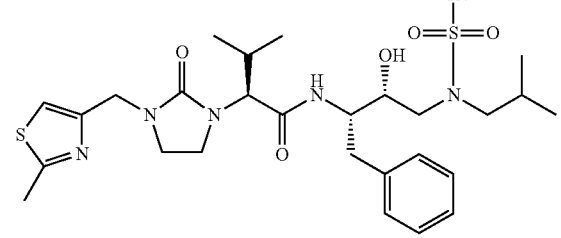
| Ex. | R4 |
|---|---|
| 746 | 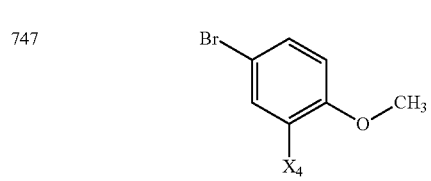 |
| 747 | 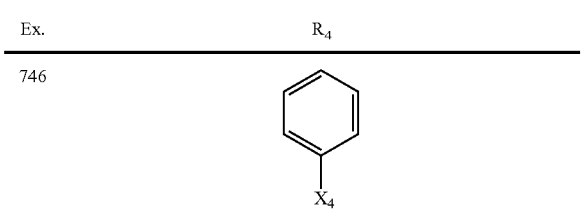 |
| 748 | 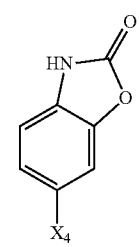 |
| 749 | 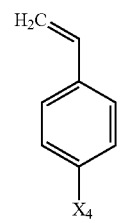 |
| 750 | 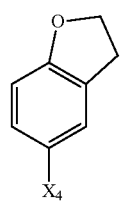 |
| 751 | 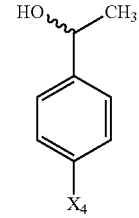 |

TABLE 17-continued

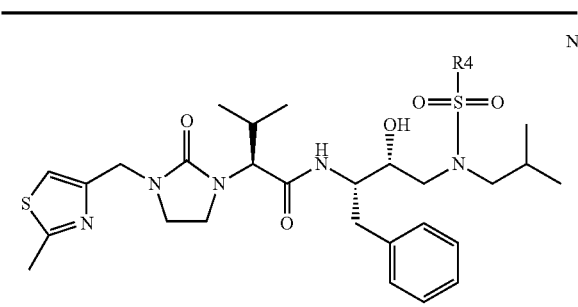

| Ex. | R4 |
|---|---|
| 752 | 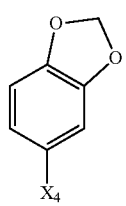 |
| 753 | 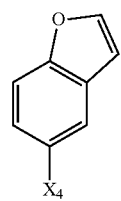 |
| 754 | 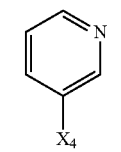 |
| 755 | 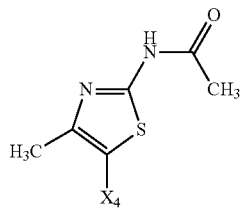 |
| 756 | 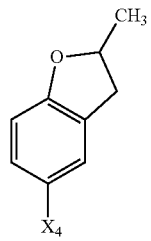 |
| 757 | 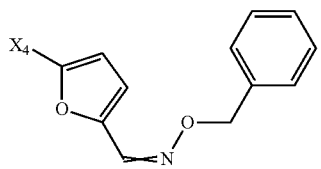 |

TABLE 17-continued

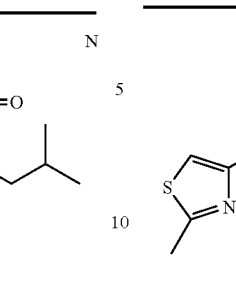

| Ex. | R4 |
|---|---|
| 758 | 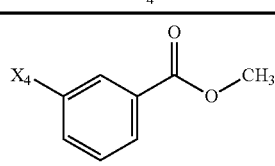 |
| 759 | 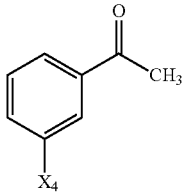 |
| 760 | 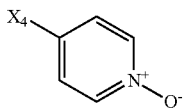 |

Example 761

(2S)—N-{(1S,2R)-1-benzyl-2-hydroxy-3-[[(3-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide Example 714 (31 mg, 0.045 mmol) in dichloromethane (3 mL) was added BBr$_3$ (20 μL, equivalents) and stirred for 2 h at 25° C. The mixture was quenched with 1N NaHCO$_3$ and extracted with ethyl acetate. The solvents were evaporated and the residue was purified using ethyl acetate to give 21 mg (69%) of the title compound.

Example 762

(2S)—N-{(1S,2R)-1-benzyl-3-[[(5-bromo-2-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide In a similar manner to Example 761, Example 747 was treated with BBr$_3$ to give the title compound.

Example 763

(2S)—N-{(1S,2R)-1-benzyl-3-[{[4-(1,2-dihydroxyethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide Example 749 (30 mg, 0.044 mmol) dissolved in tetrahydrofuran (1 mL) and water (0.2 mL) was added 4% weight OsO$_4$ in water (16.3 µL, 6 mol %) and NMMO (5.2 mg, 1.2 equivalents). The mixture was stirred at 25° C. for 4 h and quenched with 10% NaHSO$_3$. The mixture was extracted with ethyl acetate, the solvents were evaporated, and the residue was purified using 5% methanol/dichloromethane to give 21 mg (67%) of the title compound.

Example 764

(2S)—N-{(1S,2R)-1-benzyl-3-[[(4-formylphenyl) sulfonyl](isobutyl)amino]-2-hydroxypropyl}-3-methyl-2-{3-[(2-methyl-1,3-thiazol-4-yl)methyl]-2-oxo-1-imidazolidinyl}butanamide Example 749 (81 mg, 0.12 mmol) in tetrahydrofuran (3 mL) and water (0.6 mL) was added 4% weight OsO$_4$ in water (44 µL, 6 mol %) followed by NaIO$_4$ (56 mg, 2.2 equivalents). The mixture was stirred at 25° C. for 16 h and quenched with 10% NaHSO$_3$, extracted with ethyl acetate, solvents were evaporated, and the residue was purified using ethyl acetate to give 68 mg (84%) of the title compound.

Example 765

(2S)—N-{(1S,2R)-1-benzyl-2-hydroxy-3-[{[4-(hydroxymethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide Example 764 (14 mg, 0.02 mmol) was dissolved in ethanol (0.5 mL) and combined with NaBH$_4$ (2.2 mg, 3 equivalent) and stirred at 25° C. for 1 h. The solvents were evaporated, and the residue was purified using 5% methanol/dichloromethane to give 9 mg (69%) of the title compound.

Example 766

(2S)—N-{(1S,2R)-1-benzyl-3-[{[4-(formylamino) phenyl]sulfonyl}(isobutyl)amino]-2-hydroxypropyl}-3-methyl-2-{3-[(2-methyl-1,3-thiazol-4-yl) methyl]-2-oxo-1-imidazolidinyl}butanamide Example 650 (10 mg, 0.014 mmol) was dissolved in tetrahydrofuran (0.25 mL) and combined with formic acetic anhydride (2 drops) and the mixture was stirred for 1 h. The solvent was evaporated, and the residue was purified by using 5% methanol/dichloromethane to give 8.5 mg (83%) of the title compound.

Example 767

(2S)—N-{(1S,2R)-3-[[(3-amino-4-chlorophenyl) sulfonyl](isobutyl)amino]-1-benzyl-2-hydroxypropyl}-2-(3-{[2-(hydroxymethyl)-1,3-thiazol-4-yl] methyl}-2-oxo-1-imidazolidinyl)-3-methylbutanamide Example 687 (45 mg, 0.059 mmol) was dissolved in water: tetrahydrofuran (1 mL, 2:1) and treated with lithium hydroxide (8 mg, 3 equivalents) at 25° C. for 30 min. The mixture was neutralized with 1N HCl (0.2 mL) and extracted with ethyl acetate. The organic layer was separated and washed with water, brine, dried over magnesium sulfate and the solvents were evaporated to give 43 mg (100%) of the title compound.

Example 768

(2S)—N-{(1S,2R)-3-[{[3-(acetylamino)-4-hydroxyphenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 768A (2S)—N-{(1S,2R)-1-benzyl-2-hydroxy-3-[[(4-hydroxy-3-nitrophenyl)sulfonyl](isobutyl)amino]propyl}-3-methyl-2-{3-[(2-methyl-1,3-thiazol-4-yl) methyl]-2-oxo-1-imidazolidinyl}butanamide To 4-hydroxy-3-nitrobenzenesulfonyl chloride (69 mg, 0.27 mmol) in dichloromethane (1.2 mL) was added bistrimethylsilylacetamide (72 µL, 1 equivalent) at 25° C. for 3 h. To this mixture was added the Example 713B (150 mg, 1 equivalent) followed by triethylamine (0.12 mL, 3 equivalents). The mixture was stirred for 16 h, and the solvents were evaporated. The crude residue was treated with tetrabutylammonium fluoride (TBAF) (0.9 mL, 3 equivalents 1M tetrabutyl ammonium fluoride/tetrahydrofuran) for 2 h and the solvents were evaporated. The residue was purified by HPLC reverse phase chromatography using water (0.1% trifluoroacetic acid):acetonitrile (95:5) to acetonitrile (100%) to give 132 mg (62%) of the title compound.

Example 768B (2S)—N-{(1S,2R)-3-[[(3-amino-4-hydroxyphenyl) sulfonyl](isobutyl)amino]-1-benzyl-2-hydroxypropyl}-3-methyl-2-{3-[(2-methyl-1,3-thiazol-4-yl) methyl]-2-oxo-1-imidazolidinyl}butanamide Example 768A (132 mg, 0.184 mmol) in ethanol/acetic acid (2 mL, 1:1) is added Fe powder (40 mg, 4 equivalents) at 70° C. for 2 h. The mixture was evaporated and partitioned between CHCl$_3$ and 10% EDTA disodium salt. The organic layer was washed with brine, dried over MgSO$_4$, filtered, and evaporated to give 112 mg (90% crude yield) of the title compound.

Example 768C (2S)—N-{(1S,2R)-3-[{[3-(acetylamino)-4-hydroxyphenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 768B (20 mg, 0.029 mmol) was dissolved in dichloromethane (0.3 mL) and treated with pyridine (2 µL, 1 equivalent) and acetyl chloride (1.2 µL, 0.6 equivalent) at 25° C. for 1 h. The mixture was quenched with methanol, and the solvents were evaporated. The residue was purified by HPLC reverse phase chromatography using water (0.1% trifluoroacetic acid):acetonitrile (95:5) to acetonitrile (100%) to give 16.9 mg (75%) of the title compound.

The compounds listed in Table 18, wherein $X_{4a}$, represents the points of connection to the core structure (O), were prepared by coupling the corresponding activated acylating agents with Example 768B:

TABLE 18

[Structure shown with R$_{4a}$ group having NHR$_{4a}$ substituent on hydroxyphenyl sulfonyl core]

| Ex# | R$_{4a}$ |
|---|---|
| 769 | X$_{4a}$—C(O)—CH$_2$—NH—CO$_2$t-Bu |
| 770 | X$_{4a}$—CHO |
| 771 | X$_{4a}$—C(O)—CH$_2$—phenyl |
| 772 | X$_{4a}$—C(O)—CH$_2$—CH$_2$—NH—CO$_2$t-Bu |

Example 773

(2S)—N-{(1S,2R)-1-benzyl-2-hydroxy-3-[isobutyl({4-[(methoxyimino)methyl]phenyl}sulfonyl)amino]propyl}-3-methyl-2-{3-[(2-methyl-1,3-thiazol-4-yl)methyl]-2-oxo-1-imidazolidinyl}butanamide Example 764 (14.7 mg, 0.022 mmol) was dissolved in ethanol (0.5 mL) and treated with N,N-diisopropylethylamine (6.1 μL, 2.2 equivalents) and hydroxylamine-O-methyl ether hydrochloride (3.6 mg, 2 equivalents) at 25° C. for 2 h. The mixture was partitioned between 1N NaHCO$_3$ and ethyl acetate. The organic layer was evaporated, and the residue was purified using 5% methanol/chloroform to give 7.1 mg (46%) of the title compound.

Example 774

(2S)—N-{(1S,2R)-1-benzyl-3-[(2,3-dihydro-1H-indol-5-ylsulfonyl)(isobutyl)amino]-2-hydroxypropyl}-3-methyl-2-{3-[(2-methyl-1,3-thiazol-4-yl)methyl]-2-oxo-1-imidazolidinyl}butanamide Example 693 (25 mg, 0.034 mmol) was dissolved in methanol (2 mL) and treated with 1N HCl (3 mL) at 60° C. for 5 h. The solvents were evaporated, and the residue was purified using 5% methanol/dichloromethane to give 12 mg (51%) of the title compound.

Example 775

(2S)—N-{(1S,2R)-3-[[(2-amino-4-methyl-1,3-thiazol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 755 was treated in a similar manner to Example 774 to give the title compound.

Example 776

(2S)—N-{(1S,2R)-3-[({3-[(3-aminopropanoyl)amino]-4-hydroxyphenyl}sulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide Example 772 (10 mg, 0.012 mmol) was dissolved in dichloromethane (0.2 mL) and trifluoroacetic acid (0.1 mL), and the mixture was stirred at 25° C. for 1 h. The solvents were evaporated, and the residue was purified by HPLC reverse phase chromatography using water (0.1% trifluoroacetic acid):acetonitrile (95:5) to acetonitrile (100%) to give 8 mg (79%) of the title compound.

Example 777 tert-butyl 2-(3-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate

Example 777A (2S)—N-((1S,2R)-1-benzyl-2-hydroxy-3-{isobutyl[(3-nitrophenyl)sulfonyl]amino}propyl)-3-methyl-2-{3-[(2-methyl-1,3-thiazol-4-yl)methyl]-2-oxo-1-imidazolidinyl}butanamide Example 713B (50 mg, 0.097 mmol) was dissolved in dichloromethane (1 mL) and treated with 3-nitrobenzenesulfonyl chloride (26 mg, 1.2 equivalents) and triethylamine (27 μL, 2 equivalents) at 25° for 18 h. The solvents were evaporated and the crude residue was purified using chloroform-chloroform/2% methanol to give 66.8 mg (97%) of the title compound.

Example 777B tert-butyl 2-(3-{[{(2R,3S)-2-hydroxy-3-[((2S)-3-methyl-2-(3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate Example 777A (66 mg, 0.094 mmol) was dissolved in ethanol:acetic acid (1 mL, 1:1) and treated with iron powder (21 mg, 4 equivalents) at 70° C. for 1.5 h. The mixture was diluted with chloroform and washed twice with 10% EDTA disodium salt. The aqueous layers were reextracted with chloroform, the organic layers combined, washed with brine, dried over magnesium sulfate, and the solvents were evaporated to give crude product amine. This amine was dissolved in dichloromethane (1 mL) and treated with Boc-glycine N-Hydroxysuccinimide ester (38 mg, 1.5 equivalents) and pyridine (0.011 mL, 1.5 equivalents) and stirred at 25° C. for 18 h. The solvents were evaporated, and the crude residue was purified by HPLC reverse phase chromatography using water (0.1% trifluoroacetic acid):acetonitrile (95:5) to acetonitrile (100%) to give 35.3 mg (45%) of the title compound.

Example 778

(2S)—N-{(1S,2R)-1-benzyl-2-hydroxy-3-[{[3-(hydroxymethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide Example 758 (88 mg, 0.123 mmol) was dissolved in dichloromethane (1 mL) and treated with diisobutyl aluminum hydride (0.62 mL, 5 equivalents, 1M solution in dichloromethane) at −78° C. for 1 h. The mixture was quenched with acetone (0.1 mL), warmed to 25° C., and partitioned between dichloromethane and saturated Rochelle's salt solution. After stirring for 1 h, the organic layer was separated, dried over $Na_2SO_4$, filtered, and evaporated, and the residue was purified using ethyl acetate to give 68 mg (80%) of the title compound.

Example 779

(2S)—N-{(1S,2R)-1-benzyl-3-[[(5-formyl-2-furyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide Example 757 (103 mg, 0.134 mmol) in acetonitrile (1 mL) at 0° C. was added trimethylsilyl iodide (0.2 mL, 10 equivalents). The mixture was warmed to 25° C. for 2 h, partitioned between ethyl acetate and $NaS_2O_3$, and the organic layer was separated. The layer was dried over $Na_2SO_4$ and evaporated. The residue was purified using ethyl acetate to give 35 mg (39%) of the title compound.

Example 780

(2S)—N-{(1S,2R)-1-benzyl-2-hydroxy-3-[({5-[(E)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide

Example 780A (2S)—N-[(1S,2R)-1-benzyl-2-hydroxy-3-(isobutyl{[5-({[(4-nitrobenzyl)oxy]imino}methyl)-2-furyl]sulfonyl}amino)propyl]-3-methyl-2-{3-[(2-methyl-1,3-thiazol-4-yl)methyl]-2-oxo-1-imidazolidinyl}butanamide Example 713B (50 mg, 0.097 mmol) in dichloromethane (0.5 mL) was treated with triethylamine (30 μL, 2 equivalents) followed by 5-(p-nitrobenzyloxyimino)-2-furan sulfonyl chloride (40 mg, 1.2 equivalents) at 25° C. for 16 h. The solvents were evaporated, and the residue was purified using ethyl acetate:hexanes (3:1) to give 63 mg (79%) of the title compound.

Example 780B (2S)—N-{(1S,2R)-1-benzyl-2-hydroxy-3-[({5-[(E)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide

Examples 781

(2S)—N-{(1S,2R)-1-benzyl-2-hydroxy-3-[({5-[(Z)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide Example 780A (60 mg, 0.073 mmol) was dissolved in ethanol:acetic acid (1:1) (1 mL), treated with iron powder (20 mg, 5 equivalents) and heated at 70° C. for 4 h. The mixture was cooled, evaporated, and partitioned between $CHCl_3$ and 10% EDTA. The organic layer was dried over $Na_2SO_4$, filtered, and evaporated. The residue was purified using ethyl acetate:hexanes (3:1) to give 11 mg (22%) of Example 780B and 12 mg (24%) of Example 781.

Example 782

(2S)—N-{(1S,2R)-3-[({4-[amino(hydroxyimino)methyl]phenyl}sulfonyl)(isobutyl)amino]-1-benzyl-2-hydroxypropyl}-3-methyl-2-{3-[(2-methyl-1,3-thiazol-4-yl)methyl]-2-oxoimidazolidin-1-yl}butanamide

Example 783

4-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzamide Example 721 (33 mg, 0.048 mmol) was dissolved in ethanol (1 mL) and treated with triethylamine (70 μL, 10 equivalents) and hydroxylamine hydrochloride (14 mg, 4 equivalents). The mixture was heated at 50° C. for 3 hrs. The solvents were evaporated, and the residue was purified using 5% methanol/dichloromethane to give 13 mg (37%) of Example 782 and 8.5 mg (25%) of Example 783.

Example 784

4-{[[(2R,3S)-2-hydroxy-3-({(2S,3S)-3-methyl-2-[2-oxo-3-(3-pyridinylmethyl)-1-imidazolidinyl]pentanoyl}amino)-4-phenylbutyl](isobutyl)amino]sulfonyl}benzamide Example 785 (36 mg, 0.053 mmol) was dissolved in methanol (1 mL) and treated with triethylamine (75 μL, 10 equivalents) and hydroxylamine hydrochloride (15 mg, 4 equivalents). The mixture was heated to 80° C. for 1 h. The solvents were evaporated, and the residue was purified using 8% methanol/ethyl acetate to give 20 mg (53%) of the p-hydroxyamidine and 4 mg (11%) of the title compound.

Example 785

(2S,3S)—N-{(1S,2R)-1-benzyl-3-[[(4-cyanophenyl)sulfonyl](isobutyl)amino]-2-hydroxypropyl}-3-methyl-2-[2-oxo-3-(3-pyridinylmethyl)-1-imidazolidinyl]pentanamide Example 785A (2S,3S)—N-[(1S,2R)-1-benzyl-2-hydroxy-3-(isobutylamino)propyl]-3-methyl-2-[2-oxo-3-(3-pyridinylmethyl)-1-imidazolidinyl]pentanamide Example 103 (0.266 g, 0.9 mmol) was combined with Example 713A (0.153 g, 1 equivalent) in N,N-dimethylformamide (2 mL) and to this mixture was added HOBT (0.1 g, 1.5 equivalents) and EDAC (0.15 g, 1.5 equivalents). The mixture was stirred for 16 h at 25° C. and quenched with NaHCO$_3$, extracted with ethyl acetate, and evaporated under vacuum. The residue was purified using 10% methanol/dichloromethane/0.5% NH$_4$OH to give 50 mg (19%) of the amine.

Example 785B (2S,3S)—N-{(1S,2R)-1-benzyl-3-[[(4-cyanophenyl)sulfonyl](isobutyl)amino]-2-hydroxypropyl}-3-methyl-2-[2-oxo-3-(3-pyridinylmethyl)-1-imidazolidinyl]pentanamide Example 785A (50 mg, 0.098 mmol) was dissolved in dichloromethane (1 mL) and combined with p-cyanobenzenesulfonyl chloride (24 mg, 1.2 equivalents) and triethylamine (41 µL, 3 equivalents) at 25° C. for 16 h. The mixture was quenched with 1N NaHCO$_3$ and extracted with ethyl acetate. The organic layer was evaporated, and the residue was purified using ethyl acetate to give 49 mg (74%) of the title compound.

Example 786

(2S)—N-{(1S,2R)-1-benzyl-2-hydroxy-3-[[(4-hydroxyphenyl)sulfonyl](isobutyl)amino]propyl}-2-{3-[(2-ethyl-1,3-thiazol-4-yl)methyl]-2,4-dioxo-1-imidazolidinyl}-3-methylbutanamide Example 290 (75 mg, 0.23 mmol) was combined with N-hydroxysuccinimide (24.8 mg, 1.1 equivalents) and DCC (44.5 mg, 1.1 equivalents) in dichloromethane (1 mL) and stirred for 1 h at 25° C. The solids are filtered, and to this mixture was added N-methylmorpholine (24 µL, 1 equivalent) and 625B (77 mg, 1 equivalent). The mixture was stirred for 16 h, evaporated, and was purified using 1% methanol/CHCl$_3$ to give 54 mg (40%) of the title compound. $^1$H NMR (300 MHz, CDCl$_3$) δ ppm 0.79 (t, J=6.61 Hz, 6H), 0.88 (d, J=6.44 Hz, 3H), 0.92 (d, J=6.44 Hz, 3H), 1.32 (t, J=7.63 Hz, 3H), 1.77 (d, J=10.17 Hz, 1H), 1.83 (m, 1H), 2.07 (m, 1H), 2.66 (dd, J=14.24, 10.85 Hz, 1H), 2.83 (dd, J=13.56, 6.78 Hz, 1H), 2.98 (m, 2H), 3.03 (m, 1H), 3.17 (m, 1H), 3.27 (d, J=17.97 Hz, 1H), 3.61 (d, J=17.97 Hz, 1H), 3.85 (m, 2H), 3.89 (d, J=11.19 Hz, 1H), 4.19 (m, 1H), 4.75 (m, 2H), 6.33 (d, J=9.49 Hz, 2H), 6.93 (d, J=8.82 Hz, 2H), 7.04 (s, 1H), 7.07 (s, 5H), 7.66 (m, 2H).

The compounds listed in Table 19, wherein X$_7$, X$_{11}$, X$_4$ represent respectively the points of connection to the core structure (P), were prepared by coupling the corresponding acids (Examples 287-359) with the amines (Examples 625-648), as exemplified in Example 362 (Method A), Example 162 (Method B) and Example 524 (Method C):

TABLE 19

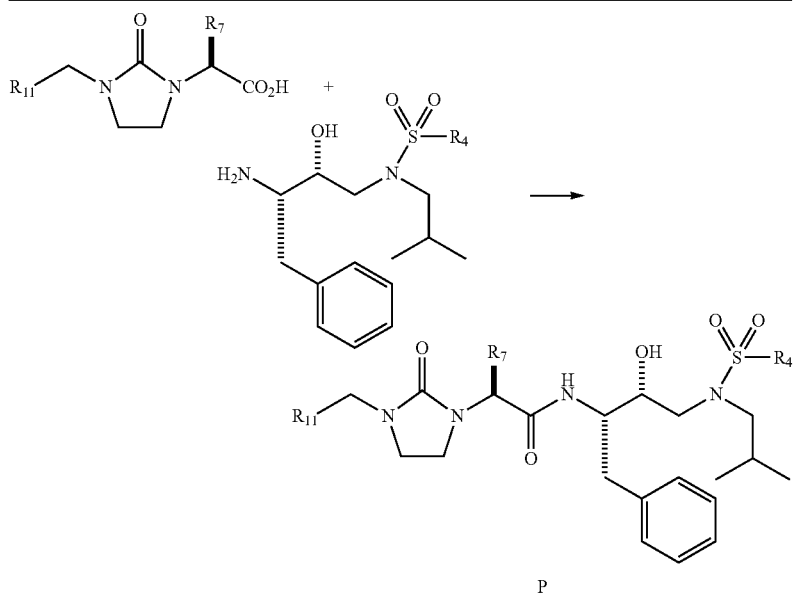

| Ex. | Method | R$_{11}$ | R$_7$ | R$_4$ |
|---|---|---|---|---|
| 787 | C | (2-ethylthiazol-4-yl)-X$_{11}$ | (CH$_3$)$_2$CH-X$_7$ | 4-aminophenyl-X$_4$ |

TABLE 19-continued

| 788 | C | 2-ethyl-thiazol-4-yl ($X_{11}$) | isopropyl ($X_7$) | 3-amino-4-chloro-phenyl ($X_4$) |
| 789 | C | 2-methyl-thiazol-4-yl ($X_{11}$) | isopropyl ($X_7$) | 4-hydroxy-phenyl ($X_4$) |
| 790 | C | 2-methyl-thiazol-4-yl ($X_{11}$) | isopropyl ($X_7$) | 3-amino-4-chloro-phenyl ($X_4$) |
| 791 | C | 2-methyl-thiazol-4-yl ($X_{11}$) | isopropyl ($X_7$) | 2-amino-4-hydroxy-phenyl ($X_4$) |
| 792 | C | 2-(methoxymethyl)-thiazol-4-yl ($X_{11}$) | isopropyl ($X_7$) | 3-amino-4-chloro-phenyl ($X_4$) |
| 793 | C | 2-(methoxymethyl)-thiazol-4-yl ($X_{11}$) | isopropyl ($X_7$) | 2-methyl-thiazol-4-yl ($X_1$) |
| 794 | C | 2-(methoxymethyl)-thiazol-4-yl ($X_{11}$) | isopropyl ($X_7$) | 4-amino-phenyl ($X_4$) |
| 795 | A | phenyl ($X_{11}$) | isopropyl ($X_7$) | 3-amino-4-chloro-phenyl ($X_4$) |
| 796 | A | 3-methyl-phenyl ($X_{11}$) | isopropyl ($X_7$) | 3-amino-4-chloro-phenyl ($X_4$) |

TABLE 19-continued
| | | | | |
|---|---|---|---|---|
| 797 | A | 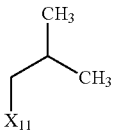 |  | 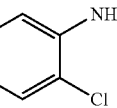 |
| 798 | A | 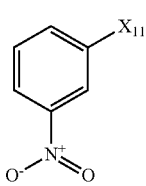 | 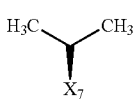 | 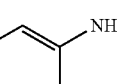 |
| 800 | A | 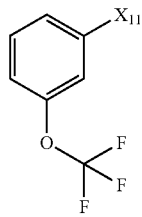 | 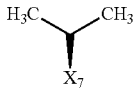 | 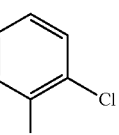 |
| 801 | A | 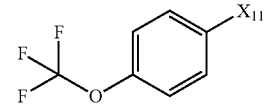 | 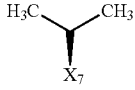 | 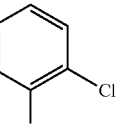 |
| 802 | A | 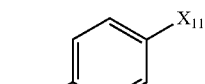 | 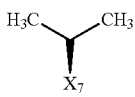 | 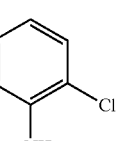 |
| 803 | A | 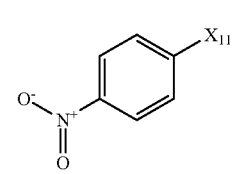 | 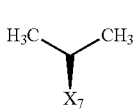 | 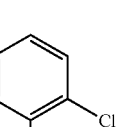 |
| 804 | B | 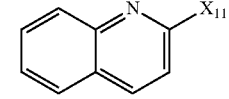 | 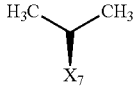 | 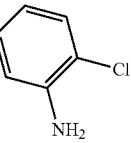 |
| 805 | B | 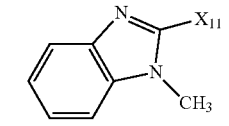 | 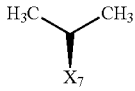 | 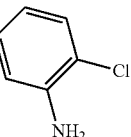 |
| 806 | A | 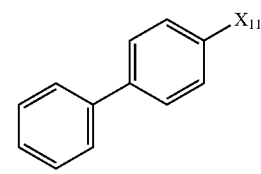 | 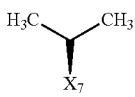 | 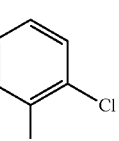 |

TABLE 19-continued

| 807 | A | (4-benzoylphenyl)-X₁₁ | H₃C-CH(X₇)-CH₃ | 2-chloro-5-X₄-phenyl-NH₂ |
| 808 | A | (4-benzoylphenyl)-X₁₁ | H₃C-CH(X₇)-CH₃ | 2-chloro-5-X₄-phenyl-NH₂ |
| 809 | A | 2-X₁₁-naphthyl | H₃C-CH(X₇)-CH₃ | 2-chloro-5-X₄-phenyl-NH₂ |
| 810 | A | 4-(CH₂=CH)-phenyl-X₁₁ | H₃C-CH(X₇)-CH₃ | 2-chloro-5-X₄-phenyl-NH₂ |
| 811 | A | 3-methyl-4-nitro-phenyl-X₁₁ | H₃C-CH(X₇)-CH₃ | 2-chloro-5-X₄-phenyl-NH₂ |
| 812 | A | 2-nitro-phenyl-X₁₁ | H₃C-CH(X₇)-CH₃ | 2-chloro-5-X₄-phenyl-NH₂ |
| 813 | A | 2-methyl-3-nitro-phenyl-X₁₁ | H₃C-CH(X₇)-CH₃ | 2-chloro-5-X₄-phenyl-NH₂ |

TABLE 19-continued

| 814 | A | 4-(thiadiazol-4-yl)phenyl-$X_{11}$ | $H_3C$-CH($X_7$)-$CH_3$ | 2-chloro-5-$X_4$-aniline |
| 815 | A | pyridin-3-yl-$X_{11}$ | $H_3C$-CH($X_7$)-$CH_3$ | 2-chloro-5-$X_4$-aniline |
| 816 | A | pyridin-2-yl-$X_{11}$ | $H_3C$-CH($X_7$)-$CH_3$ | 2-chloro-5-$X_4$-aniline |
| 817 | A | pyridin-4-yl-$X_{11}$ | $H_3C$-CH($X_7$)-$CH_3$ | 2-chloro-5-$X_4$-aniline |
| 818 | A | 2-methoxy-5-nitrophenyl-$X_{11}$ | $H_3C$-CH($X_7$)-$CH_3$ | 2-chloro-5-$X_4$-aniline |
| 819 | A | 2-fluoro-6-nitrophenyl-$X_{11}$ | $H_3C$-CH($X_7$)-$CH_3$ | 2-chloro-5-$X_4$-aniline |
| 820 | A | 3-methyl-4-nitrophenyl-$X_{11}$ | $H_3C$-CH($X_7$)-$CH_3$ | 2-chloro-5-$X_4$-aniline |

TABLE 19-continued
| 821 | A | 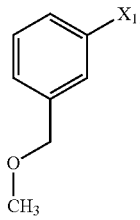 |  | 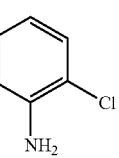 |
| 822 | A | 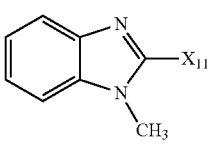 | 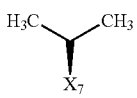 | 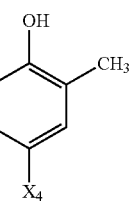 |
| 823 | A | 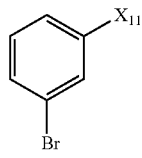 | 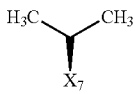 | 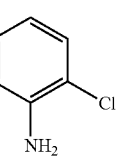 |
| 824 | A | 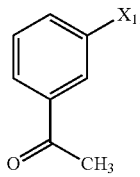 | 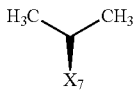 | 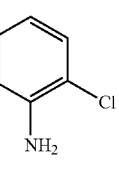 |
| 825 | A | 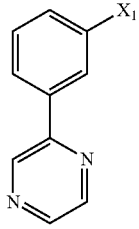 | 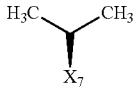 | 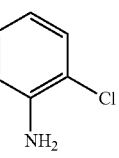 |
| 826 | A | 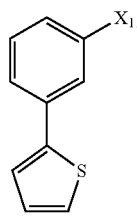 | 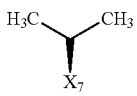 | 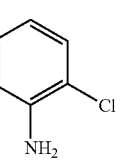 |
| 827 | A | 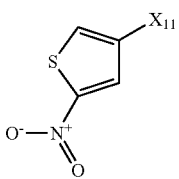 | 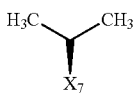 | 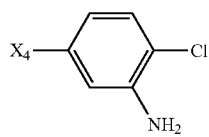 |
| 828 | A | 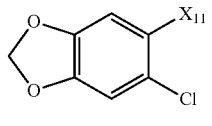 | 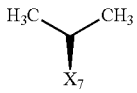 | 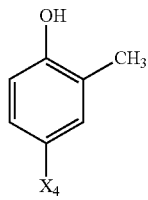 |

TABLE 19-continued
| 829 | A | 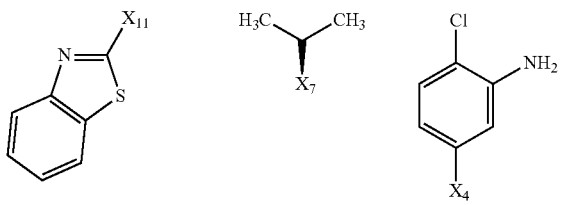 |
| 830 | A | 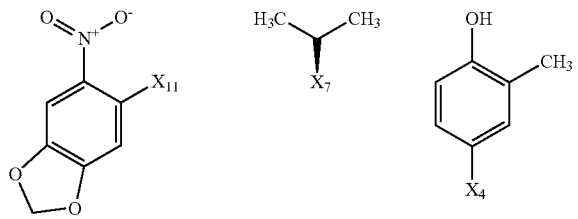 |
| 831 | A | 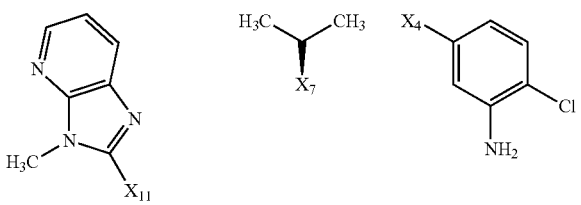 |
| 832 | A | 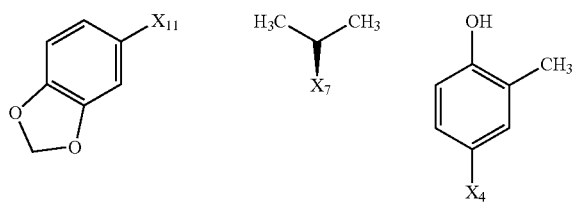 |
| 833 | B | 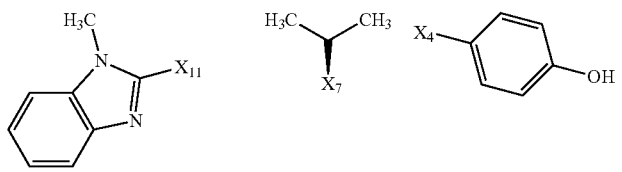 |
| 834 | A | 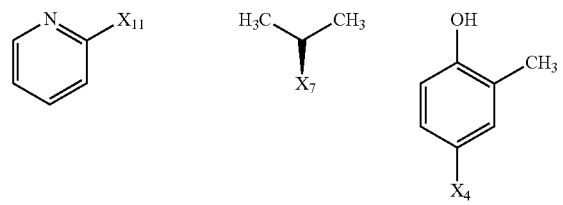 |
| 835 | A | 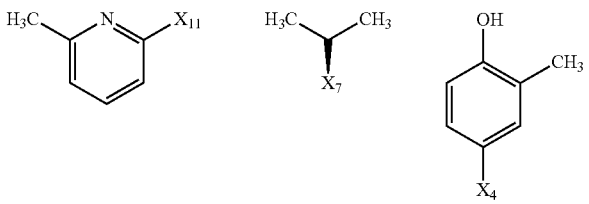 |

TABLE 19-continued

| | | | | |
|---|---|---|---|---|
| 836 | A | 4-methyl-3-X₁₁-pyridine | isopropyl-X₇ | 2-methyl-4-X₄-phenol |
| 837 | A | N-(4-X₁₁-thiazol-2-yl)acetamide | isopropyl-X₇ | 2-amino-1-chloro-4-X₄-benzene |
| 838 | A | 4-X₁₁-pyridine-2-carbonitrile | isopropyl-X₇ | 2-methyl-4-X₄-phenol |
| 839 | A | 1-(4-X₁₁-pyridin-2-yl)ethanone | isopropyl-X₇ | 2-methyl-4-X₄-phenol |
| 840 | A | (3-X₁-phenyl)methanol | isopropyl-X₇ | 2-amino-1-chloro-4-X₄-benzene |
| 841 | A | N-(4-X₁₁-thiazol-2-yl)acetamide | sec-butyl-X₇ | 2-amino-1-chloro-4-X₄-benzene |
| 842 | B | 6-amino-2-X₁₁-quinoline | sec-butyl-X₇ | 2-amino-1-chloro-4-X₄-benzene |
| 843 | A | 4-X₁₁-quinoline | sec-butyl-X₇ | 2-amino-1-chloro-4-X₄-benzene |

Example 844

(2S)—N-{(1S,2R)-3-[{[4-((E)-{[(3-aminopropanoyl)oxy]imino}methyl)phenyl]sulfonyl}(cyclopentylmethyl)amino]-1-benzyl-2-hydroxypropyl}-3-methyl-2-{3-[(2-methyl-1,3-thiazol-4-yl)methyl]-2,4-dioxo-1-imidazolidinyl}butanamide

Example 844A tert-butyl 3-{[((E)-{4-[(((cyclopentylmethyl){(2R,3S)-2-hydroxy-3-[((2S)-3-methyl-2-{3-[(2-methyl-1,3-thiazol-4-yl)methyl]-2,4-dioxo-1-imidazolidinyl}butanoyl)amino]-4-phenylbutyl}amino)sulfonyl]phenyl}methylidene)amino]oxy}-3-oxopropylcarbamate Example 372 (78 mg, 0.1 mmol) was dissolved in dichloromethane (1 mL) and treated with Boc-β-alanine hydroxysuccinimide ester (45 mg, 1.4 equivalents), N-methylmorpholine (25 μL, 2 equivalents) and DMAP (20 mg, 1.4 equivalents) at 25° C. for 18 h. The solvents were evaporated and the crude residue was purified by HPLC reverse phase chromatography using water (0.1% trifluoroacetic acid):acetonitrile (95:5) to acetonitrile (100%) to give 62 mg (65%) of the title compound.

Example 844B (2S)—N-{(1S,2R)-3-[{[4-((E)-{[(3-aminopropanoyl)oxy]imino}methyl)phenyl]sulfonyl}(cyclopentylmethyl)amino]-1-benzyl-2-hydroxypropyl}-3-methyl-2-{3-[(2-methyl-1,3-thiazol-4-yl)methyl]-2,4-dioxo-1-imidazolidinyl}butanamide Example 844A (60 mg, 0.066 mmol) was dissolved in dichloromethane:trifluoroacetic acid (3 mL, 2:1) at 25° C. for 30 min. The solvents were evaporated and the crude residue was purified by HPLC reverse phase chromatography using water (0.1% trifluoroacetic acid):acetonitrile (95:5) to acetonitrile (100%) to give 46 mg (75%) of the title compound.

NMR Data

Example 163

$^1$H NMR (300 MHz, CDCl$_3$) δ ppm 0.79 (d, J=6.44 Hz, 3H), 0.83 (d, J=6.78 Hz, 3H), 0.87 (d, J=6.78 Hz, 3H), 0.91 (d, J=6.78 Hz, 3H), 1.53 (s, 1H), 1.85 (m, 1H), 2.17 (m, 1H), 3.00 (m, 9H), 3.66 (d, J=10.85 Hz, 1H), 3.77 (d, J=3.39 Hz, 1H), 3.82 (m, 1H), 4.16 (d, J=15.26 Hz, 1H), 4.23 (m, 1H), 4.40 (d, J=15.60 Hz, 1H), 6.45 (d, J=9.16 Hz, 1H), 7.19 (m, 5H), 7.33 (d, J=1.70 Hz, 1H), 7.71 (d, J=8.48 Hz, 2H), 7.79 (d, J=8.48 Hz, 2H), 8.16 (s, 1H)

Example 164

$^1$H NMR (300 MHz, CDCl$_3$) δ ppm 0.76 (t, J=6.27 Hz, 6H), 0.82 (d, J=6.44 Hz, 3H), 0.89 (d, J=6.44 Hz, 3H), 1.39 (d, J=9.83 Hz, 1H), 1.75 (dd, J=14.24, 6.78 Hz, 1H), 2.12 (m, 1H), 2.62 (dd, J=14.41, 10.34 Hz, 1H), 2.80 (dd, J=13.56, 6.78 Hz, 1H), 3.05 (m, 3H), 3.30 (m, 1H), 3.30 (m, 1H), 3.54 (d, J=10.85 Hz, 1H), 3.59 (d, J=2.71 Hz, 1H), 3.70 (m, 1H), 3.94 (m, 2H), 4.21 (m, 1H), 5.92 (d, J=9.49 Hz, 1H), 7.13 (dd, J=6.44, 2.71 Hz, 2H), 7.24 (m, J=3.73 Hz, 3H), 7.33 (d, J=4.07 Hz, 1H), 7.54 (t, J=7.12 Hz, 1H), 7.66 (d, J=8.48 Hz, 2H), 7.70 (d, J=8.82 Hz, 2H), 7.77 (d, J=10.85 Hz, 2H), 8.15 (s, 1H), 8.18 (d, J=8.48 Hz, 1H), 8.39 (s, 1H), 8.99 (d, J=4.41 Hz, 1H)

Example 165

$^1$H NMR (300 MHz, CDCl$_3$) δ ppm 0.74 (d, J=6.44 Hz, 3H), 0.84 (d, J=6.44 Hz, 9H), 1.89 (m, 1H), 2.22 (s, 3H), 3.01 (m, 11H), 3.61 (d, J=10.51 Hz, 1H), 3.95 (s, 1H), 4.20 (m, 2H), 4.35 (s, 2H), 6.72 (s, 1H), 6.93 (m, 1H), 7.18 (m, 5H), 7.69 (d, J=8.48 Hz, 2H), 7.79 (d, Hz, 2H), 8.16 (s, 1H)

Example 166

$^1$H NMR (300 MHz, CD$_3$OD) δ ppm 0.78 (d, J=6.44 Hz, 6H), 0.87 (d, J=6.78 Hz, 3H), 0.91 (d, J=6.44 Hz, 3H), 2.05 (m, 2H), 2.52 (dd, J=13.90, 11.53 Hz, 1H), 2.68 (m, 1H), 2.97 (s, 6H), 3.15 (m, 7H), 3.47 (dd, J=14.58, 3.73 Hz, 1H), 3.75 (m, 2H), 4.11 (s, 1H), 4.40 (d, J=15.60 Hz, 1H), 4.63 (d, J=16.28 Hz, 1H), 4.69 (s, 2H), 7.16 (m, 5H), 7.57 (s, 1H), 7.78 (d, J=8.48 Hz, 2H), 7.83 (d, J=8.48 Hz, 2H), 7.95 (d, J=9.83 Hz, 1H), 8.14 (s, 1H)

Example 167

$^1$H NMR (300 MHz, CD$_3$OD) δ ppm 0.78 (d, J=6.44 Hz, 6H), 1.75 (m, 4H), 2.00 (m, 4H), 2.56 (m, 4H), 2.69 (s, 3H), 3.22 (m, 7H), 3.74 (m, 2H), 4.12 (m, 1H), 4.42 (s, 2H), 7.13 (m, 5H), 7.78 (d, J=8.82 Hz, 2H), 7.84 (d, J=8.82 Hz, 2H), 7.97 (d, J=9.49 Hz, 1H), 8.14 (s, 1H)

Example 168

$^1$H NMR (300 MHz, CD$_3$OD) δ ppm 0.76 (m, 6H), 1.57 (m, 1H), 1.89 (m, 2H), 2.01 (m, 2H), 2.55 (m, 2H), 2.69 (d, J=1.36 Hz, 3H), 3.12 (m, 6H), 3.42 (m, J=14.92, 3.05 Hz, 1H), 3.59 (m, 1H), 3.79 (m, 4H), 4.13 (m, 2H), 4.42 (s, 2H), 7.11 (m, 5H), 7.20 (d, J=2.37 Hz, 1H), 7.77 (d, J=7.80 Hz, 2H), 7.83 (t, J=2.03 Hz, 2H), 7.93 (t, J=10.17 Hz, 1H), 8.14 (s, 1H)

Example 169

$^1$H NMR (300 MHz, CD$_3$OD) δ ppm 0.74 (d, J=6.44 Hz, 3H), 0.79 (d, J=6.78 Hz, 3H), 2.03 (m, 1H), 2.52 (m, 2H), 2.70 (s, 3H), 2.76 (dd, J=15.09, 10.00 Hz, 1H), 3.02 (d, J=12.89 Hz, 6H), 3.15 (m, 6H), 3.57 (m, 2H), 3.75 (d, J=11.19 Hz, 1H), 4.00 (m, 3H), 4.42 (s, 2H), 7.12 (m, 5H), 7.20 (s, 1H), 7.84 (d, J=8.82 Hz, 2H), 7.90 (d, J=8.82 Hz, 2H), 8.06 (d, J=9.83 Hz, 1H), 8.16 (s, 1H)

Example 170

$^1$H NMR (300 MHz, CD$_3$OD) δ ppm 0.76 (d, J=2.71 Hz, 3H), 0.79 (m, 3H), 1.23 (m, 1H), 1.61 (m, 5H), 2.04 (m, 1H), 2.26 (dd, J=15.09, 7.29 Hz, 1H), 2.52 (m, 1H), 2.70 (s, 3H), 3.13 (m, 11H), 3.46 (dd, J=14.92, 3.73 Hz, 1H), 3.72 (d, J=0.85 Hz, 1H), 3.77 (m, 1H), 4.12 (m, 1H), 4.42 (d, J=1.36 Hz, 2H), 7.08 (m, 3H), 7.14 (m, 2H), 7.21 (s, 1H), 7.78 (d, J=8.82 Hz, 2H), 7.83 (d, J=8.82 Hz, 2H), 7.96 (m, 1H)

Example 171

$^1$H NMR (300 MHz, CD$_3$OD) δ ppm 0.71 (d, J=6.78 Hz, 3H), 0.76 (d, J=6.78 Hz, 3H), 2.02 (m, 1H), 2.51 (m, 2H), 2.69 (d, J=4.07 Hz, 3H), 3.12 (m, 2H), 3.35 (s, 3H), 3.42 (m, 1H), 3.70 (d, J=11.19 Hz, 1H), 3.79 (m, 1H), 4.09 (s, 1H), 4.41 (m, 2H), 4.64 (s, 2H), 6.20 (d, J=3.39 Hz, 1H), 6.25 (m, 1H), 7.08 (m, 3H), 7.15 (m, 2H), 7.20 (s, 1H), 7.25 (d, J=2.71 Hz, 1H), 7.71 (m, 4H), 7.95 (d, J=9.83 Hz, 1H), 8.12 (s, 1H)

Example 172

$^1$H NMR (300 MHz, CD$_3$OD) δ ppm 0.78 (t, J=6.44 Hz, 6H), 2.05 (m, 1H), 2.48 (dd, J=13.90, 11.19 Hz, 1H), 2.56 (m, 1H), 2.69 (s, 3H), 3.16 (m, 8H), 3.70 (m, 1H), 3.75 (s, 1H), 3.78 (m, 1H), 4.03 (m, 1H), 4.41 (d, J=2.37 Hz, 2H), 4.64 (d, J=17.63 Hz, 1H), 4.91 (d, J=17.63 Hz, 2H), 7.10 (m, 5H), 7.20 (s, 1H), 7.83 (m, 4H), 8.00 (d, J=8.14 Hz, 1H), 8.17 (s, 1H)

Example 173

$^1$H NMR (300 MHz, CDCl$_3$) δ ppm 0.76 (d, J=6.78 Hz, 3H), 0.79 (d, J=6.78 Hz, 3H), 0.86 (d, J=6.78 Hz, 3H), 0.91 (d, J=6.44 Hz, 3H), 1.87 (m, 1H), 2.14 (m, 1H), 2.41 (s, 3H), 2.61 (s, 3H), 2.70 (m, 1H), 2.88 (dd, J=13.56, 6.78 Hz, 1H), 2.98 (m, 1H), 3.13 (m, 7H), 3.62 (d, J=11.19 Hz, 1H), 3.77 (m, 1H), 4.11 (m, 1H), 4.38 (d, J=4.07 Hz, 2H), 6.48 (d, J=9.16 Hz, 1H), 7.16 (m, 5H), 7.70 (d, J=8.48 Hz, 2H), 7.79 (d, J=8.48 Hz, 2H), 8.15 (s, 1H)

Example 174

$^1$H NMR (300 MHz, CDCl$_3$) δ ppm 0.80 (d, J=6.44 Hz, 3H), 0.86 (t, J=6.44 Hz, 6H), 0.91 (d, J=6.78 Hz, 3H), 1.53 (d, J=5.09 Hz, 1H), 1.87 (m, J=6.44 Hz, 1H), 2.18 (m, 1H), 2.82 (m, 3H), 3.09 (m, 5H), 3.69 (d, J=11.19 Hz, 1H), 3.79 (m, 2H), 4.22 (m, 1H), 4.30 (d, J=15.60 Hz, 1H), 4.54 (d, J=15.60 Hz, 1H), 6.48 (d, J=8.82 Hz, 1H), 7.20 (m, 4H), 7.52 (t, J=7.80 Hz, 1H), 7.59 (m, 1H), 7.68 (s, 1H), 7.71 (d, J=8.48 Hz, 2H), 7.79 (d, J=8.48 Hz, 2H), 8.09 (m, 1H), 8.13 (m, 1H), 8.16 (s, 1H)

Example 175

$^1$H NMR (300 MHz, CDCl$_3$) δ ppm 0.78 (d, J=6.44 Hz, 3H), 0.81 (d, J=6.44 Hz, 3H), 0.87 (d, J=6.44 Hz, 3H), 0.91 (d, J=6.78 Hz, 3H), 1.87 (m, 1H), 2.15 (m, 1H), 2.96 (m, 10H), 3.67 (d, J=10.85 Hz, 1H), 3.78 (d, J=8.65, 5.26 Hz, 1H), 4.17 (dd, J=10.00, 4.58 Hz, 1H), 4.24 (d, J=15.26 Hz, 1H), 4.45 (d, J=15.26 Hz, 1H), 6.53 (d, J=8.82 Hz, 1H), 7.17 (m, 5H), 7.30 (m, 1H), 7.60 (m, 1H), 7.71 (d, J=8.48 Hz, 2H), 7.79 (d, J=8.48 Hz, 2H), 8.16 (s, 1H), 8.55 (m, 2H)

Example 176

$^1$H NMR (300 MHz, CDCl$_3$) δ ppm 0.74 (d, J=6.44 Hz, 3H), 0.82 (t, J=7.46 Hz, 3H), 0.87 (d, J=6.44 Hz, 3H), 0.91 (d, J=6.78 Hz, 3H), 0.98 (m, 1H), 1.29 (m, 1H), 1.92 (m, 2H), 2.99 (m, 9H), 3.75 (m, 2H), 3.80 (s, 3H), 3.85 (q, J=5.76 Hz, 1H), 4.06 (m, 1H), 4.63 (d, J=15.26 Hz, 1H), 4.86 (d, J=15.26 Hz, 1H), 6.45 (d, J=8.48 Hz, 1H), 7.15 (m, 5H), 7.33 (m, 2H), 7.74 (m, 6H), 8.18 (s, 1H)

Example 177

$^1$H NMR (300 MHz, CD$_3$OD) δ ppm 0.77 (t, J=5.76 Hz, 6H), 2.04 (m, 1H), 2.54 (m, 2H), 2.71 (m, 3H), 3.14 (m, 5H), 3.28 (s, 3H), 3.49 (m, 5H), 3.73 (d, J=10.85 Hz, 1H), 3.79 (m, 1H), 4.07 (m, 1H), 4.42 (d, J=1.70 Hz, 2H), 7.12 (m, 5H), 7.21 (s, 1H), 7.77 (d, J=8.48 Hz, 2H), 7.84 (d, J=8.82 Hz, 2H), 7.98 (d, J=9.49 Hz, 1H), 8.14 (d, J=3.39 Hz, 1H)

Example 178

$^1$H NMR (300 MHz, CD$_3$OD) δ ppm 0.78 (d, J=6.44 Hz, 6H), 1.77 (m, 2H), 2.00 (m, 2H), 2.55 (m, 3H), 3.12 (m, 7H), 3.40 (m, 4H), 3.46 (s, 3H), 3.73 (m, 2H), 4.12 (m, 1H), 4.45 (s, 2H), 4.70 (s, 2H), 7.08 (m, 3H), 7.15 (m, 2H), 7.37 (s, 1H), 7.76 (d, J=8.82 Hz, 2H), 7.83 (d, J=8.82 Hz, 2H), 7.96 (d, J=9.49 Hz, 1H), 8.14 (s, 1 µl Example 179

$^1$H NMR (300 MHz, CDCl$_3$) δ ppm 0.72 (d, J=6.78 Hz, 3H), 0.83 (m, J=7.46 Hz, 3H), 0.87 (d, J=6.44 Hz, 3H), 0.92 (d, J=6.78 Hz, 1H), 0.97 (m, 1H), 1.35 (m, 1H), 1.86 (d, J=6.78 Hz, 1H), 1.98 (m, 1H), 2.89 (m, 4H), 3.12 (m, 4H), 3.74 (d, J=10.85 Hz, 1H), 3.83 (m, 2H), 4.20 (m, 3H), 4.48 (d, J=15.26 Hz, 1H), 6.53 (d, J=8.48 Hz, 1H), 7.19 (m, 7H), 7.37 (m, 1H), 7.67 (d, J=7.80 Hz, 1H), 7.71 (d, J=8.82 Hz, 2H), 7.79 (d, J=8.48 Hz, 2H), 8.16 (s, 1H)

Example 180

$^1$H NMR (300 MHz, CDCl$_3$) δ ppm 0.70 (d, J=6.44 Hz, 3H), 0.85 (t, J=7.29 Hz, 3H), 1.02 (s, 1H), 1.36 (m, 1H), 1.65 (dd, J=11.02, 7.97 Hz, 4H), 1.85 (m, 2H), 1.98 (m, 4H), 2.52 (m, 1H), 2.80 (dd, J=14.24, 10.17 Hz, 1H), 2.91 (s, 1H), 3.16 (m, 5H), 3.72 (d, J=10.85 Hz, 1H), 3.79 (m, 1H), 4.20 (m, J=15.26 Hz, 2H), 4.52 (d, J=15.60 Hz, 1H), 6.65 (s, 1H), 7.20 (m, 7H), 7.45 (s, 1H), 7.71 (d, J=8.48 Hz, 2H), 7.79 (d, J=8.48 Hz, 3H), 8.16 (s, 1H)

Example 181

$^1$H NMR (300 MHz, CDCl$_3$) δ ppm 0.76 (d, J=6.44 Hz, 3H), 0.87 (m, 9H), 1.01 (d, J=22.72 Hz, 1H), 1.37 (m, 1H), 1.87 (d, J=6.78 Hz, 2H), 2.00 (m, 1H), 2.96 (m, 9H), 3.79 (m, J=10.85 Hz, 2H), 4.27 (m, J=15.94 Hz, 2H), 4.49 (d, J=15.94 Hz, 1H), 6.53 (d, J=8.82 Hz, 1H), 7.20 (m, 5H), 7.30 (s, 2H), 7.69 (d, J=8.48 Hz, 2H), 7.80 (d, J=8.14 Hz, 2H), 8.16 (s, 1H), 8.60 (s, 2H)

Example 182

$^1$H NMR (300 MHz, CDCl$_3$) δ ppm 0.77 (d, J=6.44 Hz, 3H), 0.87 (t, J=7.29 Hz, 3H), 1.03 (s, 1H), 1.43 (s, 1H), 1.69 (m, 2H), 1.86 (m, 2H), 1.98 (m, 4H), 2.50 (m, 1H), 2.82 (m, 1H), 3.13 (m, 8H), 3.82 (m, J=10.51 Hz, 2H), 4.28 (m, J=16.62 Hz, 2H), 4.51 (d, J=16.28 Hz, 1H), 6.59 (d, J=8.82 Hz, 1H), 7.21 (m, J=13.05, 4.24 Hz, 5H), 7.34 (s, 2H), 7.68 (d, J=8.48 Hz, 2H), 7.80 (d, J=8.48 Hz, 2H), 8.16 (s, 1H), 8.61 (s, 2H)

Example 183

$^1$H NMR (300 MHz, CD$_3$OD) δ ppm 0.75 (m, 6H), 1.16 (t, J=6.44 Hz, 3H), 2.01 (m, 1H), 2.52 (m, 2H), 2.70 (s, 3H), 2.91 (m, 1H), 3.13 (m, 9H), 3.63 (m, 1H), 3.72 (m, 1H), 3.89 (m, 1H), 4.06 (m, 1H), 4.42 (d, J=2.03 Hz, 2H), 7.08 (m, 3H), 7.14 (m, 2H), 7.21 (s, 1H), 7.78 (d, J=8.82 Hz, 2H), 7.83 (d, J=8.82 Hz, 2H), 8.14 (s, 1H)

Example 184

$^1$H NMR (300 MHz, CDCl$_3$) δ ppm 0.77 (d, J=6.44 Hz, 3H), 0.85 (t, J=7.29 Hz, 3H), 1.00 (m, 2H), 1.35 (m, 2H), 1.66 (m, 4H), 1.82 (m, 1H), 1.98 (m, 4H), 2.48 (dd, J=15.26, 7.46 Hz, 2H), 2.81 (m, 3H), 3.11 (m, 3H), 3.79 (m, 2H), 3.86 (m, 1H), 4.24 (m, 1H), 4.80 (t, J=15.60 Hz, 2H), 6.60 (d, J=8.82 Hz, 1H), 7.16 (m, 5H), 7.27 (m, 1H), 7.60 (m, 1H), 7.72 (m, 4H), 7.79 (d, J=8.48 Hz, 2H), 8.16 (s, 1H), 8.17 (m, 2H)

Example 185

¹H NMR (300 MHz, CD₃OD) δ ppm 0.78 (d, J=6.78 Hz, 6H), 2.07 (m, 1H), 2.55 (m, 2H), 2.70 (s, 3H), 3.14 (m, 6H), 3.43 (m, 2H), 3.58 (m, 2H), 3.77 (m, 2H), 4.10 (m, 1H), 4.42 (d, J=1.36 Hz, 2H), 6.82 (d, J=2.37 Hz, 1H), 6.90 (dd, J=509, 3.39 Hz, 1H), 7.09 (m, 3H), 7.18 (m, 3H), 7.20 (s, 1H), 7.77 (d, J=8.82 Hz, 2H), 7.82 (d, J=8.82 Hz, 2H), 8.02 (d, J=9.83 Hz, 1H), 8.14 (s, 1H)

Example 186

¹H NMR (300 MHz, DMSO-d₆) δ ppm 0.61 (d, J=6.44 Hz, 3H), 0.76 (d, J=7.46 Hz, 3H), 0.81 (d, J=6.78 Hz, 6H), 0.92 (m, 2H), 1.06 (m, 1H), 1.26 (m, 1H), 1.76 (s, 1H), 1.98 (d, J=6.78 Hz, 1H), 2.40 (dd, J=13.56, 11.19 Hz, 1H), 2.59 (m, 2H), 2.63 (s, 3H), 2.98 (m, 2H), 3.13 (d, J=7.80 Hz, 1H), 3.25 (d, J=17.29 Hz, 2H), 3.58 (d, J=7.46 Hz, 1H), 3.85 (m, J=10.85 Hz, 2H), 4.31 (d, J=8.48 Hz, 2H), 4.95 (d, J=6.44 Hz, 1H), 7.06 (m, 5H), 7.22 (s, 1H), 7.76 (d, J=8.82 Hz, 2H), 7.80 (d, J=8.82 Hz, 2H), 8.24 (s, 1H)

Example 187

¹H NMR (300 MHz, DMSO-d₆) δ ppm 0.63 (d, J=6.78 Hz, 3H), 0.78 (t, J=7.12 Hz, 3H), 0.92 (m, 2H), 1.24 (s, 1H), 1.60 (m, J=29.84, 8.82 Hz, 2H), 1.73 (m, 4H), 1.89 (m, 2H), 2.42 (dd, J=13.73, 11.02 Hz, 1H), 2.59 (m, 2H), 2.64 (s, 3H), 3.09 (m, 6H), 3.56 (d, J=3.73 Hz, 1H), 3.86 (d, J=10.85 Hz, 2H), 4.32 (m, 2H), 4.99 (d, J=6.44 Hz, 1H), 7.06 (m, 3H), 7.22 (s, 1H), 7.79 (m, 4H), 7.91 (m, 2H), 8.24 (s, 1H)

Example 188

¹H NMR (300 MHz, CDCl₃) δ ppm 0.76 (d, J=6.78 Hz, 3H), 0.85 (t, J=6.78 Hz, 6H), 0.90 (d, J=6.44 Hz, 3H), 0.94 (m, 1H), 1.37 (m, 1H), 1.85 (m, 1H), 2.04 (s, 1H), 2.83 (m, 4H), 3.06 (m, 6H), 3.83 (m, 2H), 4.23 (s, 1H), 4.81 (m, J=13.90 Hz, 2H), 6.53 (d, J=8.48 Hz, 1H), 7.16 (m, 5H), 7.61 (t, J=7.46 Hz, 1H), 7.74 (m, 5H), 8.15 (m, 3H), 8.24 (m, 2H)

Example 189

¹H NMR (300 MHz, DMSO-d₆) δ ppm 0.64 (d, J=6.78 Hz, 3H), 0.79 (m, 3H), 0.88 (m, 1H), 1.19 (m, 1H), 1.60 (m, 1H), 1.73 (m, 4H), 1.87 (dd, J=13.22, 7.80 Hz, 2H), 2.12 (s, 3H), 2.43 (dd, J=13.56, 10.85 Hz, 1H), 2.57 (m, 1H), 2.67 (m, J=7.12 Hz, 1H), 3.09 (m, 8H), 3.56 (s, 1H), 3.85 (m, J=10.85 Hz, 2H), 4.26 (t, J=15.26 Hz, 2H), 4.99 (d, J=6.10 Hz, 1H), 6.88 (s, 1H), 7.07 (m, 5H), 7.79 (m, 4H), 7.87 (d, J=9.49 Hz, 1H), 8.24 (s, 1H)

Example 190

¹H NMR (300 MHz, DMSO-d₆) δ ppm 0.62 (d, J=6.78 Hz, 3H), 0.80 (m, 9H), 0.89 (m, 1H), 1.22 (m, 1H), 1.72 (d, J=2.37 Hz, 1H), 1.99 (m, 1H), 2.12 (s, 3H), 2.41 (dd, J=13.39, 11.02 Hz, 1H), 2.67 (m, 1H), 2.87 (dd, J=13.73, 6.61 Hz, 1H), 3.10 (m, 6H), 3.58 (d, J=6.10 Hz, 1H), 3.85 (m, 2H), 4.26 (t, J=15.26 Hz, 2H), 4.95 (d, J=6.44 Hz, 1H), 6.88 (s, 1H), 7.06 (m, 5H), 7.78 (m, 4H), 7.88 (d, J=9.49 Hz, 1H), 8.24 (s, 1H)

Example 191

¹H NMR (300 MHz, CD₃OD) δ ppm 0.72 (d, J=6.44 Hz, 3H), 0.86 (m, 6H), 0.91 (d, J=6.78 Hz, 3H), 0.99 (m, 1H), 1.32 (m, 1H), 1.85 (m, 1H), 2.02 (m, 1H), 2.48 (m, 2H), 3.07 (m, 8H), 3.44 (dd, J=14.92, 3.39 Hz, 1H), 3.75 (m, 1H), 3.85 (d, J=11.19 Hz, 1H), 4.10 (m, 1H), 4.41 (d, J=14.58 Hz, 1H), 4.57 (d, J=14.92 Hz, 1H), 6.98 (dd, J=4.92, 1.87 Hz, 3H), 7.13 (m, 2H), 7.25 (m, 1H), 7.59 (m, 2H), 7.78 (d, J=8.48 Hz, 2H), 7.84 (d, J=8.82 Hz, 2H), 8.14 (s, 1H), 8.16 (s, 1H)

Example 192

¹H NMR (300 MHz, CD₃OD) δ ppm 0.79 (m, 9H), 0.95 (d, J=6.78 Hz, 3H), 2.04 (m, 2H), 2.52 (m, 1H), 2.69 (d, J=4.07 Hz, 3H), 3.16 (m, 7H), 3.46 (m, 3H), 3.73 (m, 3H), 3.83 (m, 1H), 4.09 (s, 1H), 4.42 (s, 2H), 7.11 (m, 5H), 7.22 (m, 1H), 7.75 (d, J=8.48 Hz, 2H), 7.89 (d, J=8.48 Hz, 2H), 8.14 (s, 1H)

Example 193

¹H NMR (300 MHz, CD₃OD) δ ppm 0.65 (dd, J=9.16, 6.78 Hz, 3H), 0.82 (0=6.95 Hz, 6H), 0.95 (d, J=6.44 Hz, 3H), 1.89 (m, 1H), 2.06 (m, 1H), 2.50 (dd, J=13.73, 10.68 Hz, 1H), 2.64 (m, 1H), 2.70 (s, 3H), 3.10 (m, 6H), 3.54 (m, 1H), 3.65 (m, 2H), 3.76 (m, 2H), 4.00 (m, 2H), 4.43 (s, 2H), 7.17 (m, 6H), 7.73 (m, 3H), 7.87 (m, 1H), 8.06 (m, 1H), 8.14 (s, 1H)

Example 194

¹H NMR (300 MHz, DMSO-d₆) δ ppm 0.64 (d, J=6.78 Hz, 3H), 0.80 (m, 3H), 0.92 (m, 1H), 1.20 (m, 4H), 1.53 (m, 6H), 1.77 (d, J=3.05 Hz, 1H), 2.25 (m, J=7.46 Hz, 1H), 2.40 (dd, J=13.39, 11.02 Hz, 1H), 3.09 (m, 8H), 3.60 (s, 1H), 3.91 (m, J=10.85 Hz, 2H), 4.80 (d, J=3.05 Hz, 2H), 4.96 (d, J=6.44 Hz, 1H), 6.93 (m, 3H), 7.05 (d, J=6.44 Hz, 2H), 7.42 (d, J=4.41 Hz, 1H), 7.62 (t, J=7.12 Hz, 1H), 7.79 (m, 4H), 7.97 (d, J=9.49 Hz, 1H), 8.06 (d, J=7.80 Hz, 1H), 8.24 (s, 1H), 8.30 (d, J=7.80 Hz, 1H), 8.89 (d, J=4.41 Hz, 1H)

Example 195

¹H NMR (300 MHz, CDCl₃) δ ppm 0.73 (d, J=6.44 Hz, 3H), 0.84 (dd, J=12.72, 6.95 Hz, 6H), 0.90 (d, J=6.44 Hz, 3H), 1.00 (m, 1H), 1.33 (s, 1H), 1.87 (d, J=6.78 Hz, 1H), 1.99 (s, 1H), 2.34 (s, 3H), 2.75 (dd, J=14.24, 9.83 Hz, 1H), 2.88 (m, 3H), 3.09 (m, 6H), 3.76 (d, J=10.85 Hz, 1H), 3.81 (s, 1H), 4.17 (m, 1H), 4.28 (d, J=14.92 Hz, 1H), 4.44 (d, J=14.92 Hz, 1H), 6.49 (d, J=8.82 Hz, 1H), 7.19 (m, 6H), 7.71 (d, J=8.48 Hz, 2H), 7.79 (d, J=8.48 Hz, 2H), 8.16 (s, 1H), 8.42 (m, 2H)

Example 196

¹H NMR (300 MHz, CDCl₃) δ ppm 0.73 (d, J=6.44 Hz, 3H), 0.85 (m, 6H), 0.91 (d, J=6.44 Hz, 3H), 1.03 (m, 1H), 1.35 (d, J=3.05 Hz, 1H), 1.86 (m, 1H), 1.96 (s, 1H), 2.56 (s, 3H), 2.74 (dd, J=14.24, 10.17 Hz, 1H), 3.02 (m, 8H), 3.80 (m, 2H), 3.88 (d, J=3.39 Hz, 1H), 4.12 (m, 1H), 4.38 (d, J=15.60 Hz, 1H), 4.59 (d, J=15.60 Hz, 1H), 6.49 (d, J=8.82 Hz, 1H), 7.06 (d, J=7.46 Hz, 2H), 7.18 (m, 5H), 7.58 (m, 1H), 7.70 (d, J=8.48 Hz, 2H), 7.79 (d, J=8.48 Hz, 2H), 8.16 (s, 1H)

Example 197

¹H NMR (300 MHz, CDCl₃) δ ppm 0.73 (d, J=6.44 Hz, 3H), 0.89 (m, 9H), 1.01 (s, 1H), 1.39 (s, 1H), 1.87 (m, 1H), 1.97 (s, 1H), 2.75 (dd, J=14.24, 10.17 Hz, 1H), 3.03 (m, 8H), 3.77 (d, J=10.85 Hz, 1H), 3.79 (s, 1H), 3.90 (d, J=3.05 Hz, 1H), 4.16 (m, 1H), 4.40 (d, J=15.60 Hz, 1H), 4.59 (d, J=15.60 Hz, 1H), 6.53 (d, J=8.82 Hz, 1H), 7.18 (m, 7H), 7.70 (m, J=8.48 Hz, 3H), 7.79 (d, J=8.48 Hz, 2H), 8.16 (s, 1H), 8.56 (d, J=4.07 Hz, 1H)

Example 198

¹H NMR (300 MHz, CDCl₃) δ ppm 0.74 (d, J=6.78 Hz, 3H), 0.85 (t, J=7.29 Hz, 6H), 0.91 (d, J=6.78 Hz, 3H), 1.01 (m, 1H), 1.39 (m, 1H), 1.88 (m, 1H), 1.98 (m, 1H), 2.75 (dd, J=14.41, 10.00 Hz, 1H), 2.87 (dd, J=13.73, 6.95 Hz, 2H), 2.99 (m, 1H), 3.17 (m, 4H), 3.48 (s, 3H), 3.81 (m, 3H), 4.17 (m, 1H), 4.37 (d, J=15.60 Hz, 1H), 4.56 (s, 2H), 4.60 (d, J=15.94 Hz, 1H), 6.50 (d, J=8.48 Hz, 1H), 7.17 (m, 5H), 7.32 (d, J=7.80 Hz, 1H), 7.68 (m, 4H), 7.79 (d, J=8.82 Hz, 2H), 8.15 (s, 1H), 8.17 (s, 1H)

Example 199

¹H NMR (300 MHz, CDCl₃) δ ppm 0.73 (d, J=6.44 Hz, 3H), 0.83 (t, J=7.12 Hz, 3H), 0.98 (m, 1H), 1.39 (m, 2H), 1.55 (m, 6H), 1.96 (s, 2H), 2.13 (m, 2H), 2.78 (m, 2H), 3.11 (m, 7H), 3.47 (s, 3H), 3.80 (d, J=10.85 Hz, 1H), 3.86 (m, 1H), 4.20 (m, 1H), 4.37 (d, J=15.94 Hz, 1H), 4.56 (s, 2H), 4.61 (d, J=15.60 Hz, 1H), 6.66 (d, J=9.16 Hz, 1H), 7.17 (m, 6H), 7.33 (d, J=7.80 Hz, 1H), 7.68 (m, 3H), 7.79 (d, J=8.48 Hz, 2H), 8.15 (s, 1H)

Example 200

¹H NMR (300 MHz, CD₃OD) δ ppm 0.74 (d, J=6.44 Hz, 3H), 0.88 (m, J=6.95, 2.20 Hz, 6H), 0.91 (d, J=6.44 Hz, 3H), 1.03 (m, 1H), 1.41 (m, 1H), 1.89 (m, 1H), 2.02 (m, 1H), 2.51 (dd, J=13.73, 11.36 Hz, 1H), 2.64 (m, 1H), 3.10 (m, 8H), 3.45 (dd, J=14.92, 3.39 Hz, 1H), 3.76 (m, 1H), 3.87 (d, J=11.19 Hz, 1H), 4.14 (m, 1H), 4.53 (d, J=15.94 Hz, 1H), 4.78 (d, J=10.17 Hz, 1H), 7.09 (m, 3H), 7.18 (m, 2H), 7.47 (d, J=8.48 Hz, 1H), 7.60 (m, 1H), 7.76 (m, 3H), 7.84 (d, J=8.48 Hz, 2H), 7.92 (m, 1H), 8.02 (m, 1H), 8.14 (s, 1H), 8.34 (d J=8.48 Hz, 1H)

Example 201

¹H NMR (300 MHz, CD₃OD) δ ppm 0.73 (d, J=6.78 Hz, 3H), 0.87 (m, 6H), 0.91 (d, J=6.44 Hz, 3H), 1.00 (m, 1H), 1.30 (m, 1H), 1.86 (m, 1H), 2.02 (m, 1H), 2.49 (m, 1H), 2.58 (m, 1H), 3.07 (m, 6H), 3.45 (dd, J=14.92, 3.39 Hz, 1H), 3.75 (m, 1H), 3.84 (d, J=11.19 Hz, 1H), 4.13 (m, 1H), 4.31 (d, J=15.26 Hz, 1H), 4.52 (d, J=15.60 Hz, 1H), 7.07 (m, 3H), 7.17 (m, 2H), 7.59 (m, 2H), 7.67 (m, 1H), 7.78 (d, J=8.48 Hz, 2H), 7.84 (d, J=8.82 Hz, 2H), 7.98 (s, 1H), 8.14 (s, 1H)

Example 202

¹H NMR (300 MHz, DMSO-d₆) δ ppm 0.61 (d, J=6.78 Hz, 3H), 0.78 (dd, J=16.95, 7.12 Hz, 9H), 0.91 (m, 1H), 1.26 (m, 1H), 1.73 (s, 1H), 1.98 (m, J=6.44 Hz, 1H), 2.39 (dd, J=13.22, 11.19 Hz, 1H), 2.58 (t, J=7.97 Hz, 1H), 3.05 (m, 9H), 3.58 (m, 1H), 3.84 (m, J=10.85 Hz, 2H), 4.49 (m, 2H), 7.05 (m, 5H), 7.76 (d, J=8.82 Hz, 2H), 7.80 (d, J=8.82 Hz, 2H), 7.94 (s, 1H), 8.24 (s, 1H)

Example 203

¹H NMR (300 MHz, CDCl₃) δ ppm 0.74 (d, J=6.44 Hz, 3H), 0.82 (t, J=7.29 Hz, 3H), 0.95 (m, 1H), 1.24 (m, 5H), 1.53 (m, 4H), 1.96 (m, 1H), 2.15 (m, 1H), 2.99 (m, 12H), 3.76 (d, J=11.19 Hz, 1H), 3.88 (m, 1H), 3.96 (d, J=2.71 Hz, 1H), 4.11 (m, 1H), 4.62 (d, J=14.92 Hz, 1H), 4.86 (d, J=15.26 Hz, 1H), 6.45 (d, J=8.82 Hz, 1H), 7.15 (m, 5H), 7.33 (m, 2H), 7.74 (m, 6H), 8.18 (s, 1H)

Example 204

¹H NMR (300 MHz, CDCl₃) δ ppm 0.74 (d, J=6.44 Hz, 3H), 0.84 (t, J=7.29 Hz, 3H), 0.98 (m, 2H), 1.21 (m, 2H), 1.38 (m, 2H), 1.64 (m, 6H), 1.97 (s, 1H), 2.10 (m, 1H), 2.74 (m, 3H), 3.09 (m, 5H), 3.81 (m, 2H), 4.13 (m, 1H), 5.10 (d, J=2.03 Hz, 2H), 6.58 (d, J=8.82 Hz, 1H), 7.13 (m, 5H), 7.44 (dd, J=8.31, 4.24 Hz, 1H), 7.52 (m, 1H), 7.69 (m, 3H), 7.77 (m, 3H), 8.15 (s, 1H), 8.18 (dd, J=8.31, 1.53 Hz, 1H), 8.95 (d, J=2.37 Hz, 1H)

Example 205

¹H NMR (300 MHz, CDCl₃) δ ppm 0.72 (s, 3H), 0.87 (s, 9H), 1.01 (s, 1H), 1.40 (s, 1H), 1.90 (m, 2H), 2.98 (s, 11H), 3.82 (m, 3H), 4.17 (s, 1H), 5.09 (m, 2H), 7.14 (m, 5H), 7.45 (dd, J=8.14, 4.07 Hz, 1H), 7.52 (m, 1H), 7.69 (m, 3H), 7.78 (m, 3H), 8.18 (d, J=8.14 Hz, 1H), 8.96 (d, J=2.37 Hz, 1H)

Example 206

¹H NMR (300 MHz, DMSO-d₆) δ ppm 0.79 (m, J=15.77, 6.95 Hz, 6H), 1.23 (dd, J=14.07, 6.27 Hz, 6H), 1.32 (d, J=7.12 Hz, 6H), 1.75 (s, 1H), 1.96 (d, J=7.80 Hz, 1H), 2.39 (dd, J=13.39, 11.02 Hz, 1H), 3.07 (m, 11H), 3.61 (m, 1H), 3.84 (m, J=10.85 Hz, 2H), 4.36 (m, 2H), 4.95 (d, J=6.44 Hz, 1H), 7.05 (m, 5H), 7.24 (s, 1H), 7.78 (t, J=8.82 Hz, 4H), 7.89 (d, J=9.49 Hz, 1H), 8.24 (s, 1H)

Example 207

¹H NMR (300 MHz, DMSO-d₆), δ ppm 0.63 (d, J=6.44 Hz, 3H), 0.77 (t, J=7.12 Hz, 3H), 0.90 (m, 1H), 1.23 (dd, J=14.07, 6.61 Hz, 4H), 1.32 (d, J=6.78 Hz, 6H), 1.52 (m, 6H), 1.71 (d, J=16.28 Hz, 1H), 2.26 (m, 1H), 2.40 (dd, J=13.22, 10.85 Hz, 1H), 2.57 (m, 1H), 3.11 (m, 7H), 3.59 (d, J=12.55 Hz, 1H), 3.85 (m, J=11.19 Hz, 2H), 4.30 (d, J=15.60 Hz, 1H), 4.39 (d, J=15.26 Hz, 1H), 4.95 (d, J=6.44 Hz, 1H), 7.05 (m, 5H), 7.25 (s, 1H), 7.78 (t, J=8.82 Hz, 4H), 7.89 (d, J=9.49 Hz, 1H), 8.24 (s, 1H)

Example 208

¹H NMR (300 MHz, DMSO-d₆) δ ppm 0.66 (d, J=6.44 Hz, 3H), 0.70 (d, J=6.44 Hz, 3H), 0.81 (d, J=6.78 Hz, 6H), 1.23 (dd, J=13.73, 5.93 Hz, 6H), 1.32 (d, J=7.12 Hz, 6H), 1.94 (m, 1H), 2.40 (dd, J=13.22, 11.19 Hz, 1H), 3.00 (m, 2H), 3.21 (m, 2H), 3.59 (m, 1H), 3.75 (d, J=10.85 Hz, 1H), 3.85 (s, 1H), 4.30 (d, J=15.26 Hz, 1H), 4.39 (d, J=15.26 Hz, 1H), 4.96 (d, J=6.78 Hz, 1H), 7.05 (m, 5H), 7.24 (s, 1H), 7.78 (t, J=8.82 Hz, 4H), 7.89 (d, J=9.49 Hz, 1H), 8.24 (s, 1H)

Example 209

¹H NMR (300 MHz, DMSO-d₆), δ ppm 0.69 (t, J=7.12 Hz, 6H), 0.85 (m, 1H), 1.19 (m, 4H), 1.32 (d, J=6.78 Hz, 6H), 1.53 (m, 6H), 1.94 (m, 1H), 2.22 (m, 1H), 2.40 (dd, J=13.39, 11.02 Hz, 1H), 3.11 (m, 6H), 3.61 (m, 1H), 3.76 (d, J=10.85 Hz, 1H), 3.88 (s, 1H), 4.35 (dd, J=15.60, 14.92 Hz, 2H), 4.96 (d, J=6.44 Hz, 1H), 7.06 (m, 5H), 7.24 (s, 1H), 7.78 (dd, J=9.16, 8.48 Hz, 4H), 7.88 (d, J=9.49 Hz, 1H), 8.24 (s, 1H)

Example 210

¹H NMR (300 MHz, DMSO-d₆), δ ppm 0.61 (d, J=6.44 Hz, 3H), 0.76 (d, J=7.12 Hz, 3H), 0.81 (d, J=6.78 Hz, 3H), 1.26 (d, J=5.76 Hz, 3H), 1.73 (s, 1H), 1.97 (s, 1H), 2.40 (dd, J=13.39, 10.68 Hz, 1H), 2.60 (d, J=7.46 Hz, 1H), 2.89 (m, 1H), 2.99 (m, 3H), 3.01 (m, 4H), 3.13 (d, J=8.14 Hz, 1H), 3.23 (m, 1H), 3.38 (s, 3H), 3.61 (m, J=10.85 Hz, 1H), 3.85 (m, J=11.19 Hz, 2H), 4.37 (s, 1H), 4.67 (d, J=4.07 Hz, 2H), 4.95 (d, J=6.44 Hz, 1H), 7.05 (m, 5H), 7.41 (s, 1H), 7.78 (t, J=12.21 Hz, 4H), 7.90 (d, J=9.83 Hz, 1H), 8.24 (s, 1H)

Example 211

$^1$H NMR (300 MHz, DMSO-$d_6$) δ ppm 0.63 (d, J=6.44 Hz, 3H), 0.77 (t, J=7.29 Hz, 3H), 0.89 (m, 1H), 1.24 (m, 7H), 1.56 (d, J=7.80 Hz, 6H), 1.72 (d, J=23.06 Hz, 1H), 2.22 (s, 1H), 2.42 (m, 1H), 2.60 (d, J=7.12 Hz, 1H), 2.99 (m, 1H), 3.13 (m, 1H), 3.38 (s, 3H), 3.61 (m, 2H), 3.85 (m, J=11.19 Hz, 2H), 4.37 (s, 2H), 4.68 (s, 2H), 4.95 (d, J=6.44 Hz, 1H), 7.07 (m, 5H), 7.41 (s, 1H), 7.78 (m, 4H), 7.90 (d, J=9.16 Hz, 1H), 8.24 (s, 1H)

Example 212

$^1$H NMR (300 MHz, CDCl$_3$) δ ppm 0.81 (m, 12H), 1.03 (m, J=15.94 Hz, 1H), 1.43 (m, 1H), 1.85 (m, 1H), 1.99 (m, 1H), 2.35 (s, 3H), 2.87 (m, 4H), 3.12 (m, 7H), 3.78 (d, J=11.19 Hz, 1H), 3.95 (m, 1H), 4.20 (m, J=15.94 Hz, 2H), 4.51 (d, J=15.94 Hz, 1H), 6.63 (d, J=7.46 Hz, 1H), 7.14 (m, 5H), 7.71 (m, 3H), 7.80 (m, 3H), 8.15 (s, 1H), 8.55 (d, J=5.09 Hz, 1H)

Example 213

$^1$H NMR (300 MHz, CDCl$_3$) δ ppm 0.69 (d, J=6.44 Hz, 3H), 0.87 (m, 9H), 0.98 (m, 1H), 1.39 (m, 1H), 1.89 (dd, J=13.73, 6.95 Hz, 1H), 2.03 (m, 1H), 3.02 (m, 9H), 3.72 (m, 1H), 3.87 (m, 1H), 4.17 (m, 2H), 4.44 (d, J=14.92 Hz, 1H), 4.67 (d, J=15.26 Hz, 1H), 6.83 (d, J=8.82 Hz, 1H), 7.18 (m, 5H), 7.45 (m, 2H), 7.79 (m, 5H), 8.10 (s, 1H), 8.18 (s, 1H), 8.19 (m, 1H), 8.94 (d, J=2.71 Hz, 1H)

Example 214

$^1$H NMR (300 MHz, CDCl$_3$) δ ppm 0.69 (d, J=6.44 Hz, 3H), 0.87 (m, 12H), 0.99 (m, 1H), 1.39 (m, 1H), 1.89 (dd, J=13.73, 6.95 Hz, 2H), 2.02 (m, 2H), 3.01 (m, 5H), 3.71 (d, J=11.19 Hz, 1H), 3.87 (m, 1H), 4.17 (m, 1H), 4.44 (d, J=14.92 Hz, 1H), 4.66 (m, 1H), 6.83 (d, J=8.82 Hz, 1H), 7.18 (m, 5H), 7.45 (m, 2H), 7.79 (m, 5H), 810 (s, 1H), 8.20 (m, 1H), 8.18 (s, 1H), 8.94 (d, J=2.71 Hz, 1H)

Example 215

$^1$H NMR (300 MHz, DMSO-$d_6$), δ ppm 0.62 (d, J=6.44 Hz, 3H), 0.77 (d, J=7.46 Hz, 3H), 0.81 (d, J=6.44 Hz, 6H), 0.92 (m, 1H), 1.26 (m, 2H), 1.74 (s, 1H), 1.98 (m, J=5.09 Hz, 1H), 2.40 (dd, J=13.39, 11.02 Hz, 1H), 2.60 (m, J=8.14 Hz, 1H), 3.06 (m, 8H), 3.58 (m, 1H), 3.87 (d, J=10.85 Hz, 2H), 4.47 (m, 2H), 7.01 (m, 5H), 7.49 (dd, J=6.44, 4.75 Hz, 1H), 7.57 (s, 1H), 7.78 (m, 4H), 7.94 (m, 2H), 8.09 (m, 1H), 8.24 (s, 1H)

Example 216

$^1$H NMR (300 MHz, CDCl$_3$) δ ppm 0.69 (d, J=6.78 Hz, 3H), 0.85 (t, J=7.29 Hz, 3H), 0.97 (m, 1H), 1.24 (m, 3H), 1.38 (m, 1H), 1.55 (m, 6H), 2.01 (m, 1H), 2.15 (m, 1H), 3.03 (m, 7H), 3.72 (m, 1H), 3.90 (m, 1H), 4.19 (m, 2H), 4.43 (d, J=14.92 Hz, 1H), 4.67 (d, J=15.26 Hz, 1H), 6.82 (d, J=8.82 Hz, 1H), 7.16 (m, 6H), 7.46 (m, 2H), 7.78 (m, 5H), 8.10 (s, 1H), 8.20 (m, 1H), 8.18 (s, 1H), 8.94 (dd, J=4.41, 1.70 Hz, 1H)

Example 217

$^1$H NMR (300 MHz, CDCl$_3$) δ ppm 0.76 (d, J=6.44 Hz, 3H), 0.86 (t, J=7.29 Hz, 3H), 1.01 (m, 1H), 1.23 (m, 2H), 1.38 (m, 1H), 1.57 (m, 6H), 2.01 (m, 1H), 2.11 (dd, J=14.75, 7.29 Hz, 1H), 2.99 (m, 9H), 3.84 (m, 3H), 4.24 (m, 1H), 4.41 (d, J=15.26 Hz, 1H), 4.63 (d, J=14.92 Hz, 1H), 6.58 (d, J=8.82 Hz, 1H), 7.17 (m, 5H), 7.42 (dd, J=8.31, 4.24 Hz, 1H), 7.62 (dd, J=8.48, 2.03 Hz, 1H), 7.69 (m, 3H), 7.79 (d, J=8.82 Hz, 2H), 8.12 (dd, J=8.82, 6.78 Hz, 2H), 8.16 (s, 1H), 8.91 (d, J=3.05 Hz, 1H)

Example 218

$^1$H NMR (300 MHz, DMSO-$d_6$), δ ppm 0.62 (t, J=6.61 Hz, 3H), 0.76 (d, J=7.46 Hz, 3H), 0.81 (d, J=6.78 Hz, 6H), 0.91 (m, 1H), 1.24 (m, 2H), 1.73 (0=10.51 Hz, 1H), 1.98 (m, 1H), 2.41 (dd, J=13.22, 11.19 Hz, 1H), 2.63 (t, J=7.63 Hz, 1H), 2.87 (dd, J=13.56, 6.44 Hz, 1H), 3.00 (s, 6H), 3.14 (m, 6H), 3.56 (m, 1H), 3.85 (d, J=11.19 Hz, 2H), 4.32 (s, 2H), 4.95 (d, J=6.44 Hz, 1H), 7.05 (m, 5H), 7.33 (s, 1H), 7.78 (m, 4H), 7.90 (d, J=9.49 Hz, 1H), 8.24 (s, 1H).

Example 219

$^1$H NMR (300 MHz, CD$_3$OD) δ ppm 0.71 (d, J=6.78 Hz, 3H), 0.85 (t, J=7.29 Hz, 3H), 1.00 (s, 9H), 1.37 (m, 1H), 1.89 (s, 1H), 2.56 (dd, J=14.07, 11.02 Hz, 1H), 3.15 (m, 7H), 3.39 (m, 2H), 3.48 (m, 1H), 3.81 (d, J=11.19 Hz, 1H), 3.91 (m, 1H), 4.02 (m, 2H), 4.07 (s, 3H), 4.74 (d, J=16.95 Hz, 1H), 5.01 (d, J=16.95 Hz, 1H), 7.13 (m, 5H), 7.66 (m, 2H), 7.78 (m, 3H), 7.83 (d, J=8.48 Hz, 2H), 7.89 (m, 1H), 8.14 (s, 1H)

Example 220

$^1$H NMR (300 MHz, CD$_3$OD) δ ppm 0.65 (d, J=6.44 Hz, 3H), 0.73 (d, J=6.78 Hz, 3H), 0.96 (m, 2H), 1.97 (m, 1H), 2.45 (m, 2H), 2.69 (s, 3H), 3.12 (m, 4H), 3.52 (m, 3H), 3.98 (s, 1H), 4.41 (m, 2H), 4.69 (dd, J=36.11, 16.11 Hz, 2H), 7.08 (m, 5H), 7.19 (s, 1H), 7.62 (d, J=8.48 Hz, 2H), 7.87 (m, 7H), 8.15 (s, 1H), 8.28 (d, J=8.14 Hz, 1H), 8.53 (m, 1H), 8.78 (d, J=4.75 Hz, 1H)

Example 221

$^1$H NMR (300 MHz, CDCl$_3$) δ ppm 0.77 (d, J=6.44 Hz, 3H), 0.86 (t, J=7.29 Hz, 3H), 1.02 (m, 1H), 1.12 (s, 2H), 1.44 (m, 8H), 2.00 (s, 1H), 2.10 (m, 1H), 2.35 (s, 3H), 2.87 (dd, J=14.24, 10.17 Hz, 1H), 3.01 (dd, J=11.19, 7.80 Hz, 2H), 3.12 (m, 5H), 3.26 (m, 1H), 3.79 (d, J=10.85 Hz, 1H), 3.99 (s, 1H), 4.18 (m, 2H), 4.51 (d, J=15.94 Hz, 1H), 6.63 (m, 1H), 7.10 (dd, J=5.09, 1.70 Hz, 1H), 7.18 (m, 5H), 7.71 (m, J=8.31, 8.31 Hz, 3H), 7.79 (d, J=8.48 Hz, 2H), 8.15 (s, 1H), 8.55 (d, J=5.09 Hz, 1H)

Example 222

$^1$H NMR (300 MHz, CD$_3$OD) δ ppm 0.72 (d, J=6.44 Hz, 3H), 0.86 (m, J=12.21, 6.78 Hz, 6H), 0.91 (d, J=6.44 Hz, 3H), 1.00 (m, 1H), 1.36 (s, 1H), 1.89 (s, 1H), 1.99 (d, J=15.26 Hz, 1H), 2.28 (s, 3H), 2.49 (m, J=13.73, 11.36 Hz, 1H), 2.60 (m, J=8.48 Hz, 1H), 3.00 (m, 1H), 3.09 (m, 6H), 3.08 (m, 1H), 3.18 (m, 1H), 3.44 (m, J=18.65 Hz, 1H), 3.75 (m, 1H), 3.83 (m, J=11.53 Hz, 1H), 4.12 (m, 1H), 4.37 (d, J=15.60 Hz, 1H), 4.63 (m, 1H), 7.12 (m, 5H), 7.26 (d, J=7.80 Hz, 1H), 7.75 (m, 3H), 7.84 (d, J=8.48 Hz, 2H), 8.15 (s, 1H)

Example 223

¹H NMR (300 MHz, CD₃OD) δ ppm 0.73 (d, J=6.78 Hz, 3H), 0.86 (dd, J=9.16, 7.12 Hz, 6H), 0.91 (d, J=6.44 Hz, 3H), 1.03 (d, J=10.85 Hz, 1H), 1.35 (s, 1H), 1.87 (s, 1H), 2.02 (m, 1H), 2.17 (d, J=6.10 Hz, 3H), 2.50 (dd, J=13.73, 11.36 Hz, 1H), 2.63 (m, 1H), 3.07 (m, 8H), 3.11 (s, 3H), 3.44 (dd, J=14.92, 3.05 Hz, 1H), 3.75 (dd, J=15.60, 3.73 Hz, 1H), 3.82 (dd, J=11.19, 2.71 Hz, 1H), 4.10 (m, J=6.78 Hz, 1H), 4.35 (d, J=15.94 Hz, 1H), 4.58 (d, J=15.60 Hz, 1H), 4.68 (s, 2H), 7.13 (m, 5H), 7.24 (m, 1H), 7.80 (m, 5H), 7.95 (d, J=9.83 Hz, 1H), 8.14 (s, 1H)

Example 224

¹H NMR (300 MHz, CD₃OD) δ ppm 0.71 (d, J=6.78 Hz, 3H), 0.85 (m, J=14.75, 6.95 Hz, 6H), 0.91 (d, J=6.78 Hz, 3H), 0.96 (m, 1H), 1.34 (m, 1H), 1.86 (m, J=17.97 Hz, 1H), 2.01 (m, 1H), 2.49 (m, 2H), 3.08 (m, 9H), 3.28 (s, 3H), 3.44 (dd, J=14.58, 3.39 Hz, 1H), 3.73 (m, 1H), 3.81 (d, J=11.19 Hz, 1H), 4.10 (m, 1H), 4.21 (d, J=6.10 Hz, 1H), 4.57 (m, 2H), 6.40 (s, 1H), 7.13 (m, 5H), 7.78 (d, J=8.48 Hz, 2H), 7.84 (m, J=8.48 Hz, 2H), 8.15 (s, 1H)

Example 225

¹H NMR (300 MHz, DMSO-d₆), δ ppm 0.62 (d, J=6.44 Hz, 3H), 0.77 (d, J=7.12 Hz, 3H), 0.81 (d, J=6.78 Hz, 6H), 0.89 (m, 1H), 1.28 (m, 1H), 1.74 (s, 1H), 1.96 (m, 1H), 2.40 (dd, J=13.39, 11.02 Hz, 1H), 2.61 (m, 1H), 3.06 (m, 10H), 3.59 (m, 1H), 3.87 (d, J=10.85 Hz, 1H), 4.48 (s, 2H), 7.01 (m, 5H), 7.56 (m, 1H), 7.60 (s, 1H), 7.76 (d, J=9.16 Hz, 2H), 7.81 (d, J=8.82 Hz, 2H), 7.92 (d, J=9.49 Hz, 1H), 8.24 (s, 1H), 8.31 (s, 1H), 8.33 (m, 1H), 8.67 (dd, J=4.75, 1.70 Hz, 1H), 9.15 (d, J=1.70 Hz, 1H)

Example 226

¹H NMR (300 MHz, CD₃OD) δ ppm 0.73 (d, J=6.78 Hz, 3H), 0.84 (m, 6H), 0.91 (d, J=6.44 Hz, 3H), 0.99 (m, 1H), 1.39 (m, 1H), 1.90 (m, 1H), 2.03 (m, 1H), 2.49 (dd, J=13.73, 11.36 Hz, 1H), 2.62 (m, 1H), 3.11 (m, 8H), 3.44 (dd, J=14.92, 3.39 Hz, 1H), 3.75 (m, 1H), 3.85 (d, J=11.19 Hz, 1H), 4.13 (m, 1H), 4.46 (d, J=15.94 Hz, 1H), 4.71 (d, J=15.94 Hz, 1H), 7.09 (m, 5H), 7.37 (d, J=6.78 Hz, 1H), 7.43 (m, 1H), 7.78 (d, J=8.82 Hz, 2H), 7.84 (d, J=6.78 Hz, 2H), 7.92 (m, 2H), 8.14 (s, 1H), 8.23 (d, J=7.12 Hz, 1H), 8.41 (d, J=8.14 Hz, 1H), 8.63 (m, 1 H)

Example 227

¹H NMR (300 MHz, CDCl₃) δ ppm 0.76 (d, J=6.44 Hz, 3H), 0.85 (dd, J=8.99, 6.95 Hz, 6H), 0.90 (d, J=6.44 Hz, 3H), 1.01 (m, 1H), 1.33 (m, 1H), 1.85 (m, 1H), 1.99 (m, 1H), 2.75 (s, 3H), 2.99 (m, 9H), 3.83 (m, 3H), 4.22 (dd, J=9.49, 4.75 Hz, 1H), 4.68 (d, J=15.60 Hz, 1H), 4.82 (d, J=15.26 Hz, 1H), 6.54 (d, J=8.82 Hz, 1H), 7.17 (m, 5H), 7.51 (t, J=7.63 Hz, 1H), 7.69 (m, 4H), 7.79 (d, J=8.48 Hz, 2H), 8.08 (d, J=8.48 Hz, 2H), 8.16 (s, 1H)

Example 228

¹H NMR (300 MHz, CDCl₃) δ ppm 0.76 (d, J=6.78 Hz, 3H), 0.86 (dd, J=7.12, 3.39 Hz, 6H), 0.90 (d, J=6.44 Hz, 3H), 1.03 (m, 1H), 1.41 (m, 1H), 1.87 (m, 1H), 1.99 (m, 1H), 2.67 (s, 3H), 2.76 (m, 1H), 2.88 (m, 1H), 2.99 (m, 1H), 3.15 (m, 5H), 3.81 (m, 3H), 3.89 (d, J=3.39 Hz, 1H), 4.16 (m, 1H), 4.51 (d, J=15.26 Hz, 1H), 4.78 (d, J=15.26 Hz, 1H), 6.56 (d, J=8.82 Hz, 1H), 7.17 (m, 6H), 7.56 (t, J=7.12 Hz, 1H), 7.72 (m, 3H), 7.79 (d, J=8.48 Hz, 2H), 7.98 (d, J=7.46 Hz, 1H), 8.07 (d, J=8.48 Hz, 1H), 8.17 (s, 1H)

Example 229

¹H NMR (300 MHz, CDCl₃) δ ppm 0.73 (d, J=6.44 Hz, 3H), 0.88 (m, 9H), 1.29 (m, 6H), 1.87 (s, 2H), 2.97 (m, 12H), 3.75 (d, J=11.53 Hz, 2H), 3.86 (d, J=3.39 Hz, 1H), 4.12 (q, J=7.12 Hz, 1H), 4.39 (s, 1H), 4.58 (s, 1H), 6.50 (d, J=8.82 Hz, 1H), 7.08 (s, 2H), 7.19 (s, 5H), 7.69 (m, J=7.80 Hz, 3H), 7.78 (d, J=8.48 Hz, 2H), 8.15 (s, 1H)

Example 230

¹H NMR (300 MHz, CDCl₃) δ ppm 0.74 (d, J=6.78 Hz, 3H), 0.86 (m, 3H), 1.00 (m, 1H), 1.16 (m, 2H), 1.26 (m, J=7.29, 7.29 Hz, 1H), 1.39 (m, 2H), 1.64 (m, 6H), 1.97 (m, J=11.53 Hz, 1H), 2.13 (m, 1H), 2.55 (s, 3H), 2.79 (m, 2H), 3.10 (m, 5H), 3.79 (m, 3H), 4.15 (m, 1H), 4.40 (m, 1H), 4.59 (d, J=15.60 Hz, 1H), 6.52 (d, J=8.82 Hz, 1H), 7.06 (d, J=7.12 Hz, 2H), 7.16 (m, 1H), 7.21 (m, 4H), 7.58 (m, 1H), 7.70 (d, J=8.48 Hz, 2H), 7.79 (d, J=8.48 Hz, 2H), 8.16 (s, 1H)

Example 231

¹H NMR (300 MHz, CDCl₃) δ ppm 0.74 (d, J=6.44 Hz, 3H), 0.84 (t, J=7.46 Hz, 3H), 0.99 (m, 1H), 1.15 (s, 1H), 1.34 (m, 2H), 1.59 (m, 6H), 1.96 (m, 1H), 2.11 (m, J=7.80 Hz, 1H), 2.34 (s, 3H), 2.80 (m, 3H), 3.04 (m, 7H), 3.79 (m, 2H), 4.22 (m, 1H), 4.28 (d, J=15.26 Hz, 1H), 4.44 (d, J=14.92 Hz, 1H), 6.51 (d, J=8.82 Hz, 1H), 7.17 (m, 6H), 7.71 (d, J=8.48 Hz, 2H), 7.79 (d, J=8.48 Hz, 2H), 8.16 (s, 1H), 8.41 (m, 2H)

Example 232

¹H NMR (300 MHz, CDCl₃) δ ppm 0.72 (d, J=6.62 Hz, 3H), 0.85 (m, 6H), 0.90 (d, J=6.25 Hz, 3H), 1.00 (m, 1H), 1.85 (m, 1H), 1.95 (m, 1H), 2.99 (m, 11H), 3.40 (s, 3H), 3.76 (d, J=11.03 Hz, 1H), 3.82 (m, 1H), 4.16 (m, 1H), 4.38 (d, J=15.44 Hz, 1H), 4.44 (s, 2H), 4.58 (d, J=15.44 Hz, 1H), 6.62 (d, J=8.82 Hz, 1H), 7.17 (m, 7H), 7.70 (d, J=8.46 Hz, 2H), 7.80 (d, J=8.46 Hz, 2H), 8.15 (s, 1H), 8.50 (d, J=5.15 Hz, 1H)

Example 233

¹H NMR (300 MHz, CD₃OD) δ ppm 0.87 (m, 6H), 0.91 (s, 9H), 1.29 (d, J=2.94 Hz, 1H), 2.02 (m, 1H), 2.26 (m, 1H), 2.43 (dd, J=13.79, 11.58 Hz, 1H), 3.06 (m, 8H), 3.43 (dd, J=14.71, 3.31 Hz, 1H), 3.74 (m, 1H), 4.07 (m, 1H), 4.58 (s, 2H), 7.10 (m, 5H), 7.58 (s, 1H), 7.78 (m, 5H), 7.96 (m, 1H), 8.14 (s, 1H), 8.60 (m, 1H), 8.68 (m, 1H)

Example 234

¹H NMR (300 MHz, CDCl₃) δ ppm 0.88 (d, J=6.62 Hz, 3H), 0.91 (d, J=6.62 Hz, 3H), 0.98 (s, 9H), 1.82 (m, 2H), 2.54 (q, J=9.19 Hz, 1H), 2.67 (dd, J=14.34, 10.30 Hz, 1H), 3.04 (m, 5H), 3.31 (m, 1H), 3.82 (m, 2H), 4.07 (s, 1H), 4.24 (m, 1H), 4.81 (s, 2H), 6.26 (d, J=8.82 Hz, 1H), 7.04 (m, 5H), 7.28 (d, J=4.41 Hz, 1H), 7.61 (m, 1H), 7.72 (m, 3H), 7.80 (d, J=8.46 Hz, 2H), 8.17 (m, 3H), 8.89 (d, J=4.41 Hz, 1H)

Example 235

¹H NMR (300 MHz, CDCl₃) δ ppm 0.74 (d, J=6.62 Hz, 3H), 0.84 (t, J=7.35 Hz, 3H), 0.97 (m, 2H), 1.31 (m, 4H), 1.61

(s, 8H), 1.96 (s, 1H), 2.11 (dd, J=15.08, 7.35 Hz, 1H), 2.79 (m, 1H), 3.06 (m, 5H), 3.79 (m, 2H), 4.22 (m, 2H), 4.45 (d, J=15.08 Hz, 1H), 6.50 (d, J=8.82 Hz, 1H), 7.17 (m, 5H), 7.29 (m, 1H), 7.60 (m, 1H), 7.71 (d, J=8.46 Hz, 2H), 7.79 (d, J=8.82 Hz, 2H), 8.16 (s, 1H), 8.54 (m, 2H)

Example 236

$^1$H NMR (300 MHz, CDCl$_3$) δ ppm 0.88 (d, J=6.62 Hz, 3H), 0.92 (d, J=6.62 Hz, 3H), 0.96 (s, 9H), 1.87 (m, 1H), 2.59 (q, J=8.95 Hz, 1H), 2.70 (dd, J=14.16, 10.48 Hz, 1H), 3.01 (m, 6H), 3.32 (m, 1H), 3.79 (m, 1H), 4.00 (s, 1H), 4.23 (m, 2H), 4.46 (d, J=15.08 Hz, 1H), 6.24 (d, J=9.19 Hz, 1H), 7.13 (m, 5H), 7.30 (dd, J=7.35, 4.41 Hz, 1H), 7.62 (m, 1H), 7.72 (d, J=8.46 Hz, 2H), 7.80 (d, J=8.46 Hz, 3H), 8.17 (s, 1H), 8.55 (m, 2H)

Example 237

$^1$H NMR (300 MHz, DMSO-d$_6$), δ ppm 0.61 (d, J=6.62 Hz, 3H), 0.76 (d, J=7.35 Hz, 3H), 0.81 (d, J=6.62 Hz, 6H), 0.91 (m, 1H), 1.22 (m, 1H), 1.73 (s, 1H), 1.96 (dd, J=13.42, 6.07 Hz, 1H), 2.04 (s, 2H), 2.07 (s, 1H), 2.40 (dd, J=13.24, 11.03 Hz, 1H), 2.61 (m, J=7.35 Hz, 1H), 2.92 (m, 6H), 3.03 (s, 3H), 3.15 (m, 1H), 3.24 (m, 1H), 3.58 (m, 1H), 3.84 (d, J=11.03 Hz, 1H), 4.02 (m, 1H), 4.37 (m, 2H), 4.71 (s, 1H), 4.83 (s, 1H), 7.06 (m, 5H), 7.35 (m, 1H), 7.79 (t, J=8.82 Hz, 4H), 7.90 (d, J=9.19 Hz, 1H), 8.24 (s, 1H)

Example 238

$^1$H NMR (300 MHz, CDCl$_3$) δ ppm 0.88 (d, J=6.62 Hz, 3H), 0.91 (d, J=6.62 Hz, 3H), 0.98 (s, 9H), 1.86 (m, 1H), 2.53 (m, 1H), 2.67 (dd, J=14.34, 10.30 Hz, 1H), 2.75 (s, 3H), 3.07 (m, 7H), 3.81 (m, 2H), 4.07 (s, 1H), 4.24 (m, 1H), 4.74 (d, J=16.18 Hz, 2H), 6.23 (d, J=8.82 Hz, 1H), 7.05 (m, 5H), 7.18 (s, 1H), 7.52 (t, J=7.72 Hz, 1H), 7.71 (m, 3H), 7.80 (d, J=8.46 Hz, 2H), 8.09 (t, J=9.38 Hz, 2H), 8.17 (s, 1H)

Example 239

$^1$H NMR (300 MHz, CDCl$_3$) δ ppm 0.88 (d, J=6.62 Hz, 3H), 0.91 (d, J=6.62 Hz, 3H), 0.98 (s, 9H), 1.87 (m, 1H), 2.67 (m, 2H), 3.01 (m, 5H), 3.34 (m, 1H), 3.83 (m, 2H), 4.06 (s, 2H), 4.24 (m, 1H), 4.45 (d, J=15.08 Hz, 1H), 4.65 (d, J=15.08 Hz, 1H), 6.31 (d, J=8.82 Hz, 1H), 7.14 (m, 5H), 7.42 (dd, J=8.27, 4.23 Hz, 1H), 7.65 (m, 1H), 7.71 (d, J=8.82 Hz, 2H), 7.79 (d, J=8.46 Hz, 2H), 8.14 (dd, J=8.64, 3.13 Hz, 2H), 8.18 (s, 1H), 8.88 (s, 1H), 8.91 (dd, J=4.23, 1.65 Hz, 1H)

Example 240

$^1$H NMR (300 MHz, CDCl$_3$) δ ppm 0.87 (d, J=6.62 Hz, 3H), 0.91 (d, J=6.62 Hz, 3H), 0.98 (s, 9H), 1.89 (m, 1H), 2.71 (m, 2H), 3.04 (m, 6H), 3.35 (m, 1H), 3.84 (m, 1H), 4.04 (m, J=4.78 Hz, 2H), 4.22 (m, 1H), 4.50 (d, J=15.08 Hz, 1H), 4.65 (d, J=15.08 Hz, 1H), 6.41 (d, J=8.82 Hz, 1H), 7.14 (m, 5H), 7.43 (dd, J=8.27, 4.23 Hz, 1H), 7.50 (dd, J=8.46, 1.47 Hz, 1H), 7.73 (d, J=8.46 Hz, 2H), 7.80 (d, J=8.46 Hz, 2H), 8.05 (s, 1H), 8.17 (d, J=4.78 Hz, 1H), 8.94 (dd, J=4.41, 1.47 Hz, 1H), 9.03 (s, 1H)

Example 241

$^1$H NMR (300 MHz, CD$_3$OD) δ ppm 0.88 (d, J=6.99 Hz, 6H), 0.92 (s, 9H), 2.02 (m, 1H), 2.22 (m, 1H), 2.42 (dd, J=13.60, 11.77 Hz, 1H), 3.12 (m, 8H), 3.42 (m, J=15.08, 3.31 Hz, 1H), 3.73 (m, 1H), 4.00 (s, 1H), 4.05 (m, 1H), 4.54 (m, 2H), 7.05 (m, 5H), 7.43 (m, 1H), 7.49 (s, 1H), 7.77 (d, J=8.82 Hz, 2H), 7.84 (d, J=8.46 Hz, 2H), 7.90 (m, 1H), 8.14 (s, 1H), 8.21 (d, J=8.09 Hz, 1H), 8.57 (m, 1H)

Example 242

$^1$H NMR (300 MHz, DMSO-d$_6$), δ ppm 0.61 (d, J=6.62 Hz, 3H), 0.77 (m, 3H), 0.81 (d, J=6.62 Hz, 6H), 0.92 (m, 1H), 1.21 (m, 2H), 1.73 (m, 1H), 1.97 (m, 1H), 2.08 (s, 3H), 2.40 (dd, J=13.42, 10.85 Hz, 1H), 2.60 (m, 1H), 2.94 (m, 4H), 3.13 (m, 1H), 3.25 (dd, J=14.52, 2.76 Hz, 1H), 3.57 (m, 2H), 3.86 (m, 2H), 4.38 (s, 2H), 5.32 (s, 2H), 7.05 (m, 5H), 7.47 (s, 1H), 7.78 (m, 4H), 7.91 (d, J=9.56 Hz, 1H), 8.24 (s, 1H)

Example 243

$^1$H NMR (300 MHz, CDCl$_3$) δ ppm 0.87 (d, J=6.62 Hz, 3H), 0.92 (d, J=6.62 Hz, 3H), 0.97 (s, 9H), 1.53 (s, 1H), 1.84 (m, 1H), 2.61 (q, J=9.19 Hz, 1H), 2.71 (dd, J=14.34, 10.30 Hz, 1H), 2.87 (dd, J=13.42, 6.80 Hz, 1H), 3.09 (m, 5H), 3.34 (m, 1H), 3.48 (s, 3H), 3.79 (m, 1H), 4.00 (s, 1H), 4.16 (m, 1H), 4.39 (d, J=15.81 Hz, 1H), 4.57 (s, 2H), 4.64 (d, J=15.81 Hz, 1H), 6.18 (d, J=9.19 Hz, 1H), 7.15 (m, 5H), 7.33 (d, J=7.72 Hz, 1H), 7.68 (m, 2H), 7.72 (d, J=6.25 Hz, 2H), 7.80 (d, J=8.46 Hz, 2H), 8.16 (s, 1

Example 244

$^1$H NMR (300 MHz, CDCl$_3$) δ ppm 0.87 (d, J=7.35 Hz, 3H), 0.91 (d, J=6.62 Hz, 3H), 0.95 (s, 9H), 1.86 (m, 1H), 2.58 (q, J=8.95 Hz, 1H), 2.69 (dd, J=13.97, 10.30 Hz, 1H), 2.86 (dd, J=13.42, 6.80 Hz, 1H), 3.01 (m, 3H), 3.13 (m, 3H), 3.32 (m, 1H), 3.49 (s, 3H), 3.76 (m, 2H), 3.98 (s, 1H), 4.18 (m, 1H), 4.43 (d, J=14.71 Hz, 1H), 4.52 (d, J=15.44 Hz, 1H), 4.70 (d, J=2.57 Hz, 2H), 6.19 (d, J=8.82 Hz, 1H), 7.11 (s, 1H), 7.15 (m, 5H), 7.71 (d, J=8.46 Hz, 2 H), 7.79 (d, J=8.82 Hz, 2H), 7.93 (s, 1H), 8.16 (s, 1H)

Example 245

$^1$H NMR (300 MHz, CD$_3$OD) δ ppm 0.71 (d, J=6.62 Hz, 3H), 0.81 (t, J=7.35 Hz, 3H), 0.88 (d, J=6.62 Hz, 3H), 0.91 (d, J=6.25 Hz, 3H), 0.99 (m, 1H), 1.30 (m, 1H), 1.85 (t, J=15.08 Hz, 1H), 2.01 (m, J=14.71 Hz, 1H), 2.48 (m, 2H), 3.07 (m, 8H), 3.44 (dd, J=14.89, 3.49 Hz, 1H), 3.74 (m, 1H), 3.85 (d, J=11.03 Hz, 1H), 4.10 (m, 1H), 4.38 (d, J=15.08 Hz, 1H), 4.56 (d, J=15.08 Hz, 1H), 7.02 (m, 3H), 7.12 (m, 2H), 7.38 (d, J=7.35 Hz, 1H), 7.52 (m, 2H), 7.61 (m, 2H), 7.78 (d, J=8.82 Hz, 2H), 7.83 (d, J=9.93 Hz, 2H), 8.08 (m, 1H), 8.14 (s, 1H), 8.52 (dd, J=4.96, 1.65 Hz, 1H), 8.79 (d, J=3.31 Hz, 1H)

Example 246

$^1$H NMR (300 MHz, DMSO-d$_6$) δ ppm 0.82 (t, J=2.94 Hz, 15H), 1.23 (m, 1H), 1.47 (d, J=7.35 Hz, 3H), 1.88 (s, 3H), 1.97 (m, 1H), 2.17 (q, J=8.95 Hz, 1H), 2.33 (m, 1H), 3.05 (m, 6H), 3.53 (t, J=8.27 Hz, 1H), 3.84 (m, 1H), 3.96 (s, 1H), 4.30 (d, J=15.44 Hz, 1H), 4.42 (d, J=15.44 Hz, 1H), 4.95 (d, J=6.62 Hz, 1H), 5.14 (m, 1H), 7.03 (m, 5H), 7.27 (s, 1H), 7.76 (d, J=8.82 Hz, 2H), 7.80 (d, J=8.82 Hz, 2H), 7.98 (d, J=9.56 Hz, 1H), 8.23 (s, 1H), 8.62 (d, J=7.72 Hz, 1H)

Example 247

$^1$H NMR (300 MHz, CD$_3$OD) δ ppm 0.87 (m, 6H), 0.91 (s, 9H), 2.00 (dd, J=14.52, 6.80 Hz, 1H), 2.28 (m, 1H), 2.44 (dd, J=13.42, 11.58 Hz, 1H), 2.73 (s, 3H), 3.10 (m, 9H), 3.43 (dd, J=14.89, 3.49 Hz, 1H), 3.73 (m, 1H), 4.00 (s, 1H), 4.03 (s, 1H), 4.57 (s, 2H), 7.06 (m, 5H), 7.61 (s, 1H), 7.78 (m, 2H), 7.83 (d, J=8.46 Hz, 2H), 7.96 (m, 1H), 8.14 (s, 1H), 8.69 (dd, J=8.46, 2.21 Hz, 1H)

Example 248

¹H NMR (300 MHz, CD₃OD) δ ppm 0.88 (m, 6H), 0.91 (s, 9H), 1.99 (s, 1H), 2.28 (d, J=8.46 Hz, 1H), 2.44 (m, 1H), 3.06 (m, 8H), 3.41 (d, J=3.68 Hz, 1H), 3.73 (s, 1H), 4.00 (s, 1H), 4.07 (m, 1H), 4.59 (s, 2H), 7.07 (m, 5H), 7.72 (s, 1H), 7.77 (d, J=8.46 Hz, 2H), 7.82 (m, 3H), 7.94 (s, 1H), 8.14 (s, 1H), 8.21 (m, 1H), 8.74 (m, 1H)

Example 249

¹H NMR (300 MHz, CD₃OD) δ ppm 0.88 (d, J=6.99 Hz, 6H), 0.91 (s, 9H), 2.02 (m, 1H), 2.18 (m, 1H), 2.42 (dd, J=13.42, 11.58 Hz, 1H), 3.11 (m, 7H), 3.42 (dd, J=14.71, 3.31 Hz, 1H), 3.72 (m, 1H), 3.98 (s, 1H), 4.05 (m, 1H), 4.42 (d, J=14.71 Hz, 1H), 4.53 (m, J=13.24 Hz, 2H), 7.06 (m, 6H), 7.31 (s, 1H), 7.54 (d, J=5.15 Hz, 1H), 7.60 (d, J=3.68 Hz, 1H), 7.77 (d, J=8.82 Hz, 2H), 7.85 (d, J=8.82 Hz, 2H), 8.14 (s, 1H)

Example 250

¹H NMR (300 MHz, CDCl₃) δ ppm 0.75 (d, J=6.62 Hz, 3H), 0.85 (t, J=7.35 Hz, 6H), 0.90 (d, J=6.62 Hz, 3H), 1.35 (m, 3H), 1.85 (m, 1H), 2.00 (m, 1H), 2.55 (s, 3H), 2.99 (m, 9H), 3.79 (m, J=11.03 Hz, 2H), 4.20 (m, J=4.78 Hz, 1H), 4.26 (d, J=15.44 Hz, 1H), 4.42 (d, J=15.08 Hz, 1H), 6.49 (d, J=8.82 Hz, 1H), 7.17 (m, 6H), 7.45 (dd, J=7.72, 1.47 Hz, 1H), 7.71 (d, J=8.46 Hz, 2H), 7.79 (d, J=8.46 Hz, 2H), 8.16 (s, 1H), 8.43 (dd, J=4.96, 1.65 Hz, 1H)

Example 251

¹H NMR (300 MHz, CDCl₃) δ ppm 0.73 (d, J=6.62 Hz, 3H), 0.84 (dd, J=15.44, 6.99 Hz, 6H), 0.91 (d, J=6.62 Hz, 3H), 0.99 (m, 1H), 1.27 (m, 1H), 1.85 (m, J=7.72 Hz, 2H), 2.55 (s, 3H), 2.96 (m, 10H), 3.76 (m, 2H), 4.19 (m, J=15.08 Hz, 2H), 4.41 (d, J=15.08 Hz, 1H), 6.45 (d, J=8.82 Hz, 1H), 7.18 (m, 5H), 7.49 (dd, J=7.91, 2.39 Hz, 1H), 7.72 (d, J=8.82 Hz, 2H), 7.80 (d, J=8.46 Hz, 2H), 8.16 (s, 1H), 8.17 (s, 1H), 8.40 (d, J=2.57 Hz, 1H)

Example 252

¹H NMR (300 MHz, CD₃OD) δ ppm 0.73 (d, J=6.62 Hz, 3H), 0.86 (dd, J=9.74, 6.80 Hz, 9H), 0.91 (d, J=6.62 Hz, 4H), 0.99 (m, 1H), 1.16 (s, 1H), 1.34 (m, 2H), 1.87 (d, J=10.66 Hz, 1H), 2.03 (m, 1H), 2.50 (dd, J=13.60, 11.40 Hz, 1H), 2.63 (m, 1H), 2.97 (s, 3H), 3.12 (m, 4H), 3.44 (dd, J=14.71, 3.68 Hz, 1H), 3.75 (m, 1H), 3.83 (d, J=11.40 Hz, 1H), 4.12 (m, 2H), 4.35 (d, J=15.81 Hz, 1H), 4.57 (m, 3H), 4.77 (d, J=9.93 Hz, 2H), 7.09 (m, 3H), 7.17 (m, 2H), 7.22 (d, J=7.72 Hz, 1H), 7.78 (m, 4H), 7.83 (d, J=8.82 Hz, 2H), 8.14 (s, 1H)

Example 253

¹H NMR (300 MHz, CD₃OD) δ ppm 0.87 (m, 6H), 0.92 (s, 9H), 2.02 (m, 1H), 2.29 (q, J=9.19 Hz, 1H), 2.45 (dd, J=13.60, 11.40 Hz, 1H), 3.11 (m, 9H), 3.43 (dd, J=14.71, 3.31 Hz, 1H), 3.73 (m, 1H), 3.99 (s, 1H), 4.07 (m, 1H), 4.39 (d, J=15.81 Hz, 1H), 4.56 (d, J=15.44 Hz, 1H), 4.70 (s, 2H), 7.12 (m, 5H), 7.22 (d, J=7.72 Hz, 1H), 7.45 (d, J=8.09 Hz, 1H), 7.81 (m, 5H), 8.14 (s, 1H)

Example 254

¹H NMR (300 MHz, CD₃OD) δ ppm 0.72 (d, J=6.25 Hz, 3H), 0.85 (dd, J=15.08, 6.99 Hz, 6H), 0.91 (d, J=6.62 Hz, 3H), 1.00 (m, 1H), 1.32 (m, 1H), 1.85 (m, 1H), 2.03 (m, 1H), 2.51 (m, 2H), 3.09 (m, 8H), 3.44 (dd, J=14.71, 3.31 Hz, 1H), 3.75 (m, 1H), 3.85 (d, J=11.03 Hz, 1H), 4.11 (dd, J=0.11, 7.91 Hz, 1H), 4.36 (d, J=15.44 Hz, 1H), 4.54 (d, J=15.08 Hz, 1H), 7.04 (m, 3H), 7.14 (m, 2H), 7.42 (d, J=7.72 Hz, 1H), 7.50 (t, J=7.91 Hz, 1H), 7.61 (d, J=3.31 Hz, 1H), 7.78 (d, J=8.82 Hz, 2H), 7.84 (d, J=8.46 Hz, 2H), 7.88 (m, 2H), 7.98 (d, J=9.56 Hz, 1H), 8.14 (s, 1H)

Example 255

¹H NMR (300 MHz, CD₃OD) δ ppm 0.72 (d, J=6.62 Hz, 3H), 0.82 (t, J=7.35 Hz, 3H), 0.87 (d, J=6.99 Hz, 3H), 0.91 (d, J=6.62 Hz, 3H), 0.99 (m, 1H), 1.33 (m, 1H), 1.85 (s, 1H), 2.01 (m, 1H), 2.47 (dd, J=13.79, 11.21 Hz, 1H), 2.57 (m, 1H), 3.06 (m, 8H), 3.45 (dd, J=14.71, 3.31 Hz, 1H), 3.75 (m, 1H), 3.85 (d, J=11.40 Hz, 1H), 4.11 (m, 1H), 4.40 (d, J=15.08 Hz, 1H), 4.57 (d, J=15.08 Hz, 1H), 7.03 (dd, J=6.43, 3.86 Hz, 3H), 7.14 (m, 2H), 7.47 (d, J=7.72 Hz, 1H), 7.56 (m, 2H), 7.77 (d, J=8.46 Hz, 2H), 7.83 (d, J=8.82 Hz, 2H), 7.88 (m, 1H), 7.98 (m, 2H), 8.11 (m, 1H), 8.14 (s, 1H), 8.67 (d, J=4.41 Hz, 1H)

Example 256

¹H NMR (300 MHz, CD₃OD) δ ppm 0.88 (d, J=7.72 Hz, 6H), 0.91 (s, 9H), 2.00 (d, J=6.25 Hz, 1H), 2.22 (q, J=9.07 Hz, 1H), 2.43 (m, 1H), 2.50 (s, 3H), 3.10 (m, 10H), 3.42 (dd, J=14.71, 3.31 Hz, 1H), 3.72 (m, 1H), 3.98 (s, 1H), 4.06 (d, J=10.66 Hz, 1H), 4.54 (t, J=15.08 Hz, 2H), 7.06 (m, 5H), 7.54 (s, 1H), 7.77 (d, J=8.46 Hz, 1H), 7.83 (d, J=8.46 Hz, 1H), 7.96 (d, J=9.19 Hz, 1H), 8.14 (s, 1H)

Example 257

¹H NMR (300 MHz, CDCl₃) δ ppm 0.87 (d, J=6.62 Hz, 3H), 0.90 (d, J=6.62 Hz, 3H), 0.95 (s, 9H), 1.88 (m, 1H), 2.93 (m, 8H), 3.34 (m, 1H), 3.83 (m, 1H), 3.89 (s, 3H), 3.94 (d, J=3.31 Hz, 1H), 4.00 (s, 1H), 4.15 (m, 1H), 4.63 (d, J=15.44 Hz, 1H), 4.83 (d, J=15.44 Hz, 1H), 6.21 (d, J=8.82 Hz, 1H), 7.09 (m, 5H), 7.25 (m, 1H), 7.71 (d, J=8.82 Hz, 2H), 7.79 (d, J=8.46 Hz, 2H), 8.03 (m, 1H), 8.18 (s, 1H), 8.40 (dd, J=4.78, 1.47 Hz, 1H)

Example 258

¹H NMR (300 MHz, CDCl₃) δ ppm 0.73 (t, J=5.52 Hz, 3H), 0.84 (dd, J=12.50, 6.99 Hz, 6H), 0.90 (d, J=6.25 Hz, 3H), 0.97 (m, 1H), 1.33 (m, 1H), 1.85 (m, 1H), 1.97 (m, J=8.82 Hz, 1H), 2.34 (s, 3H), 2.59 (s, 3H), 2.97 (m, 8H), 3.79 (m, 3H), 4.20 (m, 1H), 4.39 (d, J=14.71 Hz, 1H), 4.48 (d, J=14.71 Hz, 1H), 6.52 (d, J=8.46 Hz, 1H), 6.97 (d, J=5.15 Hz, 1H), 7.20 (m, 5H), 7.70 (d, J=8.46 Hz, 2H), 7.79 (d, J=8.82 Hz, 2H), 8.16 (s, 1H), 8.30 (d, J=5.15 Hz, 2H)

Example 259

¹H NMR (300 MHz, CD₃OD) δ ppm 0.72 (d, J=6.62 Hz, 3H), 0.85 (m, 6H), 0.91 (d, J=6.62 Hz, 3H), 1.00 (m, 1H), 1.32 (m, 1H), 1.86 (m, 1H), 2.02 (m, 1H), 2.47 (m, 3H), 3.08 (m, 7H), 3.44 (dd, J=14.89, 3.49 Hz, 1H), 3.75 (m, 1H), 3.85 (d, J=11.03 Hz, 1H), 4.11 (m, 1H), 4.30 (d, J=14.71 Hz, 1H), 4.48 (d, J=14.71 Hz, 1H), 6.79 (d, J=1.84 Hz, 1H), 7.04 (m, 3H), 7.13 (m, 2H), 7.19 (d, J=7.72 Hz, 1H), 7.37 (m, 1H), 7.49 (m, 1H), 7.55 (m, 1H), 7.78 (d, J=8.46 Hz, 2H), 7.84 (d, J=8.82 Hz, 2H), 7.88 (m, 1H, 7.96 (d, J=9.56 Hz, 1H), 8.14 (s, 1H)

Example 260

$^1$H NMR (300 MHz, CD$_3$OD) δ ppm 0.72 (d, J=6.62 Hz, 3H), 0.82 (t, J=7.35 Hz, 3H), 0.88 (d, J=6.62 Hz, 3H), 0.91 (d, J=6.62 Hz, 3H), 1.00 (m, 2H), 1.31 (m, 1H), 1.86 (m, 1H), 2.00 (m, 1H), 2.51 (m, 2H), 3.07 (m, 8H), 3.75 (m, 1H), 3.85 (d, J=11.03 Hz, 1H), 4.11 (m, 1H), 4.39 (d, J=15.08 Hz, 1H), 4.57 (d, J=15.08 Hz, 1H), 7.04 (m, 3H), 7.13 (m, 2H), 7.44 (d, J=7.72 Hz, 1H), 7.56 (t, J=7.54 Hz, 1H), 7.66 (m, 2H), 7.77 (d, J=8.46 Hz, 2H), 7.83 (d, J=8.46 Hz, 2H), 7.97 (d, J=9.93 Hz, 1H), 8.14 (s, 1H), 9.06 (s, 1H), 9.14 (s, 1H)

Example 261

$^1$H NMR (300 MHz, CD$_3$OD) δ ppm 0.71 (d, J=6.62 Hz, 3H), 0.85 (dd, J=16.18, 6.99 Hz, 6H), 0.91 (d, J=6.62 Hz, 3H), 0.97 (m, 1H), 1.28 (m, 1H), 1.83 (s, 1H), 2.01 (m, 1H), 2.51 (m, 2H), 3.08 (m, 8H), 3.44 (m, 1H), 3.74 (m, 1H), 3.84 (m, 1H), 3.90 (s, 3H), 4.12 (m, 1H), 4.24 (m, 1H), 4.39 (d, J=15.08 Hz, 1H), 6.81 (d, J=8.46 Hz, 1H), 7.06 (m, 3H), 7.15 (m, 2H), 7.63 (dd, 8.64, 2.39 Hz, 1H), 7.78 (m, 2H), 7.84 (d, J=8.82 Hz, 2H), 8.08 (d, J=1.84 Hz, 1H), 8.14 (s, 1H)

Example 262

$^1$H NMR (300 MHz, CD$_3$OD) δ ppm 0.87 (m, 6H), 0.92 (s, 9H), 2.03 (d, J=6.25 Hz, 1H), 2.22 (t, J=8.46 Hz, 1H), 2.43 (m, 1H), 3.09 (m, 9H), 3.42 (m, 1H), 3.74 (m, 1H), 4.00 (s, 1H), 4.05 (m, 1H), 4.58 (s, 2H), 7.08 (m, 5H), 7.60 (s, 1H), 7.77 (d, J=8.46 Hz, 2H), 7.84 (d, J=6.62 Hz, 2H), 8.14 (s, 1H), 8.62 (d, J=2.57 Hz, 1H), 9.37 (s, 1H)

Example 263

$^1$H NMR (300 MHz, CD$_3$OD) δ ppm 0.88 (d, J=7.72 Hz, 6H), 0.92 (s, 9H), 1.53 (d, J=4.04 Hz, 6H), 2.00 (m, 1H), 2.24 (m, 1H), 2.44 (dd, J=13.60, 11.77 Hz, 1H), 3.12 (m, 10H), 3.42 (dd, J=14.71, 3.31 Hz, 1H), 3.73 (m, 1H), 3.98 (s, 1H), 4.08 (m, 1H), 4.38 (d, J=15.44 Hz, 1H), 4.62 (d, J=15.44 Hz, 1H), 7.11 (m, 5H), 7.53 (d, J=8.09 Hz, 1H), 7.77 (m, 3H), 7.84 (d, J=8.46 Hz, 2H), 8.14 (s, 1H)

Example 264

$^1$H NMR (300 MHz, CDCl$_3$) δ ppm 0.76 (d, J=6.62 Hz, 3H), 0.85 (t, J=7.35 Hz, 3H), 1.00 (d, J=22.43 Hz, 2H), 1.26 (s, 4H), 1.58 (s, 8H), 1.99 (s, 1H), 2.11 (m, 1H), 2.98 (m, 8H), 3.81 (m, 3H), 4.24 (m, 2H), 4.43 (d, J=15.44 Hz, 1H), 652 (d, J=8.82 Hz, 1H), 7.17 (m, 5H), 7.45 (d, J=6.62 Hz, 1H), 7.70 (d, J=8.46 Hz, 2H), 7.78 (d, J=8.46 Hz, 2H), 8.16 (s, 1H), 8.25 (s, 1H), 8.43 (d, J=3.68 Hz, 1H)

Example 265

$^1$H NMR (300 MHz, CDCl$_3$) δ ppm 0.88 (d, J=6.62 Hz, 3H), 0.92 (d, J=6.62 Hz, 3H), 0.96 (s, 9H), 1.85 (dd, J=14.34, 6.99 Hz, 1H), 2.56 (s, 3H), 2.69 (dd, J=13.97, 10.30 Hz, 1H), 3.02 (m, 7H), 3.31 (m, 1H), 3.77 (d, J=3.68 Hz, 2H), 4.00 (s, 1H), 4.20 (m, 2H), 4.42 (d, J=14.71 Hz, 1H), 6.18 (d, J=9.19 Hz, 1H), 7.14 (m, 5H), 7.51 (dd, J=7.72, 2.21 Hz, 1H), 7.72 (d, J=8.46 Hz, 2H), 7.80 (d, J=8.46 Hz, 2H), 7.87 (m, 1H), 8.17 (s, 1H), 8.42 (m, 1H)

Example 266

$^1$H NMR (300 MHz, CDCl$_3$) δ ppm 0.89 (t, J=6.62 Hz, 6H), 0.98 (m, 9H), 1.88 (m, 1H), 2.95 (m, 8H), 3.41 (m, 1H), 3.88 (m, 2H), 4.04 (d, J=3.31 Hz, 1H), 4.29 (m, 2H), 4.51 (d, J=16.18 Hz, 1H), 6.42 (d, J=9.19 Hz, 1H), 7.15 (m, 5H), 7.36 (dd, J=5.15, 2.57 Hz, 1H), 7.70 (d, J=8.46 Hz, 2H), 7.80 (m, 2H), 8.16 (s, 1H), 9.15 (m, 2H)

Example 267

$^1$H NMR (300 MHz, CDCl$_3$) δ ppm 0.76 (d, J=6.62 Hz, 3H), 0.88 (m, 9H), 1.00 (m, 1H), 1.35 (m, 1H), 1.86 (m, 1H), 1.98 (m, 1H), 2.77 (dd, J=14.34, 10.30 Hz, 1H), 2.88 (dd, J=13.60, 6.99 Hz, 1H), 3.09 (m, 7H), 3.82 (m, 3H), 4.23 (m, 2H), 4.50 (d, J=16.18 Hz, 1H), 6.54 (d, J=8.82 Hz, 1H), 7.18 (m, 5H), 7.34 (dd, J=5.15, 2.21 Hz, 1H), 7.70 (d, J=8.82 Hz, 2H), 7.79 (d, J=8.46 Hz, 2H), 8.16 (s, 1H), 9.15 (m, 2H)

Example 268

$^1$H NMR (300 MHz, CDCl$_3$) δ ppm 0.75 (d, J=6.62 Hz, 3H), 0.84 (m, 6H), 0.89 (d, J=6.62 Hz, 3H), 0.98 (m, 1H), 1.33 (m, 1H), 1.86 (m, 1H), 1.98 (m, 1H), 2.76 (dd, J=14.34, 10.30 Hz, 1H), 2.88 (m, 2H), 2.98 (m, 1H), 3.17 (m, 6H), 3.84 (m, 1H), 3.93 (t, J=3.86 Hz, 1H), 4.21 (m, 1H), 4.59 (d, J=15.44 Hz, 1H), 4.75 (d, J=15.81 Hz, 1H), 6.54 (d, J=8.82 Hz, 1H), 7.18 (m, 5H), 7.49 (m, 2H), 7.70 (d, J=8.46 Hz, 2H), 7.79 (d, J=8.46 Hz, 2H), 8.16 (s, 1H), 8.34 (s, 1H)

Example 269

$^1$H NMR (300 MHz, CDCl$_3$) δ ppm 0.75 (d, J=6.25 Hz, 3H), 0.84 (m, 6H), 0.90 (d, J=6.62 Hz, 3H), 0.97 (m, 1H), 1.29 (m, 1H), 1.93 (m, 2H), 2.76 (dd, J=14.52, 10.48 Hz, 1H), 3.05 (m, 8H), 3.77 (d, J=11.03 Hz, 1H), 3.87 (s, 3H), 3.87 (m, 2H), 4.14 (m, 1H), 4.58 (d, J=15.08 Hz, 1H), 4.85 (d, J=15.44 Hz, 1H), 6.44 (d, J=8.46 Hz, 1H), 7.14 (m, 5H), 7.25 (dd, J=8.09, 4.78 Hz, 1H), 7.70 (d, J=8.46 Hz, 2H), 7.79 (d, J=8.46 Hz, 2H), 8.01 (dd, J=8.09, 1.47 Hz, 1H), 8.18 (s, 1H), 8.40 (dd, J=4.78, 1.47 Hz, 1H)

Example 270

$^1$H NMR (300 MHz, CDCl$_3$) δ ppm 0.76 (d, J=6.78 Hz, 3H), 0.82 (d, J=6.44 Hz, 3H), 0.86 (d, J=6.44 Hz, 3H), 0.91 (d, J=6.44 Hz, 3H), 1.86 (s, 1H), 2.13 (d, J=21.02 Hz, 1H), 2.93 (td, J=8.82, 7.12 Hz, 2H), 3.14 (m, 9H), 3.63 (d, J=10.51 Hz, 1H), 3.78 (s, 1H), 4.15 (s, 1H), 4.40 (d, J=14.92 Hz, 1H), 4.48 (d, J=15.26 Hz, 1H), 6.52 (d, J=8.14 Hz, 1H), 6.96 (s, 1H), 7.19 (m, 5H), 7.70 (d, J=8.48 Hz, 2H), 7.79 (d, J=8.48 Hz, 2H), 8.16 (s, 1H)

Example 273

$^1$H NMR (300 MHz, CD$_3$OD) δ ppm 0.78 (d, J=6.44 Hz, 6H), 0.87 (d, J=6.78 Hz, 3H), 0.91 (d, J=6.44 Hz, 3H), 1.40 (m, 1H), 2.04 (m, 2H), 2.52 (dd, J=13.90, 11.53 Hz, 1H), 2.67 (m, 1H), 2.81 (s, 3H), 3.09 (m, 4H), 3.47 (dd, J=14.92, 3.73 Hz, 1H), 3.75 (m, 2H), 4.14 (m, 1H), 4.37 (d, J=15.60 Hz, 1H), 4.55 (s, 2H), 4.64 (d, J=15.60 Hz, 1H), 4.80 (s, 1H), 7.15

(m, 5H), 7.51 (s, 1H), 7.77 (d, J=8.48 Hz, 2H), 7.83 (d, J=8.48 Hz, 2H), 7.95 (d, J=9.83 Hz, 1H), 8.14 (s, 1H)

Example 274

$^1$H NMR (300 MHz, CD$_3$OD) δ ppm 0.78 (m, 6H), 1.73 (s, 1H), 2.15 (m, 4H), 2.54 (m, 2H), 2.69 (s, 3H), 2.81 (dd, J=14.58, 8.82 Hz, 1H), 2.97 (d, J=14.92 Hz, 1H), 3.17 (m, 4H), 3.40 (m, 2H), 3.68 (m, 4H), 3.88 (m, 1H), 4.11 (s, 2H), 442 (s, 2H), 7.13 (m, 5H), 7.20 (s, 1H), 7.83 (d, J=8.82 Hz, 2H), 7.88 (m, 2H), 8.04 (m, 1H), 8.16 (s, 1H)

Example 275

$^1$H NMR (300 MHz, CDCl$_3$) δ ppm 0.66 (d, J=6.78 Hz, 3H) 0.74 (d, J=6.78 Hz, 3H) 0.86 (t, J=6.44 Hz, 6H) 1.88 (dd, J=13.73, 6.95 Hz, 1H) 2.29 (m, 1H) 2.68 (s, 3H) 2.79 (dd, J=14.07, 10.00 Hz, 1H) 2.94 (t, J=6.78 Hz, 1H) 3.08 (dd, J=14.07, 4.92 Hz, 1H) 3.17 (m, 2H) 3.90 (m, 1H) 4.03 (d, J=10.51 Hz, 1H) 4.18 (m, 1H) 4.88 (s, 2H) 6.22 (d, J=3.05 Hz, 1H) 6.33 (d, J=2.71 Hz, 1H) 6.94 (s, 1H) 7.08 (m, 3H) 7.43 (m, 2H) 7.61 (m, 1H) 7.66 (d, J=8.48 Hz, 2H) 7.78 (m, 2H) 7.83 (d, J=7.46 Hz, 1H) 8.13 (s, 1H)

Example 276

$^1$H NMR (300 MHz, CDCl$_3$) δ ppm 0.77 (d, J=6.44 Hz, 3H), 0.83 (d, J=6.78 Hz, 3H), 0.86 (d, J=6.78 Hz, 3H), 0.90 (d, J=6.44 Hz, 3H), 1.86 (m, 1H), 2.16 (m, 1H), 2.97 (m, 10H), 3.66 (d, J=10.85 Hz, 1H), 3.82 (d, J=5.43 Hz, 1H), 4.18 (d, J=14.92 Hz, 2H), 4.31 (d, J=14.92 Hz, 1H), 6.63 (m, 5H), 7.16 (m, 5H), 7.70 (d, J=8.48 Hz, 2H), 7.79 (d, J=8.48 Hz, 2H), 8.15 (s, 1H)

Example 277

$^1$H NMR (300 MHz, CD$_3$OD) δ ppm 0.72 (d, J=6.78 Hz, 3H), 0.84 (m, 6H), 0.88 (d, J=6.78 Hz, 3H), 0.91 (d, J=6.44 Hz, 3H), 0.97 (dd, J=8.14, 5.76 Hz, 1H), 1.30 (m, 1H), 1.85 (s, 1H), 2.03 (d, J=7.12 Hz, 1H), 2.51 (dd, J=13.90, 11.53 Hz, 1H), 2.67 (m, 1H), 3.09 (m, 5H), 3.45 (dd, J=14.75, 3.56 Hz, 1H), 3.75 (m, 1H), 3.82 (d, J=11.19 Hz, 1H), 4.13 (s, 1H), 4.28 (d, J=15.94 Hz, 1H), 4.52 (d, J=15.60 Hz, 1H), 7.12 (m, 3H), 7.17 (m, 2H), 7.56 (m, 1H), 7.78 (d, J=8.82 Hz, 2H), 7.84 (d, J=8.48 Hz, 2H), 7.97 (m, 1H), 8.14 (s, 1H), 8.28 (m, 1H), 8.31 (s, 1H)

Example 278

$^1$H NMR (300 MHz, CD$_3$OD) δ ppm 0.73 (d, J=6.44 Hz, 3H), 0.86 (m, 6H), 0.91 (d, J=6.44 Hz, 3H), 1.00 (m, 1H), 1.33 (m, 1H), 1.87 (s, 1H), 2.03 (m, 1H), 2.53 (dd, J=13.90, 11.19 Hz, 1H), 2.76 (m, 1H), 3.09 (m, 8H), 3.46 (dd, J=14.92, 3.39 Hz, 1H), 3.76 (m, 1H), 3.82 (d, J=11.19 Hz, 1H), 4.11 (d, J=6.78 Hz, 1H), 4.28 (d, J=16.62 Hz, 1H), 4.55 (d, J=16.28 Hz, 1H), 7.16 (m, 5H), 7.45 (d, J=7.12 Hz, 1H), 7.78 (d, J=8.48 Hz, 2H), 7.84 (d, J=8.48 Hz, 2H), 7.97 (m, 1H), 8.14 (s, 1H), 8.31 (d, J=7.12 Hz, 2H)

Example 279

$^1$H NMR (300 MHz, CD$_3$OD) δ ppm 0.73 (d, J=6.78 Hz, 3H), 0.85 (m, 6H), 0.91 (d, J=6.44 Hz, 3H), 0.97 (d, J=9.16 Hz, 1H), 1.32 (m, 1H), 1.84 (s, 1H), 1.99 (d, J=14.58 Hz, 1H), 2.52 (dd, J=14.07, 11.36 Hz, 1H), 2.72 (m, 1H), 3.10 (m, 9 μl), 3.47 (dd, J=14.92, 3.73 Hz, 1H), 3.76 (m, 1H), 3.82 (d, J=11.19 Hz, 1H), 4.14 (d, J=10.85 Hz, 1H), 4.36 (d, J=15.60 Hz, 1H), 4.47 (s, 2H), 4.63 (d, J=15.94 Hz, 1H), 7.15 (m, 5H), 7.47 (s, 1H), 7.78 (d, J=8.82 Hz, 2H), 7.83 (d, J=8.48 Hz, 2H), 7.94 (d, J=9.49 Hz, 1H), 8.14 (s, 1H)

Example 280

$^1$H NMR (300 MHz, CD$_3$OD) δ ppm 0.75 (d, J=6.78 Hz, 3H), 0.85 (t, J=7.12 Hz, 3H), 0.97 (m, 1H), 1.29 (s, 1H), 1.67 (m, J=18.65 Hz, 1H), 1.81 (dd, J=10.34, 6.61 Hz, 4H), 2.02 (d, J=10.85 Hz, 2H), 2.52 (m, 1H), 2.61 (m, 1H), 2.71 (d, J=7.80 Hz, 1H), 3.11 (m, 6H), 3.36 (m, 1H), 3.45 (m, 1H), 3.75 (d, J=6.44 Hz, 1H), 3.84 (d, J=10.85 Hz, 1H), 4.14 (s, 1H), 4.36 (d, J=15.26 Hz, 1H), 4.47 (s, 2H), 4.63 (d, J=15.94 Hz, 1H), 7.16 (m, 5H), 7.47 (s, 1H), 7.78 (d, J=8.82 Hz, 2H), 7.83 (d, J=8.48 Hz, 2H), 7.94 (d, J=9.16 Hz, 1H), 8.15 (s, 1H)

Example 281

$^1$H NMR (300 MHz, CD$_3$OD) δ ppm 0.75 (d, J=6.44 Hz, 3H), 0.84 (t, J=7.29 Hz, 3H), 0.97 (m, 1H), 1.17 (m, 1H), 1.32 (m, 3H), 1.58 (m, 6H), 1.85 (s, 1H), 2.26 (m, 1H), 2.53 (dd, J=13.73, 11.36 Hz, 1H), 2.70 (m, 1H), 3.14 (m, 6H), 3.48 (dd, J=14.92, 4.07 Hz, 1H), 3.78 (dd, J=11.19, 4.75 Hz, 1H), 3.83 (d, J=11.19 Hz, 1H), 4.15 (s, 1H), 4.36 (d, J=15.60 Hz, 1H), 4.47 (s, 2H), 4.63 (d, J=15.94 Hz, 1H), 7.16 (m, 5H), 7.47 (s, 1H), 7.78 (d, J=8.82 Hz, 2H), 7.84 (d, J=8.48 Hz, 2H), 7.94 (d, J=9.49 Hz, 1H), 8.14 (s, 1H)

Example 282

$^1$H NMR (300 MHz, CD$_3$OD) δ ppm 0.79 (m, 6H) 0.87 (d, J=6.78 Hz, 3H) 0.91 (d, J=6.78 Hz, 3H) 0.97 (m, 1H) 1.16 (m, 1H) 1.98 (m, 2H) 2.24 (s, 3H) 2.56 (dd, J=13.90, 10.85 Hz, 1H) 2.98 (m, 1H) 3.10 (m, 3H) 3.43 (dd, J=14.92, 2.37 Hz, 1H) 3.77 (m, 1H) 4.05 (m, 1H) 4.16 (d, J=10.85 Hz, 1H) 4.81 (m, J=9.49 Hz, 2H) 4.86 (m, 1H) 4.95 (m, 1H) 6.38 (m, 1H) 6.42 (d, J=3.05 Hz, 1H) 6.99 (m, 3H) 7.07 (m, 2H) 7.19 (dd, J=5.09, 1.70 Hz, 1H) 7.76 (s, 1H) 7.79 (m, 1H) 7.86 (d, J=8.82 Hz, 2H) 8.17 (d, J=8.48 Hz, 2H) 8.48 (d, J=5.09 Hz, 1H)

Example 283

$^1$H NMR (300 MHz, CD$_3$OD) δ ppm 0.73 (d, J=6.78 Hz, 3H), 0.84 (t, J=7.29 Hz, 3H), 0.95 (d, J=16.28 Hz, 1H), 1.08 (d, J=6.10 Hz, 6H), 1.31 (m, 3H), 1.59 (d, J=16.95 Hz, 6H), 1.89 (s, 1H), 2.27 (m, 1H), 2.48 (m, 1H), 2.57 (m, 1H), 2.86 (m, 1H), 3.13 (m, 9H), 3.46 (dd, J=14.75, 3.90 Hz, 1H), 3.77 (m, 1H), 3.82 (d, J=11.19 Hz, 1H), 4.07 (s, 2H), 4.11 (m, 1H), 4.44 (m, 2H), 7.12 (m, 5H), 7.30 (s, 1H), 7.77 (d, J=8.48 Hz, 2H), 7.83 (d, J=8.48 Hz, 2H), 8.14 (s, 1H)

Example 284

$^1$H NMR (300 MHz, CD$_3$OD) δ ppm 0.55 (m, 2H), 0.63 (m, 3H), 0.71 (d, J=6.44 Hz, 3H), 1.08 (d, J=6.44 Hz, 6H), 1.22 (s, 3H), 1.61 (m, 6H), 2.29 (m, 1H), 2.52 (dd, J=14.24, 11.53 Hz, 1H), 2.84 (m, 1H), 3.20 (m, 9H), 3.44 (m, 1H), 3.60 (m, 1H), 3.79 (d, J=11.19 Hz, 1H), 4.01 (s, 2H), 4.10 (m, 1H), 4.28 (d, J=15.94 Hz, 1H), 4.42 (d, J=15.94 Hz, 1H), 7.17 (m, 5H), 7.24 (s, 1H), 7.76 (d, J=8.82 Hz, 2H), 7.81 (d, J=8.82 Hz, 2H), 8.13 (s, 1H)

Example 285

$^1$H NMR (300 MHz, CD$_3$OD) δ ppm 0.72 (d, J=6.44 Hz, 3H), 0.86 (dd, J=12.72, 6.95 Hz, 6H), 0.91 (d, J=6.44 Hz, 3H), 0.99 (m, 1H), 1.32 (m, 1H), 1.85 (m, 1H), 2.02 (m, 1H), 2.51

(m, 2H), 3.07 (m, 9H), 3.44 (dd, J=14.92, 3.39 Hz, 1H), 3.75 (m, 1H), 3.83 (d, J=11.19 Hz, 1H), 4.13 (m, 1H), 4.29 (d, J=14.92 Hz, 1H), 4.49 (d, J=14.92 Hz, 1H), 7.06 (m, 3H), 7.15 (m, 2H), 7.38 (t, J=3.05 Hz, 1H), 7.38 (m, 2H), 7.59 (m, 2H), 7.78 (d, J=8.82 Hz, 2H), 7.84 (d, J=8.82 Hz, 2H), 7.89 (s, 1H), 8.14 (s, 1H)

Example 286

$^1$H NMR (300 MHz, CDCl$_3$) δ ppm 0.73 (d, J=6.78 Hz, 3H), 0.85 (dd, J=8.99, 6.95 Hz, 6H), 0.91 (t, J=5.76 Hz, 3H), 1.00 (m, 1H), 1.26 (s, 1H), 1.38 (m, 1H), 1.53 (s, 1H), 1.87 (m, 1H), 1.98 (m, 1H), 2.87 (m, 3H), 3.15 (m, 5H), 3.82 (m, 3H), 4.17 (m, 1H), 4.37 (d, J=15.60 Hz, 1H), 4.59 (d, J=15.60 Hz, 1H), 4.74 (d, J=4.75 Hz, 2H), 6.53 (d, J=8.82 Hz, 1H), 7.17 (m, 6H), 7.66 (m, 1H), 7.70 (d, J=6.78 Hz, 2H), 7.79 (d, J=8.48 Hz, 2H), 7.97 (s, 1H), 8.15 (s, 1H)

Example 287

$^1$H NMR (300 MHz, CDCl$_3$) δ ppm 0.74 (d, J=6.78 Hz, 3H), 0.85 (t, J=6.27 Hz, 6H), 0.90 (d, J=6.44 Hz, 3H), 1.03 (dd, J=12.55, 9.16 Hz, 1H), 1.52 (s, 1H), 1.86 (s, 1H), 1.99 (m, 1H), 2.86 (m, 4H), 3.14 (m, 5H), 3.78 (m, J=10.85 Hz, 2H), 3.88 (d, J=3.73 Hz, 1H), 4.12 (d, J=7.12 Hz, 1H), 4.16 (s, 1H), 4.41 (d, J=15.94 Hz, 1H), 4.58 (d, J=15.60 Hz, 1H), 6.53 (m, 1H), 7.19 (m, 6H), 7.66 (m, 3H), 7.79 (d, J=8.82 Hz, 2H), 8.15 (s, 1H), 8.20 (s, 1H)

Example 288

$^1$H NMR (300 MHz, CD$_3$OD) δ ppm 0.88 (d, J=6.99 Hz, 6H), 0.92 (s, 9H), 1.47 (dd, J=6.62, 1.84 Hz, 3H), 2.02 (m, 1H), 2.29 (m, 1H), 2.45 (t, J=12.13 Hz, 1H), 3.09 (m, 10H), 3.43 (dd, J=15.08, 3.31 Hz, 1H), 3.73 (m, 1H), 3.99 (s, 1H), 4.07 (m, 1H), 4.38 (d, J=15.44 Hz, 1H), 4.59 (d, J=15.44 Hz, 1H), 7.15 (m, 5H), 7.45 (dd, J=7.72, 2.21 Hz, 1H), 7.81 (m, 6H), 8.14 (s, 1H)

Example 363

$^1$H NMR (300 MHz, CDCl$_3$) δ ppm 0.78 (d, J=6.44 Hz, 3H), 0.83 (d, J=6.44 Hz, 3H), 0.87 (d, J=6.78 Hz, 3H), 0.93 (d, J=6.44 Hz, 3H), 1.83 (d, J=6.44 Hz, 1H), 2.09 (m, 1H), 2.68 (dd, J=14.24, 10.85 Hz, 1H), 2.84 (dd, J=13.56, 6.44 Hz, 1H) 3.02 (m, 4H), 3.21 (m, 1H), 3.32 (d, J=17.97 Hz, 1H), 3.61 (d, J=17.97 Hz, 1H), 3.87 (m, J=10.85 Hz, 2H), 4.25 (m, 1H), 4.70 (t, J=14.92 Hz, 2H), 6.08 (d, J=9.16 Hz, 1H), 7.09 (m, 5H), 7.53 (m, 1H), 7.56 (d, J=2.37 Hz, 1H), 7.72 (d, J=8.48 Hz, 2H), 7.79 (d, J=8.48 Hz, 2H), 8.16 (dd, J=8.99, 1.53 Hz, 1H), 8.17 (s, 1H), 8.24 (d, J=2.03 Hz, 1H)

Example 364

$^1$H NMR (300 MHz, CD$_3$OD) δ ppm 0.79 (J=6.44 Hz, 3H), 0.82 (d, J=6.78 Hz, 3H), 0.86 (d, J=6.78 Hz, 3H), 0.90 (d, J=6.44 Hz, 3H), 2.02 (m, 2H), 2.50 (dd, J=13.90, 11.53 Hz, 1H), 2.95 (m, 1H), 3.09 (m, 5H), 3.21 (dd, J=13.90, 3.73 Hz, 1H), 3.44 (dd, J=14.92, 3.39 Hz, 1H), 3.78 (m, 2H), 3.96 (s, 3H), 4.02 (d, J=10.85 Hz, 1H), 4.14 (m, 1H), 4.95 (d, J=16.28 Hz, 1H), 5.02 (d, J=16.28 Hz, 1H), 7.01 (m, 3H), 7.15 (m, 2H), 7.27 (m, 2H), 7.51 (d, J=7.80 Hz, 1H), 7.59 (d, J=7.46 Hz, 1H), 7.76 (d, J=8.82 Hz, 2H), 7.82 (d, J=8.82 Hz, 1H), 8.13 (s, 1H).

Example 365

$^1$H NMR (300 MHz, CDCl$_3$) δ ppm 0.82 (d, J=6.44 Hz, 3H), 0.86 (d, J=6.44 Hz, 3H), 0.89 (d, J=3.39 Hz, 3H), 0.92 (d, J=3.39 Hz, 3H), 1.85 (d, J=7.12 Hz, 1H), 2.16 (m, 1H), 2.70 (dd, J=14.24, 10.51 Hz, 1H), 2.84 (dd, J=13.56, 6.78 Hz, 1H), 3.00 (m, 1H), 3.07 (m, 2H), 3.21 (m, 1H), 3.45 (d, J=17.63 Hz, 1H), 3.76 (m, 2H), 3.84 (d, J=3.05 Hz, 1H), 3.92 (d, Hz, 1H), 4.25 (m, 1H), 4.94 (d, J=15.94 Hz, 1H), 5.03 (d, J=16.28 Hz, 1H), 6.20 (d, J=9.16 Hz, 1H), 7.16 (m, 5H), 7.32 (d, J=8.48 Hz, 1H), 7.49 (t, J=7.46 Hz, 1H), 7.64 (m, 1H), 7.72 (d, J=8.48 Hz, 2H), 7.79 (m, 2H), 7.82 (d, J=7.46 Hz, 1H), 7.95 (d, J=8.82 Hz, 1H), 8.12 (d, J=8.48 Hz, 1H), 8.16 (s, 1H).

Example 366

$^1$H NMR (300 MHz, DMSO-d$_6$) δ ppm 0.68 (d, J=6.44 Hz, 3H), 0.75 (d, J=6.78 Hz, 3H), 0.82 (d, J=6.44 Hz, 6H), 1.96 (m, 1H), 2.37 (dd, J=13.05, 11.70 Hz, 1H), 3.01 (m, 8H), 3.59 (d, J=7.12 Hz, 1H), 3.85 (m, 1H), 3.91 (s, 3H), 4.02 (d, J=10.85 Hz, 1H), 5.01 (d, J=5.09 Hz, 2H), 6.98 (m, 1H), 7.12 (d, J=4.07 Hz, 5H), 7.23 (dd, J=8.14, 4.75 Hz, 1H), 7.77 (d, J=8.82 Hz, 2H), 7.81 (d, J=8.82 Hz, 2H), 7.89 (m, 1H), 8.24 (s, 1H), 8.33 (dd, J=4.75, 1.36 Hz, 1H).

Example 367

$^1$H NMR (300 MHz, CDCl$_3$) δ ppm 0.76 (d, J=6.78 Hz, 3H), 0.81 (d, J=6.44 Hz, 3H), 0.87 (d, J=6.44 Hz, 3H), 0.93 (d, J=6.44 Hz, 3H), 1.83 (s, 1H), 2.06 (m, 1H), 2.65 (dd, J=14.24, 10.51 Hz, 1H), 2.82 (m, 1H), 3.04 (m, 3H), 3.20 (m, 2H), 3.54 (d, J=17.97 Hz, 1H), 3.85 (d, J=11.19 Hz, 2H), 4.22 (s, 1H), 4.51 (d, J=2.37 Hz, 2H), 5.92 (s, 2H), 6.06 (d, J=9.49 Hz, 1H), 6.75 (d, J=7.80 Hz, 1H), 6.91 (m, 2H), 7.07 (m, 5H), 7.72 (d, J=8.48 Hz, 2H), 7.79 (d, J=8.48 Hz, 2H), 8.16 (s, 1H).

Example 368

$^1$H NMR (300 MHz, CDCl$_3$) δ ppm 0.88 (d, J=2.71 Hz, 3H), 0.91 (d, J=3.05 Hz, 3H), 1.86 (dd, J=14.07, 7.29 Hz, 1H), 2.99 (m, 6H), 3.45 (d, J=17.29 Hz, 1H), 3.67 (m, 1H), 3.73 (d, J=12.21 Hz, 1H), 3.90 (m, 1H), 3.98 (d, J=16.28 Hz, 1H), 4.20 (s, 1H), 4.63 (s, 2H), 6.13 (d, J=8.82 Hz, 1H), 7.13 (dd, J=6.78, 2.71 Hz, 2H), 7.22 (m, 3H), 7.31 (m, 2H), 7.39 (m, 3H), 7.73 (d, J=8.48 Hz, 2H), 7.80 (m, 2H), 8.16 (s, 1H)

Example 369

$^1$H NMR (300 MHz, CDCl$_3$) δ ppm 0.78 (d, J=6.78 Hz, 3H), 0.84 (d, J=6.44 Hz, 3H), 0.87 (d, J=6.44 Hz, 3H), 0.91 (d, J=6.44 Hz, 3H), 1.86 (s, 1H), 2.09 (s, 1H), 3.00 (m, 6H), 3.49 (d, J=17.97 Hz, 1H), 3.69 (d, J=17.97 Hz, 1H), 3.92 (m, J=10.51 Hz, 2H), 4.28 (s, 1H), 4.71 (m, 2H), 6.45 (d, J=7.80 Hz, 1H), 7.14 (m, 5H), 7.51 (m, 2H), 7.70 (d, J=8.48 Hz, 2H), 7.79 (d, J=8.48 Hz, 2H), 8.16 (s, 1H), 8.66 (s, 2H)

Example 370

$^1$H NMR (300 MHz, CD$_3$OD) δ ppm 0.76 (d, J=3.73 Hz, 3H), 0.79 (d, J=3.39 Hz, 3H), 0.87 (d, J=6.78 Hz, 3H), 0.90 (d, J=6.78 Hz, 3H), 2.01 (m, 2H), 2.40 (s, 6H), 2.45 (m, 1H), 3.03 (m, 4H), 3.21 (dd, J=13.73, 3.56 Hz, 2H), 3.45 (dd, J=14.75, 3.56 Hz, 1H), 3.69 (d, Hz, 1H), 3.76 (m, 1H), 3.90 (s, 2H), 4.00 (d, J=11.19 Hz, 1H), 4.11 (m, 1H), 4.75 (m, 2H), 6.99 (m, 3H), 7.12 (m, 2H), 7.42 (s, 1H), 7.78 (m, 2H), 7.83 (d, J=8.82 Hz, 2H), 8.14 (s, 1H)

Example 371

$^1$H NMR (300 MHz, CDCl$_3$) δ ppm 0.80 (t, J=6.78 Hz, 6H), 0.87 (d, J=6.78 Hz, 3H), 0.92 (d, J=6.44 Hz, 3H), 1.84

(dd, J=14.58, 6.78 Hz, 1H), 2.09 (m, 1H), 2.86 (dd, J=13.39, 6.95 Hz, 2H), 3.12 (m, 8H), 3.61 (d, J=17.63 Hz, 1H), 3.83 (m, 1H), 3.92 (d, J=10.85 Hz, 1H), 4.23 (d, J=4.41 Hz, 1H), 4.76 (m, 2H), 6.37 (s, 1H), 7.05 (s, 1H), 7.13 (m, 5H), 7.72 (d, J=8.48 Hz, 2H), 7.80 (d, J=8.48 Hz, 2H), 8.16 (s, 1H)

Example 372

$^1$H NMR (300 MHz, CD$_3$OD) δ ppm 0.77 (d, J=4.07 Hz, 3H), 0.80 (d, J=3.73 Hz, 3H), 1.23 (d, J=28.82 Hz, 2H), 1.63 (m, 6H), 2.02 (m, 1H), 2.27 (m, 1H), 2.46 (m, 1H), 2.65 (s, 3H), 3.10 (m, 6H), 3.47 (dd, J=14.75, 3.90 Hz, 1H), 3.69 (d, J=17.97 Hz, 1H), 3.79 (m, 1H), 4.01 (d, J=11.19 Hz, 1H), 4.16 (m, 1H), 4.73 (m, 2H), 6.98 (m, 3H), 7.13 (dd, J=6.44, 3.05 Hz, 2H), 7.24 (s, 1H), 7.77 (d, J=8.82 Hz, 2H), 7.83 (d, J=8.82 Hz, 2H), 8.14 (s, 1H)

Example 373

$^1$H NMR (300 MHz, CDCl$_3$) δ ppm 0.81 (dd, J=6.78, 3.05 Hz, 6H), 0.86 (d, J=6.44 Hz, 3H), 0.91 (d, J=6.78 Hz, 3H), 1.87 (m, 1H), 2.13 (m, J=10.17 Hz, 1H), 2.93 (m, 5H), 3.20 (m, 1H), 3.47 (d, J=18.31 Hz, 1H), 3.71 (d, J=17.97 Hz, 1H), 3.85 (s, 1H), 3.93 (d, J=10.51 Hz, 1H), 4.27 (s, 1H), 4.85 (d, J=1.70 Hz, 2H), 6.38 (s, 1H), 7.17 (m, 5H), 7.26 (m, 2H), 7.71 (m, J=8.48 Hz, 3H), 7.80 (d, J=8.82 Hz, 2H), 8.16 (s, 1H), 8.55 (s, 1H)

Example 374

$^1$H NMR (300 MHz, CDCl$_3$) δ ppm 0.83 (dd, J=6.27, 4.58 Hz, 6H), 0.87 (d, J=6.78 Hz, 3H), 0.92 (d, J=6.78 Hz, 3H), 1.85 (m, 1H), 2.13 (s, 1H), 2.76 (m, 1H), 2.84 (m, 1H), 2.96 (s, 3H), 3.01 (m, 2H), 3.20 (m, 1H), 3.40 (d, J=17.29 Hz, 1H), 3.69 (d, J=17.29 Hz, 2H), 3.84 (s, 1H), 3.91 (d, J=10.51 Hz, 1H), 4.24 (s, 1H), 4.83 (m, 2H), 6.21 (s, 1H), 7.16 (s, 5H), 7.24 (m, 1H), 7.72 (d, J=8.48 Hz, 2H), 7.79 (d, J=8.48 Hz, 2H), 7.88 (s, 1H), 8.02 (s, 1H), 8.16 (s, 1H),

Example 375

$^1$H NMR (300 MHz, CDCl$_3$) δ ppm 0.76 (d, J=6.78 Hz, 3H), 0.81 (d, J=6.44 Hz, 3H), 0.87 (d, J=6.78 Hz, 3H), 0.93 (d, J=6.78 Hz, 3H), 1.86 (m, 1H), 2.05 (m, 1H), 2.64 (dd, J=14.24, 10.85 Hz, 1H), 2.84 (m, 1H), 3.01 (m, 3H), 3.20 (d, J=17.97 Hz, 1H), 3.54 (d, J=17.97 Hz, 1H), 3.81 (m, 1H), 3.86 (d, J=11.19 Hz, 1H), 4.23 (d, J=4.41 Hz, 1H), 4.62 (m, 2H), 6.06 (d, J=9.83 Hz, 1H), 7.02 (m, 5H), 7.32 (m, 4H), 7.41 (m, 2H), 7.72 (d, J=8.82 Hz, 2H), 7.79 (d, J=8.82 Hz, 2H), 8.16 (s, 1H)

Example 376

$^1$H NMR (300 MHz, CD$_3$OD) δ ppm 0.76 (t, J=6.78 Hz, 6H), 0.87 (d, J=6.78 Hz, 3H), 0.90 (d, J=6.44 Hz, 3H), 2.00 (m, 1H), 2.42 (dd, J=13.56, 11.87 Hz, 1H), 2.59 (s, 3H), 3.02 (m, 6H), 3.20 (dd, J=13.73, 3.22 Hz, 1H), 3.44 (dd, J=14.92, 3.39 Hz, 1H), 3.68 (d, J=17.97 Hz, 1H), 3.75 (m, 1H), 4.01 (d, J=10.85 Hz, 1H), 4.11 (m, 1H), 4.73 (d, J=2.71 Hz, 2H), 6.88 (m, 3H), 7.07 (m, 2H), 7.51 (t, J=7.63 Hz, 1H), 7.66 (d, J=8.14 Hz, 1H), 7.77 (d, J=8.48 Hz, 2H), 7.82 (d, J=8.82 Hz, 2H), 7.94 (d, J=7.80 Hz, 1H), 8.03 (s, 1H), 8.14 (s, 1H)

Example 377

$^1$H NMR (300 MHz, CD$_3$OD) δ ppm 0.78 (dd, J=6.44, 4.75 Hz, 6H), 1.21 (m, 2H), 1.59 (m, 8H), 2.01 (m, 1H), 2.27 (m, 1H), 2.46 (dd, J=13.56, 11.87 Hz, 1H), 2.99 (d, J=17.97 Hz, 1H), 3.07 (m, 1H), 3.22 (m, 2H), 3.43 (m, 3H), 3.48 (m, 1H), 3.69 (d, J=17.97 Hz, 1H), 3.79 (m, 1H), 4.01 (d, J=11.19 Hz, 1H), 4.14 (m, 1H), 4.66 (s, 2H), 4.77 (d, J=5.76 Hz, 2H), 6.99 (m, 3H), 7.13 (m, 2H), 7.41 (s, 1H), 7.77 (d, J=8.82 Hz, 2H), 7.83 (d, J=8.48 Hz, 2H), 8.14 (s, 1H)

Example 378

$^1$H NMR (300 MHz, CD$_3$OD) δ ppm 0.79 (m, 6H), 1.78 (m, 7H), 1.99 (m, 2H), 2.47 (dd, J=13.73, 11.70 Hz, 1H), 2.60 (m, 1H), 2.66 (s, 3H), 3.00 (m, 1H), 3.20 (m, 2H), 3.40 (m, 2H), 3.69 (d, J=18.31 Hz, 1H), 3.76 (m, 1H), 4.02 (d, J=10.85 Hz, 1H), 4.13 (m, 1H), 4.73 (t, J=15.60 Hz, 2H), 6.99 (m, 3H), 7.12 (m, 2H), 7.25 (s, 1H), 7.77 (d, J=8.48 Hz, 2H), 7.84 (d, J=4.75 Hz, 2H), 8.14 (s, 1H)

Example 379

$^1$H NMR (300 MHz, CD$_3$OD) δ ppm 0.79 (t, J=6.27 Hz, 6H), 1.76 (m, 3H), 2.00 (m, 4H), 2.46 (dd, J=13.39, 11.70 Hz, 1H), 2.62 (m, 1H), 3.00 (m, 1H), 3.20 (m, 2H), 3.43 (m, 2H), 3.43 (s, 3H), 3.69 (d, J=18.31 Hz, 1H), 3.76 (m, 1H), 4.01 (d, J=10.85 Hz, 1H), 4.11 (s, 1H), 4.66 (s, 2H), 4.77 (d, J=5.76 Hz, 2H), 6.99 (m, 3H), 7.13 (dd, 6.27, 3.56 Hz, 2H), 7.41 (s, 1H), 7.77 (d, J=8.82 Hz, 2H), 7.83 (d, J=8.82 Hz, 2H), 8.14 (s, 1H), 8.22 (d, J=9.49 Hz, 1H)

Example 380

$^1$H NMR (300 MHz, CDCl$_3$) δ ppm 0.79 (d, J=6.78 Hz, 3H), 0.83 (d, J=4.75 Hz, 3H), 0.87 (m, 3H), 0.93 (d, J=6.78 Hz, 3H), 1.86 (m, J=7.12 Hz, 1H), 2.07 (m, 1H), 2.77 (m, 2H), 3.04 (m, 3H), 3.22 (m, 1H), 3.44 (d, J=18.31 Hz, 1H), 3.66 (d, J=17.97 Hz, 1H), 3.88 (m, 2H), 4.28 (m, 1H), 4.63 (m, 2H), 6.12 (d, J=9.49 Hz, 1H), 7.12 (m, 3H), 7.22 (m, 2H), 7.45 (m, 1H), 7.70 (m, 4H), 7.82 (d, J=8.48 Hz, 2H), 8.17 (s, 1H)

Example 381

$^1$H NMR (300 MHz, CDCl$_3$) δ ppm 0.82 (dd, J=8.48, 6.78 Hz, 6H), 0.87 (d, J=6.44 Hz, 3H), 0.93 (d, J=6.78 Hz, 2H), 1.84 (m, 1H), 2.09 (m, 1H), 2.70 (s, 3H), 2.83 (d, J=13.56 Hz, 1H), 3.02 (m, 5H), 3.21 (m, 1H), 3.21 (s, 1H), 3.36 (d, J=17.97 Hz, 1H), 3.65 (d, J=17.97 Hz, 1H), 3.86 (m, J=10.85 Hz, 2H), 4.30 (s, 1H), 4.67 (m, 2H), 6.15 (d, J=9.49 Hz, 1H), 7.10 (d, J=7.12 Hz, 3H), 7.24 (s, 2H), 7.40 (s, 1H), 7.72 (d, J=8.48 Hz, 2H), 7.79 (d, J=8.82 Hz, 2H), 7.95 (s, 1H), 8.16 (s, 1H)

Example 382

$^1$H NMR (300 MHz, CDCl$_3$) δ ppm 0.76 (d, J=6.78 Hz, 3H), 0.82 (d, J=6.44 Hz, 3H), 0.87 (d, J=6.44 Hz, 3H), 0.93 (d, J=6.78 Hz, 3H), 1.81 (m, 1H), 2.06 (m, 1H), 2.64 (dd, J=14.41, 10.68 Hz, 1H), 2.83 (dd, J=13.56, 6.78 Hz, 1H), 3.03 (m, 2H), 3.21 (m, 2H), 3.55 (d, J=17.97 Hz, 1H), 3.82 (m, 2H), 3.86 (d, J=11.19 Hz, 1H), 4.24 (m, 1H), 4.33 (s, 2H), 4.62 (m, 2H), 6.08 (d, J=9.16 Hz, 1H), 7.04 (m, 5H), 7.24 (s, 1H), 7.38 (m, 3H), 7.72 (d, J=8.48 Hz, 2H), 7.79 (d, J=8.82 Hz, 2H), 8.16 (s, 1H)

Example 383

$^1$H NMR (300 MHz, CDCl$_3$) δ ppm 0.81 (m, 6H), 0.87 (d, J=6.44 Hz, 3H), 0.93 (d, J=6.44 Hz, 3H), 1.18 (s, 1H), 1.84 (m, 2H), 2.70 (dd, J=14.24, 10.51 Hz, 1H), 2.84 (dd, J=13.56, 6.44 Hz, 1H), 3.04 (m, 3H), 3.22 (m, 1H), 3.41 (d, J=17.97

Hz, 1H), 3.61 (d, J=18.31 Hz, 2H), 3.85 (s, 1H), 3.96 (d, J=11.19 Hz, 1H), 4.26 (s, 1H), 4.57 (d, J=15.26 Hz, 1H), 4.64 (d, J=14.92 Hz, 1H), 6.14 (d, J=9.16 Hz, 1H), 7.11 (m, 5H), 7.26 (m, 2H), 7.72 (d, J=8.48 Hz, 2 H), 7.79 (d, J=8.82 Hz, 2H), 8.17 (s, 1H), 8.59 (s, 2H)

Example 384

$^1$H NMR (300 MHz, CDCl$_3$) δ ppm 0.77 (d, J=6.78 Hz, 4H), 0.82 (d, J=7.46 Hz, 3H), 0.87 (d, J=6.44 Hz, 3H), 0.92 (d, J=6.44 Hz, 3H), 1.19 (s, 1H), 1.85 (m, 2H), 2.64 (dd, J=14.07, 10.68 Hz, 1H), 2.86 (dd, J=13.56, 6.78 Hz, 1H), 3.04 (m, 3H), 3.20 (m, 1H), 3.31 (d, J=17.63 Hz, 1H), 3.56 (d, J=17.97 Hz, 1H), 3.62 (s, 1H), 3.78 (s, 1H), 3.93 (d, J=11.19 Hz, 1H), 4.23 (m, 1H), 4.63 (m, 2H), 6.12 (d, J=8.82 Hz, 1H), 7.05 (m, 5H), 7.32 (s, 1H), 7.74 (d, J=8.48 Hz, 2H), 7.79 (d, J=8.82 Hz, 2H), 8.09 (s, 1H), 8.17 (s, 1H), 8.57 (s, 1H), 8.73 (s, 1 μl Example 385

$^1$H NMR (300 MHz, DMSO-d$_6$) δ ppm 0.64 (d, J=6.78 Hz, 3H), 0.76 (t, J=7.12 Hz, 3H), 0.86 (m, 1H), 1.18 (m, 3H), 1.50 (m, 8H), 1.74 (s, 1H), 2.10 (s, 3H), 2.23 (m, 1H), 2.37 (m, 1H), 3.06 (m, 3H), 3.62 (m, 1H), 3.77 (d, J=18.31 Hz, 1H), 3.94 (d, J=9.49 Hz, 1H), 4.08 (d, J=11.19 Hz, 1H), 4.58 (s, 2H), 5.00 (d, J=6.44 Hz, 1H), 6.90 (s, 1H), 6.97 (m, 3H), 7.05 (m, 2H), 7.77 (d, J=8.82 Hz, 2H), 7.81 (d, J=8.82 Hz, 2H), 8.20 (d, J=9.49 Hz, 1H), 8.24 (s, 1H)

Example 386

$^1$H NMR (300 MHz, DMSO-d$_6$) δ ppm 0.62 (d, J=6.78 Hz, 3H), 0.76 (t, J=7.12 Hz, 3H), 0.81 (dd, J=6.61, 1.87 Hz, 6H), 1.23 (s, 1H), 1.72 (s, 1H), 1.96 (s, 1H), 2.10 (s, 3H), 2.33 (m, 1H), 2.88 (m, 1H), 3.01 (m, 3H), 3.15 (m, 1H), 3.26 (d, J=13.56 Hz, 2H), 3.60 (m, 1H), 3.76 (d, J=17.97 Hz, 1H), 3.91 (m, J=9.49 Hz, 1H), 4.07 (m, 1H), 4.56 (m, 2H), 5.00 (d, J=6.44 Hz, 1H), 6.89 (s, 1H), 6.95 (m, 3H), 7.05 (m, 2H), 7.79 (m, 4H), 8.20 (d, J=9.49 Hz, 1H), 8.24 (s, 1H)

Example 387

$^1$H NMR (300 MHz, CDCl$_3$) δ ppm 0.81 (d, J=3.73 Hz, 3H), 0.83 (d, J=3.39 Hz, 3H), 0.87 (d, J=6.78 Hz, 3H), 0.93 (d, J=6.44 Hz, 3H), 1.85 (m, 1H), 2.10 (dd, J=11.02, 6.27 Hz, 1H), 2.71 (dd, J=14.24, 10.51 Hz, 1H), 2.84 (dd, J=13.56, 6.78 Hz, 1H), 3.05 (m, 3H), 3.22 (m, 1H), 3.40 (d, J=17.97 Hz, 1H), 3.63 (d, J=3.05 Hz, 1H), 3.69 (d, J=17.97 Hz, 1H), 3.81 (d, J=5.43 Hz, 1H), 3.87 (d, J=11.19 Hz, 1H), 4.24 (dd, J=10.00, 5.26 Hz, 1H), 4.79 (d, J=15.94 Hz, 1H), 4.87 (d, J=15.94 Hz, 1H), 6.10 (d, J=9.49 Hz, 1H), 7.15 (d, J=7.12 Hz, 5H), 7.24 (s, 1H), 7.60 (s, 1H), 7.73 (d, J=8.48 Hz, 2H), 7.79 (d, J=8.48 Hz, 2H), 8.17 (s, 1H), 8.48 (s, 1H)

Example 388

$^1$H NMR (300 MHz, CDCl$_3$) δ ppm 0.78 (t, J=6.61 Hz, 6H), 0.88 (dd, J=6.78, 3.39 Hz, 6H), 3.01 (m, 7H), 2.96 (s, 3H), 3.03 (m, 1H), 3.11 (d, J=3.73 Hz, 1H), 3.51 (m, 2H), 3.66 (d, J=17.97 Hz, 1H), 3.97 (s, 2H), 4.23 (s, 1H), 4.67 (d, J=7.12 Hz, 1H), 6.51 (s, 1H), 6.83 (s, 1H), 7.09 (s, 1H), 7.19 (m, J=32.21 Hz, 5H), 7.73 (d, J=8.48 Hz, 2H), 7.80 (d, J=8.48 Hz, 2H), 8.02 (s, 1H), 8.17 (s, 1H)

Example 389

$^1$H NMR (300 MHz, CD$_3$OD) δ ppm 0.74 (d, J=6.44 Hz, 3H), 0.77 (d, J=6.44 Hz, 3H), 0.87 (d, J=6.78 Hz, 3H), 0.90 (d, J=6.78 Hz, 3H), 1.25 (m, 1H), 2.00 (m, 1H), 2.35 (s, 2H), 2.37 (s, 3H), 2.44 (m, 1H), 2.91 (m, 1H), 2.98 (m, 1H), 3.05 (m, 1H), 3.12 (m, 1H), 3.20 (dd, J=13.73, 3.22 Hz, 1H), 3.44 (dd, J=14.92, 3.39 Hz, 1H), 3.65 (m, 1H), 3.74 (m, 2H), 4.00 (d, J=10.85 Hz, 1H), 4.04 (s, 1H), 4.10 (m, 1H), 4.66 (m, 2H), 6.87 (m, 3H), 7.07 (m, 2H), 7.31 (m, 3H), 7.38 (s, 1H), 7.77 (d, J=8.48 Hz, 2H), 7.83 (d, J=8.48 Hz, 2H)

Example 390

$^1$H NMR (300 MHz, CD$_3$OD) δ ppm 0.73 (d, J=6.78 Hz, 3H), 0.82 (t, J=7.29 Hz, 3H), 0.87 (d, J=6.78 Hz, 3H), 0.91 (d, J=6.78 Hz, 3H), 0.97 (m, 1H), 1.24 (t, J=7.12 Hz, 1H), 1.82 (s, 1H), 2.01 (s, 1H), 2.44 (dd, J=13.73, 11.70 Hz, 1H), 3.03 (m, 5H), 3.19 (s, 1H), 3.44 (dd, J=14.92, 3.39 Hz, 1H), 3.68 (d, J=18.31 Hz, 1H), 3.76 (s, 1H), 4.11 (m, 2H), 4.78 (d, J=5.43 Hz, 2H), 6.90 (m, 3H), 7.10 (m, 2H), 7.63 (t, J=7.80 Hz, 1H), 7.78 (d, J=8.48 Hz, 2H), 7.82 (m, 3H), 8.14 (s, 1H), 8.18 (d, J=8.48 Hz, 1H), 8.26 (m, 1H)

Example 391

$^1$H NMR (300 MHz, CDCl$_3$) δ ppm 0.79 (d, J=6.78 Hz, 3H), 0.83 (s, 3H), 0.87 (m, 3H), 0.92 (d, J=6.44 Hz, 3H), 1.84 (m, 1H), 2.08 (m, 1H), 2.67 (dd, J=14.24, 10.51 Hz, 1H), 2.83 (dd, J=13.39, 6.61 Hz, 1H), 3.03 (m, 3H), 3.03 (m, 3H), 3.21 (m, 1H), 3.37 (d, J=17.97 Hz, 1H), 3.64 (m, 2H), 3.85 (s, 1H), 3.88 (d, J=10.85 Hz, 1H), 4.26 (s, 1H), 5.08 (m, 2H), 6.10 (d, J=9.49 Hz, 1H), 7.06 (m, 5H), 7.34 (d, J=4.41 Hz, 1H), 7.64 (m, 1H), 7.77 (m, 2H), 8.14 (m, 1H), 8.16 (s, 1H), 8.28 (d, J=7.46 Hz, 1H)

Example 392

$^1$H NMR (300 MHz, DMSO-d$_6$) δ ppm 0.63 (d, J=6.78 Hz, 3H), 0.80 (m, 9H), 0.94 (s, 1H), 1.34 (dd, J=10.34, 3.22 Hz, 1H), 1.80 (s, 1H), 1.97 (m, 1H), 2.37 (m, 1H), 3.04 (m, 5H), 3.58 (s, 1H), 3.83 (d, J=17.97 Hz, 1H), 4.08 (m, 2H), 4.80 (t, J=16.28 Hz, 2H), 5.01 (d, J=6.78 Hz, 1H), 5.53 (s, 2H), 6.78 (d, J=2.37 Hz, 1H), 6.96 (m, 1H), 7.07 (m, 5H), 7.23 (d, J=8.82 Hz, 1H), 7.53 (d, J=9.16 Hz, 1H), 7.79 (m, 4H), 7.93 (d, J=8.48 Hz, 1H), 8.24 (s, 1H), 8.25 (d, J=9.49 Hz, 1H)

Example 393

$^1$H NMR (300 MHz, CD$_3$OD) δ ppm 0.74 (d, J=6.78 Hz, 3H), 0.83 (d, J=7.12 Hz, 3H), 0.87 (d, J=6.44 Hz, 3H), 0.91 (d, J=6.78 Hz, 3H), 0.97 (d, J=8.48 Hz, 1H), 1.29 (s, 1H), 1.84 (s, 1H), 2.02 (s, 1H), 2.47 (dd, J=13.73, 11.70 Hz, 1H), 2.65 (s, 3H), 3.08 (m, 6H), 3.45 (dd, J=14.75, 3.56 Hz, 1H), 3.74 (m, 1H), 3.77 (m, 1H), 4.12 (m, 2H), 4.74 (m, 2H), 6.97 (m, 3H), 7.13 (d, J=6.78, 3.05 Hz, 2H), 7.56 (dd, J=5.09, 1.70 Hz, 1H), 7.77 (d, J=8.48 Hz, 2H), 7.83 (d, J=8.48 Hz, 2H), 7.95 (s, 1H), 8.14 (s, 1H), 8.65 (d, J=4.75 Hz, 1H)

Example 394

$^1$H NMR (300 MHz, DMSO-d$_6$) δ ppm 0.65 (d, J=6.78 Hz, 3H), 0.76 (t, J=6.95 Hz, 3H), 0.85 (m, 1H), 1.23 (m, 1H), 1.61 (m, 2H), 1.73 (m, 4H), 1.87 (m, 2H), 2.10 (s, 3H), 2.38 (dd, J=13.05, 11.36 Hz, 1H), 2.57 (m, 1H), 3.11 (m, 6H), 3.51 (s, 1H), 3.77 (d, J=18.31 Hz, 1H), 3.92 (d, J=5.76 Hz, 1H), 4.09 (d, J=10.85 Hz, 1H), 4.58 (s, 2H), 5.04 (d, J=6.44 Hz, 1H), 6.90 (s, 1H), 6.96 (m, 3H), 7.06 (m, 2H), 7.78 (m, 4H), 8.20 (d, J=9.49 Hz, 1H)

Example 395

$^1$H NMR (300 MHz, DMSO-d$_6$) δ ppm 0.70 (d, J=6.78 Hz, 3H), 0.76 (d, J=6.44 Hz, 3H), 0.90 (m, 1H), 1.69 (m, 4H), 1.95

(m, 2H), 2.39 (m, 1H), 2.57 (m, 1H), 3.03 (m, 4H), 3.23 (m, 1H), 3.60 (m, 1H), 3.84 (m, 2H), 3.91 (s, 3H), 4.04 (m, 2H), 4.14 (m, 1H), 5.00 (m, 2H), 6.98 (m, 1H), 7.11 (dd, J=7.97, 4.24 Hz, 3H), 7.23 (m, 2H), 7.79 (d, J=2.71 Hz, 4H), 7.90 (m, 1H), 8.24 (s, 1H), 8.33 (dd, J=4.92, 1.53 Hz, 1H)

Example 396

$^1$H NMR (300 MHz, DMSO-d$_6$) δ ppm 0.69 (d, J=6.44 Hz, 3H), 0.75 (d, J=6.78 Hz, 3H), 1.12 (s, 2H), 1.50 (m, 8H), 1.97 (m, 1H), 2.26 (m, 1H), 2.38 (dd, J=12.89, 11.53 Hz, 1H), 3.07 (m, 5H), 3.60 (s, 1H), 3.84 (m, 1H), 3.91 (s, 3H), 4.03 (d, J=10.85 Hz, 1H), 5.01 (d, J=6.44 Hz, 3H), 6.98 (m, 1H), 7.12 (d, J=4.41 Hz, 3H), 7.22 (m, 2H), 7.78 (m, 4H), 7.90 (dd, J=8.14, 1.36 Hz, 1H), 8.24 (s, 1H), 8.33 (dd, P4.75, 1.36 Hz, 1H)

Example 397

$^1$H NMR (300 MHz, CDCl$_3$) δ ppm 0.77 (m, 3H), 0.86 (m, 6H), 0.92 (d, J=6.44 Hz, 3H), 0.96 (s, 1H), 1.26 (t, J=7.12 Hz, 1H), 1.83 (m, 2H), 2.71 (dd, J=14.07, 10.34 Hz, 1H), 2.85 (dd, J=13.56, 6.78 Hz, 1H), 3.04 (m, 4H), 3.21 (m, 1H), 3.44 (d, J=17.63 Hz, 1H), 3.67 (d, J=17.97 Hz, 1H), 3.75 (s, 1H), 3.83 (s, 1H), 3.99 (d, J=10.85 Hz, 1H), 4.25 (d, J=5.76 Hz, 1H), 4.80 (m, 2H), 6.22 (s, 1H), 7.15 (s, 5H), 7.22 (d, J=7.12 Hz, 1H), 7.64 (m, 1H), 7.72 (d, J=8.48 Hz, 2H), 7.79 (d, J=8.48 Hz, 2H), 7.85 (m, 1H), 8.16 (s, 1H), 8.52 (d, J=3.73 Hz, 1H)

Example 398

$^1$H NMR (300 MHz, CDCl$_3$) δ ppm 0.81 (m, 6H), 0.87 (d, J=6.44 Hz, 3H), 0.92 (d, J=6.44 Hz, 3H), 1.26 (t, J=7.12 Hz, 1H), 1.86 (s, 2H), 2.68 (s, 1H), 2.84 (dd, J=13.56, 7.12 Hz, 1H), 3.01 (m, 3H), 3.20 (s, 1H), 3.44 (d, P17.97 Hz, 1H), 3.64 (m, 2H), 3.85 (s, 1H), 3.98 (d, J=11.19 Hz, 1H), 4.26 (s, 1H), 5.09 (d, P5.09 Hz, 2H), 6.16 (d, J=8.14 Hz, 1H), 7.07 (m, 6H), 7.41 (s, 1H), 7.71 (m, J=8.14 Hz, 1H), 7.80 (m, 2H), 7.87 (s, 1H), 8.16 (s, 1H), 8.24 (d, J=6.44 Hz, 1H), 8.31 (d, J=8.48 Hz, 1H)

Example 399

$^1$H NMR (300 MHz, CDCl$_3$) δ ppm 0.82 (t, J=7.29 Hz, 6H), 0.95 (m, 1H), 1.26 (t, P7.12 Hz, 1H), 1.70 (m, 2H), 1.92 (m, 4H), 2.49 (m, 1H), 2.70 (dd, J=14.24, 10.51 Hz, 1H), 3.07 (m, 4H), 3.25 (m, 1H), 3.44 (d, J=17.97 Hz, 1H), 3.50 (d, J=2.37 Hz, 1H), 3.64 (d, J=17.97 Hz, 1H), 3.82 (s, 1H), 4.00 (d, J=11.19 Hz, 1H), 4.28 (s, 1H), 5.09 (d, J=4.41 Hz, 2H), 6.22 (d, J=9.49 Hz, 1H), 7.06 (m, 5H), 7.38 (d, J=3.73 Hz, 1H), 7.65 (d, J=7.12 Hz, 1H), 7.71 (d, J=8.48 Hz, 2H), 7.79 (d, J=8.48 Hz, 2H), 7.99 (s, 1H), 8.16 (s, 1H), 8.20 (d, J=8.48 Hz, 1H), 8.29 (d, J=8.48 Hz, 1H), 8.89 (d, J=4.07 Hz, 1H)

Example 400

$^1$H NMR (300 MHz, CDCl$_3$) δ ppm 0.80 (d, J=6.44 Hz, 3H), 0.83 (m, 3H), 0.96 (m, 1H), 1.23 (m, 2H), 1.58 (m, 8H), 1.93 (m, 1H), 2.10 (m, 1H), 2.69 (dd, J=14.41, 10.68 Hz, 1H), 3.07 (m, 3H), 3.43 (d, J=17.97 Hz, 1H), 3.63 (m, 2H), 3.89 (m, 1H), 3.99 (d, J=11.19 Hz, 1H), 4.27 (m, 1H), 5.08 (m, 2H), 6.19 (d, P9.49 Hz, 1H), 7.06 (m, 5H), 7.36 (d, J=4.41 Hz, 1H), 7.65 (m, 2H), 7.72 (m, 2H), 7.77 (d, P8.48 Hz, 2H), 8.17 (m, 1H), 8.16 (s, 1H), 8.29 (d, J=8.48 Hz, 1H), 8.88 (d, J=4.41 Hz, 1H)

Example 401

$^1$H NMR (300 MHz, CDCl$_3$) δ ppm 0.77 (d, P6.78 Hz, 3H), 0.81 (d, J=6.44 Hz, 3H), 0.87 (d, J=6.78 Hz, 3H), 0.92 (d, J=6.44 Hz, 3H), 1.84 (dd, J=8.31, 6.61 Hz, 1H), 2.06 (m, 1H), 2.63 (dd, J=14.07, 10.68 Hz, 1H), 2.84 (dd, J=13.56, 6.78 Hz, 1H), 3.03 (m, 4H), 3.22 (m, 2H), 3.55 (d, J=17.63 Hz, 1H), 3.67 (s, 1H), 3.82 (d, J=2.71 Hz, 1H), 3.86 (d, J=10.85 Hz, 1H), 4.19 (m, 1H), 4.49 (d, J=14.24 Hz, 1H), 4.52 (d, J=14.24 Hz, 1H), 6.14 (d, J=9.16 Hz, 1H), 6.60 (dd, J=7.63, 1.86 Hz, 1H), 6.76 (s, 1H), 6.80 (d, J=7.80 Hz, 1H), 7.04 (m, 5H), 7.10 (m, 1H), 7.72 (d, J=8.48 Hz, 2H), 7.79 (d, J=8.48 Hz, 2H), 8.16 (s, 1H)

Example 402

$^1$H NMR (300 MHz, CD$_3$OD) δ ppm 0.76 (m, 6H), 0.87 (d, J=6.44 Hz, 3H), 0.90 (d, J=6.44 Hz, 3H), 2.01 (m, 1H), 2.21 (s, 3H), 2.41 (dd, J=13.56, 11.87 Hz, 1H), 3.06 (m, 7H), 3.44 (m, 1H), 3.65 (d, J=17.97 Hz, 1H), 3.75 (m, 1H), 4.00 (d, J=11.19 Hz, 1H), 4.11 (m, 1H), 4.67 (s, 2H), 6.85 (m, 3H), 7.06 (m, 2H), 7.39 (m, 2H), 7.59 (m, 1H), 7.72 (s, 1H), 7.77 (d, J=8.82 Hz, 2H), 7.83 (d, J=8.48 Hz, 2H), 8.14 (s, 1H)

Example 403

$^1$H NMR (300 MHz, CD$_3$OD) δ ppm 0.75 (d, J=6.78 Hz, 3H), 0.78 (d, J=6.78 Hz, 3H), 0.87 (d, J=6.78 Hz, 3H), 0.90 (d, J=6.78 Hz, 3H), 1.29 (s, 2H), 2.02 (m, 2H), 2.44 (dd, J=13.56, 11.87 Hz, 1H), 2.98 (m, 3H), 3.11 (m, 1H), 3.20 (m, 1H), 3.44 (m, 1H), 3.67 (m, 1H), 3.76 (m, 1H), 3.86 (d, J=4.07 Hz, 2H), 4.00 (d, J=10.85 Hz, 1H), 4.12 (m, 1H), 4.66 (m, 1H), 4.79 (s, 2H), 6.89 (m, 3H), 7.08 (m, 2H), 7.32 (m, 3H), 7.40 (s, 1H), 7.77 (d, J=8.82 Hz, 2H), 7.83 (d, J=8.48 Hz, 2H), 8.14 (s, 1H)

Example 404

$^1$H NMR (300 MHz, CD$_3$OD) δ ppm 0.73 (d, J=6.44 Hz, 3H), 0.82 (t, J=7.29 Hz, 3H), 0.87 (d, J=6.78 Hz, 3H), 0.91 (d, J=6.78 Hz, 3H), 1.24 (m, 2H), 1.80 (s, 1H), 2.01 (m, 1H), 2.41 (dd, J=13.73, 11.70 Hz, 1H), 0.00 (none, 3H), 3.11 (m, 1H), 3.20 (dd, J=13.56, 3.39 Hz, 2H), 3.44 (dd, J=14.75, 3.56 Hz, 1H), 3.60 (d, J=17.97 Hz, 1H), 3.75 (m, 1H), 4.11 (m, 2H), 4.53 (s, 2H), 6.64 (m, 1H), 6.64 (m, 1H), 6.71 (d, J=7.46 Hz, 1H), 6.71 (d, J=7.46 Hz, 1H), 6.77 (d, J=1.70 Hz, 1H), 6.77 (d, J=1.70 Hz, 1H), 6.90 (m, 5H), 6.90 (m, 3H), 7.07 (m, 4H), 7.83 (d, J=8.48 Hz, 2H), 8.14 (s, 1H)

Example 405

$^1$H NMR (300 MHz, CD$_3$OD) δ ppm 0.74 (d, J=6.78 Hz, 3H), 0.82 (t, J=7.46 Hz, 3H), 0.87 (d, J=6.78 Hz, 3H), 0.91 (d, J=6.44 Hz, 3H), 1.27 (dd, J=13.90, 4.41 Hz, 1H), 1.83 (s, 1H), 2.01 (m, 1H), 2.25 (s, 3H), 2.46 (dd, J=13.73, 11.70 Hz, 1H), 3.03 (m, 6H), 3.21 (dd, J=13.56, 3.39 Hz, 1H), 3.45 (dd, J=14.75, 3.56 Hz, 1H), 3.71 (d, J=17.97 Hz, 1H), 3.77 (m, 1H), 4.13 (m, 2H), 4.70 (d, J=7.80 Hz, 2H), 6.94 (m, 3H), 7.11 (m, 2H), 7.32 (dd, J=5.09, 1.70 Hz, 1H), 7.80 (q, J=8.48 Hz, 4H), 7.85 (d, J=3.73 Hz, 1H), 8.14 (s, 1H), 8.51 (d, J=5.09 Hz, 1H)

Example 436

$^1$H NMR (300 MHz, CDCl$_3$) δ ppm 0.85 (m, 12H), 1.91 (m, 1H), 2.22 (s, 1H), 2.95 (m, 7H), 2.98 (s, 3H), 3.36 (dd, J=15.26, 4.41 Hz, 1H), 3.85 (s, 1H), 4.11 (m, 1H), 4.22 (s, 1H), 4.31 (d, J=15.94 Hz, 1H), 7.18 (m, 5H), 7.29 (s, 1H), 7.70 (d, J=8.48 Hz, 2H), 7.76 (s, 1H), 7.82 (d, J=8.48 Hz, 2H), 8.13 (s, 1H), 8.29 (s, 1H), 8.51 (s, 1H)

Example 437

$^1$H NMR (300 MHz, CDCl$_3$) δ ppm 0.68 (d, J=6.78 Hz, 3H), 0.87 (m, 9H), 1.89 (dd, J=13.73, 6.95 Hz, 1H), 2.23 (m, 1H), 2.68 (s, 3H), 2.85 (dd, J=13.39, 7.29 Hz, 1H), 2.93 (s, 3H), 3.02 (m, 4H), 3.35 (dd, J=15.09, 4.58 Hz, 1H), 3.85 (m, 1H), 4.10 (d, J=4.75 Hz, 1H), 4.21 (d, J=15.94 Hz, 2H), 4.53 (d, J=15.94 Hz, 1H), 6.16 (s, 1H), 6.76 (s, 1H), 6.96 (s, 1H), 7.18 (m, 5H), 7.71 (d, J=8.48 Hz, 2H), 7.82 (d, J=8.48 Hz, 2H), 8.13 (s, 1H)

Example 438

$^1$H NMR (300 MHz, CDCl$_3$) δ ppm 0.67 (d, J=6.78 Hz, 3H), 0.87 (m, 9H), 1.69 (s, 1H), 1.89 (m, 1H), 2.20 (s, 1H), 2.86 (dd, J=13.56, 7.46 Hz, 1H), 2.94 (s, 3H), 3.02 (m, 3H), 3.33 (dd, J=15.26, 4.75 Hz, 1H), 3.50 (s, 3H), 3.85 (m, 1H), 4.09 (s, 1H), 4.22 (s, 1H), 4.28 (d, J=16.28 Hz, 1H), 4.56 (d, J=16.62 Hz, 1H), 4.68 (s, 2H), 6.77 (s, 1H), 7.11 (s, 1H), 7.20 (m, 5H), 7.71 (d, J=8.48 Hz, 2H), 7.82 (d, J=8.48 Hz, 2H), 8.13 (s, 1H)

Example 439

$^1$H NMR (300 MHz, DMSO-d$_6$) δ ppm 0.77 (d, J=6.78 Hz, 3H), 0.82 (d, J=6.44 Hz, 3H), 0.99 (t, J=6.95 Hz, 3H), 1.08 (d, J=7.12 Hz, 3H), 1.29 (d, J=6.78 Hz, 6H), 1.96 (m, 1H), 2.57 (dd, J=13.90, 10.51 Hz, 1H), 2.85 (m, 2H), 3.02 (m, 2H), 3.26 (m, 6H), 3.78 (m, 2H), 4.10 (m, 1H), 6.38 (s, 1H), 7.12 (m, 5H), 7.22 (s, 1H), 7.62 (d, J=8.82 Hz, 1H), 7.76 (d, J=8.82 Hz, 2H), 7.80 (d, J=8.82 Hz, 2H), 8.23 (s, 1H)

Example 440

$^1$H NMR (300 MHz, CD$_3$OD) δ ppm 0.76 (d, J=3.39 Hz, 3H), 0.78 (d, J=3.39 Hz, 3H), 1.13 (m, 2H), 1.26 (m, 2H), 1.37 (d, J=6.78 Hz, 6H), 1.59 (m, 8H), 1.90 (m, 1H), 2.23 (dd, J=15.09, 7.63 Hz, 1H), 2.65 (dd, J=13.90, 10.51 Hz, 1H), 2.94 (s, 3H), 3.07 (m, 2H), 3.21 (m, 1H), 3.46 (dd, J=14.92, 3.73 Hz, 1H), 3.82 (m, 1H), 3.96 (d, J=7.46 Hz, 1H), 4.10 (m, 1H), 4.48 (m, 2H), 7.15 (m, 6H), 7.76 (d, J=8.82 Hz, 2H), 7.81 (d, J=8.82 Hz, 2H), 8.13 (s, 1H)

Example 441

$^1$H NMR (300 MHz, CD$_3$OD) δ ppm 0.76 (d, J=3.05 Hz, 3H), 0.78 (d, J=3.05 Hz, 3H), 1.36 (d, J=6.78 Hz, 6H), 1.66 (m, 2H), 1.78 (m, 2H), 1.96 (m, 4H), 2.58 (dd, J=14.92, 7.46 Hz, 1H), 2.65 (m, 1H), 2.94 (s, 3H), 3.11 (m, 6H), 3.42 (dd, J=14.75, 3.90 Hz, 1H), 3.78 (m, 1H), 3.95 (d, J=7.46 Hz, 1H), 4.08 (m, 1H), 4.48 (m, 2H), 7.15 (m, 6H), 7.77 (d, J=8.82 Hz, 2H), 7.82 (d, J=8.48 Hz, 2H), 8.14 (s, 1H)

Example 442

$^1$H NMR (300 MHz, CD$_3$OD) δ ppm 0.71 (d, J=6.78 Hz, 3H), 0.78 (t, J=7.46 Hz, 3H), 0.97 (m, 1H), 1.14 (d, J=6.10 Hz, 1H), 1.24 (m, 2H), 1.61 (m, 8H), 2.24 (m, 1H), 2.66 (dd, J=14.07, 10.68 Hz, 1H), 2.94 (s, 3H), 3.12 (m, 5H), 3.47 (dd, J=14.92, 3.73 Hz, 1H), 3.83 (m, 1H), 4.01 (d, J=7.46 Hz, 1H), 4.13 (m, 1H), 4.55 (s, 2H), 7.16 (m, 5H), 7.31 (t, J=7.46 Hz, 2H), 7.77 (m, 3H), 7.82 (d, J=6.44 Hz, 2H), 8.13 (s, 1H), 8.48 (d, J=4.07 Hz, 1H)

Example 443

$^1$H NMR (300 MHz, CD$_3$OD) δ ppm 0.71 (d, J=6.78 Hz, 3H), 0.78 (m, 3H), 0.98 (m, 1H), 1.24 (m, 1H), 1.73 (m, 5H), 1.96 (m, 2H), 2.57 (dd, J=15.26, 7.46 Hz, 1H), 2.66 (m, 2H), 2.94 (s, 3H), 3.02 (dd, J=14.75, 8.65 Hz, 1H), 3.17 (m, 2H), 3.43 (m, 1H), 3.79 (m, 1H), 4.01 (m, 2H), 4.12 (m, 1H), 4.55 (s, 2H), 6.23 (d, J=7.80 Hz, 1H), 7.16 (m, 5H), 7.31 (m, J=7.12, 7.12 Hz, 2H), 7.78 (m, 3H), 7.83 (d, J=8.82 Hz, 2H), 8.13 (s, 1H), 8.48 (d, J=4.41 Hz, 1H)

Example 444

$^1$H NMR (300 MHz, DMSO-d$_6$) δ ppm 0.85 (d, J=6.44 Hz, 3H), 1.03 (s, 9H), 1.08 (m, 1H), 1.57 (d, J=28.14 Hz, 1H), 1.71 (m, 1H), 1.76 (s, 1H), 1.84 (d, J=20.35 Hz, 1H), 2.54 (m, 1H), 2.67 (dd, J=13.73, 9.66 Hz, 1H), 2.87 (s, 3H), 2.97 (m, 1H), 3.08 (m, 1H), 3.25 (d, J=7.80 Hz, 1H), 3.35 (d, J=4.07 Hz, 1H), 3.38 (s, 3H), 3.61 (s, 1H), 3.81 (m, 1H), 3.93 (dd, J=6.44, 4.41 Hz, 1H), 4.00 (s, 1H), 4.47 (d, J=4.41 Hz, 2H), 4.65 (s, 2H), 5.05 (d, J=6.44 Hz, 1H), 5.80 (d, J=6.78 Hz, 1H), 7.15 (m, 1H), 7.22 (m, 5H), 7.37 (s, 1H), 7.40 (d, J=9.16 Hz, 1H), 7.77 (d, J=8.48 Hz, 2H), 7.81 (d, J=8.82 Hz, 2H), 8.24 (s, 1H)

Example 445

$^1$H NMR (300 MHz, DMSO-d$_6$) δ ppm 0.84 (d, J=6.44 Hz, 3H), 1.03 (s, 9H), 1.08 (m, 2H), 1.19 (m, 2H), 1.50 (s, 6H), 2.19 (s, 1H), 2.87 (s, 3H), 2.96 (m, 2H), 3.14 (dd, J=14.07, 8.65 Hz, 1H), 3.38 (s, 3H), 3.65 (0=10.85 Hz, 1H), 3.81 (dd, J=6.10, 4.41 Hz, 1H), 3.94 (dd, J=6.61, 4.58 Hz, 1H), 4.03 (s, 1H), 4.47 (d, J=4.41 Hz, 2H), 4.65 (s, 2H), 5.02 (d, J=6.44 Hz, 1H), 5.80 (d, J=6.78 Hz, 1H), 7.16 (m, 1H), 7.20 (d, J=8.14 Hz, 5H), 7.23 (s, 1H), 7.38 (m, 1H), 7.76 (d, J=8.48 Hz, 2H), 7.81 (d, J=8.48 Hz, 2H)

Example 446

$^1$H NMR (300 MHz, DMSO-d$_6$) δ ppm 0.59 (d, J=6.44 Hz, 3H), 0.70 (t, J=7.29 Hz, 3H), 1.27 (m, 2H), 1.56 (m, 3H), 1.74 (m, 2H), 1.86 (m, 2H), 2.57 (m, 1H), 2.85 (s, 3H), 2.92 (m, 1H), 3.01 (m, 1H), 3.07 (m, 1H), 3.26 (m, 1H), 3.38 (s, 3H), 3.60 (m, J=4.41 Hz, 1H), 3.94 (t, J=7.97 Hz, 2H), 4.41 (d, J=15.94 Hz, 1H), 4.51 (d, J=16.28 Hz, 1H), 4.64 (s, 2H), 5.02 (d, J=6.10 Hz, 1H), 5.98 (d, J=8.48 Hz, 1H), 7.14 (m, 5H), 7.32 (s, 1H), 7.67 (d, J=8.82 Hz, 1H), 7.79 (t, J=8.82 Hz, 4H)

Example 447

$^1$H NMR (300 MHz, DMSO-d$_6$) δ ppm 0.59 (d, J=6.78 Hz, 3H), 0.70 (t, J=7.46 Hz, 3H), 0.88 (m, 1H), 1.07 (m, 1H), 1.24 (m, 2H), 1.52 (m, 8H), 2.57 (m, 1H), 2.84 (s, 3H), 2.98 (m, 2H), 3.13 (m, 1H), 3.28 (s, 1H), 3.38 (s, 3H), 3.61 (s, 1H), 3.95 (t, J=8.14 Hz, 2H), 4.41 (d, J=16.28 Hz, 1H), 4.50 (d, J=16.28 Hz, 1H), 4.64 (s, 2H), 4.99 (d, J=6.10 Hz, 1H), 5.97 (d, J=8.14 Hz, 1H), 7.14 (m, 5H), 7.31 (s, 1H), 7.69 (d, J=9.16 Hz, 1H), 7.76 (d, J=8.82 Hz, 2H), 7.78 (d, J=8.82 Hz, 2H), 8.23 (s, 1H)

Example 448

$^1$H NMR (300 MHz, CD$_3$OD) δ ppm 0.77 (dd, J=6.78, 1.70 Hz, 6H), 0.98 (m, 1H), 1.64 (m, 2H), 1.80 (m, 2H), 1.96 (m, 4H), 2.59 (m, 2H), 2.67 (s, 3H), 2.70 (m, 1H), 2.93 (s, 3H), 2.99 (m, 1H), 3.17 (m, 2H), 3.43 (dd, J=14.75, 3.90 Hz, 1H), 3.78 (m, 1H), 3.96 (d, J=7.12 Hz, 1H), 4.10 (m, 1H), 4.43 (d, J=15.94 Hz, 1H), 4.52 (d, J=16.28 Hz, 1H), 7.16 (m, 6H), 7.77 (d, J=8.48 Hz, 2H), 7.82 (d, J=8.82 Hz, 2H), 8.14 (s, 1H)

Example 449

$^1$H NMR (300 MHz, DMSO-d$_6$) δ ppm 0.59 (d, J=6.78 Hz, 3H), 0.69 (t, J=7.46 Hz, 3H), 0.77 (d, J=6.44 Hz, 3H), 0.81 (d, J=6.44 Hz, 3H), 0.93 (m, 1H), 1.19 (m, 1H), 1.59 (s, 1H), 1.96

(m, 1H), 2.60 (s, 3H), 2.83 (s, 3H), 2.90 (m, 1H), 2.98 (m, 1H), 3.03 (m, 1H), 3.31 (m, 2H), 3.59 (s, 1H), 3.95 (m, 2H), 4.35 (d, J=16.28 Hz, 1H), 4.47 (d, J=15.94 Hz, 1H), 4.97 (d, J=6.44 Hz, 1H), 6.02 (d, J=8.48 Hz, 1H), 7.14 (m, 6H), 7.67 (d, J=9.16 Hz, 1H), 7.76 (d, J=8.82 Hz, 2H), 7.80 (d, J=8.82 Hz, 2H), 8.23 (s, 1H)

Example 450

$^1$H NMR (300 MHz, CDCl$_3$) δ ppm 0.76 (t, J=7.29 Hz, 3H), 0.84 (d, J=7.12 Hz, 3H), 0.96 (m, 1H), 1.66 (m, 2H), 1.83 (m, 3H), 1.98 (m, 4H), 2.52 (dd, J=14.92, 7.46 Hz, 1H), 2.65 (s, 3H), 2.91 (s, 3H), 3.03 (m, 2H), 3.25 (m, 1H), 3.41 (dd, J=14.75, 5.93 Hz, 1H), 3.82 (m, 1H), 4.17 (d, J=16.28 Hz, 1H), 4.24 (m, 3H), 4.53 (d, J=16.28 Hz, 1H), 6.23 (s, 1H), 6.82 (d, J=8.14 Hz, 1H), 6.95 (s, 1H), 7.19 (m, 5H), 7.73 (d, J=8.48 Hz, 2H), 7.85 (d, J=8.48 Hz, 2H), 8.14 (s, 1H)

Example 451

$^1$H NMR (300 MHz, DMSO-d$_6$) δ ppm 0.77 (d, J=6.78 Hz, 3H), 0.83 (dd, J=8.14, 6.44 Hz, 6H), 1.02 (s, 9H), 1.95 (m, 1H), 2.62 (s, 3H), 2.68 (dd, J=13.90, 9.49 Hz, 1H), 2.86 (s, 3H), 2.93 (m, 4H), 3.62 (s, 1H), 3.79 (dd, J=10.85, 6.44 Hz, 1H), 3.94 (dd, J=6.61, 4.58 Hz, 1H), 4.03 (m, 1H), 4.42 (t, J=16.62 Hz, 2H), 5.01 (d, J=6.44 Hz, 1H), 5.84 (d, J=6.44 Hz, 1H), 7.16 (m, 5H), 7.22 (s, 1H), 7.36 (d, J=9.49 Hz, 1H), 7.76 (d, J=8.82 Hz, 2H), 7.80 (d, J=8.82 Hz, 2H), 8.23 (s, 1H)

Example 452

$^1$H NMR (300 MHz, DMSO-d$_6$) δ ppm 0.85 (d, J=6.10 Hz, 3H), 1.03 (s, 9H), 1.57 (d, J=27.13 Hz, 2H), 1.71 (m, 3H), 1.87 (s, 2H), 2.62 (s, 3H), 2.68 (dd, J=13.90, 9.83 Hz, 1H), 2.86 (s, 3H), 2.95 (m, 2H), 3.08 (m, 1H), 3.26 (m, 1H), 3.61 (s, 1H), 3.81 (dd, J=6.10, 4.41 Hz, 1H), 3.93 (dd, J=6.44, 4.41 Hz, 2H), 4.38 (d, J=16.28 Hz, 1H), 4.42 (d, J=16.28 Hz, 2H), 5.05 (d, J=6.10 Hz, 1H), 5.85 (d, J=6.44 Hz, 1H), 7.17 (m, 5H), 7.23 (s, 1H), 7.38 (d, J=9.16 Hz, 1H), 7.77 (d, J=8.82 Hz, 2H), 7.81 (d, J=8.48 Hz, 2H), 8.23 (s, 1H)

Example 453

$^1$H NMR (300 MHz, CDCl$_3$) δ ppm 0.79 (t, J=6.44 Hz, 6H), 0.87 (d, J=6.78 Hz, 6H), 1.16 (m, 1H), 1.52 (s, 1H), 1.88 (m, 1H), 2.88 (s, 3H), 2.94 (d, J=11.19 Hz, 1H), 3.07 (m, 2H), 3.07 (m, 2H), 3.21 (m, 1H), 3.87 (m, 1H), 3.99 (d, J=3.73 Hz, 1H), 4.13 (m, 2H), 4.13 (dd, J=7.63, 5.93 Hz, 1H), 4.23 (m, 1H), 4.45 (d, J=15.94 Hz, 1H), 4.67 (m, 2H), 6.43 (d, J=8.14 Hz, 1H), 7.21 (m, 5H), 7.51 (m, 2H), 7.70 (d, J=6.44 Hz, 2H), 7.71 (s, 1H), 7.79 (d, J=8.48 Hz, 2H), 8.05 (s, 1H), 8.14 (s, 1H)

Example 454

$^1$H NMR (300 MHz, CD$_3$OD) δ ppm 0.71 (d, J=6.78 Hz, 3H), 0.78 (t, J=7.46 Hz, 3H), 0.85 (d, J=6.78 Hz, 3H), 0.90 (d, J=6.78 Hz, 3H), 0.97 (m, 1H), 1.28 (m, 1H), 1.64 (s, 1H), 2.00 (m, 1H), 2.61 (dd, J=13.90, 10.85 Hz, 1H), 2.94 (s, 3H), 3.07 (m, 7H), 3.46 (dd, J=14.92, 3.73 Hz, 1H), 3.83 (s, 3H), 3.96 (d, J=8.14 Hz, 1H), 4.09 (m, 1H), 4.23 (d, J=16.28 Hz, 1H), 4.38 (d, J=16.28 Hz, 1H), 6.81 (s, 1H), 7.09 (m, 5H), 7.80 (q, J=8.48 Hz, 4H), 7.87 (m, 1H), 8.13 (s, 1H)

Example 455

$^1$H NMR (300 MHz, DMSO-d$_6$) δ ppm 0.65 (dd, J=9.16, 6.78 Hz, 6H), 1.57 (dd, J=16.62, 8.82 Hz, 2H), 1.71 (m, 2H), 1.84 (dd, J=13.73, 6.61 Hz, 4H), 2.56 (m, J=20.01 Hz, 1H), 2.85 (s, 3H), 2.91 (m, 1H), 3.00 (m, 1H), 3.07 (m, 1H), 3.26 (d, J=9.83 Hz, 2H), 3.37 (s, 3H), 3.60 (d, J=3.05 Hz, 1H), 3.90 (m, 2H), 4.42 (d, J=16.28 Hz, 1H), 4.51 (d, J=16.28 Hz, 1H), 4.64 (s, 2H), 5.03 (d, J=6.44 Hz, 1H), 5.96 (d, J=8.48 Hz, 1H), 7.14 (m, 5H), 7.32 (s, 1H), 7.70 (d, J=9.49 Hz, 1H), 7.78 (m, 4H), 8.23 (s, 1H)

Example 456

$^1$H NMR (300 MHz, CD$_3$OD) δ ppm 0.74 (t, J=7.29 Hz, 3H), 0.80 (d, J=7.12 Hz, 3H), 0.93 (m, 1H), 1.29 (s, 1H), 1.66 (dd, J=16.62, 9.16 Hz, 2H), 1.81 (m, 2H), 1.97 (m, 2H), 2.61 (m, 1H), 2.86 (s, 3H), 2.99 (d, J=2.03 Hz, 3H), 3.03 (m, 1H), 3.12 (m, 3H), 3.16 (m, 2H), 3.44 (dd, J=14.58, 4.07 Hz, 1H), 3.80 (m, 1H), 3.98 (m, 1H), 4.10 (s, 1H), 4.28 (d, J=15.94 Hz, 1H), 4.36 (d, J=15.94 Hz, 1H), 6.16 (s, 1H), 6.84 (s, 1H), 7.06 (m, 3H), 7.18 (m, 2H), 7.80 (q, J=8.59 Hz, 4H), 7.87 (d, J=9.16 Hz, 1H), 8.14 (s, 1H)

Example 457

$^1$H NMR (300 MHz, CD$_3$OD) δ ppm 0.69 (d, J=6.44 Hz, 3H), 0.80 (t, J=7.29 Hz, 3H), 0.85 (d, J=6.78 Hz, 3H), 0.89 (d, J=6.78 Hz, 3H), 0.99 (m, 1H), 1.35 (m, 1H), 1.64 (m, 1H), 2.00 (m, 1H), 2.63 (dd, J=13.90, 10.85 Hz, 1H), 2.86 (s, 3H), 2.95 (m, 1H), 3.06 (m, 2H), 3.15 (m, 2H), 3.28 (s, 1H), 3.46 (dd, J=14.92, 3.39 Hz, 1H), 3.79 (m, 1H), 4.00 (d, J=8.48 Hz, 1H), 4.09 (m, 1H), 4.45 (d, J=15.94 Hz, 1H), 4.62 (d, J=15.94 Hz, 1H), 7.15 (m, 5H), 7.39 (dd, J=7.46, 4.41 Hz, 1H), 7.70 (m, 1H), 7.79 (q, J=8.82 Hz, 4H), 8.13 (s, 1H), 8.43 (dd, J=4.92, 1.53 Hz, 2H)

Example 458

$^1$H NMR (300 MHz, CD$_3$OD) δ ppm 0.70 (d, J=6.44 Hz, 3H), 0.80 (t, J=7.29 Hz, 3H), 1.00 (m, 1H), 1.35 (m, 1H), 1.66 (m, 2H), 1.80 (m, 3H), 1.95 (m, 3H), 1.95 (m, 2H), 2.62 (m, 2H), 2.91 (s, 3H), 3.00 (dd, J=14.75, 8.65 Hz, 1H), 3.17 (m, 1H), 3.27 (s, 2H), 3.45 (dd, J=14.58, 4.07 Hz, 1H), 3.79 (m, 1H), 4.00 (d, J=8.48 Hz, 1H), 4.10 (m, 1H), 4.47 (d, J=16.95 Hz, 1H), 4.62 (d, J=17.29 Hz, 1H), 7.17 (m, 7H), 7.76 (d, J=8.82 Hz, 2H), 7.79 (d, J=6.78 Hz, 2H), 8.13 (s, 1H), 8.44 (m, 1H)

Example 459

$^1$H NMR (300 MHz, CDCl$_3$) δ ppm 0.78 (dd, J=14.92, 6.78 Hz, 6H), 0.87 (m, 6H), 2.93 (s, 3H), 2.89 (m, 8H), 3.33 (s, 1H), 3.50 (s, 3H), 3.85 (s, 2H), 4.21 (m, 3H), 4.57 (d, J=15.94 Hz, 1H), 4.67 (s, 2H), 6.68 (d, J=8.82 Hz, 1H), 7.11 (s, 1H), 7.20 (dd, J=18.31, 8.14 Hz, 5H), 7.55 (d, J=8.82 Hz, 1H), 7.71 (d, J=8.14 Hz, 2H), 7.82 (d, J=8.48 Hz, 2H), 8.14 (s, 1H)

Example 460

$^1$H NMR (300 MHz, CD$_3$OD) δ ppm 0.71 (d, J=6.78 Hz, 3H), 0.79 (t, J=7.46 Hz, 3H), 0.99 (m, 1H), 1.14 (m, 1H), 1.30 (m, 2H), 1.60 (m, 8H), 2.24 (m, 1H), 2.65 (dd, J=13.90, 10.51 Hz, 1H), 2.95 (s, 3H), 3.12 (m, 5H), 3.44 (m, 3H), 3.46 (m, 1H), 3.82 (m, 1H), 4.00 (d, J=8.14 Hz, 1H), 4.11 (m, 1H), 4.45 (d, J=16.28 Hz, 1H), 4.50 (s, 2H), 4.55 (d, J=16.28 Hz, 1H), 7.11 (m, 5H), 7.19 (m, 2H), 7.37 (d, J=7.80 Hz, 1H), 7.76 (d, J=7.12 Hz, 2H), 7.82 (d, J=8.82 Hz, 2H), 8.13 (s, 1H)

Example 461

$^1$H NMR (300 MHz, DMSO-d$_6$) δ ppm 0.59 (d, J=6.78 Hz, 3H), 0.69 (t, J=7.46 Hz, 3H), 0.77 (d, J=6.44 Hz, 3H), 0.81 (d, J=6.44 Hz, 3H), 0.92 (m, 1H), 1.22 (m, 1H), 1.30 (d, J=6.78 Hz, 6H), 1.59 (s, 1H), 1.94 (m, 1H), 2.56 (m, 1H), 2.85 (s, 3H), 2.96 (m, 4H), 3.21 (dd, J=13.90, 6.78 Hz, 1H), 3.61 (m, 1H), 3.94 (t, J=7.97 Hz, 2H), 4.37 (d, J=16.28 Hz, 1H), 4.47 (d, J=16.28 Hz, 1H), 4.97 (d, J=6.44 Hz, 1H), 5.98 (d, J=8.82 Hz, 1H), 7.14 (m, 6H), 7.69 (d, J=9.16 Hz, 1H), 7.76 (d, J=8.82 Hz, 2H), 7.80 (d, J=8.82 Hz, 2H), 8.23 (s, 1H)

Example 462

$^1$H NMR (300 MHz, DMSO-$d_6$) δ ppm 0.60 (d, J=6.78 Hz, 3H), 0.69 (t, J=7.29 Hz, 3H), 0.91 (m, 1H), 1.07 (m, 1H), 1.20 (m, 3H), 1.30 (d, J=6.78 Hz, 6H), 1.48 (dd, J=17.80, 7.29 Hz, 8H), 2.19 (m, 1H), 2.57 (m, 1H), 2.85 (s, 3H), 2.97 (m, 1H), 3.14 (m, 1H), 3.36 (m, J=3.73 Hz, 1H), 3.59 (s, 1H), 3.95 (m, J=7.97, 7.97 Hz, 2H), 4.37 (d, J=16.28 Hz, 1H), 4.46 (d, J=16.28 Hz, 1H), 4.98 (d, J=6.44 Hz, 1H), 5.98 (d, J=8.48 Hz, 1H), 7.13 (m, 6H), 7.69 (d, J=8.82 Hz, 1H), 7.76 (d, J=8.82 Hz, 2H), 7.80 (d, J=8.82 Hz, 2H), 8.23 (s, 1H)

Example 463

$^1$H NMR (300 MHz, CD$_3$OD) δ ppm 0.69 (d, J=6.78 Hz, 3H), 0.75 (t, J=7.46 Hz, 3H), 0.91 (m, 1H), 1.14 (m, 1H), 1.29 (m, 2H), 1.60 (m, 8H), 2.23 (dd, J=14.92, 7.46 Hz, 1H), 2.64 (dd, J=13.90, 10.85 Hz, 1H), 2.99 (s, 3H), 3.12 (m, 6H), 3.46 (dd, J=14.58, 3.73 Hz, 1H), 3.82 (m, 1H), 3.98 (d, J=8.14 Hz, 1H), 4.10 (m, 1H), 4.46 (d, J=16.28 Hz, 1H), 4.60 (d, J=16.62 Hz, 1H), 4.79 (s, 2H), 7.14 (m, 6H), 7.29 (dd, J=6.78, 2.03 Hz, 1H), 7.76 (m, 3H), 7.82 (d, J=8.82 Hz, 2H), 8.13 (s, 1H)

Example 464

$^1$H NMR (300 MHz, CD$_3$OD) δ ppm 0.86 (s, 9H), 1.19 (m, 3H), 1.62 (m, 8H), 2.23 (m, 1H), 2.61 (dd, J=13.73, 10.68 Hz, 1H), 2.96 (s, 3H), 3.08 (m, 2H), 3.20 (m, 1H), 3.43 (s, 3H), 3.47 (m, 1H), 3.82 (m, 1H), 4.03 (s, 1H), 4.11 (m, 1H), 4.38 (d, J=16.28 Hz, 1H), 4.49 (s, 2H), 4.58 (d, J=16.28 Hz, 1H), 7.00 (m, 1H), 7.13 (m, 5H), 7.37 (d, J=7.80 Hz, 1H), 7.77 (m, 3H), 7.81 (d, J=2.37 Hz, 2H), 8.13 (s, 1H)

Example 465

$^1$H NMR (300 MHz, CDCl$_3$) δ ppm 0.91 (s, 9H), 1.19 (m, 3H), 1.27 (m, 2H), 1.29 (s, 9H), 1.55 (m, 8H), 2.12 (m, 1H), 2.87 (m, 1H), 3.02 (d, J=7.72 Hz, 2H), 3.08 (m, 1H), 3.25 (m, 1H), 3.88 (m, 1H), 3.94 (d, J=7.72 Hz, 1H), 4.12 (m, 1H), 4.33 (d, J=15.81 Hz, 1H), 4.44 (d, J=15.81 Hz, 1H), 4.52 (s, 2H), 6.42 (d, J=8.09 Hz, 1H), 7.11 (m, 6H), 7.47 (d, J=7.72 Hz, 1H), 7.69 (m, 3H), 7.78 (d, J=8.46 Hz, 2H), 8.14 (s, 1H)

Example 466

$^1$H NMR (300 MHz, DMSO-$d_6$) δ ppm 0.87 (d, J=6.10 Hz, 3H), 1.55 (d, J=27.80 Hz, 2H), 1.70 (d, J=14.92 Hz, 3H), 1.86 (s, 2H), 2.62 (m, 1H), 2.84 (d, J=3.39 Hz, 2H), 2.86 (s, 3H), 2.94 (d, J=3.39 Hz, 1H), 2.99 (d, J=10.17 Hz, 1H), 3.07 (dd, J=14.07, 6.95 Hz, 1H), 3.25 (m, 1H), 3.37 (d, J=3.39 Hz, 3H), 3.59 (s, 1H), 3.82 (m, 1H), 3.89 (s, 1H), 3.96 (dd, J=7.46, 5.09 Hz, 1H), 4.48 (s, 2H), 4.65 (s, 2H), 5.98 (d, J=7.80 Hz, 1H), 7.17 (m, 5H), 7.32 (s, 1H), 7.61 (d, J=9.16 Hz, 1H), 7.76 (d, J=8.48 Hz, 2H), 7.82 (d, J=8.82 Hz, 2H), 8.23 (s, 1H)

Example 467

$^1$H NMR (300 MHz, DMSO-$d_6$) δ ppm 0.87 (d, J=6.10 Hz, 3H), 1.06 (d, J=20.01 Hz, 2H), 1.25 (s, 1H), 1.44 (d, J=32.89 Hz, 8H), 2.20 (d, J=7.80 Hz, 1H), 2.60 (dd, J=13.90, 10.17 Hz, 1H), 2.86 (s, 3H), 2.97 (m, 5H), 3.11 (m, 1H), 3.62 (s, 1H), 3.82 (m, 1H), 3.89 (s, 1H), 3.97 (dd, J=7.46, 5.43 Hz, 1H), 4.48 (s, 2H), 4.65 (s, 2H), 5.97 (d, J=7.46 Hz, 1H), 7.16 (m, 5H), 7.32 (s, 1H), 7.62 (d, J=9.16 Hz, 1H), 7.75 (d, J=8.48 Hz, 2H), 7.81 (d, J=8.82 Hz, 2H), 8.22 (s, 1H)

Example 468

$^1$H NMR (300 MHz, CD$_3$OD) δ ppm 0.65 (d, J=6.78 Hz, 3H), 0.74 (t, J=7.29 Hz, 3H), 0.84 (d, J=6.78 Hz, 3H), 0.90 (d, J=6.44 Hz, 3H), 1.20 (m, 1H), 1.59 (s, 1H), 2.00 (m, 1H), 2.61 (dd, J=14.07, 10.68 Hz, 1H), 2.88 (s, 3H), 3.05 (m, 4H), 3.45 (dd, J=14.75, 3.56 Hz, 1H), 3.81 (m, 1H), 4.00 (d, J=7.46 Hz, 1H), 4.08 (m, 1H), 4.31 (d, J=16.28 Hz, 1H), 4.44 (d, J=15.94 Hz, 1H), 4.79 (s, 3H), 6.54 (d, J=7.46 Hz, 1H), 6.61 (m, 2H), 7.06 (t, J=7.63 Hz, 1H), 7.16 (m, 5H), 7.77 (d, J=8.48 Hz, 2H), 7.83 (d, J=8.82 Hz, 2H), 8.13 (s, 1H)

Example 469

$^1$H NMR (300 MHz, DMSO-$d_6$) δ ppm 0.76 (d, J=6.78 Hz, 3H), 0.80 (d, J=6.44 Hz, 3H), 0.87 (d, J=6.44 Hz, 3H), 1.93 (s, 1H), 2.61 (s, 3H), 2.85 (s, 3H), 2.99 (m, 1H), 3.38 (m, 1H), 3.54 (s, 5H), 3.81 (m, 2H), 3.97 (m, 1H), 4.44 (s, 2H), 6.00 (d, J=6.78 Hz, 1H), 7.14 (s, 1H), 7.15 (m, 5H), 7.61 (d, J=9.16 Hz, 1H), 7.76 (d, J=8.48 Hz, 2H), 7.81 (d, J=8.48 Hz, 2H), 8.23 (s, 1H)

Example 470

$^1$H NMR (300 MHz, DMSO-$d_6$) δ ppm 0.88 (d, J=6.44 Hz, 3H), 1.55 (d, J=27.47 Hz, 2H), 1.70 (m, 3H), 1.86 (s, 2H), 2.61 (s, 3H), 2.85 (s, 3H), 2.94 (m, 1H), 3.06 (m, 2H), 3.27 (m, 5H), 3.85 (m, 3H), 4.44 (s, 2H), 6.01 (d, J=6.78 Hz, 1H), 7.15 (s, 1H), 7.17 (m, 5H), 7.60 (d, J=9.16 Hz, 1H), 7.76 (d, J=8.48 Hz, 2H), 7.82 (d, J=8.48 Hz, 2H), 8.23 (s, 1H)

Example 471

$^1$H NMR (300 MHz, DMSO-$d_6$) δ ppm 0.64 (d, J=6.44 Hz, 3H), 0.73 (t, J=7.46 Hz, 3H), 0.78 (d, J=6.44 Hz, 3H), 0.81 (d, J=6.44 Hz, 3H), 0.96 (m, 1H), 1.38 (s, 1H), 1.60 (s, 1H), 1.96 (m, 1H), 2.55 (m, 1H), 2.82 (d, J=6.78 Hz, 1H), 2.88 (s, 3H), 2.98 (m, 2H), 3.34 (m, 1H), 3.62 (s, 2H), 3.91 (s, 1H), 4.01 (m, 1H), 4.40 (d, J=16.28 Hz, 3H), 4.55 (d, J=15.94 Hz, 1H), 6.14 (d, J=8.48 Hz, 1H), 7.09 (m, 5H), 7.42 (s, 1H), 7.78 (m, 4H), 7.94 (d, J=9.16 Hz, 1H), 8.24 (s, 1H), 8.42 (s, 2H)

Example 472

$^1$H NMR (300 MHz, DMSO-$d_6$) δ ppm 0.65 (d, J=6.44 Hz, 3H), 0.74 (t, J=7.46 Hz, 3H), 0.95 (m, J=6.44 Hz, 1H), 1.24 (d, J=2.71 Hz, 1H), 1.31 (s, 1H), 1.68 (m, 4H), 1.86 (m, 2H), 2.56 (m, 1H), 2.88 (s, 3H), 2.95 (m, 2H), 3.08 (dd, J=14.07, 6.61 Hz, 1H), 3.29 (m, 2H), 3.69 (s, 3H), 3.90 (s, 1H), 4.01 (m, 1H), 4.41 (m, 2H), 4.55 (d, J=15.94 Hz, 1H), 6.13 (d, J=8.82 Hz, 1H), 7.11 (m, 5H), 7.42 (s, 1H), 7.79 (m, 4H), 7.92 (d, J=9.49 Hz, 1H), 8.24 (s, 1H), 8.42 (s, 2H)

Example 473

$^1$H NMR (300 MHz, DMSO-$d_6$) δ ppm 0.65 (d, J=6.78 Hz, 3H), 0.74 (t, J=7.29 Hz, 3H), 0.95 (d, J=6.78 Hz, 1H), 1.07 (s, 2H), 1.19 (m, 2H), 1.43 (dd, J=10.51, 6.10 Hz, 2H), 1.53 (m, 6H), 2.20 (s, 1H), 2.56 (m, 1H), 2.88 (s, 3H), 2.99 (m, 2H), 3.14 (m, 1H), 3.34 (m, 1H), 3.63 (s, 1H), 4.01 (m, 2H), 4.37

(m, 2H), 4.55 (d, J=15.94 Hz, 1H), 6.13 (d, J=8.48 Hz, 1H), 7.09 (m, 5H), 7.42 (s, 1H), 7.76 (d, J=8.82 Hz, 2H), 7.81 (d, J=8.82 Hz, 2H), 7.94 (d, J=9.16 Hz, 1H), 8.24 (s, 1H), 8.42 (s, 2H)

Example 474

$^1$H NMR (300 MHz, DMSO-d$_6$) δ ppm 0.65 (d, J=6.78 Hz, 3H), 0.74 (t, J=7.46 Hz, 3H), 0.85 (m, 1H), 0.98 (dd, J=16.62, 6.44 Hz, 1H), 1.18 (t, J=7.29 Hz, 4H), 1.49 (d, J=6.78 Hz, 3H), 1.48 (m, J=35.26 Hz, 6H), 2.18 (d, J=7.12 Hz, 1H), 2.58 (m, 1H), 2.89 (s, 3H), 2.97 (s, 2H), 3.10 (m, 2H), 3.32 (d, J=3.05 Hz, 1H), 3.63 (s, 1H), 3.94 (s, 1H), 4.02 (t, J=8.31 Hz, 1H), 4.25 (s, 1H), 4.41 (d, J=15.94 Hz, 1H), 4.56 (d, J=16.28 Hz, 1H), 4.82 (s, 1H), 6.17 (d, J=8.48 Hz, 1H), 7.12 (m, 5H), 7.43 (s, 1H), 7.76 (d, J=8.82 Hz, 2H), 7.79 (d, J=8.82 Hz, 2H), 7.97 (d, J=9.49 Hz, 1H), 8.24 (s, 1H), 8.52 (s, 2H)

Example 475

$^1$H NMR (300 MHz, DMSO-d$_6$) δ ppm 0.65 (d, J=6.44 Hz, 3H), 0.74 (t, J=7.29 Hz, 3H), 0.95 (d, J=6.44 Hz, 2H), 1.17 (s, 1H), 1.34 (s, 2H), 1.47 (m, 8H), 1.57 (d, J=6.78 Hz, 3H), 2.18 (d, J=6.78 Hz, 1H), 2.55 (m, 1H), 2.88 (s, 3H), 2.98 (m, 2H), 3.14 (m, 1H), 3.34 (dd, J=14.24, 3.39 Hz, 1H), 3.64 (s, 1H), 4.02 (m, 1H), 4.40 (d, J=16.28 Hz, 1H), 4.55 (d, J=16.28 Hz, 1H), 4.71 (s, 1H), 6.17 (d, J=8.14 Hz, 1H), 7.09 (m, 5H), 7.45 (s, 1H), 7.76 (d, J=8.82 Hz, 2H), 7.81 (d, J=8.82 Hz, 2H), 7.98 (d, J=9.16 Hz, 1H), 8.24 (s, 1H), 8.49 (d, J=4.41 Hz, 2H)

Example 476

$^1$H NMR (300 MHz, CD$_3$OD) δ ppm 0.66 (d, J=6.78 Hz, 3H), 0.74 (t, J=7.29 Hz, 3H), 0.90 (m, 1H), 1.15 (d, J=6.10 Hz, 1H), 1.25 (m, 2H), 1.59 (m, 8H), 2.22 (m, 1H), 2.26 (s, 3H), 2.63 (dd, J=13.73, 10.68 Hz, 1H), 3.00 (s, 3H), 3.11 (m, 5H), 3.45 (dd, J=14.92, 3.73 Hz, 1H), 3.81 (m, 1H), 3.97 (m, 1H), 4.10 (m, 1H), 4.48 (d, J=16.62 Hz, 1H), 4.61 (d, J=16.62 Hz, 1H), 7.16 (m, 7H), 7.70 (t, J=7.63 Hz, 1H), 7.76 (d, J=8.82 Hz, 2H), 7.82 (d, J=8.48 Hz, 2 H), 8.13 (s, 1H)

Example 477

$^1$H NMR (300 MHz, DMSO-d$_6$) δ ppm 0.61 (d, J=6.99 Hz, 2H), 0.70 (t, J=7.35 Hz, 3H), 0.85 (m, 1H), 0.94 (m, 1H), 1.08 (s, 1H), 1.21 (m, 3H), 1.44 (d, J=6.99 Hz, 3H), 1.47 (d, J=32.72 Hz, 8H), 1.87 (s, 3H), 2.19 (m, 1H), 2.57 (m, 1H), 2.84 (s, 3H), 2.97 (m, 2H), 3.13 (m, 1H), 3.33 (m, 1H), 3.60 (s, 2H), 4.42 (s, 2H), 5.10 (dd, J=14.89, 7.17 Hz, 1H), 6.04 (d, J=8.46 Hz, 1H), 7.15 (s, 1H), 7.14 (m, 5H), 7.75 (m, 3H), 7.80 (d, J=8.82 Hz, 2H), 8.23 (s, 1H), 8.58 (d, J=8.09 Hz, 1H)

Example 480

$^1$H NMR (300 MHz, CDCl$_3$) δ ppm 0.86 (d, J=6.44 Hz, 3H), 0.91 (d, J=6.44 Hz, 3H), 1.26 (s, 1H), 1.85 (d, J=7.46 Hz, 2H), 2.09 (s, 1H), 2.87 (d, J=6.78 Hz, 1H), 2.99 (m, 3H), 3.16 (m, 1H), 3.63 (d, J=10.51 Hz, 1H), 3.68 (s, 1H), 3.78 (dd, J=10.68, 4.58 Hz, 1H), 3.84 (s, 3H), 4.84 (d, J=8.14 Hz, 1H), 5.12 (s, 1H), 7.26 (m, 5H), 7.71 (d, J=8.48 Hz, 2H), 7.78 (d, J=8.48 Hz, 2H), 8.16 (s, 1H)

Example 481

$^1$H NMR (300 MHz, DMSO-d$_6$) δ ppm 0.77 (d, J=6.44 Hz, 3H), 0.82 (d, J=6.44 Hz, 3H), 1.99 (s, 1H), 2.27 (m, 2H), 2.60 (dd, J=13.90, 10.17 Hz, 1H), 2.83 (m, 1H), 2.97 (m, 4H), 3.63 (s, 1H), 3.80 (s, 1H), 4.25 (dd, J=8.48, 5.43 Hz, 1H), 5.00 (m, 3H), 6.83 (s, 1H), 7.12 (dd, J=8.65, 4.24 Hz, 1H), 7.21 (m, 5H), 7.35 (s, 4H), 7.78 (m, 6H), 8.23 (s, 1H)

Example 482

$^1$H NMR (300 MHz, CDCl$_3$) δ ppm 0.87 (m, 15H), 1.86 (m, 1H), 2.83 (dd, J=13.56, 6.78 Hz, 1H), 2.91 (dd, J=13.73, 4.58 Hz, 1H), 3.01 (m, 2H), 3.11 (s, 1H), 3.65 (s, 3H), 3.74 (m, 1H), 3.86 (m, 1H), 4.21 (s, 1H), 5.07 (s, 1H), 5.99 (d, J=8.48 Hz, 1H), 7.23 (m, 5H), 7.56 (s, 1H), 7.71 (d, J=8.48 Hz, 2H), 7.77 (d, J=8.48 Hz, 2H), 8.16 (s, 1H)

Example 483

$^1$H NMR (300 MHz, CD$_3$OD) δ ppm 0.86 (d, J=6.78 Hz, 3H), 0.91 (d, J=6.44 Hz, 3H), 1.80 (s, 3H), 2.01 (m, 1H), 2.60 (m, 1H), 2.90 (m, 1H), 2.97 (m, 1H), 3.12 (m, 2H), 3.41 (dd, J=14.92, 3.05 Hz, 1H), 3.78 (m, 1H), 4.01 (m, 1H), 4.80 (s, 1H), 7.19 (m, 5H), 7.79 (m, 4H), 8.14 (s, 1H)

Example 484

$^1$H NMR (300 MHz, CDCl$_3$) δ ppm 0.54 (d, J=6.44 Hz, 3H), 0.75 (d, J=6.78 Hz, 3H), 0.88 (d, J=6.78 Hz, 3H), 0.96 (d, J=6.44 Hz, 3H), 1.70 (s, 1H), 1.92 (s, 1H), 2.79 (s, 1H), 2.81 (m, 1H), 2.97 (m, 2H), 3.26 (dd, J=14.92, 3.05 Hz, 1H), 3.95 (d, J=4.41 Hz, 2H), 4.19 (s, 1H), 5.30 (m, 2H), 5.40 (m, 2H), 5.82 (d, J=8.48 Hz, 1H), 7.23 (m, 5H), 7.40 (d, J=7.46 Hz, 1H), 7.74 (m, 6H), 8.15 (s, 1H), 8.57 (d, J=4.75 Hz, 1H)

Example 485

$^1$H NMR (300 MHz, CDCl$_3$) δ ppm 0.60 (d, J=6.78 Hz, 3H), 0.83 (s, 1H), 0.85 (m, 9H), 1.26 (s, 1H), 1.86 (s, 1H), 2.12 (m, 1H), 2.92 (d, J=8.14 Hz, 2H), 3.05 (d, J=4.75 Hz, 1H), 3.12 (d, J=8.14 Hz, 2H), 3.19 (m, 1H), 3.80 (s, 1H), 3.91 (s, 1H), 4.12 (s, 1H), 5.09 (s, 1H), 5.23 (s, 2H), 6.28 (s, 1H), 7.21 (dd, J=13.39, 6.61 Hz, 7H), 7.30 (m, 1H), 7.71 (d, J=8.14 Hz, 2H), 7.78 (d, J=8.48 Hz, 2H), 8.16 (s, 1H)

Example 486

$^1$H NMR (300 MHz, CDCl$_3$) δ ppm 0.88 (d, J=6.44 Hz, 3H), 0.92 (d, J=6.44 Hz, 2H), 1.90 (m, 1H), 2.10 (s, 6H), 3.02 (m, 1H), 3.17 (m, 3H), 3.97 (m, 1H), 4.09 (d, J=14.92 Hz, 1H), 4.19 (m, 1H), 4.28 (m, 1H), 6.96 (m, 5H), 7.05 (d, J=8.48 Hz, 1H), 7.23 (m, 6H), 7.30 (s, 1H), 7.71 (d, J=8.48 Hz, 2H), 7.80 (d, J=8.48 Hz, 2H), 8.02 (s, 1H), 8.15 (s, 1H)

Example 487

$^1$H NMR (300 MHz, CDCl$_3$) δ ppm 0.61 (d, J=6.78 Hz, 3H), 0.83 (d, J=6.78 Hz, 3H), 0.87 (d, J=6.78 Hz, 6H), 1.86 (m, 1H), 2.10 (d, J=5.76 Hz, 1H), 2.90 (m, 2H), 3.04 (m, 1H), 3.10 (d, J=7.80 Hz, 2H), 3.15 (d, J=4.07 Hz, 1H), 3.83 (dd, J=8.31, 3.90 Hz, 1H), 3.89 (dd, J=8.14, 5.43 Hz, 1H), 4.19 (m, 1H), 4.89 (d, J=1.36 Hz, 1H), 5.07 (s, 2H), 6.23 (d, J=8.14 Hz, 1H), 7.20 (m, 5H), 7.33 (m, 5H), 7.60 (s, 1H), 7.71 (d, J=8.48 Hz, 2H), 7.80 (d, J=8.48 Hz, 2H), 8.15 (s, 1H)

Example 488

$^1$H NMR (300 MHz, CDCl$_3$) δ ppm 0.89 (t, J=6.44 Hz, 6H), 1.08 (d, J=6.44 Hz, 3H), 1.84 (dd, J=14.24, 7.12 Hz, 1H), 2.80 (dd, J=14.24, 10.17 Hz, 2H), 2.97 (m, 2H), 3.11 (m, 5H), 3.86 (m, 1H), 3.96 (dd, J=7.80, 1.70 Hz, 1H), 4.20 (m, J=4.75 Hz, 2H), 5.10 (s, 2H), 5.40 (d, J=6.78 Hz, 1H), 6.60 (d, J=7.80

Hz, 1H), 7.21 (m, 4H), 7.34 (m, 5H), 7.72 (d, J=8.48 Hz, 2H), 7.80 (d, J=8.48 Hz, 2H), 8.16 (s, 1H)

Example 489

$^1$H NMR (300 MHz, CDCl$_3$) δ ppm 0.87 (dd, J=6.78, 5.09 Hz, 3H), 0.92 (m, 3H), 1.65 (s, 2H), 1.85 (d, J=2.71 Hz, 4H), 2.11 (m, 3H), 2.11 (m, 2H), 3.46 (m, 1H), 3.85 (m, 6H), 4.13 (dd, J=10.17, 6.10 Hz, 1H), 5.04 (m, 1H), 5.22 (s, 1H), 7.26 (m, 5H), 7.74 (m, 4H), 8.16 (s, 1H)

Example 490

$^1$H NMR (300 MHz, CDCl$_3$) δ ppm 0.84 (d, J=6.44 Hz, 3H), 0.89 (d, J=6.78 Hz, 3H), 1.81 (s, 1H), 2.82 (m, 1H), 2.98 (m, 2H), 3.15 (m, 1H), 3.83 (s, 2H), 4.88 (m, 3H), 6.32 (s, 1H), 6.90 (m, 1H), 7.26 (m, 6H), 7.37 (m, J=5.43, 5.43 Hz, 1H), 7.70 (d, J=8.48 Hz, 2H), 7.76 (d, J=8.82 Hz, 2H), 8.17 (m, 2H)

Example 491

$^1$H NMR (300 MHz, CDCl$_3$) δ ppm 0.87 (dd, J=10.34, 6.61 Hz, 6H), 1.88 (m, 1H), 2.95 (m, 6H), 3.19 (m, 1H), 3.75 (m, 1H), 3.88 (s, 1H), 4.13 (s, 1H), 5.29 (m, 2H), 5.71 (s, 1H), 6.44 (m, 1H), 7.20 (t, J=7.46 Hz, 4H), 7.42 (m, 3H), 7.72 (q, J=8.48 Hz, 4H), 7.85 (m, 1H), 8.15 (s, 1H), 8.61 (d, J=4.75 Hz, 1H)

Example 492

$^1$H NMR (300 MHz, CDCl$_3$) δ ppm 0.79 (dd, J=6.10, 3.39 Hz, 6H), 0.88 (dd, J=6.44, 3.05 Hz, 6H), 1.42 (s, 9H), 1.89 (m, 1H), 2.89 (m, 4H), 3.09 (m, 5H), 3.84 (s, 2H), 4.15 (s, 1H), 4.61 (s, 1H), 6.25 (d, J=7.46 Hz, 1H), 7.26 (m, 5H), 7.75 (m, 4H), 8.15 (s, 1H)

Example 493

$^1$H NMR (300 MHz, CDCl$_3$) δ ppm 0.77 (t, J=6.95 Hz, 6H), 0.88 (d, J=6.44 Hz, 6H), 1.01 (s, 1H), 1.84 (s, 2H), 2.90 (s, 4H), 3.06 (s, 4H), 3.84 (s, 1H), 3.93 (s, 1H), 4.15 (m, 1H), 4.87 (s, 1H), 5.07 (s, 2H), 6.24 (s, 1H), 7.21 (m, 5H), 7.36 (m, 5H), 7.71 (d, J=7.80 Hz, 2H), 7.80 (m, 2H), 8.15 (s, 1H)

Example 494

$^1$H NMR (300 MHz, CDCl$_3$) δ ppm 0.88 (d, J=6.78 Hz, 3H), 0.92 (d, J=6.44 Hz, 3H), 1.85 (m, 1H), 2.79 (s, 3H), 2.87 (m, 2H), 2.98 (dd, J=12.55, 4.41 Hz, 1H), 3.07 (m, 1H), 3.16 (m, 3H), 3.89 (d, J=7.80 Hz, 2H), 4.41 (t, J=5.43 Hz, 2H), 4.95 (s, 1H), 7.27 (m, 5H), 7.59 (m, 1 H), 7.72 (d, J=8.48 Hz, 2H), 7.79 (m, 2H), 8.17 (s, 1H)

Example 495

$^1$H NMR (300 MHz, CDCl$_3$) δ ppm 0.88 (dd, J=6.61, 4.24 Hz, 6H), 0.92 (d, J=6.78 Hz, 1H), 1.43 (s, 9H), 1.86 (m, 1H), 2.89 (s, 3H), 2.93 (m, 3H), 2.99 (m, 1H), 3.06 (m, 1H), 3.14 (m, 2H), 3.88 (m, 1H), 4.20 (m, 2H), 5.11 (d, J=8.14 Hz, 1H), 6.58 (d, J=8.14 Hz, 1H), 7.25 (m, 5H), 7.49 (m, 1H), 7.72 (d, J=8.82 Hz, 2H), 7.81 (m, 3H), 8.16 (s, 1H)

Example 496

$^1$H NMR (300 MHz, CDCl$_3$) δ ppm 0.88 (d, J=6.44 Hz, 3H), 0.92 (d, J=6.44 Hz, 3H), 1.43 (s, 1H), 1.66 (m, 2H), 1.86 (d, J=7.12 Hz, 1H), 2.10 (m, 1H), 2.85 (m, 2H), 3.02 (m, 3H), 3.18 (m, 1H), 3.42 (m, 1H), 3.56 (d, J=7.46 Hz, 1H), 3.86 (m, 3H), 4.15 (m, 1H) 4.93 (d, J=8.82 Hz, 1H), 5.02 (d, J=4.07 Hz, 1H), 5.21 (dd, J=6.27, 3.22 Hz, 1H), 7.25 (m, 5H), 7.67 (s, 1H), 7.75 (m, 4H), 8.16 (s, 1H)

Example 497

$^1$H NMR (300 MHz, CDCl$_3$) δ ppm 0.86 (d, J=6.78 Hz, 3H), 0.91 (d, J=6.44 Hz, 3H), 1.34 (m, 1H), 1.84 (s, 2H), 2.17 (s, 1H), 2.85 (m, 2H), 2.94 (d, J=5.76 Hz, 2H), 3.02 (m, 4H), 3.11 (s, 1H), 3.46 (m, 1H), 3.88 (m, 3H), 4.13 (dd, P10.17, 6.44 Hz, 1H), 5.05 (d, J=3.73 Hz, 1H), 5.21 (s, 1H), 7.27 (m, 5H), 7.60 (s, 1H), 7.74 (m, 4H), 8.16 (s, 1H)

Example 498

$^1$H NMR (300 MHz, CD$_3$OD) δ ppm 0.83 (d, J=6.78 Hz, 3H), 0.89 (m, 3H), 1.99 (d, J=7.12 Hz, 1H), 2.67 (dd, J=13.90, 10.51 Hz, 1H), 2.92 (m, 1H), 2.99 (d, J=9.16 Hz, 1H), 3.04 (dd, J=8.48, 4.75 Hz, 1H), 3.12 (dd, J=14.41, 8.31 Hz, 3H), 3.36 (d, J=5.09 Hz, 1H), 3.49 (d, J=11.87 Hz, 1H), 3.83 (m, 1H), 4.05 (s, 1H), 4.52 (dd, J=8.31, 4.92 Hz, 1H), 4.80 (s, 4H), 5.09 (s, 2H), 7.14 (dd, J=8.14, 4.07 Hz, 1H), 7.20 (d, J=4.41 Hz, 4H), 7.30 (d, J=8.82 Hz, 1H), 7.34 (m, 3H), 7.76 (d, J=8.48 Hz, 2H), 7.83 (m, 2H), 8.13 (s, 1H)

Example 499

$^1$H NMR (300 MHz, CD$_3$OD) δ ppm 0.83 (d, J=6.78 Hz, 3H), 0.89 (d, J=6.44 Hz, 3H), 1.63 (m, 1H), 1.75 (m, 1H), 1.99 (s, 3H), 2.01 (m, 1H), 2.31 (m, 2H), 2.66 (dd, J=13.73, 10.68 Hz, 1H), 2.93 (dd, J=14.24, 7.46 Hz, 2H), 3.02 (m, 2H), 3.09 (m, 1H), 3.16 (dd, J=14.07, 3.90 Hz, 1H), 3.45 (d, J=16.95 Hz, 1H), 3.80 (m, 1H), 4.02 (s, 1H), 4.10 (m, 1H), 5.06 (d, J=6.10 Hz, 2H), 7.14 (m, 1H), 7.20 (d, J=4.41 Hz, 5H), 7.31 (m, 4H), 7.77 (d, J=8.48 Hz, 2H), 7.84 (d, J=8.48 Hz, 2H), 8.13 (s, 1H)

Example 500

$^1$H NMR (300 MHz, CD$_3$OD) δ ppm 0.83 (m, 9H), 0.89 (m, 3H), 1.25 (m, 2H), 1.49 (m, 1H), 2.01 (s, 1H), 2.66 (dd, J=13.90, 10.51 Hz, 1H), 2.93 (dd, J=13.56, 7.12 Hz, 2H), 2.99 (d, J=9.16 Hz, 1H), 3.07 (m, 2H), 3.17 (dd, J=13.73, 3.90 Hz, 1H), 3.45 (dd, J=15.26, 2.71 Hz, 1H), 3.79 (m, 1H), 4.01 (dd, J=9.32, 5.93 Hz, 1H), 5.05 (m, 2H), 7.13 (m, 1H), 7.19 (d, J=4.41 Hz, 5H), 7.29 (dd, J=8.31, 5.26 Hz, 5H), 7.76 (d, J=8.14 Hz, 2H), 7.83 (m, 2H), 8.13 (s, 1H)

Example 501

$^1$H NMR (300 MHz, CD$_3$OD) δ ppm 0.82 (s, 9H), 0.84 (d, J=6.78 Hz, 3H), 0.88 (d, J=6.78 Hz, 3H), 1.98 (m, 1H), 2.62 (dd, J=13.90, 10.85 Hz, 1H), 2.95 (dd, J=13.90, 7.12 Hz, 2H), 3.05 (m, 2H), 3.13 (m, 1H), 3.44 (dd, J=14.58, 3.39 Hz, 1H), 3.78 (m, 1H), 3.86 (s, 1H), 4.10 (m, 1H), 5.07 (s, 2H), 7.06 (d, J=7.12 Hz, 1H), 7.13 (t, J=7.29 Hz, 2H), 7.20 (m, 3H), 7.32 (m, 5H), 7.76 (d, J=8.82 Hz, 2H), 7.82 (d, J=8.48 Hz, 2H), 8.13 (s, 1H)

Example 502

$^1$H NMR (300 MHz, CD$_3$OD) δ ppm 0.83 (d, J=6.44 Hz, 3H), 0.89 (m, 3H), 1.43 (m, 6H), 1.93 (s, 1H), 2.59 (t, J=6.95 Hz, 2H), 2.66 (dd, J=13.90, 10.51 Hz, 1H), 2.94 (m, 2H), 3.05 (m, 2H), 3.15 (m, 1H), 3.48 (d, J=15.60 Hz, 1H), 3.79 (m, 1H), 3.96 (m, 1H), 4.05 (d, J=7.12 Hz, 1H), 5.07 (s, 2H), 7.12

(m, 1H), 7.19 (m, 5H), 7.30 (dd, J=8.48, 5.43 Hz, 5H), 7.76 (d, J=8.48 Hz, 2H), 7.84 (d, J=8.48 Hz, 2H), 8.13 (s, 1H)

Example 503

$^1$H NMR (300 MHz, CD$_3$OD) δ ppm 0.83 (d, J=6.78 Hz, 3H), 0.88 (d, J=6.78 Hz, 3H), 1.97 (m, 1H), 2.64 (dd, J=15.09, 9.32 Hz, 1H), 2.71 (d, J=10.17 Hz, 1H), 2.84 (m, 2H), 2.94 (m, 1H), 3.02 (dd, J=8.65, 6.61 Hz, 2H), 3.11 (m, 1H), 3.38 (dd, J=15.09, 2.88 Hz, 1H), 3.79 (m, 1H), 4.04 (m, 1H), 4.25 (dd, J=9.16, 5.09 Hz, 1H), 5.02 (m, 2H), 6.74 (s, 1H), 7.12 (m, 1H), 7.19 (m, 7H), 7.29 (m, 6H), 7.55 (s, 1H), 7.74 (d, J=8.14 Hz, 2H), 7.82 (m, 2H), 8.11 (s, 1H)

Example 504

$^1$H NMR (300 MHz, CD$_3$OD) δ ppm 0.82 (d, J=6.44 Hz, 3H), 0.85 (d, J=6.44 Hz, 3H), 1.92 (m, 1H), 2.01 (s, 1H), 2.65 (dd, J=13.90, 9.83 Hz, 1H), 2.80 (d, J=14.58 Hz, 1H), 2.85 (m, 1H), 2.91 (m, 2H), 2.98 (m, 2H), 3.08 (m, 2H), 3.71 (d, J=9.83 Hz, 1H), 3.99 (s, 1H), 4.32 (m, 1H), 4.97 (d, J=7.12 Hz, 2H), 6.95 (s, 1H), 6.98 (d, J=7.12 Hz, 1H), 7.07 (m, 2H), 7.16 (m, 6H), 7.26 (m, 6H), 7.54 (d, J=7.80 Hz, 1H), 7.73 (d, J=8.48 Hz, 2H), 7.80 (m, 2H), 8.09 (s, 1H)

Example 505

$^1$H NMR (300 MHz, CD$_3$OD) δ ppm 0.82 (d, J=6.78 Hz, 3H), 0.88 (d, J=6.78 Hz, 3H), 1.05 (d, J=6.10 Hz, 3H), 1.97 (d, J=14.24 Hz, 1H), 2.70 (dd, J=13.90, 10.17 Hz, 1H), 2.91 (dd, J=13.73, 6.95 Hz, 2H), 2.99 (d, J=9.16 Hz, 1H), 3.04 (m, 2H), 3.12 (m, 2H), 3.44 (dd, J=14.92, 3.05 Hz, 1H), 3.68 (d, J=15.60 Hz, 1H), 3.79 (m, 2H), 3.89 (d, J=15.60 Hz, 1H), 4.10 (m, 2H), 5.11 (m, 2H), 7.12 (m, 1H), 7.19 (m, 5H), 7.31 (m, 5H), 7.79 (m, 4H), 8.13 (s, 1H)

Example 506

$^1$H NMR (300 MHz, CD$_3$OD) δ ppm 0.84 (d, J=6.44 Hz, 3H), 0.89 (d, J=6.44 Hz, 3H), 2.01 (s, 2H), 2.44 (dd, J=16.78, 7.97 Hz, 1H), 2.93 (dd, J=14.41, 7.29 Hz, 2H), 3.04 (m, 3H), 3.14 (m, 1H), 3.40 (d, J=2.71 Hz, 1H), 3.57 (s, 3H), 3.79 (m, 1H), 3.98 (s, 1H), 4.40 (t, J=6.95 Hz, 1H), 5.09 (m, 2H), 7.13 (m, 1H), 7.19 (m, 5H), 7.32 (m, 5H), 7.80 (m, 4H), 8.13 (s, 1H)

Example 507

$^1$H NMR (300 MHz, CD$_3$OD) δ ppm 0.70 (d, J=6.78 Hz, 3H), 0.77 (t, J=7.46 Hz, 3H), 1.03 (m, 2H), 1.24 (m, 2H), 1.57 (m, 8H), 2.22 (dd, J=14.92, 7.46 Hz, 1H), 2.66 (dd, J=13.90, 10.85 Hz, 1H), 3.02 (d, J=7.12 Hz, 1H), 3.08 (m, 1H), 3.18 (m, 3H), 3.45 (dd, J=14.92, 3.73 Hz, 1H), 3.80 (dd, J=6.44, 3.39 Hz, 1H), 3.85 (m, 1H), 4.12 (m, 1H), 5.16 (s, 2H), 7.09 (m, 1H), 7.20 (m, 5H), 7.33 (dd, J=6.95, 5.59 Hz, 1H), 7.45 (d, J=7.80 Hz, 1H), 7.79 (m, 4H), 8.13 (s, 1H), 8.50 (d, J=4.07 Hz, 1H)

Example 508

$^1$H NMR (300 MHz, CD$_3$OD) δ ppm 0.70 (d, J=6.78 Hz, 3H), 0.77 (t, J=7.46 Hz, 3H), 0.98 (m, 1H), 1.12 (m, 1H), 1.24 (m, 2H), 1.58 (m, 8H), 2.23 (m, 1H), 2.66 (dd, J=13.90, 10.85 Hz, 1H), 3.05 (m, 2H), 3.19 (m, 2H), 3.44 (s, 3H), 3.45 (m, 1H), 3.81 (m, 1H), 3.85 (d, J=7.12 Hz, 1H), 4.11 (m, 1H), 4.52 (s, 2H), 5.14 (s, 2H), 7.09 (m, 1H), 7.20 (m, 5H), 7.36 (dd, J=15.60, 7.80 Hz, 2H), 7.79 (m, 5H), 8.12 (s, 1H)

Example 509

$^1$H NMR (300 MHz, CD$_3$OD) δ ppm 0.84 (s, 9H), 1.15 (s, 1H), 1.23 (s, 1H), 1.56 (d, J=3.68 Hz, 8H), 2.22 (dd, J=14.71, 6.99 Hz, 1H), 2.65 (dd, J=13.79, 10.48 Hz, 1H), 3.06 (m, 1H), 3.15 (m, 1H), 3.44 (s, 3H), 3.46 (m, 3H), 3.82 (m, 1H), 3.87 (s, 1H), 4.14 (m, 1H), 4.53 (s, 2H), 5.15 (s, 2H), 7.07 (d, J=6.62 Hz, 1H), 7.18 (m, 5H), 7.37 (dd, J=16.73, 7.91 Hz, 2H), 7.79 (m, 5H), 8.13 (s, 1H)

Example 510

$^1$H NMR (300 MHz, CDCl$_3$) δ ppm 0.85 (d, J=6.62 Hz, 3H), 0.89 (d, J=6.62 Hz, 3H), 1.80 (m, 1H), 2.84 (dd, J=13.24, 6.99 Hz, 1H), 2.96 (m, 2H), 3.05 (d, J=5.15 Hz, 2H), 3.14 (m, 1H), 3.85 (s, 2H), 4.93 (d, J=7.35 Hz, 1H), 5.02 (s, 2H), 7.20 (d, J=8.09 Hz, 4H), 7.27 (m, 3H), 7.55 (s, 1H), 7.73 (q, J=8.58 Hz, 4H), 8.17 (s, 1H), 8.56 (dd, J=4.96, 1.65 Hz, 1H)

Example 511

$^1$H NMR (300 MHz, CDCl$_3$) δ ppm 0.86 (d, J=6.62 Hz, 3H), 0.90 (d, J=6.62 Hz, 3H), 1.82 (d, J=7.72 Hz, 1H), 2.84 (dd, J=13.60, 6.99 Hz, 1H), 2.97 (m, 1H), 3.06 (m, 2H), 3.17 (m, 1H), 3.64 (s, 1H), 3.89 (s, 2H), 5.02 (d, J=3.31 Hz, 2H), 7.07 (d, J=4.41 Hz, 2H), 7.28 (m, 5H), 7.70 (d, J=8.46 Hz, 2H), 7.77 (m, 2H), 8.13 (s, 1H), 8.16 (s, 1H), 8.54 (d, J=5.88 Hz, 2H)

Example 512

$^1$H NMR (300 MHz, CDCl$_3$) δ ppm 0.85 (m, 3H), 0.90 (m, 3H), 1.86 (m, 1H), 2.82 (m, 1H), 2.98 (m, 2H), 3.15 (m, 1H), 3.62 (s, 1H), 3.85 (s, 2H), 4.88 (s, 1H), 5.20 (m, 2H), 6.90 (m, 1H), 7.24 (m, 6H), 7.76 (m, 5H), 8.17 (m, 2H), 8.78 (m, 1H)

Example 513

$^1$H NMR (300 MHz, CD$_3$OD) δ ppm 0.85 (d, J=7.46 Hz, 12H), 0.89 (d, J=6.78 Hz, 3H), 1.98 (m, 1H), 2.59 (m, 1H), 2.97 (m, 1H), 3.04 (m, 2H), 3.12 (m, 2H), 3.20 (m, 3H), 3.45 (dd, J=14.92, 3.39 Hz, 1H), 3.63 (s, 3H), 3.78 (m, 1H), 4.09 (m, 1H), 4.14 (s, 1H), 7.03 (m, 2H), 7.18 (m, 6H), 7.31 (m, 1H), 7.76 (m, 2H), 7.82 (d, J=8.82 Hz, 2H), 8.14 (s, 1H)

Example 514

$^1$H NMR (300 MHz, CD$_3$OD) δ ppm 0.63 (s, 9H), 0.81 (d, J=6.78 Hz, 3H), 0.86 (d, J=6.78 Hz, 3H), 1.97 (m, 1H), 2.59 (dd, J=14.58, 11.53 Hz, 1H), 2.89 (m, 1H), 3.06 (m, 2H), 3.21 (d, J=4.07 Hz, 4H), 3.26 (d, J=4.07 Hz, 1H), 3.43 (m, 1H), 3.63 (s, 2H), 3.72 (m, 1H), 4.08 (s, 1H), 4.17 (m, 1H), 6.95 (m, 1H), 7.12 (m, 2H), 7.23 (m, 6H), 7.31 (m, 1H), 7.74 (m, 2H), 7.79 (m, 2H), 8.12 (s, 1H)

Example 515

$^1$H NMR (300 MHz, CD$_3$OD) δ ppm 0.73 (d, J=6.78 Hz, 3H), 0.80 (m, 3H), 0.83 (m, 3H), 0.90 (t, J=5.93 Hz, 3H), 1.00 (m, 1H), 1.69 (m, 1H), 1.97 (m, J=6.78 Hz, 1H), 2.64 (m, 1H), 2.94 (m, 2H), 3.02 (d, J=5.76 Hz, 1H), 3.07 (m, 3H), 3.17 (m, 2H), 3.45 (m, 1H), 3.76 (m, 1H), 3.92 (m, 1H), 4.09 (m, 4H), 7.15 (m, 1H), 7.22 (m, 5H), 7.80 (m, 4H), 8.14 (s, 1H)

Example 516

¹H NMR (300 MHz, CD₃OD) δ ppm 0.73 (d, J=6.78 Hz, 3H), 0.78 (m, 3H), 0.83 (m, 3H), 0.89 (d, J=6.78 Hz, 3H), 0.97 (m, 1H), 1.26 (m, 1H), 1.64 (d, J=6.78 Hz, 1H), 2.00 (m, 1H), 2.62 (m, 1H), 2.94 (m, 1H), 3.03 (m, 1H), 3.08 (m, 1H), 3.13 (d, J=4.41 Hz, 1H), 3.20 (m, 4H), 3.45 (m, 1H), 3.66 (m, 2H), 3.78 (m, 1H), 4.09 (m, 1H), 4.13 (m, 1H), 6.98 (m, 1H), 7.09 (m, 3H), 7.12 (m, 1H), 7.18 (d, J=6.78 Hz, 3H), 7.23 (t, J=3.90 Hz, 1H), 7.31 (m, 1H), 7.76 (m, 2H), 7.83 (m, 2H), 8.13 (s, 1H)

Example 517

¹H NMR (300 MHz, CD₃OD) δ ppm 0.74 (d, J=6.78 Hz, 3H), 0.77 (d, J=7.12 Hz, 3H), 0.84 (m, 3H), 0.89 (d, J=6.44 Hz, 3H), 1.28 (s, 1H), 1.67 (d, J=9.83 Hz, 1H), 2.02 (d, J=5.76 Hz, 1H), 2.62 (dd, J=13.90, 10.85 Hz, 1H), 2.97 (m, 2H), 3.07 (m, 1H), 3.14 (m, 1H), 3.21 (d, J=2.71 Hz, 2H), 3.25 (s, 2H), 3.47 (m, 1H), 3.64 (m, 2H), 3.79 (d, J=3.39 Hz, 1H), 4.08 (m, 1H), 4.13 (d, J=7.12 Hz, 1H), 7.10 (m, 3H), 7.20 (m, 5H), 7.60 (d, J=1.70 Hz, 1H), 7.72 (d, J=8.48 Hz, 1H), 7.80 (m, 4H), 7.96 (d, J=2.03 Hz, 1H), 8.13 (s, 1H)

Example 518

¹H NMR (300 MHz, CD₃OD) δ ppm 0.82 (d, J=6.44 Hz, 3H), 0.89 (d, J=6.78 Hz, 3H), 1.36 (m, 2H), 1.47 (m, 2H), 1.95 (s, 1H), 2.64 (dd, J=13.90, 10.51 Hz, 1H), 2.94 (m, 2H), 3.05 (m, 5H), 3.16 (m, 2H), 3.49 (s, 1H), 3.78 (m, 1H), 3.98 (t, J=7.12 Hz, 1H), 4.08 (m, 1H), 5.08 (m, 2H), 7.14 (m, 1H), 7.19 (m, 5H), 7.30 (dd, J=7.97, 4.92 Hz, 5H), 7.81 (m, 4H), 8.14 (s, 1H)

Example 519

¹H NMR (300 MHz, CDCl₃) δ ppm 0.80 (d, J=6.62 Hz, 3H), 0.86 (s, 3H), 0.95 (s, 9H), 1.81 (dd, J=14.89, 8.27 Hz, 4H), 2.80 (dd, J=13.05, 6.43 Hz, 1H), 2.95 (d, J=5.15 Hz, 2H), 3.04 (d, J=12.87 Hz, 1H), 3.25 (s, 1H), 3.74 (s, 1H), 4.00 (s, 1H), 4.36 (s, 1H), 7.22 (m, 5H), 7.40 (s, 1H), 7.66 (d, J=8.46 Hz, 2H), 7.74 (d, J=8.82 Hz, 2H), 8.16 (s, 1H)

Example 520

¹H NMR (300 MHz, CD₃OD) δ ppm 0.80 (d, J=6.62 Hz, 3H), 0.89 (d, J=6.62 Hz, 3H), 1.95 (m, 1H), 2.53 (dd, J=13.97, 9.93 Hz, 1H), 2.90 (m, 3H), 2.98 (dd, J=9.93, 4.04 Hz, 1H), 3.07 (m, 1H), 3.56 (m, 2H), 3.88 (m, 1H), 7.01 (s, 5H), 7.4 g (m, 4H), 7.78 (m, 4H), 8.08 (s, 1H), 8.15 (s, 1H)

Example 525

¹H NMR (300 MHz, DMSO-d₆) δ ppm 0.67 (d, J=6.44 Hz, 3H), 0.70 (d, J=6.78 Hz, 3H), 0.81 (dd, J=6.61, 3.22 Hz, 6H), 1.94 (m, 2H), 2.42 (dd, J=13.39, 11.02 Hz, 1H), 2.59 (m, 1H), 2.63 (s, 3H), 2.80 (dd, J=13.73, 6.61 Hz, 1H), 2.90 (m, 1H), 3.00 (m, 2H), 3.19 (m, 2H), 3.59 (s, 1H), 3.75 (d, J=10.85 Hz, 1H), 3.83 (s, 3H), 3.89 (d, J=10.17 Hz, 1H), 4.33 (s, 2H), 4.93 (d, J=6.44 Hz, 1H), 7.07 (m, 7H), 7.22 (s, 1H), 7.72 (d, J=8.82 Hz, 2H), 7.87 (d, J=9.49 Hz, 1H)

Example 526

¹H NMR (300 MHz, CDCl₃) δ ppm 0.78 (d, J=6.44 Hz, 3H), 0.81 (d, J=6.78 Hz, 3H), 0.87 (d, J=6.44 Hz, 3H), 0.92 (d, J=6.78 Hz, 3H), 1.51 (s, 1H), 2.13 (m, 1H), 2.68 (t, J=4.41 Hz, 1H), 2.78 (m, 1H), 2.83 (s, 1H), 2.98 (m, 2H), 3.06 (m, 2H), 3.16 (m, 2H), 3.33 (dd, J=3.90, 2.20 Hz, 1H), 3.66 (d, J=10.85 Hz, 1H), 3.76 (m, 1H), 3.86 (m, 1H), 3.87 (s, 3H), 4.17 (m, 1H), 4.25 (d, J=14.92 Hz, 1H), 4.42 (m, 2H), 6.40 (d, J=8.82 Hz, 1H), 6.99 (m, 3H), 7.16 (m, 5H), 7.29 (m, 1H), 7.73 (d, J=8.82 Hz, 2H)

Example 527

¹H NMR (300 MHz, CDCl₃) δ ppm 0.77 (d, J=6.78 Hz, 3H), 0.81 (d, J=6.78 Hz, 3H), 0.86 (d, J=6.44 Hz, 3H), 0.92 (d, J=6.44 Hz, 3H), 1.37 (t, J=7.63 Hz, 3H), 1.54 (s, 1H), 1.85 (m, 1H), 2.13 (m, 1H), 2.28 (t, J=5.76 Hz, 2H), 2.68 (m, 1H), 2.80 (m, 1H), 3.01 (m, 2H), 3.12 (m, 2H), 3.20 (m, 2H), 3.30 (m, 1H), 3.65 (m, 2H), 3.75 (m, 1H), 3.87 (d, J=6.44 Hz, 1H), 3.87 (s, 3H), 4.17 (m, 1H), 4.39 (d, J=14.92 Hz, 1H), 4.46 (d, J=16.28 Hz, 1H), 6.42 (d, J=8.82 Hz, 1H), 6.97 (m, 4H), 7.16 (m, 3H), 7.73 (d, J=8.82 Hz, 2H)

Example 528

¹H NMR (300 MHz, CDCl₃) δ ppm 0.78 (d, J=6.44 Hz, 3H), 0.81 (d, J=6.78 Hz, 3H), 0.87 (d, J=6.78 Hz, 3H), 0.92 (d, J=6.44 Hz, 3H), 1.83 (s, 1H), 2.04 (s, 3H), 2.70 (m, 1H), 2.80 (m, 1H), 2.99 (m, 2H), 3.11 (m, 2H), 3.19 (m, 3H), 3.48 (s, 2H), 3.65 (d, J=10.85 Hz, 1H), 3.76 (s, 1H), 3.87 (s, 3H), 4.17 (m, 1H), 4.39 (d, J=15.60 Hz, 1H), 4.49 (d, J=15.60 Hz, 1H), 4.70 (s, 2H), 6.44 (d, J=9.16 Hz, 1H), 6.99 (d, J=8.82 Hz, 2H), 7.10 (s, 1H), 7.16 (m, 5H), 7.72 (d, J=8.82 Hz, 2H)

Example 529

¹H NMR (300 MHz, CDCl₃) δ ppm 0.78 (d, J=6.44 Hz, 3H), 0.82 (d, J=6.78 Hz, 3H), 0.86 (d, J=6.44 Hz, 3H), 0.92 (d, J=6.44 Hz, 3H), 1.83 (m, 1H), 2.15 (m, 1H), 2.73 (m, 1H), 2.80 (m, 1H), 2.99 (m, 2H), 3.13 (m, 3H), 3.22 (m, 1H), 3.67 (d, J=10.85 Hz, 1H), 3.77 (m, 1H), 3.87 (s, 3H), 4.20 (m, 1H), 4.58 (d, J=15.94 Hz, 1H), 4.73 (d, J=15.94 Hz, 1H), 6.38 (d, J=9.16 Hz, 1H), 6.96 (s, 1H), 6.99 (s, 1H), 7.17 (d, J=3.39 Hz, 1H), 7.21 (m, 5H), 7.31 (d, J=3.39 Hz, 1H), 7.71 (m, 2H), 7.74 (d, J=1.70 Hz, 2H)

Example 530

¹H NMR (300 MHz, CDCl₃) δ ppm 0.78 (m, 6H), 0.87 (d, J=6.78 Hz, 3H), 0.92 (d, J=6.44 Hz, 3H), 1.84 (m, 1H), 2.12 (s, 1H), 2.28 (s, 3H), 2.29 (s, 3H), 2.71 (m, 1H), 2.78 (m, 1H), 2.97 (m, 2H), 3.03 (d, J=2.71 Hz, 2H), 3.07 (d, J=5.43 Hz, 3H), 3.12 (d, J=3.05 Hz, 1H), 3.16 (m, 1H), 3.67 (d, J=10.85 Hz, 1H), 3.77 (s, 1H), 3.87 (s, 3H), 4.12 (d, J=14.92 Hz, 1H), 4.19 (m, 1H), 4.33 (d, J=15.26 Hz, 1H), 6.46 (d, J=8.82 Hz, 1H), 6.97 (d, J=8.82 Hz, 1H), 7.19 (m, 5H), 7.40 (m, 4H), 7.71 (s, 1H), 7.74 (s, 1H)

Example 531

¹H NMR (300 MHz, CDCl₃) δ ppm 0.78 (t, J=6.95 Hz, 6H), 0.86 (d, J=6.44 Hz, 3H), 0.92 (d, J=6.78 Hz, 3H), 1.31 (t, J=7.46 Hz, 3H), 1.83 (m, 1H), 2.10 (m, 1H), 2.65 (m, 1H), 2.78 (m, 1H), 2.93 (m, 4H), 3.03 (m, 1H), 3.16 (m, 1H), 3.27 (m, 1H), 3.65 (m, 1H), 3.74 (m, 1H), 3.87 (s, 3H), 4.17 (m, 1H), 4.44 (q, J=14.69 Hz, 2H), 6.36 (d, J=8.82 Hz, 1H), 6.98 (m, 2H), 7.10 (m, 2H), 7.18 (m, 5H), 7.40 (m, 4H), 7.72 (m, 2H), 7.87 (m, 2H)

Example 532

¹H NMR (300 MHz, CDCl₃) δ ppm 0.77 (t, J=6.61 Hz, 6H), 0.86 (d, J=6.44 Hz, 3H), 0.92 (m, 3H), 1.23 (t, J=7.63

Hz, 3H), 1.83 (m, 1H), 2.11 (m, 1H), 2.62 (s, 3H), 2.68 (m, 1H), 2.78 (dd, J=12.55, 5.76 Hz, 1H), 2.85 (m, 2H), 2.96 (m, 2H), 3.04 (m, 1H), 3.16 (m, 5H), 3.64 (d, J=11.19 Hz, 1H), 3.74 (m, 1H), 3.87 (s, 3H), 4.14 (m, 1H), 4.35 (m, 2H), 6.37 (d, J=9.16 Hz, 1H), 6.98 (m, 2H), 7.16 (m, 5H), 7.72 (m, 2H)

Example 533

$^1$H NMR (300 MHz, CDCl$_3$) δ ppm 0.76 (d, J=6.78 Hz, 3H), 0.79 (d, J=6.78 Hz, 3H), 0.86 (d, J=6.44 Hz, 3H), 0.92 (d, J=6.78 Hz, 3H), 1.83 (m, 1H), 2.10 (m, 1H), 2.41 (s, 3H), 2.60 (s, 3H), 2.67 (m, 1H), 2.78 (m, 1H), 2.96 (dd, J=13.39, 8.65 Hz, 1H), 3.06 (m, 1H), 3.16 (m, 6H), 3.63 (d, J=10.85 Hz, 1H), 3.73 (m, 1H), 3.87 (s, 3H), 4.15 (m, 1H), 4.34 (d, J=3.39 Hz, 2H), 6.38 (d, J=9.16 Hz, 1H), 6.97 (m, 2H), 7.14 (m, 5H), 7.72 (m, 2H)

Example 534

$^1$H NMR (300 MHz, CDCl$_3$) δ ppm 0.81 (m, 6H), 0.87 (d, J=6.78 Hz, 3H), 0.92 (d, J=6.78 Hz, 3H), 1.84 (m, 1H), 2.16 (dd, J=17.63, 6.78 Hz, 1H), 2.78 (m, 3H), 2.94 (d, J=8.48 Hz, 1H), 3.01 (m, 2H), 3.12 (m, 4H), 3.67 (d, J=10.85 Hz, 1H), 3.79 (s, 1H), 3.87 (s, 3H), 4.15 (d, J=15.60 Hz, 1H), 4.20 (s, 1H), 4.41 (d, J=15.94 Hz, 1H), 6.40 (d, J=8.82 Hz, 1H), 6.98 (d, J=9.16 Hz, 2H), 7.19 (m, 5H), 7.33 (d, J=1.70 Hz, 1H), 7.73 (d, J=8.82 Hz, 2H), 7.80 (d, J=1.70 Hz, 1H)

Example 535

$^1$H NMR (300 MHz, CDCl$_3$) δ ppm 0.79 (d, J=6.44 Hz, 6H), 0.87 (d, J=6.78 Hz, 3H), 0.92 (d, J=6.44 Hz, 3H), 1.55 (m, 1H), 1.84 (m, 1H), 2.12 (m, 1H), 2.67 (m, 1H), 2.79 (m, 1H), 2.99 (m, 2H), 3.12 (m, 1H), 3.72 (d, J=10.85 Hz, 1H), 3.78 (m, 1H), 3.85 (d, J=3.05 Hz, 1H), 3.87 (s, 3H), 4.18 (m, 1H), 4.53 (d, J=14.92 Hz, 2H), 4.64 (d, J=14.58 Hz, 2H), 6.39 (d, J=9.16 Hz, 2H), 6.98 (d, J=8.82 Hz, 2H), 7.11 (m, 5H), 7.30 (s, 1H), 7.37 (m, 2H), 7.74 (d, J=8.82 Hz, 2H), 7.86 (m, 1H), 7.92 (m, 1H)

Example 536

$^1$H NMR (300 MHz, CDCl$_3$) δ ppm 0.78 (d, J=3.73 Hz, 3H), 0.81 (d, J=3.39 Hz, 3H), 0.86 (d, J=6.44 Hz, 3H), 0.91 (d, J=6.44 Hz, 3H), 1.83 (m, 1H), 2.15 (m, 1H), 2.73 (m, 1H), 2.79 (m, 1H), 2.97 (m, 1H), 3.06 (m, 3H), 3.17 (m, 4H), 3.67 (d, J=10.85 Hz, 1H), 3.80 (s, 3H), 3.87 (s, 3H), 3.90 (d, J=2.71 Hz, 1H), 4.20 (m, 1H), 4.51 (d, J=15.26 Hz, 1H), 4.76 (d, J=15.26 Hz, 1H), 6.36 (d, J=8.82 Hz, 1H), 6.98 (d, J=9.16 Hz, 2H), 7.16 (m, 5H), 7.32 (m, 4H), 7.72 (d, J=9.16 Hz, 2H)

Example 537

$^1$H NMR (300 MHz, CDCl$_3$) δ ppm 0.79 (d, J=6.78 Hz, 6H), 0.87 (d, J=6.78 Hz, 3H), 0.92 (d, J=6.78 Hz, 3H), 1.83 (m, 1H), 2.15 (m, 1H), 2.77 (m, 4H), 2.97 (m, 3H), 3.04 (m, 3H), 3.12 (m, 2H), 3.70 (s, 3H), 3.78 (m, 1H), 3.87 (s, 3H), 419 (m, 1H), 4.36 (d, J=15.26 Hz, 1H), 4.65 (d, J=15.26 Hz, 1H), 6.41 (d, J=7.12 Hz, 1H), 6.98 (d, J=9.16 Hz, 2H), 7.15 (m, 9H), 7.57 (d, J=7.80 Hz, 1H), 7.72 (d, J=9.16 Hz, 1H)

Example 538

$^1$H NMR (300 MHz, CDCl$_3$) δ ppm 0.80 (d, J=6.44 Hz, 3H), 0.87 (d, J=6.44 Hz, 6H), 0.92 (d, J=6.78 Hz, 3H), 1.83 (dd, J=14.58, 6.78 Hz, 1H), 2.17 (m, 1H), 2.77 (m, 3H), 3.00 (m, 2H), 3.16 (m, 5H), 3.71 (d, J=10.85 Hz, 1H), 3.78 (m, 1H), 3.87 (s, 3H), 3.89 (d, J=3.05 Hz, 1H), 4.20 (m, 1H), 4.53 (d, J=15.26 Hz, 1H), 4.77 (d, J=15.26 Hz, 1H), 6.45 (d, J=8.82 Hz, 1H), 6.98 (d, J=9.16 Hz, 2H), 7.18 (m, 5H), 7.38 (d, J=8.48 Hz, 1H), 7.53 (m, 1H), 7.73 (d, J=8.82 Hz, 2H), 7.80 (d, J=8.14 Hz, 1H), 8.05 (d, J=8.82 Hz, 1H), 8.14 (d, J=8.48 Hz, 1H)

Example 539

$^1$H NMR (300 MHz, CDCl$_3$) δ ppm 0.77 (d, J=6.44 Hz, 3H), 0.81 (d, J=6.44 Hz, 3H), 0.86 (d, J=6.44 Hz, 3H), 0.92 (d, J=6.78 Hz, 3H), 1.70 (m, 2H), 1.83 (m, 1H), 1.94 (m, 3H), 2.13 (m, 1H), 2.29 (m, 1H), 2.69 (m, 2H), 2.80 (m, 2H), 3.00 (m, 2H), 3.11 (m, 2H), 3.19 (m, 1H), 3.49 (m, 1H), 3.64 (d, J=10.85 Hz, 1H), 3.73 (d, J=11.87 Hz, 1H), 3.87 (s, 3H), 4.17 (m, 1H), 4.38 (t, J=15.26 Hz, 2H), 6.41 (d, J=9.16 Hz, 1H), 6.83 (s, 1H), 6.98 (d, J=8.82 Hz, 2H), 7.16 (m, 5H), 7.72 (d, J=8.82 Hz, 1H)

Example 540

$^1$H NMR (300 MHz, CDCl$_3$) δ ppm 0.81 (t, J=6.95 Hz, 6H), 0.87 (d, J=6.78 Hz, 3H), 0.91 (d, J=6.44 Hz, 3H), 1.84 (m, 1H), 2.17 (m, 1H), 2.75 (m, 2H), 2.86 (m, 2H), 2.96 (m, 1H), 3.13 (m, 7H), 3.25 (m, 1H), 3.29 (m, 2H), 3.64 (d, J=10.85 Hz, 1H), 3.79 (m, 1H), 3.87 (s, 3H), 4.20 (m, 1H), 4.39 (d, J=15.94 Hz, 1H), 6.98 (d, J=9.16 Hz, 2H), 7.20 (m, 5H), 7.50 (s, 1H), 7.72 (d, J=9.16 Hz, 2H)

Example 541

$^1$H NMR (300 MHz, CDCl$_3$) δ ppm 0.80 (t, J=6.78 Hz, 6H), 0.87 (m, 3H), 0.92 (d, J=6.78 Hz, 3H), 1.25 (dd, J=6.95, 1.87 Hz, 6H), 1.84 (m, 1H), 2.12 (m, 1H), 2.76 (m, 2H), 2.98 (m, 2H), 3.19 (m, 6H), 3.67 (d, J=10.85 Hz, 1H), 3.78 (m, 2H), 3.87 (s, 3H), 4.19 (m, 1H), 4.42 (d, J=15.60 Hz, 1H), 4.61 (d, J=15.60 Hz, 1H), 6.43 (d, J=9.16 Hz, 1H), 6.98 (d, J=8.82 Hz, 2H), 7.16 (m, 5H), 7.43 (s, 1H), 7.73 (d, J=8.82 Hz, 2H)

Example 542

$^1$H NMR (300 MHz, CDCl$_3$) δ ppm 0.80 (dd, J=9.32, 6.61 Hz, 6H), 0.86 (d, J=6.44 Hz, 3H), 0.92 (d, J=6.44 Hz, 3H), 1.00 (m, 3H), 1.80 (m, 3H), 2.13 (m, 2H), 2.76 (m, 4H), 2.98 (m, 2H), 3.19 (m, 5H), 3.67 (d, J=11.19 Hz, 1H), 3.78 (m, 1H), 3.87 (s, 3H), 4.18 (m, 1H), 4.42 (d, J=15.60 Hz, 1H), 4.60 (m, 1H), 6.49 (d, J=8.82 Hz, 1H), 6.98 (d, J=8.82 Hz, 2H), 7.16 (m, 5H), 7.43 (s, 1H), 7.73 (d, J=9.16 Hz, 2H)

Example 543

$^1$H NMR (300 MHz, CDCl$_3$) δ ppm 0.79 (d, J=4.78 Hz, 3H), 0.82 (d, J=4.78 Hz, 3H), 0.87 (d, J=6.62 Hz, 3H), 0.92 (d, J=6.62 Hz, 3H), 1.84 (m, 1H), 2.16 (s, 1H), 2.75 (m, 1H), 2.82 (d, J=9.19 Hz, 2H), 2.94 (d, J=8.09 Hz, 1H), 3.04 (d, J=3.31 Hz, 2H), 3.16 (m, 4H), 3.68 (d, J=10.66 Hz, 1H), 3.81 (s, 1H), 3.87 (s, 3H), 4.23 (s, 1H), 4.33 (d, J=15.81 Hz, 1H), 4.61 (d, J=15.81 Hz, 1H), 6.42 (s, 1H), 6.90 (m, 1H), 6.98 (m, 2H), 7.19 (m, 5H), 7.48 (m, 1H), 7.72 (m, 2H), 7.79 (d, J=4.04 Hz, 1H)

Example 544

$^1$H NMR (300 MHz, CDCl$_3$) δ ppm 0.81 (t, J=6.95 Hz, 6H), 0.87 (d, J=6.78 Hz, 3H), 0.91 (d, J=6.44 Hz, 3H), 1.84 (m, 1H), 2.17 (m, 1H), 2.75 (m, 1H), 2.93 (m, 3H), 3.13 (m, 5H), 3.30 (m, 1H), 3.64 (d, J=10.85 Hz, 1H), 3.79 (m, 1H), 3.87 (s, 3H), 4.20 (m, 1H), 4.39 (d, J=15.94 Hz, 1H), 4.57 (d, J=16.28 Hz, 1H), 6.44 (d, J=8.82 Hz, 1H), 6.98 (d, J=9.16 Hz, 2H), 7.19 (m, 5H), 7.50 (s, 1H), 7.72 (d, J=9.16 Hz, 2H)

Example 545

$^1$H NMR (300 MHz, CDCl$_3$) δ ppm 0.77 (d, J=6.44 Hz, 3H), 0.81 (d, J=6.78 Hz, 3H), 0.86 (d, J=6.44 Hz, 3H), 0.92 (d, J=6.44 Hz, 3H), 1.84 (m, 1H), 2.13 (m, 1H), 2.75 (m, 2H), 2.97 (m, 2H), 3.12 (m, 4H), 3.21 (m, 3H), 3.65 (d, J=10.85 Hz, 1H), 3.76 (m, 1H), 3.87 (s, 3H), 4.18 (m, 1H), 4.38 (d, J=15.60 Hz, 1H), 4.51 (d, J=16.28 Hz, 1H), 4.62 (s, 2H), 6.45 (d, J=9.16 Hz, 1H), 6.98 (d, J=9.16 Hz, 2H), 7.14 (s, 1H), 7.19 (m, 5H), 7.72 (d, J=8.82 Hz, 2H)

Example 546

$^1$H NMR (300 MHz, CDCl$_3$) δ ppm 0.80 (m, 6H), 0.86 (d, J=6.44 Hz, 3H), 0.92 (d, J=6.44 Hz, 3H), 1.22 (t, J=7.29 Hz, 3H), 1.83 (m, 1H), 2.14 (m, 1H), 2.72 (m, 2H), 2.80 (m, 2H), 2.98 (m, 2H), 3.17 (m, 6H), 3.67 (d, J=10.85 Hz, 1H), 3.76 (m, 1H), 3.87 (s, 3H), 4.18 (m, 1H), 4.42 (d, J=15.60 Hz, 1H), 4.59 (d, J=15.60 Hz, 1H), 6.39 (d, J=9.16 Hz, 1H), 6.98 (d, J=8.82 Hz, 2H), 7.16 (m, 5H), 7.42 (s, 1H), 7.72 (d, J=8.82 Hz, 2H)

Example 547

$^1$H NMR (300 MHz, CDCl$_3$) δ ppm 0.87 (d, J=6.44 Hz, 3H), 0.93 (d, J=6.44 Hz, 3H), 0.95 (s, 9H), 1.11 (m, 1H), 1.83 (dd, J=14.75, 6.61 Hz, 1H), 2.51 (q, J=8.82 Hz, 1H), 2.70 (s, 3H), 2.80 (m, 1H), 3.01 (m, 2H), 3.11 (m, 4H), 3.29 (m, 1H), 3.76 (m, 1H), 3.87 (s, 3H), 3.98 (s, 1H), 4.18 (m, 1H), 4.44 (d, J=7.46 Hz, 2H), 6.11 (d, J=9.49 Hz, 1H), 6.94 (s, 1H), 6.98 (d, J=9.16 Hz, 2H), 7.14 (m, 5H), 7.73 (d, J=9.16 Hz, 2H)

Example 548

$^1$H NMR (300 MHz, CDCl$_3$) δ ppm 0.73 (d, J=6.78 Hz, 3H), 0.84 (dd, J=13.73, 6.95 Hz, 6H), 0.92 (d, J=6.78 Hz, 3H), 0.99 (m, 1H), 1.36 (m, 1H), 1.84 (m, 1H), 1.94 (m, 1H), 2.69 (s, 3H), 2.76 (m, 3H), 2.97 (m, 1H), 3.13 (m, 6H), 3.76 (m, 2H), 3.87 (s, 3H), 4.18 (m, 1H), 4.36 (d, J=15.26 Hz, 1H), 4.46 (d, J=15.26 Hz, 1H), 6.40 (d, J=8.82 Hz, 1H), 6.93 (s, 1H), 6.98 (d, J=9.16 Hz, 2H), 7.16 (m, 5H), 7.73 (d, J=8.82 Hz, 2H)

Example 549

$^1$H NMR (300 MHz, CDCl$_3$) δ ppm 0.90 (d, J=3.39 Hz, 3H), 0.92 (d, J=3.39 Hz, 3H), 1.89 (m, 1H), 2.43 (m, 2H), 2.69 (s, 3H), 2.77 (m, 1H), 2.91 (m, 2H), 3.14 (m, 9H), 3.87 (s, 3H), 4.26 (m, 1H), 4.41 (d, J=12.55 Hz, 1H), 4.71 (m, 1H), 5.23 (s, 1H), 5.85 (s, 1H), 6.79 (d, J=9.16 Hz, 1H), 6.98 (s, 1H), 6.99 (d, J=7.80 Hz, 2H), 7.15 (m, 5H), 7.75 (d, J=8.82 Hz, 2H)

Example 550

$^1$H NMR (300 MHz, CDCl$_3$) δ ppm 0.78 (d, J=6.44 Hz, 3H), 0.81 (d, J=6.78 Hz, 3H), 0.86 (d, J=6.44 Hz, 3H), 0.92 (d, J=6.44 Hz, 3H), 1.84 (m, 1H), 2.11 (m, 1H), 2.71 (m, 2H), 2.79 (m, 2H), 2.96 (m, 1H), 3.02 (m, 1H), 3.16 (m, 7H), 3.65 (d, J=10.85 Hz, 1H), 3.76 (m, 1H), 3.87 (s, 3H), 4.17 (m, 1H), 4.40 (d, J=15.26 Hz, 1H), 4.50 (d, J=15.94 Hz, 1H), 5.33 (s, 2H), 6.41 (d, J=8.82 Hz, 1H), 6.98 (d, J=8.82 Hz, 2H), 7.14 (s, 1H), 7.18 (m, 5H), 7.72 (d, J=9.16 Hz, 2H)

Example 551

$^1$H NMR (300 MHz, CDCl$_3$) δ ppm 0.90 (d, J=6.44 Hz, 6H), 1.67 (s, 2H), 1.89 (m, 2H), 2.09 (m, 2H), 2.40 (m, 1H), 2.70 (s, 3H), 2.81 (dd, J=14.41, 11.02 Hz, 1H), 2.90 (d, J=7.46 Hz, 2H), 3.09 (m, 4H), 3.15 (m, 3H), 3.87 (s, 3H), 4.30 (m, 2H), 4.54 (d, J=15.26 Hz, 1H), 5.52 (s, 1H), 6.10 (s, 1H), 6.74 (d, J=8.82 Hz, 1H), 6.97 (m, 1H), 7.00 (d, J=8.82 Hz, 2H), 7.16 (m, 5H), 7.74 (d, J=9.16 Hz, 2H)

Example 552

$^1$H NMR (300 MHz, CDCl$_3$) δ ppm 0.78 (d, J=6.44 Hz, 3H), 0.82 (d, J=6.44 Hz, 3H), 0.86 (d, J=6.44 Hz, 3H), 0.92 (d, J=6.44 Hz, 3H), 1.84 (m, 1H), 2.13 (m, 1H), 2.70 (m, 1H), 2.78 (m, 1H), 2.99 (m, 2H), 3.14 (m, 5H), 3.68 (d, J=10.85 Hz, 1H), 3.76 (m, 1H), 3.87 (s, 3H), 4.20 (m, 1H), 4.47 (d, J=4.07 Hz, 2H), 6.36 (d, J=9.16 Hz, 1H), 6.61 (s, 1H), 6.98 (d, J=8.82 Hz, 2H), 7.11 (m, 2H), 7.21 (m, 6H), 7.43 (d, J=8.14 Hz, 1H), 7.53 (m, 1H), 7.73 (d, J=9.16 Hz, 2H)

Example 553

$^1$H NMR (300 MHz, CDCl$_3$) δ ppm 0.81 (dd, J=9.83, 6.78 Hz, 6H), 0.87 (d, J=6.78 Hz, 3H), 0.92 (d, J=6.44 Hz, 3H), 1.84 (m, 1H), 2.14 (m, 1H), 2.78 (m, 5H), 3.06 (m, 7H), 3.70 (d, J=11.19 Hz, 1H), 3.82 (d, J=3.39 Hz, 1H), 3.87 (s, 3H), 4.21 (m, 1H), 4.38 (d, J=15.26 Hz, 1H), 4.67 (d, J=15.26 Hz, 1H), 6.43 (d, J=8.82 Hz, 1H), 6.98 (d, J=8.82 Hz, 2H), 7.16 (m, 6H), 7.56 (m, 1H), 7.80 (d, J=8.14 Hz, 1H), 8.03 (s, 1H), 8.12 (d, J=8.48 Hz, 1H), 8.83 (d, J=2.03 Hz, 1H)

Example 554

$^1$H NMR (300 MHz, CDCl$_3$) δ ppm 0.80 (dd, J=6.61, 3.56 Hz, 3H), 0.88 (m, 6H), 0.92 (m, 3H), 1.67 (s, 1H), 1.85 (d, J=6.78 Hz, 1H), 2.03 (m, 2H), 2.16 (m, 1H), 2.59 (m, 1H), 2.79 (m, 2H), 2.90 (m, 1H), 3.10 (m, 4H), 3.66 (m, 1H), 3.80 (d, J=5.76 Hz, 1H), 3.87 (s, 2H), 4.07 (s, 1H), 4.10 (m, 2H), 4.20 (m, 1H), 4.32 (m, 1H), 4.94 (m, 1H), 5.02 (m, 1H), 5.37 (d, J=11.19 Hz, 1H), 6.43 (d, J=8.82 Hz, 1H), 6.98 (m, 2H), 7.19 (m, 5H), 7.73 (m, 2H)

Example 555

$^1$H NMR (300 MHz, CDCl$_3$) δ ppm 0.77 (d, J=6.44 Hz, 3H), 0.81 (d, J=6.78 Hz, 3H), 0.86 (d, J=6.44 Hz, 3H), 0.92 (d, J=6.44 Hz, 3H), 1.85 (m, 1H), 2.14 (s, 3H), 2.70 (m, 2H), 2.79 (m, 2H), 2.99 (m, 2H), 3.17 (m, 5H), 3.66 (d, J=10.85 Hz, 1H), 3.77 (m, 1H), 3.87 (s, 3H), 3.95 (s, 2H), 4.18 (m, 1H), 4.42 (m, 2H), 6.49 (d, J=9.16 Hz, 1H), 6.97 (m, 2H), 7.08 (m, 1H), 7.14 (m, 5H), 7.72 (d, J=9.16 Hz, 2H)

Example 556

$^1$H NMR (300 MHz, CDCl$_3$) δ ppm 0.77 (d, J=6.44 Hz, 3H), 0.81 (d, J=6.44 Hz, 3H), 0.87 (d, J=6.78 Hz, 3H), 0.91 (d, J=6.44 Hz, 3H), 1.85 (m, 1H), 2.14 (m, 1H), 2.72 (m, 1H), 2.80 (m, 2H), 2.95 (m, 1H), 3.07 (m, 2H), 3.16 (m, 2H), 3.24 (m, 1H), 3.66 (d, J=10.85 Hz, 1H), 3.79 (m, 1H), 3.87 (s, 3H), 4.08 (s, 2H), 4.18 (m, 1H), 4.44 (m, 2H), 6.51 (d, J=9.16 Hz, 1H), 6.98 (d, J=9.16 Hz, 2H), 7.14 (s, 1H), 7.18 (m, 5H), 7.72 (d, J=8.82 Hz, 2H)

Example 557

¹H NMR (300 MHz, CDCl₃) δ ppm 0.73 (d, J=6.44 Hz, 3H), 0.85 (m, 9H), 1.88 (m, 1H), 2.23 (s, 3H), 2.88 (m, 5H), 3.12 (m, 7H), 3.60 (d, J=10.51 Hz, 1H), 3.87 (s, 3H), 3.95 (m, 1H), 4.17 (m, 1H), 4.35 (m, 2H), 6.71 (s, 1H), 6.97 (m, 2H), 7.18 (m, 5H), 7.73 (m, 2H)

Example 558

¹H NMR (300 MHz, CDCl₃) δ ppm 0.81 (d, J=6.44 Hz, 3H), 0.87 (d, J=6.78 Hz, 6H), 0.92 (d, J=6.44 Hz, 3H), 1.85 (m, 1H), 2.18 (m, 1H), 2.78 (m, 3H), 3.00 (m, 2H), 3.18 (m, 4H), 3.71 (d, J=10.85 Hz, 1H), 3.78 (s, 1H), 3.87 (d, J=3.05 Hz, 3H), 4.21 (m, 1H), 4.51 (d, J=15.94 Hz, 1H), 4.80 (d, J=15.60 Hz, 1H), 6.43 (d, J=8.82 Hz, 1H), 6.98 (m, 2H), 7.18 (m, 7H), 7.33 (d, J=7.46 Hz, 1H), 7.44 (m, 2H), 7.73 (m, 2H), 8.17 (d, J=8.48 Hz, 1H)

Example 559

¹H NMR (300 MHz, CDCl₃) δ ppm 0.76 (d, J=6.44 Hz, 3H), 0.84 (t, J=6.95 Hz, 6H), 0.91 (d, J=6.44 Hz, 3H), 0.97 (m, 1H), 1.29 (m, 1H), 1.82 (dd, J=14.75, 6.95 Hz, 1H), 1.97 (m, 1H), 2.79 (m, 2H), 2.99 (m, 3H), 3.10 (m, 2H), 3.24 (t, J=7.80 Hz, 2H), 3.76 (d, J=10.85 Hz, 2H), 3.85 (s, 3H), 3.87 (s, 3H), 4.22 (m, 1H), 4.61 (d, J=15.26 Hz, 1H), 4.81 (m, 1H), 6.35 (d, J=8.82 Hz, 1H), 6.98 (m, 2H), 7.15 (m, 6H), 7.35 (m, 3H), 7.71 (m, 2H), 7.79 (m, 1H)

Example 560

¹H NMR (300 MHz, CDCl₃) δ ppm 0.81 (d, J=6.44 Hz, 3H), 0.86 (t, J=6.78 Hz, 6H), 0.92 (d, J=6.44 Hz, 3H), 1.84 (m, 1H), 2.16 (m, 1H), 2.75 (m, 3H), 3.01 (m, 3H), 3.14 (m, 3H), 3.72 (d, J=11.19 Hz, 1H), 3.79 (m, 1H), 3.87 (m, 3H), 398 (s, 3H), 4.19 (m, 1H), 4.45 (s, 1H), 4.79 (d, J=15.26 Hz, 1H), 6.41 (d, J=9.16 Hz, 1H), 6.76 (s, 1H), 6.98 (d, J=9.16 Hz, 2H), 7.18 (m, 6H), 7.50 (t, J=7.46 Hz, 1H), 7.68 (s, 1H), 7.72 (m, 2H), 8.00 (s, 1H), 8.16 (d, J=8.14 Hz, 1H)

Example 561

¹H NMR (300 MHz, CDCl₃) δ ppm 0.79 (t, J=6.10 Hz, 3H), 0.86 (m, 6H), 0.92 (d, J=6.78 Hz, 3H), 1.85 (m, 3H), 2.16 (m, 1H), 2.78 (m, 2H), 3.00 (m, 2H), 3.21 (m, 4H), 3.70 (d, J=10.85 Hz, 1H), 3.78 (m, 1H), 3.87 (s, 3H), 4.22 (d, J=9.49 Hz, 1H), 4.54 (d, J=15.94 Hz, 1H), 4.84 (d, J=15.94 Hz, 1H), 6.40 (d, J=8.82 Hz, 1H), 6.98 (d, J=8.82 Hz, 2H), 7.17 (m, 6H), 7.72 (m, 2H), 7.78 (m, 2H), 8.05 (m, 1H), 8.12 (m, 1H)

Example 562

¹H NMR (300 MHz, CDCl₃) δ ppm 0.91 (d, J=3.73 Hz, 3H), 0.93 (d, J=4.07 Hz, 3H), 1.87 (m, 1H), 2.37 (dd, J=14.58, 6.44 Hz, 1H), 2.49 (m, 1H), 2.63 (d, J=4.75 Hz, 3H), 2.70 (m, 3H), 2.75 (m, 1H), 2.92 (m, 2H), 3.13 (m, 5H), 3.79 (s, 1H), 3.87 (s, 3H), 4.23 (m, 1H), 4.41 (m, 2H), 4.64 (dd, J=8.14, 6.44 Hz, 1H), 5.79 (s, 1H), 6.78 (d, J=9.16 Hz, 1H), 6.99 (m, 3H), 7.16 (m, 6H), 7.75 (m, 2H)

Example 563

¹H NMR (300 MHz, CDCl₃) δ ppm 0.91 (d, J=5.09 Hz, 3H), 0.93 (d, J=4.75 Hz, 3H), 0.99 (t, J=7.29 Hz, 3H), 1.88 (dd, J=13.73, 6.95 Hz, 1H), 2.35 (dd, J=14.58, 6.44 Hz, 1H), 2.48 (q, J=8.48 Hz, 1H), 2.69 (s, 3H), 2.76 (m, 1H), 2.92 (m, 2H), 3.14 (m, 6H), 3.81 (m, 1H), 3.87 (s, 3H), 3.91 (d, J=3.39 Hz, 1H), 4.22 (dd, J=9.66, 5.26 Hz, 1H), 4.41 (m, 2H), 4.64 (dd, J=8.31, 6.61 Hz, 1H), 5.76 (s, 1H), 6.75 (d, J=8.82 Hz, 1H), 6.99 (m, 3H), 7.16 (m, 6H), 7.75 (m, 2H)

Example 564

¹H NMR (300 MHz, CDCl₃) δ ppm 0.77 (d, J=6.78 Hz, 3H), 0.83 (d, J=7.12 Hz, 3H), 0.87 (d, J=6.78 Hz, 3H), 0.92 (d, J=6.44 Hz, 3H), 1.01 (m, 1H), 1.32 (m, 1H), 1.84 (m, 3H), 1.97 (m, 1H), 2.78 (m, 3H), 3.06 (m, 4H), 3.81 (m, 2H), 3.87 (s, 3H), 3.91 (d, J=2.71 Hz, 1H), 4.23 (m, 1H), 4.79 (m, 2H), 6.47 (d, J=8.82 Hz, 1H), 6.97 (m, 2H), 7.15 (m, 6H), 7.27 (s, 1H), 7.59 (m, 1H), 7.75 (m, 2H), 8.15 (d, J=8.48 Hz, 2H), 8.88 (d, J=4.41 Hz, 1H)

Example 565

¹H NMR (300 MHz, CD₃OD) δ ppm 0.73 (d, J=6.44 Hz, 3H), 0.86 (m, 6H), 0.91 (m, 3H), 0.99 (m, 1H), 1.31 (m, 1H), 1.85 (m, 1H), 2.00 (m, 1H), 2.48 (m, 2H), 2.90 (m, 1H), 3.05 (m, 4H), 3.18 (m, 1H), 3.41 (m, 1H), 3.76 (m, 1H), 3.83 (s, 1H), 3.87 (s, 3H), 4.13 (m, 1H), 4.49 (m, 2H), 6.99 (m, 5H), 7.08 (m, 2H), 7.14 (m, 2H), 7.25 (m, 1H), 7.59 (s, 2H), 7.78 (m, 2H), 8.16 (s, 1H)

Example 566

¹H NMR (300 MHz, CDCl₃) δ ppm 0.76 (t, J=6.61 Hz, 3H), 0.80 (d, J=6.78 Hz, 3H), 1.16 (d, J=6.44 Hz, 1H), 1.29 (d, J=11.19 Hz, 1H), 1.59 (m, 8H), 2.13 (m, 2H), 2.71 (m, 1H), 2.90 (m, 1H), 3.11 (m, 4H), 3.48 (d, J=5.76 Hz, 3H), 3.67 (d, J=10.85 Hz, 1H), 3.80 (m, 1H), 3.86 (d, J=3.73 Hz, 3H), 3.88 (s, 1H), 4.23 (m, 1H), 4.45 (q, J=15.60 Hz, 2H), 4.70 (d, J=4.07 Hz, 2H), 6.53 (d, J=8.82 Hz, 1H), 6.98 (m, 2H), 7.11 (d, J=2.37 Hz, 1H), 7.20 (m, 6H), 7.72 (d, J=9.16 Hz, 2-H)

Example 567

¹H NMR (300 MHz, CD₃OD) δ ppm 0.74 (d, J=6.44 Hz, 3H), 0.88 (m, 6H), 0.90 (m, 3H), 1.02 (m, 1H), 1.41 (m, 1H), 1.88 (m, 1H), 1.98 (m, 1H), 2.51 (dd, J=13.73, 11.36 Hz, 1H), 2.62 (m, 1H), 2.90 (dd, J=13.73, 6.95 Hz, 1H), 3.00 (dd, J=14.41, 8.65 Hz, 2H), 3.13 (m, 3H), 3.24 (m, 2H), 3.41 (dd, J=14.58, 3.73 Hz, 1H), 3.77 (m, 1H), 3.87 (d, J=11.19 Hz, 1H), 3.87 (s, 3H), 4.16 (m, 1H), 4.52 (d, J=15.94 Hz, 1H), 4.78 (m, 1H), 7.08 (m, 4H), 7.16 (m, 3H), 7.46 (d, J=8.48 Hz, 1H), 7.59 (m, 1H), 7.76 (m, 3H), 7.92 (d, J=8.14 Hz, 1H), 8.02 (d, J=8.48 Hz, 1H), 8.33 (d, J=8.48 Hz, 1H)

Example 568

¹H NMR (300 MHz, CDCl₃) δ ppm 0.76 (d, J=6.78 Hz, 3H), 0.82 (t, J=7.29 Hz, 3H), 0.96 (m, 1H), 1.18 (m, 1H), 1.29 (m, 2H), 1.59 (m, 8H), 1.95 (m, 1H), 2.10 (dd, J=15.26, 7.80 Hz, 1H), 2.77 (m, 2H), 2.91 (dd, J=13.22, 7.12 Hz, 1H), 3.06 (m, 3H), 3.17 (m, 2H), 3.77 (m, 1H), 3.80 (s, 3H), 3.87 (s, 3H), 4.24 (m, 1H), 4.50 (d, J=15.26 Hz, 1H), 4.76 (d, J=15.26 Hz, 1H), 6.38 (d, J=9.16 Hz, 1H), 6.98 (m, 2H), 7.15 (m, 6H), 7.31 (m, 3H), 7.72 (m, 2H), 7.75 (m, 1H)

Example 569

¹H NMR (300 MHz, DMSO-d₆) δ ppm 0.62 (d, J=6.44 Hz, 3H), 0.78 (m, 6H), 0.82 (d, J=3.05 Hz, 3H), 0.89 (m, 1H), 1.73 (s, 1H), 1.97 (m, 1H), 2.41 (dd, J=13.73, 11.02 Hz, 1H), 2.61 (t, J=7.12 Hz, 1H), 2.80 (dd, J=13.90, 6.78 Hz, 1H), 2.97 (m, 3H), 3.10 (m, 1H), 3.21 (dd, J=14.58, 2.37 Hz, 1H), 3.38 (s, 3H), 3.44 (m, 1H), 3.51 (s, 1H), 3.60 (m, 1H), 3.83 (s, 3H), 3.89 (m, 2H), 4.37 (s, 2H), 4.68 (s, 2H), 4.93 (d, J=6.44 Hz, 1H), 7.07 (m, 7H), 7.41 (s, 1H), 7.72 (d, J=8.82 Hz, 2H), 7.87 (d, J=9.16 Hz, 1H)

Example 570

$^1$H NMR (300 MHz, CDCl$_3$) δ ppm 0.76 (d, J=6.44 Hz, 3H), 0.86 (dd, J=8.82, 6.78 Hz, 6H), 0.92 (d, J=6.78 Hz, 3H), 1.02 (m, 1H), 1.35 (m, 1H), 1.84 (m, 1H), 1.97 (d, J=10.85 Hz, 1H), 2.79 (m, 1H), 2.88 (s, 3H), 2.96 (s, 3H), 3.08 (m, 2H), 3.79 (m, 2H), 3.87 (s, 3H), 4.20 (m, 2H), 4.49 (d, J=15.60 Hz, 1H), 6.41 (d, J=8.82 Hz, 1H), 6.98 (m, 2H), 7.18 (m, 5H), 7.47 (m, 3H), 7.58 (m, 1H), 7.73 (m, 2H), 8.02 (s, 1H)

Example 571

$^1$H NMR (300 MHz, CDCl$_3$) δ ppm 0.87 (d, J=6.44 Hz, 3H), 0.92 (d, J=6.44 Hz, 3H), 0.96 (s, 9H), 1.84 (m, 1H), 2.56 (q, J=8.93 Hz, 1H), 2.71 (dd, J=14.41, 10.68 Hz, 1H), 2.82 (m, 1H), 2.97 (m, 2H), 3.10 (m, 4H), 3.29 (m, 1H), 3.56 (dd, J=7.80, 5.43 Hz, 1H), 3.82 (m, 3H), 3.87 (d, J=4.07 Hz, 3H), 3.97 (d, J=11.53 Hz, 1H), 4.24 (m, 1H), 4.57 (d, J=15.26 Hz, 1H), 4.75 (m, 1H), 6.13 (d, J=9.16 Hz, 1H), 6.99 (m, 2H), 7.12 (m, 5H), 7.32 (m, 3H), 7.72 (m, 2H), 7.76 (m, 1H)

Example 572

$^1$H NMR (300 MHz, CDCl$_3$) δ ppm 0.89 (d, J=6.78 Hz, 3H), 1.90 (d, J=6.44 Hz, 1H), 2.31 (s, 1H), 2.68 (m, 3H), 2.79 (s, 2H), 2.89 (t, J=7.80 Hz, 2H), 3.08 (m, 4H), 3.25 (m, 1H), 3.49 (s, 1H), 3.75 (s, 1H), 3.87 (s, 3H), 3.91 (d, J=7.46 Hz, 1H), 3.97 (t, J=4.75 Hz, 2H), 4.46 (d, J=13.90 Hz, 5H), 6.97 (m, 4H), 7.20 (m, 5H), 7.75 (m, 2H), 7.98 (m, 1H)

Example 573

$^1$H NMR (300 MHz, CDCl$_3$) δ ppm 0.86 (m, 6H), 1.87 (m, 2H), 2.65 (s, 1H), 2.69 (s, 3H), 2.88 (m, 2H), 3.05 (m, 1H), 3.27 (m, 2H), 3.57 (dd, J=14.07, 7.63 Hz, 2H), 3.57 (dd, J=14.07, 7.63 Hz, 1H), 3.86 (d, J=3.39 Hz, 3H), 3.92 (m, 1H), 4.23 (dd, J=14.41, 4.92 Hz, 1H), 4.33 (m, 2H), 4.43 (m, 2H), 4.51 (d, J=2.37 Hz, 1H), 4.73 (d, J=11.19 Hz, 2H), 5.43 (s, 1H), 6.98 (m, 5H), 7.16 (m, 3H), 7.22 (d, J=6.10 Hz, 1H), 7.59 (m, 1H), 7.73 (m, 2H)

Example 574

$^1$H NMR (300 MHz, CDCl$_3$) δ ppm 0.75 (d, J=6.44 Hz, 3H), 0.85 (m, 6H), 0.92 (d, J=6.44 Hz, 3H), 0.99 (m, 1H), 1.39 (d, J=25.77 Hz, 1H), 1.86 (m, 1H), 1.96 (s, 1H), 2.73 (m, 1H), 2.79 (m, 2H), 2.96 (m, 1H), 3.01 (m, 1H), 3.14 (m, 5H), 3.48 (s, 3H), 3.76 (m, 2H), 3.88 (m, 3H), 4.19 (d, J=9.49 Hz, 1H), 4.35 (d, J=15.60 Hz, 1H), 4.55 (s, 2H), 4.58 (m, 1H), 6.40 (d, J=8.82 Hz, 1H), 6.98 (m, 2H), 7.12 (d, J=8.14 Hz, 1H), 7.19 (m, 5H), 7.31 (d, J=7.46 Hz, 1H), 7.67 (t, J=7.63 Hz, 1H), 7.72 (m, 2H)

Example 575

$^1$H NMR (300 MHz, CDCl$_3$) δ ppm 0.79 (m, 9H), 0.86 (t, J=7.29 Hz, 3H), 1.02 (m, 1H), 1.43 (m, 2H), 1.83 (m, 1H), 2.02 (d, J=13.56 Hz, 1H), 2.34 (d, J=5.09 Hz, 3H), 2.85 (m, 3H), 3.08 (m, 5H), 3.78 (d, J=10.85 Hz, 1H), 3.87 (s, 3H), 3.95 (m, 1H), 4.20 (m, 2H), 4.51 (d, J=16.28 Hz, 1H), 4.64 (d, J=3.39 Hz, 1H), 6.57 (d, J=7.80 Hz, 1H), 6.98 (m, 2H), 7.10 (dd, J=5.09, 1.70 Hz, 1H), 7.18 (m, 5H), 7.72 (m, 3H), 8.55 (d, J=5.09 Hz, 1H)

Example 576

$^1$H NMR (300 MHz, DMSO-d$_6$) δ ppm 0.63 (d, J=6.44 Hz, 3H), 0.81 (m, 9H), 0.93 (m, 1H), 1.29 (m, 1H), 1.75 (s, 1H), 1.95 (m, 1H), 2.41 (dd, J=13.56, 10.85 Hz, 1H), 2.59 (m, 1H), 2.80 (dd, J=13.56, 6.78 Hz, 1H), 2.92 (dd, J=13.90, 8.48 Hz, 2H), 3.07 (m, 1H), 3.21 (m, 1H), 3.59 (m, 1H), 3.84 (s, 3H), 3.88 (m, 2H), 4.47 (d, J=3.05 Hz, 2H), 4.93 (d, J=6.44 Hz, 1H), 6.98 (m, 1H), 7.07 (dd, J=14.92, 8.14 Hz, 7H), 7.48 (m, 1H), 7.57 (s, 1H), 7.72 (m, 2H), 7.91 (m, 1H), 7.96 (m, 1H), 8.11 (d, J=7.80 Hz, 1H), 8.63 (d, J=4.07 Hz, 1H)

Example 577

$^1$H NMR (300 MHz, CDCl$_3$) δ ppm 0.75 (d, J=6.25 Hz, 3H), 0.86 (m, 6H), 0.92 (d, J=6.62 Hz, 3H), 1.00 (m, 1H), 1.37 (m, 1H), 1.84 (m, 1H), 1.96 (m, 1H), 2.76 (m, 2H), 2.97 (m, 1H), 3.02 (dd, J=11.95, 3.13 Hz, 1H), 3.10 (m, 2H), 3.27 (m, 2H), 3.76 (m, 2H), 3.87 (m, 4H), 4.13 (m, 1H), 4.20 (m, 1H), 4.52 (m, 2H), 6.40 (d, J=9.19 Hz, 1H), 6.97 (m, 2H), 7.16 (m, 6H), 7.37 (dd, J=8.46, 4.41 Hz, 1H), 7.73 (m, 2H), 8.21 (m, 1H), 8.65 (dd, J=4.78, 1.84 Hz, 1H), 9.15 (d, J=2.21 Hz, 1H)

Example 578

$^1$H NMR (300 MHz, CDCl$_3$) δ ppm 0.88 (d, J=6.62 Hz, 3H), 0.93 (d, J=6.62 Hz, 3H), 0.95 (s, 9H), 1.84 (dd, J=7.91, 6.43 Hz, 1H), 2.52 (q, J=8.82 Hz, 1H), 2.69 (dd, J=14.16, 10.48 Hz, 1H), 2.79 (m, 1H), 2.97 (m, 1H), 3.06 (m, 1H), 3.17 (m, 2H), 3.18 (m, 1H), 3.30 (m, 1H), 3.49 (s, 3H), 3.75 (m, 1H), 3.85 (d, J=2.57 Hz, 1H), 3.87 (s, 3H), 3.98 (s, 1H), 4.20 (m, 1H), 4.47 (m, 2H), 4.71 (s, 2H), 6.14 (d, J=8.82 Hz, 1H), 6.98 (m, 2H), 7.11 (s, 1H), 7.15 (m, 5H), 7.73 (m, 2H)

Example 579

$^1$H NMR (300 MHz, DMSO-d$_6$) δ ppm 0.83 (m, 15H), 1.96 (m, 1H), 2.22 (m, 1H), 2.36 (dd, J=13.24, 11.40 Hz, 1H), 2.81 (m, 2H), 2.93 (dd, J=15.26, 5.70 Hz, 1H), 3.02 (m, 3H), 3.15 (m, 3H), 3.83 (s, 3H), 3.99 (s, 1H), 4.49 (m, 2H), 6.94 (m, 1H), 7.07 (m, 7H), 7.56 (dd, J=7.54, 5.33 Hz, 1H), 7.61 (s, 1H), 7.72 (m, 2H), 7.98 (d, J=9.56 Hz, 1H), 8.33 (m, 1H), 8.67 (dd, J=4.78, 1.47 Hz, 1H), 9.15 (d, J=1.47 Hz, 1H)

Example 580

$^1$H NMR (500 MHz, DMSO-d$_6$) δ ppm 0.62 (m, 3H), 0.78 (m, 6H), 0.82 (m, 3H), 0.92 (m, 1H), 1.27 (m, 1H), 1.75 (m, 1H), 1.95 (m, 1H), 2.42 (dd, J=13.43, 10.99 Hz, 1H), 2.60 (m, 1H), 2.71 (s, 3H), 2.81 (m, 1H), 2.92 (dd, J=14.04, 8.54 Hz, 1H), 2.97 (dd, J=9.46, 5.80 Hz, 1H), 3.02 (m, 1H), 3.09 (m, 1H), 320 (m, 1H), 3.35 (d, J=8.54 Hz, 1H), 3.58 (m, 1H), 3.84 (s, 3H), 3.86 (m, 1H), 3.92 (m, 1H), 4.43 (m, 2H), 4.92 (d, J=6.71 Hz, 1H), 6.99 (t, Hz, 1H), 7.08 (m, 8H), 7.43 (s, 1H), 7.72 (d, J=8.54 Hz, 2H), 7.86 (d, J=9.77 Hz, 1H)

Example 581

$^1$H NMR (300 MHz, DMSO-d$_6$) δ ppm 0.62 (t, J=6.62 Hz, 3H), 0.80 (m, 9H), 0.91 (m, 1H), 1.24 (t, J=7.54 Hz, 3H), 1.73 (d, J=8.09 Hz, 1H), 1.95 (m, 1H), 2.41 (dd, J=13.42, 11.21 Hz, 1H), 2.60 (m, 1H), 2.80 (m, 1H), 2.92 (dd, J=13.79, 8.64 Hz, 2H), 3.04 (m, 4H), 3.08 (m, 1H), 3.21 (m, 3H), 3.58 (m, 1H), 3.84 (s, 3H), 3.87 (m, 1H), 4.51 (m, 2H), 4.93 (m, 1H), 6.97 (m, 1H), 7.07 (m, 5H), 7.66 (s, 1H), 7.70 (m, 2H), 7.73 (m, 2H), 7.90 (d, J=9.56 Hz, 1H), 8.59 (d, J=5.15 Hz, 1H)

Example 582

$^1$H NMR (300 MHz, CD$_3$OD) δ ppm 0.73 (d, J=6.62 Hz, 3H), 0.85 (dd, J=16.55, 6.99 Hz, 6H), 0.91 (d, J=6.62 Hz, 3H), 1.00 (m, 1H), 1.33 (m, 1H), 1.83 (dd, J=11.40, 3.68 Hz, 1H), 2.00 (m, 1H), 2.51 (m, 1H), 2.58 (s, 3H), 2.91 (m, 2H), 3.06 (m, 6H), 3.23 (m, 3H), 3.40 (dd, J=14.71, 3.68 Hz, 1H), 3.75 (m, 1H), 3.82 (s, 1H), 3.87 (s, 3H), 4.11 (m, 1H), 4.54 (m, 2H), 7.01 (m, 1H), 7.09 (m, 5H), 7.40 (d, J=8.82 Hz, 1H), 7.46 (s, 1H), 7.77 (d, J=8.82 Hz, 2H), 8.23 (d, J=2.21 Hz, 1H), 8.26 (d, J=2.57 Hz, 1H), 9.00 (d, J=2.21 Hz, 1H)

Example 583

$^1$H NMR (300 MHz, CDCl$_3$) δ ppm 0.88 (d, J=6.62 Hz, 3H), 0.92 (d, J=6.62 Hz, 3H), 0.96 (s, 9H), 1.84 (m, 1H), 2.60 (q, J=8.70 Hz, 1H), 2.72 (dd, J=14.16, 10.48 Hz, 2H), 2.80 (m, 2H), 2.97 (m, 2H), 3.04 (d, J=3.68 Hz, 1H), 3.13 (m, 6H), 3.32 (m, 1H), 3.80 (m, 1H), 3.85 (t, J=2.94 Hz, 1H), 4.00 (s, 1H), 4.26 (m, 1H), 4.67 (dd, J=65.63, 15.26 Hz, 2H), 6.11 (d, J=9.19 Hz, 1H), 6.99 (m, 2H), 7.11 (m, 5H), 7.23 (m, 1H), 7.73 (m, 2H), 8.01 (dd, J=8.09, 1.47 Hz, 1H), 8.39 (dd, J=4.78, 1.47 Hz, 1H)

Example 584

$^1$H NMR (300 MHz, CDCl$_3$) δ ppm 0.76 (d, J=6.62 Hz, 3H), 0.84 (m, 6H), 0.92 (d, J=6.25 Hz, 3H), 1.33 (m, 2H), 1.83 (m, 2H), 1.97 (m, 2H), 2.78 (m, 3H), 3.01 (m, 2H), 3.14 (m, 2H), 3.80 (m, 3H), 3.87 (s, 3H), 4.10 (m, 1H), 4.23 (m, 1H), 4.49 (d, J=15.08 Hz, 1H), 4.79 (d, J=15.44 Hz, 1H), 6.33 (d, J=8.82 Hz, 2H), 6.98 (m, 2H), 7.16 (m, 7H), 7.73 (m, 2H), 8.00 (dd, J=8.09, 1.47 Hz, 1H), 8.39 (dd, J=4.78, 1.47 Hz, 1H)

Example 585

$^1$H NMR (300 MHz, CD$_3$OD) δ ppm 0.74 (d, J=6.62 Hz, 3H), 0.84 (m, 3H), 0.97 (m, 1H), 1.19 (m, 2H), 1.34 (m, 2H), 1.55 (m, 5H), 1.69 (m, 3H), 1.86 (m, 1H), 2.26 (m, 1H), 2.52 (m, 3H), 3.01 (m, 1H), 3.17 (m, 1H), 3.42 (dd, J=14.71, 4.04 Hz, 1H), 3.79 (m, 2H), 3.87 (s, 3H), 4.13 (m, 1H), 4.56 (d, J=5.52 Hz, 2H), 7.05 (m, 6H), 7.17 (m, 3H), 7.51 (s, 1H), 7.54 (m, 1H), 7.77 (m, 2H), 8.37 (m, 1H), 8.60 (dd, P4.96, 1.65 Hz, 1H), 9.14 (d, J=1.47 Hz, 1H)

Example 586

$^1$H NMR (300 MHz, DMSO-d$_6$) δ ppm 0.58 (d, J=6.62 Hz, 3H), 0.77 (m, 3H), 0.87 (q, J=7.23 Hz, 2H), 0.95 (m, 9H), 1.23 (m, 2H), 1.76 (m, 1H), 2.43 (m, 1H), 2.59 (m, 1H), 2.80 (d, J=14.71 Hz, 1H), 2.97 (m, 3H), 3.09 (m, 1H), 3.21 (d, J=9.56 Hz, 1H), 3.31 (m, 1H), 3.74 (s, 2H), 3.83 (d, J=5.88 Hz, 2H), 4.45 (d, J=15.07 Hz, 2H), 6.97 (m, 1H), 7.07 (m, 7H), 7.56 (m, 1H), 7.60 (s, 1H), 7.75 (m, 2H), 7.87 (d, J=9.19 Hz, 1H), 8.33 (m, 1H), 8.68 (dd, J=4.78, 1.47 Hz, 1H), 9.15 (d, J=1.47 Hz, 1H)

Example 587

$^1$H NMR (300 MHz, CDCl$_3$) δ ppm 0.77 (d, J=6.44 Hz, 3H), 0.82 (d, J=6.78 Hz, 3H), 0.86 (d, J=6.78 Hz, 3H), 0.92 (d, J=6.44 Hz, 3H), 1.84 (m, 1H), 2.14 (m, 1H), 2.75 (m, 3H), 2.99 (m, 3H), 3.19 (m, 4H), 3.66 (d, J=10.85 Hz, 1H), 3.76 (m, 1H), 3.87 (s, 3H), 4.19 (m, 3H), 4.38 (d, J=15.26 Hz, 1H), 4.47 (d, J=15.60 Hz, 1H), 6.48 (d, J=8.82 Hz, 1H), 6.98 (m, 4H), 7.16 (m, 6H), 7.72 (d, J=8.82 Hz, 2H)

Example 588

$^1$H NMR (300 MHz, CDCl$_3$) δ ppm 0.77 (d, J=6.44 Hz, 3H), 0.83 (d, J=6.78 Hz, 3H), 0.86 (d, J=6.78 Hz, 3H), 0.91 (d, J=6.44 Hz, 3H), 1.84 (m, 2H), 2.02 (s, 3H), 2.15 (m, 1H), 2.76 (m, 4H), 2.95 (m, 1H), 3.05 (dd, J=14.92, 3.73 Hz, 1H), 3.18 (m, 3H), 3.65 (d, J=10.85 Hz, 1H), 3.78 (m, 1H), 3.87 (s, 3H), 4.15 (m, 1H), 4.38 (d, J=15.60 Hz, 1H), 4.48 (d, J=15.26 Hz, 1H), 4.70 (d, J=5.43 Hz, 2H), 6.32 (s, 1H), 6.56 (d, J=9.16 Hz, 1H), 6.98 (d, J=8.82 Hz, 2H), 7.05 (s, 1H), 7.16 (m, 5H), 7.71 (d, J=9.16 Hz, 2H)

Example 589

$^1$H NMR (300 MHz, CDCl$_3$) δ ppm 0.75 (s, 3H), 0.82 (d, J=6.78 Hz, 3H), 0.86 (d, J=6.44 Hz, 3H), 0.91 (d, J=6.44 Hz, 3H), 1.84 (m, 1H), 2.15 (m, 1H), 2.71 (m, 1H), 2.75 (m, 2H), 2.81 (m, 1H), 2.95 (m, 1H), 3.04 (dd, J=14.41, 11.36 Hz, 1H), 3.11 (m, 4H), 3.21 (m, 1H), 3.64 (d, J=10.85 Hz, 1H), 3.78 (m, 1H), 3.87 (s, 3H), 4.17 (m, 1H), 4.44 (q, J=15.37 Hz, 2H), 4.92 (s, 2H), 6.55 (d, J=9.16 Hz, 1H), 6.98 (d, J=9.16 Hz, 2H), 7.09 (s, 1H), 7.17 (m, 5H), 7.72 (d, J=9.16 Hz, 2H)

Example 590

$^1$H NMR (300 MHz, CDCl$_3$) δ ppm 0.80 (t, J=6.61 Hz, 6H), 0.86 (d, J=6.44 Hz, 3H), 0.91 (d, J=6.44 Hz, 3H), 1.83 (m, 1H), 2.16 (m, 1H), 2.70 (s, 1H), 2.75 (d, J=2.03 Hz, 6H), 2.80 (m, 1H), 2.94 (m, 1H), 3.00 (dd, J=12.04, 3.22 Hz, 1H), 3.10 (dd, J=9.32, 4.92 Hz, 2H), 3.16 (m, 3H), 3.24 (m, 1H), 3.65 (d, J=10.85 Hz, 1H), 3.78 (m, 1H), 3.87 (s, 3H), 4.19 (m, 1H), 4.28 (s, 2H), 4.49 (m, 2H), 6.45 (d, J=8.82 Hz, 1H), 6.97 (m, 2H), 7.17 (m, 5H), 7.25 (s, 1H), 7.72 (m, 2H)

Example 591

$^1$H NMR (300 MHz, CDCl$_3$) δ ppm 0.77 (d, J=6.78 Hz, 3H), 0.82 (d, J=6.44 Hz, 3H), 0.86 (d, J=6.44 Hz, 3H), 0.90 (d, J=6.44 Hz, 3H), 1.85 (m, 1H), 2.16 (m, 1H), 2.72 (m, 1H), 2.79 (dd, J=13.73, 6.27 Hz, 2H), 2.92 (m, 1H), 2.98 (s, 3H), 3.06 (dd, J=14.24, 3.73 Hz, 2H), 3.18 (m, 4H), 3.64 (d, J=10.85 Hz, 1H), 3.79 (m, 1H), 3.87 (s, 3H), 4.18 (m, 1H), 4.41 (m, 2H), 4.60 (d, J=6.10 Hz, 2H), 5.51 (t, J=6.27 Hz, 1H), 6.61 (d, J=9.16 Hz, 1H), 6.98 (m, 2H), 7.08 (s, 1H), 7.18 (m, 5H), 7.72 (m, 2H)

Example 592

$^1$H NMR (300 MHz, CDCl$_3$) δ ppm 0.75 (d, J=6.44 Hz, 3H), 0.79 (d, J=6.44 Hz, 3H), 0.84 (d, J=6.44 Hz, 3H), 0.91 (d, J=6.78 Hz, 3H), 1.86 (m, 1H), 2.14 (m, 1H), 2.71 (m, 2H), 2.81 (m, 2H), 2.99 (m, 2H), 3.19 (m, 4H), 3.69 (d, J=10.85 Hz, 1H), 3.82 (s, 1H), 3.87 (s, 3H), 4.22 (s, 1H), 4.54 (m, 2H), 6.88 (m, 1H), 6.98 (d, J=8.82 Hz, 2H), 7.13 (d, J=6.10 Hz, 5H), 7.45 (s, 1H), 7.72 (d, J=9.16 Hz, 2H), 8.02 (s, 1H)

Example 593

$^1$H NMR (300 MHz, CDCl$_3$) δ ppm 0.76 (d, J=6.44 Hz, 3H), 0.81 (d, J=6.44 Hz, 3H), 0.86 (d, J=6.78 Hz, 3H), 0.91 (d, J=6.44 Hz, 3H), 1.84 (m, 1H), 2.15 (m, 1H), 2.69 (m, 1H), 2.78 (m, 2H), 2.94 (m, 8.14 Hz, 1H), 2.98 (dd, J=5.76, 2.71 Hz, 1H), 3.04 (d, J=3.05 Hz, 1H), 3.13 (m, 3H), 3.21 (m, 1H), 3.66 (d, J=10.85 Hz, 1H), 3.71 (s, 3H), 3.78 (m, 1H), 3.87 (s, 3H), 4.17 (m, 1H), 4.42 (m, 2H), 4.63 (d, J=6.10 Hz, 2H), 5.53 (s, 1H), 6.60 (d, J=9.16 Hz, 1H), 6.97 (m, 2H), 7.06 (s, 1H), 7.16 (m, 5H), 7.72 (m, 2H)

Example 594

$^1$H NMR (300 MHz, CDCl$_3$) δ ppm 0.79 (dd, J=9.16, 6.44 Hz, 6H), 0.86 (d, J=6.44 Hz, 3H), 0.91 (d, J=6.44 Hz, 3H), 1.83 (dd, J=14.41, 6.61 Hz, 1H), 2.14 (m, 1H), 2.72 (m, 1H), 2.80 (m, 2H), 2.97 (s, 3H), 3.16 (m, 7H), 3.66 (d, J=10.85 Hz, 1H), 3.79 (m, 1H), 3.87 (s, 3H), 4.20 (m, 1H), 4.47 (m, 2H), 4.59 (s, 2H), 6.55 (d, J=9.16 Hz, 1H), 6.98 (d, J=9.16 Hz, 2H), 7.18 (m, 6H), 7.71 (m, 2H)

Example 595

$^1$H NMR (300 MHz, CDCl$_3$) δ ppm 0.80 (m, 6H), 0.86 (d, J=6.44 Hz, 3H), 0.91 (d, J=6.78 Hz, 3H), 1.39 (t, J=7.29 Hz, 6H), 1.83 (m, 1H), 2.15 (m, 1H), 2.73 (m, 2H), 2.82 (m, 2H), 2.95 (m, 1H), 3.05 (dd, J=16.28, 3.73 Hz, 2H), 3.17 (m, 7H), 3.66 (d, J=10.85 Hz, 1H), 3.78 (m, 1H), 3.87 (s, 3H), 4.18 (m, 1H), 4.37 (d, J=15.94 Hz, 1H), 4.57 (s, 2H), 4.57 (m, 1H), 6.52 (d, J=9.16 Hz, 1H), 6.98 (m, 2H), 7.17 (m, 5H), 7.24 (s, 1H), 7.72 (m, 2H)

Example 596

$^1$H NMR (300 MHz, CD$_3$OD) δ ppm 0.76 (d, J=6.44 Hz, 3H), 0.81 (d, J=6.78 Hz, 3H), 0.87 (d, J=6.44 Hz, 3H), 0.90 (d, J=6.78 Hz, 3H), 1.15 (d, J=6.78 Hz, 6H), 1.27 (d, J=8.48 Hz, 1H), 2.02 (m, 2H), 2.51 (dd, J=13.90, 11.19 Hz, 1H), 2.59 (m, 1H), 2.90 (m, 1H), 3.02 (m, 2H), 3.10 (m, 2H), 3.19 (m, 2H), 3.37 (m, 1H), 3.66 (d, J=9.16 Hz, 1H), 3.74 (m, 2H), 3.87 (s, 3H), 3.98 (m, 1H), 4.10 (m, 1H), 4.14 (m, 1H), 7.08 (m, 2H), 7.17 (m, 5H), 7.76 (m, 2H), 7.93 (d, J=9.49 Hz, 1H)

Example 597

$^1$H NMR (300 MHz, CD$_3$OD) δ ppm 0.78 (d, J=6.44 Hz, 6H), 0.86 (d, J=6.78 Hz, 3H), 0.90 (d, J=6.44 Hz, 3H), 2.02 (m, 2H), 2.53 (dd, J=13.73, 11.36 Hz, 1H), 2.67 (m, 1H), 2.81 (s, 3H), 2.88 (dd, J=13.73, 6.95 Hz, 1H), 2.97 (dd, J=14.58, 8.14 Hz, 1H), 3.05 (m, 1H), 3.14 (m, 2H), 3.24 (m, 2H), 3.27 (s, 2H), 3.43 (dd, J=14.75, 3.90 Hz, 1H), 3.72 (d, J=11.19 Hz, 1H), 3.78 (m, 1H), 3.87 (s, 2H), 4.16 (d, J=10.85 Hz, 1H), 4.37 (d, J=15.60 Hz, 1H), 4.55 (s, 1H), 4.64 (m, 1H), 4.80 (s, 2H), 7.07 (m, 2H), 7.17 (m, 4H), 7.51 (s, 1H), 7.76 (m, 2H), 7.93 (d, J=10.17 Hz, 1H)

Example 598

$^1$H NMR (300 MHz, DMSO-d$_6$) δ ppm 0.68 (d, J=6.44 Hz, 3H), 0.71 (d, J=6.78 Hz, 3H), 0.80 (d, J=3.05 Hz, 3H), 0.82 (d, J=3.05 Hz, 3H), 0.87 (m, 1H), 1.96 (d, J=7.12 Hz, 2H), 2.22 (s, 1H), 2.34 (s, 3H), 2.43 (d, J=12.89 Hz, 1H), 2.80 (dd, J=13.73, 6.61 Hz, 1H), 2.95 (m, 3H), 3.59 (s, 1H), 3.76 (d, J=10.85 Hz, 1H), 3.83 (s, 3H), 3.90 (d, J=8.14 Hz, 1H), 4.40 (d, J=5.09 Hz, 1H), 4.47 (s, 2H), 4.93 (d, J=6.44 Hz, 1H), 7.06 (m, 7H), 7.37 (s, 1H), 7.64 (s, 1H), 7.72 (d, J=8.82 Hz, 2H), 7.87 (d, J=9.49 Hz, 1H)

Example 599

$^1$H NMR (300 MHz, CD$_3$OD) δ ppm 0.75 (d, J=6.44 Hz, 3H), 0.85 (t, J=7.29 Hz, 3H), 0.98 (d, J=6.44 Hz, 1H), 1.18 (s, 1H), 1.33 (m, 3H), 1.55 (s, 4H), 1.71 (s, 2H), 1.85 (s, 1H), 2.25 (m, 1H), 2.54 (dd, J=13.73, 11.36 Hz, 1H), 2.71 (m, 1H), 2.99 (m, 1H), 3.05 (m, 1H), 3.12 (d, J=8.82 Hz, 2H), 3.17 (d, J=4.75 Hz, 2H), 3.23 (m, 2H), 3.45 (dd, J=14.75, 4.24 Hz, 1H), 3.80 (dd, J=6.10, 3.73 Hz, 1H), 3.83 (d, J=10.85 Hz, 1H), 3.87 (s, 3H), 4.18 (s, 1H), 4.36 (d, J=15.60 Hz, 1H), 4.47 (s, 2H), 4.63 (m, 1H), 7.08 (m, 2H), 7.13 (d, J=6.10 Hz, 3H), 7.20 (m, 2H), 7.48 (s, 1H), 7.77 (m, 2H)

Example 600

$^1$H NMR (300 MHz, CDCl$_3$) δ ppm 0.76 (d, J=6.44 Hz, 3H), 0.83 (m, 6H), 0.87 (d, J=3.73 Hz, 3H), 0.95 (m, 1H), 1.28 (s, 1H), 1.90 (m, 3H), 3.82 (d, J=10.85 Hz, 1H), 3.86 (s, 3H), 4.27 (m, J=15.26 Hz, 2H), 4.44 (m, 1H), 5.41 (s, 1H), 672 (d, J=8.82 Hz, 1H), 6.96 (d, J=8.82 Hz, 2H), 7.11 (m, 3H), 7.18 (m, 2H), 7.32 (d, P7.46 Hz, 1H), 7.40 (t, J=7.46 Hz, 1H), 7.58 (m, 2H), 7.72 (m, 2H)

Example 601

$^1$H NMR (300 MHz, CDCl$_3$) δ ppm 0.90 (d, J=6.78 Hz, 6H), 1.70 (m, 1H), 1.87 (dd, J=13.73, 6.95 Hz, 1H), 2.04 (m, 1H), 2.37 (m, 1H), 2.89 (m, 2H), 2.99 (m, 1H), 3.12 (m, 2H), 3.17 (m, 2H), 3.25 (m, 1H), 3.45 (m, 1H), 3.62 (m, 1H), 3.79 (s, 3H), 3.87 (s, 3H), 3.91 (m, 1H), 4.31 (m, 1H), 4.54 (m, 2H), 4.78 (d, J=15.60 Hz, 1H), 6.75 (d, J=8.82 Hz, 1H), 7.00 (m, 2H), 7.12 (m, 1H), 7.19 (m, 6H), 7.32 (m, 2H), 7.74 (m, 3H)

Example 603

$^1$H NMR (300 MHz, CDCl$_3$) δ ppm 0.78 (d, J=6.78 Hz, 3H), 0.82 (d, J=6.44 Hz, 3H), 0.87 (d, J=6.44 Hz, 3H), 0.94 (d, J=6.44 Hz, 3H), 1.82 (m, 1H), 2.08 (m, 1H), 2.25 (d, J=6.44 Hz, 2H), 2.66 (dd, J=13.90, 10.85 Hz, 1H), 2.78 (dd, J=13.39, 6.61 Hz, 1H), 2.95 (dd, J=12.89, 2.03 Hz, 1H), 3.08 (m, 1H), 3.22 (m, 1H), 3.45 (s, 3H), 3.58 (d, J=17.97 Hz, 1H), 3.81 (m, 1H), 3.88 (s, 3H), 3.88 (m, 1H), 4.23 (m, 1H), 4.69 (m, 2H), 4.76 (d, J=7.12 Hz, 2H), 6.22 (d, J=9.16 Hz, 1H), 6.98 (m, 2H), 7.09 (m, 5H), 7.19 (s, 1H), 7.72 (m, 2H)

Example 604

$^1$H NMR (300 MHz, CDCl$_3$) δ ppm 0.75 (d, J=6.78 Hz, 3H), 0.82 (d, J=6.44 Hz, 3H), 0.87 (d, J=6.78 Hz, 3H), 0.94 (m, 3H), 1.81 (m, 1H), 2.04 (d, J=3.39 Hz, 1H), 2.05 (m, 1H), 2.63 (dd, J=14.07, 10.68 Hz, 1H), 2.77 (dd, J=13.56, 6.44 Hz, 1H), 2.91 (d, J=2.71 Hz, 1H), 2.99 (m, 2H), 3.06 (m, 1H), 3.18 (m, 2H), 3.53 (d, J=17.97 Hz, 1H), 3.80 (m, 2H), 3.88 (s, 3H), 4.22 (m, 1H), 4.62 (m, 2H), 6.05 (d, P9.49 Hz, 1H), 6.97 (s, 1H), 6.98 (m, 5H), 7.05 (m, 2H), 7.33 (m, 1H), 7.42 (m, 1H), 7.72 (m, 2H)

Example 605

$^1$H NMR (300 MHz, CDCl$_3$) δ ppm 0.83 (d, J=6.44 Hz, 3H), 0.86 (d, J=6.78 Hz, 3H), 0.91 (t, J=6.78 Hz, 6H), 1.28 (s, 1H), 1.83 (m, 1H), 2.15 (m, 1H), 2.70 (m, 1H), 2.78 (dd, J=13.39, 6.61 Hz, 1H), 2.98 (m, 1H), 3.08 (dd, J=14.24, 4.41 Hz, 1H), 3.19 (m, 1H), 3.40 (m, 1H), 3.74 (d, J=17.97 Hz, 1H), 3.82 (s, 2H), 3.88 (s, 3H), 3.92 (d, P10.85 Hz, 1H), 4.25 (m, 1H), 4.98 (m, 2H), 6.17 (d, J=9.49 Hz, 1H), 6.98 (m, 2H), 7.15 (m, 5H), 7.33 (d, J=8.48 Hz, 1H), 7.49 (m, 1H), 7.65 (m, 1H), 7.72 (m, 2H), 7.77 (d, J=7.80 Hz, 1H), 7.95 (d, J=8.48 Hz, 1H), 8.13 (d, J=8.48 Hz, 1H)

Example 606

$^1$H NMR (300 MHz, CDCl$_3$) δ ppm 0.77 (d, J=6.44 Hz, 3H), 0.80 (d, J=6.78 Hz, 3H), 0.86 (d, J=6.44 Hz, 3H), 0.92

(m, 3H), 1.83 (m, 1H), 2.08 (m, 1H), 2.71 (dd, J=13.90, 10.85 Hz, 1H), 2.81 (m, 1H), 2.97 (m, 2H), 3.06 (dd, P8.31, 3.56 Hz, 1H), 3.18 (m, 2H), 3.36 (d, J=17.97 Hz, 1H), 3.66 (m, 1H), 3.87 (s, 3H), 3.88 (s, 3H), 3.96 (d, J=10.85 Hz, 1H), 4.28 (m, 1H), 4.90 (m, 2H), 6.39 (d, J=9.49 Hz, 1H), 6.97 (m, 2H), 7.06 (s, 3H), 7.17 (m, 3H), 7.26 (m, 1H), 7.32 (m, 1H), 7.72 (m, 3H)

Example 607

$^1$H NMR (300 MHz, CD$_3$OD) δ ppm 0.79 (d, J=6.44 Hz, 6H), 0.87 (d, J=6.44 Hz, 3H), 0.90 (d, J=6.44 Hz, 3H), 1.27 (m, 3H), 2.02 (m, 1H), 2.47 (dd, J=13.56, 11.53 Hz, 1H), 2.89 (m, 1H), 3.02 (m, 3H), 3.23 (dd, J=13.73, 3.56 Hz, 1H), 3.40 (dd, J=14.92, 3.73 Hz, 1H), 3.71 (d, J=17.97 Hz, 2H), 3.78 (m, 1H), 3.87 (s, 3H), 4.01 (d, J=11.19 Hz, 1H), 4.16 (m, 3H), 4.32 (m, 1H), 7.08 (m, 2H), 7.19 (m, 6H), 7.77 (m, 2H), 8.22 (d, J=9.83 Hz, 1H)

Example 608

$^1$H NMR (300 MHz, CDCl$_3$) δ ppm 0.84 (m, 9H), 0.92 (m, 3H), 1.81 (s, 1H), 2.11 (s, 1H), 2.72 (m, 1H), 2.79 (m, 1H), 2.88 (s, 1H), 3.00 (m, 1H), 3.08 (dd, J=14.24, 4.41 Hz, 1H), 3.18 (m, 1H), 3.41 (d, J=17.97 Hz, 1H), 3.71 (d, J=17.97 Hz, 1H), 3.81 (s, 1H), 3.88 (s, 3H), 3.92 (s, 1H), 3.96 (s, 3H), 4.26 (s, 1H), 4.91 (m, 2H), 6.20 (d, J=9.16 Hz, 1H), 6.98 (m, 2H), 7.16 (m, 5H), 7.72 (m, 2H), 7.94 (dd, J=8.14, 1.36 Hz, 1H), 8.02 (s, 1H), 8:36 (dd, J=4.75, 1.36 Hz, 1H)

Example 609

$^1$H NMR (300 MHz, CD$_3$OD) δ ppm 0.80 (d, J=6.78 Hz, 3H), 0.86 (dd, J=6.44, 1.70 Hz, 6H), 0.90 (d, J=6.44 Hz, 3H), 2.04 (m, 2H), 2.49 (dd, J=13.73, 11.70 Hz, 1H), 2.86 (s, 2H), 3.03 (m, 1H), 3.12 (d, J=17.97 Hz, 1H), 3.23 (dd, J=13.73, 3.56 Hz, 1H), 3.41 (dd, J=14.92, 3.73 Hz, 1H), 3.78 (m, 2H), 3.87 (s, 3H), 3.92 (s, 3H), 4.03 (d, J=11.19 Hz, 1H), 4.15 (m, 1H), 4.95 (m, 2H), 7.04 (m, 5H), 7.17 (m, 2H), 7.25 (d, J=2.71 Hz, 1H), 7.35 (dd, J=9.32, 2.88 Hz, 1H), 7.41 (d, J=8.82 Hz, 1H), 7.76 (m, 2H), 7.84 (d, J=9.16 Hz, 1H), 7.97 (s, 1H), 8.20 (d, J=8.48 Hz, 1H)

Example 610

$^1$H NMR (300 MHz, CDCl$_3$) δ ppm 0.78 (d, J=6.78 Hz, 3H), 0.86 (m, 6H), 0.93 (d, J=6.44 Hz, 3H), 1.82 (m, 1H), 2.09 (m, 1H), 2.67 (dd, J=14.24, 10.85 Hz, 1H), 2.78 (dd, J=13.56, 6.44 Hz, 1H), 2.95 (s, 2H), 3.04 (m, 1H), 3.19 (m, 1H), 3.35 (d, J=17.97 Hz, 1H), 3.64 (m, 1H), 3.75 (m, 1H), 3.81 (m, 1H), 3.88 (s, 3H), 4.26 (m, 1H), 5.11 (m, 2H), 6.12 (d, J=9.16 Hz, 1H), 6.99 (d, J=8.82 Hz, 2H), 7.06 (m, 5H), 7.37 (d, J=2.71 Hz, 1H), 7.68 (m, 1H), 7.72 (d, J=9.16 Hz, 2H), 7.76 (m, 1H), 8.02 (s, 1H), 8.19 (d, J=8.14 Hz, 1H), 8.30 (d, J=8.14 Hz, 1H), 8.88 (d, J=4.07 Hz, 1H)

Example 611

$^1$H NMR (300 MHz, CD$_3$OD) δ ppm 0.82 (d, J=6.78 Hz, 3H), 0.87 (d, J=6.78 Hz, 3H), 0.90 (d, J=6.44 Hz, 6H), 2.07 (m, 2H), 2.51 (dd, J=13.56, 11.53 Hz, 1H), 2.91 (m, 2H), 3.03 (m, 1H), 3.18 (m, 2H), 3.26 (d, J=3.39 Hz, 1H), 3.42 (dd, J=14.75, 3.56 Hz, 1H), 3.79 (m, 2H), 3.87 (d, J=18.31 Hz, 1H), 3.87 (s, 3H), 4.04 (d, J=11.19 Hz, 1H), 4.16 (m, 1H), 5.06 (m, 2H), 7.07 (m, 2H), 7.16 (m, 5H), 7.67 (d, J=8.48 Hz, 1H), 7.76 (m, 2H), 8.06 (d, J=9.49 Hz, 1H), 8.45 (dd, J=9.32, 2.54 Hz, 1H), 8.54 (d, J=8.48 Hz, 1H), 8.91 (d, J=2.71 Hz, 1H)

Example 612

$^1$H NMR (300 MHz, CDCl$_3$) δ ppm 0.80 (d, J=6.44 Hz, 3H), 0.85 (d, J=6.44 Hz, 6H), 0.92 (t, J=5.93 Hz, 3H), 0.90 (m, 2H), 1.83 (m, 1H), 2.15 (m, 1H), 2.71 (m, 1H), 2.79 (dd, J=13.39, 6.61 Hz, 1H), 2.98 (m, 2H), 3.08 (dd, J=13.73, 4.24 Hz, 1H), 3.18 (m, 1H), 3.42 (d, J=17.63 Hz, 1H), 3.71 (d, J=17.63 Hz, 1H), 3.87 (s, 3H), 3.95 (d, J=10.85 Hz, 1H), 4.26 (s, 1H), 4.96 (m, 2H), 6.33 (s, 1H), 6.88 (m, 1H), 6.97 (m, 2H), 7.15 (s, 5H), 7.24 (d, J=3.39 Hz, 1H), 7.71 (m, 2H), 7.90 (d, J=15.26 Hz, 2H)

Example 613

$^1$H NMR (300 MHz, CDCl$_3$) δ ppm 0.70 (d, J=6.78 Hz, 3H), 0.75 (d, J=6.78 Hz, 3H), 0.87 (d, J=3.39 Hz, 3H), 0.89 (d, J=3.39 Hz, 3H), 1.89 (m, 1H), 2.05 (m, 1H), 2.21 (s, 3H), 2.24 (s, 1H), 2.76 (dd, J=13.90, 10.85 Hz, 1H), 2.88 (s, 1H), 2.94 (m, 1H), 2.99 (d, J=4.07 Hz, 1H), 3.01 (d, J=9.16 Hz, 1H), 3.07 (m, 2H), 3.62 (q, J=17.97 Hz, 2H), 3.88 (s, 3H), 4.10 (m, 2H), 4.23 (d, J=9.16 Hz, 1H), 4.74 (m, 2H), 6.83 (s, 1H), 6.99 (m, 2H), 7.11 (m, 5H), 7.74 (m, 2H)

Example 614

$^1$H NMR (300 MHz, DMSO-d$_6$) δ ppm 0.64 (d, J=6.78 Hz, 3H), 0.78 (m, 6H), 0.82 (d, J=4.07 Hz, 3H), 1.20 (s, 1H), 1.72 (s, 1H), 1.92 (m, 1H), 2.10 (s, 3H), 2.38 (dd, J=13.22, 11.53 Hz, 1H), 2.73 (s, 1H), 2.79 (dd, J=13.39, 6.61 Hz, 1H), 2.89 (s, 1H), 293 (m, 1H), 3.05 (m, 1H), 3.09 (m, 1H), 3.20 (m, J=3.05 Hz, 1H), 3.59 (s, 1H), 3.76 (d, J=17.97 Hz, 1H), 3.84 (s, 3H), 3.94 (d, J=8.82 Hz, 1H), 4.08 (d, J=10.85 Hz, 1H), 4.55 (d, J=15.94 Hz, 2H), 4.97 (d, J=6.44 Hz, 1H), 6.90 (s, 1H), 7.01 (m, 5H), 7.10 (m, 2H), 7.72 (d, J=8.82 Hz, 2H), 8.19 (d, J=9.49 Hz, 1H)

Example 615

$^1$H NMR (300 MHz, CD$_3$OD) δ ppm 0.76 (d, J=6.78 Hz, 3H), 0.87 (d, J=6.44 Hz, 6H), 0.90 (d, J=6.44 Hz, 3H), 1.01 (m, 1H), 1.40 (m, 1H), 1.88 (m, 1H), 2.00 (m, 1H), 2.48 (dd, J=13.56, 11.53 Hz, 1H), 2.89 (dd, J=13.73, 6.95 Hz, 1H), 3.02 (m, 1H), 3.02 (d, J=7.80 Hz, 2H), 3.15 (d, J=18.31 Hz, 1H), 3.22 (dd, J=13.56, 3.39 Hz, 1H), 3.41 (dd, J=14.58, 3.73 Hz, 1H), 3.77 (m, 2H), 3.87 (s, 3H), 4.12 (m, 1H), 4.18 (m, 1H), 4.82 (m, 1H), 4.95 (m, 1H), 6.93 (d, J=2.71 Hz, 1H), 7.03 (m, 6H), 7.16 (m, 1H), 7.21 (dd, J=8.99, 2.54 Hz, 1H), 7.28 (d, J=8.48 Hz, 1H), 7.70 (d, J=9.16 Hz, 1H), 7.76 (m, 2H), 7.96 (d, J=8.48 Hz, 1H)

Example 616

$^1$H NMR (300 MHz, CDCl$_3$) δ ppm 0.82 (m, 6H), 0.87 (d, J=6.44 Hz, 3H), 0.93 (d, J=6.44 Hz, 3H), 1.22 (m, 1H), 1.82 (m, 2H), 2.67 (dd, J=14.24, 10.51 Hz, 1H), 2.78 (dd, J=13.39, 6.27 Hz, 1H), 2.97 (m, 3H), 3.05 (dd, J=9.32, 4.92 Hz, 1H), 3.19 (m, 1H), 3.37 (d, J=17.97 Hz, 1H), 3.61 (m, 1H), 3.74 (d, J=2.71 Hz, 1H), 3.83 (m, 1H), 3.88 (s, 3H), 3.98 (d, J=11.19 Hz, 1H), 4.26 (m, 1H), 5.08 (m, 2H), 6.12 (d, J=9.16 Hz, 1H), 6.99 (m, 2H), 7.05 (m, 6H), 7.35 (d, J=4.41 Hz, 1H), 7.64 (m, 1H), 7.72 (d, J=9.16 Hz, 2H), 7.77 (m, 1H), 8.16 (d, J=8.14 Hz, 1H), 8.29 (d, J=7.80 Hz, 1H)

Example 617

$^1$H NMR (300 MHz, CD$_3$OD) δ ppm 0.75 (d, J=6.44 Hz, 3H), 0.83 (t, J=7.29 Hz, 3H), 0.96 (m, 1H), 1.18 (m, 1H), 1.55 (m, 6H), 1.70 (m, 3H), 1.82 (m, 1H), 2.24 (m, 1H), 2.47 (dd, J=13.56, 11.87 Hz, 1H), 2.95 (m, 2H), 3.04 (m, 2H), 3.15 (d, J=8.48 Hz, 1H), 3.22 (m, 2H), 3.41 (d, J=4.07 Hz, 1H), 3.43 (s, 3H), 3.45 (m, 1H), 3.66 (m, 1H), 3.80 (m, 1H), 4.11 (m, 1H), 4.18 (m, 1H), 4.66 (s, 2H), 4.77 (d, J=6.78 Hz, 2H), 6.99 (m, 3H), 7.08 (m, 2H), 7.12 (m, 2H), 7.41 (s, 1H), 7.77 (m, 2H)

Example 618

$^1$H NMR (300 MHz, CD$_3$OD) δ ppm 0.74 (d, J=6.78 Hz, 3H), 0.83 (m, 3H), 0.87 (d, J=6.78 Hz, 3H), 0.90 (d, J=6.44 Hz, 3H), 0.97 (m, 1H), 1.29 (m, 1H), 1.80 (dd, J=11.19, 3.39 Hz, 1H), 2.00 (m, 1H), 2.46 (dd, J=13.73, 11.70 Hz, 1H), 2.89 (m, 1H), 2.94 (m, 1H), 3.00 (m, 2H), 3.06 (m, 1H), 3.22 (dd, J=13.56, 3.39 Hz, 1H), 3.41 (m, 1H), 3.43 (s, 2H), 3.66 (d, J=17.97 Hz, 1H), 3.77 (m, 1H), 3.87 (s, 3H), 4.10 (m, 1H), 4.66 (s, 2H), 4.77 (m, 2H), 4.78 (m, 2H), 6.99 (m, 3H), 7.08 (m, 2H), 7.12 (m, 2H), 7.41 (s, 1H), 7.77 (m, 2H), 8.20 (d, J=9.83 Hz, 1H)

Example 619

$^1$H NMR (300 MHz, CD$_3$OD) δ ppm 0.70 (d, J=6.78 Hz, 3H), 0.83 (t, J=7.29 Hz, 3H), 0.98 (m, 9H), 1.28 (m, 1H), 1.78 (m, 1H), 2.44 (dd, J=13.90, 11.53 Hz, 1H), 2.95 (dd, J=17.97, 3.39 Hz, 2H), 3.09 (m, 1H), 3.15 (dd, J=10.17, 5.09 Hz, 2H), 3.36 (m, 1H), 3.43 (s, 2H), 3.65 (m, 1H), 3.85 (d, J=8.82 Hz, 1H), 3.88 (m, 3H), 3.94 (m, 1H), 4.07 (m, 2H), 4.66 (s, 2H), 4.76 (d, J=6.44 Hz, 2H), 4.80 (s, 2H), 6.98 (m, 3H), 7.08 (m, 4H), 7.41 (s, 1H), 7.79 (m, 2H)

Example 620

$^1$H NMR (300 MHz, DMSO-d$_6$) δ ppm 0.68 (d, J=6.78 Hz, 3H), 0.69 (dd, J=9.16, 6.78 Hz, 3H), 0.80 (d, J=3.39 Hz, 3H), 0.81 (m, 3H), 0.84 (d, J=6.78 Hz, 6H), 1.68 (m, 1H), 1.91 (m, 1H), 2.38 (dd, J=13.05, 11.36 Hz, 1H), 2.76 (m, 1H), 2.91 (m, 5H), 2.99 (m, 1H), 3.07 (m, 2H), 3.22 (m, 1H), 3.57 (m, 1H), 3.74 (d, J=18.31 Hz, 1H), 3.84 (s, 2H), 4.03 (m, 2H), 4.98 (d, J=6.44 Hz, 1H), 6.99 (m, 1H), 7.10 (m, 7H), 7.72 (d, J=8.82 Hz, 1H), 8.06 (m, 1H), 8.19 (d, J=9.83 Hz, 1H)

Example 621

$^1$H NMR (300 MHz, DMSO-d$_6$) δ ppm 0.69 (dd, J=9.16, 6.78 Hz, 6H), 0.81 (m, 6H), 0.84 (d, J=6.78 Hz, 6H), 1.68 (m, 1H), 1.92 (m, 2H), 2.38 (dd, J=13.05, 11.36 Hz, 1H), 2.77 (m, 1H), 2.83 (m, 2H), 2.93 (m, 5H), 3.07 (m, 2H), 3.21 (dd, J=14.24, 2.71 Hz, 1H), 3.59 (d, J=6.44 Hz, 1H), 3.74 (d, J=18.31 Hz, 1H), 3.84 (s, 2H), 4.03 (m, 2H), 4.98 (d, J=6.44 Hz, 1H), 7.00 (dd, J=8.99, 4.58 Hz, 1H), 7.10 (m, 7H), 7.72 (d, J=8.82 Hz, 2H)

Example 622

$^1$H NMR (300 MHz, DMSO-d$_6$) δ ppm 0.69 (m, 6H), 0.81 (dd, 2.71 Hz, 6H), 1.93 (m, 1H), 2.37 (dd, J=13.22, 11.19 Hz, 1H), 2.79 (m, 1H), 2.83 (s, 3H), 2.93 (m, 1H), 3.05 (s, 3H), 3.08 (m, 1H), 3.21 (dd, J=14.24, 3.05 Hz, 1H), 3.59 (t, J=6.44 Hz, 1H), 3.73 (d, J=18.31 Hz, 1H), 3.84 (s, 3H), 3.91 (d, J=9.49 Hz, 1H), 3.99 (d, J=10.85 Hz, 1H), 4.31 (m, 2H), 7.00 (m, 1H), 7.11 (m, 7H), 7.71 (m, 2H), 8.21 (d, J=9.49 Hz, 1H)

Example 623

$^1$H NMR (300 MHz, DMSO-d$_6$) δ ppm 0.69 (t, J=6.78 Hz, 6H), 0.81 (dd, J=6.61, 2.88 Hz, 6H), 1.93 (m, 2H), 2.37 (dd, J=13.05, 11.36 Hz, 1H), 2.80 (dd, J=13.56, 6.44 Hz, 1H), 2.94 (m, 3H), 3.07 (dd, J=13.05, 2.88 Hz, 1H), 3.21 (dd, J=14.24, 3.05 Hz, 1H), 3.43 (d, J=4.41 Hz, 2H), 3.57 (m, J=3.73 Hz, 4H), 3.63 (d, J=4.41 Hz, 2H), 3.74 (d, J=17.97 Hz, 1H), 3.84 (s, 3H), 3.91 (d, J=9.83 Hz, 1H), 3.99 (d, J=11.19 Hz, 1H), 4.35 (m, 2H), 7.00 (m, 1H), 7.11 (m, 7 H), 7.72 (d, J=8.82 Hz, 2H), 8.21 (d, J=9.49 Hz, 1H)

Example 624

$^1$H NMR (300 MHz, DMSO-d$_6$) δ ppm 0.69 (d, J=6.44 Hz, 3H), 0.73 (d, J=6.44 Hz, 3H), 0.81 (dd, J=6.44, 3.73 Hz, 6H), 1.94 (m, 2H), 2.40 (dd, J=13.22, 11.19 Hz, 1H), 2.80 (dd, J=13.56, 6.44 Hz, 1H), 2.93 (m, 2H), 3.06 (m, 2H), 3.22 (dd, J=14.07, 3.22 Hz, 1H), 3.58 (m, 1H), 3.82 (m, 1H), 3.84 (s, 3H), 3.91 (m, 1H), 4.01 (d, J=10.85 Hz, 1H), 4.27 (m, 2H), 4.99 (d, J=6.44 Hz, 1H), 7.01 (m, 1H), 7.10 (m, 8H), 7.32 (t, J=7.80 Hz, 2H), 7.56 (d, J=7.46 Hz, 2H), 7.71 (m, 2H)

Example 650

$^1$H NMR (300 MHz, DMSO-d$_6$) δ ppm 0.70 (dd, J=6.61, 4.58 Hz, 6H), 0.80 (dd, J=6.61, 4.58 Hz, 6H), 1.94 (m, 2H), 2.42 (dd, J=13.56, 11.19 Hz, 1H), 2.63 (s, 3H), 2.71 (m, 1H), 2.83 (m, 2H), 3.00 (m, 3H), 3.18 (m, 2H), 3.61 (m, 1H), 3.76 (d, J=10.85 Hz, 1H), 3.92 (m, 1H), 4.33 (d, J=1.36 Hz, 2H), 4.86 (d, J=6.10 Hz, 1H), 5.94 (s, 2H), 6.60 (d, J=8.82 Hz, 2H), 7.07 (m, 5H), 7.21 (d, J=3.73 Hz, 1H), 7.39 (d, J=8.82 Hz, 2H), 7.84 (d, J=9.49 Hz, 1H)

Example 651

$^1$H NMR (300 MHz, DMSO-d$_6$) δ ppm 0.69 (dd, J=9.32, 6.61 Hz, 6H), 0.82 (dd, J=6.78, 1.36 Hz, 6H), 1.94 (m, 2H), 2.42 (dd, J=13.56, 10.85 Hz, 1H), 2.63 (d, J=2.37 Hz, 3H), 2.84 (m, 2H), 2.98 (m, 3H), 3.13 (m, 1H), 3.22 (dd, J=14.58, 3.39 Hz, 1H), 3.59 (d, J=5.76 Hz, 1H), 3.75 (d, J=10.51 Hz, 1H), 3.91 (m, 1H), 4.34 (m, 3H), 4.95 (d, J=6.10 Hz, 1H), 5.81 (s, 2H), 6.86 (d, J=2.03 Hz, 1H), 6.89 (d, J=2.37 Hz, 1H), 7.06 (m, 6H), 7.36 (d, J=8.48 Hz, 1H), 7.85 (d, J=9.49 Hz, 1H)

Example 652

$^1$H NMR (300 MHz, CDCl$_3$) δ ppm 0.74 (d, J=6.44 Hz, 3H), 0.80 (d, J=6.78 Hz, 3H), 0.90 (m, 6H), 1.87 (m, 1H), 2.13 (m, 1H), 2.65 (m, 1H), 2.69 (s, 3H), 2.78 (m, 2H), 2.93 (dd, J=7.63, 2.88 Hz, 2H), 3.04 (d, J=3.39 Hz, 2H), 3.10 (m, 1H), 3.16 (dd, J=9.16, 4.07 Hz, 1H), 3.24 (m, 2H), 3.59 (d, J=11.19 Hz, 1H), 3.78 (m, 1H), 4.04 (m, 1H), 4.42 (s, 2H), 6.46 (d, J=8.82 Hz, 1H), 6.92 (m, 2H), 6.96 (s, 1H), 7.15 (m, 5H), 7.64 (m, 2H)

Example 653

$^1$H NMR (300 MHz, DMSO-d$_6$) δ ppm 0.67 (d, J=6.78 Hz, 3H), 0.70 (d, J=6.78 Hz, 3H), 0.79 (d, J=3.39 Hz, 3H), 0.81 (d, J=3.39 Hz, 3H), 1.32 (m, 6H), 1.93 (m, 2H), 2.40 (dd, J=13.39, 11.02 Hz, 1H), 2.77 (dd, J=13.73, 6.61 Hz, 1H), 2.88 (m, 3H), 2.99 (m, 2H), 3.15 (m, 1H), 3.23 (m, 1H), 3.60 (m, 1H), 3.75 (d, J=10.85 Hz, 1H), 3.88 (m, 1H), 4.02 (s, 1H), 4.35 (m, 2H), 4.91 (d, J=6.44 Hz, 1H), 6.88 (d, J=8.82 Hz, 2H), 7.06 (m, 6H), 7.59 (d, J=8.82 Hz, 2H), 7.85 (d, J=9.49 Hz, 1H)

Example 654

¹H NMR (300 MHz, DMSO-d₆) δ ppm 0.70 (t, J=6.27 Hz, 6H), 0.80 (dd, J=6.44, 4.41 Hz, 6H), 1.32 (m, 6H), 1.93 (m, 2H), 2.41 (dd, J=13.56, 10.85 Hz, 1H), 2.71 (m, 1H), 2.83 (m, 2H), 3.01 (m, 2H), 3.17 (m, 2H), 3.60 (m, 1H), 3.76 (d, J=10.85 Hz, 1H), 3.89 (d, J=10.51 Hz, 1H), 4.02 (s, 1H), 4.35 (m, 2H), 4.87 (d, J=6.10 Hz, 1H), 5.94 (s, 2H), 6.60 (d, J=8.82 Hz, 2 H), 7.03 (s, 1H), 7.08 (m, 5H), 7.38 (m, 2H), 7.83 (d, J=9.49 Hz, 1H)

Example 655

¹H NMR (300 MHz, DMSO-d₆) δ ppm 0.67 (d, J=6.78 Hz, 3H), 0.70 (m, 3H), 0.83 (m, 6H), 1.33 (m, 6H), 1.96 (s, 1H), 2.45 (s, 1H), 2.83 (m, 2H), 3.00 (m, 4H), 3.22 (m, 4H), 3.75 (d, J=10.85 Hz, 1H), 3.92 (s, 2H), 4.35 (m, 2H), 4.99 (m, 1H), 5.81 (s, 1H), 6.86 (d, J=2.03 Hz, 1H), 6.89 (m, 1H), 7.05 (m, 5H), 7.21 (s, 1H), 7.23 (m, 1H), 7.35 (d, J=8.48 Hz, 1H), 7.84 (d, J=9.83 Hz, 1H)

Example 656

¹H NMR (300 MHz, CDCl₃) δ ppm 0.74 (d, J=6.44 Hz, 3H), 0.80 (d, J=6.78 Hz, 3H), 0.90 (dd, J=8.48, 6.78 Hz, 6H), 1.38 (t, J=7.29 Hz, 3H), 1.68 (s, 2H), 1.87 (m, 2H), 2.12 (s, 1H), 2.70 (d, J=14.92 Hz, 1H), 2.83 (s, 1H), 2.93 (dd, J=7.29, 4.58 Hz, 3H), 3.04 (s, 2H), 3.11 (d, J=8.14 Hz, 3H), 3.24 (d, J=8.48 Hz, 2H), 3.58 (s, 1H), 3.77 (s, 1H), 4.06 (s, 1H), 4.42 (s, 1H), 6.92 (d, J=8.82 Hz, 2H), 7.00 (s, 1H), 7.15 (m, 5H), 7.65 (d, J=8.48 Hz, 2H)

Example 657

¹H NMR (300 MHz, CDCl₃) δ ppm 0.78 (d, J=6.44 Hz, 3H), 0.81 (d, J=6.78 Hz, 3H), 0.86 (d, J=6.44 Hz, 3H), 0.92 (d, J=6.44 Hz, 3H), 1.38 (m, 3H), 1.82 (m, 1H), 2.12 (m, 1H), 2.67 (m, 1H), 2.71 (m, 1H), 2.77 (m, 1H), 2.94 (m, 1H), 3.00 (m, 2H), 3.17 (m, 2H), 3.24 (d, J=8.82 Hz, 1H), 3.65 (d, J=11.19 Hz, 1H), 3.74 (m, 1H), 3.89 (m, 1H), 4.12 (s, 2H), 4.18 (m, 1H), 4.43 (m, 2H), 4.52 (d, J=8.14 Hz, 1H), 4.65 (d, J=10.51 Hz, 1H), 6.38 (d, J=9.16 Hz, 1H), 6.67 (m, 2H), 6.95 (s, 1H), 7.15 (m, 5H), 7.57 (m, 2H)

Example 658

¹H NMR (300 MHz, CDCl₃) δ ppm 0.78 (d, J=6.44 Hz, 3H), 0.82 (d, J=6.78 Hz, 3H), 0.90 (d, J=3.39 Hz, 3H), 0.92 (d, J=3.73 Hz, 3H), 1.37 (t, J=7.63 Hz, 3H), 1.87 (m, 1H), 2.17 (m, 1H), 2.65 (q, J=8.36 Hz, 1H), 2.78 (dd, J=14.24, 10.51 Hz, 1H), 2.90 (dd, J=7.46, 4.41 Hz, 2H), 3.00 (m, 2H), 3.12 (m, 2H), 3.23 (m, 1H), 3.72 (d, J=3.73 Hz, 1H), 3.76 (d, J=10.17 Hz, 1H), 3.83 (m, 1H), 4.24 (m, 1H), 4.42 (m, 2H), 4.57 (d, J=6.78 Hz, 2H), 6.58 (d, J=8.82 Hz, 1H), 6.94 (s, 1H), 7.01 (d, J=2.03 Hz, 1H), 7.04 (t, J=2.54 Hz, 1H), 7.17 (m, 7H), 7.35 (m, 1H)

Example 659

¹H NMR (300 MHz, CDCl₃) δ ppm 0.75 (d, J=6.78 Hz, 3H), 0.80 (d, J=6.78 Hz, 3H), 0.90 (m, 3H), 0.93 (d, J=3.05 Hz, 3H), 1.38 (t, J=7.63 Hz, 3H), 1.88 (m, 1H), 2.13 (m, 1H), 2.74 (m, 2H), 2.79 (m, 1H), 2.94 (m, 1H), 3.01 (m, 2H), 3.05 (d, J=4.07 Hz, 2H), 3.14 (m, 1H), 3.23 (m, 2H), 3.62 (m, 1H), 3.77 (m, 2H), 4.06 (m, 1H), 4.43 (d, J=2.37 Hz, 2H), 6.42 (d, J=8.48 Hz, 1H), 6.98 (s, 1H), 7.01 (d, J=2.37 Hz, 1H), 7.04 (d, J=2.37 Hz, 1H), 7.11 (d, J=2.03 Hz, 2H), 7.15 (m, 5H)

Example 660

¹H NMR (300 MHz, CDCl₃) δ ppm 0.74 (d, J=6.44 Hz, 3H), 0.80 (d, J=6.44 Hz, 3H), 0.90 (m, 6H), 1.86 (m, 1H), 2.11 (m, 1H), 2.69 (dd, J=14.24, 10.17 Hz, 1H), 2.79 (m, 1H), 2.93 (m, 1H), 3.03 (m, 2H), 3.12 (m, 3H), 3.23 (m, 2H), 3.48 (s, 3H), 3.61 (d, J=10.85 Hz, 1H), 3.77 (m, 2H), 4.11 (m, 1H), 4.47 (m, 2H), 4.70 (s, 2H), 6.51 (d, J=9.16 Hz, 1H), 6.92 (m, 2H), 7.12 (s, 1H), 7.17 (m, 5H), 7.65 (m, 2H)

Example 661

¹H NMR (300 MHz, CDCl₃) δ ppm 0.80 (m, 6H), 0.86 (m, 3H), 0.92 (d, J=6.44 Hz, 3H), 1.82 (dd, J=8.31, 6.61 Hz, 1H), 2.13 (m, 1H), 2.71 (m, 2H), 2.77 (m, 1H), 2.93 (m, 1H), 2.97 (m, 2H), 3.11 (m, 4H), 3.21 (m, 1H), 3.48 (d, J=3.73 Hz, 3H), 3.65 (d, J=10.85 Hz, 1H), 3.74 (d, J=12.55 Hz, 1H), 4.17 (m, 2H), 4.45 (q, J=15.26 Hz, 2H), 4.70 (s, 2H), 6.39 (d, J=8.82 Hz, 1H), 6.67 (m, 2H), 7.09 (d, J=3.73 Hz, 1H), 7.16 (m, 5H), 7.56 (m, 2H)

Example 662

¹H NMR (300 MHz, CDCl₃) δ ppm 0.78 (d, J=6.44 Hz, 3H), 0.81 (d, J=6.78 Hz, 3H), 0.90 (d, J=3.39 Hz, 3H), 0.92 (d, J=3.39 Hz, 3H), 1.85 (m, 1H), 2.18 (m, 1H), 2.67 (q, J=8.48 Hz, 1H), 2.79 (dd, J=14.41, 10.34 Hz, 1H), 2.90 (dd, J=7.46, 3.73 Hz, 2H), 3.04 (m, 1H), 3.14 (m, 2H), 3.23 (m, 1H), 3.48 (s, 3H), 3.72 (d, J=4.07 Hz, 1H), 3.76 (d, J=10.17 Hz, 1H), 3.82 (m, 1H), 4.25 (m, 1H), 4.45 (m, 2H), 4.57 (s, 2H), 4.70 (s, 2H), 6.58 (d, J=8.48 Hz, 1H), 7.01 (d, J=2.37 Hz, 1H), 7.03 (d, J=2.03 Hz, 1H), 7.09 (s, 1H), 7.19 (m, 6H), 7.35 (m, 1H)

Example 663

¹H NMR (300 MHz, CDCl₃) δ ppm 0.75 (d, J=6.78 Hz, 3H), 0.80 (d, J=6.78 Hz, 3H), 0.90 (d, J=3.05 Hz, 3H), 0.93 (d, J=3.39 Hz, 3H), 1.26 (t, J=7.12 Hz, 3H), 1.87 (s, 1H), 2.13 (s, 1H), 2.71 (s, 1H), 2.81 (d, J=13.90 Hz, 2H), 2.92 (t, J=7.12 Hz, 2H), 3.07 (m, 3H), 3.21 (m, 2H), 3.49 (s, 3H), 3.64 (d, J=10.51 Hz, 1H), 3.77 (s, 1H), 4.12 (q, J=7.12 Hz, 2H), 4.46 (s, 2H), 4.70 (s, 2H), 6.39 (s, 1H), 6.81 (d, J=8.48 Hz, 1H), 7.02 (m, 1H), 7.13 (s, 1H), 7.17 (m, 5H)

Example 664

¹H NMR (300 MHz, CD₃OD) δ ppm 0.78 (dd, J=6.44, 1.70 Hz, 6H), 0.87 (d, J=6.78 Hz, 3H), 0.91 (d, J=6.78 Hz, 3H), 2.01 (m, 1H), 2.46 (s, 1H), 2.52 (m, 1H), 2.68 (d, J=7.46 Hz, 1H), 2.71 (s, 3H), 2.91 (m, 1H), 2.99 (m, 2H), 3.11 (m, 4H), 3.21 (m, 2H), 3.43 (dd, J=14.92, 3.73 Hz, 1H), 3.71 (s, 1H), 3.72 (d, J=2.71 Hz, 3H), 3.78 (d, J=11.19 Hz, 1H), 4.12 (s, 1H), 4.44 (m, 2H), 6.88 (d, J=8.48 Hz, 1H), 7.08 (m, 3H), 7.16 (m, 2H), 7.22 (s, 1H), 7.43 (dd, J=8.48, 2.37 Hz, 1H), 7.68 (d, J=1.36 Hz, 1H), 7.75 (s, 1H), 7.81 (d, J=2.37 Hz, 1H), 7.91 (d, J=9.49 Hz, 1H)

Example 665

¹H NMR (300 MHz, CDCl₃) δ ppm 0.79 (d, J=6.44 Hz, 3H), 0.83 (d, J=6.44 Hz, 3H), 0.89 (d, J=6.44 Hz, 3H), 0.91

(m, 3H), 1.88 (d, J=7.46 Hz, 1H), 2.17 (d, J=11.53 Hz, 1H), 2.69 (s, 3H), 2.74 (m, 1H), 2.84 (m, 2H), 2.96 (m, 3H), 3.15 (m, 5H), 3.63 (d, J=11.19 Hz, 1H), 3.77 (s, 1H), 4.16 (s, 1H), 4.40 (d, J=2.37 Hz, 2H), 6.56 (d, J=9.16 Hz, 1H), 6.93 (s, 1H), 7.18 (m, 5H), 7.71 (d, J=3.73 Hz, 1H), 8.02 (s, 1H)

Example 666

$^1$H NMR (300 MHz, CD$_3$OD) δ ppm 0.76 (d, J=6.62 Hz, 6H), 0.86 (t, J=6.62 Hz, 3H), 0.90 (m, 3H), 1.29 (s, 1H), 2.02 (d, J=6.62 Hz, 1H), 2.47 (dd, J=13.42, 11.21 Hz, 1H), 2.87 (dd, J=13.97, 6.99 Hz, 2H), 2.95 (m, 2H), 3.03 (m, 2H), 3.07 (m, 2H), 3.18 (s, 2H), 3.37 (m, 1H), 3.70 (m, 1H), 3.75 (s, 1H), 4.14 (s, 1H), 4.31 (d, J=6.62 Hz, 2H), 4.55 (s, 1H), 6.91 (m, 1H), 7.03 (m, 3H), 7.14 (m, 2H), 7.32 (m, 1H), 7.67 (m, 2H), 7.92 (s, 1H)

Example 667

$^1$H NMR (300 MHz, CD$_3$OD) δ ppm 0.77 (m, 6H), 0.87 (m, 3H), 0.91 (d, J=6.78 Hz, 3H), 1.02 (t, J=7.29 Hz, 1H), 2.03 (m, 1H), 2.52 (m, 1H), 2.71 (m, 3H), 2.71 (m, 2H), 2.91 (m, 2H), 3.01 (m, 2H), 3.09 (m, 1H), 3.20 (m, 2H), 3.41 (dd, J=14.75, 3.56 Hz, 1H), 3.73 (m, 1H), 3.78 (m, 1H), 4.13 (s, 1H), 4.42 (m, 2H), 6.81 (m, 1H), 7.08 (m, 3H), 7.16 (m, 2H), 7.23 (m, 1H), 7.48 (m, 1H), 7.54 (dd, J=8.14, 5.76 Hz, 1H), 7.85 (t, J=2.71 Hz, 1H), 7.96 (d, J=9.83 Hz, 1H), 8.16 (m, 2H), 8.71 (dd, J=4.92, 1.53 Hz, 1H), 8.88 (d, J=2.37 Hz, 1H)

Example 668

$^1$H NMR (300 MHz, CD$_3$OD) δ ppm 0.78 (d, J=6.78 Hz, 6H), 0.87 (d, J=6.78 Hz, 3H), 0.90 (d, J=6.44 Hz, 3H), 2.02 (m, 2H), 2.51 (m, 2H), 2.70 (s, 3H), 2.93 (dd, J=13.39, 7.29 Hz, 2H), 2.98 (s, 3H), 3.07 (m, 3H), 3.14 (m, 2H), 3.22 (m, 2H), 3.42 (dd, J=14.75, 3.56 Hz, 1H), 3.73 (m, 1H), 3.75 (m, 1H), 4.10 (s, 1H), 4.41 (d, J=7.12 Hz, 2H), 7.01 (m, 1H), 7.08 (m, 3H), 7.16 (m, 2H), 7.21 (s, 1H), 7.52 (m, 1H), 7.82 (m, 1H), 7.91 (d, J=9.49 Hz, 1H)

Example 669

$^1$H NMR (300 MHz, CDCl$_3$) δ ppm 0.74 (d, J=6.44 Hz, 3H), 0.79 (d, J=6.44 Hz, 3H), 0.88 (m, 3H), 0.92 (d, J=6.44 Hz, 3H), 0.99 (m, 2H), 1.12 (m, 2H), 1.27 (m, 1H), 1.86 (dd, J=13.56, 6.78 Hz, 1H), 2.10 (m, 1H), 2.30 (m, 1H), 2.69 (m, 2H), 2.93 (m, 2H), 3.06 (dd, J=661, 3.56 Hz, 2H), 3.13 (m, 3H), 3.23 (m, 2H), 3.62 (d, J=10.85 Hz, 1H), 3.78 (m, 2H), 4.09 (m, 1H), 4.38 (s, 2H), 6.57 (d, J=9.16 Hz, 1H), 6.88 (m, 1H), 6.93 (m, 1H), 7.14 (m, 5H), 7.65 (m, 1H)

Example 670

$^1$H NMR (300 MHz, CDCl$_3$) δ ppm 0.78 (d, J=6.44 Hz, 3H), 0.81 (d, J=6.78 Hz, 3H), 0.90 (d, J=4.07 Hz, 3H), 0.92 (d, J=4.07 Hz, 3H), 0.99 (m, 3H), 1.11 (m, 2H), 1.86 (dd, J=13.39, 6.95 Hz, 1H), 2.17 (m, 1H), 2.28 (m, 1H), 2.64 (q, J=8.48 Hz, 1H), 2.78 (dd, J=14.24, 10.51 Hz, 2H), 2.89 (m, 2H), 3.04 (dd, J=15.26, 8.14 Hz, 1H), 3.12 (m, 3H), 3.22 (m, 1H), 3.74 (m, 2H), 4.26 (m, 1H), 4.38 (m, 2H), 4.57 (s, 1H), 6.55 (d, J=9.16 Hz, 1H), 6.83 (s, 1H), 7.02 (dd, J=8.48, 2.03 Hz, 1H), 7.17 (m, 7H), 7.35 (d, P8.48 Hz, 1H)

Example 671

$^1$H NMR (300 MHz, CDCl$_3$) δ ppm 0.78 (d, J=6.78 Hz, 3H), 0.81 (d, J=6.78 Hz, 3H), 0.86 (d, J=6.44 Hz, 3H), 0.92 (d, J=6.44 Hz, 3H), 1.00 (m, 2H), 1.11 (m, 3H), 1.82 (m, 1H), 2.13 (m, 1H), 2.29 (m, 1H), 2.68 (m, 1H), 2.75 (m, 2H), 2.96 (m, 2H), 3.10 (m, 4H), 3.21 (m, 1H), 3.65 (d, J=10.85 Hz, 1H), 3.74 (s, 1H), 3.89 (s, 1H), 4.16 (m, 2H), 4.38 (m, 2H), 6.38 (d, J=8.82 Hz, 1H), 6.68 (m, 2H), 6.84 (s, 1H), 7.16 (m, 5H), 3.56 (m, 2H)

Example 672

$^1$H NMR (300 MHz, CDCl$_3$) δ ppm 0.75 (d, J=6.44 Hz, 3H), 0.81 (d, J=6.78 Hz, 3H), 0.88 (d, J=6.78 Hz, 3H), 0.92 (d, J=6.44 Hz, 3H), 1.23 (t, J=7.63 Hz, 3H), 1.86 (m, 1H), 2.12 (m, 1H), 2.64 (d, J=7.80 Hz, 1H), 2.69 (m, 3H), 2.76 (m, 2H), 2.87 (m, 1H), 2.97 (m, 1H), 3.04 (m, 2H), 3.11 (dd, J=8.48, 3.73 Hz, 2H), 3.21 (m, 3H), 3.60 (d, J=10.85 Hz, 1H), 3.76 (m, 1H), 4.05 (m, 1H), 4.41 (s, 2H), 6.35 (d, J=9.16 Hz, 1H), 6.84 (m, 1H), 6.95 (m, 1H), 7.16 (m, 6H), 7.47 (dd, J=8.48, 2.37 Hz, 1H), 7.56 (d, J=2.37 Hz, 1H)

Example 673

$^1$H NMR (300 MHz, CDCl$_3$) δ ppm 0.79 (d, J=6.44 Hz, 3H), 0.85 (m, 9H), 1.87 (s, 1H), 2.22 (s, 1H), 2.69 (s, 3H), 2.76 (s, 1H), 3.00 (m, 5H), 3.23 (m, 3H), 3.32 (s, 2H), 3.60 (d, J=10.51 Hz, 1H), 3.85 (s, 1H), 4.18 (s, 1H), 4.43 (m, 2H), 6.80 (s, 1H), 6.92 (d, J=8.48 Hz, 1H), 7.19 (m, 5H), 7.52 (d, J=2.03 Hz, 1H), 7.56 (d, J=2.37 Hz, 1H)

Example 674

$^1$H NMR (300 MHz, CDCl$_3$) δ ppm 0.73 (d, J=6.44 Hz, 3H), 0.79 (d, J=6.78 Hz, 3H), 0.89 (d, J=6.44 Hz, 3H), 0.93 (d, J=6.44 Hz, 3H), 1.88 (s, 1H), 2.12 (m, 1H), 2.28 (s, 3H), 2.69 (s, 3H), 2.75 (m, 1H), 2.92 (m, 2H), 3.14 (m, 4H), 3.60 (d, J=10.85 Hz, 1H), 3.76 (d, J=8.48 Hz, 1H), 4.06 (s, 1H), 4.42 (s, 2H), 6.43 (d, J=8.48 Hz, 1H), 6.86 (d, J=8.48 Hz, 1H), 6.95 (s, 1H), 7.16 (m, 5H), 7.47 (m, 2H), 7.55 (d, P1.70 Hz, 2H), 7.75 (d, J=8.82 Hz, 1H), 7.85 (s, 1H)

Example 675

$^1$H NMR (300 MHz, CDCl$_3$) δ ppm 0.75 (d, J=6.44 Hz, 3H), 0.80 (d, J=6.44 Hz, 3H), 0.88 (d, J=6.44 Hz, 3H), 0.92 (d, J=6.78 Hz, 3H), 1.88 (d, J=6.78 Hz, 1H), 2.14 (m, 1H), 2.69 (s, 3H), 2.75 (m, 2H), 2.92 (m, 2H), 3.00 (m, 2H), 3.10 (s, 3H), 3.13 (m, 1H), 3.22 (m, 2H), 3.65 (d, J=10.85 Hz, 1H), 3.78 (d, J=9.83 Hz, 2H), 4.12 (q, J=7.12 Hz, 1H), 4.42 (m, 2H), 6.53 (d, J=8.82 Hz, 1H), 6.93 (s, 1H), 7.15 (m, 5H), 7.33 (d, J=8.82 Hz, 2H), 7.57 (s, 1H), 7.77 (d, J=8.82 Hz, 2H)

Example 676

$^1$H NMR (300 MHz, CDCl$_3$) δ ppm 0.79 (d, J=6.44 Hz, 3H), 0.82 (d, J=6.44 Hz, 3H), 0.86 (d, J=6.78 Hz, 3H), 0.88 (m, 3H), 1.88 (m, 1H), 2.16 (m, 1H), 2.49 (s, 3H), 2.67 (m, 2H), 2.71 (m, 3H), 2.89 (m, 1H), 3.00 (dd, J=14.24, 4.41 Hz, 1H), 3.14 (d, J=7.46 Hz, 2H), 3.22 (m, 4H), 3.49 (s, 1H), 3.58 (d, J=11.19 Hz, 1H), 3.67 (d, J=6.44 Hz, 1H), 3.95 (s, 1H), 4.42 (m, 2H), 6.39 (d, J=8.14 Hz, 1H), 6.87 (d, J=8.14 Hz, 1H), 6.97 (s, 1H), 7.17 (m, 5H), 7.24 (s, 1H), 7.67 (d, J=10.85 Hz, 1H)

Example 677

$^1$H NMR (300 MHz, CDCl$_3$) δ ppm 0.82 (dd, J=10.85, 6.44 Hz, 9H), 0.88 (m, 3H), 1.86 (d, J=6.78 Hz, 1H), 2.17 (m, 1H), 2.51 (s, 3H), 2.68 (d, J=3.73 Hz, 3H), 2.68 (m, 1H), 2.84 (s, 1H), 3.04 (m, 1H), 3.11 (m, 2H), 3.19 (m, 2H), 3.25 (m, 2H), 3.49 (d, J=5.09 Hz, 1H), 3.61 (d, J=10.85 Hz, 1H), 3.72 (s, 1H), 3.82 (d, J=3.39 Hz, 1H), 4.02 (s, 1H), 4.41 (d, J=1.70 Hz, 2H), 6.44 (d, J=8.82 Hz, 1H), 6.60 (s, 1H), 6.92 (m, 1H), 7.17 (m, 5H), 7.91 (s, 1H)

Example 678

$^1$H NMR (300 MHz, CDCl$_3$) δ ppm 0.78 (d, J=6.44 Hz, 3H), 0.83 (m, 3H), 0.88 (d, J=6.78 Hz, 3H), 0.93 (m, 3H), 1.85 (dd, J=8.48, 6.78 Hz, 1H), 2.15 (m, 1H), 2.34 (s, 3H), 2.69 (s, 3H), 2.74 (m, 1H), 2.83 (m, 1H), 2.97 (m, 2H), 3.09 (m, 2H), 3.15 (m, 1H), 3.22 (m, 2H), 3.64 (d, J=11.19 Hz, 1H), 3.74 (dd, J=8.65, 2.88 Hz, 1H), 3.89 (d, J=3.05 Hz, 1H), 4.16 (m, 1H), 4.41 (m, 2H), 6.11 (s, 1H), 6.46 (d, J=8.82 Hz, 1H), 6.92 (d, J=6.44 Hz, 1H), 7.17 (m, 5H), 7.48 (d, J=1.70 Hz, 1H), 7.64 (d, J=2.37 Hz, 1H)

Example 679

$^1$H NMR (300 MHz, CD$_3$OD) δ ppm 0.78 (d, J=6.78 Hz, 6H), 0.90 (m, 6H), 2.01 (m, 2H), 2.46 (m, 1H), 2.51 (m, 1H), 2.63 (d, J=3.39 Hz, 3H), 2.69 (m, 3H), 2.92 (dd, J=13.56, 7.12 Hz, 2H), 3.01 (m, 2H), 3.08 (m, 2H), 3.15 (m, 1H), 3.21 (m, 2H), 3.30 (dd, J=3.05, 1.70 Hz, 2H), 3.42 (dd, J=14.92, 3.73 Hz, 1H), 3.74 (m, 2H), 4.11 (m, 1H), 4.41 (s, 2H), 6.94 (d, J=8.48 Hz, 1H), 7.09 (m, 3H), 7.15 (m, 2H), 7.20 (s, 1H), 7.42 (dd, 8.65, 2.20 Hz, 1H), 7.84 (d, J=2.37 Hz, 1H)

Example 680

$^1$H NMR (300 MHz, CD$_3$OD) δ ppm 0.77 (dd, J=6.78, 1.36 Hz, 6H), 0.89 (d, J=6.44 Hz, 3H), 0.92 (d, J=6.78 Hz, 3H), 1.32 (m, 3H), 2.01 (m, 2H), 2.51 (m, 2H), 2.69 (s, 3H), 2.93 (m, 1H), 2.97 (m, 1H), 3.06 (m, 2H), 3.15 (m, 1H), 3.22 (m, 2H), 3.29 (m, 2H), 3.46 (dd, J=14.92, 3.39 Hz, 1H), 3.73 (m, 2H), 4.10 (m, 1H), 4.26 (q, J=7.12 Hz, 2H), 4.41 (m, 2H), 6.94 (d, J=8.48 Hz, 1H), 7.09 (m, 3H), 7.15 (m, 2H), 7.18 (s, 1H), 7.38 (dd, J=8.48, 2.37 Hz, 1H), 7.91 (m, 1H), 8.34 (d, J=1.70 Hz, 1H)

Example 681

$^1$H NMR (300 MHz, CDCl$_3$) δ ppm 0.75 (d, J=6.44 Hz, 3H), 0.81 (d, J=6.78 Hz, 3H), 0.88 (d, J=6.78 Hz, 3H), 0.92 (d, J=6.44 Hz, 3H), 1.25 (d, J=6.78 Hz, 6H), 1.62 (s, 1H), 1.86 (d, J=6.10 Hz, 1H), 2.14 (d, J=6.78 Hz, 1H), 2.72 (s, 3H), 2.80 (d, J=18.65 Hz, 1H), 2.89 (m, 1H), 2.96 (m, 2H), 3.02 (m, 2H), 3.11 (m, 2H), 3.17 (d, J=9.16 Hz, 1H), 3.26 (m, 2H), 3.57 (d, J=11.19 Hz, 1H), 3.77 (d, J=5.43 Hz, 1H), 3.99 (s, 1H), 4.43 (s, 2H), 6.30 (d, J=8.82 Hz, 1H), 6.84 (d, J=8.48 Hz, 1H), 6.99 (s, 1H), 7.18 (m, 5H), 7.46 (dd, J=8.31, 2.20 Hz, 1H), 7.60 (d, J=2.37 Hz, 1H)

Example 682

$^1$H NMR (300 MHz, CDCl$_3$) δ ppm 0.74 (d, J=6.44 Hz, 3H), 0.78 (d, J=6.44 Hz, 3H), 0.90 (d, J=6.78 Hz, 3H), 0.91 (d, J=2.37 Hz, 3H), 1.88 (dd, J=14.41, 6.95 Hz, 1H), 2.13 (m, 1H), 2.74 (m, 1H), 2.89 (d, J=7.80 Hz, 1H), 2.95 (m, 2H), 3.00 (m, 2H), 3.05 (dd, J=6.44, 2.71 Hz, 2H), 3.17 (m, 1H), 3.25 (m, 1H), 3.56 (d, J=10.85 Hz, 1H), 3.74 (s, 1H), 3.82 (s, 3H), 3.96 (s, 1H), 3.99 (d, J=2.37 Hz, 1H), 4.65 (m, 2H), 6.42 (d, J=8.48 Hz, 1H), 6.95 (d, J=8.82 Hz, 2H), 7.12 (m, 5H), 7.33 (m, 3H), 7.63 (d, J=8.82 Hz, 2H), 7.73 (m, 1H)

Example 683

$^1$H NMR (300 MHz, CDCl$_3$) δ ppm 0.77 (d, J=6.44 Hz, 3H), 0.81 (m, 3H), 0.88 (d, J=6.78 Hz, 3H), 0.94 (d, J=6.78 Hz, 3H), 1.85 (d, J=6.78 Hz, 1H), 2.13 (m, 1H), 2.29 (s, 6H), 2.70 (s, 3H), 2.73 (d, J=3.05 Hz, 1H), 2.79 (m, 1H), 2.96 (d, J=8.14 Hz, 1H), 3.02 (d, J=1.36 Hz, 1H), 3.15 (m, 7H), 3.63 (d, J=10.85 Hz, 1H), 3.74 (m, 1H), 4.16 (d, J=9.16 Hz, 1H), 4.41 (m, 2H), 6.38 (d, J=9.49 Hz, 1H), 6.94 (s, 1H), 7.16 (m, 5H), 7.41 (d, J=10.17 Hz, 2H)

Example 684

$^1$H NMR (300 MHz, CDCl$_3$) δ ppm 0.82 (dd, J=6.44, 4.41 Hz, 6H), 0.91 (d, J=3.05 Hz, 3H), 0.93 (d, J=3.39 Hz, 3H), 1.55 (s, 1H), 1.87 (s, 1H), 2.19 (s, 1H), 2.81 (s, 1H), 2.90 (d, J=7.12 Hz, 2H), 3.05 (s, 2H), 3.15 (s, 4H), 3.81 (s, 2H), 4.17 (s, 1H), 4.28 (s, 2H), 4.38 (s, 1H), 6.52 (s, 1H), 7.03 (s, 1H), 7.22 (m, 7H), 7.35 (m, 2H), 7.80 (d, J=1.70 Hz, 1H)

Example 685

$^1$H NMR (300 MHz, CDCl$_3$) δ ppm 0.77 (d, J=6.44 Hz, 3H), 0.81 (d, J=6.78 Hz, 3H), 0.90 (m, 6H), 1.84 (m, 1H), 2.16 (m, 1H), 2.73 (dd, J=14.41, 10.34 Hz, 1H), 2.86 (m, 3H), 3.07 (dd, J=9.66, 3.22 Hz, 2H), 3.16 (m, 1H), 3.24 (m, 1H), 3.31 (t, J=8.99 Hz, 1H), 3.62 (d, J=10.85 Hz, 1H), 3.82 (s, 2H), 4.18 (s, 1H), 4.41 (d, J=15.94 Hz, 1H), 4.59 (m, 1H), 6.50 (d, J=8.82 Hz, 1H), 6.93 (m, 2H), 7.18 (m, 6H), 7.51 (s, 1H), 7.66 (d, J=8.82 Hz, 2H)

Example 686

$^1$H NMR (300 MHz, CDCl$_3$) δ ppm 0.80 (t, J=6.61 Hz, 6H), 0.90 (d, J=6.44 Hz, 3H), 0.97 (d, J=6.78 Hz, 3H), 1.91 (m, 1H), 2.21 (m, 1H), 2.66 (m, 2H), 2.70 (s, 3H), 2.84 (m, 2H), 2.94 (d, J=8.48 Hz, 1H), 3.05 (m, 1H), 3.13 (m, 1H), 3.20 (m, 1H), 3.28 (m, 1H), 3.39 (s, 1H), 3.93 (d, J=9.16 Hz, 2H), 4.32 (m, 1H), 4.45 (m, 2H), 6.67 (d, J=7.12 Hz, 1H), 6.70 (d, J=8.14 Hz, 1H), 6.96 (d, J=3.05 Hz, 1H), 7.14 (m, 3H), 7.19 (m, 7H)

Example 687

$^1$H NMR (300 MHz, CDCl$_3$) δ ppm 0.78 (d, J=6.44 Hz, 3H), 0.82 (d, J=6.78 Hz, 3H), 0.90 (d, J=3.39 Hz, 3H), 0.92 (d, J=3.05 Hz, 3H), 1.86 (m, 1H), 2.14 (s, 3H), 2.67 (m, 1H), 2.79 (dd, J=14.41, 10.68 Hz, 1H), 2.90 (dd, J=7.46, 4.07 Hz, 2H), 3.04 (dd, J=15.26, 8.14 Hz, 1H), 3.11 (dd, J=8.99, 4.24 Hz, 3H), 3.16 (m, 3H), 3.23 (m, 2H), 3.77 (d, J=10.17 Hz, 1H), 3.83 (m, 1H), 4.25 (m, 1H), 4.45 (m, 2H), 5.34 (s, 2H), 6.57 (d, J=8.48 Hz, 1H), 7.01 (d, J=2.03 Hz, 1H), 7.03 (d, J=2.37 Hz, 1H), 7.14 (s, 1H), 7.18 (m, 5H), 7.35 (m, 1H)

Example 688

$^1$H NMR (300 MHz, CD$_3$OD) δ ppm 0.76 (t, J=6.78 Hz, 6H), 0.89 (m, 3H), 0.92 (d, J=6.44 Hz, 3H), 2.01 (m, 2H), 2.50 (m, 2H), 2.67 (d, J=1.70 Hz, 1H), 2.69 (s, 3H), 2.78 (m, 1H), 2.85 (d, J=3.73 Hz, 3H), 2.90 (m, 1H), 2.98 (m, 2H), 3.04 (m, 1H), 3.11 (m, 1H), 3.20 (m, 2H), 3.37 (m, 1H), 3.71 (m, 1H), 3.77 (m, 1H), 4.13 (m, 1H), 4.42 (s, 2H), 6.75 (d, J=8.14 Hz, 1H), 6.85 (d, J=2.37 Hz, 1H), 6.98 (dd, J=8.14, 2.37 Hz, 1H), 7.07 (m, 3H), 7.15 (m, 2H), 7.19 (s, 1H)

Example 689

$^1$H NMR (300 MHz, CD$_3$OD) δ ppm 0.76 (t, J=6.27 Hz, 6H), 0.87 (d, J=6.78 Hz, 3H), 0.90 (d, J=6.78 Hz, 3H), 2.02 (m, 2H), 2.50 (m, 2H), 2.69 (s, 3H), 2.76 (s, 6H), 2.91 (dd, J=13.73, 6.95 Hz, 1H), 2.99 (m, 1H), 3.04 (m, 1H), 3.11 (m, 1H), 3.17 (m, 1H), 3.23 (m, 2H), 3.34 (d, J=2.37 Hz, 1H), 3.37 (m, 1H), 3.71 (d, J=11.19 Hz, 1H), 3.77 (m, 1H), 4.13 (m, 1H), 4.42 (s, 2H), 6.90 (m, 1H), 7.08 (m, 3H), 7.15 (m, 2H), 7.19 (s, 1H), 7.37 (m, 2H)

Example 690

$^1$H NMR (300 MHz, CD$_3$OD) δ ppm 0.77 (dd, J=6.61, 2.20 Hz, 6H), 0.91 (dd, J=9.49, 6.44 Hz, 6H), 1.16 (t, J=7.29 Hz, 3H), 2.03 (m, 1H), 2.50 (m, 1H), 2.70 (s, 3H), 2.94 (m, 1H), 3.12 (m, 2H), 3.28 (m, 9H), 3.46 (dd, J=15.09, 3.56 Hz, 1H), 3.75 (d, J=11.19 Hz, 2H), 4.09 (s, 1H), 4.40 (m, 2H), 6.90 (d, J=8.48 Hz, 1H), 7.07 (m, 3H), 7.16 (m, 2H), 7.19 (d, J=4.07 Hz, 1H), 7.30 (dd, J=8.48, 2.37 Hz, 1H), 7.99 (d, J=9.49 Hz, 1H), 8.45 (m, 1H)

Example 691

$^1$H NMR (300 MHz, CD$_3$OD) δ ppm 0.77 (dd, J=6.61, 1.53 Hz, 6H), 0.89 (d, J=6.78 Hz, 3H), 0.92 (d, J=6.44 Hz, 3H), 2.02 (m, 1H), 2.51 (m, 1H), 2.70 (s, 3H), 2.94 (dd, J=13.90, 7.12 Hz, 2H), 3.11 (m, 4H), 3.21 (m, 3H), 3.46 (dd, J=14.75, 3.22 Hz, 1H), 3.77 (m, 3H), 3.79 (m, 3H), 4.08 (m, 1H), 4.42 (m, 2H), 6.94 (d, J=8.48 Hz, 1H), 7.08 (m, 3H), 7.15 (m, 2H), 7.20 (s, 1H), 7.39 (dd, J=8.48, 2.37 Hz, 1H), 7.90 (d, J=9.49 Hz, 1H), 8.34 (s, 1H)

Example 692

$^1$H NMR (300 MHz, CD$_3$OD) δ ppm 0.77 (d, J=6.78 Hz, 6H), 0.89 (d, J=6.44 Hz, 3H), 0.92 (d, J=6.44 Hz, 3H), 2.02 (m, 1H), 2.47 (m, 1H), 2.50 (m, 2H), 2.69 (s, 3H), 2.94 (dd, J=14.07, 6.61 Hz, 2H), 3.05 (m, 2H), 3.14 (m, 1H), 3.20 (m, 1H), 3.48 (dd, J=15.09, 3.22 Hz, 1H), 3.75 (m, 2H), 4.12 (m, 1H), 4.41 (m, 2H), 5.27 (s, 2H), 6.95 (d, J=8.48 Hz, 1H), 7.07 (m, 3H), 7.14 (dd, J=5.93, 3.90 Hz, 2H), 7.17 (s, 1H), 7.31 (m, 1H), 7.37 (m, 6H), 7.44 (m, 1H), 7.89 (d, J=9.49 Hz, 1H)

Example 693

$^1$H NMR (300 MHz, CDCl$_3$) δ ppm 0.78 (d, J=6.44 Hz, 3H), 0.82 (d, J=6.78 Hz, 3H), 0.86 (d, J=6.44 Hz, 3H), 0.92 (d, J=6.78 Hz, 3H), 1.83 (dd, J=8.14, 6.78 Hz, 1H), 2.14 (m, 1H), 2.26 (s, 3H), 2.69 (s, 3H), 2.72 (m, 2H), 2.79 (m, 1H), 2.97 (m, 1H), 3.03 (m, 1H), 3.10 (m, 2H), 3.17 (m, 2H), 3.26 (m, 2H), 3.64 (d, J=10.85 Hz, 1H), 3.75 (m, 1H), 3.92 (d, J=3.05 Hz, 1H), 4.17 (m, 3H), 4.41 (m, 2H), 6.43 (d, J=8.82 Hz, 1H), 6.92 (d, J=6.44 Hz, 1H), 7.14 (dd, J=8.82, 4.07 Hz, 1H), 7.19 (m, 5H), 7.60 (d, J=3.39 Hz, 1H), 7.63 (s, 1H)

Example 694

$^1$H NMR (300 MHz, CDCl$_3$) δ ppm 0.80 (d, J=5.09 Hz, 3H), 0.82 (d, J=6.44 Hz, 3H), 0.89 (d, J=6.44 Hz, 3H), 0.92 (d, J=6.78 Hz, 3H), 1.92 (d, J=7.46 Hz, 1H), 2.21 (d, J=5.09 Hz, 3H), 2.69 (s, 3H), 2.74 (d, J=10.51 Hz, 1H), 2.93 (m, 2H), 3.25 (m, 6H), 3.49 (s, 1H), 3.56 (d, J=11.19 Hz, 1H), 3.70 (d, J=5.43 Hz, 2H), 4.09 (s, 1H), 4.43 (m, 2H), 6.21 (d, J=7.80 Hz, 1H), 6.85 (s, 1H), 6.99 (s, 1H), 7.10 (m, 2H), 7.19 (m, 3H), 7.85 (s, 1H)

Example 695

$^1$H NMR (300 MHz, CDCl$_3$) δ ppm 0.74 (d, J=6.78 Hz, 3H), 0.82 (d, J=6.78 Hz, 3H), 0.88 (d, J=6.44 Hz, 3H), 0.92 (d, J=6.78 Hz, 3H), 1.27 (M, 1H), 1.87 (m, 1H), 2.15 (m, 1H), 2.68 (d, J=4.07 Hz, 3H), 2.72 (s, 3H), 3.08 (m, 1H), 3.12 (m, 1H), 3.19 (m, 2H), 3.26 (m, 1H), 3.38 (m, 1H), 3.40 (m, 1H), 3.62 (m, 1H), 3.64 (m, 1H), 3.78 (m, 2H), 4.17 (m, 1H), 4.41 (m, 2H), 4.47 (s, 1H), 6.54 (d, J=8.82 Hz, 1H), 7.08 (m, 1H), 7.17 (m, 5H), 7.86 (m, 1H), 8.24 (d, J=2.37 Hz, 1H)

Example 696

$^1$H NMR (300 MHz, CDCl$_3$) δ ppm 0.81 (d, J=3.39 Hz, 3H), 0.83 (d, J=3.73 Hz, 3H), 0.91 (d, J=3.73 Hz, 3H), 0.93 (d, J=4.07 Hz, 3H), 1.91 (dd, J=13.39, 6.61 Hz, 1H), 2.18 (m, 1H), 2.69 (s, 3H), 2.75 (m, 1H), 2.83 (d, J=8.48 Hz, 1H), 2.90 (dd, J=7.46, 2.37 Hz, 1H), 3.11 (dd, J=14.24, 4.07 Hz, 1H), 3.18 (m, 2H), 3.25 (m, 2H), 3.68 (d, P10.85 Hz, 1H), 3.86 (m, 2H), 4.10 (s, 1H), 4.41 (s, 2H), 5.61 (d, J=4.75 Hz, 2H), 6.51 (d, J=8.82 Hz, 1H), 6.92 (d, J=6.78 Hz, 1H), 7.18 (m, 5H), 7.54 (s, 1H)

Example 697

$^1$H NMR (300 MHz, CDCl$_3$) δ ppm 0.73 (d, J=6.44 Hz, 3H), 0.78 (d, J=6.78 Hz, 3H), 0.91 (t, J=6.27 Hz, 6H), 1.86 (t, J=6.78 Hz, 1H), 2.17 (s, 1H), 2.29 (s, 3H), 2.87 (m, 6H), 3.10 (m, 4H), 3.49 (s, 1H), 3.68 (d, J=10.85 Hz, 1H), 3.90 (m, 1H), 4.21 (s, 1H), 4.39 (d, J=15.26 Hz, 1H), 4.62 (m, 1H), 6.71 (d, J=8.82 Hz, 1H), 6.98 (d, J=8.48 Hz, 1H), 7.16 (m, 2H), 7.42 (m, 2H), 7.51 (m, 1H), 7.55 (s, 1H), 7.60 (m, 1H), 7.76 (m, 2H), 7.84 (d, J=8.14 Hz, 2H), 8.10 (d, J=1.36 Hz, 1H), 8.17 (d, J=8.82 Hz, 1H)

Example 698

$^1$H NMR (300 MHz, CDCl$_3$) δ ppm 0.80 (dd, J=8.14, 6.78 Hz, 6H), 0.89 (d, J=6.44 Hz, 3H), 0.93 (d, J=6.44 Hz, 3H), 1.84 (d, J=1.70 Hz, 1H), 2.16 (m, 1H), 2.29 (s, 3H), 2.76 (dd, J=14.07, 10.00 Hz, 1H), 2.84 (m, 2H), 2.94 (m, 2H), 3.04 (m, 1H), 3.13 (m, 3H), 3.65 (d, J=10.85 Hz, 1H), 3.79 (s, 1H), 4.15 (d, J=15.26 Hz, 1H), 4.19 (m, 1H), 4.42 (d, J=15.60 Hz, 1H), 6.06 (s, 1H), 6.33 (d, J=9.16 Hz, 1H), 6.85 (d, J=8.14 Hz, 1H), 7.19 (m, 5H), 7.34 (d, J=1.70 Hz, 1H), 7.50 (dd, J=8.48, 2.37 Hz, 1H), 7.56 (d, J=1.70 Hz, 1H), 7.80 (d, J=1.70 Hz, 1H)

Example 699

$^1$H NMR (300 MHz, CDCl$_3$) δ ppm 0.83 (t, J=6.27 Hz, 6H), 0.90 (t, J=7.12 Hz, 6H), 1.89 (m, 1H), 2.21 (m, 1H), 2.69 (d, J=8.82 Hz, 1H), 2.82 (m, 1H), 2.91 (m, 1H), 3.06 (m, 5H), 3.17 (m, 1H), 3.73 (m, 1H), 3.86 (m, 2H), 4.31 (m, 1H), 4.55 (s, 2H), 4.68 (d, J=15.60 Hz, 1H), 4.88 (m, 1H), 6.56 (d, J=8.82 Hz, 1H), 7.04 (dd, J=8.48, 2.03 Hz, 1H), 7.15 (m, 5H), 7.22 (d, J=2.03 Hz, 1H), 7.28 (s, 1H), 7.36 (d, J=8.14 Hz, 1H), 7.59 (m, 1H), 7.75 (m, 1H), 8.02 (s, 1H), 8.11 (d, J=8.48 Hz, 1H), 8.16 (d, J=7.80 Hz, 1H)

Example 700

$^1$H NMR (300 MHz, CDCl$_3$) δ ppm 0.76 (d, J=6.44 Hz, 3H), 0.81 (d, J=6.78 Hz, 3H), 0.88 (d, J=6.44 Hz, 3H), 0.93 (d, J=6.44 Hz, 3H), 1.87 (m, 1H), 2.13 (m, 1H), 2.69 (s, 3H), 2.74 (m, 1H), 2.88 (dd, J=13.56, 7.12 Hz, 2H), 2.94 (m, 2H), 3.02 (m, 1H), 3.07 (t, J=3.73 Hz, 2H), 3.17 (m, 4H), 3.61 (d, J=10.85 Hz, 1H), 3.71 (m, 1H), 3.90 (t, J=6.27 Hz, 2H), 4.05 (m, 1H), 4.40 (m, 2H), 6.47 (d, J=8.82 Hz, 1H), 6.92 (d, J=6.44 Hz, 1H), 7.16 (m, 5H), 7.38 (d, J=8.48 Hz, 2H), 7.73 (d, J=8.48 Hz, 2H)

Example 701

$^1$H NMR (300 MHz, CDCl$_3$) δ ppm 0.78 (d, J=6.78 Hz, 3H), 0.86 (t, J=6.61 Hz, 6H), 0.92 (d, J=6.44 Hz, 3H), 1.93

(m, 1H), 2.24 (s, 3H), 2.78 (dd, J=13.39, 6.61 Hz, 1H), 2.86 (m, 1H), 3.17 (m, 1H), 3.32 (dd, J=15.09, 3.90 Hz, 1H), 3.84 (d, J=9.16 Hz, 1H), 4.00 (dd, J=7.97, 4.24 Hz, 1H), 4.06 (m, 1H), 4.27 (m, 2H), 4.47 (m, 1H), 4.81 (d, J=7.12 Hz, 2H), 6.72 (s, 2H), 6.88 (m, 1H), 7.00 (d, J=2.03 Hz, 1H), 7.03 (d, J=2.03 Hz, 1H), 7.16 (m, 6H), 7.28 (d, J=2.03 Hz, 2H), 7.32 (s, 1H), 7.34 (d, J=3.39 Hz, 1H)

Example 702

$^1$H NMR (300 MHz, CDCl$_3$) δ ppm 0.77 (m, 3H), 0.81 (m, 3H), 0.92 (d, J=3.05 Hz, 6H), 1.92 (s, 1H), 2.15 (s, 1H), 2.73 (s, 3H), 2.79 (s, 2H), 3.01 (s, 3H), 3.18 (m, 3H), 3.27 (s, 3H), 3.59 (d, J=10.85 Hz, 1H), 3.80 (s, 1H), 4.06 (s, 1H), 4.43 (d, J=20.35 Hz, 2H), 6.57 (s, 1H), 7.01 (s, 1H), 7.17 (s, 5H), 7.82 (s, 1H), 8.03 (d, J=2.03 Hz, 1H)

Example 703

$^1$H NMR (300 MHz, CDCl$_3$) δ ppm 0.75 (d, J=6.44 Hz, 3H), 0.83 (t, J=7.29 Hz, 3H), 0.90 (m, 3H), 0.92 (d, J=4.75 Hz, 3H), 0.97 (m, 1H), 1.30 (m, 2H), 1.87 (m, 1H), 1.98 (m, 1H), 2.73 (m, 1H), 2.81 (m, 1H), 2.89 (d, J=7.12 Hz, 2H), 2.93 (d, J=15.26 Hz, 1H), 3.10 (m, 2H), 3.19 (m, 2H), 3.78 (s, 3H), 3.87 (d, J=10.17 Hz, 2H), 4.26 (m, 1H), 4.49 (d, J=15.26 Hz, 1H), 4.51 (s, 2H), 4.77 (d, J=15.26 Hz, 1H), 6.47 (d, J=8.82 Hz, 1H), 7.03 (dd, J=8.48, 2.03 Hz, 1H), 7.12 (m, 1H), 7.19 (m, 5H), 7.30 (m, 2H), 7.35 (m, 2H), 7.74 (m, 1H)

Example 704

$^1$H NMR (300 MHz, CDCl$_3$) δ ppm 0.77 (d, J=6.78 Hz, 3H), 0.85 (t, J=7.29 Hz, 3H), 0.93 (m, 6H), 1.00 (m, 1H), 1.32 (m, 1H), 1.69 (s, 2H), 1.90 (m, 2H), 1.98 (m, 1H), 2.77 (m, 1H), 2.89 (m, 2H), 3.08 (m, 2H), 3.16 (m, 1H), 3.80 (d, J=3.73 Hz, 1H), 3.85 (dd, J=8.31, 3.90 Hz, 1H), 3.97 (d, J=9.83 Hz, 1H), 4.31 (m, 1H), 4.57 (s, 2H), 4.66 (d, J=15.60 Hz, 1H), 4.91 (d, J=15.60 Hz, 1H), 6.59 (d, J=8.82 Hz, 1H), 7.05 (m, 1H), 7.16 (m, 6H), 7.29 (m, 1H), 7.36 (d, J=8.48 Hz, 1H), 7.60 (t, J=7.29 Hz, 1H), 7.76 (t, J=7.12 Hz, 1H), 8.11 (d, J=8.14 Hz, 1H), 8.20 (d, J=8.14 Hz, 1H), 8.88 (d, J=4.41 Hz, 1H)

Example 705

$^1$H NMR (300 MHz, CD$_3$OD) δ ppm 0.71 (d, J=6.78 Hz, 3H), 0.84 (d, J=7.46 Hz, 3H), 0.89 (d, J=6.78 Hz, 3H), 0.92 (d, J=6.44 Hz, 3H), 0.99 (m, 1H), 1.29 (m, 1H), 1.84 (m, 1H), 2.02 (m, 1H), 2.49 (m, 2H), 2.93 (dd, J=13.73, 6.95 Hz, 1H), 3.03 (m, 2H), 3.11 (m, 2H), 3.19 (dd, J=13.73, 3.22 Hz, 1H), 3.41 (dd, J=14.92, 3.73 Hz, 1H), 3.76 (m, 1H), 3.85 (d, J=11.19 Hz, 1H), 4.12 (m, 2H), 4.41 (d, J=14.92 Hz, 1H), 4.57 (m, 1H), 6.99 (m, 4H), 7.02 (d, J=2.37 Hz, 1H), 7.14 (m, 2H), 7.23 (d, J=1.36 Hz, 1H), 7.26 (d, J=2.03 Hz, 2H), 7.36 (d, J=8.14 Hz, 1H), 7.60 (m, 2H), 7.92 (d, J=9.49 Hz, 1H), 8.16 (s, 1H)

Example 706

$^1$H NMR (300 MHz, CD$_3$OD) δ ppm 0.73 (m, 3H), 0.88 (m, 6H), 0.94 (d, J=6.44 Hz, 3H), 1.04 (m, 2H), 1.41 (s, 1H), 1.90 (s, 1H), 2.02 (s, 1H), 2.93 (m, 2H), 3.02 (m, 2H), 3.10 (m, 2H), 3.17 (m, 1H), 3.25 (m, 2H), 3.42 (dd, J=14.92, 3.73 Hz, 1H), 3.78 (s, 1H), 3.87 (m, 1H), 4.18 (m, 1H), 4.53 (d, J=15.60 Hz, 1H), 4.79 (d, J=15.94 Hz, 1H), 7.01 (m, 1H), 7.11 (m, 4H), 7.19 (m, 2H), 7.26 (m, 1H), 7.36 (d, J=8.14 Hz, 1H), 7.47 (d, J=8.48 Hz, 1H), 7.59 (t, J=6.95 Hz, 1H), 7.77 (m, 1H), 7.93 (d, J=8.14 Hz, 1H), 8.03 (d, J=8.48 Hz, 1H), 8.34 (d, J=8.48 Hz, 1H)

Example 707

$^1$H NMR (300 MHz, CD$_3$OD) δ ppm 0.91 (m, 15H), 1.09 (m, 1H), 1.29 (d, J=2.94 Hz, 2H), 2.01 (m, 1H), 2.28 (m, 1H), 2.45 (dd, J=13.60, 11.77 Hz, 1H), 2.91 (m, 1H), 2.98 (m, 1H), 3.06 (m, 1H), 3.14 (m, 1H), 3.23 (m, 2H), 3.27 (m, 1H), 3.38 (dd, J=14.71, 3.68 Hz, 1H), 3.75 (m, 1H), 4.00 (s, 1H), 4.05 (m, 1H), 4.59 (m, 2H), 6.99 (m, 2H), 7.11 (m, 3H), 7.24 (m, 1H), 7.35 (m, 1H), 7.57 (d, J=10.66 Hz, 1H), 7.75 (dd, J=7.91, 5.33 Hz, 1H), 7.92 (m, 1H), 8.64 (m, 2H), 9.25 (s, 1H)

Example 708

$^1$H NMR (300 MHz, CD$_3$OD) δ ppm 0.87 (m, 3H), 0.90 (d, J=6.62 Hz, 3H), 0.93 (s, 9H), 1.98 (m, 1H), 2.28 (m, 1H), 2.44 (dd, J=13.79, 11.58 Hz, 1H), 2.92 (m, 1H), 2.98 (m, 1H), 3.12 (m, 1H), 3.17 (m, 1H), 3.23 (m, 2H), 3.29 (m, 3H), 3.35 (m, 1H), 3.75 (m, 1H), 4.01 (s, 1H), 4.06 (s, 1H), 4.58 (s, 1H), 4.81 (s, 2H), 6.73 (m, 2H), 6.99 (m, 1H), 7.11 (m, 3H), 7.24 (m, 1H), 7.51 (m, 2H), 7.61 (s, 1H), 7.81 (dd, J=8.27, 5.33 Hz, 1H), 7.95 (d, J=9.56 Hz, 1H), 8.70 (m, 1H), 9.27 (s, 1H)

Example 709

$^1$H NMR (300 MHz, CDCl$_3$) δ ppm 0.92 (d, J=4.78 Hz, 3H), 0.94 (d, J=4.78 Hz, 3H), 0.97 (s, 9H), 1.89 (m, 1H), 2.44 (m, 1H), 2.82 (m, 1H), 2.87 (m, 1H), 2.91 (m, 1H), 2.94 (d, J=2.94 Hz, 1H), 2.98 (m, 1H), 3.13 (t, J=5.15 Hz, 2H), 3.18 (m, 2H), 3.25 (m, 1H), 3.49 (s, 2H), 3.77 (d, J=4.04 Hz, 1H), 3.84 (m, 1H), 4.12 (s, 1H), 4.34 (m, 2H), 4.53 (m, 1H), 4.67 (s, 1H), 4.70 (s, 2H), 6.40 (d, J=9.19 Hz, 1H), 7.00 (dd, J=8.09, 2.21 Hz, 1H), 7.10 (m, 1H), 7.14 (dd, J=8.27, 3.13 Hz, 1H), 7.18 (d, J=2.94 Hz, 4H), 7.20 (s, 1H), 7.35 (d, J=8.46 Hz, 1H)

Example 710

$^1$H NMR (500 MHz, DMSO-d$_6$) δ ppm 0.63 (d, J=6.71 Hz, 3H), 0.78 (t, J=7.32 Hz, 3H), 0.82 (dd, J=6.41, 3.36 Hz, 6H), 0.90 (m, 1H), 1.26 (m, 1H), 1.75 (m, 1H), 1.96 (m, 1H), 2.42 (m, 1H), 2.50 (s, 2H), 2.61 (q, J=8.54 Hz, 1H), 2.71 (s, 3H), 2.84 (dd, J=13.43, 6.71 Hz, 1H), 2.99 (m, 2H), 3.09 (m, 1H), 3.21 (m, 2H), 3.59 (s, 1H), 3.87 (t, J=11.60 Hz, 1H), 3.92 (m, 1H), 4.43 (m, 2H), 4.94 (d, J=6.10 Hz, 1H), 5.80 (s, 2H), 6.87 (d, J=8.54 Hz, 1H), 6.99 (t, J=7.02 Hz, 1H), 7.07 (m, 3H), 7.22 (s, 1H), 7.36 (d, J=8.54 Hz, 1H), 7.43 (s, 1H), 7.85 (d, J=9.16 Hz, 1H), 8.03 (s, 1H)

Example 711

$^1$H NMR (300 MHz, CD$_3$OD) δ ppm 0.71 (d, J=6.44 Hz, 3H), 0.77 (d, J=6.78 Hz, 3H), 1.00 (d, J=6.10 Hz, 9H), 2.03 (m, 1H), 2.49 (m, 2H), 2.70 (s, 3H), 3.06 (m, 2H), 3.22 (m, 3H), 3.38 (s, 1H), 3.47 (m, 2H), 3.68 (d, J=10.85 Hz, 1H), 3.87 (m, 1H), 4.00 (m, 1H), 4.42 (m, 2H), 7.10 (m, 5H), 7.22 (s, 1H), 7.77 (m, 2H), 7.87 (m, 3H), 8.14 (s, 1H)

Example 712

$^1$H NMR (300 MHz, DMSO-d$_6$) δ ppm 0.69 (m, 6H), 0.81 (d, J=5.43 Hz, 6H), 1.95 (m, 2H), 2.40 (m, 1H), 2.57 (m, 1H), 2.63 (s, 3H), 2.91 (q, J=6.78 Hz, 4H), 3.02 (d, J=10.17 Hz, 4H), 3.13 (m, 4H), 3.25 (s, 1H), 3.57 (s, 1H), 3.76 (d, J=10.85

Hz, 1H), 3.89 (s, 1H), 4.33 (s, 2H), 7.08 (m, 4H), 7.22 (s, 1H), 7.78 (d, J=3.05 Hz, 2H), 7.90 (s, 1H), 7.93 (s, 4H), 8.85 (s, 1H)

Example 715

¹H NMR (300 MHz, CDCl₃) δ ppm 0.77 (d, J=6.78 Hz, 3H), 0.83 (d, J=6.78 Hz, 3H), 0.86 (d, J=6.44 Hz, 3H), 0.91 (d, J=6.78 Hz, 3H), 1.85 (m, 1H), 2.15 (m, 1H), 2.69 (s, 3H), 2.74 (m, 1H), 2.85 (dd, J=13.56, 7.12 Hz, 1H), 2.95 (d, J=8.14 Hz, 1H), 3.02 (m, 1H), 3.08 (m, 2H), 3.13 (m, 1H), 3.21 (m, 1H), 3.49 (d, J=5.43 Hz, 1H), 3.63 (d, J=11.19 Hz, 1H), 3.75 (d, J=9.16 Hz, 2H), 4.17 (d, J=1.70 Hz, 1H), 4.41 (m, 2H), 6.50 (d, J=9.16 Hz, 1H), 6.93 (s, 1H), 7.18 (m, 5H), 7.48 (m, 2H), 7.73 (m, 2H)

Example 716

¹H NMR (300 MHz, CDCl₃) δ ppm 0.77 (d, J=6.44 Hz, 3H), 0.82 (d, J=6.78 Hz, 3H), 0.86 (d, J=6.78 Hz, 3H), 0.91 (d, J=6.78 Hz, 3H), 1.85 (s, 1H), 2.15 (m, 1H), 2.69 (m, 3H), 2.73 (m, 1H), 2.84 (dd, J=13.56, 6.78 Hz, 1H), 2.98 (m, 1H), 3.09 (m, 2H), 3.15 (m, 2H), 3.22 (m, 2H), 3.64 (d, J=10.85 Hz, 1H), 3.76 (m, 1H), 4.17 (s, 1H), 4.42 (m, 2H), 6.49 (d, J=8.82 Hz, 1H), 6.92 (d, J=6.44 Hz, 1H), 7.18 (m, 6H), 7.79 (m, 2H), 7.82 (m, 2H)

Example 717

¹H NMR (300 MHz, CDCl₃) δ ppm 0.78 (d, J=6.44 Hz, 3H), 0.84 (d, J=6.44 Hz, 3H), 0.88 (d, J=6.44 Hz, 3H), 0.91 (d, J=6.44 Hz, 3H), 1.87 (d, J=7.46 Hz, 1H), 2.17 (m, 1H), 2.69 (s, 3H), 2.72 (d, J=4.41 Hz, 1H), 2.79 (m, 1H), 2.89 (m, 1H), 2.94 (dd, J=12.38, 7.63 Hz, 1H), 3.01 (d, J=7.80 Hz, 1H), 3.08 (m, 1H), 3.13 (m, 2H), 3.19 (m, 2H), 3.24 (m, 1H), 3.63 (d, J=10.85 Hz, 1H), 3.77 (s, 1H), 4.16 (s, 1H), 4.41 (m, 2H), 6.56 (d, J=8.48 Hz, 1H), 6.92 (m, 1H), 7.19 (m, 5H), 7.56 (dd, J=8.31, 2.20 Hz, 1H), 7.75 (m, 1H)

Example 718

¹H NMR (300 MHz, CDCl₃) δ ppm 0.81 (d, J=6.78 Hz, 3H), 0.85 (d, J=6.44 Hz, 3H), 0.89 (d, J=6.44 Hz, 6H), 1.94 (m, 1H), 2.13 (m, 1H), 2.42 (m, 3H), 2.64 (m, 1H), 2.69 (d, J=3.39 Hz, 3H), 2.89 (m, 2H), 3.05 (m, 1H), 3.14 (m, 2H), 3.20 (m, 1H), 3.39 (dd, J=15.09, 2.20 Hz, 1H), 3.50 (d, J=7.80 Hz, 1H), 3.57 (m, 1H), 3.62 (s, 3H), 3.71 (d, J=10.85 Hz, 1H), 3.93 (m, 1H), 4.24 (m, 1H), 4.46 (m, 2H), 6.35 (d, J=9.49 Hz, 1H), 6.95 (s, 1H), 7.16 (m, 5H), 7.36 (s, 1H)

Example 719

¹H NMR (300 MHz, CDCl₃) δ ppm 0.81 (d, J=6.44 Hz, 3H), 0.84 (d, J=6.78 Hz, 3H), 0.90 (d, J=6.44 Hz, 6H), 1.95 (m, 1H), 2.13 (m, 1H), 2.60 (m, 1H), 2.68 (m, 1H), 2.69 (s, 3H), 2.92 (dd, J=7.46, 2.03 Hz, 2H), 3.05 (m, 1H), 3.12 (m, 2H), 3.20 (m, 1H), 3.41 (dd, J=15.26, 2.37 Hz, 1H), 3.51 (m, 1H), 3.77 (s, 3H), 3.92 (s, 1H), 4.24 (dd, J=9.66, 6.27 Hz, 1H), 4.44 (m, 2H), 5.98 (s, 1H), 6.41 (d, J=9.83 Hz, 1H), 6.95 (s, 1H), 7.12 (m, 5H), 7.46 (d, J=1.36 Hz, 1H), 7.51 (d, J=1.02 Hz, 1H)

Example 720

¹H NMR (300 MHz, CDCl₃) δ ppm 0.79 (d, J=6.44 Hz, 3H), 0.86 (d, J=6.78 Hz, 3H), 0.90 (d, J=6.44 Hz, 6H), 1.88 (s, 1H), 2.22 (m, 1H), 2.68 (d, J=5.76 Hz, 3H), 2.75 (m, 1H), 2.90 (d, J=8.82 Hz, 1H), 3.00 (m, 2H), 3.26 (m, 6H), 3.60 (d, JA 1.19 Hz, 1H), 3.79 (m, 1H), 4.15 (s, 1H), 4.41 (s, 2H), 6.76 (d, J=7.80 Hz, 1H), 6.93 (s, 1H), 7.20 (m, 5H), 8.30 (d, J=2.37 Hz, 1H), 8.69 (d, J=2.03 Hz, 1H)

Example 721

¹H NMR (300 MHz, CDCl₃) δ ppm 0.77 (d, J=6.44 Hz, 2H), 0.85 (t, J=6.27 Hz, 6H), 0.89 (d, J=6.44 Hz, 3H), 1.52 (s, 2H), 1.88 (d, J=6.10 Hz, 1H), 2.17 (d, J=10.85 Hz, 1H), 2.69 (s, 3H), 2.76 (m, 2H), 2.97 (t, J=7.29 Hz, 1H), 3.07 (m, 1H), 3.20 (m, 4H), 3.62 (d, J=10.85 Hz, 1H), 3.73 (d, J=4.07 Hz, 2H), 4.16 (s, 1H), 4.41 (d, J=2.03 Hz, 2H), 6.61 (d, J=8.14 Hz, 1H), 6.93 (s, 1H), 7.20 (m, 5H), 7.79 (m, 2H), 7.91 (d, J=8.82 Hz, 21-j Example 722

¹H NMR (300 MHz, CDCl₃) δ ppm 0.78 (d, J=6.44 Hz, 3H), 0.83 (d, J=6.78 Hz, 3H), 0.87 (m, 3H), 0.91 (d, J=6.44 Hz, 3H), 1.86 (m, 1H), 2.16 (m, 1H), 2.69 (s, 3H), 2.74 (m, 1H), 2.87 (m, 1H), 3.00 (m, 1H), 3.15 (m, 4H), 3.25 (m, 1H), 3.64 (d, J=11.19 Hz, 1H), 3.77 (m, 2H), 4.17 (m, 1H), 4.41 (m, 2H), 6.51 (d, J=8.82 Hz, 1H), 6.93 (s, 1H), 7.17 (m, 6H), 7.29 (m, 1 H), 7.50 (m, 2H), 7.59 (m, 1H)

Example 723

¹H NMR (300 MHz, CDCl₃) δ ppm 0.77 (d, J=6.44 Hz, 3H), 0.83 (d, J=6.44 Hz, 3H), 0.86 (d, J=6.44 Hz, 3H), 0.90 (d, J=6.44 Hz, 3H), 1.85 (m, 1H), 2.16 (m, 1H), 2.68 (d, J=5.09 Hz, 3H), 2.74 (m, 1H), 2.85 (dd, J=13.39, 6.95 Hz, 1H), 2.97 (m, 1H), 3.07 (m, 2H), 3.13 (m, 2H), 3.23 (m, 2H), 3.64 (d, J=11.19 Hz, 1H), 3.76 (m, 2H), 4.17 (m, 1H), 4.39 (m, 2H), 6.53 (d, J=8.48 Hz, 1H), 6.92 (d, J=6.44 Hz, 1H), 7.16 (m, 5H), 7.64 (m, 4H)

Example 724

¹H NMR (300 MHz, CDCl₃) δ ppm 0.78 (d, J=6.44 Hz, 3H), 0.83 (d, J=6.78 Hz, 3H), 0.87 (d, J=6.78 Hz, 3H), 0.91 (m, 3H), 1.86 (m, 1H), 2.17 (m, 1H), 2.69 (s, 3H), 2.76 (m, 1H), 2.94 (dd, J=14.41, 7.63 Hz, 2H), 3.13 (m, 2H), 3.23 (m, 2H), 3.64 (d, J=11.19 Hz, 1H), 3.77 (m, 2H), 4.17 (m, 1H), 4.41 (m, 2H), 6.58 (d, J=8.48 Hz, 1H), 6.93 (m, 1H), 7.16 (m, 6H), 7.69 (m, 2H), 7.88 (dd, J=6.78, 2.37 Hz, 1H), 7.88 (dd, J=6.78, 2.37 Hz, 1H)

Example 725

¹H NMR (300 MHz, CDCl₃) δ ppm 0.76 (d, J=6.44 Hz, 3H), 0.81 (d, J=6.78 Hz, 3H), 0.87 (d, J=6.44 Hz, 3H), 0.93 (d, J=6.44 Hz, 3H), 1.85 (dd, J=8.14, 6.78 Hz, 1H), 2.14 (m, 1H), 2.69 (s, 3H), 2.73 (m, 1H), 2.81 (dd, J=13.56, 6.78 Hz, 1H), 2.99 (m, 1H), 3.04 (m, 1H), 3.11 (m, 1H), 3.20 (m, 4H), 3.64 (d, J=10.85 Hz, 1H), 3.75 (s, 1H), 3.85 (s, 1H), 3.93 (s, 3H), 3.94 (s, 3H), 4.18 (m, 1H), 4.41 (m, 2H), 6.43 (d, J=8.82 Hz, 1H), 6.92 (d, J=5.76 Hz, 1H), 6.95 (s, 1H), 7.15 (m, 5H), 7.40 (d, J=2.37 Hz, 1H), 7.43 (d, J=2.37 Hz, 1H)

Example 726

¹H NMR (300 MHz, CDCl₃) δ ppm 0.78 (d, J=6.78 Hz, 3H), 0.83 (d, J=6.78 Hz, 3H), 0.87 (d, J=6.44 Hz, 3H), 0.91 (d, J=6.78 Hz, 3H), 1.86 (m, 1H), 2.17 (m, 1H), 2.69 (s, 3H), 2.74 (m, 1H), 2.80 (d, J=8.82 Hz, 1H), 2.94 (dd, J=13.22, 7.46 Hz, 2H), 3.07 (m, 1H), 3.14 (dd, J=6.44, 3.05 Hz, 2H), 3.18 (m, 1H), 3.24 (m, 1H), 3.63 (d, J=11.19 Hz, 1H), 3.76 (m, 2H), 4.17 (m, 1H), 4.41 (m, 2H), 6.57 (d, J=8.48 Hz, 1H), 6.93 (s, 1H), 7.17 (m, 5H), 7.59 (m, 2H), 7.88 (d, J=2.03 Hz, 1H)

Example 727

$^1$H NMR (300 MHz, CDCl$_3$) δ ppm 0.76 (d, J=6.44 Hz, 3H), 0.82 (d, J=6.78 Hz, 3H), 0.86 (d, J=6.44 Hz, 3H), 0.90 (d, J=6.44 Hz, 3H), 1.86 (m, 1H), 2.14 (m, 1H), 2.65 (m, 3H), 2.69 (m, 3H), 2.74 (m, 1H), 2.89 (dd, J=13.56, 7.12 Hz, 1H), 3.01 (m, 1H), 3.10 (m, 3H), 3.19 (m, 2H), 3.26 (m, 1H), 3.63 (d, J=10.85 Hz, 1H), 3.76 (m, 2H), 4.16 (dd, J=8.82, 5.09 Hz, 1H), 4.41 (m, 2H), 6.53 (d, J=8.48 Hz, 1H), 6.92 (d, J=5.76 Hz, 1H), 7.17 (m, 5H), 7.88 (m, 2H), 8.06 (m, 2H)

Example 728

$^1$H NMR (300 MHz, CDCl$_3$) δ ppm 0.80 (d, J=7.46 Hz, 6H), 0.85 (dd, J=7.12, 4.41 Hz, 6H), 1.86 (m, 1H), 2.17 (m, 1H), 2.68 (d, J=3.73 Hz, 3H), 2.77 (m, 1H), 3.02 (dd, J=14.07, 4.58 Hz, 1H), 3.19 (m, 5H), 3.43 (m, 2H), 3.48 (d, J=4.41 Hz, 1H), 3.61 (d, J=11.19 Hz, 1H), 3.82 (m, 1H), 4.16 (m, 1H), 4.41 (m, 2H), 6.56 (d, J=8.48 Hz, 1H), 6.92 (d, J=6.78 Hz, 1H), 7.15 (m, 5H), 7.45 (m, 2H)

Example 729

$^1$H NMR (300 MHz, CDCl$_3$) δ ppm 0.81 (m, 6H), 0.86 (m, 6H), 1.86 (d, P6.78 Hz, 1H), 2.18 (m, 1H), 2.68 (d, J=5.76 Hz, 3H), 2.80 (m, 1H), 3.04 (dd, J=14.41, 4.58 Hz, 1H), 3.18 (m, 4H), 3.39 (m, 2H), 3.62 (m, 2H), 3.84 (d, J=4.07 Hz, 1H), 4.18 (d, J=8.48 Hz, 1H), 4.42 (m, 2H), 6.65 (d, J=8.14 Hz, 1H), 6.94 (s, 1H), 7.18 (m, 5H), 7.65 (m, 1H), 7.70 (dd, J=5.76, 1.70 Hz, 1H), 7.74 (m, 1H), 7.85 (m, 1H), 8.08 (m, 1H)

Example 730

$^1$H NMR (300 MHz, CDCl$_3$) δ ppm 0.79 (d, J=6.78 Hz, 3H), 0.84 (d, J=6.78 Hz, 3H), 0.86 (s, 3H), 0.89 (m, 3H), 1.86 (m, 1H), 2.18 (m, 1H), 2.69 (s, 3H), 2.75 (m, 1H), 2.86 (m, 1H), 2.96 (m, 2H), 3.07 (m, 1H), 3.20 (m, 4H), 3.63 (d, J=10.85 Hz, 1H), 3.76 (m, 2H), 4.18 (d, J=9.16 Hz, 1H), 4.41 (m, 2H), 6.63 (d, J=8.48 Hz, 1H), 6.92 (d, J=7.12 Hz, 1H), 7.20 (m, 5H), 7.63 (m, 1H), 7.84 (m, 1H), 8.02 (dd, J=9.49, 1.70 Hz, 1H), 8.08 (s, 1H)

Example 731

$^1$H NMR (300 MHz, CDCl$_3$) δ ppm 0.83 (t, J=6.44 Hz, 6H), 0.88 (m, 3H), 0.90 (m, 3H), 1.89 (m, 1H), 2.18 (m, 1H), 2.68 (d, J=5.76 Hz, 3H), 2.76 (m, 1H), 3.08 (m, 3H), 3.16 (dd, J=9.32, 4.58 Hz, 1H), 3.22 (m, 1H), 3.29 (m, 2H), 3.49 (d, J=5.43 Hz, 1H), 3.64 (d, J=10.85 Hz, 1H), 3.70 (d, J=3.73 Hz, 1H), 3.81 (dd, J=7.63, 4.24 Hz, 1H), 4.19 (m, 1H), 4.41 (m, 2H), 6.57 (d, J=8.48 Hz, 1H), 6.92 (d, J=7.46 Hz, 1H), 6.93 (s, 1H), 7.16 (m, 5H)

Example 732

$^1$H NMR (300 MHz, CDCl$_3$) δ ppm 0.78 (d, J=6.44 Hz, 3H), 0.82 (d, J=6.44 Hz, 3H), 0.90 (d, J=6.44 Hz, 3H), 0.93 (d, J=6.78 Hz, 3H), 1.90 (m, 1H), 2.15 (m, 1H), 2.67 (s, 1H), 2.68 (d, J=5.43 Hz, 3H), 2.73 (m, 1H), 2.87 (m, 1H), 2.98 (m, 1H), 3.13 (m, 4H), 3.22 (m, 1H), 3.64 (d, J=11.19 Hz, 1H), 3.73 (d, J=3.05 Hz, 1H), 3.81 (dd, J=8.48, 4.75 Hz, 1H), 4.18 (d, J=8.82 Hz, 1H), 4.41 (m, 2H), 6.49 (d, J=8.48 Hz, 1H), 6.93 (s, 1H), 7.11 (m, 1H), 7.17 (m, 5H), 7.58 (m, 2H)

Example 733

$^1$H NMR (300 MHz, CDCl$_3$) δ ppm 0.79 (d, J=3.73 Hz, 3H), 0.83 (m, 6H), 0.85 (d, J=6.44 Hz, 3H), 1.81 (d, J=6.44 Hz, 1H), 2.17 (m, 1H), 2.68 (d, J=5.76 Hz, 3H), 2.80 (t, J=8.82 Hz, 1H), 3.03 (dd, J=14.24, 4.41 Hz, 1H), 3.19 (m, 5H), 3.35 (d, J=5.43 Hz, 2H), 3.54 (d, J=4.41 Hz, 1H), 3.62 (d, J=11.19 Hz, 1H), 3.77 (d, J=5.76 Hz, 1H), 4.15 (s, 1H), 4.39 (m, 2H), 6.51 (d, J=8.82 Hz, 1H), 6.92 (d, J=6.44 Hz, 1H), 7.17 (m, 5H), 7.37 (dd, 8.65, 2.20 Hz, 1H), 7.51 (d, J=2.03 Hz, 1H), 8.02 (d, J=8.48 Hz, 1H)

Example 734

$^1$H NMR (300 MHz, CDCl$_3$) δ ppm 0.81 (dd, J=6.44, 5.09 Hz, 9H), 0.86 (d, J=6.78 Hz, 3H), 1.83 (m, 1H), 2.15 (m, 1H), 2.67 (m, 3H), 2.79 (q, J=8.59 Hz, 1H), 3.02 (dd, J=14.24, 4.41 Hz, 1H), 3.18 (m, 5H), 3.35 (d, J=5.76 Hz, 2H), 3.56 (d, J=4.41 Hz, 1H), 3.61 (m, 1H), 3.78 (m, 1H), 4.13 (m, 1H), 4.41 (m, 2H), 6.51 (d, J=8.82 Hz, 1H), 6.92 (d, J=6.44 Hz, 1H), 7.17 (m, 5H), 7.34 (t, J=7.97 Hz, 1H), 7.66 (dd, J=8.14, 1.70 Hz, 1H), 8.03 (dd, J=7.97, 1.53 Hz, 1H)

Example 735

$^1$H NMR (300 MHz, CDCl$_3$) δ ppm 0.79 (d, J=6.44 Hz, 3H), 0.83 (d, J=6.78 Hz, 3H), 0.88 (m, 3H), 0.90 (d, J=6.78 Hz, 3H), 1.86 (s, 1H), 2.17 (m, 1H), 2.39 (d, J=3.73 Hz, 3H), 2.65 (s, 3H), 2.70 (m, 3H), 2.75 (m, 1H), 2.97 (dd, J=14.24, 7.46 Hz, 1H), 3.04 (d, J=5.76 Hz, 1H), 3.10 (m, 1H), 3.20 (m, 5H), 3.61 (d, J=10.85 Hz, 1H), 3.68 (d, J=4.07 Hz, 1H), 3.77 (s, 1H), 4.14 (s, 1H), 4.41 (m, 2H), 6.56 (d, J=8.82 Hz, 1H), 7.18 (m, 6H)

Example 736

$^1$H NMR (300 MHz, CDCl$_3$) δ ppm 0.81 (m, 9H), 0.88 (d, J=6.44 Hz, 3H), 1.79 (m, 1H), 2.14 (m, 1H), 2.41 (m, 3H), 2.68 (d, J=6.44 Hz, 3H), 2.69 (m, 1H), 2.90 (m, 1H), 3.09 (m, 3H), 3.19 (m, 2H), 3.45 (m, 1H), 3.45 (m, 1H), 3.65 (d, J=10.85 Hz, 1H), 3.71 (m, 1H), 3.82 (d, J=3.05 Hz, 1H), 3.90 (s, 3H), 4.15 (m, 1H), 4.41 (m, 2H), 6.31 (d, J=9.16 Hz, 1H), 6.78 (s, 1H), 6.85 (d, J=8.14 Hz, 1H), 6.93 (s, 1H), 7.13 (m, 5H), 7.79 (d, J=8.14 Hz, 1H)

Example 737

$^1$H NMR (300 MHz, CDCl$_3$) δ ppm 0.79 (d, J=6.44 Hz, 3H), 0.83 (d, J=6.78 Hz, 3H), 0.87 (d, J=6.78 Hz, 3H), 0.91 (d, J=6.44 Hz, 3H), 1.86 (m, 1H), 2.16 (m, 1H), 2.28 (d, J=2.71 Hz, 3H), 2.69 (s, 3H), 2.74 (m, 2H), 2.86 (m, 1H), 2.98 (m, 1H), 3.15 (m, 3H), 3.64 (d, J=10.85 Hz, 1H), 3.76 (m, 1H), 3.82 (m, 1H), 4.16 (m, 1H), 4.41 (m, 2H), 6.52 (d, J=8.82 Hz, 1H), 6.92 (d, J=6.78 Hz, 1H), 7.16 (m, 6H), 7.67 (dd, J=8.82, 2.03 Hz, 1H), 7.79 (m, 1H), 7.83 (d, J=2.03 Hz, 1H), 8.61 (d, J=8.82 Hz, 1H)

Example 738

$^1$H NMR (300 MHz, CDCl$_3$) δ ppm 0.44 (s, 2H), 0.70 (d, J=6.44 Hz, 3H), 0.89 (d, J=6.78 Hz, 3H), 0.99 (d, J=6.44 Hz, 3H), 1.90 (d, 5.60 Hz, 2H), 2.37 (d, J=36.28 Hz, 4H), 2.64 (s, 3H), 2.84 (m, 4H), 3.09 (m, 6H), 3.68 (s, 1H), 4.17 (s, 2H), 4.45 (d, J=31.87 Hz, 2H), 6.61 (s, 1H), 6.96 (m, 6H), 7.67 (s, 1H), 8.39 (s, 1H)

Example 739

$^1$H NMR (300 MHz, CDCl$_3$) δ ppm 0.76 (d, J=6.44 Hz, 2H), 0.82 (d, J=6.44 Hz, 3H), 0.88 (d, J=6.78 Hz, 3H), 0.92 (m, 3H), 1.89 (d, J=6.44 Hz, 1H), 2.16 (d, J=6.78 Hz, 1H), 2.68 (s, 1H), 2.69 (d, J=3.73 Hz, 3H), 2.74 (m, 1H), 2.82 (d, J=8.82 Hz, 1H), 2.87 (s, 1H), 2.94 (dd, J=10.68, 7.63 Hz, 1H), 3.05 (m, 1H), 3.10 (m, 1H), 3.15 (d, J=6.44 Hz, 1H), 3.22 (m, 1H), 3.60 (m, 1H), 3.75 (s, 1H), 3.87 (d, J=3.05 Hz, 1H), 4.08 (d, J=4.75 Hz, 1H), 4.41 (s, 2H), 6.49 (d, J=8.48 Hz, 1H), 6.95 (s, 1H), 7.08 (d, J=8.48 Hz, 1H), 7.18 (m, 5H), 7.47 (d, J=1.36 Hz, 1H), 7.51 (m, 1H), 7.55 (d, J=2.03 Hz, 1H)

Example 740

$^1$H NMR (300 MHz, CDCl$_3$) δ ppm 0.74 (dd, J=6.61, 3.22 Hz, 6H), 0.81 (dd, J=6.61, 2.54 Hz, 6H), 1.85 (m, 1H), 2.14 (m, 1H), 2.67 (m, 3H), 2.76 (m, 1H), 3.03 (m, 1H), 3.16 (m, 5H), 3.33 (m, 2H), 3.60 (d, J=11.19 Hz, 1H), 3.70 (d, J=4.07 Hz, 1H), 3.79 (m, 1H), 4.15 (m, 1H), 4.40 (d, J=3.73 Hz, 2H), 6.51 (d, J=8.82 Hz, 1H), 6.91 (m, 1H), 7.15 (m, 5H), 7.70 (m, 1H), 8.19 (d, J=8.48 Hz, 1H), 8.36 (m, 1H), 8.44 (d, J=6.10 Hz, 1H), 8.70 (d, J=6.10 Hz, 1H), 9.34 (s, 1H)

Example 741

$^1$H NMR (300 MHz, CDCl$_3$) δ ppm 0.75 (d, J=6.44 Hz, 3H), 0.81 (d, J=6.78 Hz, 3H), 0.88 (d, J=6.44 Hz, 3H), 0.94 (d, J=6.44 Hz, 3H), 1.86 (dd, J=8.14, 6.78 Hz, 1H), 2.14 (m, 1H), 2.69 (s, 3H), 2.70 (m, 1H), 2.83 (dd, J=13.39, 6.61 Hz, 1H), 3.03 (m, 1H), 3.14 (m, 3H), 3.26 (m, 2H), 3.62 (d, J=11.19 Hz, 1H), 3.75 (m, 1H), 3.84 (d, J=3.39 Hz, 1H), 3.90 (s, 3H), 3.91 (s, 6H), 4.17 (m, 1H), 4.36 (d, J=15.60 Hz, 1H), 4.44 (d, J=15.60 Hz, 1H), 6.45 (d, J=8.82 Hz, 1H), 6.92 (s, 1H), 7.03 (s, 2H), 7.17 (m, 5H)

Example 742

$^1$H NMR (300 MHz, CDCl$_3$) δ ppm 0.78 (d, J=6.44 Hz, 3H), 0.82 (d, J=6.78 Hz, 3H), 0.87 (d, J=6.78 Hz, 3H), 0.92 (d, J=6.44 Hz, 3H), 1.84 (d, J=8.14 Hz, 1H), 2.15 (m, 1H), 2.44 (d, J=4.41 Hz, 3H), 2.49 (d, J=10.51 Hz, 1H), 2.68 (d, J=7.12 Hz, 3H), 2.69 (m, 2H), 2.76 (m, 1H), 2.85 (dd, J=13.56, 6.78 Hz, 1H), 3.00 (m, 1H), 3.11 (m, 3H), 3.21 (m, 2H), 3.64 (d, J=11.19 Hz, 1H), 3.78 (m, 1H), 4.16 (m, 1H), 4.41 (m, 1H), 6.48 (d, J=8.82 Hz, 1H), 6.92 (d, J=9.16 Hz, 1H), 7.17 (m, 5H), 7.36 (d, J=7.80 Hz, 1H), 7.56 (dd, J=7.97, 1.87 Hz, 1H), 7.77 (d, J=2.03 Hz, 1H)

Example 743

$^1$H NMR (300 MHz, CDCl$_3$) δ ppm 0.80 (d, J=6.78 Hz, 6H), 0.84 (dd, J=6.61, 1.53 Hz, 6H), 1.83 (m, 1H), 2.18 (m, 1H), 2.68 (d, J=3.73 Hz, 3H), 2.83 (q, J=8.36 Hz, 1H), 3.00 (dd, J=14.41, 4.58 Hz, 1H), 3.19 (m, 6H), 3.41 (m, 2H), 3.60 (m, 2H), 3.81 (dd, J=6.95, 4.92 Hz, 1H), 4.15 (m, 1H), 4.38 (d, J=16.28 Hz, 1H), 6.58 (d, J=8.14 Hz, 1H), 6.93 (s, 1H), 7.17 (m, 6H), 7.62 (m, 1H), 7.72 (m, 1H)

Example 744

$^1$H NMR (300 MHz, CDCl$_3$) δ ppm 0.80 (m, 6H), 0.83 (d, J=4.41 Hz, 3H), 0.85 (d, J=3.73 Hz, 3H), 1.85 (m, 1H), 2.17 (m, 1H), 2.69 (m, 3H), 2.83 (m, 1H), 3.02 (dd, J=14.41, 4.58 Hz, 1H), 3.19 (m, 4H), 3.38 (d, J=5.76 Hz, 2H), 3.55 (d, J=4.41 Hz, 1H), 3.61 (d, J=10.85 Hz, 1H), 3.79 (d, J=5.09 Hz, 1H), 4.15 (s, 1H), 4.41 (s, 2H), 6.55 (d, J=8.48 Hz, 1H), 6.93 (s, 1H), 7.16 (m, 5H), 7.23 (d, J=6.10 Hz, 1H), 7.64 (d, J=8.48 Hz, 1H), 7.75 (s, 1H), 8.22 (d, J=7.80 Hz, 1H)

Example 745

$^1$H NMR (300 MHz, CDCl$_3$) δ ppm 0.79 (dd, J=9.32, 6.61 Hz, 6H), 0.89 (m, 6H), 1.92 (m, 2H), 2.14 (m, 2H), 2.70 (m, 3H), 2.78 (m, 2H), 3.05 (m, 4H), 3.21 (m, 3H), 3.78 (d, J=10.85 Hz, 1H), 3.89 (d, J=5.43 Hz, 1H), 4.29 (s, 1H), 4.44 (m, 2H), 6.96 (m, 1H), 7.13 (m, 5H), 7.91 (m, 2H), 8.14 (d, J=8.82 Hz, 2H)

Example 746

$^1$H NMR (300 MHz, CDCl$_3$) δ ppm 0.76 (d, J=6.78 Hz, 3H), 0.81 (d, J=6.78 Hz, 3H), 0.86 (d, J=6.44 Hz, 3H), 0.92 (d, J=6.44 Hz, 3H), 1.85 (m, 1H), 2.15 (m, 1H), 268 (d, J=6.78 Hz, 3H), 2.72 (m, 1H), 2.83 (m, 1H), 2.97 (d, J=8.14 Hz, 1H), 3.02 (dd, J=5.59, 2.54 Hz, 1H), 3.08 (dd, J=10.51, 3.73 Hz, 1H), 3.14 (s, 1H), 3.17 (m, 1H), 3.24 (m, 1H), 3.64 (d, J=10.85 Hz, 1H), 3.76 (m, 1H), 3.83 (d, J=3.39 Hz, 1H), 4.17 (m, 1H), 4.41 (m, 2H), 6.45 (d, J=8.82 Hz, 1H), 6.92 (d, J=6.44 Hz, 1H), 7.14 (m, 1H), 7.20 (m, 5H), 7.53 (m, 2H), 7.58 (m, 1H), 7.78 (t, J=1.87 Hz, 1H), 7.81 (m, 1H)

Example 747

$^1$H NMR (300 MHz, CDCl$_3$) δ ppm 0.80 (m, 6H), 0.85 (d, J=6.44 Hz, 3H), 0.87 (d, J=6.44 Hz, 3H), 1.77 (m, 1H), 2.16 (m, 1H), 2.68 (d, J=4.41 Hz, 3H), 2.75 (m, 1H), 2.96 (dd, J=14.24, 6.78 Hz, 1H), 3.11 (m, 4H), 3.24 (m, 1H), 3.46 (m, 1H), 3.65 (d, J=11.19 Hz, 1H), 3.71 (m, 2H), 3.90 (d, J=3.73 Hz, 3H), 4.08 (m, 1H), 4.15 (m, 1H), 4.41 (m, 2H), 6.41 (d, J=8.82 Hz, 1H), 6.87 (m, 1H), 6.92 (d, J=6.78 Hz, 1H), 7.16 (m, 5H), 7.61 (m, 1H), 8.05 (m, 1H)

Example 748

$^1$H NMR (300 MHz, CDCl$_3$) δ ppm 0.81 (d, J=6.78 Hz, 3H), 0.86 (m, 6H), 0.90 (m, 3H), 1.91 (m, 1H), 2.16 (m, 1H), 2.67 (s, 3H), 2.77 (dd, J=14.24, 10.17 Hz, 1H), 2.87 (dd, J=13.73, 7.29 Hz, 1H), 2.96 (m, 2H), 3.24 (m, 4H), 3.33 (m, 2H), 3.82 (d, J=10.85 Hz, 1H), 3.95 (dd, J=7.97, 4.24 Hz, 1H), 4.43 (t, J=4.58 Hz, 1H), 4.48 (m, 2H), 6.92 (s, 1H), 7.09 (m, 3H), 7.16 (m, 4H), 7.32 (m, 1H), 7.71 (dd, J=8.14, 1.70 Hz, 1H), 7.97 (d, J=1.70 Hz, 1H)

Example 749

$^1$H NMR (300 MHz, CDCl$_3$) δ ppm 0.76 (d, J=6.44 Hz, 3H), 0.81 (d, J=6.78 Hz, 3H), 0.87 (d, J=6.78 Hz, 3H), 0.92 (d, J=6.78 Hz, 3H), 1.85 (m, 1H), 2.14 (m, 1H), 2.68 (d, J=5.76 Hz, 3H), 2.73 (m, 1H), 2.83 (dd, J=13.39, 6.95 Hz, 1H), 2.99 (m, 1H), 3.08 (m, 1H), 3.15 (d, J=8.14 Hz, 2H), 3.21 (m, 2H), 3.64 (d, J=10.85 Hz, 1H), 3.77 (m, 1H), 3.83 (d, J=3.39 Hz, 1H), 4.18 (m, 1H), 4.41 (m, 2H), 5.43 (m, 1H), 5.88 (d, J=17.63 Hz, 1H), 6.45 (d, J=8.82 Hz, 1H), 6.74 (dd, J=17.63, 10.85 Hz, 1H), 6.93 (s, 1H), 7.17 (m, 6H), 7.51 (m, 2H), 7.76 (m, 2H)

Example 750

$^1$H NMR (300 MHz, CDCl$_3$) δ ppm 0.78 (d, J=6.44 Hz, 3H), 0.82 (d, J=6.44 Hz, 3H), 0.87 (d, J=6.78 Hz, 3H), 0.93 (d, J=6.44 Hz, 3H), 1.83 (dd, J=8.48, 6.78 Hz, 1H), 2.14 (m, 1H), 2.69 (s, 3H), 2.72 (m, 1H), 2.78 (m, 1H), 2.95 (d, J=8.48 Hz, 1H), 3.00 (m, 1H), 3.14 (m, 4H), 3.27 (m, 2H), 3.65 (d, J=10.85 Hz, 1H), 3.76 (m, 1H), 3.93 (d, J=2.71 Hz, 1H), 4.18 (d, J=9.49 Hz, 1H), 4.41 (m, 2H), 4.68 (t, J=8.82 Hz, 2H), 6.41 (d, J=9.49 Hz, 1H), 6.84 (d, J=8.48 Hz, 1H), 6.93 (s, 1H), 7.17 (m, 5H), 7.56 (d, J=2.37 Hz, 1H), 7.59 (d, J=2.03 Hz, 1H), 7.61 (s, 1H)

Example 751

$^1$H NMR (300 MHz, CDCl$_3$) δ ppm 0.77 (d, J=6.44 Hz, 3H), 0.82 (d, J=6.44 Hz, 3H), 0.88 (d, J=6.78 Hz, 3H), 0.93 (d, J=6.44 Hz, 3H), 1.51 (d, J=6.44 Hz, 3H), 1.89 (m, 1H), 2.15 (m, 1H), 2.69 (m, 3H), 2.74 (m, 1H), 2.86 (m, 1H), 3.01 (m, 1H), 3.10 (m, 3H), 3.18 (m, 1H), 3.25 (m, 1H), 3.59 (dd, J=10.85, 2.37 Hz, 1H), 3.75 (d, J=9.16 Hz, 2H), 4.09 (dd, J=8.99, 4.24 Hz, 1H), 4.35 (m, 3H), 4.97 (q, J=6.67 Hz, 1H), 6.41 (t, J=8.99 Hz, 1H), 6.92 (s, 1H), 7.15 (m, 5H), 7.53 (d, J=8.48 Hz, 2H), 7.76 (d, J=8.48 Hz, 2H)

Example 752

$^1$H NMR (300 MHz, CDCl$_3$) δ ppm 0.79 (d, J=6.44 Hz, 3H), 0.82 (d, J=6.78 Hz, 3H), 0.87 (d, J=6.44 Hz, 3H), 0.93 (d, J=6.44 Hz, 3H), 1.84 (m, 1H), 2.15 (m, 1H), 2.69 (s, 3H), 2.71 (m, 2H), 2.80 (m, 1H), 2.99 (m, 3H), 3.16 (m, 5H), 3.65 (d, J=10.85 Hz, 1H), 3.75 (m, 1H), 3.87 (s, 1H), 4.16 (d, J=14.92 Hz, 1H), 4.41 (m, 2H), 6.08 (s, 2H), 6.46 (d, J=8.82 Hz, 1H), 6.90 (m, 2H), 7.17 (m, 5H), 7.35 (dd, J=8.31, 1.86 Hz, 1H)

Example 753

$^1$H NMR (300 MHz, CDCl$_3$) δ ppm 0.86 (m, 12H), 1.85 (s, 1H), 2.13 (s, 1H), 2.69 (s, 3H), 2.73 (m, 3H), 3.08 (m, 7H), 3.64 (m, 1H), 3.78 (d, J=14.58 Hz, 1H), 4.17 (s, 1H), 4.38 (m, 2H), 6.44 (s, 1H), 6.88 (d, J=8.14 Hz, 1H), 6.93 (s, 1H), 7.14 (m, 3H), 7.24 (s, 1H), 7.28 (d, J=2.03 Hz, 1H), 7.35 (m, 1H), 7.43 (d, J=7.80 Hz, 1H), 7.71 (s, 1H), 7.78 (d, J=2.03 Hz, 1H)

Example 754

$^1$H NMR (300 MHz, CDCl$_3$) δ ppm 0.77 (d, J=6.44 Hz, 3H), 0.83 (d, J=6.78 Hz, 3H), 0.88 (dd, J=7.97, 6.61 Hz, 6H), 1.87 (m, 1H), 2.16 (m, 1H), 2.69 (d, J=3.73 Hz, 3H), 2.73 (d, J=4.07 Hz, 1H), 2.81 (m, 1H), 2.97 (m, 2H), 3.07 (m, 1H), 3.18 (m, 3H), 3.25 (m, 1H), 3.62 (d, J=10.85 Hz, 1H), 3.80 (m, 1H), 4.16 (dd, J=8.99, 4.92 Hz, 1H), 4.42 (m, 2H), 6.62 (d, J=8.48 Hz, 1H), 6.95 (s, 1H), 7.18 (m, 6H), 7.46 (dd, J=7.63, 4.58 Hz, 1H), 8.09 (m, 1H), 8.80 (dd, J=4.92, 1.53 Hz, 1H), 9.02 (d, J=1.70 Hz, 1H)

Example 755

$^1$H NMR (300 MHz, CD$_3$OD) δ ppm 0.76 (t, J=6.10 Hz, 6H), 0.89 (d, J=6.78 Hz, 3H), 0.92 (d, J=6.44 Hz, 3H), 1.45 (d, J=6.44 Hz, 9H), 2.02 (m, 1H), 2.48 (m, 2H), 2.69 (m, 3H), 2.94 (m, 2H), 3.06 (m, 3H), 3.15 (m, 2H), 3.20 (m, 4H), 3.35 (s, 1H), 3.47 (m, 1H), 3.75 (m, 2H), 3.95 (d, J=12.89 Hz, 1H), 4.04 (s, 1H), 4.44 (q, J=15.26 Hz, 2H), 6.98 (d, J=8.48 Hz, 1H), 7.09 (m, 2H), 7.18 (m, 3H), 7.45 (dd, J=8.48, 2.37 Hz, 1H), 7.94 (d, J=9.83 Hz, 1H), 8.53 (d, J=2.03 Hz, 1H)

Example 756

$^1$H NMR (300 MHz, CDCl$_3$) δ ppm 0.78 (d, J=6.78 Hz, 3H), 0.81 (d, J=6.78 Hz, 3H), 0.87 (d, J=6.44 Hz, 3H), 0.93 (d, J=6.44 Hz, 3H), 1.50 (d, J=6.44 Hz, 3H), 1.83 (s, 1H), 2.14 (m, 1H), 2.69 (s, 3H), 2.74 (m, 1H), 2.78 (m, 1H), 2.88 (s, 1H), 2.96 (m, 1H), 3.00 (m, 1H), 3.11 (m, 3H), 3.21 (m, 1H), 3.35 (m, 1H), 3.65 (d, J=10.85 Hz, 1H), 3.74 (s, 1H), 3.95 (d, J=2.71 Hz, 1H), 4.16 (s, 1H), 4.41 (m, 2H), 5.04 (m, 1H), 6.39 (d, J=9.16 Hz, 1H), 6.80 (d, J=8.82 Hz, 1H), 6.93 (s, 1H), 7.17 (m, 5H), 7.56 (m, 2H)

Example 757

$^1$H NMR (300 MHz, CDCl$_3$) δ ppm 0.80 (d, J=6.78 Hz, 3H), 0.83 (dd, J=6.78, 1.70 Hz, 3H), 0.88 (m, 6H), 1.53 (s, 2H), 1.91 (s, 1H), 2.17 (s, 1H), 2.69 (s, 3H), 2.76 (m, 1H), 3.05 (d, J=7.46 Hz, 2H), 3.10 (m, 1H), 3.23 (m, 4H), 136 (d, J=3.05 Hz, 1H), 3.62 (d, J=11.53 Hz, 1H), 3.72 (s, 1H), 3.88 (s, 1H), 4.17 (s, 1H), 4.39 (m, 2H), 5.20 (d, J=3.73 Hz, 1H), 5.30 (s, 1H), 6.54 (s, 1H), 6.69 (d, J=3.39 Hz, 1H), 6.92 (d, J=5.43 Hz, 1H), 7.03 (d, J=3.73 Hz, 1H), 7.19 (m, 4H), 7.37 (m, 3H), 7.46 (s, 1H), 8.01 (s, 1H)

Example 758

$^1$H NMR (300 MHz, CDCl$_3$) δ ppm 0.76 (d, J=6.44 Hz, 3H), 0.82 (d, J=6.78 Hz, 3H), 0.86 (d, J=6.78 Hz, 3H), 0.91 (m, 3H), 1.87 (m, 1H), 2.14 (m, 1H), 2.69 (m, 3H), 2.75 (m, 1H), 2.90 (m, 1H), 3.02 (m, 1H), 3.11 (m, 3H), 3.22 (m, 3H), 3.62 (d, J=10.85 Hz, 1H), 3.77 (m, 1H), 3.84 (m, 1H), 3.97 (s, 3H), 4.13 (m, 1H), 4.41 (m, 2H), 6.49 (d, J=9.16 Hz, 1H), 6.93 (s, 1H), 7.17 (m, 5H), 7.61 (m, 1H), 7.98 (d, J=7.80 Hz, 1H), 8.25 (d, J=7.80 Hz, 1H), 8.44 (d, J=1.70 Hz, 1H)

Example 759

$^1$H NMR (300 MHz, CDCl$_3$) δ ppm 0.75 (d, J=6.44 Hz, 3H), 0.82 (d, J=6.44 Hz, 3H), 0.87 (d, J=6.78 Hz, 3H), 0.91 (d, J=6.78 Hz, 3H), 2.65 (m, 3H), 2.69 (s, 3H), 2.75 (m, 2H), 2.91 (m, 2H), 3.01 (d, J=7.80 Hz, 1H), 3.10 (d, J=19.67 Hz, 2H), 3.21 (m, 3H), 3.27 (m, 3H), 3.62 (d, J=11.19 Hz, 2H), 3.78 (d, J=5.76 Hz, 1H), 3.90 (s, 1H), 4.19 (s, 1H), 4.43 (m, 2H), 6.54 (s, 1H), 6.93 (s, 1H), 7.19 (m, 4H), 7.63 (m, 1H), 7.99 (d, J=7.80 Hz, 1H), 8.15 (m, 1H), 8.36 (s, 1H)

Example 760

$^1$H NMR (300 MHz, CDCl$_3$) δ ppm 0.80 (d, J=6.78 Hz, 3H), 0.88 (m, 9H), 1.88 (m, 4H), 2.19 (m, 1H), 2.70 (s, 3H), 2.75 (m, 1H), 2.89 (t, J=7.97 Hz, 1H), 3.01 (m, 2H), 3.24 (m, 2H), 3.63 (d, J=10.85 Hz, 1H), 3.77 (dd, J=7.63, 4.24 Hz, 2H), 4.16 (m, 1H), 4.41 (m, 2H), 6.75 (d, J=8.14 Hz, 1H), 6.93 (d, J=9.83 Hz, 1H), 7.18 (m, 5H), 7.63 (t, J=5.76 Hz, 2H), 8.20 (d, J=6.44 Hz, 2H)

Example 761

$^1$H NMR (300 MHz, CDCl$_3$) δ ppm 0.80 (dd, J=9.83, 6.78 Hz, 6H), 0.92 (m, 3H), 0.96 (d, J=6.78 Hz, 3H), 1.93 (d, J=8.14 Hz, 1H), 2.19 (dd, J=9.16, 6.78 Hz, 1H), 2.68 (d, J=9.16 Hz, 3H), 2.77 (m, 2H), 2.89 (m, 2H), 3.11 (m, 3H), 3.30 (d, J=7.46 Hz, 2H), 3.39 (m, 1H), 3.88 (m, 2H), 4.29 (s, 1H), 4.43 (s, 2H), 6.71 (d, J=8.14 Hz, 1H), 6.96 (s, 1H), 7.07 (m, 1H), 7.17 (m, 5H), 7.31 (s, 1H), 7.37 (t, J=7.80 Hz, 1H), 8.95 (s, 1 FD Example 762

$^1$H NMR (300 MHz, CDCl$_3$) δ ppm 0.80 (m, 3H), 0.84 (d, J=3.39 Hz, 3H), 0.87 (m, 6H), 1.91 (d, J=7.46 Hz, 1H), 2.22

(m, 1H), 2.71 (m, 3H), 2.73 (m, 1H), 2.89 (t, J=8.65 Hz, 1H), 2.99 (m, 3H), 3.23 (m, 3H), 3.31 (m, 2H), 3.62 (d, J=11.19 Hz, 1H), 3.83 (dd, J=6.95, 4.92 Hz, 1H), 4.17 (m, 1H), 4.41 (d, J=5.09 Hz, 2H), 6.74 (d, J=8.48 Hz, 1H), 6.93 (m, 2H), 7.18 (m, 5H), 7.51 (dd, J=8.82, 2.37 Hz, 1H), 7.73 (d, J=2.37 Hz, 1H)

Example 763

$^1$H NMR (300 MHz, CDCl$_3$) δ ppm 0.77 (m, 3H), 0.82 (d, J=6.78 Hz, 3H), 0.90 (m, 3H), 0.94 (dd, J=6.44, 2.37 Hz, 3H), 1.90 (s, 1H), 2.11 (m, 1H), 2.69 (d, J=2.03 Hz, 3H), 2.78 (d, J=14.92 Hz, 1H), 2.93 (m, 1H), 3.07 (m, 4H), 3.19 (m, 2H), 3.58 (m, 2H), 3.68 (m, 2H), 3.83 (m, 1H), 4.01 (s, 1H), 4.36 (m, 2H), 4.89 (m, 1H), 6.35 (d, J=8.82 Hz, 1H), 6.52 (d, J=9.16 Hz, 1H), 6.93 (s, 1H), 7.17 (m, 5H), 7.56 (m, 2H), 7.79 (dd, J=8.48, 2.37 Hz, 2H)

Example 764

$^1$H NMR (300 MHz, CDCl$_3$) δ ppm 0.76 (d, J=6.44 Hz, 3H), 0.84 (dd, J=10.00, 6.61 Hz, 6H), 0.90 (d, J=6.78 Hz, 3H), 1.86 (m, 1H), 2.16 (m, 1H), 2.69 (s, 3H), 2.76 (m, 1H), 2.93 (m, 2H), 3.16 (m, 4H), 3.63 (d, J=11.19 Hz, 1H), 3.77 (s, 2H), 4.12 (q, J=7.12 Hz, 2H), 4.41 (m, 2H), 6.55 (d, J=8.14 Hz, 1H), 6.92 (d, J=6.78 Hz, 1H), 7.17 (m, 6H), 7.98 (m, 4H), 10.09 (d, J=7.46 Hz, 1H)

Example 765

$^1$H NMR (300 MHz, CDCl$_3$) δ ppm 0.77 (d, J=6.44 Hz, 3H), 0.82 (d, J=6.44 Hz, 3H), 0.88 (d, J=6.44 Hz, 3H), 0.93 (d, J=6.78 Hz, 3H), 1.89 (m, 1H), 2.14 (m, 1H), 2.69 (d, J=4.75 Hz, 3H), 2.74 (dd, J=15.26, 4.75 Hz, 2H), 2.87 (dd, J=13.56, 6.78 Hz, 1H), 3.00 (m, 1H), 3.07 (m, 2H), 3.14 (m, 2H), 3.21 (m, 1H), 3.58 (d, J=10.85 Hz, 1H), 3.76 (m, 1H), 4.08 (m, 1H), 4.36 (m, 2H), 4.78 (s, 2H), 6.41 (d, J=8.82 Hz, 1H), 6.92 (s, 1H), 7.17 (m, 6H), 7.52 (d, J=8.48 Hz, 2H), 7.78 (d, J=8.48 Hz, 2H)

Example 766

$^1$H NMR (300 MHz, CDCl$_3$) δ ppm 0.77 (d, J=6.44 Hz, 3H), 0.82 (d, J=6.78 Hz, 3H), 0.87 (d, J=6.44 Hz, 3H), 0.91 (d, J=6.44 Hz, 3H), 1.86 (s, 1H), 2.14 (m, 1H), 2.68 (d, J=4.41 Hz, 3H), 2.75 (m, 2H), 2.85 (dd, J=13.05, 6.27 Hz, 1H), 2.98 (m, 1H), 3.16 (m, 4H), 3.63 (d, J=10.85 Hz, 1H), 3.76 (s, 1H), 3.85 (s, 1H), 4.12 (dd, J=14.24, 7.12 Hz, 1H), 4.43 (m, 2H), 6.50 (s, 1H), 6.94 (s, 1H), 7.16 (m, 6H), 7.58 (m, 1H), 7.75 (m, 4H), 8.44 (s, 1H)

Example 767

$^1$H NMR (300 MHz, CDCl$_3$) δ ppm 0.77 (d, J=6.78 Hz, 3H), 0.81 (d, J=6.78 Hz, 3H), 0.91 (dd, J=6.61, 1.87 Hz, 6H), 1.88 (m, 2H), 2.20 (m, 1H), 2.66 (q, J=8.14 Hz, 1H), 2.81 (m, 1H), 2.86 (d, J=7.12 Hz, 1H), 2.93 (d, J=7.80 Hz, 1H), 2.97 (dd, J=8.14, 2.37 Hz, 1H), 3.02 (d, J=8.14 Hz, 1H), 3.09 (m, 1H), 3.15 (m, 2H), 3.25 (t, J=7.80 Hz, 2H), 3.79 (d, J=9.49 Hz, 1H), 3.85 (m, 1H), 4.27 (t, J=10.00 Hz, 1H), 4.43 (s, 2H), 4.91 (s, 2H), 6.73 (d, J=8.82 Hz, 1H), 7.00 (dd, J=8.14, 2.03 Hz, 1H), 7.07 (s, 1H), 7.15 (d, J=2.37 Hz, 2H), 7.21 (m, 5H), 7.34 (d, J=8.14 Hz, 1H)

Example 768

$^1$H NMR (300 MHz, CD$_3$OD) δ ppm 0.77 (dd, J=6.44, 5.09 Hz, 6H), 0.89 (d, J=6.78 Hz, 3H), 0.92 (d, J=6.44 Hz, 3H), 2.02 (m, 1H), 2.21 (s, 3H), 2.51 (m, 2H), 2.69 (m, 3H), 2.94 (m, 2H), 3.05 (m, 3H), 3.15 (m, 2H), 3.22 (m, 1H), 3.25 (m, 1H), 3.43 (dd, J=14.92, 3.73 Hz, 1H), 3.75 (m, 2H), 4.10 (m, 1H), 4.42 (m, 2H), 6.97 (d, J=8.48 Hz, 1H), 7.08 (m, 3H), 7.16 (m, 2H), 7.21 (s, 1H), 7.45 (dd, J=8.48, 2.37 Hz, 1H), 7.95 (d, J=9.49 Hz, 1H), 8.38 (d, J=2.37 Hz, 1H)

Example 769

$^1$H NMR (300 MHz, CD$_3$OD) δ ppm 0.76 (m, 6H), 0.89 (d, J=6.44 Hz, 3H), 0.93 (d, J=6.78 Hz, 3H), 1.45 (d, J=6.44 Hz, 9H), 2.02 (m, 1H), 2.47 (dd, J=13.73, 11.36 Hz, 2H), 2.70 (s, 3H), 2.94 (m, 2H), 3.03 (m, 2H), 3.11 (m, 2H), 3.19 (m, 2H), 3.28 (s, 3H), 3.46 (d, J=3.73 Hz, 1H), 3.75 (t, J=10.85 Hz, 2H), 3.95 (d, J=12.89 Hz, 1H), 4.03 (s, 1H), 4.44 (q, J=15.60 Hz, 2H), 4.80 (s, 2H), 6.98 (d, J=8.48 Hz, 1H), 7.10 (m, 3H), 7.19 (m, 3H), 7.45 (dd, J=8.48, 2.37 Hz, 1H), 7.94 (d, J=9.83 Hz, 1H)

Example 770

$^1$H NMR (300 MHz, CD$_3$OD) δ ppm 0.76 (t, J=6.27 Hz, 6H), 0.89 (d, J=6.78 Hz, 3H), 0.92 (d, J=6.44 Hz, 3H), 2.01 (m, 1H), 2.48 (dd, J=13.90, 11.19 Hz, 2H), 2.69 (s, 3H), 2.94 (m, 2H), 3.08 (m, 3H), 3.15 (m, 2H), 3.22 (d, J=6.44 Hz, 2H), 3.42 (m, 1H), 3.75 (m, 2H), 4.06 (d, J=23.39 Hz, 1H), 4.41 (s, 2H), 6.99 (m, 1H), 7.07 (m, 3H), 7.15 (m, 2H), 7.19 (s, 1H), 7.45 (dd, J=8.48, 2.37 Hz, 1H), 7.95 (d, J=9.49 Hz, 1H), 8.37 (s, 1H), 8.66 (d, J=2.03 Hz, 1H)

Example 771

$^1$H NMR (300 MHz, CD$_3$OD) δ ppm 0.73 (d, J=6.78 Hz, 3H), 0.76 (d, J=6.78 Hz, 3H), 0.88 (d, J=6.78 Hz, 3H), 0.91 (d, J=6.44 Hz, 3H), 2.00 (m, 1H), 2.49 (m, 2H), 2.69 (d, J=5.09 Hz, 3H), 2.93 (dd, J=14.07, 6.95 Hz, 2H), 3.04 (m, 2H), 3.10 (s, 1H), 3.12 (m, 2H), 3.21 (m, 2H), 3.34 (s, 1H), 3.44 (dd, J=15.09, 3.22 Hz, 1H), 3.74 (m, 1H), 3.82 (s, 1H), 4.07 (m, 1H), 4.42 (m, 2H), 6.97 (t, J=8.14 Hz, 1H), 7.07 (m, 3H), 7.13 (m, 2H), 7.20 (s, 1H), 7.25 (m, 2H), 7.26 (m, 1H), 7.34 (m, 1H), 7.40 (m, 2H), 7.44 (dd, J=8.48, 2.37 Hz, 1H), 7.96 (m, 1H), 8.44 (d, J=2.37 Hz, 1H)

Example 772

$^1$H NMR (300 MHz, CD$_3$OD) δ ppm 0.76 (d, J=3.39 Hz, 3H), 0.78 (m, 3H), 0.89 (d, J=6.78 Hz, 3H), 0.92 (m, 3H), 1.42 (s, 9H), 2.03 (m, 2H), 2.49 (m, 2H), 2.66 (d, J=6.44 Hz, 2H), 2.70 (s, 3H), 2.95 (m, 2H), 3.01 (s, 1H), 3.10 (m, 3H), 3.16 (d, J=4.41 Hz, 3H), 3.43 (t, J=6.61 Hz, 2H), 3.49 (s, 1H), 3.74 (m, 2H), 4.08 (s, 1H), 4.42 (s, 2H), 6.98 (d, J=8.48 Hz, 1H), 7.08 (m, 3H), 7.15 (m, 2H), 7.20 (s, 1H), 7.45 (dd, J=8.48, 2.37 Hz, 1H), 7.94 (d, J=9.49 Hz, 1H), 8.41 (s, 1H)

Example 773

$^1$H NMR (300 MHz, CDCl$_3$) δ ppm 0.77 (d, J=6.44 Hz, 3H), 0.82 (d, J=6.78 Hz, 3H), 0.86 (d, J=6.78 Hz, 3H), 0.91 (d, J=6.44 Hz, 3H), 1.86 (d, J=6.78 Hz, 1H), 2.15 (m, 1H), 2.67 (s, 1H), 2.68 (d, J=4.41 Hz, 3H), 2.73 (m, 2H), 2.85 (dd, J=13.56, 7.12 Hz, 1H), 2.99 (m, 1H), 3.06 (dd, J=15.09, 3.22 Hz, 2H), 3.14 (m, 3H), 3.21 (m, 2H), 3.63 (d, J=10.85 Hz, 1H), 3.76 (m, 2H), 4.16 (dd, J=9.32, 4.92 Hz, 1H), 4.41 (m, 2H), 6.47 (d, J=9.16 Hz, 1H), 6.92 (d, J=6.10 Hz, 1H), 7.16 (m, 5H), 7.71 (d, J=8.48 Hz, 2H), 7.78 (m, 2H), 8.07 (s, 1H)

Example 774

$^1$H NMR (300 MHz, CDCl$_3$) δ ppm 0.80 (m, 6H), 0.86 (m, 3H), 0.94 (d, J=6.44 Hz, 3H), 1.53 (s, 1H), 1.81 (m, 1H), 2.13

(m, 1H), 2.66 (m, 1H), 2.69 (s, 3H), 2.75 (m, 1H), 2.96 (m, 2H), 3.08 (m, 4H), 3.17 (m, 2H), 3.23 (d, J=8.82 Hz, 1H), 3.65 (m, 1H), 3.68 (d, J=2.71 Hz, 1H), 3.74 (m, 1H), 4.00 (d, J=2.71 Hz, 1H), 4.17 (m, 2H), 4.41 (m, 2H), 6.35 (d, J=9.16 Hz, 1H), 6.56 (m, 1H), 6.93 (s, 1H), 7.17 (m, 4H), 7.44 (dd, J=3.90, 2.54 Hz, 2H)

Example 775

$^1$H NMR (300 MHz, CDCl$_3$) δ ppm 0.82 (d, J=6.44 Hz, 6H), 0.91 (d, J=2.71 Hz, 3H), 0.93 (d, J=3.05 Hz, 3H), 1.90 (dd, J=13.56, 6.78 Hz, 1H), 2.16 (m, 1H), 2.46 (s, 3H), 2.69 (s, 3H), 2.73 (m, 2H), 2.96 (dd, J=7.46, 3.39 Hz, 2H), 3.12 (m, 2H), 3.21 (dd, J=8.48, 3.39 Hz, 2H), 3.71 (m, 2H), 3.85 (d, J=2.71 Hz, 1H), 4.15 (m, 1H), 4.41 (s, 2H), 5.56 (s, 2H), 6.44 (d, J=8.82 Hz, 1H), 6.94 (s, 1H), 7.16 (m, 6H)

Example 776

$^1$H NMR (300 MHz, CD$_3$OD) δ ppm 0.76 (t, J=6.61 Hz, 6H), 0.90 (d, J=6.44 Hz, 3H), 0.93 (d, J=6.78 Hz, 3H), 2.03 (s, 2H), 2.46 (m, 1H), 2.48 (d, J=3.05 Hz, 1H), 2.70 (s, 3H), 2.96 (m, 4H), 3.10 (m, 3H), 3.18 (m, 3H), 3.35 (m, 1H), 3.51 (m, 1H), 3.75 (d, J=11.19 Hz, 2H), 4.05 (s, 1H), 4.42 (s, 2H), 4.76 (s, 2H), 7.00 (d, J=8.48 Hz, 1H), 7.06 (m, 3H), 7.14 (m, 2H), 7.22 (s, 1H), 7.46 (dd, J=8.48, 2.37 Hz, 1H), 7.79 (d, J=9.83 Hz, 1H), 8.52 (d, J=2.03 Hz, 1H)

Example 777

$^1$H NMR (300 MHz, CD$_3$OD) δ ppm 0.77 (dd, J=6.78, 2.71 Hz, 6H), 0.91 (m, 6H), 1.45 (s, 9H), 2.02 (s, 1H), 2.47 (s, 1H), 2.70 (s, 3H), 3.02 (m, 3H), 3.17 (m, 3H), 3.19 (d, J=13.90 Hz, 2H), 3.52 (s, 1H), 3.75 (d, J=10.85 Hz, 2H), 3.91 (s, 1H), 4.08 (s, 1H), 4.47 (m, 2H), 4.72 (d, J=6.10 Hz, 2H), 4.92 (m, 2H), 7.09 (m, 3H), 7.17 (m, 2H), 7.53 (d, J=7.46 Hz, 1H), 7.66 (s, 1H), 7.89 (s, 1H), 8.20 (d, J=1.70 Hz, 1H), 8.47 (s, 1H)

Example 778

$^1$H NMR (300 MHz, CDCl$_3$) δ ppm 0.76 (d, J=6.44 Hz, 3H), 0.80 (d, J=6.78 Hz, 3H), 0.92 (m, 6H), 1.95 (m, 1H), 2.13 (m, 1H), 2.56 (dd, J=14.07, 10.68 Hz, 1H), 2.61 (m, 1H), 2.69 (d, J=3.73 Hz, 3H), 3.04 (m, 3H), 3.14 (m, 2H), 3.22 (s, 1H), 3.30 (m, 1H), 3.45 (d, J=7.12 Hz, 1H), 3.68 (d, J=10.85 Hz, 1H), 4.07 (m, 1H), 4.36 (d, J=15.26 Hz, 2H), 4.47 (m, 3H), 4.74 (m, 1H), 4.85 (m, 1H), 6.94 (s, 1H), 6.98 (d, J=9.16 Hz, 1H), 7.14 (m, 5H), 7.51 (m, 1H), 7.69 (m, 1H), 7.93 (s, 1H)

Example 779

$^1$H NMR (300 MHz, CDCl$_3$) δ ppm 0.79 (d, J=6.44 Hz, 3H), 0.84 (d, J=6.44 Hz, 3H), 0.89 (d, J=6.44 Hz, 6H), 1.94 (s, 1H), 2.19 (d, J=10.85 Hz, 1H), 2.73 (s, 3H), 2.88 (s, 1H), 3.06 (m, 1H), 3.13 (dd, J=10.51, 7.46 Hz, 2H), 3.23 (d, J=1221 Hz, 1H), 3.31 (m, 1H), 3.42 (m, 1H), 3.62 (d, J=10.85 Hz, 1H), 3.87 (s, 1H), 4.12 (q, J=7.12 Hz, 2H), 4.17 (s, 1H), 4.43 (s, 2H), 6.70 (d, J=8.82 Hz, 1H), 6.98 (s, 1H), 7.09 (d, J=3.39 Hz, 1H), 7.19 (m, 5H), 7.24 (m, 2H), 9.74 (s, 1H)

Example 780

$^1$H NMR (300 MHz, CDCl$_3$) δ ppm 0.79 (d, J=6.44 Hz, 3H), 0.91 (dd, J=6.78, 4.41 Hz, 6H), 0.96 (d, J=6.44 Hz, 3H), 1.52 (s, 2H), 2.08 (m, 2H), 2.43 (m, 1H), 2.69 (d, J=3.73 Hz, 3H), 2.83 (m, 1H), 3.04 (m, 1H), 3.11 (m, 1H), 3.14 (m, 3H), 3.24 (m, 1H), 3.30 (m, 1H), 3.62 (s, 1H), 3.92 (d, J=11.19 Hz, 1H), 4.06 (m, 1H), 4.24 (m, 1H), 4.47 (m, 2H), 6.57 (d, J=3.73 Hz, 1H), 6.96 (d, J=3.39 Hz, 1H), 7.13 (m, 5H), 8.05 (s, 1H)

Example 781

$^1$H NMR (300 MHz, CDCl$_3$) δ ppm 0.82 (d, J=3.73 Hz, 3H), 0.84 (d, J=3.39 Hz, 3H), 0.87 (d, J=4.07 Hz, 3H), 0.89 (d, J=4.07 Hz, 3H), 1.94 (m, 1H), 2.17 (m, 1H), 2.65 (m, 1H), 2.69 (m, 3H), 2.76 (m, 1H), 3.05 (dd, J=7.46, 3.39 Hz, 1H), 3.12 (m, 1H), 3.20 (m, 1H), 3.27 (m, 1H), 3.48 (d, J=2.71 Hz, 1H), 3.53 (d, J=4.75 Hz, 1H), 3.67 (d, J=10.85 Hz, 1H), 3.85 (s, 1H), 4.12 (q, J=7.12 Hz, 1H), 4.20 (s, 1H), 4.44 (s, 2H), 6.69 (d, J=8.82 Hz, 1H), 6.96 (s, 1H), 7.06 (d, J=3.73 Hz, 2H), 7.12 (m, 2H), 7.17 (m, 4H), 7.44 (s, 1H)

Example 782

$^1$H NMR (300 MHz, CDCl$_3$) δ ppm 0.76 (d, J=6.44 Hz, 3H), 0.87 (d, J=6.44 Hz, 3H), 0.90 (d, J=6.78 Hz, 3H), 1.87 (m, 1H), 2.15 (m, 1H), 2.69 (s, 3H), 2.74 (m, 2H), 3.07 (m, 11H), 3.63 (d, J=10.85 Hz, 1H), 3.76 (m, J=20.35 Hz, 2H), 4.12 (m, 1H), 4.39 (d, J=15.60 Hz, 1H), 4.46 (d, J=15.94 Hz, 1H), 4.99 (s, 1H), 6.54 (d, J=8.14 Hz, 1H), 6.94 (s, 1H), 7.17 (m, 5H), 7.77 (d, J=8.82 Hz, 2H), 7.81 (d, J=8.82 Hz, 2H)

Example 783

$^1$H NMR (300 MHz, CDCl$_3$) δ ppm 0.76 (d, J=6.44 Hz, 3H), 0.82 (d, J=6.78 Hz, 3H), 0.88 (d, J=6.44 Hz, 3H), 0.91 (d, J=6.44 Hz, 3H), 1.88 (m, 1H), 2.14 (m, 1H), 2.68 (m, 3H), 2.75 (m, 1H), 2.96 (dd, J=12.89, 7.12 Hz, 2H), 3.09 (m, 4H), 3.23 (m, 3H), 3.61 (d, J=10.85 Hz, 1H), 3.72 (d, J=8.82 Hz, 2H), 4.12 (q, J=7.12 Hz, 1H), 4.41 (m, 2H), 6.52 (d, J=8.82 Hz, 1H), 6.93 (s, 1H), 7.18 (m, 6H), 7.87 (d, J=8.48 Hz, 2H), 7.94 (m, 2H)

Example 784

$^1$H NMR (300 MHz, CDCl$_3$) δ ppm 0.74 (d, J=6.62 Hz, 3H), 0.85 (dd, J=14.34, 6.99 Hz, 6H), 0.91 (m, 3H), 1.00 (m, 1H), 1.34 (m, 1H), 1.89 (dd, J=13.97, 6.99 Hz, 2H), 2.75 (dd, J=14.16, 9.74 Hz, 1H), 2.85 (m, 1H), 2.89 (m, 1H), 2.97 (m, 2H), 3.01 (m, 1H), 3.08 (m, 3H), 3.16 (m, 2H), 3.75 (d, J=11.03 Hz, 2H), 4.17 (d, J=6.62 Hz, 1H), 4.23 (d, J=15.08 Hz, 1H), 4.45 (m, 1H), 6.49 (d, J=8.46 Hz, 1H), 7.19 (m, 5H), 7.29 (d, J=5.15 Hz, 1H), 7.59 (m, 1H), 7.88 (m, 2H), 7.94 (m, 2H), 8.51 (s, 1H), 8.55 (d, J=3.31 Hz, 1H)

Example 785

$^1$H NMR (300 MHz, CDCl$_3$) δ ppm 0.75 (d, J=6.62 Hz, 3H), 0.88 (m, 9H), 1.00 (m, 1H), 1.36 (m, 1H), 1.87 (m, 1H), 1.97 (m, 1H), 2.78 (m, 1H), 2.89 (m, 1H), 2.96 (m, 2H), 3.04 (m, 3H), 3.17 (m, 2H), 3.24 (m, 1H), 3.77 (m, 3H), 4.20 (m, 2H), 4.45 (m, 1H), 6.58 (d, J=8.46 Hz, 1H), 7.19 (m, 5H), 7.59 (m, 1H), 7.80 (m, 2H), 7.91 (m, 2H), 8.51 (d, J=1.84 Hz, 1H), 8.55 (dd, J=4.78, 1.47 Hz, 1H)

Example 787

$^1$H NMR (300 MHz, CDCl$_3$) δ ppm 0.79 (d, J=6.78 Hz, 3H), 0.82 (d, J=6.44 Hz, 3H), 0.86 (s, 3H), 0.94 (d, J=6.44 Hz, 3H), 1.33 (t, J=7.63 Hz, 3H), 1.82 (m, 1H), 2.08 (m, 1H), 2.65 (dd, J=14.07, 10.68 Hz, 2H), 2.76 (dd, J=13.22, 6.44 Hz, 1H), 2.97 (m, 4H), 3.07 (dd, J=13.90, 4.07 Hz, 1H), 3.16 (d, J=8.82 Hz, 1H), 3.22 (d, J=17.97 Hz, 1H), 3.58 (d, J=17.97 Hz, 1H), 3.80 (m, 1H), 3.83 (d, J=3.73 Hz, 1H), 3.90 (d, J=11.19 Hz, 1H), 4.16 (s, 2H), 4.23 (m, 1H), 4.76 (m, 2H), 6.16 (d, J=9.49 Hz, 1H), 6.68 (m, 2H), 7.00 (s, 1H), 7.09 (s, 5H), 7.56 (m, 2H)

Example 788

$^1$H NMR (300 MHz, CDCl$_3$) δ ppm 0.80 (t, J=6.10 Hz, 6H), 0.89 (m, 3H), 0.94 (d, J=6.44 Hz, 3H), 1.33 (m, 3H), 1.84 (m, 1H), 2.08 (m, 1H), 2.67 (dd, J=14.07, 10.68 Hz, 1H), 2.85 (m, 2H), 3.06 (t, J=3.39 Hz, 1H), 3.25 (d, J=17.63 Hz, 1H), 3.60 (d, J=17.63 Hz, 1H), 3.64 (s, 1H), 3.87 (m, 2H), 3.96 (m, 1H), 4.24 (m, 1H), 4.43 (s, 2H), 4.75 (d, J=6.10 Hz, 2H), 4.83 (m, 2H), 6.26 (d, J=9.16 Hz, 1H), 7.01 (s, 1H), 7.03 (t, J=2.54 Hz, 1H), 7.06 (t, J=2.37 Hz, 1H), 7.13 (m, 5H), 7.18 (d, J=2.03 Hz, 1H), 7.37 (d, J=8.48 Hz, 1H)

Example 789

$^1$H NMR (300 MHz, CD$_3$OD) δ ppm 0.78 (dd, J=6.61, 2.88 Hz, 6H), 0.87 (d, J=6.78 Hz, 3H), 0.90 (d, J=6.44 Hz, 3H), 2.00 (m, 2H), 2.45 (m, 1H), 2.65 (s, 3H), 2.88 (m, 3H), 3.03 (m, 1H), 3.22 (m, 1H), 3.39 (dd, J=14.58, 3.73 Hz, 1H), 3.68 (d, J=18.31 Hz, 1H), 3.77 (m, 1H), 4.00 (d, J=10.85 Hz, 1H), 4.15 (m, 2H), 4.73 (d, J=6.44 Hz, 2H), 6.90 (m, 2H), 6.99 (m, 3H), 7.13 (m, 2H), 7.22 (m, 1H), 7.67 (m, 2H), 8.21 (d, J=9.83 Hz, 1H)

Example 790

$^1$H NMR (300 MHz, CDCl$_3$) δ ppm 0.80 (m, 6H), 0.89 (d, J=6.78 Hz, 3H), 0.94 (d, J=6.44 Hz, 3H), 1.85 (m, 1H), 2.09 (m, 1H), 2.65 (s, 3H), 2.74 (d, J=11.87 Hz, 1H), 2.87 (m, 3H), 3.07 (m, 2H), 3.15 (m, 1H), 3.23 (m, 1H), 3.59 (m, 1H), 3.83 (m, 1H), 3.92 (m, 2H), 4.23 (m, 1H), 4.43 (s, 2H), 4.73 (d, J=6.78 Hz, 2H), 4.80 (d, J=6.44 Hz, 1H), 6.30 (d, J=9.16 Hz, 1H), 7.01 (s, 1H), 7.03 (t, J=2.54 Hz, 1H), 7.06 (m, 1H), 7.10 (s, 5H), 7.19 (m, 1H), 7.37 (d, J=8.14 Hz, 1H)

Example 791

$^1$H NMR (300 MHz, CDCl$_3$) δ ppm 0.77 (m, 6H), 0.89 (d, J=6.44 Hz, 3H), 0.93 (d, J=6.44 Hz, 3H), 1.86 (m, 1H), 2.65 (m, 2H), 2.74 (s, 3H), 2.85 (m, 2H), 2.95 (m, 2H), 2.98 (m, 2H), 3.07 (m, 2H), 3.15 (m, 1H), 3.57 (d, J=17.97 Hz, 1H), 3.83 (m, 1H), 3.92 (d, J=11.19 Hz, 1H), 4.15 (m, 1H), 4.72 (m, 2H), 6.68 (d, J=9.16 Hz, 1H), 6.79 (d, J=8.48 Hz, 1H), 7.04 (m, 7 H), 7.14 (d, J=2.37 Hz, 1H)

Example 792

$^1$H NMR (300 MHz, CDCl$_3$) δ ppm 0.80 (t, J=6.95 Hz, 6H), 0.89 (d, J=6.78 Hz, 3H), 0.94 (d, J=6.78 Hz, 3H), 1.84 (m, 1H), 2.08 (m, 1H), 2.68 (dd, J=14.24, 10.85 Hz, 1H), 2.84 (m, 1H), 2.98 (m, 1H), 3.18 (m, 1H), 3.27 (d, J=17.97 Hz, 1H), 3.44 (s, 3H), 3.48 (d, J=6.10 Hz, 1H), 3.60 (d, J=17.63 Hz, 1H), 3.84 (m, 2H), 3.91 (m, 1H), 4.25 (m, 1H), 4.67 (s, 2H), 4.76 (m, 2H), 6.24 (d, J=9.16 Hz, 1H), 7.02 (d, J=2.03 Hz, 1H), 7.05 (d, J=2.37 Hz, 1H), 7.11 (s, 6H), 7.18 (m, 2H), 7.37 (d, J=8.48 Hz, 1H)

Example 793

$^1$H NMR (300 MHz, CD$_3$OD) δ ppm 0.78 (dd, J=6.61, 3.90 Hz, 6H), 0.87 (d, J=6.44 Hz, 3H), 0.90 (d, J=6.44 Hz, 3H), 1.99 (m, 2H), 2.46 (m, 1H), 2.87 (dd, J=13.56, 11.87 Hz, 1H), 3.00 (m, 2H), 3.22 (m, 1H), 3.35 (m, 2H) 3.42 (m, 3H), 3.68 (d, J=18.31 Hz, 1H), 3.78 (m, 1H), 4.00 (d, J=10.85 Hz, 1H), 4.13 (m, 1H), 4.65 (m, 1H)=5.09 Hz, 2H), 4.77 (d, J=5.76 Hz, 2H), 6.90 (m, 2H), 6.99 (q, J=3.50 Hz, 3H), 7.12 (m, 2H), 7.41 (s, 1H), 7.65 (m, 2H), 8.20 (d, J=9.49 Hz, 1H)

Example 794

$^1$H NMR (300 MHz, CDCl$_3$) δ ppm 0.77 (d, J=6.78 Hz, 3H), 0.81 (d, J=6.78 Hz, 3H), 0.86 (s, 3H), 0.94 (d, J=6.78 Hz, 3H), 1.82 (m, 1H), 2.06 (m, 1H), 2.65 (dd, J=14.24, 10.85 Hz, 1H), 2.76 (dd, J=13.22, 6.44 Hz, 1H), 2.95 (m, 1H), 3.08 (dd, J=13.90, 4.07 Hz, 1H), 3.20 (m, 2H), 3.46 (s, 3H), 3.51 (s, 2H), 3.59 (m, 1H), 3.82 (m, 1H), 3.88 (d, J=10.85 Hz, 1H), 4.21 (m, 2H), 4.70 (s, 2H), 4.79 (m, 2H), 6.34 (d, J=9.49 Hz, 1H), 6.69 (d, J=8.82 Hz, 2H), 7.05 (m, 6H), 7.24 (s, 1H), 7.56 (d, J=8.48 Hz, 2H)

Example 795

$^1$H NMR (300 MHz, CDCl$_3$) δ ppm 0.76 (d, J=6.44 Hz, 3H), 0.81 (d, J=6.44 Hz, 3H), 0.88 (d, J=6.44 Hz, 3H), 0.94 (d, J=6.78 Hz, 3H), 1.83 (m, 1H), 2.06 (m, 1H), 2.65 (dd, J=14.07, 10.68 Hz, 1H), 2.80 (m, 1H), 2.98 (m, 1H), 3.05 (m, 1H), 3.18 (m, 2H), 3.54 (d, J=17.63 Hz, 1H), 3.59 (s, 1H), 3.81 (s, 1H), 3.87 (d, J=11.19 Hz, 1H), 4.21 (m, 1H), 4.38 (s, 2H), 4.62 (m, 2H), 6.06 (d, J=9.49 Hz, 1H), 7.03 (m, 6H), 7.16 (d, J=2.03 Hz, 1H), 7.33 (m, 5H), 7.41 (m, 2H)

Example 796

$^1$H NMR (300 MHz, CDCl$_3$) δ ppm 0.76 (d, J=6.78 Hz, 3H), 0.81 (d, J=6.78 Hz, 3H), 0.88 (d, J=6.78 Hz, 3H), 0.94 (d, J=6.78 Hz, 3H), 1.83 (m, 1H), 2.06 (m, 1H), 2.33 (s, 3H), 2.64 (dd, J=14.24, 10.51 Hz, 1H), 2.81 (m, 1H), 2.98 (m, 1H), 3.05 (m, 2H), 3.18 (m, 2H), 3.54 (d, J=17.97 Hz, 1H), 3.59 (s, 1H), 3.84 (s, 1H), 3.88 (d, J=10.85 Hz, 1H), 4.21 (m, 1H), 4.38 (s, 2H), 4.58 (d, J=2.03 Hz, 2H), 6.06 (d, J=9.49 Hz, 1H), 7.05 (m, 6H), 7.16 (d, J=2.37 Hz, 1H), 7.22 (m, 4H), 7.37 (d, J=8.48 Hz, 1H)

Example 797

$^1$H NMR (300 MHz, CDCl$_3$) δ ppm 0.80 (d, J=6.78 Hz, 3H), 0.83 (d, J=6.78 Hz, 3H), 0.89 (d, J=6.78 Hz, 3H), 0.94 (d, J=6.44 Hz, 3H), 1.85 (m, 1H), 2.12 (m, 1H), 2.73 (dd, J=14.24, 10.85 Hz, 1H), 2.83 (dd, J=13.56, 6.78 Hz, 1H), 2.97 (m, 1H), 3.07 (m, 2H), 3.16 (m, 1H), 3.37 (d, J=17.97 Hz, 1H), 3.57 (s, 1H), 3.66 (d, J=17.97 Hz, 1H), 3.86 (m, 1H), 3.93 (d, J=10.51 Hz, 1H), 4.26 (m, 1H), 4.85 (m, 2H), 6.17 (d, J=8.82 Hz, 1H), 7.03 (dd, J=8.48, 2.03 Hz, 1H), 7.15 (d, J=4.07 Hz, 5H), 7.35 (t, J=3.90 Hz, 2H), 7.39 (m, 1H), 7.56 (m, 2H), 7.66 (d, J=7.80 Hz, 1H)

Example 798

$^1$H NMR (300 MHz, CDCl$_3$) δ ppm 0.78 (d, J=6.78 Hz, 3H), 0.83 (d, J=6.44 Hz, 3H), 0.90 (m, 3H), 0.94 (d, J=6.44 Hz, 3H), 1.83 (m, 1H), 2.09 (m, 1H), 2.69 (dd, J=14.07, 10.68 Hz, 1H), 2.82 (dd, J=13.56, 6.78 Hz, 1H), 3.02 (m, 4H), 3.17 (m, 1H), 3.30 (d, J=17.97 Hz, 1H), 3.61 (d, J=17.97 Hz, 2H), 3.84 (s, 1H), 3.89 (d, J=10.85 Hz, 1H), 4.26 (m, 1H), 4.70 (m, 2H), 6.11 (d, J=9.16 Hz, 1H), 7.03 (dd, J=8.14, 2.03 Hz, 1H), 7.11 (m, 5H), 7.15 (d, J=2.37 Hz, 1H), 7.37 (d, J=8.48 Hz, 1H), 7.52 (t, J=7.97 Hz, 1H), 7.72 (d, J=7.80 Hz, 1H), 8.15 (d, Hz, 1H), 8.24 (t, J=1.87 Hz, 1H)

Example 800

$^1$H NMR (300 MHz, CDCl$_3$) δ ppm 0.75 (d, J=6.78 Hz, 3H), 0.82 (d, J=6.44 Hz, 3H), 0.89 (d, J=6.44 Hz, 3H), 0.95 (d, J=6.44 Hz, 3H), 1.82 (m, 1H), 2.07 (m, 1H), 2.65 (dd, J=14.24, 10.85 Hz, 1H), 2.82 (m, 1H), 2.99 (m, 2H), 3.06 (m, 1H), 3.19 (m, 1H), 3.53 (s, 1H), 3.60 (d, J=4.41 Hz, 2H), 3.82 (m, 1H), 3.87 (d, J=11.19 Hz, 1H), 4.24 (m, 1H), 4.37 (d, J=6.78 Hz, 2H), 4.62 (m, 2H), 6.06 (d, J=9.49 Hz, 1H), 7.05 (m, 4H), 7.09 (d, J=1.70 Hz, 1H), 7.14 (s, 1H), 7.17 (d, J=2.37 Hz, 2H), 7.26 (d, J=9.83 Hz, 2H), 7.39 (t, J=3.73 Hz, 1H)

Example 801

$^1$H NMR (300 MHz, CDCl$_3$) δ ppm 0.76 (d, J=6.44 Hz, 3H), 0.83 (d, J=6.44 Hz, 3H), 0.89 (d, J=6.78 Hz, 3H), 0.95 (d, J=6.44 Hz, 3H), 1.83 (dd, J=8.31, 6.61 Hz, 1H), 2.07 (m, 1H), 2.67 (dd, J=14.24, 10.85 Hz, 1H), 2.82 (dd, J=13.56, 6.78 Hz, 1H), 3.01 (m, 3H), 3.20 (m, 2H), 3.58 (m, 2H), 3.82 (m, 1H), 3.87 (d, J=10.85 Hz, 1H), 4.23 (d, J=4.75 Hz, 1H), 4.37 (d, J=6.78 Hz, 2H), 4.60 (m, 2H), 6.06 (d, J=9.49 Hz, 1H), 7.04 (m, 6H), 7.17 (m, 2H), 7.37 (d, J=8.14 Hz, 1H), 7.44 (m, 2H)

Example 802

$^1$H NMR (300 MHz, CDCl$_3$) δ ppm 0.75 (d, J=6.44 Hz, 3H), 0.81 (d, J=6.44 Hz, 3H), 0.88 (d, J=6.44 Hz, 3H), 0.94 (d, J=6.44 Hz, 3H), 1.84 (m, 1H), 2.05 (m, 2H), 2.30 (s, 3H), 2.65 (dd, J=14.24, 10.85 Hz, 1H), 2.81 (m, 1H), 3.01 (m, 2H), 3.17 (m, 2H), 3.53 (d, J=17.97 Hz, 1H), 3.60 (d, J=3.05 Hz, 1H), 3.81 (m, 1H), 3.87 (d, J=10.85 Hz, 1H), 4.12 (q, J=7.12 Hz, 2H), 4.22 (m, 1H), 4.37 (d, J=6.78 Hz, 2H), 4.57 (m, 2H), 6.07 (d, J=9.49 Hz, 1H), 7.02 (d, J=2.37 Hz, 1H), 7.06 (m, 2H), 7.13 (d, J=7.80 Hz, 2H), 7.16 (d, J=2.37 Hz, 1H), 7.30 (d, J=8.14 Hz, 2H), 7.37 (d, J=8.48 Hz, 1H)

Example 803

$^1$H NMR (300 MHz, CDCl$_3$) δ ppm 0.77 (d, J=6.78 Hz, 3H), 0.84 (d, J=6.78 Hz, 3H), 0.89 (d, J=6.44 Hz, 3H), 0.94 (d, J=6.78 Hz, 3H), 1.83 (dd, J=8.14, 6.78 Hz, 1H), 2.09 (m, 1H), 2.70 (dd, J=14.24, 10.85 Hz, 1H), 2.82 (m, 1H), 3.01 (m, 3H), 3.16 (m, 1H), 3.32 (d, J=17.97 Hz, 1H), 3.61 (m, 1H), 3.62 (m, 1H), 3.84 (m, 1H), 3.89 (d, J=10.85 Hz, 1H), 4.27 (m, 1H), 4.37 (d, J=6.78 Hz, 2H), 4.69 (m, 2H), 6.12 (d, J=9.16 Hz, 1H), 7.03 (m, 1H), 7.10 (m, 5H), 7.14 (t, J=2.71 Hz, 1H), 7.37 (d, J=8.14 Hz, 1H), 7.54 (m, 2H), 8.19 (m, 1H)

Example 804

$^1$H NMR (300 MHz, CDCl$_3$) δ ppm 0.81 (d, J=6.44 Hz, 3H), 0.89 (m, 6H), 0.92 (d, J=6.78 Hz, 3H), 1.84 (m, 1H), 2.17 (m, 1H), 2.72 (dd, J=14.07, 10.68 Hz, 1H), 2.83 (dd, J=13.22, 6.78 Hz, 1H), 2.96 (m, 1H), 3.08 (m, 1H), 3.17 (m, 1H), 3.43 (d, J=17.97 Hz, 1H), 3.76 (m, 2H), 3.85 (m, 1H), 3.96 (d, J=10.85 Hz, 1H), 4.27 (m, 1H), 4.40 (s, 1H), 4.98 (m, 2H), 6.26 (d, J=9.16 Hz, 1H), 7.03 (dd, J=8.31, 2.20 Hz, 1H), 7.17 (m, 7H), 7.34 (t, J=8.14 Hz, 2H), 7.48 (m, 1H), 7.64 (m, 1H), 7.76 (d, J=7.80 Hz, 1H), 7.93 (d, J=8.48 Hz, 1H), 8.12 (d, J=8.48 Hz, 1H)

Example 805

$^1$H NMR (300 MHz, DMSO-d$_6$) δ ppm 0.69 (t, J=7.12 Hz, 3H), 0.75 (d, J=6.78 Hz, 3H), 0.81 (t, J=6.10 Hz, 6H), 1.96 (m, 2H), 2.38 (dd, J=13.05, 11.70 Hz, 1H), 2.83 (m, 2H), 2.94 (dd, J=8.99, 4.24 Hz, 1H), 3.02 (d, J=18.31 Hz, 2H), 3.09 (d, J=3.39 Hz, 1H), 0.00 (none, 1H), 3.59 (s, 1H), 3.88 (s, 3H), 3.94 (d, J=7.12 Hz, 1H), 4.02 (d, J=10.85 Hz, 1H), 4.12 (m, 1H), 4.93 (d, J=17.29 Hz, 3H), 5.81 (s, 2H), 6.88 (dd, J=8.48, 2.03 Hz, 1H), 6.97 (m, 1H), 7.13 (m, 5H), 7.25 (m, 1H), 7.35 (m, 1H), 7.48 (d, J=8.14 Hz, 1H), 7.55 (d, J=7.80 Hz, 1H), 8.23 (d, J=9.83 Hz, 1H)

Example 806

$^1$H NMR (300 MHz, CDCl$_3$) δ ppm 0.77 (d, J=6.78 Hz, 3H), 0.82 (d, J=6.78 Hz, 3H), 0.88 (d, J=6.78 Hz, 3H), 0.94 (d, J=6.44 Hz, 3H), 1.83 (m, 1H), 2.09 (m, 1H), 2.66 (dd, J=14.07, 10.68 Hz, 1H), 2.81 (dd, J=13.56, 6.44 Hz, 1H), 2.97 (m, 1H), 3.04 (m, 2H), 3.18 (m, 1H), 3.23 (m, 1H), 3.58 (m, 2H), 3.82 (m, 1H), 3.89 (d, J=10.85 Hz, 1H), 4.24 (s, 1H), 4.36 (d, J=6.78 Hz, 2H), 4.66 (m, 2H), 6.07 (d, J=9.16 Hz, 1H), 7.02 (m, 1H), 7.05 (m, 6H), 7.17 (m, 1H), 7.34 (m, 1H), 7.41 (m, 2H), 7.48 (d, J=8.48 Hz, 2H), 7.55 (m, 3H)

Example 807

$^1$H NMR (300 MHz, CDCl$_3$) δ ppm 0.78 (d, J=6.78 Hz, 3H), 0.83 (d, J=6.44 Hz, 3H), 0.88 (d, J=6.78 Hz, 3H), 0.94 (d, J=6.78 Hz, 3H), 1.82 (dd, J=15.09, 6.61 Hz, 1H), 2.09 (m, 1H), 2.67 (dd, J=14.24, 10.51 Hz, 1H), 2.81 (dd, J=13.39, 6.61 Hz, 1H), 2.98 (m, 1H), 3.05 (m, 2H), 3.19 (m, 1H), 3.29 (d, J=17.97 Hz, 1H), 3.61 (m, 2H), 3.84 (m, 1H), 3.89 (d, J=10.85 Hz, 1H), 4.24 (m, 1H), 4.39 (d, J=6.78 Hz, 2H), 4.70 (m, 2H), 6.09 (d, J=9.16 Hz, 1H), 7.03 (m, 1H), 7.08 (d, J=1.70 Hz, 5H), 7.17 (d, J=2.03 Hz, 1H), 7.37 (d, J=8.48 Hz, 1H), 7.42 (s, 1H), 7.46 (d, J=7.80 Hz, 2H), 7.50 (d, J=8.48 Hz, 2H), 7.58 (m, 1H), 7.74 (m, 2H), 7.78 (d, J=8.48 Hz, 1H)

Example 808

$^1$H NMR (300 MHz, DMSO-d$_6$) δ ppm 0.68 (d, J=6.78 Hz, 3H), 0.72 (d, J=6.78 Hz, 3H), 0.82 (d, J=6.10 Hz, 6H), 0.92 (m, 1H), 1.94 (m, 1H), 2.32 (m, 1H), 2.83 (dd, J=13.90, 6.78 Hz, 1H), 2.92 (m, 2H), 3.03 (m, 1H), 3.21 (dd, J=14.07, 2.88 Hz, 1H), 3.58 (s, 1H), 3.83 (d, J=17.97 Hz, 1H), 3.92 (s, 1H), 4.02 (d, J=10.51 Hz, 1H), 5.00 (d, J=6.44 Hz, 1H), 5.06 (m, 2H), 5.81 (s, 2H), 6.81 (m, 3H), 6.87 (m, 1H), 7.00 (m, 2H), 7.22 (d, J=2.03 Hz, 1H), 7.38 (m, 2H), 7.49 (m, 1H), 7.61 (m, 2H), 7.89 (d, J=8.14 Hz, 1H), 7.97 (m, 1H), 8.21 (d, J=9.49 Hz, 1H), 8.38 (d, J=8.48 Hz, 1H)

Example 809

$^1$H NMR (300 MHz, DMSO-d$_6$) δ ppm 0.70 (dd, J=9.16, 6.78 Hz, 6H), 0.82 (m, 6H), 1.94 (m, 2H), 2.37 (m, 1H), 2.83 (dd, J=13.73, 6.95 Hz, 1H), 2.93 (m, 2H), 3.03 (m, 1H), 3.22 (m, 1H), 3.58 (s, 1H), 3.81 (d, J=18.31 Hz, 1H), 3.96 (s, 1H), 4.01 (d, J=10.85 Hz, 1H), 4.77 (d, J=7.46 Hz, 2H), 5.00 (d, J=6.44 Hz, 1H), 5.81 (s, 2H), 6.82 (m, 3H), 6.87 (dd, J=8.31, 2.20 Hz, 1H), 7.03 (m, 2H), 7.22 (d, J=2.03 Hz, 1H), 7.36 (d, J=8.48 Hz, 1H), 7.51 (m, 3H), 7.82 (s, 1H), 7.89 (m, 2H), 7.93 (m, 1H), 8.22 (d, J=9.49 Hz, 1H)

Example 810

$^1$H NMR (300 MHz, CDCl$_3$) δ ppm 0.76 (dd, J=6.61, 2.54 Hz, 3H), 0.82 (dd, J=6.44, 1.70 Hz, 3H), 0.89 (d, J=6.44 Hz, 3H), 0.93 (t, J=6.10 Hz, 3H), 1.62 (d, J=6.44 Hz, 2H), 1.85 (m, 1H), 2.07 (m, 1H), 2.66 (dd, J=14.07, 10.68 Hz, 1H), 2.81 (m, 1H), 2.97 (dd, J=5.59, 2.54 Hz, 1H), 3.00 (m, 3H), 3.20 (m, 1H), 3.52 (d, J=4.07 Hz, 1H), 3.59 (m, 1H), 3.82 (s, 1H), 3.87 (d, J=11.19 Hz, 1H), 4.23 (s, 1H), 4.37 (d, J=6.44 Hz, 2H), 4.61 (m, 2H), 7.04 (m, 6H), 7.16 (s, 1H), 7.36 (d, J=2.37 Hz, 3H), 7.37 (m, 1H), 7.41 (m, 1H)

Example 811

¹H NMR (300 MHz, CDCl₃) δ ppm 0.77 (d, J=6.44 Hz, 3H), 0.83 (d, J=6.78 Hz, 3H), 0.89 (d, J=6.44 Hz, 3H), 0.94 (d, J=6.44 Hz, 3H), 1.86 (m, 1H), 2.08 (m, 1H), 2.55 (s, 3H), 2.69 (dd, J=14.24, 10.85 Hz, 1H), 2.82 (dd, J=13.39, 6.61 Hz, 1H), 2.97 (m, 1H), 3.06 (m, 1H), 3.17 (m, 1H), 3.27 (d, J=17.97 Hz, 1H), 3.59 (m, 2H), 3.83 (s, 1H), 3.88 (d, J=10.85 Hz, 1H), 4.24 (m, 1H), 4.39 (s, 2H), 4.63 (m, 2H), 6.07 (d, J=9.49 Hz, 1H), 7.03 (dd, J=8.14, 2.03 Hz, 1H), 7.10 (m, 5H), 7.14 (m, 1H), 7.31 (d, J=7.80 Hz, 1H), 7.37 (m, 1H), 7.52 (dd, J=7.80, 1.70 Hz, 1H), 7.99 (d, J=1.70 Hz, 1H)

Example 812

¹H NMR (300 MHz, CDCl₃) δ ppm 0.83 (m, 6H), 0.89 (d, J=6.78 Hz, 3H), 0.94 (d, J=6.44 Hz, 3H), 1.83 (m, 1H), 2.12 (m, 1H), 2.73 (dd, J=14.24, 10.85 Hz, 1H), 2.82 (m, 1H), 3.00 (m, 2H), 3.08 (m, 1H), 3.18 (m, 1H), 3.41 (d, J=17.97 Hz, 1H), 3.60 (s, 1H), 3.69 (d, J=17.97 Hz, 1H), 3.84 (s, 1H), 3.90 (d, J=10.85 Hz, 1H), 4.29 (m, 1H), 4.38 (s, 1H), 5.04 (m, 2H), 6.08 (d, J=9.49 Hz, 1H), 7.03 (dd, J=8.31, 2.20 Hz, 1H), 7.16 (m, 7H), 7.37 (d, J=8.14 Hz, 1H), 7.44 (m, 1H), 7.57 (m, 1H), 8.07 (dd, J=8.14, 1.36 Hz, 1H)

Example 813

¹H NMR (300 MHz, CDCl₃) δ ppm 0.80 (d, J=6.44 Hz, 3H), 0.84 (d, J=6.44 Hz, 3H), 0.89 (d, J=6.78 Hz, 3H), 0.94 (d, J=6.78 Hz, 3H), 1.83 (d, J=1.36 Hz, 1H), 2.10 (m, 1H), 2.56 (m, 3H), 2.72 (dd, J=14.41, 10.68 Hz, 1H), 2.82 (m, 1H), 2.98 (m, 1H), 3.06 (m, 2H), 3.18 (m, 1H), 3.36 (d, J=18.31 Hz, 1H), 3.63 (m, 2H), 3.86 (s, 1H), 3.88 (d, J=10.85 Hz, 1H), 4.27 (d, J=5.76 Hz, 1H), 4.38 (s, 1H), 4.69 (m, 2H), 6.09 (d, J=9.49 Hz, 1H), 7.03 (dd, J=8.31, 2.20 Hz, 1H), 7.11 (d, J=7.12 Hz, 5H), 7.15 (d, J=2.03 Hz, 1H), 7.30 (m, 1H), 7.37 (d, J=8.48 Hz, 1H), 7.52 (d, J=7.46 Hz, 1H), 7.67 (m, 1H)

Example 814

¹H NMR (300 MHz, CDCl₃) δ ppm 0.78 (d, J=6.78 Hz, 3H), 0.83 (d, J=6.44 Hz, 3H), 0.88 (d, J=6.78 Hz, 3H), 0.94 (d, J=6.44 Hz, 3H), 1.83 (m, 1H), 2.10 (m, 1H), 2.67 (dd, J=13.90, 10.85 Hz, 1H), 2.81 (m, 1H), 2.98 (m, 2H), 3.03 (m, 1H), 3.16 (m, 1H), 3.26 (d, J=17.97 Hz, 1H), 3.60 (m, 2H), 3.82 (m, 1H), 3.90 (d, J=10.85 Hz, 1H), 4.25 (m, 1H), 4.39 (s, 1H), 4.67 (m, 2H), 6.11 (d, J=9.49 Hz, 1H), 7.02 (m, 1H), 7.08 (m, 5H), 7.15 (d, J=2.03 Hz, 1H), 7.24 (s, 1H), 7.35 (d, J=8.14 Hz, 1H), 7.55 (d, J=8.48 Hz, 2H), 8.02 (m, 2H)

Example 815

¹H NMR (300 MHz, CD₃OD) δ ppm 0.75 (dd, J=8.48, 6.78 Hz, 6H), 0.89 (m, 6H), 1.98 (m, 1H), 2.46 (m, 1H), 2.99 (m, 3H), 3.21 (dd, J=13.90, 3.39 Hz, 1H), 3.31 (m, 3H), 3.40 (dd, J=14.92, 3.73 Hz, 1H), 3.69 (d, J=18.31 Hz, 1H), 3.78 (m, 1H), 3.98 (m, 1H), 4.13 (m, 1H), 4.67 (m, 2H), 6.88 (m, 2H), 6.99 (dd, J=8.31, 2.20 Hz, 1H), 7.09 (m, 2H), 7.23 (m, 2H), 7.35 (d, J=8.14 Hz, 1H), 7.45 (dd, J=7.46, 4.41 Hz, 1H), 7.89 (m, 1H), 8.49 (m, 1H), 8.62 (d, J=1.70 Hz, 1H)

Example 816

¹H NMR (300 MHz, CD₃OD) δ ppm 0.79 (m, 6H), 0.90 (m, 6H), 2.02 (m, 2H), 2.49 (dd, J=13.56, 11.87 Hz, 1H), 2.92 (m, 1H), 3.03 (m, 2H), 3.11 (d, J=3.05 Hz, 1H), 3.22 (m, 2H), 3.30 (d, J=1.70 Hz, 3H), 3.41 (dd, J=14.92, 3.73 Hz, 1H), 3.78 (m, 2H), 4.00 (d, J=10.85 Hz, 1H), 4.16 (m, 1H), 4.55 (s, 1H), 4.73 (m, 1H), 6.98 (d, J=2.03 Hz, 1H), 7.01 (t, J=2.20 Hz, 1H), 7.07 (m, 3H), 7.16 (m, 2H), 7.22 (s, 1H), 7.25 (d, J=2.03 Hz, 1H), 7.30 (dd, J=6.78, 5.43 Hz, 1H), 7.35 (m, 1H), 7.37 (m, 1H)

Example 817

¹H NMR (300 MHz, CD₃OD) δ ppm 0.77 (d, J=6.44 Hz, 6H), 0.88 (m, 3H), 0.91 (d, J=6.78 Hz, 3H), 2.01 (m, 2H), 2.49 (dd, J=13.73, 11.70 Hz, 1H), 2.86 (s, 2H), 2.93 (m, 1H), 2.99 (m, 2H), 3.05 (d, J=9.49 Hz, 2H), 3.11 (m, 1H), 3.22 (dd, J=13.73, 3.56 Hz, 1H), 3.41 (dd, J=14.75, 3.90 Hz, 1H), 3.77 (m, 2H), 4.00 (d, J=10.85 Hz, 1H), 4.09 (m, 1H), 4.55 (s, 1H), 4.72 (d, J=10.17 Hz, 1H), 6.99 (m, 3H), 7.01 (d, J=2.37 Hz, 1H), 7.14 (dd, J=6.10, 3.05 Hz, 2H), 7.22 (d, J=4.41 Hz, 1H), 7.25 (d, J=2.03 Hz, 1H), 7.35 (d, J=8.14 Hz, 1H), 7.40 (d, Hz, 2H)

Example 818

¹H NMR (300 MHz, CDCl₃) δ ppm 0.85 (d, J=6.78 Hz, 6H), 0.89 (d, J=6.44 Hz, 3H), 0.94 (d, J=6.44 Hz, 3H), 1.84 (m, 1H), 2.14 (m, 1H), 2.74 (dd, J=14.07, 11.02 Hz, 1H), 2.83 (m, 1H), 2.98 (m, 1H), 3.06 (dd, J=10.85, 3.73 Hz, 1H), 3.15 (m, 1H), 3.28 (d, J=17.97 Hz, 1H), 3.66 (m, 2H), 3.85 (m, 1H), 3.94 (d, J=10.85 Hz, 1H), 3.98 (s, 3H), 4.27 (m, 1H), 4.40 (s, 2H), 4.70 (m, 2H), 6.10 (d, J=9.16 Hz, 1H), 6.92 (d, J=9.16 Hz, 1H), 7.02 (m, 1H), 7.13 (m, 1H), 7.16 (d, J=7.46 Hz, 6H), 7.36 (d, J=8.48 Hz, 1H), 7.93 (d, J=2.71 Hz, 1H), 8.15 (dd, J=8.99, 2.88 Hz, 1H)

Example 819

¹H NMR (300 MHz, CDCl₃) δ ppm 0.73 (d, J=6.78 Hz, 3H), 0.79 (d, J=6.44 Hz, 3H), 0.88 (d, J=6.44 Hz, 3H), 0.94 (d, J=6.78 Hz, 3H), 1.83 (d, J=6.78 Hz, 1H), 2.04 (m, 1H), 2.71 (dd, J=14.24, 10.51 Hz, 1H), 2.80 (m, 1H), 2.98 (m, 1H), 308 (dd, J=14.41, 4.24 Hz, 1H), 3.16 (m, 1H), 3.26 (d, J=17.63 Hz, 1H), 3.54 (d, J=17.97 Hz, 1H), 3.62 (d, J=3.05 Hz, 1H), 3.82 (d, J=10.85 Hz, 2H), 4.25 (s, 1H), 4.38 (s, 2H), 5.02 (m, 2H), 5.97 (d, J=9.49 Hz, 1H), 7.03 (dd, J=8.31, 2.20 Hz, 1H), 7.15 (m, 7H), 7.35 (m, 2H), 7.44 (m, 1H), 7.73 (d, J=8.14 Hz, 1H)

Example 820

¹H NMR (300 MHz, CDCl₃) δ ppm 0.78 (d, J=6.44 Hz, 3H), 0.84 (d, J=6.44 Hz, 3H), 0.89 (d, J=6.78 Hz, 3H), 0.94 (d, J=6.78 Hz, 3H), 1.83 (m, 1H), 2.08 (m, 1H), 2.58 (s, 3H), 2.69 (dd, J=14.24, 10.51 Hz, 1H), 2.82 (dd, J=13.56, 6.78 Hz, 1H), 2.92 (d, J=21.70 Hz, 1H), 3.04 (m, 1H), 3.17 (m, 1H), 3.31 (d, J=17.97 Hz, 1H), 3.57 (s, 1H), 3.62 (m, 1H), 3.83 (dd, J=8.31, 3.22 Hz, 1H), 3.89 (d, J=10.51 Hz, 1H), 4.25 (m, 1H), 4.38 (d, J=6.78 Hz, 2H), 4.62 (m, 2H), 6.11 (d, J=9.49 Hz, 1H), 7.03 (dd, J=8.48, 2.03 Hz, 1H), 7.11 (m, 5H), 7.14 (m, 1H), 7.34 (m, 2H), 7.37 (d, J=8.14 Hz, 1H), 7.93 (d, J=9.16 Hz, 1H)

Example 821

¹H NMR (300 MHz, CDCl₃) δ ppm 0.76 (d, J=6.78 Hz, 3H), 0.81 (d, J=6.44 Hz, 3H), 0.88 (d, J=6.44 Hz, 3H), 0.94 (d, J=6.78 Hz, 3H), 1.85 (m, 1H), 2.06 (m, 1H), 2.64 (dd, J=14.07, 10.68 Hz, 1H), 2.81 (m, 1H), 2.98 (m, 1H), 3.05 (m, 1H), 3.18 (m, 2H), 3.37 (s, 3H), 3.55 (d, J=17.97 Hz, 1H), 3.60 (s, 1H), 3.79 (s, 1H), 3.87 (d, J=10.85 Hz, 1H), 4.12 (q, J=7.12 Hz, 1H), 4.22 (m, 1H), 4.43 (s, 3H), 4.62 (m, 2H), 6.06

(d, J=9.49 Hz, 1H), 7.04 (m, 7H) 7.17 (d, J=2.03 Hz, 1H), 7.32 (m, 1H), 7.34 (m, 2H), 7.38 (s, 1H)

Example 822

¹H NMR (300 MHz, CDCl₃) δ ppm 0.80 (dd, J=6.44, 2.03 Hz, 6H), 0.89 (d, J=6.78 Hz, 3H), 0.94 (d, J=6.44 Hz, 3H), 1.86 (s, 1H), 2.12 (m, 1H), 2.30 (s, 3H), 2.75 (dd, J=14.07, 10.68 Hz, 1H), 2.95 (m, 1H), 3.06 (m, 1H), 3.14 (m, 2H), 3.49 (m, 1H), 3.59 (d, J=18.31 Hz, 1H), 3.64 (s, 1H), 3.76 (m, 1H), 3.80 (d, J=9.49 Hz, 1H), 3.87 (m, 3H), 3.88 (d, J=4.07 Hz, 1H), 4.11 (s, 1H), 4.93 (m, 1H), 6.11 (d, J=8.48 Hz, 1H), 6.87 (d, J=8.48 Hz, 1H), 7.15 (m, 6H), 7.33 (m, 2H), 7.45 (d, J=8.31, 2.20 Hz, 1H), 7.56 (d, J=2.03 Hz, 1H), 7.65 (d, J=7.80 Hz, 1H)

Example 823

¹H NMR (300 MHz, CDCl₃) δ ppm 0.77 (d, J=6.78 Hz, 3H), 0.82 (d, J=6.44 Hz, 3H), 0.89 (d, J=6.44 Hz, 3H), 0.95 (d, J=6.44 Hz, 3H), 1.83 (m, 1H), 2.07 (m, 1H), 2.66 (dd, J=14.24, 10.85 Hz, 1H), 2.81 (dd, J=13.39, 6.61 Hz, 1H), 2.98 (m, 1H), 3.06 (m, 1H), 3.20 (m, 2H), 3.57 (m, 2H), 3.83 (m, 1H), 3.88 (d, J=10.85 Hz, 1H), 4.24 (m, 1H), 4.38 (s, 2H), 4.57 (m, 2H), 6.05 (d, J=9.49 Hz, 1H), 7.04 (m, 6H), 7.16 (d, J=2.03 Hz, 1H), 7.22 (d, J=7.80 Hz, 1H), 7.33 (s, 1H), 7.37 (d, J=8.48 Hz, 1H), 7.43 (d, J=8.14 Hz, 1H), 7.57 (s, 1H)

Example 824

¹H NMR (300 MHz, CDCl₃) δ ppm 0.77 (d, J=6.44 Hz, 3H), 0.82 (d, J=6.44 Hz, 3H), 0.89 (d, J=6.44 Hz, 3H), 0.94 (d, J=6.44 Hz, 3H), 1.81 (m, 1H), 2.07 (m, 1H), 2.59 (d, J=5.76 Hz, 3H), 2.66 (m, 1H), 2.82 (dd, J=13.22, 6.78 Hz, 1H), 3.01 (m, 2H), 3.17 (m, 1H), 3.22 (m, 1H), 3.58 (d, J=17.97 Hz, 1H), 3.62 (d, J=3.05 Hz, 1H), 3.83 (dd, J=8.65, 5.26 Hz, 1H), 3.89 (d, J=10.85 Hz, 1H), 4.25 (m, 1H), 4.40 (d, J=6.78 Hz, 2H), 4.68 (m, 2H), 6.13 (d, J=9.49 Hz, 1H), 7.04 (m, 6H), 7.16 (d, J=2.37 Hz, 1H), 7.37 (d, J=8.14 Hz, 1H), 7.44 (t, J=7.63 Hz, 1H), 7.61 (m, 1H), 7.88 (d, J=7.80 Hz, 1H), 7.99 (s, 1H)

Example 825

¹H NMR (300 MHz, CDCl₃) δ ppm 0.77 (d, J=6.44 Hz, 3H), 0.82 (d, J=6.78 Hz, 3H), 0.88 (d, J=6.78 Hz, 3H), 0.94 (d, J=6.44 Hz, 3H), 1.83 (m, 1H), 2.07 (m, 1H), 2.63 (dd, J=14.24, 10.85 Hz, 1H), 2.81 (m, 1H), 3.00 (m, 2H), 3.19 (m, 2H), 3.58 (m, 2H), 3.82 (m, 1H), 3.90 (d, J=10.85 Hz, 1H), 4.21 (s, 1H), 4.39 (d, J=6.78 Hz, 2H), 4.72 (m, 2H), 6.12 (d, J=9.49 Hz, 1H), 7.04 (m, 7H), 7.16 (d, J=2.03 Hz, 1H), 7.51 (m, 1H), 7.94 (m, 1H), 8.10 (s, 1H), 8.51 (d, J=2.37 Hz, 1H), 8.62 (m, 1H), 9.02 (d, J=1.36 Hz, 1H)

Example 826

¹H NMR (300 MHz, CDCl₃) δ ppm 0.77 (d, J=6.78 Hz, 3H), 0.81 (d, J=6.44 Hz, 3H), 0.88 (d, J=6.78 Hz, 3H), 0.94 (d, J=6.78 Hz, 3H), 1.62 (m, 3H), 1.82 (m, 1H), 2.07 (m, 1H), 2.62 (dd, J=14.24, 10.85 Hz, 1H), 2.81 (dd, J=13.56, 6.78 Hz, 1H), 3.18 (m, 2H), 3.56 (d, J=17.97 Hz, 1H), 3.61 (d, J=3.05 Hz, 1H), 3.82 (m, 1H), 3.90 (d, J=10.85 Hz, 1H), 4.22 (m, 1H), 4.38 (d, J=6.78 Hz, 2H), 4.65 (m, 2H), 6.10 (d, J=9.49 Hz, 1H), 7.03 (m, 8H), 7.18 (m, 1H), 7.31 (m, 2H), 7.36 (m, 2H), 7.53 (m, 1H), 7.66 (s, 1H)

Example 827

¹H NMR (300 MHz, CDCl₃) δ ppm 0.78 (d, J=6.78 Hz, 3H), 0.84 (d, J=6.44 Hz, 3H), 0.89 (d, J=6.44 Hz, 3H), 0.94 (d, J=6.44 Hz, 3H), 1.86 (m, 1H), 2.08 (m, 1H), 2.70 (dd, J=14.07, 10.68 Hz, 1H), 2.82 (m, 1H), 2.98 (m, 2H), 3.05 (m, 2H), 3.18 (m, 1H), 3.32 (d, J=17.97 Hz, 1H), 3.88 (d, J=10.85 Hz, 2H), 4.25 (m, 1H), 4.40 (s, 1H), 4.57 (m, 2H), 6.12 (d, J=9.49 Hz, 1H), 7.03 (dd, J=8.14, 2.03 Hz, 1H), 7.11 (m, 6H), 7.16 (d, J=2.37 Hz, 1H), 7.37 (m, 1H), 7.53 (d, J=1.70 Hz, 1H), 7.94 (d, J=1.70 Hz, 1H)

Example 828

¹H NMR (300 MHz, CDCl₃) δ ppm 0.81 (dd, J=8.99, 6.61 Hz, 6H), 0.88 (d, J=6.44 Hz, 3H), 0.95 (d, J=6.44 Hz, 3H), 1.83 (d, J=7.46 Hz, 1H), 2.09 (m, 1H), 2.29 (d, J=6.78 Hz, 3H), 2.70 (dd, J=14.24, 10.51 Hz, 1H), 2.78 (m, 1H), 2.92 (d, J=2.37 Hz, 1H), 2.99 (m, 2H), 3.08 (m, 1H), 3.20 (m, 1H), 3.31 (d, J=17.63 Hz, 1H), 3.61 (d, J=17.97 Hz, 1H), 3.83 (m, 2H), 4.24 (s, 1H), 4.66 (m, 2H), 5.60 (s, 1H), 5.94 (s, 2H), 6.05 (d, J=9.49 Hz, 1H), 6.85 (m, 1H), 7.14 (s, 5H), 7.51 (dd, J=8.48, 2.37 Hz, 1H), 7.55 (s, 1H)

Example 829

¹H NMR (300 MHz, CDCl₃) δ ppm 0.84 (t, J=6.27 Hz, 6H), 0.88 (m, 3H), 0.94 (d, J=6.44 Hz, 3H), 1.82 (d, J=8.14 Hz, 1H), 2.11 (s, 1H), 2.71 (dd, J=14.07, 10.68 Hz, 1H), 2.82 (m, 1H), 2.97 (m, 1H), 3.05 (m, 2H), 3.11 (d, J=4.41 Hz, 1H), 3.19 (m, 2H), 3.40 (d, J=18.31 Hz, 1H), 3.64 (s, 1H), 3.71 (d, J=17.97 Hz, 1H), 3.84 (s, 1H), 3.92 (d, J=10.85 Hz, 1H), 4.25 (d, J=9.83 Hz, 1H), 5.06 (m, 2H), 6.15 (d, J=9.16 Hz, 1H), 7.04 (dd, J=8.31, 2.20 Hz, 1H), 7.16 (m, 5H), 7.37 (m, 1H), 7.44 (m, 1H), 7.83 (d, J=8.14 Hz, 1H), 7.97 (d, J=7.46 Hz, 1H)

Example 830

¹H NMR (300 MHz, CDCl₃) δ ppm 0.83 (m, 6H), 0.88 (d, J=6.78 Hz, 3H), 0.95 (d, J=6.78 Hz, 3H), 1.83 (s, 1H), 2.10 (s, 1H), 2.30 (s, 3H), 2.76 (m, 2H), 2.91 (m, 1H), 2.98 (m, 2H), 3.06 (s, 1H), 3.18 (d, J=8.48 Hz, 1H), 3.41 (d, J=17.97 Hz, 1H), 3.68 (m, 1H), 3.82 (d, J=3.39 Hz, 1H), 3.86 (d, J=10.85 Hz, 1H), 4.28 (s, 1H), 5.00 (m, 2H), 6.08 (m, 2H), 6.53 (s, 2H), 6.85 (d, J=8.14 Hz, 2H), 7.18 (m, 5H), 7.51 (m, 1H), 7.59 (m, 1H)

Example 831

¹H NMR (300 MHz, CDCl₃) δ ppm 0.71 (d, J=6.44 Hz, 3H), 0.79 (d, J=6.78 Hz, 3H), 0.88 (d, J=6.44 Hz, 3H), 0.91 (d, J=6.78 Hz, 3H), 1.87 (m, 1H), 2.09 (m, 1H), 2.75 (dd, J=14.07, 10.68 Hz, 1H), 2.91 (m, 2H), 3.08 (dd, J=14.07, 4.24 Hz, 1H), 3.15 (m, 2H), 3.50 (d, J=17.97 Hz, 1H), 3.74 (m, 1H), 3.93 (s, 3H), 3.97 (d, J=10.85 Hz, 1H), 4.10 (s, 1H), 4.30 (m, 1H), 4.45 (s, 2H), 4.94 (m, 2H), 6.49 (d, J=9.16 Hz, 1H), 7.04 (dd, J=8.31, 2.20 Hz, 1H), 7.13 (m, 7H), 7.35 (d, J=8.48 Hz, 1H), 7.90 (dd, J=7.97, 1.53 Hz, 1H), 8.36 (dd, J=4.92, 1.53 Hz, 1H)

Example 832

¹H NMR (300 MHz, CDCl₃) δ ppm 0.75 (d, J=6.78 Hz, 3H), 0.81 (d, J=6.44 Hz, 3H), 0.88 (d, J=6.78 Hz, 3H), 0.94 (t, J=6.44 Hz, 3H), 1.80 (dd, J=14.58, 7.80 Hz, 2H), 2.05 (m, 1H), 2.29 (s, 3H), 2.64 (dd, J=14.07, 10.68 Hz, 1H), 2.77 (m, 1H), 3.04 (m, 1H), 3.18 (m, 2H), 3.53 (d, J=17.97 Hz, 1H), 3.78 (m, 1H), 3.85 (d, J=10.85 Hz, 1H), 4.21 (q, J=7.12 Hz, 1H), 4.52 (m, 2H), 5.93 (m, 2H), 6.07 (d, J=9.49 Hz, 1H), 6.76

(d, J=8.14 Hz, 1H), 6.87 (d, J=8.48 Hz, 1H), 6.91 (m, 2H), 7.03 (m, 5H), 7.50 (dd, J=8.48, 2.37 Hz, 1H), 7.55 (d, J=2.03 Hz, 1H), 8.02 (s, 2H)

Example 833

¹H NMR (300 MHz, CD₃OD) δ ppm 0.79 (d, J=6.44 Hz, 3H), 0.83 (d, J=6.44 Hz, 3H), 0.86 (d, J=6.44 Hz, 3H), 0.89 (d, J=6.78 Hz, 3H), 2.01 (m, 2H), 2.50 (dd, J=13.73, 11.70 Hz, 1H), 2.86 (dd, J=13.56, 6.78 Hz, 1H), 2.99 (m, 2H), 3.11 (d, J=17.97 Hz, 1H), 3.22 (dd, J=13.90, 3.39 Hz, 1H), 3.38 (dd, J=14.92, 3.73 Hz, 1H), 3.78 (m, 2H), 3.96 (s, 3H), 4.02 (d, J=10.85 Hz, 1H), 4.16 (m, 1H), 4.97 (m, 2H), 6.90 (m, 2H), 7.00 (m, 3H), 7.16 (m, 2H), 7.24 (m, 1H), 7.31 (m, 1H), 7.52 (d, J=7.80 Hz, 1H), 7.59 (d, J=7.46 Hz, 1H), 7.65 (m, 2H), 7.89 (s, 1H)

Example 834

¹H NMR (300 MHz, CDCl₃) δ ppm 0.83 (m, 6H), 0.88 (d, J=6.78 Hz, 3H), 0.95 (d, J=6.44 Hz, 3H), 1.80 (s, 1H), 2.10 (s, 1H), 2.30 (s, 3H), 2.73 (dd, J=14.24, 10.51 Hz, 1H), 2.80 (m, 1H), 2.95 (d, J=4.41 Hz, 3H), 3.02 (m, 2H), 3.17 (m, 1H), 3.39 (d, J=17.63 Hz, 1H), 3.69 (d, J=17.97 Hz, 1H), 3.83 (s, 1H), 3.87 (d, J=10.85 Hz, 1H), 4.16 (d, J=14.92 Hz, 1H), 4.80 (s, 2H), 6.13 (s, 1H), 6.63 (s, 1H), 6.89 (m, 1H), 6.98 (s, 1H), 7.04 (s, 1H), 7.14 (s, 5H), 7.50 (dd, J=8.48, 2.03 Hz, 1H), 7.55 (d, J=2.03 Hz, 2H)

Example 835

¹H NMR (300 MHz, CDCl₃) δ ppm 0.78 (d, J=6.44 Hz, 6H), 0.90 (d, J=6.44 Hz, 6H), 1.86 (s, 2H), 2.12 (s, 2H), 2.30 (s, 3H), 2.60 (s, 3H), 2.85 (m, 2H), 3.07 (m, 3H), 3.38 (d, J=17.97 Hz, 1H), 3.66 (d, J=18.31 Hz, 1H), 3.86 (s, 2H), 4.17 (m, 1H), 4.69 (s, 2H), 6.46 (s, 1H), 6.94 (m, 1H), 7.12 (s, 6H), 7.34 (s, 1H), 7.44 (d, J=7.12 Hz, 1H), 7.49 (s, 1H)

Example 836

¹H NMR (300 MHz, CDCl₃) δ ppm 0.70 (d, J=6.44 Hz, 3H), 0.75 (d, J=6.44 Hz, 3H), 0.91 (m, 6H), 1.90 (m, 2H), 2.08 (m, 2H), 2.24 (s, 3H), 2.79 (m, 1H), 3.07 (m, 2H), 3.57 (d, J=18.31 Hz, 1H), 3.70 (m, 1H), 4.12 (m, 1H), 4.18 (d, J=10.51 Hz, 1H), 4.27 (t, J=10.17 Hz, 1H), 4.74 (s, 2H), 6.83 (s, 1H), 7.05 (dd, J=8.31, 2.20 Hz, 3H), 7.11 (m, 5H), 7.22 (m, 2H), 7.37 (m, 1H), 8.02 (s, 1H)

Example 837

¹H NMR (300 MHz, CDCl₃) δ ppm 0.70 (d, J=6.44 Hz, 3H), 0.75 (d, J=6.44 Hz, 3H), 0.88 (d, J=6.78 Hz, 3H), 0.91 (m, 3H), 1.90 (m, 2H), 2.08 (m, 2H), 2.24 (s, 3H), 2.78 (m, 2H), 3.04 (m, 2H), 3.11 (m, 1H), 3.63 (m, 2H), 4.12 (m, 1H), 4.18 (d, J=10.51 Hz, 1H), 4.27 (t, J=10.17 Hz, 1H), 4.74 (s, 2H), 6.83 (s, 1H), 7.05 (dd, J=8.31, 2.20 Hz, 2H), 7.11 (m, 6H), 7.22 (m, 2H), 7.37 (m, 1H), 8.02 (s, 1H)

Example 838

¹H NMR (300 MHz, CDCl₃) δ ppm 0.79 (d, J=6.44 Hz, 3H), 0.87 (m, 6H), 0.94 (d, J=6.44 Hz, 3H), 1.81 (d, J=6.78 Hz, 1H), 2.06 (m, 1H), 2.30 (d, J=3.05 Hz, 3H), 2.71 (m, 1H), 2.79 (m, 1H), 3.07 (m, 1H), 3.19 (m, 1H), 3.40 (d, J=17.97 Hz, 1H), 3.65 (d, J=17.97 Hz, 1H), 3.87 (m, 2H), 4.29 (d, J=18.31 Hz, 2H), 4.62 (m, 2H), 6.14 (m, 2H), 6.87 (d, J=8.48 Hz, 1H), 7.11 (m, 3H), 7.22 (m, 2H), 7.48 (m, 2H), 7.58 (m, 1H), 7.66 (s, 1H), 8.02 (s, 1H), 8.68 (d, J=4.75 Hz, 1H)

Example 839

¹H NMR (300 MHz, CDCl₃) δ ppm 0.80 (d, J=6.78 Hz, 3H), 0.83 (d, J=6.78 Hz, 3H), 0.88 (d, J=6.44 Hz, 3H), 0.95 (d, J=6.44 Hz, 3H), 1.83 (s, 1H), 2.09 (d, J=10.51 Hz, 1H), 2.30 (d, J=3.73 Hz, 4H), 2.70 (s, 3H), 2.79 (dd, J=13.56, 6.44 Hz, 1H), 3.02 (m, 2H), 3.19 (m, 1H), 3.33 (d, J=17.97 Hz, 1H), 3.64 (d, J=17.97 Hz, 1H), 3.86 (m, 2H), 4.32 (d, J=17.63 Hz, 1H), 4.68 (m, 2H), 5.71 (s, 1H), 6.13 (d, J=9.16 Hz, 1H), 6.86 (d, J=8.48 Hz, 1H), 7.10 (m, 5H), 7.23 (m, 2H), 7.41 (m, 1H), 7.54 (m, 1H), 7.56 (m, 1H), 7.96 (m, 1H), 8.02 (s, 1H)

Example 840

¹H NMR (300 MHz, CDCl₃) δ ppm 0.77 (d, J=6.78 Hz, 3H), 0.80 (d, J=6.78 Hz, 3H), 0.89 (d, J=6.78 Hz, 3H), 0.93 (d, J=6.78 Hz, 3H), 1.83 (m, 1H), 2.07 (m, 1H), 2.62 (dd, J=14.07, 10.68 Hz, 1H), 2.83 (dd, J=13.39, 6.95 Hz, 1H), 2.91 (d, J=13.22 Hz, 1H), 3.01 (m, 2H), 3.17 (m, 1H), 3.56 (d, J=17.97 Hz, 1H), 3.66 (s, 1H), 3.83 (s, 1H), 3.89 (d, J=10.51 Hz, 1H), 4.20 (m, 1H), 4.41 (s, 1H), 4.63 (s, 2H), 4.69 (s, 2H), 6.27 (d, J=9.83 Hz, 1H), 7.01 (m, 2H), 7.06 (m, 5H), 7.16 (d, J=2.03 Hz, 1H), 7.24 (s, 1H), 7.29 (d, J=5.09 Hz, 1H), 7.33 (m, 2H), 7.36 (d, J=8.48 Hz, 1H), 7.43 (s, 1H)

Example 841

¹H NMR (300 MHz, CDCl₃) δ ppm 0.65 (d, J=6.44 Hz, 3H), 0.81 (m, 3H), 0.88 (d, J=6.44 Hz, 3H), 0.92 (m, 3H), 1.23 (m, 2H), 1.89 (m, 2H), 2.21 (s, 3H), 2.75 (m, 1H), 2.81 (m, 1H), 2.95 (m, 2H), 3.05 (m, 2H), 3.11 (m, 1H), 3.67 (s, 2H), 4.12 (q, J=7.35 Hz, 1H), 4.25 (m, 2H), 4.53 (s, 1H), 4.70 (m, 2H), 6.80 (s, 1H), 6.93 (s, 1H), 7.04 (m, 1H), 7.12 (m, 5H), 7.21 (d, J=2.03 Hz, 1H), 7.38 (m, 1H)

Example 842

¹H NMR (300 MHz, CDCl₃) δ ppm 0.74 (d, J=6.44 Hz, 3H), 0.86 (m, 6H), 0.92 (d, J=6.44 Hz, 3H), 1.01 (m, 1H), 1.37 (m, 1H), 1.83 (m, 1H), 1.93 (d, J=16.95 Hz, 1H), 2.70 (dd, J=14.07, 10.68 Hz, 1H), 2.83 (dd, J=13.22, 6.78 Hz, 1H), 2.90 (d, J=8.48 Hz, 1H), 2.96 (m, 1H), 3.05 (m, 1H), 3.42 (d, J=17.97 Hz, 1H), 3.70 (d, J=17.63 Hz, 1H), 3.77 (d, J=2.71 Hz, 1H), 3.87 (m, 3H), 4.04 (m, 1H), 4.24 (m, 1H), 4.42 (s, 2H), 4.90 (m, 2H), 6.31 (d, J=9.16 Hz, 1H), 6.85 (t, J=2.71 Hz, 1H), 7.03 (dd, J=8.48, 2.03 Hz, 1H), 7.08 (dd, J=8.99, 2.54 Hz, 1H), 7.14 (m, 5H), 7.17 (d, J=2.03 Hz, 1H), 7.20 (m, 1H), 7.35 (d, J=8.14 Hz, 1H), 7.75 (m, 1H), 7.85 (m, 1H)

Example 843

¹H NMR (300 MHz, CDCl₃) δ ppm 0.79 (d, J=6.44 Hz, 3H), 0.84 (m, 3H), 0.88 (d, J=6.44 Hz, 3H), 0.93 (d, J=6.78 Hz, 3H), 1.22 (m, 1H), 1.86 (m, 2H), 2.68 (dd, J=14.24, 10.85 Hz, 1H), 2.82 (dd, J=13.22, 6.78 Hz, 1H), 3.02 (m, 3H), 3.18 (m, 1H), 3.40 (m, 1H), 3.63 (d, J=17.97 Hz, 2H), 3.84 (m, 1H), 4.00 (d, J=10.85 Hz, 1H), 4.27 (m, 1H), 4.39 (s, 2H), 5.08 (m, 2H), 6.16 (d, J=9.49 Hz, 1H), 7.06 (m, 7H), 7.17 (m, 1H), 7.36 (m, 2H), 7.64 (m, 1H), 7.76 (m, 1H), 8.15 (d, J=7.46 Hz, 1H), 8.28 (d, J=7.46 Hz, 1H), 8.88 (d, J=4.41 Hz, 1H)

Example 844

¹H NMR (300 MHz, DMSO-d₆) δ ppm 0.70 (m, 6H), 0.85 (m, 1H), 1.17 (t, J=7.12 Hz, 4H), 1.24 (d, J=3.05 Hz, 1H), 1.50 (m, 6H), 1.94 (m, 1H), 2.23 (s, 1H), 2.36 (m, 1H), 2.59 (s, 3H), 2.73 (s, 1H), 2.88 (d, J=6.78 Hz, 1H), 2.95 (m, 1H), 3.03 (m, 1H), 3.09 (m, 1H), 3.19 (m, 2H), 3.31 (m, 1H), 3.76 (d, J=17.97 Hz, 1H), 3.90 (s, 1H), 4.01 (m, 1H), 4.64 (s, 2H), 6.99 (m, 3H), 7.07 (m, 2H), 7.24 (s, 1H), 7.79 (s, 2H), 7.95 (m, 3H), 8.24 (d, J=9.49 Hz, 1H), 8.85 (s, 1H)

The foregoing is merely illustrative of the invention and is not intended to limit the invention to the disclosed compounds. Variations and changes which are obvious to one skilled in the art are intended to be within the scoped of the nature of the invention which are defined in the appended claims.

What is claimed is:
1. A compound of formula (I),

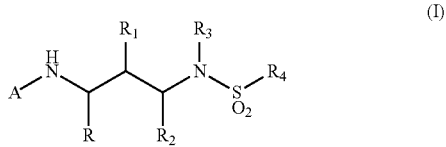

or a pharmaceutically acceptable salt form, stereoisomer, ester, salt of an ester, or combination thereof, wherein:
A is

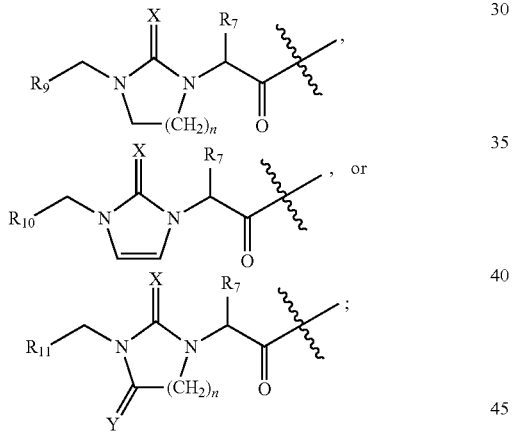

X is O, S or NH;
Y is O, S or NH;
R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —$NH_2$, —N(H)alkyl, —N(alkyl)$_2$, —C(=O)OH, —C(=O)Oalkyl, haloalkyl, hydroxyalkyl and alkoxyalkyl;
$R_1$ is $OR_a$, —$OSO_2R_a$, —$OSO_3R_a$, —$OPO_3R_a$, —OC(=O)C(H)($R_{1a}$)$NR_aR_b$ or —OC(=O)C(H)($R_{1a}$)N(H)C(O)$OR_a$;
$R_{1a}$ is hydrogen, alkyl, alkenyl, alkynyl, cycloalkyl, cycloalkenyl, aryl, arylalkyl, heteroaryl or heteroarylalkyl; wherein each $R_{1a}$ is substituted with 0, 1 or 2 substituents independently selected from the group consisting of halo, alkyl, alkenyl, alkynyl, —$OR_a$, —$SR_a$, —$SOR_a$, —$SO_2R_a$, —$SO_2NR_aR_b$, —C(=O)$R_a$, —$NR_aR_b$, —N($R_b$)C(=O)$R_a$, —N($R_b$)C(=O)$OR_a$, —N($R_b$)$SO_2R_a$, —N($R_b$)$SO_2NR_aR_b$, —N($R_b$)C(=NH)$NR_aR_b$, —N($R_b$)C(=O)$NR_aR_b$, —C(=O)$NR_aR_b$ and —C(=O)$OR_a$;
$R_2$ is H;
$R_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkyl$SR_a$, -alkyl$SOR_a$, -alkyl$SO_2R_a$, -alkyl$NR_aR_b$, -alkylN($R_b$)C(=O)$OR_a$, -alkylN($R_b$)C(=O)$R_a$, -alkylN($R_b$)$SO_2R_a$ or -alkylN($R_b$)$SO_2NR_aR_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —$SO_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$, -alkylC(=O)alkyl and $R_{3a}$;
$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —$SO_2$(alkyl), —$NH_2$, —N(H)(alkyl), —N(alkyl)$_2$, —N(H)C(=O)alkyl, —N(alkyl)C(=O)alkyl, —C(=O)OH, —C(=O)O(alkyl), —C(=O)$NH_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkyl$SO_2$(alkyl), -alkyl$NH_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)$NH_2$, -alkylC(=O)N(H)(alkyl), -alkylC(=O)N(alkyl)$_2$ and -alkylC(=O)alkyl;
$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —$OR_{4a}$, —$SR_{4a}$, —$SOR_{4a}$, —$SO_2R_{4a}$, —$NR_{4a}R_{4b}$, —OC(=O)$R_{4a}$, —C(=O)$R_{4a}$, —C(=O)$OR_{4a}$, —C(=O)$NR_{4a}R_{4b}$, —N($R_{4b}$)C(=O)$R_{4a}$, —N($R_{4b}$)C(=O)$OR_{4a}$, —N($R_{4b}$)$SO_2R_{4a}$, —N($R_{4b}$)C(=O)$NR_{4a}R_{4b}$, —N($R_{4b}$)$SO_2NR_{4a}R_{4b}$, -alkyl$SR_{4a}$, -alkyl$SOR_{4a}$, -alkyl$SO_2R_{4a}$, -alkyl$NR_{4a}R_{4b}$, -alkylOC(=O)$R_{4a}$, -alkylC(=O)$R_{4a}$, -alkylC(=O)$OR_{4a}$, -alkylC(=O)$NR_{4a}R_{4b}$, -alkylN($R_{4b}$)C(=O)$R_{4a}$, -alkylN($R_{4b}$)C(=O)$OR_{4a}$, -alkylN($R_{4b}$)$SO_2R_{4a}$, -alkylN($R_{4b}$)C(=O)$NR_{4a}R_{4b}$, -alkylN($R_{4b}$)$SO_2NR_{4a}R_{4b}$, —N(H)C(=O)alkylN(H)C(=O)$OR_{4a}$, —N(H)C(=O)alkylN$R_{4a}R_{4b}$, —C($R_{4b}$)=$NOR_{4a}$, —C($NR_{4a}R_{4b}$)=$NOR_{4a}$ and —C($R_{4b}$)=NOC(=O)alkyl$NR_{4a}R_{4b}$;

$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_5$ is alkyl, haloalkyl, cyanoalkyl, hydroxyalkyl, alkoxyalkyl, haloalkoxyalkyl, —OalkylSO$_2$alkyl, —O-heterocycle, -alkyl-O-aryl or —O-alkyl-heteroaryl; wherein the heterocycle, aryl or heteroaryl moiety of —O-heterocycle, -alkyl-O-aryl and —O-alkyl-heteroaryl is independently substituted with 0, 1, 2 or 3 substituents independently selected from the group consisting of cyano, halo, nitro, oxo, alkyl, alkenyl, alkynyl, hydroxy, alkoxy, —NH$_2$, —N(H)(alkyl), —N(alkyl), —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_6$ is aryl or heteroaryl; wherein each $R_6$ is substituted with 0 or 1 substituent selected from the group consisting of —C(H)=NOH, —C(alkyl)=NOH, —C(H)=NO(alkyl), —C(alkyl)=NO(alkyl), —C(H)=NO(arylalkyl) and —C(alkyl)=NO(arylalkyl);

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and $R_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_8$ is —C(=O)OR$_{8a}$ or —C(=O)alkylNR$_{8a}$R$_{8b}$, $R_{8a}$ and $R_{8b}$ are, at each occurrence, independently selected from the group consisting of alkyl, arylalkyl and heteroarylalkyl; wherein each $R_{8a}$ and $R_{8b}$ is independently substituted with 0, 1, 2, 3 or 4 substituents independently selected from the group consisting of alkyl, nitro, hydroxy, alkoxy, amino, formyl, halo, haloalkyl, hydroxyalkyl, alkoxyalky aminoalkyl and formylalkyl;

$R_9$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{10}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{10}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{10a}$;

$R_{10a}$ is cycloalkyl, cycloalkenyl, heterocycle, aryl or heteroaryl; wherein each $R_{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{11}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{11}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{11a}$;

$R_{11a}$ is cycloalkyl, cycloalkenyl, heterocycle, aryl or heteroaryl; wherein each $R_{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_{12}$ is alkyl, alkenyl, cycloalkyl, cycloalkenyl, cycloalkylalkyl or cycloalkenylalkyl; wherein each $R_{12}$ is substituted with 0, 1 or 2 substituents independently selected from the group consisting of hydroxy, alkoxy cyano, nitro and halo;

$R_{13}$ is alkyl, alkenyl, alkynyl, cycloalkyl, cycloalkenyl, aryl, heteroaryl or heterocycle; wherein each $R_{13}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{13a}$;

$R_{13a}$ is cycloalkyl, cycloalkenyl, heterocycle, aryl or heteroaryl; wherein each $R_{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$;

alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and R$_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$; and n is 1 or 2.

2. The compound of claim 1 having formula (III)

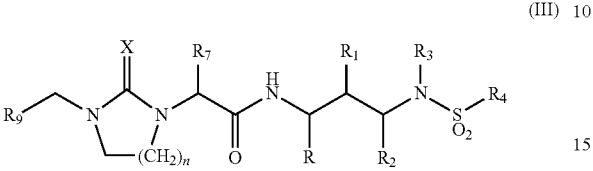

(III)

or a pharmaceutically acceptable salt form, stereoisomer, ester, salt of an ester or combination thereof, wherein X is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

R$_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

R$_{1a}$ is hydrogen, alkyl, alkenyl, alkynyl, cycloalkyl, cycloalkenyl, aryl, arylalkyl, heteroaryl or heteroarylalkyl; wherein each R$_{1a}$ is substituted with 0, 1 or 2 substituents independently selected from the group consisting of halo, alkyl, alkenyl, alkynyl, —OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_2$ is H;

R$_3$ is alkyl, haloalkyl, alkenyl, haloalkenyl, alkynyl, haloalkynyl, cycloalkyl, cycloalkenyl, cycloalkylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSR$_a$, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

R$_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)

NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, haloalkyl, hydroxyalkyl, alkoxyalkyl, -alkylNH₂, -alkylN(H)(alkyl), -alkylN(alkyl)₂, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkyl-C(=O)N(alkyl)₂;

$R_9$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_9$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO₂R$_a$, —SO₂NR$_a$, —SO₂OR$_a$, —NR$_a$R$_b$, —N(R$_b$)NR$_a$R$_b$, —N(R$_b$)C(=O)R$_a$, —N(R$_b$)SO₂R$_a$, —N(R$_b$)C(=O)OR$_a$, —N(R$_b$)C(=O)NR$_a$R$_b$, —N(R$_b$)SO₂NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO₂R$_a$, -alkylSO₂NR$_a$, -alkylSO₂OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO₂NR$_a$R$_b$, -alkylN(R$_b$)SO₂R$_a$, -alkylC(=O)R$_a$, -alkylC(=O)OR$_a$, -alkylC(=O)NR$_a$R$_b$ and $R_{9a}$;

$R_{9a}$ is cycloalkyl, cycloalkenyl, heterocycle, aryl or heteroaryl; wherein each $R_{9a}$ is substituted with 0, 1, 2, 3 or 4 substituents independently selected from the group consisting of cyano, halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, haloalkyl, hydroxyalkyl, alkoxyalkyl, -alkylNH₂, -alkylN(H)(alkyl), -alkylN(alkyl)₂, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl) and -alkylC(=O)N(alkyl)₂;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, nitroalkyl, haloalkyl, hydroxyalkyl, alkoxyalkyl, -alkylNH₂, -alkylN(H)(alkyl), -alkylN(alkyl)₂, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl)-alkylC(=O)N(alkyl)₂ and $R_c$;

alternatively, $R_a$ and $R_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, cyanoalkyl, formylalkyl, nitroalkyl, haloalkyl, hydroxyalkyl, alkoxyalkyl, -alkylNH₂, -alkylN(H)(alkyl), -alkylN(alkyl)₂, -alkylN(H)C(=O)NH₂, -alkylN(H)C(=O)N(H)(alkyl), -alkylN(H)C(=O)N(alkyl)₂, -alkylC(=O)OH, -alkylC(=O)Oalkyl, -alkylC(=O)NH₂, -alkylC(=O)N(H)(alkyl), -alkylC(=O)N(alkyl)₂ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(=O)alkyl, —N(alkyl)C(=O)alkyl, —N(H)C(=O)NH₂, —N(H)C(=O)N(H)(alkyl), —N(H)C(=O)N(alkyl)₂, —C(=O)OH, —C(=O)Oalkyl, —C(=O)NH₂, —C(=O)N(H)(alkyl), —C(=O)N(alkyl)₂, haloalkyl, hydroxyalkyl, alkoxyalkyl, -alkylNH₂, -alkyl-N(H)(alkyl), -alkyl-N(alkyl)₂, -alkyl-N(H)C(=O)NH₂, -alkyl-N(H)C(=O)N(H)(alkyl), -alkyl-N(H)C(=O)N(alkyl)₂, -alkyl-C(=O)OH, -alkyl-C(=O)Oalkyl, -alkyl-C(=O)NH₂, -alkyl-C(=O)N(H)(alkyl) and -alkyl-C(=O)N(alkyl)₂; and n is 1 or 2.

3. The compound of claim 2 wherein $R_1$ is OH and $R_2$ is H.

4. The compound of claim 2 wherein $R_1$ is OH, $R_2$ is H, X is O and $R_3$ is alkyl, cycloalkenylalkyl, cycloalkylalkyl, heterocyclealkyl, heteroarylalkyl, arylalkyl, hydroxyalkyl, alkoxyalkyl, -alkylSR$_a$, -alkylSOR$_a$, -alkylSO₂R$_a$ or -alkyl-NR$_a$R$_b$.

5. The compound of claim 2 wherein $R_1$ is OH, $R_2$ is H, X is O, $R_3$ is alkyl or cycloalkyl and $R_4$ is aryl or heteroaryl.

6. The compound of claim 2 wherein $R_1$ is OH, $R_2$ is H, X is O, $R_3$ is alkyl or cycloalkylalkyl and $R_4$ is phenyl.

7. The compound of claim 2 wherein $R_1$ is OH, $R_2$ is H, X is O, $R_3$ is alkyl or cycloalkylalkyl and $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$; wherein R$_{4a}$ and R$_{4b}$ are independently selected from the group consisting of hydrogen and alkyl.

8. The compound of claim 2 wherein $R_1$ is OH, $R_2$ is H, X is O, $R_3$ is alkyl or cycloalkylalkyl, $R_4$ is phenyl substituted with 0, 1, 2, 3 or 4 substituents selected from the group consisting of halo, —OR$_{4a}$, —NR$_{4a}$R$_{4b}$ and —C(R$_{4b}$)=NOR$_{4a}$, and $R_7$ is alkyl; wherein R$_{4a}$ and R$_{4b}$ are independently selected from the group consisting of hydrogen and alkyl.

9. The compound of claim 1 having formula (IV)

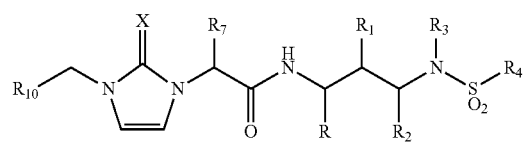

(IV)

or a pharmaceutically acceptable salt form, stereoisomer, ester, salt of an ester, or combination thereof, wherein X is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

R$_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

R$_{1a}$ is hydrogen, alkyl, alkenyl, alkynyl, cycloalkyl, cycloalkenyl, aryl, arylalkyl, heteroaryl or heteroarylalkyl; wherein each R$_{1a}$ is substituted with 0, 1 or 2 substituents independently selected from the group consisting of halo, alkyl, alkenyl, alkynyl, —OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_2$ is H;

R$_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocyclealkyl, heteroaryl, heteroarylalkyl, aryl, arylalkyl, hydroxyalkyl, alkoxyalkyl, haloalkoxyalkyl, -alkylSR$_a$, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocyclealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and R$_{3a}$;

R$_{3a}$ is cycloalkyl, cycloalkenyl, aryl, heteroaryl or heterocycle, wherein each R$_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylC(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

R$_4$ is cycloalkyl, cycloalkenyl, heterocycle, aryl or heteroaryl wherein each R$_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)OR$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

R$_{4a}$ and R$_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each R$_{4a}$ and R$_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

R$_7$ is hydrogen, alkyl, alkenyl, alkynyl, cycloalkyl, cycloalkenyl, aryl or heteroaryl; wherein each R$_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and R$_{7a}$;

R$_{7a}$ is cycloalkyl, cycloalkenyl, heterocycle, aryl or heteroaryl; wherein each R$_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl), —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

R$_{10}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each R$_{10}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)

$SO_2NR_aR_b$, —C(=O)$R_a$, —C(=O)N$R_aR_b$, —C(=O)O$R_a$, azidoalkyl, haloalkyl, nitroalkyl, cyanoalkyl, -alkylOR$_a$, -alkylOC(=O)$R_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and R$_{10a}$;

R$_{10a}$ is cycloalkyl, cycloalkenyl, heterocycle, aryl or heteroaryl; wherein each R$_{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

R$_a$ and R$_b$ at each occurrence are independently selected from the group consisting of hydrogen, alkyl, alkenyl, alkynyl, cycloalkyl, aryl, heteroaryl or heterocycle; wherein each R$_a$ and R$_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl)-alkylC(=O)N(alkyl)$_2$ and R$_c$;

alternatively, R$_a$ and R$_b$, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl), -alkylC(=O)N(alkyl)$_2$ and R$_c$; and R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkyl-N(H)(alkyl), -alkyl-N(alkyl)$_2$, -alkyl-N(H)C(=O)NH$_2$, -alkyl-N(H)C(=O)N(H)(alkyl), -alkyl-N(H)C(=O)N(alkyl)$_2$, -alkyl-C(=O)OH, -alkyl-C(=O)Oalkyl, -alkyl-C(=O)NH$_2$, -alkyl-C(=O)N(H)(alkyl) and -alkyl-C(=O)N(alkyl)$_2$.

10. The compound of claim 1 having formula (V)

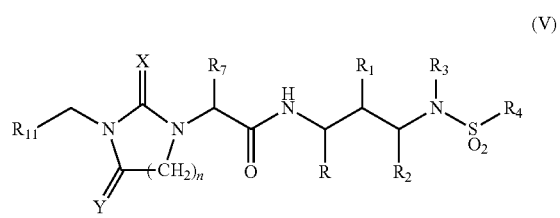

(V)

or a pharmaceutically acceptable salt form, stereoisomer, ester, salt of an ester, or combination thereof, wherein X is O, S or NH;

Y is O, S or NH;

R is alkyl, alkenyl, cycloalkyl, cycloalkenyl, cycloalkylalkyl, cycloalkenylalkyl, arylalkyl or heteroarylalkyl; wherein each R is substituted with 0, 1, or 2 substituents selected from the group consisting of alkyl, alkenyl, alkynyl, cyano, halo, formyl, nitro, hydroxy, alkoxy, —NH$_2$, —N(H)alkyl, —N(alkyl)$_2$, —C(=O)OH, —C(=O)Oalkyl, haloalkyl, hydroxyalkyl and alkoxyalkyl;

R$_1$ is OR$_a$, —OSO$_2$R$_a$, —OSO$_3$R$_a$, —OPO$_3$R$_a$, —OC(=O)C(H)(R$_{1a}$)NR$_a$R$_b$ or —OC(=O)C(H)(R$_{1a}$)N(H)C(O)OR$_a$;

R$_{1a}$ is hydrogen, alkyl, alkenyl, alkynyl, cycloalkyl, cycloalkenyl, aryl, arylalkyl, heteroaryl or heteroarylalkyl; wherein each R$_{1a}$ is substituted with 0, 1 or 2 substituents independently selected from the group consisting of halo, alkyl, alkenyl, alkynyl, —OR$_a$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_a$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$ and —C(=O)OR$_a$;

R$_2$ is H;

R$_3$ is alkyl, haloalkyl, alkenyl, haloalkenyl, alkynyl, haloalkynyl, cycloalkyl, cycloalkenyl, cycloalkenylalkyl, cycloalkylalkyl, heterocycle, heterocylealkyl, heteroaryl, heteroarylalkyl, aryl, arylalkyl, hydroxyalkyl, alkoxyalkyl, haloalkoxyalkyl, -alkylSR$_a$, -alkylSOR$_a$, -alkylSO$_2$R$_a$, -alkylNR$_a$R$_b$, -alkylN(R$_b$)C(=O)OR$_a$, -alkylN(R$_b$)C(=O)R$_a$, -alkylN(R$_b$)SO$_2$R$_a$ or -alkylN(R$_b$)SO$_2$NR$_a$R$_b$; wherein each of the cycloalkyl, cycloalkenyl, aryl, heteroaryl, heterocycle, cycloalkyl moiety of the cycloalkylalkyl, cycloalkenyl moiety of the cycloalkenylalkyl, heterocycle moiety of the heterocylealkyl, heteroaryl moiety of the heteroarylalkyl, aryl moiety of the arylalkyl is independently substituted with 0, 1, 2 or 3 substituents independently selected from the group consisting of halo, nitro, cyano, formyl, alkyl, alkenyl, alkynyl, hydroxy, alkoxy, —SH, —S(alkyl), —SO$_2$(alkyl), —NH$_2$, —N(H)(alkyl), —N(alkyl)$_2$, —N(H)C(=O)alkyl, —N(alkyl)C(=O)alkyl, —C(=O)OH, —C(=O)O(alkyl), —C(=O)NH$_2$, —C(=O)N(H)(alkyl), —C(=O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$, -alkylC(=O)alkyl and $R_{3a}$;

$R_{3a}$ is cycloalkyl, cycloalkenyl, aryl, heteroaryl or heterocycle, wherein each $R_{3a}$ is independently substituted with 0, 1, 2 or 3 substituents independently selected from the group consisting of halo, nitro, cyano, formyl, alkyl, alkenyl, alkynyl, hydroxyl, alkoxy, —SH, —S(alkyl), —SO$_2$(alkyl), —NH$_2$, —N(H)(alkyl), —N(alkyl), —N(H)C(=O)alkyl, —N(alkyl)C(=O)alkyl, —C(=O)OH, —C(=O)O(alkyl), —C(=O)NH$_2$, —C(=O)N(H)(alkyl), —C(O)N(alkyl)$_2$, —C(=O)alkyl, haloalkyl, hydroxyalkyl, alkoxyalkyl, cyanoalkyl, formylalkyl, nitroalkyl, -alkylSH, -alkylS(alkyl), -alkylSO$_2$(alkyl), -alkylNH$_2$, -alkylN(H)(alkyl), -alkylN(alkyl)$_2$, -alkylN(H)C(=O)alkyl, -alkylN(alkyl)C(=O)alkyl, -alkylC(=O)OH, -alkylC(=O)O(alkyl), -alkylC(=O)NH$_2$, -alkylC(=O)N(H)(alkyl), -alkylC(=O)N(alkyl)$_2$ and -alkylC(=O)alkyl;

$R_4$ is cycloalkyl, cycloalkenyl, heterocycle, aryl or heteroaryl wherein each $R_4$ is substituted with 0, 1, 2, 3 or 4 substituents independently selected from the group consisting of halo, alkyl, oxo, alkenyl, alkynyl, nitro, cyano, haloalkyl, cyanoalkyl, hydroxyalkyl, alkoxyalkyl, nitroalkyl, —OR$_{4a}$, —SR$_{4a}$, —SOR$_{4a}$, —SO$_2$R$_{4a}$, —NR$_{4a}$R$_{4b}$, —OC(=O)R$_{4a}$, —C(=O)R$_{4a}$, —C(=O)OR$_{4a}$, —C(=O)NR$_{4a}$R$_{4b}$, —N(R$_{4b}$)C(=O)R$_{4a}$, —N(R$_{4b}$)C(=O)OR$_{4a}$, —N(R$_{4b}$)SO$_2$R$_{4a}$, —N(R$_{4b}$)C(=O)NR$_{4a}$R$_{4b}$, —N(R$_{4b}$)SO$_2$NR$_{4a}$R$_{4b}$, -alkylSR$_{4a}$, -alkylSOR$_{4a}$, -alkylSO$_2$R$_{4a}$, -alkylNR$_{4a}$R$_{4b}$, -alkylOC(=O)R$_{4a}$, -alkylC(=O)R$_{4a}$, -alkylC(=O)OR$_{4a}$, -alkylC(=O)NR$_{4a}$R$_{4b}$, -alkylN(R$_{4b}$)C(=O)R$_{4a}$, -alkylN(R$_{4b}$)C(=O)OR$_{4a}$, -alkylN(R$_{4b}$)SO$_2$R$_{4a}$, -alkylN(R$_{4b}$)C(=O)NR$_{4a}$R$_{4b}$, -alkylN(R$_{4b}$)SO$_2$NR$_{4a}$R$_{4b}$, —N(H)C(=O)alkylN(H)C(=O)R$_{4a}$, —N(H)C(=O)alkylNR$_{4a}$R$_{4b}$, —C(R$_{4b}$)=NOR$_{4a}$, —C(NR$_{4a}$R$_{4b}$)=NOR$_{4a}$ and —C(R$_{4b}$)=NOC(=O)alkylNR$_{4a}$R$_{4b}$;

$R_{4a}$ and $R_{4b}$, at each occurrence, are independently selected from the group consisting of hydrogen, alkyl, alkenyl, alkynyl, cycloalkyl, cycloalkylalkyl, aryl, arylalkyl, heterocycle, heterocyclealkyl, heteroaryl and heteroalkyl; wherein each $R_{4a}$ and $R_{4b}$, at each occurrence, is independently substituted with 0, 1 or 2 substituents independently selected from the group consisting of alkyl, alkenyl, hydroxy, alkoxy, halo, nitro, cyano, formyl, oxo, —NH$_2$, —N(H)alkyl, —N(alkyl)$_2$, —C(=O)alkyl, —C(=O)OH, —C(=O)Oalkyl, —C(=O)NH$_2$, —C(=O)N(H)alkyl, —C(=O)N(alkyl)$_2$, haloalkyl, hydroxyalkyl, cyanoalkyl, nitroalkyl, formylalkyl and alkoxyalkyl;

$R_7$ is hydrogen, alkyl, alkenyl, alkynyl, cycloalkyl, cycloalkenyl, aryl or heteroaryl; wherein each $R_7$ is substituted with 0, 1 or 2 substituents independently selected from the group consisting of halo, —OR$_a$, —OalkylC(=O)NR$_a$R$_b$, —SR$_a$, —SOR$_a$, —SO$_2$R$_a$, —SO$_2$NR$_a$R$_b$, —C(=O)R$_a$, —NR$_a$R$_b$, —N(R$_b$)C(=O)R$_a$, —N(R$_b$)C(=O)OR$_a$, —N(R$_b$)SO$_2$R$_a$, —N(R$_b$)SO$_2$NR$_a$R$_b$, —N(R$_b$)C(=NH)NR$_a$R$_b$, —N(R$_b$)C(=O)NR$_a$R$_b$, —C(=O)NR$_a$R$_b$, —C(=O)OR$_a$ and $R_{7a}$;

$R_{7a}$ is cycloalkyl, cycloalkenyl, heterocycle, aryl or heteroaryl; wherein each $R_{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkyl-C(=O)N(alkyl)$_2$;

$R_{11}$ is alkyl, alkenyl, alkynyl, —C(=O)NR$_a$R$_b$, —C(=O)OR$_a$, cycloalkyl, cycloalkenyl, aryl, heteroaryl or heterocycle; wherein each $R_{11}$ is substituted with 0, 1, 2 or 3 substituents independently selected from the group consisting of alkyl, alkenyl, alkynyl, cyano, halo, nitro, oxo, —OR$_a$, —OC(=O)R$_a$, —SR$_a$, —SOR$_a$, —SO$_2$R$_a$, —SO$_2$NR$_a$, —SO$_2$OR$_a$, —NR$_a$R$_b$, —N(R$_b$)NR$_a$R$_b$, —N(R$_b$)C(=O)R$_a$, —N(R$_b$)SO$_2$R$_a$, —N(R$_b$)C(=O)OR$_a$, —N(R$_b$)C(=O)NR$_a$R$_b$, —N(R$_b$)SO$_2$NR$_a$R$_b$, —C(=O)R$_a$, —C(=O)NR$_a$R$_b$, —C(=O)OR$_a$, azidoalkyl, haloalkyl, nitroalkyl, cyanoalkyl, -alkylOR$_a$, -alkylOC(=O)R$_a$, -alkylSR$_a$, -alkylSOR$_a$, -alkylSO$_2$R$_a$, -alkylSO$_2$NR$_a$, -alkylSO$_2$OR$_a$, -alkylNR$_a$R$_b$, —C(H)=N(OR$_a$), —C(alkyl)=N(OR$_a$), —C(H)=NNR$_a$R$_b$, —C(alkyl)=NNR$_a$R$_b$, —C(H)(=NOR$_a$)NR$_a$R$_b$, —C(alkyl)(=NOR$_a$)NR$_a$R$_b$, -alkylN(R$_b$)NR$_a$R$_b$, -alkylN(R$_b$)C(=O)R$_a$, -alkylN(R$_b$)C(=O)OR$_a$, -alkylN(R$_b$)C(=O)NR$_a$R$_b$, -alkylN(R$_b$)SO$_2$NR$_a$R$_b$, -alkylN(R$_b$)SO$_2$R$_a$, -alkylC(=O)R$_a$, -alkylC(=O)OR$_a$, -alkylC(=O)NR$_a$R$_b$ and $R_{11a}$;

$R_{11a}$ is cycloalkyl, cycloalkenyl, heterocycle, aryl or heteroaryl; wherein each $R_{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)(alkyl), —C(=O)N(alkyl)$_2$, cyanoalkyl, formylalkyl, haloalkyl, hydroxyalkyl, alkoxyalkyl, -alkylNH$_2$, -alkylN(H)(alkyl), -alkylN(alkyl)$_2$, -alkylN(H)C(=O)NH$_2$, -alkylN(H)C(=O)N(H)(alkyl), -alkylN(H)C(=O)N(alkyl)$_2$, -alkylC(=O)OH, -alkylC(=O)Oalkyl, -alkylC(=O)NH$_2$, -alkylC(=O)N(H)(alkyl) and -alkylC(=O)N(alkyl)$_2$;

$R_a$ and $R_b$ at each occurrence are independently selected from the group consisting of hydrogen, alkyl, alkenyl, alkynyl, cycloalkyl, aryl, heteroaryl or heterocycle; wherein each $R_a$ and $R_b$, at each occurrence, is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(=O)alkyl, —N(alkyl)C(=O)alkyl, —N(H)C(=O)NH$_2$, —N(H)C(=O)N(H)(alkyl), —N(H)C(=O)N(alkyl)$_2$, —C(=O)OH, —C(=O)Oalkyl, —C(=O)NH$_2$, —C(=O)N(H)

(alkyl), —C(═O)N(alkyl)₂, cyanoalkyl, formylalkyl, nitroalkyl, haloalkyl, hydroxyalkyl, alkoxyalkyl, -alkylNH₂, -alkylN(H)(alkyl), -alkylN(alkyl)₂, -alkylN(H)C(═O)NH₂, -alkylN(H)C(═O)N(H)(alkyl), -alkylN(H)C(═O)N(alkyl)₂, -alkylC(═O)OH, -alkylC(═O)Oalkyl, -alkylC(═O)NH₂, -alkylC(═O)N(H)(alkyl)- alkylC(═O)N(alkyl)₂ and R_c;

alternatively, R_a and R_b, together with the nitrogen atom they are attached, form a heterocycle ring substituted with 0, 1, 2 or 3 substituents independently selected from the group consisting of alkyl, alkenyl, alkynyl, cyano, formyl, nitro, halo, oxo, hydroxy, alkoxy, —NH₂, —N(H)(alkyl), —N(alkyl)₂, —SH, —S(alkyl), —SO₂(alkyl), —N(H)C(═O)alkyl, —N(alkyl)C(═O)alkyl, —N(H)C(═O)NH₂, —N(H)C(═O)N(H)(alkyl), —N(H)C(═O)N(alkyl)₂, —C(═O)OH, —C(═O)Oalkyl, —C(═O)NH₂, —C(═O)N(H)(alkyl), —C(═O)N(alkyl)₂, cyanoalkyl, formylalkyl, nitroalkyl, haloalkyl, hydroxyalkyl, alkoxyalkyl, -alkylNH₂, -alkylN(H)(alkyl), -alkylN(alkyl)₂, -alkylN(H)C(═O)NH₂, -alkylN(H)C(═O)N(H)(alkyl), -alkylN(H)C(═O)N(alkyl)₂, -alkylC(═O)OH, -alkylC(═O)Oalkyl, -alkylC(═O)NH₂, -alkylC(═O)N(H)(alkyl), -alkylC(═O)N(alkyl)₂ and R_c;

R_c is aryl, heteroaryl or heterocycle; wherein each R_c is independently substituted with 0, 1, 2, 3 or 4 substituents independently selected from the group consisting of halo, nitro, oxo, alkyl, alkenyl, alkynyl, hydroxy, alkoxy, —NH₂, —N(H)(alkyl), —N(alkyl)₂, —SH, —S(alkyl), —SO₂(alkyl), —N(H)C(═O)alkyl, —N(alkyl)C(═O)alkyl, —N(H)C(═O)NH₂, —N(H)C(═O)N(H)(alkyl), —N(H)C(═O)N(alkyl)₂, —C(═O)OH, —C(═O)Oalkyl, —C(═O)NH₂, —C(═O)N(H)(alkyl), —C(═O)N(alkyl)₂, haloalkyl, hydroxyalkyl, alkoxyalkyl, -alkylNH₂, -alkyl-N(H)(alkyl), -alkyl-N(alkyl)₂, -alkyl-N(H)C(═O)NH₂, -alkyl-N(H)C(═O)N(H)(alkyl), -alkyl-N(H)C(═O)N(alkyl)₂, -alkyl-C(═O)OH, -alkyl-C(═O)Oalkyl, -alkyl-C(═O)NH₂, -alkyl-C(═O)N(H)(alkyl) and -alkyl-C(═O)N(alkyl)₂; and n is 1 or 2.

11. The compound of claim 10 wherein R₁ is OH and R₂ is H.

12. The compound of claim 10 wherein R₁ is OH, R₂ is H, X is O, Y is O and R₃ is alkyl, cycloalkenylalkyl, cycloalkylalkyl, heterocyclealkyl, heteroarylalkyl, arylalkyl, hydroxyalkyl, alkoxyalkyl, -alkylSR_a, -alkylSOR_a, -alkylSO₂R_a or -alkylNR_aR_b.

13. The compound of claim 10 wherein R₁ is OH, R₂ is H, X is O, Y is O, R₃ is alkyl or cycloalkyl and R₄ is aryl or heteroaryl.

14. The compound of claim 10 wherein R₁ is OH, R₂ is H, X is O, Y is O, R₃ is alkyl or cycloalkylalkyl and R₄ is phenyl substituted with 0, 1, 2, 3 or 4 substituents selected from the group consisting of halo, —OR_{4a}, —NR_{4a}R_{4b} and —C(R_{4b})═NOR_{4a}; wherein R_{4a} and R_{4b} are independently selected from the group consisting of hydrogen and alkyl.

15. The compound of claim 10 wherein R₁ is OH, R₂ is H, X is O, Y is O, R₃ is alkyl or cycloalkylalkyl, R₄ is phenyl substituted with 0, 1, 2, 3 or 4 substituents selected from the group consisting of halo, —OR_{4a}, —NR_{4a}R_{4b} and —C(R_{4b})═NOR_{4a}, and R₇ is alkyl; wherein R_{4a} and R_{4b} are independently selected from the group consisting of hydrogen and alkyl.

16. A pharmaceutical composition comprising a therapeutically effective amount of a compound or combination of compounds of claim 1, and a pharmaceutically acceptable carrier.

17. A method of inhibiting the replication of an HIV virus comprising contacting said virus with a therapeutically effective amount of a compound or combination of compounds of claim 1.

18. A method of treating an HIV infection comprising administering to a patient in need of such treatment a therapeutically effective amount of a compound or combination of compounds of claim 1.

19. The compound of claim 2, or a pharmaceutically acceptable salt form, stereoisomer, ester, salt of an ester, or combination thereof, selected from the group consisting of (2S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxoimidazolidin-1-yl)-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(1-methyl-1H-benzimidazol-2-yl)methyl]-2-oxoimidazolidin-1-yl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-quinolinylmethyl)-1-imidazolidinyl]butanamide;

(2S)-2-(3-{[2-(acetylamino)-1,3-thiazol-4-yl]methyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-2-[3-({2-[(dimethylamino)methyl]-1,3-thiazol-4-yl}methyl)-2-oxo-1-imidazolidinyl]-3-methylbutanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(tetrahydro-2-furanylmethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[2-(dimethylamino)ethyl]({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2-furylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(2-pyridinylmethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino propyl}-2-{3-[(2,5-dimethyl-1,3-thiazol-4-yl)methyl]-2-oxo-1-imidazolidinyl}-3-methylbutanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-(3-nitrobenzyl)-2-oxo-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridinylmethyl)-1-imidazolidinyl]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-methyl-1H-benzimidazol-2-yl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(2-methoxyethyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(cyclobutylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2-oxo-1-imidazolidinyl)-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridinylmethyl)-1-imidazolidinyl]pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[2-oxo-3-(3-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridinylmethyl)-1-imidazolidinyl]pentanamide;

(2S)—N-{(1S,2R)-1-benzyl-2-hydroxy-3-[({4-[(E)-(hydroxyimino)methyl]phenyl}sulfonyl)(2-hydroxypropyl)amino]propyl}-3-methyl-2-{3-[(2-methyl-1,3-thiazol-4-yl)methyl]-2-oxo-1-imidazolidinyl}butanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-[2-oxo-3-(4-quinolinylmethyl)-1-imidazolidinyl]pentanamide;

(2S)—N-((1S,2R)-1-benzyl-2-hydroxy-3-{({4-[(E)-(hydroxyimino)methyl]phenyl}sulfonyl)[2-(2-thienyl)ethyl]amino}propyl)-3-methyl-2-{3-[(2-methyl-1,3-thiazol-4-yl)methyl]-2-oxo-1-imidazolidinyl}butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxo-1-imidazolidinyl}pentanamide;

(2S,3S)—N-{(1S,2R)-1-benzyl-3-[(cyclobutylmethyl)({4-[(E)-(hydroxyimino)methyl]phenyl}sulfonyl)amino]-2-hydroxypropyl}-3-methyl-2-{3-[(2-methyl-1,3-thiazol-4-yl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-quinolinylmethyl)-1-imidazolidinyl]pentanamide;

(2S,3S)-2-(3-{[2-(acetylamino)-1,3-thiazol-4-yl]methyl}-2-oxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)-2-(3-{[2-(acetylamino)-1,3-thiazol-4-yl]methyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-[3-(1H-benzimidazol-5-ylmethyl)-2-oxo-1-imidazolidinyl]-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S)—N-((1S,2R)-1-benzyl-2-hydroxy-3-{({4-[(E)-(hydroxyimino)methyl]phenyl}sulfonyl)[(1S)-1-(hydroxymethyl)-2-methylpropyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{({4-[(E)-(hydroxyimino)methyl]phenyl}sulfonyl)[(1R)-1-(hydroxymethyl)-2-methylpropyl]amino}propyl)-3-methyl-2-{3-[(2-methyl-1,3-thiazol-4-yl)methyl]-2-oxo-1-imidazolidinyl}butanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(4-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(4-methyl-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(6-methyl-2-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(2-pyridinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(methoxymethyl)-2-pyridinyl]methyl}-2-oxo-1-imidazolidinyl)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-(3-{[6-(methoxymethyl)-2-pyridinyl]methyl}-2-oxo-1-imidazolidinyl)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(2-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-(3-cyanobenzyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(trifluoromethyl)-1,3-thiazol-4-yl]methyl}-1-imidazolidinyl)pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(1-methyl- 1H-benzimidazol-2-yl)methyl]-2-oxo-1-imidazolidinyl}pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(8-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(8-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(2-isopropyl-1,3-thiazol-4-yl)methyl]-2-oxo-1-imidazolidinyl}-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-{3-[(2-isopropyl-1,3-thiazol-4-yl)methyl]-2-oxo-1-imidazolidinyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-{3-[(2-isopropyl-1,3-thiazol-4-yl)methyl]-2-oxo-1-imidazolidinyl}-3-methylbutanamide;

(2S)—N-{(1S,2R)-1-benzyl-3-[(cyclopentylmethyl)({4-[(E)-(hydroxyimino)methyl]phenyl}sulfonyl)amino]-2-hydroxypropyl}-2-{3-[(2-isopropyl-1,3-thiazol-4-yl)methyl]-2-oxo-1-imidazolidinyl}-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-(3-{[2-(methoxymethyl)-1,3-thiazol-4-yl]methyl}-2-oxo-1-imidazolidinyl)-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-(3-{[2-(methoxymethyl)-1,3-thiazol-4-yl]methyl}-2-oxo-1-imidazolidinyl)-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]-4-pyridinyl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(7-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(6-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(2-pyridinyl)-1,3-thiazol-4-yl]methyl}-1-imidazolidinyl)pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(7-quinolinylmethyl)-1-imidazolidinyl]pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-[2-oxo-3-(6-quinolinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[(E)-(dimethylhydrazono)methyl]-1,3-thiazol-4-yl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(neopentyl)amino]propyl}-3-methyl-2-{3-[(1-methyl-1H-benzimidazol-2-yl)methyl]-2-oxo-1-imidazolidinyl}pentanamide;

(2S)—N4(1S,2R)-1-benzyl-2-hydroxy-3-{({4-[(E)-(hydroxyimino)methyl]phenyl}sulfonyl)[4-(2-pyridinyl)benzyl]amino}propyl)-3-methyl-2-{3-[(2-methyl-1,3-thiazol-4-yl)methyl]-2-oxo-1-imidazolidinyl}butanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(1E)-N-hydroxyethanimidoyl]-4-pyridinyl}methyl)-2-oxo-1-imidazolidinyl]-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({6-[(1E)-N-hydroxyethanimidoyl]-2-pyridinyl}methyl)-2-oxo-1-imidazolidinyl]-3-methylpentanamide;

(2S,3S)-2-{3-[(6-{[acetyl(methyl)amino]methyl}-2-pyridinyl)methyl]-2-oxo-1-imidazolidinyl}-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(3-{[2-(1-methylhydrazino)-1,3-thiazol-4-yl]methyl}-2-oxo-1-imidazolidinyl)pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-(2-oxo-3-{[2-(3-pyridinyl)-1,3-thiazol-4-yl]methyl}-1-imidazolidinyl)pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{2-oxo-3-[(6-pyridin-2-yl-2-pyridinyl)methyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-4-quinolinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(4-methyl-2-quinolinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[(6-isopropyl-2-pyridinyl)methyl]-2-oxo-1-imidazolidinyl}-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(6-methyl-2-pyridinyl)methyl]-2-oxo-1-imidazolidinyl}pentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(4-methyl-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)

amino]propyl}-2-(3-{[4-(methoxymethyl)-2-pyridinyl] methyl}-2-oxo-1-imidazolidinyl)-3-methylpentanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-[2-oxo-3-(4-quinolinylmethyl)-1-imidazolidinyl]butanamide;

(2S,3S)—N-{(1S,2R)-1-benzyl-3-[(cyclopentylmethyl) ({4-[(E)-(hydroxyimino)methyl]phenyl}sulfonyl) amino]-2-hydroxypropyl}-3-methyl-2-[2-oxo-3-(3-pyridinylmethyl)-1-imidazolidinyl]pentanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-[2-oxo-3-(3-pyridinylmethyl)-1-imidazolidinyl]butanamide;

(2S,3S)-2-{3-[(2-{[acetyl(methyl)amino]methyl}-1,3-thiazol-4-yl)methyl]-2-oxo-1-imidazolidinyl}-N-{(1S,2R)-1-benzyl-2-hydroxy-3-[({4-[(E)-(hydroxyimino) methyl]phenyl}sulfonyl)(isobutyl)amino]propyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-{3-[(2-methyl-4-quinolinyl) methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-[2-oxo-3-(6-quinolinylmethyl)-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-[2-oxo-3-(7-quinolinylmethyl)-1-imidazolidinyl]butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-(2-oxo-3-{[2-(2-pyridinyl)-1,3-thiazol-4-yl]methyl}-1-imidazolidinyl)butanamide;

{4-[(3-{(1S,2S)-1-[({(1S,2R)-1-benzyl-2-hydroxy-3-[({4-[(E)-(hydroxyimino)methyl]phenyl}sulfonyl) (isobutyl)amino]propyl}amino)carbonyl]-2-methylbutyl}-2-oxo-1-imidazolidinyl)methyl]-1,3-thiazol-2-yl}methyl acetate;

(2S)—N-{(1S,2R)-1-benzyl-2-hydroxy-3-[({4-[(E)-(hydroxyimino)methyl]phenyl}sulfonyl)(isobutyl)amino] propyl}-2-(3-{[6-(methoxymethyl)-2-pyridinyl]methyl}-2-oxo-1-imidazolidinyl)-3,3-dimethylbutanamide;

(2S)—N-{(1S,2R)-1-benzyl-2-hydroxy-3-[({4-[(E)-(hydroxyimino)methyl]phenyl}sulfonyl)(isobutyl)amino] propyl}-2-(3-{[2-(methoxymethyl)-1,3-thiazol-4-yl] methyl}-2-oxo-1-imidazolidinyl)-3,3-dimethylbutanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{2-oxo-3-[3-(3-pyridinyl) benzyl]-1-imidazolidinyl}pentanamide;

(2S)-2-[3-({2-[(1S)-1-(acetylamino)ethyl]-1,3-thiazol-4-yl}methyl)-2-oxo-1-imidazolidinyl]-N-{(1S,2R)-1-benzyl-2-hydroxy-3-[({4-[(E)-(hydroxyimino)methyl] phenyl}sulfonyl)(isobutyl)amino]propyl}-3,3-dimethylbutanamide;

(2S)—N-{(1S,2R)-1-benzyl-2-hydroxy-3-[({4-[(E)-(hydroxyimino)methyl]phenyl}sulfonyl)(isobutyl)amino propyl}-3,3-dimethyl-2-(3-{[2-(6-methyl-3-pyridinyl)-1,3-thiazol-4-yl]methyl}-2-oxo-1-imidazolidinyl) butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-(2-oxo-3-{[2-(4-pyridinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-(2-oxo-3-{[2-(2-thienyl)-1,3-thiazol-4-yl]methyl}-1-imidazolidinyl)butanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{3-[(2-methyl-3-pyridinyl) methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{3-[(6-methyl-3-pyridinyl) methyl]-2-oxo-1-imidazolidinyl}pentanamide;

ethyl {6-[(3-{(1S,2S)-1-[({(1S,2R)-1-benzyl-2-hydroxy-3-[({4-[(E)-(hydroxyimino)methyl]phenyl}sulfonyl) (isobutyl)amino]propyl}amino)carbonyl]-2-methylbutyl}-2-oxo-1-imidazolidinyl)methyl]-2-pyridinyl}methyl(methyl)carbamate;

(2S)—N-{(1S,2R)-1-benzyl-2-hydroxy-3-[({4-[(E)-(hydroxyimino)methyl]phenyl}sulfonyl)(isobutyl)amino] propyl}-2-(3-{[6-(hydroxymethyl)-2-pyridinyl]methyl}-2-oxo-1-imidazolidinyl)-3,3-dimethylbutanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{2-oxo-3-[3-(1,3-thiazol-2-yl)benzyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{2-oxo-3-[3-(2-pyridinyl) benzyl]-1-imidazolidinyl}pentanamide;

(2S)—N-{(1S,2R)-1-benzyl-2-hydroxy-3-[{4-[(E)-(hydroxyimino)methyl]phenyl}sulfonyl)(isobutyl)amino] propyl}-3,3-dimethyl-2-(3-{[2-(5-methyl-3-isoxazolyl)-1,3-thiazol-4-yl]methyl}-2-oxo-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-{3-[(3-methyl-3H-imidazo[4,5-b]pyridin-2-yl)methyl]-2-oxo-1-imidazolidinyl}butanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-2-{3-[(2,4-dimethyl-3-pyridinyl)methyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-2-{3-[3-(3-furyl)benzyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-3-methyl-2-{2-oxo-3-[3-(4-pyrimidinyl)benzyl]-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl) amino]propyl}-2-{3-[(6-methoxy-3-pyridinyl)methyl]-2-oxo-1-imidazolidinyl}-3-methylpentanamide;

(2S)—N-{(1S,2R)-1-benzyl-2-hydroxy-3-[({4-[(E)-(hydroxyimino)methyl]phenyl}sulfonyl)(isobutyl)amino] propyl}-3,3-dimethyl-2-(2-oxo-3-{[2-(2-pyrazinyl)-1,3-thiazol-4-yl]methyl}-1-imidazolidinyl)butanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxy-1-methylethyl)-2-pyridinyl]methyl}-2-oxo-1-imidazolidinyl)-3,3-dimethylbutanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-3-methyl-2-{3-[(2-methyl-3-pyridinyl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-{3-[(6-methyl-3-pyridinyl)methyl]-2-oxo-1-imidazolidinyl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3,3-dimethyl-2-[2-oxo-3-(4-pyridazinylmethyl)-1-imidazolidinyl]butanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(4-pyridazinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-[2-oxo-3-(3-pyridazinylmethyl)-1-imidazolidinyl]pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(3-methyl-3H-imidazo[4,5-b]pyridin-2-yl)methyl]-2-oxo-1-imidazolidinyl}pentanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(2-methyl-1,3-thiazol-4-yl)methyl]-2-oxoimidazolidin-1-yl}butanamide;

(2S)—N-{(1S,2R)-1-benzyl-2-hydroxy-3-[({4-[(E)-(hydroxyimino)methyl]phenyl}sulfonyl)(isobutyl)amino]propyl}-3-methyl-2-[3-({2-[(methylamino)methyl]-1,3-thiazol-4-yl}methyl)-2-oxoimidazolidin-1-yl]butanamide;

(2S)—N-{(1S,2R)-1-benzyl-2-hydroxy-3-[({4-[(E)-(hydroxyimino)methyl]phenyl}sulfonyl)(pyrrolidin-2-ylmethyl)amino]propyl}-3-methyl-2-{3-[(2-methyl-1,3-thiazol-4-yl)methyl]-2-oxoimidazolidin-1-yl}butanamide;

(2S)-2-[3-(3-aminobenzyl)-2-oxoimidazolidin-1-yl]-N-{(1S,2R)-1-benzyl-2-hydroxy-3-[({4-[(E)-(hydroxyimino)methyl]phenyl}sulfonyl)(isobutyl)amino]propyl}-3-methylbutanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxido-3-pyridinyl)methyl]-2-oxo-1-imidazolidinyl}pentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-3-methyl-2-{3-[(1-oxidopyridin-4-yl)methyl]-2-oxoimidazolidin-1-yl}pentanamide;

(2S,3S)-2-(3-{[2-(aminomethyl)-1,3-thiazol-4-yl]methyl}-2-oxoimidazolidin-1-yl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)-2-(3-{[2-(aminomethyl)-1,3-thiazol-4-yl]methyl}-2-oxo-1-imidazolidinyl)-N-{(1S,2R)-1-benzyl-3-[(cyclobutylmethyl)({4-[(E)-(hydroxyimino)methyl]phenyl}sulfonyl)amino]-2-hydroxypropyl}-3-methylpentanamide;

(2S,3S)-2-(3-{[2-(aminomethyl)-1,3-thiazol-4-yl]methyl}-2-oxo-1-imidazolidinyl)-N-{(1S,2R)-1-benzyl-3-[(cyclopentylmethyl)({4-[(E)-(hydroxyimino)methyl]phenyl}sulfonyl)amino]-2-hydroxypropyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({2-[N-hydroxyethanimidoyl]pyridin-4-yl}methyl)-2-oxo-2,3-dihydro-1H-imidazol-1-yl]-3-methylpentanamide;

(2R,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide;

(2S,3S)—N-{(1S,2R)-1-benzyl-3-[(cyclopentylmethyl)({4-[(E)-(hydroxyimino)methyl]phenyl}sulfonyl)amino]-2-hydroxypropyl}-2-[3-({2-[(isopropylamino)methyl]-1,3-thiazol-4-yl}methyl)-2-oxo-1-imidazolidinyl]-3-methylpentanamide;

(2S,3S)-2-(3-{3-[amino(hydroxyimino)methyl]benzyl}-2-oxo-1-imidazolidinyl)-N-{(1S,2R)-1-benzyl-2-hydroxy-3-[({4-[(E)-(hydroxyimino)methyl]phenyl}sulfonyl)(isobutyl)amino]propyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-{3-[3-(hydroxymethyl)benzyl]-2-oxo-1-imidazolidinyl}-3-methylpentanamide;

(2S,3S)—N-{(1S,2R)-1-benzyl-2-hydroxy-3-[({4-[(E)-(hydroxyimino)methyl]phenyl}sulfonyl)(isobutyl)amino]propyl}-2-[3-({6-[(hydroxyimino)methyl]-2-pyridinyl}methyl)-2-oxo-1-imidazolidinyl]-2,3-dimethylpentanamide;

(2S)—N-{(1S,2R)-1-benzyl-2-hydroxy-3-[({4-[(E)-(hydroxyimino)methyl]phenyl}sulfonyl)(isobutyl)amino]propyl}-2-(3-{[6-(1-hydroxyethyl)-2-pyridinyl]methyl}-2-oxo-1-imidazolidinyl)-3,3-dimethylbutanamide;

(2S)—N-((1S,2R)-1-benzyl-2-hydroxy-3-{isobutyl[(4-methoxyphenyl)sulfonyl]amino}propyl)-2-{3-[(2-isopropyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-[2-oxo-3-(3-thienylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(2-ethyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3-methylbutanamide;

(2S)—N-(1S,2R)-1-benzyl-2-hydroxy-3-{isobutyl[(4-methoxyphenyl)sulfonyl]amino}propyl)-3-methyl-2-[2-oxo-3-(1,3-thiazol-2-ylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(3,5-dimethyl-1-phenyl-1H-pyrazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(5-ethyl-2-phenyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(5-ethyl-2-methyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(2,5-dimethyl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(5-nitro-3-thienyl)methyl]-2-oxo-1-imidazolidinyl}butanamide;

(2S)-2-[3-(1-benzothien-3-ylmethyl)-2-oxo-1-imidazolidinyl]-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(1-methyl-1H-benzimidazol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-{3-[(1-methyl-1H-indol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-[2-oxo-3-(2-quinolinylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(2-cyclopropyl-1,3-thiazol-4-yl)methyl]-2-oxo-1-imidazolidinyl}-3-methylbutanamide;

(2S)-2-{3-[(2-acetyl-1,3-thiazol-4-yl)methyl]-2-oxo-1-imidazolidinyl}-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-{3-[(2-isobutyryl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-2-{3-[(2-butyryl-1,3-thiazol-4-yl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(5-nitro-2-thienyl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-methyl-2-{3-[(2-nitro-1,3-thiazol-4-yl)methyl]-2-oxo-1-imidazolidinyl}butanamide;

(2S)-2(3-{[2-(azidomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)—N4(1S,2R)-1-benzyl-2-hydroxy-3-{isobutyl[(4-methoxyphenyl)sulfonyl]amino}propyl)-3-methyl-2-{2-oxo-3-[(2-propionyl-1,3-thiazol-4-yl)methyl]-1-imidazolidinyl}butanamide;

(2S)—N-((1S,2R)-1-benzyl-2-hydroxy-3-{isobutyl[(4-methoxyphenyl)sulfonyl]amino}propyl)-3,3-dimethyl-2-{3-[(2-methyl-1,3-thiazol-4-yl)methyl]-2-oxo-1-imidazolidinyl}butanamide;

(2S,3S)—N-((1S,2R)-1-benzyl-2-hydroxy-3-{isobutyl[(4-methoxyphenyl)sulfonyl]amino}propyl)-3-methyl-2-{3-[(2-methyl-1,3-thiazol-4-yl)methyl]-2-oxo-1-imidazolidinyl}pentanamide;

(2S)—N$^1$-((1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}butanediamide;

(4-{[34(1S)-1-{[((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methyl acetate;

(2S)—N' 4(1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}pentanediamide;

(2S)-2-[3-(1-benzofuran-2-ylmethyl)-2-oxo-1-imidazolidinyl]-N4(1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-3-methyl-2-[2-oxo-3-(3-quinolinylmethyl)-1-imidazolidinyl]butanamide;

(2S)—N-((1S,2R)-1-benzyl-2-hydroxy-3-{isobutyl[(4-methoxyphenyl)sulfonyl]amino}propyl)-2-{3-[(4-methoxy-5-nitro-3-thienyl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[3-({2-[(methylsulfanyl)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-(3-{[2-(cyanomethyl)-1,3-thiazol-4-yl]methyl}-2-oxo-1-imidazolidinyl)-3-methylbutanamide;

(2S)-2-(3-{[2-(acetylamino)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-{3-[(8-hydroxy-2-quinolinyl)methyl]-2-oxo-1-imidazolidinyl}-3-methylbutanamide;

(2S,3S)—N-((1S,2R)-1-benzyl-2-hydroxy-3-{isobutyl[(4-methoxyphenyl)sulfonyl]amino}propyl)-3-methyl-2-{3-[(1-methyl-1H-benzimidazol-2-yl)methyl]-2-oxo-1-imidazolidinyl}pentanamide;

(2S)—N-((1S,2R)-1-benzyl-2-hydroxy-3-{isobutyl[(4-methoxyphenyl)sulfonyl]amino}propyl)-2-{3-[(4-methoxy-2-quinolinyl)methyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[2-oxo-3-(2-quinoxalinylmethyl)-1-imidazolidinyl]butanamide;

(2S)—N$^1$-((1S,2R)-1-benzyl-2-hydroxy-3-{isobutyl[(4-methoxyphenyl)sulfonyl]amino}propyl)-N$^4$-methyl-2-{3-[(2-methyl-1,3-thiazol-4-yl)methyl]-2-oxo-1-imidazolidinyl}butanediamide;

(2S)—N$^1$-((1S,2R)-1-benzyl-2-hydroxy-3-{isobutyl[(4-methoxyphenyl)sulfonyl]amino}propyl)-N$^4$-ethyl-2-{3-[(2-methyl-1,3-thiazol-4-yl)methyl]-2-oxo-1-imidazolidinyl}butanediamide;

(2S,3S)—N-((1S,2R)-1-benzyl-2-hydroxy-3-{isobutyl[(4-methoxyphenyl)sulfonyl]amino}propyl)-3-methyl-2-[2-oxo-3-(4-quinolinylmethyl)-1-imidazolidinyl]pentanamide;

(2S,3S)-2-[3-(1H-benzimidazol-5-ylmethyl)-2-oxo-1-imidazolidinyl]-N-((1S,2R)-1-benzyl-2-hydroxy-3-{isobutyl[(4-methoxyphenyl)sulfonyl]amino}propyl)-3-methylpentanamide;

(2S)—N-((1S,2R)-1-benzyl-3-{(cyclopentylmethyl)[(4-methoxyphenyl)sulfonyl]amino}-2-hydroxypropyl)-2-(3-{[2-(methoxymethyl)-1,3-thiazol-4-yl]methyl}-2-oxo-1-imidazolidinyl)-3-methylbutanamide;

(2S,3S)—N-((1S,2R)-1-benzyl-2-hydroxy-3-{isobutyl[(4-methoxyphenyl)sulfonyl]amino}propyl)-3-methyl-2-[2-oxo-3-(2-quinolinylmethyl)-1-imidazolidinyl]pentanamide;

(2S,3S)—N-((1S,2R)-1-benzyl-3-{(cyclopentylmethyl)[(4-methoxyphenyl)sulfonyl]amino}-2-hydroxypropyl)-3-methyl-2-{3-[(1-methyl-1H-benzimidazol-2-yl)methyl]-2-oxo-1-imidazolidinyl}pentanamide;

(2S,3S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-2-[3-(3-cyanobenzyl)-2-oxo-1-imidazolidinyl]-3-methylpentanamide;

(2S)—N-((1S,2R)-1-benzyl-2-hydroxy-3-{isobutyl[(4-methoxyphenyl)sulfonyl]amino}propyl)-3,3-dimethyl-2-{3-[(1-methyl-1H-benzimidazol-2-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-3-(formylamino)-2-{3-[(2-methyl-1,3-thiazol-4-yl)methyl]-2-oxo-1-imidazolidinyl}propanamide;

(2S)-3-[(aminocarbonyl)amino]-N-((1S,2R)-1-benzyl-2-hydroxy-3-{isobutyl[(4-methoxyphenyl)sulfonyl]amino}propyl)-2-{3-[(2-methyl-1,3-thiazol-4-yl)methyl]-2-oxo-1-imidazolidinyl}propanamide;

(2S,3S)—N-((1S,2R)-1-benzyl-2-hydroxy-3-{isobutyl[(4-methoxyphenyl)sulfonyl]amino}propyl)-2-(3-{[6-(methoxymethyl)-2-pyridinyl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-2-[3-({2-[(1E)-N-hydroxyethanimidoyl]-4-pyridinyl}methyl)-2-oxo-1-imidazolidinyl]-3-methylpentanamide;

(2S,3S)—N-((1S,2R)-1-benzyl-2-hydroxy-3-{isobutyl[(4-methoxyphenyl)sulfonyl]amino}propyl)-3-methyl-2-(2-oxo-3-{[2-(2-pyridinyl)-1,3-thiazol-4-yl]methyl}-1-imidazolidinyl)pentanamide;

(2S,3S)—N-((1S,2R)-1-benzyl-2-hydroxy-3-{isobutyl[(4-methoxyphenyl)sulfonyl]amino}propyl)-3-methyl-2-(2-oxo-3-{[2-(3-pyridinyl)-1,3-thiazol-4-yl]methyl}-1-imidazolidinyl)pentanamide;

(2S)—N-((1S,2R)-1-benzyl-2-hydroxy-3-{isobutyl[(4-methoxyphenyl)sulfonyl]amino}propyl)-2-(3-{[2-(methoxymethyl)-1,3-thiazol-4-yl]methyl}-2-oxo-1-imidazolidinyl)-3,3-dimethylbutanamide;

(2S)—N-((1S,2R)-1-benzyl-2-hydroxy-3-{isobutyl[(4-methoxyphenyl)sulfonyl]amino}propyl)-3,3-dimethyl-2-(2-oxo-3-{[2-(3-pyridinyl)-1,3-thiazol-4-yl]methyl}-1-imidazolidinyl)butanamide;

(2S,3S)—N-((1S,2R)-1-benzyl-2-hydroxy-3-{isobutyl[(4-methoxyphenyl)sulfonyl]amino}propyl)-3-methyl-2-(3-{[2-(2-methyl-1,3-thiazol-4-yl)-1,3-thiazol-4-yl]methyl}-2-oxo-1-imidazolidinyl)pentanamide;

(2S,3S)—N-((1S,2R)-1-benzyl-2-hydroxy-3-{isobutyl[(4-methoxyphenyl)sulfonyl]amino}propyl)-2-(3-{[2-(2-ethyl-4-pyridinyl)-1,3-thiazol-4-yl]methyl}-2-oxo-1-imidazolidinyl)-3-methylpentanamide;

(2S,3S)—N-((1S,2R)-1-benzyl-2-hydroxy-3-{isobutyl[(4-methoxyphenyl)sulfonyl]amino}propyl)-3-methyl-2-(3-{[2-(6-methyl-3-pyridinyl)-1,3-thiazol-4-yl]methyl}-2-oxo-1-imidazolidinyl)pentanamide;

(2S)—N-((1S,2R)-1-benzyl-2-hydroxy-3-{isobutyl[(4-methoxyphenyl)sulfonyl]amino}propyl)-3,3-dimethyl-2-{3-[(3-methyl-3H-imidazo[4,5-b]pyridin-2-yl)methyl]-2-oxo-1-imidazolidinyl}butanamide;

(2S,3S)—N-((1S,2R)-1-benzyl-2-hydroxy-3-{isobutyl[(4-methoxyphenyl)sulfonyl]amino}propyl)-3-methyl-2-{3-[(3-methyl-3H-imidazo[4,5-b]pyridin-2-yl)methyl]-2-oxo-1-imidazolidinyl}pentanamide;

(2S,3S)—N-((1S,2R)-1-benzyl-3-{(cyclopentylmethyl)[(4-methoxyphenyl)sulfonyl]amino}-2-hydroxypropyl)-3-methyl-2-(2-oxo-3-{[2-(3-pyridinyl)-1,3-thiazol-4-yl]methyl}-1-imidazolidinyl)pentanamide;

(2S,3S)—N-{(1S,2R)-1-benzyl-2-hydroxy-3-[[(4-methoxyphenyl)sulfonyl](neopentyl)amino]propyl}-3-methyl-2-(2-oxo-3-{[2-(3-pyridinyl)-1,3-thiazol-4-yl]methyl}-1-imidazolidinyl)pentanamide;

(2S)-2-(3-{[2-(aminomethyl)-1,3-thiazol-4-yl]methyl}-2-oxo-1-imidazolidinyl)-N-((1S,2R)-1-benzyl-2-hydroxy-3-{isobutyl[(4-methoxyphenyl)sulfonyl]amino}propyl)-3-methylbutanamide;

(2S)-2-[3-({2-[(acetylamino)methyl]-1,3-thiazol-4-yl}methyl)-2-oxo-1-imidazolidinyl]-N-((1S,2R)-1-benzyl-2-hydroxy-3-{isobutyl[(4-methoxyphenyl)sulfonyl]amino}propyl)-3-methylbutanamide;

(2S)—N-((1S,2R)-1-benzyl-2-hydroxy-3-{isobutyl[(4-methoxyphenyl)sulfonyl]amino}propyl)-2-(3-{[2-(hydroxymethyl)-1,3-thiazol-4-yl]methyl}-2-oxo-1-imidazolidinyl)-3-methylbutanamide;

(2S)—N-((1S,2R)-1-benzyl-2-hydroxy-3-{isobutyl[(4-methoxyphenyl)sulfonyl]amino}propyl)-2-[3-({2-[(dimethylamino)methyl]-1,3-thiazol-4-yl}methyl)-2-oxo-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-3-methyl-2-{3-[(2-{[(methylsulfonyl)amino]methyl}-1,3-thiazol-4-yl)methyl]-2-oxo-1-imidazolidinyl}butanamide;

(2S)—N-((1S,2R)-1-benzyl-2-hydroxy-3-{isobutyl[(4-methoxyphenyl)sulfonyl]amino}propyl)-2-[3-({2-[(hydroxyimino)methyl]-1,3-thiazol-4-yl}methyl)-2-oxo-1-imidazolidinyl]-3-methylbutanamide;

methyl(4-{[3-((1S)-1-{[((1S,2R)-1-benzyl-2-hydroxy-3-{isobutyl[(4-methoxyphenyl)sulfonyl]amino}propyl)amino]carbonyl}-2-methylpropyl)-2-oxo-1-imidazolidinyl]methyl}-1,3-thiazol-2-yl)methylcarbamate;

(2S)—N-((1S,2R)-1-benzyl-2-hydroxy-3-{isobutyl[(4-methoxyphenyl)sulfonyl]amino}propyl)-3-methyl-2-[3-({2-[(methylsulfonyl)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-[3-({2-[(diethylamino)methyl]-1,3-thiazol-4-yl}methyl)-2-oxo-1-imidazolidinyl]-3-methylbutanamide;

(2S)—N-((1S,2R)-1-benzyl-2-hydroxy-3-{isobutyl[(4-methoxyphenyl)sulfonyl]amino}propyl)-2-{3-[2-(isopropylamino)-2-oxoethyl]-2-oxo-1-imidazolidinyl}-3-methylbutanamide;

(2S)—N-((1S,2R)-1-benzyl-2-hydroxy-3-{isobutyl[(4-methoxyphenyl)sulfonyl]amino}propyl)-3-methyl-2-[3-({2-[(methylamino)methyl]-1,3-thiazol-4-yl}methyl)-2-oxo-1-imidazolidinyl]butanamide;

(2S)—N-((1S,2R)-1-benzyl-2-hydroxy-3-{isobutyl[(4-methoxyphenyl)sulfonyl]amino}propyl)-2-[3-({2-[N-hydroxyethanimidoyl]-1,3-thiazol-4-yl}methyl)-2-oxo-1-imidazolidinyl]-3-methylbutanamide;

(2S,3S)-2-(3-{[2-(aminomethyl)-1,3-thiazol-4-yl]methyl}-2-oxo-1-imidazolidinyl)-N-((1S,2R)-1-benzyl-3-{(cyclopentylmethyl)[(4-methoxyphenyl)sulfonyl]amino}-2-hydroxypropyl)-3-methylpentanamide;

(2S,3S)-2-(3-{3-[amino(hydroxyimino)methyl]benzyl}-2-oxo-1-imidazolidinyl)-N-((1S,2R)-1-benzyl-2-hydroxy-3-{isobutyl[(4-methoxyphenyl)sulfonyl]amino}propyl)-3-methylpentanamide;

(2S)—N-((1S,2R)-1-benzyl-2-hydroxy-3-{isobutyl[(4-methoxyphenyl)sulfonyl]amino}propyl)-4-hydroxy-2-{3-[(1-methyl-1H-benzimidazol-2-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[[(4-aminophenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1R,2R)-1-benzyl-2-hydroxy-3-[[(4-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-2-{3-[(2-isopropyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-isopropyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-isopropyl-1,3-thiazol-4-yl)methyl]-2-oxo-1-imidazolidinyl}-3-methylbutanamide;

(2S)—N-{(1S,2R)-1-benzyl-2-hydroxy-3-[[(4-hydroxyphenyl)sulfonyl](isobutyl)amino]propyl}-2-{3-[(2-ethyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-3-[[(3-amino-4-hydroxyphenyl)sulfonyl](isobutyl)amino]-1-benzyl-2-hydroxypropyl}-2-{3-[(2-ethyl-1,3-thiazol-4-yl)methyl]-2-oxo-1-imidazolidinyl}-3-methylbutanamide;

(2S)—N-{(1S,2R)-1-benzyl-2-hydroxy-3-[[(4-hydroxyphenyl)sulfonyl](isobutyl)amino]propyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(4-aminophenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(3-amino-4-chlorophenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-3-[[(3-amino-4-hydroxyphenyl)sulfonyl](isobutyl)amino]-1-benzyl-2-hydroxypropyl}-2-(3-{[2-(methoxymethyl)-1,3-thiazol-4-yl]methyl}-2-oxo-1-imidazolidinyl)-3-methylbutanamide;

(2S)—N-{(1S,2R)-1-benzyl-2-hydroxy-3-{[[(4-hydroxy-3-{[(1-methyl-1H-imidazol-4-yl)sulfonyl]amino}phenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dichloro-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[({4-hydroxy-3-[(3-pyridinylsulfonyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-hydroxy-3-[(methylsulfonyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-2-{3-[(2-cyclopropyl-1,3-thiazol-4-yl)methyl]-2-oxo-1-imidazolidinyl}-3-methylbutanamide;

(2S)—N-{(1S,2R)-3-[[(3-amino-4-chlorophenyl)sulfonyl](isobutyl)amino]-1-benzyl-2-hydroxypropyl}-2-{3-[(2-cyclopropyl-1,3-thiazol-4-yl)methyl]-2-oxo-1-imidazolidinyl}-3-methylbutanamide;

(2S)—N-{(1S,2R)-3-[[(4-aminophenyl)sulfonyl](isobutyl)amino]-1-benzyl-2-hydroxypropyl}-2-{3-[(2-cyclopropyl-1,3-thiazol-4-yl)methyl]-2-oxo-1-imidazolidinyl}-3-methylbutanamide;

(2S)—N-{(1S,2R)-1-benzyl-3-[[(3-ethyl-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dichloro-2-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl({4-[(methylsulfonyl)amino]phenyl}sulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-fluoro-4-hydroxy-2-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-chloro-4-hydroxy-2-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-hydroxy-5-methylphenyl)sulfonyl]isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-{[(methylamino)sulfonyl]amino}phenyl)sulfonyl](isobutyl)amino]propyl}-3-methyl-2-{3-[(2-methyl-1,3-thiazol-4-yl)methyl]-2-oxo-1-imidazolidinyl}butanamide;

ethyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

(2S)—N-{(1S,2R)-1-benzyl-2-hydroxy-3-[[(4-hydroxy-3-isopropylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(1-methyl-1H-benzimidazol-2-yl)methyl]-2-oxo-1-imidazolidinyl}butanamide;

(2S)—N-{(1S,2R)-1-benzyl-2-hydroxy-3-[[(4-hydroxy-3,5-dimethylphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-{3-[(5-nitro-3-thienyl)methyl]-2-oxo-1-imidazolidinyl}butanamide;

(2S)—N-{(1S,2R)-1-benzyl-2-hydroxy-3-[[(4-hydroxyphenyl)sulfonyl](isobutyl)amino]propyl}-3-methyl-2-{3-[(2-nitro-1,3-thiazol-4-yl)methyl]-2-oxo-1-imidazolidinyl}butanamide;

(2S)—N-{(1S,2R)-3-[[(4-amino-3-hydroxyphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

{4-[(3-{(1S)-1-[({(1S,2R)-3-[[(3-amino-4-chlorophenyl)sulfonyl](isobutyl)amino]-1-benzyl-2-hydroxypropyl}amino)carbonyl]-2-methylpropyl}-2-oxo-1-imidazolidinyl)methyl]-1,3-thiazol-2-yl}methyl acetate;

(2S)—N-{(1S,2R)-1-benzyl-2-hydroxy-3-[{[4-hydroxy-3-(methylamino)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[3-(dimethylamino)-4-hydroxyphenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-{[(ethylamino)carbonyl]amino}-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

methyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

benzyl 2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}phenylcarbamate;

(2S)—N-{(1S,2R)-3-[[(1-acetyl-2,3-dihydro-1H-indol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2-chloro-4-hydroxy-5-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-acetyl-4-hydroxyphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(2-amino-1,3-thiazol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(4-hydroxy-3-methylphenyl)sulfonyl](isobutyl)amino]propyl}-3-methyl-2-[2-oxo-3-(3-quinolinylmethyl)-1-imidazolidinyl]butanamide;

(2S)—N-{(1S,2R)-1-benzyl-2-hydroxy-3-[[(4-hydroxy-3-methylphenyl)sulfonyl](isobutyl)amino]propyl}-3-methyl-2-{3-[(5-nitro-3-thienyl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-3-methyl-2-[2-oxo-3-(4-quinolinylmethyl)-1-imidazolidinyl]butanamide;

(2S)—N-{(1S,2R)-1-benzyl-2-hydroxy-3-[{[4-(2-hydroxyethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)-2-(3-{[2-(acetylamino)-1,3-thiazol-4-yl]methyl}-2-oxo-1-imidazolidinyl)-N-{(1S,2R)-3-[[(3-amino-4-chlorophenyl)sulfonyl](isobutyl)amino]-1-benzyl-2-hydroxypropyl}-3-methylbutanamide;

(2S)—N-{(1S,2R)-1-benzyl-3-[[(3-cyano-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S,3S)—N-{(1S,2R)-3-[[(3-amino-4-chlorophenyl)sulfonyl](isobutyl)amino]-1-benzyl-2-hydroxypropyl}-3-methyl-2-{3-[(1-methyl-1H-benzimidazol-2-yl)methyl]-2-oxo-1-imidazolidinyl}pentanamide;

(2S,3S)—N-{(1S,2R)-3-[[(3-amino-4-chlorophenyl)sulfonyl](isobutyl)amino]-1-benzyl-2-hydroxypropyl}-3-methyl-2-[2-oxo-3-(4-quinolinylmethyl)-1-imidazolidinyl]pentanamide;

(2S,3S)—N-{(1S,2R)-3-[[(3-amino-4-chlorophenyl)sulfonyl](isobutyl)amino]-1-benzyl-2-hydroxypropyl}-2-[3-(1H-benzimidazol-5-ylmethyl)-2-oxo-1-imidazolidinyl]-3-methylpentanamide;

(2S,3S)—N-{(1S,2R)-3-[[(3-amino-4-chlorophenyl)sulfonyl](isobutyl)amino]-1-benzyl-2-hydroxypropyl}-3-methyl-2-[2-oxo-3-(2-quinolinylmethyl)-1-imidazolidinyl]pentanamide;

(2S)—N-{(1S,2R)-3-[[(3-amino-4-chlorophenyl)sulfonyl](isobutyl)amino]-1-benzyl-2-hydroxypropyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-3-[[(4-aminophenyl)sulfonyl](isobutyl)amino]-1-benzyl-2-hydroxypropyl}-3,3-dimethyl-2-(2-oxo-3-{[2-(3-pyridinyl)-1,3-thiazol-4-yl]methyl}-1-imidazolidinyl)butanamide;

(2S)—N-{(1S,2R)-3-[[(3-amino-4-chlorophenyl)sulfonyl](isobutyl)amino]-1-benzyl-2-hydroxypropyl}-2-

(3-{[2-(methoxymethyl)-1,3-thiazol-4-yl]methyl}-2-oxo-1-imidazolidinyl)-3,3-dimethylbutanamide;

(2S,3S)—N-{(1S,2R)-3-[[(3-amino-4-chlorophenyl)sulfonyl](isobutyl)amino]-1-benzyl-2-hydroxypropyl}-3-methyl-2-(3-{[2-(2-methyl-1,3-thiazol-4-yl)-1,3-thiazol-4-yl]methyl}-2-oxo-1-imidazolidinyl)pentanamide;

(2S)—N-{(1S,2R)-1-benzyl-2-hydroxy-3-[({4-[(E)-(hydroxyimino)methyl]phenyl}sulfonyl)(neopentyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[{[4-((E)-{[(3-aminopropanoyl)oxy]imino}methyl)phenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(3-methoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-chlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dibromophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(1,2-dimethyl-1H-imidazol-4-yl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(1-methyl-1H-imidazol-4-yl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-bromo-5-chloro-2-pyridinyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-bromophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-fluorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dimethoxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,4-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(4-acetylphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-{isobutyl[(2,4,6-trichlorophenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-cyanophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,5-dichloro-3-thienyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(2-thienylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,4-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(2,3-dichlorophenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3,5-dimethyl-4-isoxazolyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-methoxy-4-methylphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-3-[{[4-(acetylamino)-3-chlorophenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

2-hydroxy-5-{[{[(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoic acid;

(2S)—N-{(1S,2R)-1-benzyl-3-[[(3-fluoro-4-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(5-isoquinolinylsulfonyl)amino]propyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(3,4,5-trimethoxyphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(3-chloro-4-methylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[2-chloro-5-(trifluoromethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[2-chloro-4-(trifluoromethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

4-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoic acid;

(2S)—N-{(1S,2R)-1-benzyl-2-hydroxy-3-[isobutyl(phenylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-bromo-2-methoxyphenyl)sulfonyl(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-oxo-2,3-dihydro-1,3-benzoxazol-6-yl)sulfonyl]amino}propyl)-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(4-vinylphenyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2,3-dihydro-1-benzofuran-5-ylsulfonyl)(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[{[4-(1-hydroxyethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[(1,3-benzodioxol-5-ylsulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[(1-benzofuran-5-ylsulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[isobutyl(3-pyridinylsulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[{[2-(acetylamino)-4-methyl-1,3-thiazol-5-yl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(2-methyl-2,3-dihydro-1-benzofuran-5-yl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-{(Z)-[(benzyloxy)imino]methyl}-2-furyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

methyl 3-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzoate;

(2S)—N-{(1S,2R)-3-[[(3-acetylphenyl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-((1S,2R)-1-benzyl-2-hydroxy-3-{isobutyl[(1-oxido-4-pyridinyl)sulfonyl]amino}propyl)-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[[(3-hydroxyphenyl)sulfonyl](isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-bromo-2-hydroxyphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[{[4-(1,2-dihydroxyethyl)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(4-formylphenyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[{[4-(hydroxymethyl)phenyl]sulfonyl}(isobutyl)amino]propyl}-3-methyl-2-{3-[(2-methyl-1,3-thiazol-4-yl)methyl]-2-Oxo-1-imidazolidinyl}butanamide;

(2S)—N-{(1S,2R)-1-benzyl-3-[{[4-(formylamino)phenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(3-amino-4-chlorophenyl)sulfonyl](isobutyl)amino]-1-benzyl-2-hydroxypropyl}-2-(3-{[2-(hydroxymethyl)-1,3-thiazol-4-yl]methyl}-2-oxo-1-imidazolidinyl)-3-methylbutanamide;

(2S)—N-{(1S,2R)-3-[{[3-(acetylamino)-4-hydroxyphenyl]sulfonyl}(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

tert-butyl 2-(2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate;

(2S)—N-{(1S,2R)-1-benzyl-3-[{[3-(formylamino)-4-hydroxyphenyl]sulfonyl}(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({4-hydroxy-3-[(phenylacetyl)amino]phenyl}sulfonyl)(isobutyl)amino]propyl}-3-methyl-2-{3-[(2-methyl-1,3-thiazol-4-yl)methyl]-2-oxo-1-imidazolidinyl}butanamide;

tert-butyl 3-(2-hydroxy-5-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-3-oxopropylcarbamate;

(2S)—N-{(1S,2R)-1-benzyl-2-hydroxy-3-[isobutyl({4-[(methoxyimino)methyl]phenyl}sulfonyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[(2,3-dihydro-1H-indol-5-ylsulfonyl)(isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[[(2-amino-4-methyl-1,3-thiazol-5-yl)sulfonyl](isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-3-[({3-[(3-aminopropanoyl)amino]-4-hydroxyphenyl}sulfonyl)(isobutyl)amino]-1-benzyl-2-hydroxypropyl}-3-methyl-2-{3-[(2-methyl-1,3-thiazol-4-yl)methyl]-2-oxo-1-imidazolidinyl}butanamide;

tert-butyl 2-(3-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}anilino)-2-oxoethylcarbamate;

(2S)—N-{(1S,2R)-1-benzyl-2-hydroxy-3-[{[3-(hydroxymethyl)phenyl]sulfonyl}(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-3-[[(5-formyl-2-furyl)sulfonyl](isobutyl)amino]-2-hydroxypropyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({5-[(E)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-1-benzyl-2-hydroxy-3-[({5-[(Z)-(hydroxyimino)methyl]-2-furyl}sulfonyl)(isobutyl)amino]propyl}-3-methyl-2-{3-[(2-methyl-1,3-thiazol-4-yl)methyl]-2-oxo-1-imidazolidinyl}butanamide;

(2S)—N-{(1S,2R)-3-[({4-[amino(hydroxyimino)methyl]phenyl}sulfonyl)(isobutyl)amino]-1-benzyl-2-hydroxypropyl}-3-methyl-2-{3-[(2-methyl-1,3-thiazol-4-yl)methyl]-2-oxoimidazolidin-1-yl}butanamide;

4-{[{(2R,3S)-2-hydroxy-3-[((2S)-3-methyl-2-{3-[(2-methyl-1,3-thiazol-4-yl)methyl]-2-oxo-1-imidazolidinyl}butanoyl)amino]-4-phenylbutyl}(isobutyl)amino]sulfonyl}benzamide;

4-{[[(2R,3S)-2-hydroxy-3-({(2S,3S)-3-methyl-2-[2-oxo-3-(3-pyridinylmethyl)-1-imidazolidinyl]pentanoyl}amino)-4-phenylbutyl](isobutyl)amino]sulfonyl}benzamide; and (2S,3S)—N-{(1S,2R)-1-benzyl-3-[[(4-cyanophenyl)sulfonyl](isobutyl)amino]-2-hydroxypropyl}-3-methyl-2-[2-oxo-3-(3-pyridinylmethyl)-1-imidazolidinyl]pentanamide.

\* \* \* \* \*